United States Patent
Bhide et al.

(10) Patent No.: US 10,214,537 B2
(45) Date of Patent: Feb. 26, 2019

(54) BICYCLIC HETEROARYL AMINE COMPOUNDS

(71) Applicant: BRISTOL-MYERS SQUIBB COMPANY, Princeton, NJ (US)

(72) Inventors: Rajeev S. Bhide, Bangalore (IN); Douglas G. Batt, Wilmington, DE (US); Robert J. Cherney, Newton, PA (US); Lyndon A. M. Cornelius, Jackson, NJ (US); Qingjie Liu, Newton, PA (US); David Marcoux, Pennington, NJ (US); James Neels, Holland, PA (US); Michael A. Poss, Lawrenceville, NJ (US); Zheming Ruan, Dayton, NJ (US); Qing Shi, Princeton, NJ (US); Anurag S. Srivastava, Belle Mead, NJ (US); Lan-ying Qin, Plainsboro, NJ (US); Joseph A. Tino, Lawrenceville, NJ (US); Scott Hunter Watterson, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 94 days.

(21) Appl. No.: 15/521,202

(22) PCT Filed: Oct. 21, 2015

(86) PCT No.: PCT/US2015/056576
§ 371 (c)(1),
(2) Date: Apr. 21, 2017

(87) PCT Pub. No.: WO2016/064957
PCT Pub. Date: Apr. 28, 2016

(65) Prior Publication Data
US 2017/0355707 A1   Dec. 14, 2017

Related U.S. Application Data

(60) Provisional application No. 62/067,089, filed on Oct. 22, 2014.

(51) Int. Cl.
*C07D 487/04* (2006.01)
*C07D 491/08* (2006.01)
(Continued)

(52) U.S. Cl.
CPC ......... *C07D 491/08* (2013.01); *C07D 487/04* (2013.01)

(58) Field of Classification Search
CPC combination set(s) only.
See application file for complete search history.

(56) References Cited

U.S. PATENT DOCUMENTS 8,084,620 B2   12/2011   Liu et al.
9,447,101 B2   9/2016   Yang et al.
(Continued)

FOREIGN PATENT DOCUMENTS

WO   WO 2005/097052   10/2005
WO   WO 2005/113556   12/2005
(Continued)

OTHER PUBLICATIONS

International Search Report Application No. PCT/US2015/056576 dated Jan. 18, 2016.
(Continued)

*Primary Examiner* — Amanda L Aguirre
(74) *Attorney, Agent, or Firm* — Gary Greenblatt

(57) ABSTRACT

Disclosed are compounds of Formula (I) or a salt thereof; wherein: X is N or CH; $Q_1$ is: (i) Cl, Br, I, —CN, —CH$_3$, or —CF$_3$; (ii) a 5-membered heteroaryl selected from pyrrolyl, pyrazolyl, imidazolyl, oxazolyl, thiazolyl, triazolyl, oxadiazolyl, and thiadiazolyl; (iii) a 6?membered heteroaryl selected from pyridinyl, pyridazinyl, and pyrimidinyl; or (iv) a bicyclic heteroaryl selected from indolyl, pyrrolopyridinyl, pyrazolopyridinyl and benzo[d]oxazolyl; wherein each of said 5-membered, 6-membered, and bicyclic heteroaryl is substituted with zero to 1 $R_a$ and zero to 1 $R_b$; and $R_1$, $R_2$, $R_3$, $R_4$, $R_5$, $R_6$, $R_a$, and $R_b$ are defined herein. Also disclosed are methods of using such compounds as modulators of PI3K, and pharmaceutical compositions comprising such compounds. These compounds are useful in treating, preventing, or slowing inflammatory and autoimmune diseases.

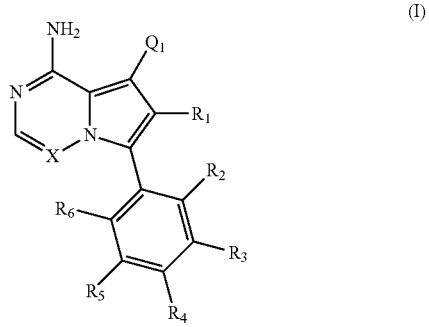

(I)

9 Claims, No Drawings

(51) Int. Cl.
*A61K 31/53* (2006.01)
*A61K 31/541* (2006.01)
*A61P 29/00* (2006.01)

(56) References Cited

U.S. PATENT DOCUMENTS

| | | | |
|---|---|---|---|
| 2007/0112005 A1 | 5/2007 | Chen et al. | |
| 2009/0281079 A1* | 11/2009 | Dixon | C07D 487/04 514/211.15 |
| 2011/0044942 A1 | 2/2011 | Puri et al. | |
| 2012/0009147 A1 | 1/2012 | Cho et al. | |
| 2012/0208819 A1* | 8/2012 | Arndt | C07D 213/82 514/243 |
| 2012/0232054 A1* | 9/2012 | Moriarty | A61K 31/53 514/210.21 |
| 2013/0023514 A1* | 1/2013 | Markwalder | C07D 487/04 514/210.02 |

FOREIGN PATENT DOCUMENTS

| | | |
|---|---|---|
| WO | WO 2007/061882 | 5/2007 |
| WO | WO-2007056170 A2 * | 5/2007 ........... C07D 487/04 |
| WO | WO 2007/064883 | 6/2007 |
| WO | WO 2007/064931 | 6/2007 |
| WO | WO 2007/079164 | 7/2007 |
| WO | WO 2007/087395 | 8/2007 |
| WO | WO 2008/089105 | 7/2008 |
| WO | WO 2009/117482 | 9/2009 |
| WO | WO 2009/136966 | 11/2009 |
| WO | WO 2010/051042 | 5/2010 |
| WO | WO 2010/051043 | 5/2010 |
| WO | WO 2010/126960 | 11/2010 |
| WO | WO 2011/011550 | 1/2011 |
| WO | WO 2011/014726 | 2/2011 |
| WO | WO 2011/123493 | 10/2011 |
| WO | WO 2011/159857 | 12/2011 |
| WO | WO 2012/007493 | 1/2012 |
| WO | WO 2012/148540 | 11/2012 |
| WO | WO 2012/151562 | 11/2012 |
| WO | WO 2013/004551 | 1/2013 |
| WO | WO 2013/028263 | 2/2013 |
| WO | WO 2013/095761 | 6/2013 |
| WO | WO 2013/104610 | 7/2013 |
| WO | WO 2013/104611 | 7/2013 |
| WO | WO 2013/124316 | 8/2013 |
| WO | WO 2013/124826 | 8/2013 |
| WO | WO 2014/011568 | 1/2014 |
| WO | WO 2014/033196 | 3/2014 |
| WO | WO 2015/058084 | 4/2015 |
| WO | WO 2016/064958 | 4/2016 |
| WO | WO 2007/056170 | 5/2017 |

OTHER PUBLICATIONS

Vanhaesebroeck et al., "The emerging mechanisms of isoform-specific PI3K signaling," Nature Review, Mol. Cell Biol. vol. 11, pp. 329-341 (2010).
Vanhaesebroeck et al., "PI3K signaling: the path to discovery and understandings," Nature Review. Mol. Cell Biol. vol. 13, pp. 195-203 (2012).
Ali et al., "Inactivation of PI92)K p110δ breaks regulatory T-cell-mediated immune tolerance to cancer," Nature, vol. 510, pp. 407-411 (2014).
Lu et al., "Suppression of Phosphoinositide 3-Kinase Signaling and Alteration of Multiple Ion Currents in Drug-Induced Long QT Syndrome," Science Translational Medicine, vol. 4, Issue 131 ra150, pp. 1-10 (2012).
Maxwell et al., "Attenuation of phosphoinositide 3-kinase δ signaling restrains autoimmune disease," Journal of Autoimmunity, 38, pp. 381-391 (2012).

* cited by examiner

BICYCLIC HETEROARYL AMINE COMPOUNDS

CROSS-REFERENCE TO RELATED APPLICATIONS

This application is a national phase application under 35 U.S.C. § 371 of International Patent Application No. PCT/US2015/056576, filed Oct. 21, 2015, which claims priority to U.S. Provisional Application 62/067,089, filed Oct. 22, 2014, which are expressly incorporated fully herein by reference.

DESCRIPTION

The present invention generally relates to heteroaryl substituted pyrrolotriazine amine compounds useful as kinase inhibitors, including the modulation of phosphoinositide 3-kinases (PI3Ks). Provided herein are heteroaryl substituted pyrrolotriazine amine compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including PI3K.

Phosphoinositide 3-kinases are lipid kinases that phosphorylate the 3-OH position of the inositol ring of membrane-based phosphoinositol substrates, i.e., phosphoinositol (PI), phosphatidylinositol-4-phosphate (PIP) and phosphatidylinositol-4,5-bisphosphate (PI-4,5-P2). The resulting 3-phosphate inositides are homing sites for signaling proteins that bind via their lipid-binding domains (Vanhaesebroeck, B. et al., *Nature Rev. Mol. Cell Biol.,* 11:329-341 (2010)). PI3Ks have been divided into 3 classes based on sequence homology and substrate specificity. Class I converts PI-4,5-P2 to PI-3,4,5 trisphosphate (PIP3); Class II converts PI-4-P to PI-3,4-P2 and PI to PI-3-P; and Class III converts PI into PI-3-P. Class I enzymes are the most extensively studied. Their activity generates PIP3 that forms a docking site for proteins with pleckstrin homology domains. These proteins are upstream components of multiple signaling pathways. (Vanhaesebroeck, B. et al., *Nature Rev. Mol. Cell Biol.,* 13:195-203 (2012)).

Class I PI3Ks are subdivided into Class IA and IB. In both subclasses, the enzymes are heterodimers consisting of a catalytic subunit and a regulatory subunit (Vanhaesebroeck, B. et al., *Nature Rev. Mol. Cell Biol.,* 11:329-341 (2010)). In Class IA, the catalytic subunits are p110α, β, and δ. Each associates with a regulatory subunit of which the most common is p85α, but others have also been identified (p85β, p55α, p55γ, p50α). The p85α regulatory subunit contains two SH2 domains that bind tyrosine phosphorylated following activation of tyrosine kinase receptors. Binding relieves the baseline inhibition that the regulatory subunit exercises on the catalytic subunit. In Class IB, the catalytic subunit p110γ is associated with regulatory subunits p101 or p87. This isoform is activated by the γ,β subunits of G protein-coupled receptors, a pathway that can also be utilized by the other isoforms including PI3kδ.

Class I PI3K isoforms α and β are ubiquitously expressed and mediate a large variety of functions in multiple cell types. They have critical roles in development such that homozygous deletion of each of the genes in mice is embryonic lethal (Vanhaesebroeck, B. et al., *Trends Biochem. Sci.,* 30:194-204 (2005)). These isoforms control important metabolic pathways including insulin-dependent glucose uptake (Shepherd, P. R., *Acta Physiol. Scand.,* 183:3-12 (2005)). In addition, PI3Kα protects against myocardial infarction (Lin, R. C. Y. et al., *Arterioscler. Thromb. Vasc. Biol.,* 30:724-732 (2010)) and its inhibition can elicit ion channel perturbation that manifests as QT prolongation (Lu, Z. et al., *Science Trans. Med.,* 4:131ra150 (2012)). PI3Kγ is also expressed within the cardiovascular system and mediates effects on blood pressure (Carnevale, D. et al., *Cardiovasc. Res.,* 93:200-209 (2012)). Its principal expression is on leukocytes, however. PI3Kδ is also expressed mainly on leukocytes. Both PI3Kγ and δ isoforms mediate a large number of functions associated with immune cell activation and survival. While gene deletion in mice is not lethal in either case, it results in marked impairment of immune function (Vanhaesebroeck, B. et al., *Trends Biochem. Sci.,* 30:194-204 (2005)). Relative to PI3γ, PI3Kδ plays a more prominent role in B cell development such that PI3Kδ knockout mice exhibit blockade of B cell differentiation. It also mediates BCR signaling, antibody generation and class switching. The PI3Kδ isoform plays an important role in T cell function and survival though the other isoforms also participate (So, L. et al., *Biochem. J.,* 442:465-481 (2012)). The involvement of PI3Kδ in autoimmunity disease has been demonstrated preclinically in mouse and rat models of a variety of autoimmune diseases including rheumatoid arthritis (Puri, K. D. et al., *J. Immunol.,* 182(Suppl. 50): 14 (2009)) and systemic lupus erythematosus (SLE) (Maxwell, M. J. et al., *J. Autoimmunity,* 38:381-391 (2012)). In the clinic, PI3Kδ has been found to be activated in peripheral T cells from patients with SLE and tracks with disease severity (Suarez-Fueyo, A. et al., *J. Immunol.,* 187:2376-2385 (2011)). These data suggest that PI3Kδ inhibition holds promise as an effective therapy for the treatment of autoimmune diseases. Furthermore, a consideration of the potential adverse effects of inhibiting the other isoforms point to δ selectivity as the preferred profile.

Thus, inhibition of PI3K activity can be useful for the treatment of allergic disorders and/or autoimmune and/or inflammatory diseases including, but not limited to: systemic lupus erythematosus (SLE), lupus nephritis, rheumatoid arthritis, multiple vasculitides, idiopathic thrombocytopenic purpura (ITP), myasthenia gravis, allergic rhinitis, multiple sclerosis (MS), transplant rejection, membranous nephritis, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, PI3K has been reported to play a role in controlling B-cell survival in certain B-cell cancers. For example, PI3K has been shown to be important for the survival of non-Hodgkins lymphoma (NHL) and chronic lymphocytic leukemia (CLL) cells. The PI3Kd inhibitor idelalisib has been approved for the treatment of these diseases in the United States. Thus inhibition of PI3K activity can be useful for the treatment of B-cell lymphoma and leukemia, including CLL and NHL.

Furthermore, inactivation of PI3Kδ has been reported to break regulatory T cell mediated immune tolerance to cancer, increasing the immune response leading to tumor regression in animal models (Ali, K. et al., *Nature,* 510:407-411 (2014)). Inhibition of PI3Kδ can therefore be useful in the treatment of tumors, particularly those types where there is evidence of inadequate immune response, including but not limited to bladder, breast, colorectal, esophageal, gastric, head and neck, liver, lung, melanoma, ovarian, pancreatic, and prostate cancers, renal cell carcinoma, leukemia and lymphoma. In the treatment of these cancers it is envisaged that the PI3Kδ inhibitor may be combined with other treatments that also stimulate immune responses to tumors, including but not limited to anti-CTLA4, anti-PD-1 and anti-PD-L1 antibodies.

In view of the numerous conditions that are contemplated to benefit by treatment involving modulation of protein kinases, it is immediately apparent that new compounds capable of modulating protein kinases such as PI3K and methods of using these compounds should provide substantial therapeutic benefits to a wide variety of patients.

U.S. Pat. No. 8,084,620 and WO 2011/159857 disclose tricyclic carboxamide compounds useful as kinase inhibitors.

There still remains a need for compounds useful as PI3K inhibitors.

Applicants have found potent compounds that have activity as PI3K inhibitors. These compounds are provided to be useful as pharmaceuticals with desirable stability, bioavailability, therapeutic index, and toxicity values that are important to their drugability.

SUMMARY OF THE INVENTION

The present invention provides bicyclic heteroaryl amine compounds, which are useful as inhibitors of PI3K and the treatment of proliferative diseases, allergic diseases, autoimmune diseases and inflammatory diseases, including prodrugs thereof.

The present invention also provides pharmaceutical compositions comprising at least one compound of Formula (I) and a pharmaceutically acceptable carrier.

The present invention also provides a method of inhibiting PI3K activity comprising administering to a mammal in need thereof at least one compound of Formula (I).

The present invention also provides a method for treating allergic disorders and/or autoimmune and/or inflammatory diseases, comprising administering to a mammal in need thereof at least one compound of Formula (I).

The present invention also provides a method for treating proliferative diseases, such as cancer, comprising administering to a mammal in need thereof at least one compound of Formula (I).

The present invention also provides a method of treating a disease or disorder associated with PI3K activity, the method comprising administering to a mammal in need thereof, at least one compound of Formula (I).

The present invention also provides processes and intermediates for making the compounds of Formula (I).

The present invention also provides a compound of Formula (I) for use in therapy.

The present invention also provides the use of the compounds of Formula (I) for the manufacture of a medicament for the treatment or prophylaxis of PI3K related conditions, such as proliferative diseases, allergic diseases, autoimmune diseases and inflammatory diseases.

The present invention also provides the use of the compounds of Formula (I) for the manufacture of a medicament for treatment of cancer.

The compounds of Formula (I) and compositions comprising the compounds of Formula (I) may be used in treating, preventing, or curing various PI3K related conditions. Pharmaceutical compositions comprising these compounds are useful in treating, preventing, or slowing the progression of diseases or disorders in a variety of therapeutic areas, such as proliferative diseases, allergic diseases, autoimmune diseases and inflammatory diseases.

These and other features of the invention will be set forth in expanded form as the disclosure continues.

DETAILED DESCRIPTION

The first aspect of the present invention provides at least one compound of Formula (I):

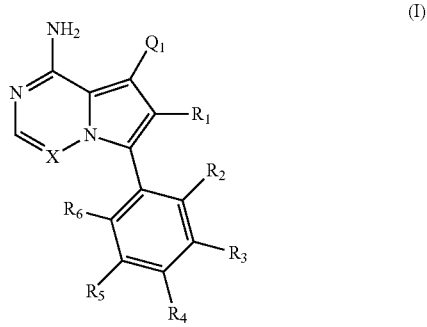

or a salt thereof; wherein:

X is N or CH;

$Q_1$ is:
(i) Cl, Br, I, —CN, —CH$_3$, —CD$_3$, or —CF$_3$;
(ii) a 5-membered heteroaryl selected from pyrrolyl, pyrazolyl, imidazolyl, isoxazolyl, thiazolyl, triazolyl, oxadiazolyl, and thiadiazolyl;
(iii) a 6-membered heteroaryl selected from pyridinyl, pyridazinyl, and pyrimidinyl; or
(iv) a bicyclic heteroaryl selected from indolyl, imidazopyridinyl, pyrrolopyridinyl, pyrazolopyridinyl and benzo[d]oxazolyl;

wherein each of said 5-membered, 6-membered, and bicyclic heteroaryls is substituted with zero to 1 $R_a$ and zero to 1 $R_b$;

$R_a$ is C$_{1-6}$ alkyl, C$_{1-6}$ deuteroalkyl, C$_{1-4}$ fluoroalkyl, C$_{1-4}$ hydroxyalkyl, C$_{1-4}$ alkoxyalkyl, C$_{1-4}$ hydroxyfluoroalkyl, —CH$_2$(C$_{3-6}$ cycloalkyl), —CH$_2$(oxetanyl), —CH$_2$(methyloxetanyl), —NH$_2$, —S(O)$_2$(C$_{1-4}$ alkyl), —S(O)$_2$(C$_{3-6}$ cycloalkyl), C$_{3-6}$ cycloalkyl, C$_{3-6}$ fluorocycloalkyl, oxetanyl, tetrahydropyranyl, pyridinyl, pyrimidinyl, pyridazinyl, phenyl, or fluorophenyl substituted with zero to 1 substituent selected from F, —CF$_3$, and —OCF$_3$;

$R_b$ is Cl, C$_{1-4}$ alkyl, —C$_{1-3}$haloalkyl, or C$_{3-5}$ cycloalkyl;

$R_1$ is H or F;

$R_2$ is H or F;

$R_3$ is H or $R_x$;

$R_4$ is H, F, Cl, —CN, —CH$_3$, —CHF$_2$, —CF$_3$, —OCH$_3$, —OCD$_3$, —(CH$_2$)$_{1-3}$OR$_c$, —CHR$_c$OH, —C(CH$_3$)$_2$OH, —C(O)OCH$_3$, —C(O)N(R$_w$)$_2$, —C(O)—NR$_w$R$_7$, —C(O)R$_8$, —C≡C—(C$_{1-4}$ alkyl), —S(O)$_{0-2}$(C$_{1-4}$ alkyl), or —S(O)$_{0-2}$(C$_{3-6}$ cycloalkyl), or triazolyl, wherein the triazolyl is substituted with 0 to 1 —CH$_3$;

$R_c$ is H, —CH$_3$, —CD$_3$, —CH$_2$CH$_3$, —CH(CH$_3$)$_2$, or cyclopropyl;

$R_5$ is H, F, Cl, —CH$_3$, or —OCH$_3$;

$R_6$ is H or F;

$R_7$ is CD$_3$, C$_{1-6}$alkyl, C$_{1-4}$haloalkyl, C$_{1-6}$alkyl substituted with 0-1 R$_{7a}$, cyclopropyl, cyanoC$_{1-6}$alkyl, or pyridinyl;

$R_{7a}$ is CN, —N(R$_w$)$_2$, —OCH$_3$, —S(O)$_2$CH$_3$;

$R_8$ is C$_{1-6}$alkyl, hydroxyC$_{1-6}$alkyl, morpholinyl, piperazinyl, wherein the piperazinyl is substituted with 0 to 1 —CH$_3$;

$R_w$ is H or —$CH_3$;
$R_x$ is:
(i) $C_{1-4}$ hydroxyalkyl, $C_{1-4}$ alkoxyalkyl, $C_{1-4}$ aminoalkyl, —$CR_wR_w$NH($C_{1-4}$ alkyl), —$CR_wR_w$N($C_{1-4}$ alkyl)$_2$, —$CR_wR_wNR_w(CH_2)_{1-3}O(C_{1-3}$ alkyl), —$CR_wR_wCR_wR_wN(C_{1-3}$ alkyl)$_2$, —$CR_wR_wCR_wR_wNR_wC(O)(C_{1-3}$ alkyl), —$CR_wR_wC(O)(C_{1-3}$ alkyl), —$CR_wR_wNR_wC(O)(C_{1-4}$ hydroxyalkyl), —$(CR_wR_w)_2R_{3a}$, —$CR_w(CF_3)R_{3a}$, —$CR_wR_wNR_wR_{3a}$, —$CH_2OR_{3a}$, or —$CR_wR_wNR_wC(O)R_{3a}$, wherein $R_{3a}$ is tetrahydropyran, morpholinyl, morpholinonyl, oxazinanonyl, oxazolidinonyl, pyrrolidinyl, pyrrolidinonyl, piperazinyl, pyridinyl, pyrrolidinium, or phenyl, each substituted with zero to 1 substituent selected from F, Cl, $C_{1-4}$ alkyl, and —$C(O)CH_3$;

(ii) —C(O)OH or —C(O)$R_{3b}$, wherein $R_{3b}$ is pyrrolidinyl, pyrrolidinonyl, azetidinyl, morpholinyl, dioxidothiomorpholinyl, thiadiazolyl, piperazinyl, piperazinonyl, 8-oxa-3-azabicyclo[3.2.1]octanyl, or piperidinyl, each substituted with zero to 2 substituents independently selected from F, —OH, —CN, $C_{1-2}$ alkyl, $C_{1-3}$ hydroxyalkyl, —C(O)($C_{1-3}$ alkyl), —C(O)$NR_wR_w$, —C(O)O($C_{1-3}$ alkyl), —$NR_wC(O)(C_{1-3}$ alkyl), —C(O)NH($C_{1-3}$ hydroxyalkyl), and —C(O)tetrahydrofuranyl; —C(O)$NR_wR_w$, —C(O)NH($C_{1-4}$ alkyl), —C(O)N($C_{1-4}$ alkyl)$_2$, —C(O)$NR_w(C_{1-3}$ fluoroalkyl), —C(O)$NR_w(C_{1-3}$ hydroxyalkyl), —C(O)$NR_w(C_{1-4}$ alkoxyalkyl), —C(O)$NR_w(CR_wR_wC(O)NR_wR_w)$, —C(O)$NR_wCR_w(C_{1-4}$ alkyl)C(O)$NR_wR_w$, —C(O)$NR_w(C_{1-6}$ hydroxyalkyl), —C(O)$NR_wR_{3c}$, —C(O)$NR_w(CR_wR_w)_{1-2}R_{3c}$, —C(O)$NR_wCR_wR_wC(O)R_{3c}$, —C(O)N($C_{1-4}$ alkyl)($C_{3-6}$ cycloalkyl), —C(O)N($C_{3-6}$ cycloalkyl)$_2$, —C(O)N($C_{3-6}$ cycloalkyl)$R_{3c}$, —C(O)N($C_{3-6}$ cycloalkyl)($CH_2R_{3c}$), or —C(O)$CR_wR_wS(O)_2(C_{1-4}$ alkyl), wherein $R_{3c}$ is phenyl, oxazolyl, oxopiperidinyl, oxopyrrolidinyl, tetrahydropyranyl, tetrazolyl, thiazolyl, piperidinyl, pyrazolyl, oxetanyl, morpholinyl, pyrrolidinyl, or isoxazolyl, each substituted with zero to 2 substituents independently selected from —$CH_3$, —$C(O)CH_3$, —C(O)$NH_2$, cyclopropyl, and —$CH_2OH$;

(iii) —$OR_{3d}$ wherein $R_{3d}$ is tetrahydropyranyl, tetrahydrothiopyranyl, piperidinyl, or pyridinyl, each substituted with zero to 3 substituents independently selected from —$CH_3$, =O, —$C(O)CH_3$, and —$C(O)CH(CH_3)_2$;

(iv) —$NR_wC(O)(C_{1-3}$ alkyl), —$NR_wS(O)_2(C_{1-3}$ alkyl), or —$S(O)_2NR_wR_w$;

(v) $C_{3-6}$ cycloalkyl substituted with zero to 3 substituents independently selected from F, —OH, $C_{1-3}$ alkyl, $C_{1-3}$ fluoroalkyl, $C_{1-3}$ alkoxy, $C_{1-3}$ fluoroalkoxy, —C(O)$NR_w(C_{1-4}$ alkyl), —C(O)$NR_w(C_{1-4}$ fluoroalkyl), —C(O)$NR_w(C_{3-6}$ cycloalkyl), and —C(O)$NR_wR_{3e}$, wherein $R_{3e}$ is oxetanyl, azetidinyl, morpholinyl, piperidinyl, pyrrolidinyl, cyclobutyl, or tetrahydropyranyl, each substituted with zero to 2 substituents independently substituted with F, —$CH_3$, and —$OCH_3$; or (vi) azetidinyl, oxetanyl, tetrahydropyranyl, piperazinyl, pyrrolidinyl, piperidinyl, 1,2-dihydropyridinonyl, morpholinyl, 4,7-diazaspiro[2.5]octanyl, octahydrobenzo[b][1,4]oxazinyl, or benzo[b][1,4]oxazinyl, each substituted with zero to 8 substituents independently selected from D, —OH, —CN, $C_{1-4}$ alkyl, $C_{1-3}$ deuteroalkyl, $C_{1-3}$ fluoroalkyl, $C_{1-4}$ cyanoalkyl, $C_{1-4}$ hydroxyalkyl, $C_{1-3}$ alkoxy, =O, —$(CH_2)O(O)CH_3$, —C(O)($C_{1-4}$ alkyl), —C(O)($C_{1-4}$ hydroxyalkyl), —C(O)$NR_wR_w$, —$C(O)CH_2CN$, —$C(O)CH_2OH$, —C(O)($C_{3-4}$ cycloalkyl), —C(O)$NH_2$, —$S(O)_2CH_3$, —$C(O)OCH_3$, —NHC(O)($C_{1-4}$ alkyl), —$NR_wS(O)(C_{1-3}$ alkyl), —$NR_wS(O)_2(C_{1-3}$ alkyl), —C(O)$CR_wR_wS(O)_2(C_{1-4}$ alkyl), —C(O)(phenyl), —C(O)(fluorophenyl), —C(O)(chlorophenyl), —C(O)(hydroxypropyl phenyl), —C(O)(difluorocyclopropyl), —C(O)(oxazolyl), —C(O)(pyrazinyl), —C(O)(pyrazolyl), —C(O)(pyridazinyl), —C(O)(pyridinyl), —C(O)(pyrimidinyl), —C(O)(pyrrolidinyl), —C(O)(tetrahydropyranyl), —C(O)(thiazolyl), —C(O)(methyl thiazolyl), —C(O)(imidazolyl), —C(O)(methyl imidazolyl), —C(O)(methyl oxazolyl), —C(O)(methyl phenyl), —C(O)(methyl pyrazolyl), —C(O)(morpholinyl), —C(O)(acetophenonyl), —$C(O)CH_2$(oxazolidinonyl), —$C(O)CH_2$(pyrrolidinyl), —$C(O)CH_2$(dioxidothiazinanyl), —$C(O)CH_2$(dioxidothiomorpholinyl), —$C(O)CH_2$(dimethyloxopyrrolidinyl), —$C(O)CH_2$(trimethyloxopyrrolidinyl), —$C(O)CH_2NHC(O)CH_3$, —$C(O)CH_2CH_2NHC(O)CH_3$, —$C(O)CH_2CH_2S(O)_2CH_3$, —$C(O)CH_2S(O)_2CH_3$, —$C(O)CH(CH_3)S(O)_2CH_3$, —$C(O)CH_2CH_2NHS(O)_2CH_3$, —$C(O)CH_2NHS(O)_2CH_3$, —$C(O)CH_2CH_2NHS(O)_2CH_3$, —$C(O)CH(CH_3)NHS(O)_2CH_3$, —$C(O)CH_2CH_2$(methyl-pyrazolyl), —$N(CH_3)_2$, —$N(CH_3)$(acetyl piperidinyl), —$CH_2C(O)NHCH_2C(CH_3)_2OH$, —$N(CH_3)C(O)CH_3$, —$N(CH_3)C(O)C(CH_3)_2OH$, —$N(CH_3)C(O)NH(CH(CH_3)_2)$, —$N(CH_3)C(O)$(furanyl), —$N(CH_3)C(O)CH_2$(pyrazinyl), —$N(CH_3)C(O)$(cyanocyclopropyl), —$N(CH_3)C(O)CH(CH_3)OH$, benzyl, carbamoyl azepanyl, carbamoyl-morpholinyl, chlorophenyl, cyclopropyl, cyclobutyl, dioxothiomorpholinyl, fluorobenzoyl, fluorophenyl, hydroxypiperidinyl, hydroxypyrrolidinyl, hydroxytetrahydropyranyl, methoxytetrahydropyranyl, methyl imidazol[1,2a]pyridinyl, methyloxadiazolyl, methylpiperazinyl, methylpiperazinonyl, methyl pyridinonyl, morpholinyl, oxetanyl, phenyl, piperidinonyl, pyridinyl, and pyrimidinyl;

(vii) phenyl, pyrazolyl, dioxothiazinanyl, pyrrolidinonyl, dimethyloxazolindinonyl, oxazolyl, tetrazolyl, pyridinyl, dioxothiomorpholinyl, quinazolinyl, thiazolyl, octahydropyrrolo[3,4-c]pyrrole, 1H-pyrido[1,2-c]pyrimidine-1,3(2H)-dione, 1,3-oxazinan-2-onyl, 1H,2H,3H,4H,6H-pyrido[1,2-a]piperazinone-1,6-dionyl, 2,3-dihydroquinazolin-4(1H)-onyl, methoxy 2,3-dihydroquinazolin-4(1H)-onyl, 2-azaspiro[4.5]decan-3-onyl, 2-oxa-6-azaspiro[3.3]heptanyl, acetyl 3,8-diazabicyclo[3.2.1]octanyl, acetyl-3,4-dihydroquinoxalin-1(2H)-yl, methyl[1,2,4]triazolo[4,3-a]pyridinyl), or dimethyl[1,2,4]triazolo[4,3-a]pyridinyl, each substituted with zero to 4 substituents independently selected from D, F, Cl, —OH, —CN, —$NH_2$, $C_{1-3}$ alkyl, $C_{1-5}$ hydroxyalkyl, $C_{1-5}$ alkoxyalkyl, —$C(O)CH_3$, —$C(O)C(CH_3)_2OH$, —C(O)$NH_2$, —C(O)NH($C_{1-4}$ alkyl), —CH($R_w$)$CH_2NR_wR_w$, —C(O)$NR_wR_w$, —$S(O)_2NH_2$, —$S(O)_2(C_{1-4}$ alkyl), —$NR_wC(O)(C_{1-4}$ alkyl), —$NR_wS(O)_{0-2}(C_{1-4}$ alkyl), =O, $C_{3-6}$ cycloalkyl, —O(piperidinyl-$S(O)_2CH_3$), —O(piperidinyl-C(O)$NR_w(C_{1-4}$ alkyl), and —O(piperidinyl-C(O)($C_{1-4}$ hydroxyalkyl);

provided that if $R_3$ is H, then $R_4$ is —C(O)N($CH_3)_2$; and if $Q_1$ is Br, then $R_3$ is not —$CH_2OH$.

In another aspect of the present invention provides at least one compound of Formula (I):

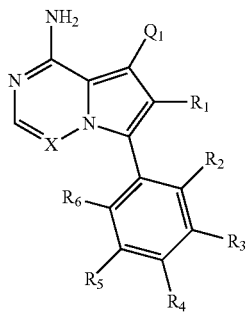

or a salt thereof; wherein:

X is N or CH;

$Q_1$ is:
(i) Cl, Br, I, —CN, —CH$_3$, or —CF$_3$;
(ii) a 5-membered heteroaryl selected from pyrrolyl, pyrazolyl, imidazolyl, isoxazolyl, thiazolyl, triazolyl, oxadiazolyl, and thiadiazolyl;
(iii) a 6-membered heteroaryl selected from pyridinyl, pyridazinyl, and pyrimidinyl; or
(iv) a bicyclic heteroaryl selected from indolyl, imidazopyridinyl, pyrrolopyridinyl, pyrazolopyridinyl and benzo[d]oxazolyl;

wherein each of said 5-membered, 6-membered, and bicyclic heteroaryls is substituted with zero to 1 $R_a$ and zero to 1 $R_b$;

$R_a$ is $C_{1-6}$ alkyl, $C_{1-6}$ deuteroalkyl, $C_{1-4}$ fluoroalkyl, $C_{1-4}$ hydroxyalkyl, $C_{1-4}$ alkoxyalkyl, $C_{1-4}$ hydroxyfluoroalkyl, —CH$_2$(C$_{3-6}$ cycloalkyl), —CH$_2$(oxetanyl), —CH$_2$(methyloxetanyl), —NH$_2$, —S(O)$_2$(C$_{1-4}$ alkyl), —S(O)$_2$(C$_{3-6}$ cycloalkyl), $C_{3-6}$ cycloalkyl, $C_{3-6}$ fluorocycloalkyl, oxetanyl, tetrahydropyranyl, pyridinyl, pyrimidinyl, pyridazinyl, phenyl, or fluorophenyl substituted with zero to 1 substituent selected from F, —CF$_3$, and —OCF$_3$;

$R_b$ is Cl, $C_{1-4}$ alkyl, —CF$_3$, or $C_{3-5}$ cycloalkyl;

$R_1$ is H or F;

$R_2$ is H or F;

$R_3$ is H or $R_x$;

$R_4$ is H, F, Cl, —CN, —CH$_3$, —CHF$_2$, —CF$_3$, —OCH$_3$, —OCD$_3$, —(CH$_2$)$_{1-3}$OR$_c$, —CHR$_c$OH, —C(CH$_3$)$_2$OH, —C(O)OCH$_3$, —C(O)N(CH$_3$)$_2$, —C≡C—(C$_{1-4}$ alkyl), —S(O)$_{0-2}$(C$_{1-4}$ alkyl), or —S(O)$_{0-2}$(C$_{3-6}$ cycloalkyl);

$R_c$ is H, —CH$_3$, —CD$_3$, —CH$_2$CH$_3$, —CH(CH$_3$)$_2$, or cyclopropyl;

$R_5$ is H, F, Cl, —CH$_3$, or —OCH$_3$;

$R_6$ is H or F;

$R_w$ is H or —CH$_3$;

$R_x$ is:
(i) $C_{1-4}$ hydroxyalkyl, $C_{1-4}$ alkoxyalkyl, $C_{1-4}$ aminoalkyl, —CR$_w$R$_w$NH(C$_{1-4}$ alkyl), —CR$_w$R$_w$N(C$_{1-4}$ alkyl)$_2$, —CR$_w$R$_w$NR$_w$(CH$_2$)$_{1-3}$O(C$_{1-3}$ alkyl), —CR$_w$R$_w$CR$_w$R$_w$N(C$_{1-3}$ alkyl)$_2$, —CR$_w$R$_w$CR$_w$R$_w$NR$_w$C(O)(C$_{1-3}$ alkyl), —CR$_w$R$_w$C(O)(C$_{1-3}$ alkyl), —CR$_w$R$_w$NR$_w$C(O)(C$_{1-4}$ hydroxyalkyl), —(CR$_w$R$_w$)$_2$R$_{3a}$, —CR$_w$(CF$_3$)R$_{3a}$, —CR$_w$R$_w$NR$_w$R$_{3a}$, —CH$_2$OR$_{3a}$, or —CR$_w$R$_w$NR$_w$C(O)R$_{3a}$, wherein R$_{3a}$ is tetrahydropyran, morpholinyl, morpholinonyl, oxazinanonyl, oxazolidinonyl, pyrrolidinyl, pyrrolidinonyl, piperazinyl, pyridinyl, pyrrolidinium, or phenyl, each substituted with zero to 1 substituent selected from F, Cl, C$_{1-4}$ alkyl, and —C(O)CH$_3$;

(ii) —C(O)OH or —C(O)R$_{3b}$, wherein R$_{3b}$ is pyrrolidinyl, pyrrolidinonyl, azetidinyl, morpholinyl, dioxidothiomorpholinyl, thiadiazolyl, piperazinyl, piperazinonyl, 8-oxa-3-azabicyclo[3.2.1]octanyl, or piperidinyl, each substituted with zero to 2 substituents independently selected from F, —OH, —CN, C$_{1-2}$ alkyl, C$_{1-3}$ hydroxyalkyl, —C(O)(C$_{1-3}$ alkyl), —C(O)NR$_w$R$_w$, —C(O)O(C$_{1-3}$ alkyl), —NR$_w$C(O)(C$_{1-3}$ alkyl), —C(O)NH(C$_{1-3}$ hydroxyalkyl), and —C(O)tetrahydrofuranyl; —C(O)NR$_w$R$_w$, —C(O)NH(C$_{1-4}$ alkyl), —C(O)N(C$_{1-4}$ alkyl)$_2$, —C(O)NR$_w$(C$_{1-3}$ fluoroalkyl), —C(O)NR$_w$(C$_{1-3}$ hydroxyalkyl), —C(O)NR$_w$(C$_{1-4}$ alkoxyalkyl), —C(O)NR$_w$(CR$_w$R$_w$C(O)NR$_w$R$_w$), —C(O)NR$_w$CR$_w$(C$_{1-4}$ alkyl)C(O)NR$_w$R$_w$, —C(O)NR$_w$(C$_{1-6}$ hydroxyalkyl), —C(O)NR$_w$R$_{3c}$, —C(O)NR$_w$(CR$_w$R$_w$)$_{1-2}$R$_{3c}$, —C(O)NR$_w$CR$_w$R$_w$C(O)R$_{3c}$, —C(O)N(C$_{1-4}$ alkyl)(C$_{3-6}$ cycloalkyl), —C(O)N(C$_{3-6}$ cycloalkyl)$_2$, —C(O)N(C$_{3-6}$ cycloalkyl)R$_{3c}$, or —C(O)N(C$_{3-6}$ cycloalkyl)(CH$_2$R$_{3c}$), wherein R$_{3c}$ is phenyl, oxazolyl, oxopiperidinyl, oxopyrrolidinyl, tetrahydropyranyl, tetrazolyl, thiazolyl, piperidinyl, pyrazolyl, oxetanyl, morpholinyl, pyrrolidinyl, or isoxazolyl, each substituted with zero to 2 substituents independently selected from —CH$_3$, —C(O)CH$_3$, —C(O)NH$_2$, cyclopropyl, and —CH$_2$OH;

(iii) —OR$_{3d}$ wherein R$_{3d}$ is tetrahydropyranyl, tetrahydrothiopyranyl, piperidinyl, or pyridinyl, each substituted with zero to 3 substituents independently selected from —CH$_3$, =O, —C(O)CH$_3$, and —C(O)CH(CH$_3$)$_2$;

(iv) —NR$_w$C(O)(C$_{1-3}$ alkyl), —NR$_w$S(O)$_2$(C$_{1-3}$ alkyl), or —S(O)$_2$NR$_w$R$_w$;

(v) $C_{3-6}$ cycloalkyl substituted with zero to 3 substituents independently selected from F, —OH, C$_{1-3}$ alkyl, C$_{1-3}$ fluoroalkyl, C$_{1-3}$ alkoxy, C$_{1-3}$ fluoroalkoxy, —C(O)NR$_w$(C$_{1-4}$ alkyl), —C(O)NR$_w$(C$_{1-4}$ fluoroalkyl), —C(O)NR$_w$(C$_{3-6}$ cycloalkyl), and —C(O)NR$_w$R$_{3e}$, wherein R$_{3e}$ is oxetanyl, azetidinyl, morpholinyl, piperidinyl, pyrrolidinyl, cyclobutyl, or tetrahydropyranyl, each substituted with zero to 2 substituents independently substituted with F, —CH$_3$, and —OCH$_3$; or (vi) azetidinyl, oxetanyl, tetrahydropyranyl, piperazinyl, pyrrolidinyl, piperidinyl, 1,2-dihydropyridinonyl, morpholinyl, or 4,7-diazaspiro[2.5]octanyl, each substituted with zero to 8 substituents independently selected from D, —OH, —CN, C$_{1-4}$ alkyl, C$_{1-3}$ deuteroalkyl, C$_{1-3}$ fluoroalkyl, C$_{1-4}$ hydroxyalkyl, C$_{1-4}$ cyanoalkyl, C$_{1-3}$ alkoxy, =O, —C(O)(C$_{1-4}$ alkyl), —C(O)(C$_{1-4}$ hydroxyalkyl), —C(O)NR$_w$R$_w$, —C(O)CH$_2$CN, —C(O)CH$_2$OH, —C(O)(C$_{3-4}$ cycloalkyl), —C(O)NH$_2$, —S(O)$_2$CH$_3$, —C(O)OCH$_3$, —NHC(O)(C$_{1-4}$ alkyl), —NR$_w$S(O)(C$_{1-3}$ alkyl), —NR$_w$S(O)$_2$(C$_{1-3}$ alkyl), —C(O)CR$_w$R$_w$S(O)$_2$(C$_{1-4}$ alkyl), —C(O)(phenyl), —C(O)(fluorophenyl), —C(O)(chlorophenyl), —C(O)(hydroxypropyl phenyl), —C(O)(difluorocyclopropyl), —C(O)(oxazolyl), —C(O)(pyrazinyl), —C(O)(pyrazolyl), —C(O)(pyridazinyl), —C(O)(pyridinyl), —C(O)(pyrimidinyl), —C(O)(tetrahydropyranyl), —C(O)(thiazolyl), —C(O)(methyl thiazolyl), —C(O)(imidazolyl), —C(O)(methyl imidazolyl), —C(O)(methyl oxazolyl), —C(O)(methyl phenyl), —C(O)(methyl pyrazolyl), —C(O)(morpholinyl), —C(O)(acetophenonyl), —N(CH$_3$)$_2$, —N(CH$_3$)(acetyl piperidinyl), —CH$_2$C(O)NHCH$_2$C(CH$_3$)$_2$OH, —N(CH$_3$)C(O)CH$_3$, —N(CH$_3$)C(O)C(CH$_3$)$_2$OH, —N(CH$_3$)C(O)NH(CH(CH$_3$)$_2$), —N(CH$_3$)C(O)(furanyl), —N(CH$_3$)C(O)CH$_2$(pyrazinyl), —N(CH$_3$)C(O)(cyanocyclopropyl), —N(CH$_3$)C(O)CH(CH$_3$)OH, benzyl, carbamoyl azepanyl, carbamoyl-morpholinyl, chlorophenyl, cyclopropyl, cyclobutyl, dioxothiomorpholinyl, fluorobenzoyl, fluorophenyl, hydroxypiperidinyl, hydroxypyrrolidinyl, hydroxytetrahydropyranyl, methoxytetrahydropyranyl, methyl imidazol[1,2a]pyridinyl, methyloxadiazolyl, methylpiperazinyl, methylpiperazinonyl, methyl pyridinonyl, morpholinyl, oxetanyl, phenyl, piperidinonyl, pyridinyl, and pyrimidinyl; phenyl, pyrazolyl, dioxothiazinanyl, pyrrolidinonyl, dimethyloxazolidinonyl, oxazolyl, tetrazolyl, pyridinyl, dioxothiomorpholinyl, quinazolinyl, thiazolyl, octahydropyrrolo[3,4-c]pyrrole, 1H-pyrido[1,2-c]pyrimidine-1,3(2H)-dione, 1,3-oxazinan-2-onyl, 1H,2H,3H,4H,6H-pyrido[1,2-a]piperazinone-1,6-dionyl, 2,3-dihydroquinazolin-4(1H)-onyl, methoxy 2,3-dihydroquinazolin-4(1H)-onyl, 2-azaspiro[4.5]decan-3-onyl, 2-oxa-6-azaspiro[3.3]heptanyl, acetyl 3,8-diazabicyclo[3.2.1]octanyl, acetyl-3,4-dihydroquinoxalin-1(2H)-yl, methyl[1,2,4]triazolo[4,3-a]pyridinyl), or dimethyl [1,2,4]triazolo[4,3-a]pyridinyl, each substituted with zero to 4 substituents independently selected from D, F, Cl, —OH, —CN, —NH$_2$, C$_{1-3}$ alkyl, C$_{1-5}$ hydroxyalkyl, C$_{1-5}$ alkoxyalkyl, —C(O)CH$_3$, —C(O)C(CH$_3$)$_2$OH, —C(O)NH$_2$, —C(O)NH(C$_{1-4}$ alkyl), —CH(R$_w$)CH$_2$NR$_w$R$_w$, —C(O)NR$_w$R$_w$, —S(O)$_2$NH$_2$, —S(O)$_2$(C$_{1-4}$ alkyl), —NR$_w$C(O)(C$_{1-4}$ alkyl), —NR$_w$S(O)$_{0-2}$(C$_{1-4}$ alkyl), =O, C$_{3-6}$ cycloalkyl, —O(piperidinyl-S(O)$_2$CH$_3$), —O(piperidinyl-C(O)NR$_w$(C$_{1-4}$ alkyl), and —O(piperidinyl-C(O)(C$_{1-4}$ hydroxyalkyl);

provided that if R$_3$ is H, then R$_4$ is —C(O)N(CH$_3$)$_2$; and if Q$_1$ is Br, then R$_3$ is not —CH$_2$OH.

One embodiment provides compounds of Formula (I) wherein Q$_1$ is pyrrolyl. Included in this embodiment, are compounds having the structure of Formula (II-A):

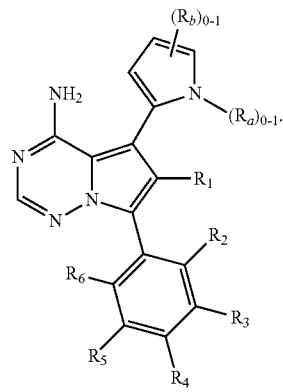

(II-A)

One embodiment provides compounds of Formula (I) wherein Q$_1$ is pyrazolyl. Included in this embodiment, are compounds having the structures of Formula (II-B) and (II-C):

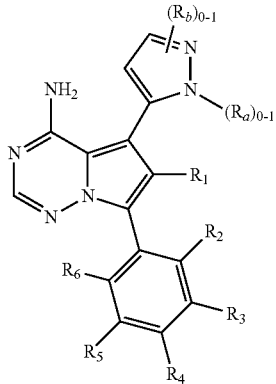

(II-B)

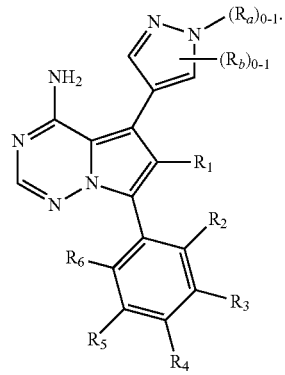

(II-C)

One embodiment provides compounds of Formula (I) wherein Q$_1$ is imidazolyl. Included in this embodiment, are compounds having the structure of Formula (II-D):

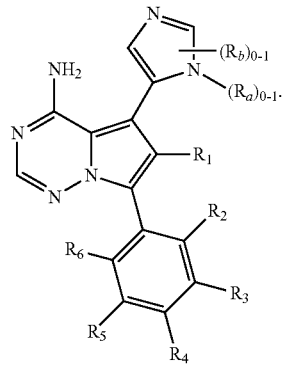

(II-D)

One embodiment provides compounds of Formula (I) wherein Q$_1$ is triazolyl. Included in this embodiment, are compounds having the structure of Formula (II-E):

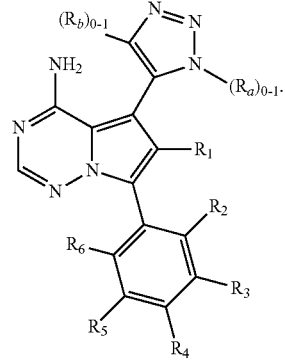

(II-E)

One embodiment provides compounds of Formula (I) wherein Q$_1$ is isoxazolyl. Included in this embodiment, are compounds having the structure of Formula (II-F):

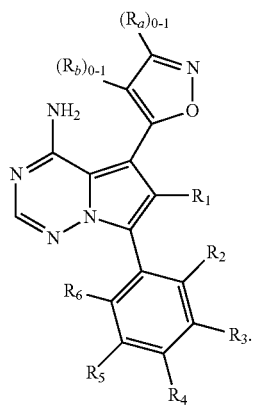

(II-F)

One embodiment provides compounds of Formula (I) wherein $Q_1$ is thiazolyl. Included in this embodiment, are compounds having the structures of Formula (II-G), Formula (II-H), and (II-I):

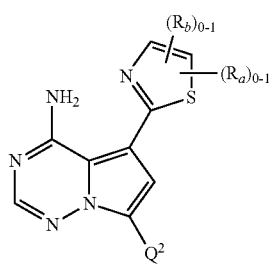

(II-G)

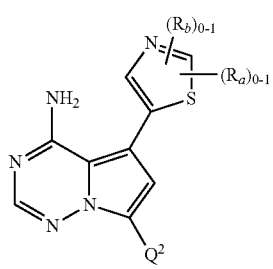

(II-H)

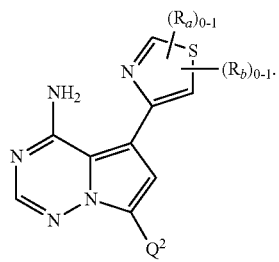

(II-I)

One embodiment provides compounds of Formula (I) wherein $Q_1$ is oxadiazolyl. Included in this embodiment, are compounds having the structure of Formula (II-J):

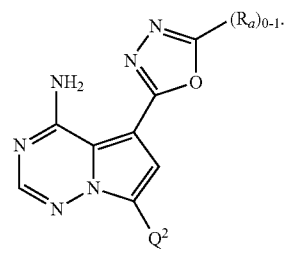

(II-J)

One embodiment provides compounds of Formula (I) wherein $Q_1$ is thiadiazolyl. Included in this embodiment, are compounds having the structure of Formula (II-K):

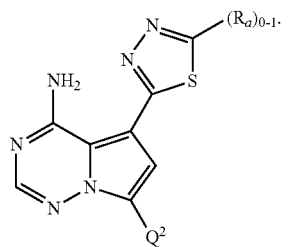

(II-K)

One embodiment provides compounds of Formula (I) wherein $Q_1$ is pyridinyl. Included in this embodiment, are compounds having the structure of Formula (III-A):

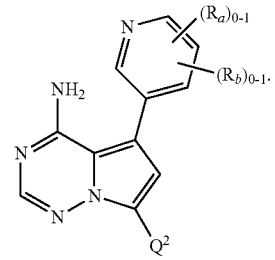

(III-A)

One embodiment provides compounds of Formula (I) wherein $Q_1$ is pyridazinyl. Included in this embodiment, are compounds having the structure of Formula (III-B):

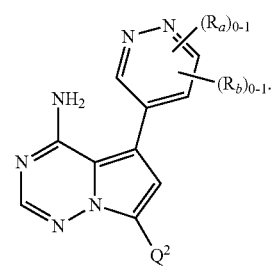

(III-B)

One embodiment provides compounds of Formula (I) wherein $Q_1$ is pyrimidinyl. Included in this embodiment, are compounds having the structure of Formula (III-C):

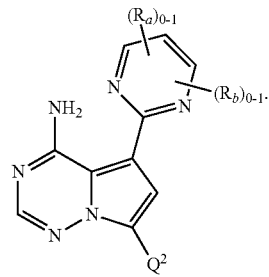
(III-C)

One embodiment provides compounds of Formula (I) wherein Q₁ is indolyl. Included in this embodiment, are compounds having the structure of Formula (IV-A):

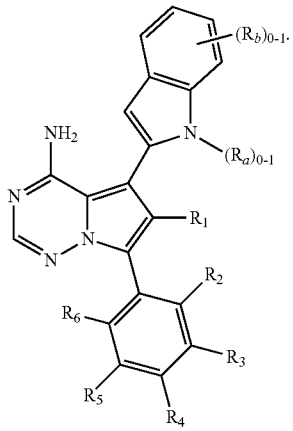
(IV-A)

One embodiment provides compounds of Formula (I) wherein Q₁ is imidazopyridinyl. Included in this embodiment are compounds having the structures of Formula (IV-B) in which Q₁ is imidazo[1,2-a]pyridinyl, and Formula (IV-C) in which Q₁ is imidazo[4,5-b]pyridinyl:

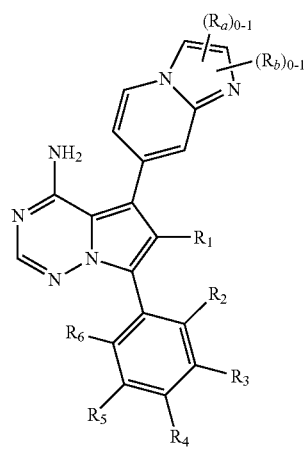
(IV-B)

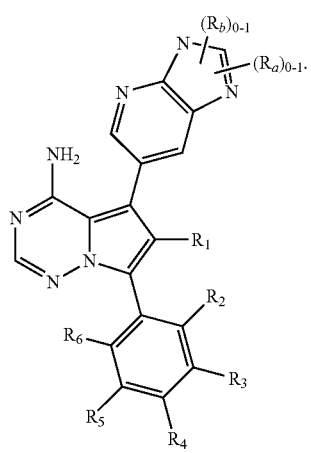
(IV-C)

One embodiment provides compounds of Formula (I) wherein Q₁ is pyrrolopyridinyl. Included in this embodiment are compounds having the structure of Formula (IV-D):

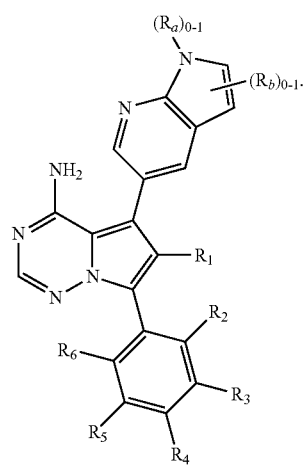
(IV-D)

One embodiment provides compounds of Formula (I) wherein Q₁ is pyrazolopyridinyl. Included in this embodiment are compounds having the structure of Formula (IV-E):

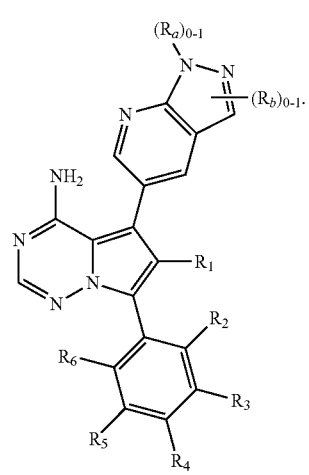
(IV-E)

One embodiment provides compounds of Formula (I) wherein Q₁ is benzo[d]oxazolyl. Included in this embodiment are compounds having the structure of Formula (IV-F):

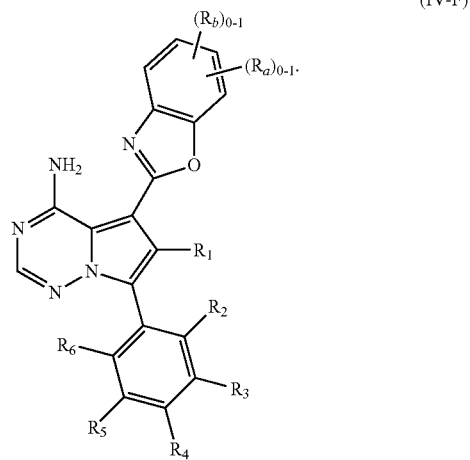

(IV-F)

One embodiment provides a compound of Formula (I) or a salt thereof, wherein:

R_a is —CH₃, —CH₂CH₂CH₃, —CH(CH₃)₂, —C(CH₃)₃, —CH₂CH(CH₃)₂, —CH(CH₃)CH₂CH₃, —CH₂C(CH₃)₃, —CD₃, —CD₂CD₃, —CH(CD₃)₂, —CD(CD₃)₂, —CF₂H, —CF₃, —CH₂CHF₂, —CH₂CF₃, —CH(CH₂F)₂, —CH(CH₃)(CF₃), —CH(CF₃)₂, —CH₂CH₂OCH₃, —CH₂C(CH₃)₂OH, —CH₂CH(OH)CF₃, —CH₂(cyclopropyl), —CH₂(cyclobutyl), —CH₂(oxetanyl), —CH₂(methyloxetanyl), —NH₂, —S(O)₂CH₃, —S(O)₂CH(CH₃)₂, —S(O)₂(cyclopropyl), cyclopropyl, cyclobutyl, cyclohexyl, difluorocyclopropyl, difluorocyclohexyl, oxetanyl, tetrahydropyranyl, pyridinyl, pyrimidinyl, pyridazinyl, phenyl, or fluorophenyl;

R_x is:
(i) —CH₂OH, —CH₂NH₂, —CH₂N(CH₃)₂, —CH₂NHS(O)₂CH₃, —CH₂N(CH₃)CH₂CH₂OCH₃, —CH₂CH(CH₃)NHCH₂CH₂OCH₃, —C(CH₃)₂N(CH₃)₂, —C(CH₃)₂N(CH₂CH₃)₂, —CH₂CH(CH₃)NH(tetrahydropyranyl), —C(CH₃)₂N(CH₃)(tetrahydropyran), —CH₂CH(CH₃)N(CH₃)₂, —C(CH₃)₂CH₂N(CH₃)₂, —CH₂(morpholinyl), —CH₂(morpholinonyl), —CH₂(oxazinanonyl), —CH₂(pyrrolidinonyl), —CH₂(hydroxypyrrolidinyl), —CH₂(t-butyl oxazolidinonyl), —CH₂(dimethyl oxazolidinonyl), —CH₂(i-propyl oxazolidinonyl), —CH₂(acetyl piperazinyl), —CH₂(methyl piperazinonyl), —CH₂(methyl pyrrolidinonyl), —CH₂(8-oxa-3-azabicyclo[3.2.1]octanyl), —CH₂N(tetrahydropyranyl)₂, —CH₂NHC(O)(methoxyphenyl), —CH₂N(cyclopropyl)(methylsulfonyl azetidinyl), —CH₂N(CH₃)(tetrahydropyranyl), —CH₂N(CH₃)(oxetanyl), —CH₂N(C(O)CH₃)(morpholinyl), —CH₂CH(CH₃)(morpholinyl), —CH₂CH(CH₃)(pyrrolidinyl), —CH(CH₃)(morpholinyl), —CH(CH₃)(dimethylazetidinyl), —CH(CH₃)(dimethylmorpholinyl), —CH(CH₃)(hydroxypyrrolidinyl), —CH(CH₃)(methoxypyrrolidinyl), —CH(CH₃)(methyl hydroxyazetidinyl), —CH(CH₃)(acetopiperazinyl), —CH(CH₃)NH(tetrahydropyranyl), —CH(CF₃)(morpholinyl), —CH₂C(O)(dioxidothiomorpholinyl), —CH₂CH(CH₃)N(CH₃)(tetrahydropyranyl), —C(CH₃)₂(pyrrolidinyl), —C(CH₃)₂(morpholinyl), —C(CH₃)₂(oxazolidinonyl), —C(CH₃)₂(methyl pyrrolidinium), —C(CH₃)₂NHC(O)CH₂C(CH₃)₂OH, or —CH₂O(pyridinyl);

(ii) —C(O)OH, —C(O)NH₂, —C(O)NHCH₃, —C(O)NHC(CH₃)₂C(O)NHCH₃, —C(O)(cyanoazetidinyl), —C(O)(methyl, hydroxyazetidinyl), —C(O)(morpholinyl), —C(O)(dioxidothiomorpholinyl), —C(O)(piperazinyl) wherein said piperazinyl is substituted with —C(O)CH₃, —C(O)CH₂CH₃, —C(O)C(CH₃)₂H, —C(O)OCH₃, or —C(O)tetrahydrofuranyl; —C(O)(methyl piperazinonyl), —C(O)(piperidinyl) wherein said piperidinyl is substituted with 1 to 2 substituents independently selected from —OH, —CH₂OH, —C(CH₃)₂OH, —C(O)NH₂—C(O)NHCH₃, —N(CH₃)₂, and —NHC(O)CH₃; —C(O)(pyrrolidinyl), —C(O)(8-oxa-3-azabicyclo[3.2.1]octanyl), —C(O)NHCH₃, —C(O)NH(oxopiperidinyl), —C(O)NH(oxopyrrolidinyl), —C(O)NH(benzamide), —C(O)NH(carbamoyl thiazolyl), —C(O)NH(acetyl piperidinyl), —C(O)NH(methyl piperidinyl), —C(O)NH(methyl, cyclopropyl-pyrazolyl), —C(O)NH(tetrahydropyranyl), —C(O)NH(hydroxymethyl tetrahydropyranyl), —C(O)N(CH₃)(methyl pyrrolidinyl), —C(O)N(CH₃)(oxetanyl), —C(O)N(CH₃)(tetrahydropyran), —C(O)N(CH₃)₂, —C(O)N(CH₃)C(O)CH₂NH₂, —C(O)N(CH₃)CH₂(dimethylisoxazolyl), —C(O)N(CH₃)CH₂(methyl pyrrolidinyl), —C(O)N(CH₃)CH₂C(CH₃)₂CH₂OH, —C(O)N(CH₃)CH₂CF₂H, —C(O)N(CH₂CH₃)₂, —C(O)N(cyclopropyl)(methyl piperidinyl), —C(O)N(cyclopropyl)(methyl pyrazolyl), —C(O)N(cyclopropyl)(acetyl piperidinyl), —C(O)N(cyclopropyl)(methyl piperidinyl), —C(O)N(cyclopropyl)(tetrahydropyranyl), —C(O)N(cyclopropyl)(thiazolyl), —C(O)N(cyclopropyl)₂, —C(O)N(cyclopropyl)(CH₂(methyl pyrazolyl)), or —C(O)N(cyclopropyl)(CH₂-thiazolyl);

(iii) —O(tetrahydropyranyl), —O(dimethyltetrahydropyranyl), —O(dioxotetrahydrothiopyranyl), —O(piperidinyl) wherein said piperidinyl is substituted with zero to 1 substituent selected from —CH₃, —C(O)CH₃, and —C(O)CH(CH₃)₂; —O(dimethylpyridinonyl), or —O(methyl pyridinonyl);

(iv) —NHC(O)CH₃ or —NHS(O)₂CH₃;

(v) cyclopropyl substituted with —C(O)NH(CH₂CH₃), —C(O)NH(CH(CH₃)₂), —C(O)NH(cyclopropyl), —C(O)NH(oxetanyl), —C(O)NH(difluorocyclobutyl), or —CH₂NH(tetrahydropyranyl); or cyclobutyl substituted with 1 to 3 substituents independently selected from F, —OH, —CH₃, —CF₃, —OCH₃, —OCHF₂, —C(O)NH(CH₃), —C(O)NH(CH₂CH₃), —C(O)NH(CH(CH₃)₂), —C(O)NH(CH₂CF₃), —C(O)NH(cyclopropyl), —C(O)NH(difluorocyclobutyl), —C(O)N(CH₃)(oxetanyl), —C(O)(morpholinyl), —C(O)(methoxypyrrolidinyl), and —C(O)(difluoroazetidinyl); or (vi) azetidinyl substituted with 1 to 2 substituents independently selected from fluorobenzoyl, dioxothiomorpholinyl, and —C(O)(hydroxypropyl phenyl); octahydropyrrolo[3,4-c]pyrrole substituted with zero to 1 substituent selected from —CH₃, —C(O)CH₃, —CH(CH₃)₂, —CH(CH₃)C(CH₃)₂OH, —CH(CH₃)CH₂OCH₃, —S(O)₂CH₃, and cyclobutyl; 1,2-dihydropyridinonyl substituted with 1 to 3 substituents independently selected from —CH₃, —CD₃, —CH₂CH₃, =O, and —CH₂CHF₂; 4,7-diazaspiro[2.5]octanyl substituted with zero to 1 substituent selected from —C(O)CH₃, —C(O)OCH₃, cyclobutyl, and oxetanyl; tetrahydropyranyl substituted with —OH, —CN, —OCH₃, —C(O)NH₂, or —NHC(O)CH₃; oxetanyl substituted with —N(CH₃)₂, —NHC(O)C(CH₃)₃, —NHS(O)C(CH₃)₃, —N(CH₃)S(O)C(CH₃)₃, —N(CH₃)(acetyl piperidinyl), piperidinonyl, hydroxypiperidinyl, hydroxypyrrolidinyl, morpholinyl, or dioxothiomorpholinyl; piperazinyl substituted with zero to 8 substituents independently selected from D, —OH, —CH₃, —CH(CH₃)₂, —CF₃, =O, —C(O)(cyclopropyl), —C(O)(cyclobutyl), —S(O)₂CH₃, —C(O)CH₃, —C(O)CH(CH₃)₂, —C(O)OCH₃, —C(O)CH₂CN, —C(O)CH₂OH, —C(O)CH₂CH₃, —C(O)CH(CH₃)OH, —C(O)C(CH₃)₂OH, —C(O)(phenyl), —N(CH₃)C(O)CH₃, —C(O)CH₂S(O)₂CH₃, cyclopropyl, cyclobutyl, oxetanyl, phenyl, fluorophenyl, chlorophenyl, pyridinyl, pyrimidinyl, and methyloxadiazolyl; pyrrolidinyl substituted with zero to 2 substituents independently selected from —OH, —CH₃, —C(CH₃)₂OH, —C(O)CH₃, —C(O)CH(CH₃)₂, —C(O)C(CH₃)₃, —NHC(O)CH₃, —N(CH₃)C(O)CH₃, —N(CH₃)C(O)C(CH₃)₂OH, —N(CH₃)C(O)CH₂(pyrazinyl), —C(O)(phenyl), —C(O)(fluorophenyl), —C(O)(methyl phenyl), —C(O)(cyclopropyl), —C(O)(difluorocyclopropyl), —C(O)(oxazolyl), —C(O)(pyrazolyl), —C(O)(pyridazinyl), —C(O)(pyridinyl), —C(O)(tetrahydropyranyl), —C(O)(thiazolyl), —C(O)(methyl thiazolyl), —C(O)(methyl pyrazolyl), and morpholinyl; piperidinyl substituted with zero to 4 substituents independently selected from —OH, —CH₃, —CN, —OCH₃, =O, —C(O)CH₃, —C(O)CH₂CN, —C(O)(morpholinyl), —C(O)NH₂, —NHC(O)CH₃, —N(CH₃)S(O)₂CH₃, —N(CH₃)C(O)NH(CH(CH₃)₂), —N(CH₃)C(O)CH₂(pyrazinyl), —N(CH₃)C(O)(furanyl), —N(CH₃)C(O)(cyanocyclopropyl), oxetanyl, morpholinyl, and piperidinonyl; phenyl substituted with 1 to 2 substituents independently selected from F and —C(O)NH₂; quinazolinyl substituted with zero to 4 substituents independently selected from F, —CH₃, and =O; carbamoyl azepanyl, imidazolyl, dimethyloxazolindinonyl, methyl imidazol[1,2a]pyridinyl, morpholinyl, carbamoyl-morpholinyl, morpholinonyl, methyl pyridinonyl, dimethyl morpholinonyl, trimethyl morpholinonyl, dioxothiomorpholinyl, methyl[1,2,4]triazolo[4,3-a]pyridinyl), dimethyl [1,2,4]triazolo[4,3-a]pyridinyl), 1-(3,4-dihydroquinoxalin-1(2H)-yl)ethanone, 2,3-dihydroquinazolin-4(1H)-one, oxetan-3-yl-1λ6,4-thiomorpholine-1,1-dione, 1,3-oxazinan-2-one, 1H,2H,3H,4H,6H-pyrido[1,2-a]piperazinone-1,6-dionyl, 1H-pyrido[1,2-c]pyrimidine-1,3(2H)-dione, or 3,8-diazabicyclo[3.2.1]octanyl ethanone;

provided that if R₃ is H, then R₄ is —C(O)N(CH₃)₂; and wherein Q₁, X, R₁, R₂, R₃, R₄, R₅, and R₆ are defined in the first aspect.

One embodiment provides a compound of Formula (I) or a salt thereof, wherein X is N; and Q₁, R₁, R₂, R₃, R₄, R₅, and R₆ are defined in the first aspect. Included in this embodiment are compounds in which:

Rₐ is —CH₃, —CH₂CH₂CH₃, —CH(CH₃)₂, —C(CH₃)₃, —CH₂CH(CH₃)₂, —CH(CH₃)CH₂CH₃, —CH₂C(CH₃)₃, —CD₃, —CD₂CD₃, —CH(CD₃)₂, —CD(CD₃)₂, —CF₂H, —CF₃, —CH₂CHF₂, —CH₂CF₃, —CH(CH₂F)₂, —CH(CH₃)(CF₃), —CH(CF₃)₂, —CH₂CH₂OCH₃, —CH₂C(CH₃)₂OH, —CH₂CH(OH)CF₃, —CH₂(cyclopropyl), —CH₂(cyclobutyl), —CH₂(oxetanyl), —CH₂(methyloxetanyl), —NH₂, —S(O)₂CH₃, —S(O)₂CH(CH₃)₂, —S(O)₂(cyclopropyl), cyclopropyl, cyclobutyl, cyclohexyl, difluorocyclopropyl, difluorocyclohexyl, oxetanyl, tetrahydropyranyl, pyridinyl, pyrimidinyl, pyridazinyl, phenyl, or fluorophenyl;

R₃ is:
(i) —CH₂OH, —CH₂NH₂, —CH₂N(CH₃)₂, —CH₂NHS(O)₂CH₃, —CH₂N(CH₃)₂CH₂CH₂OCH₃, —CH₂CH(CH₃)NHCH₂CH₂OCH₃, —C(CH₃)₂N(CH₃)₂, —C(CH₃)₂N(CH₂CH₃)₂, —CH₂CH(CH₃)NH(tetrahydropyranyl), —C(CH₃)₂N(CH₃)(tetrahydropyran), —CH₂CH(CH₃)N(CH₃)₂, —C(CH₃)₂CH₂N(CH₃)₂, —CH₂(morpholinyl), —CH₂(morpholinonyl), —CH₂(oxazinanonyl), —CH₂(pyrrolidinonyl), —CH₂(hydroxypyrrolidinyl), —CH₂(t-butyl oxazolidinonyl), —CH₂(dimethyl oxazolidinonyl), —CH₂(i-propyl oxazolidinonyl), —CH₂(acetyl piperazinyl), —CH₂(methyl piperazinonyl), —CH₂(methyl pyrrolidinonyl), —CH₂(8-oxa-3-azabicyclo[3.2.1]octanyl), —CH₂N(tetrahydropyranyl)₂, —CH₂NHC(O)(methoxyphenyl), —CH₂N(cyclopropyl)(methylsulfonyl azetidinyl), —CH₂N(CH₃)(tetrahydropyranyl), —CH₂N(CH₃)(oxetanyl), —CH₂N(C(O)CH₃)(morpholinyl), —CH₂CH(CH₃)(morpholinyl), —CH₂CH(CH₃)(pyrrolidinyl), —CH(CH₃)(morpholinyl), —CH(CH₃)(dimethylazetidinyl), —CH(CH₃)(dimethylmorpholinyl), —CH(CH₃)(hydroxypyrrolidinyl), —CH(CH₃)(methoxypyrrolidinyl), —CH(CH₃)(methyl hydroxyazetidinyl), —CH(CH₃)(acetopiperazinyl), —CH(CH₃)NH(tetrahydropyranyl), —CH(CF₃)(morpholinyl), —CH₂C(O)(dioxoidothiomorpholinyl), —CH₂CH(CH₃)N(CH₃)(tetrahydropyranyl), —C(CH₃)₂(pyrrolidinyl), —C(CH₃)₂(morpholinyl), —C(CH₃)₂(oxazolidinonyl), —C(CH₃)₂(methyl pyrrolidinium), —C(CH₃)₂NHC(O)CH₂C(CH₃)₂OH, or —CH₂O(pyridinyl);

(ii) —C(O)OH, —C(O)NH₂, —C(O)NHCH₃, —C(O)NHC(CH₃)₂C(O)NHCH₃, —C(O)(cyanoazetidinyl), —C(O)(methyl, hydroxyazetidinyl), —C(O)(morpholinyl), —C(O)(dioxidothiomorpholinyl), —C(O)(piperazinyl) wherein said piperazinyl is substituted with —C(O)CH₃, —C(O)CH₂CH₃, —C(O)C(CH₃)₂H, —C(O)OCH₃, or —C(O)tetrahydrofuranyl; —C(O)(methyl piperazinonyl), —C(O)(piperidinyl) wherein said piperidinyl is substituted with 1 to 2 substituents independently selected from —OH, —CH₂OH, —C(CH₃)₂OH, —C(O)NH₂—C(O)NHCH₃, —N(CH₃)₂, and —NHC(O)CH₃; —C(O)(pyrrolidinyl), —C(O)(8-oxa-3-azabicyclo[3.2.1]octanyl), —C(O)NHCH₃, —C(O)NH(oxopiperidinyl), —C(O)NH(oxopyrrolidinyl), —C(O)NH(benzamide), —C(O)NH(carbamoyl thiazolyl), —C(O)NH(acetyl piperidinyl), —C(O)NH(methyl piperidinyl), —C(O)NH(methyl, cyclopropyl-pyrazolyl), —C(O)NH(tetrahydropyranyl), —C(O)NH(hydroxymethyl tetrahydropyranyl), —C(O)N(CH₃)(methyl pyrrolidinyl), —C(O)N(CH₃)(oxetanyl), —C(O)N(CH₃)(tetrahydropyran), —C(O)N(CH₃)₂, —C(O)N(CH₃)C(O)CH₂NH₂, —C(O)N(CH₃)CH₂(dimethylisoxazolyl), —C(O)N(CH₃)CH₂(methyl pyrrolidinyl), —C(O)N(CH₃)CH₂C(CH₃)₂CH₂OH, —C(O)N(CH₃)CH₂CF₂H, —C(O)N(CH₂CH₃)₂, —C(O)N(cyclopropyl)(methyl piperidinyl), —C(O)N(cyclopropyl)(methyl pyrazolyl), —C(O)N(cyclopropyl)(acetyl piperidinyl), —C(O)N(cyclopropyl)(methyl piperidinyl), —C(O)N(cyclopropyl)(tetrahydropyranyl), —C(O)N(cyclopropyl)(thiazolyl), —C(O)N(cyclopropyl)₂, —C(O)N(cyclopropyl)(CH₂(methyl pyrazolyl)), or —C(O)N(cyclopropyl)(CH₂-thiazolyl);

(iii) —O(tetrahydropyranyl), —O(dimethyltetrahydropyranyl), —O(dioxotetrahydrothiopyranyl), —O(piperidinyl) wherein said piperidinyl is substituted with zero to 1 substituent selected from —CH₃, —C(O)CH₃, and —C(O)CH(CH₃)₂; —O(dimethylpyridinonyl), or —O(methyl pyridinonyl);

(iv) —NHC(O)CH₃ or —NHS(O)₂CH₃;

(v) cyclopropyl substituted with —C(O)NH(CH₂CH₃), —C(O)NH(CH(CH₃)₂), —C(O)NH(cyclopropyl), —C(O)NH(oxetanyl), —C(O)NH(difluorocyclobutyl), or —CH₂NH(tetrahydropyranyl); or cyclobutyl substituted with 1 to 3 substituents independently selected from F, —OH, —CH₃, —CF₃, —OCH₃, —OCHF₂, —C(O)NH (CH₃), —C(O)NH(CH₂CH₃), —C(O)NH(CH(CH₃)₂), —C(O)NH(CH₂CF₃), —C(O)NH(cyclopropyl), —C(O) NH(difluorocyclobutyl), —C(O)N(CH₃)(oxetanyl), —C(O)(morpholinyl), —C(O)(methoxypyrrolidinyl), and —C(O)(difluoroazetidinyl); or (vi) azetidinyl substituted with 1 to 2 substituents independently selected from fluorobenzoyl, dioxothiomorpholinyl, and —C(O)(hydroxypropyl phenyl); octahydropyrrolo[3,4-c]pyrrole substituted with zero to 1 substituent selected from —CH₃, —C(O)CH₃, —CH(CH₃)₂), —CH(CH₃)C(CH₃)₂OH, —CH(CH₃)CH₂OCH₃, —S(O)₂CH₃, and cyclobutyl; 1,2-dihydropyridinonyl substituted with 1 to 3 substituents independently selected from —CH₃, —CD₃, —CH₂CH₃, =O, and —CH₂CHF₂; 4,7-diazaspiro[2.5]octanyl substituted with zero to 1 substituent selected from —C(O)CH₃, —C(O)OCH₃, cyclobutyl, and oxetanyl; tetrahydropyranyl substituted with —OH, —CN, —OCH₃, —C(O)NH₂, or —NHC(O)CH₃; oxetanyl substituted with —N(CH₃)₂, —NHC(O)C(CH₃)₃, —NHS(O)C(CH₃)₃, —N(CH₃)S(O)C(CH₃)₃, —N(CH₃) (acetyl piperidinyl), piperidinonyl, hydroxypiperidinyl, hydroxypyrrolidinyl, morpholinyl, or dioxothiomorpholinyl; piperazinyl substituted with zero to 8 substituents independently selected from D, —OH, —CH₃, —CH(CH₃)₂, —CF₃, =O, —C(O)(cyclopropyl), —C(O)(cyclobutyl), —S(O)₂CH₃, —C(O)CH₂S(O)₂CH₃, —C(O)CH₃, —C(O)CH(CH₃)₂, —C(O)OCH₃, —C(O)CH₂CN, —C(O)CH₂OH, —C(O)CH₂CH₃, —C(O)CH(CH₃)OH, —C(O)C(CH₃)₂OH, —C(O)(phenyl), —N(CH₃)C(O)CH₃, cyclopropyl, cyclobutyl, oxetanyl, phenyl, fluorophenyl, chlorophenyl, pyridinyl, pyrimidinyl, and methyloxadiazolyl; pyrrolidinyl substituted with zero to 2 substituents independently selected from —OH, —CH₃, —C(CH₃)₂OH, —C(O)CH₃, —C(O)CH(CH₃)₂, —C(O)C(CH₃)₃, —NHC(O)CH₃, —N(CH₃)C(O)CH₃, —N(CH₃)C(O)C(CH₃)₂OH, —N(CH₃)C(O)CH₂(pyrazinyl), —C(O)(phenyl), —C(O)(fluorophenyl), —C(O)(methyl phenyl), —C(O)(cyclopropyl), —C(O)(difluorocyclopropyl), —C(O)(oxazolyl), —C(O)(pyrazolyl), —C(O)(pyridazinyl), —C(O)(pyridinyl), —C(O)(tetrahydropyranyl), —C(O)(thiazolyl), —C(O)(methyl thiazolyl), —C(O)(methyl pyrazolyl), and morpholinyl; piperidinyl substituted with zero to 4 substituents independently selected from —OH, —CH₃, —CN, —OCH₃, =O, —C(O)CH₃, —C(O)CH₂CN, —C(O)(morpholinyl), —C(O)NH₂, —NHC(O)CH₃, —N(CH₃)S(O)₂CH₃, —N(CH₃)C(O)NH(CH(CH₃)₂), —N(CH₃)C(O)CH₂(pyrazinyl), —N(CH₃)C(O)(furanyl), —N(CH₃)C(O)(cyanocyclopropyl), oxetanyl, morpholinyl, and piperidinonyl; phenyl substituted with 1 to 2 substituents independently selected from F and —C(O)NH₂; quinazolinyl substituted with zero to 4 substituents independently selected from F, —CH₃, and =O; carbamoyl azepanyl, imidazolyl, dimethyloxazolindinonyl, methyl imidazol[1,2a]pyridinyl, morpholinyl, carbamoyl-morpholinyl, morpholinonyl, methyl pyridinonyl, dimethyl morpholinonyl, trimethyl morpholinonyl, dioxothiomorpholinyl, methyl[1,2,4]triazolo[4,3-a]pyridinyl), dimethyl [1,2,4]triazolo[4,3-a]pyridinyl), 1-(3,4-dihydroquinoxalin-1(2H)-yl)ethanone, 2,3-dihydroquinazolin-4(1H)-one, 1,3-oxazinan-2-one, 1H,2H,3H,4H,6H-pyrido[1,2-a]piperazinone-1,6-dionyl, 1H-pyrido[1,2-c]pyrimidine-1,3(2H)-dione, or 3,8-diazabicyclo[3.2.1]octanyl ethanone; provided that if R₃ is H, then R₄ is —C(O)N(CH₃)₂.

One embodiment provides a compound of Formula (I) or a salt thereof, wherein X is N; Q₁ is Cl, Br, I, —CN, —CH₃, or —CF₃; and R₁, R₂, R₃, R₄, R₅, and R₆ are defined in the first aspect. Included in this embodiment are compounds in which R₃ is piperazinyl substituted with zero to 8 substituents independently selected from D, —OH, —CH₃, —CH(CH₃)₂, —CF₃, =O, —C(O)(cyclopropyl), —C(O)(cyclobutyl), —S(O)₂CH₃, —C(O)CH₃, —C(O)CH(CH₃)₂, —C(O)OCH₃, —C(O)CH₂CN, —C(O)CH₂OH, —C(O)CH₂CH₃, —C(O)CH(CH₃)OH, —C(O)C(CH₃)₂OH, —C(O)(phenyl), —C(O)CH₂S(O)₂CH₃, —N(CH₃)C(O)CH₃, cyclopropyl, oxetanyl, phenyl, fluorophenyl, chlorophenyl, pyridinyl, pyrimidinyl, and methyloxadiazolyl; —O(piperidinyl) wherein said piperidinyl is substituted with zero to 1 substituent selected from —CH₃, —C(O)CH₃, and —C(O)CH(CH₃)₂; —CH₂N(CH₃)(tetrahydropyranyl), —C(O)N(cyclopropyl)(acetyl piperidinyl), —C(O)N(cyclopropyl)(methylpiperidinyl), —C(O)N(cyclopropyl) (tetrahydropyran), or 1H,2H,3H,4H,6H-pyrido[1,2-a]piperazinone-1,6-dionyl; R₁ is H; and R₂, R₄, R₅, and R₆ are defined in the first aspect. Also included in this embodiment are compounds in which R₃ is piperazinyl substituted with zero to 8 substituents independently selected from D, —CH₃, —C(O)CH₃, —C(O)CH₂CH₃, =O, —C(O)CH₂OH, —C(O)CH(CH₃)OH, —C(O)CH₂S(O)₂CH₃, and —S(O)₂CH₃; —O(piperidinyl) wherein said piperidinyl is substituted with zero to 1 substituent selected from —C(O)CH₃; trimethyl morpholinonyl; —CH₂N(CH₃)(tetrahydropyranyl), —C(O)N(cyclopropyl)(acetyl piperidinyl), —C(O)N(cyclopropyl)(methylpiperidinyl), —C(O)N(cyclopropyl) (tetrahydropyran), or 1H,2H,3H,4H,6H-pyrido[1,2-a]piperazinone-1,6-dionyl.

One embodiment provides a compound of Formula (I) or a salt thereof, wherein said compound is selected from 3-(4-amino-5-bromopyrrolo[2,1-f][1,2,4]triazin-7-yl)-N-cyclopropyl-N-(tetrahydro-2H-pyran-4-yl)benzamide (541); 1-(4-(3-(4-amino-5-bromopyrrolo[2,1-f][1,2,4]triazin-7-yl)phenoxy)piperidin-1-yl)ethanone (542); 1-(4-(3-(4-amino-5-bromopyrrolo[2,1-f][1,2,4]triazin-7-yl)phenoxy)piperidin-1-yl)ethanone (543); 5-bromo-7-(3-((methyl(tetrahydro-2H-pyran-4-yl)amino)methyl)phenyl)pyrrolo [2,1-f][1,2,4]triazin-4-amine (544); 3-(4-amino-5-iodopyrrolo[2,1-f][1,2,4]triazin-7-yl)-N-cyclopropyl-N-(tetrahydro-2H-pyran-4-yl)benzamide (545); N-(1-acetylpiperidin-4-yl)-3-(4-amino-5-bromopyrrolo[2,1-f][1,2,4]triazin-7-yl)-N-cyclopropylbenzamide (546); 3-(4-amino-5-bromopyrrolo[2,1-f][1,2,4]triazin-7-yl)-N-cyclopropyl-N-(1-methylpiperidin-4-yl)benzamide (547); 4-acetyl-1-(3-(4-amino-5-bromopyrrolo[1,2-f][1,2,4]triazin-7-yl)phenyl)-3,3-dimethylpiperazin-2-one (548); 4-acetyl-1-(3-(4-amino-5-bromopyrrolo[2,1-f][1,2,4]triazin-7-yl)phenyl)-6,6-dimethylpiperazin-2-one (549); 4-acetyl-1-(3-(4-amino-5-iodopyrrolo[1,2-f][1,2,4]triazin-7-yl)phenyl)-3,3-dimethylpiperazin-2-one (550); 4-acetyl-1-(5-(4-amino-5-iodopyrrolo[2,1-f][1,2,4]triazin-7-yl)-2-fluorophenyl)-3,3-dimethylpiperazin-2-one (551); 4-acetyl-1-(5-{4-amino-5-bromopyrrolo[2,1-f][1,2,4]triazin-7-yl}-2-methylphenyl)-3,3-dimethylpiperazin-2-one (552); 4-acetyl-1-(5-{4-amino-5-bromopyrrolo[2,1-f][1,2,4]triazin-7-yl}-2-fluorophenyl)-3,3-dimethylpiperazin-2-one (553); 4-acetyl-1-(3-{4-amino-5-bromopyrrolo[2,1-f][1,2,4]triazin-7-yl}-5-fluorophenyl)-3,3-dimethylpiperazin-2-one (554); 4-acetyl-1-(5-{4-amino-5-bromopyrrolo[2,1-f][1,2,4]triazin-7-yl}-2-methoxyphenyl)-3,3-dimethylpiperazin-2-one (555); 2-(4-acetyl-3,3-dimethyl-2-oxopiperazin-1-yl)-4-{4-amino-5-bromopyrrolo[2,1-f][1,2,4]triazin-7-yl}benzonitrile (556); 7-(3-(4-acetyl-3,3-dimethyl-2-oxopiperazin-1-yl)-4-fluorophenyl)-4-aminopyrrolo[2,1-f][1,2,4]triazine-5-carbonitrile (557); 7-(3-(4-acetyl-3,3-dimethyl-2-oxopiperazin-1-yl)

phenyl)-4-aminopyrrolo[2,1-f][1,2,4]triazine-5-carbonitrile (558); 4-amino-7-[3-(4-methanesulfonyl-3,3-dimethyl-2-oxopiperazin-1-yl)-4-methylphenyl]pyrrolo[2,1-f][1,2,4]triazine-5-carbonitrile (559); 7-[3-(4-acetyl-3,3-dimethyl-2-oxopiperazin-1-yl)-4-cyanophenyl]-4-aminopyrrolo[2,1-f][1,2,4]triazine-5-carbonitrile (560); 7-[3-(4-acetyl-3,3-dimethyl-2-oxopiperazin-1-yl)-4-(trifluoromethyl)phenyl]-4-aminopyrrolo[2,1-f][1,2,4]triazine-5-carbonitrile (561); 7-[3-(4-acetyl-3,3-dimethyl-2-oxopiperazin-1-yl)-4-methylphenyl]-4-aminopyrrolo[2,1-f][1,2,4]triazine-5-carbonitrile (562); 7-[3-(4-acetyl-3,3-dimethyl-2-oxopiperazin-1-yl)-4-methoxyphenyl]-4-aminopyrrolo[2,1-f][1,2,4]triazine-5-carbonitrile (563); 4-acetyl-1-(3-(4-amino-5-(trifluoromethyl)pyrrolo[2,1-f][1,2,4]triazin-7-yl)phenyl)-3,3-dimethylpiperazin-2-one (564); 2-(4-acetyl-3,3-dimethyl-2-oxopiperazin-1-yl)-4-(4-amino-5-(trifluoromethyl)pyrrolo[1,2-f][1,2,4]triazin-7-yl)benzonitrile (565); 4-acetyl-1-{5-[4-amino-5-(trifluoromethyl)pyrrolo[2,1-f][1,2,4]triazin-7-yl]-2-fluorophenyl}-3,3-dimethylpiperazin-2-one (566); 4-acetyl-1-{3-[4-amino-5-(trifluoromethyl)pyrrolo[2,1-f][1,2,4]triazin-7-yl]-2,6-difluorophenyl}-3,3-dimethylpiperazin-2-one (567); 4-acetyl-1-{5-[4-amino-5-(trifluoromethyl)pyrrolo[2,1-f][1,2,4]triazin-7-yl]-2-methoxyphenyl}-3,3-dimethylpiperazin-2-one (568); 4-acetyl-1-{3-[4-amino-5-(trifluoromethyl)pyrrolo[2,1-f][1,2,4]triazin-7-yl]-2-fluorophenyl}-3,3-dimethylpiperazin-2-one (569); 4-acetyl-1-{3-[4-amino-5-(trifluoromethyl)pyrrolo[2,1-f][1,2,4]triazin-7-yl]-5-fluorophenyl}-3,3-dimethylpiperazin-2-one (570); 1-(4-{3-[4-amino-5-(trifluoromethyl)pyrrolo[2,1-f][1,2,4]triazin-7-yl]phenyl}-3,3-dimethylpiperazin-1-yl)ethan-1-one (571); 4-acetyl-1-{5-[4-amino-5-(trifluoromethyl) pyrrolo[2,1-f][1,2,4]triazin-7-yl]-2-methylphenyl}-3,3-dimethylpiperazin-2-one (572); 4-acetyl-1-{5-[4-amino-5-(trifluoromethyl)pyrrolo[2,1-f][1,2,4]triazin-7-yl]-2-(trifluoromethyl)phenyl}-3,3-dimethylpiperazin-2-one (573); 4-acetyl-1-(3-(4-amino-5-methylpyrrolo[2,1-f][1,2,4]triazin-7-yl)phenyl)-3,3-dimethylpiperazin-2-one (574); 2-(4-acetyl-3,3-dimethyl-2-oxopiperazin-1-yl)-4-{4-amino-5-methylpyrrolo[2,1-f][1,2,4]triazin-7-yl}benzonitrile (575); 4-acetyl-1-(5-{4-amino-5-methylpyrrolo[2,1-f][1,2,4]triazin-7-yl}-2-fluorophenyl)-3,3-dimethylpiperazin-2-one (576); 4-acetyl-1-(3-{4-amino-5-methylpyrrolo[2,1-f][1,2,4]triazin-7-yl}-2,6-difluorophenyl)-3,3-dimethylpiperazin-2-one (577); 4-acetyl-1-(3-{4-amino-5-methylpyrrolo[2,1-f][1,2,4]triazin-7-yl}-5-fluorophenyl)-3,3-dimethylpiperazin-2-one (578); 4-acetyl-1-(5-{4-amino-5-methylpyrrolo[2,1-f][1,2,4]triazin-7-yl}-2-methoxyphenyl)-3,3-dimethylpiperazin-2-one (579); 2-(4-acetyl-3,3-dimethyl-2-oxopiperazin-1-yl)-4-(4-amino-5-chloropyrrolo[1,2-f][1,2,4]triazin-7-yl)benzonitrile (580); 4-acetyl-1-(3-(4-amino-5-chloropyrrolo[1,2-f][1,2,4]triazin-7-yl)phenyl)-3,3-dimethylpiperazin-2-one (581); 4-acetyl-1-(3-{4-amino-5-chloropyrrolo[2,1-f][1,2,4]triazin-7-yl}-2-fluorophenyl)-3,3-dimethylpiperazin-2-one (582); 4-acetyl-1-(5-{4-amino-5-chloropyrrolo[2,1-f][1,2,4]triazin-7-yl}-2-fluorophenyl)-3,3-dimethylpiperazin-2-one (583); 4-acetyl-1-(3-{4-amino-5-chloropyrrolo[2,1-f][1,2,4]triazin-7-yl}-5-fluorophenyl)-3,3-dimethylpiperazin-2-one (584); 4-acetyl-1-(5-{4-amino-5-chloropyrrolo[2,1-f][1,2,4]triazin-7-yl}-2-methylphenyl)-3,3-dimethylpiperazin-2-one (585); 4-acetyl-1-(3-{4-amino-5-chloropyrrolo[2,1-f][1,2,4]triazin-7-yl}-4-fluorophenyl)-3,3-dimethylpiperazin-2-one (586); 4-acetyl-1-(5-{4-amino-5-chloropyrrolo[2,1-f][1,2,4]triazin-7-yl}-2-(trifluoromethyl)phenyl)-3,3-dimethylpiperazin-2-one (587); 4-acetyl-1-(3-{4-amino-5-chloropyrrolo[2,1-f][1,2,4]triazin-7-yl}-2,6-difluorophenyl)-3,3-dimethylpiperazin-2-one (588); 2-(5-{4-amino-5-chloropyrrolo[2,1-f][1,2,4]triazin-7-yl}-2-fluorophenyl)-1H,2H,3H,4H,6H-pyrido[1,2-a]piperazine-1,6-dione (589); 1-(5-{4-amino-5-chloropyrrolo[2,1-f][1,2,4]triazin-7-yl}-2-(trifluoromethyl)phenyl)-4-methanesulfonyl-3,3-dimethylpiperazin-2-one (590); 1-(5-{4-amino-5-chloropyrrolo[2,1-f][1,2,4]triazin-7-yl}-2-fluorophenyl)-4-methanesulfonyl-3,3-dimethylpiperazin-2-one (591); 1-(5-{4-amino-5-chloropyrrolo[2,1-f][1,2,4]triazin-7-yl}-2-methoxyphenyl)-4-methanesulfonyl-3,3-dimethylpiperazin-2-one (592); 4-{4-amino-5-chloropyrrolo[2,1-f][1,2,4]triazin-7-yl}-2-(4-methanesulfonyl-3,3-dimethyl-2-oxopiperazin-1-yl)benzonitrile (593); 4-acetyl-1-(5-(4-amino-5-chloropyrrolo[1,2-f][1,2,4]triazin-7-yl)-2-methoxyphenyl)-3,3-dimethylpiperazin-2-one (594); 2-(4-acetyl-3,3,6-trimethyl-2-oxopiperazin-1-yl)-4-{4-amino-5-chloropyrrolo[2,1-f][1,2,4]triazin-7-yl}benzonitrile (595); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-methoxyphenyl)-3,3-dimethylpiperazin-2-one (596); 2-(4-acetyl-3,3,6-trimethyl-2-oxopiperazin-1-yl)-4-[4-amino-5-(trifluoromethyl)pyrrolo[2,1-f][1,2,4]triazin-7-yl]benzonitrile (597); (R)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile (598); (S)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile (599); 4-acetyl-1-{3-[4-amino-5-(trifluoromethyl) pyrrolo[2,1-f][1,2,4]triazin-7-yl]phenyl}-3,3-dimethyl-5,5,6,6-tetradeuteropiperazin-2-one (600); 4-acetyl-1-(5-(4-amino-5-(trifluoromethyl)pyrrolo[2,1-f][1,2,4]triazin-7-yl)-2-(difluoromethyl)phenyl)-3,3-dimethylpiperazin-2-one (624); 4-acetyl-1-(5-(4-amino-5-(trifluoromethyl)pyrrolo[2,1-f][1,2,4]triazin-7-yl)-2-(1-hydroxyethyl)phenyl)-3,3-dimethylpiperazin-2-one (625); 4-acetyl-1-(5-(4-amino-5-chloropyrrolo[2,1-f][1,2,4]triazin-7-yl)-2-(1-hydroxyethyl)phenyl)-3,3-dimethylpiperazin-2-one (626); methyl 2-(4-acetyl-3,3-dimethyl-2-oxopiperazin-1-yl)-4-(4-amino-5-chloropyrrolo[2,1-f][1,2,4]triazin-7-yl)benzoate (627); 7-(3-(4-acetyl-3,3-dimethyl-2-oxopiperazin-1-yl)-4-chlorophenyl)-4-aminopyrrolo[2,1-f][1,2,4]triazine-5-carbonitrile (628); 4-acetyl-1-(5-(4-amino-5-(trifluoromethyl)pyrrolo[2,1-f][1,2,4]triazin-7-yl)-2-(methylsulfonyl)phenyl)-3,3-dimethylpiperazin-2-one (629); 4-acetyl-1-(5-(4-amino-5-(trifluoromethyl)pyrrolo[2,1-f][1,2,4]triazin-7-yl)-2-(2-hydroxypropan-2-yl)phenyl)-3,3-dimethylpiperazin-2-one (630); 4-acetyl-1-(5-(4-amino-5-chloropyrrolo[2,1-f][1,2,4]triazin-7-yl)-2-(difluoromethyl)phenyl)-3,3-dimethylpiperazin-2-one (631); 7-(3-(4-acetyl-3,3-dimethyl-2-oxo-5,5,6,6-tetradeuteropiperazin-1-yl)-4-fluorophenyl)-4-aminopyrrolo[2,1-f][1,2,4]triazine-5-carbonitrile (635); 4-acetyl-1-(5-(4-amino-5-chloropyrrolo[2,1-f][1,2,4]triazin-7-yl)-2-fluorophenyl)-3,3-dimethyl-5,5,6,6-tetradeuteropiperazin-2-one (636); 2-(4-acetyl-3,3-dimethyl-2-oxo-5,5,6,6-tetradeuteropiperazin-1-yl)-4-(4-amino-5-chloropyrrolo[2,1-f][1,2,4]triazin-7-yl)benzonitrile (637); 4-acetyl-1-(5-(4-amino-5-(trifluoromethyl)pyrrolo[2,1-f][1,2,4]triazin-7-yl)-2-methoxyphenyl)-3,3-dimethyl-5,5,6,6-tetradeuteropiperazin-2-one (638); 2-(4-acetyl-3,3-dimethyl-2-oxo-5,5,6,6-tetradeuteropiperazin-1-yl)-4-(4-amino-5-(trifluoromethyl)pyrrolo[2,1-f][1,2,4]triazin-7-yl)benzonitrile (639); 4-acetyl-1-(5-(4-amino-5-(trifluoromethyl)pyrrolo[2,1-f][1,2,4]triazin-7-yl)-2-fluorophenyl)-3,3-dimethyl-5,5,6,6-tetradeuteropiperazin-2-one (640); (S)-2-(4-acetyl-3,3,6-trimethyl-2-oxopiperazin-1-yl)-4-(4-amino-5-chloropyrrolo[2,1-f][1,2,4]triazin-7-yl)benzonitrile (642); (S)-2-(4-acetyl-3,3,6- trimethyl-2-oxopiperazin-1-yl)-4-(4-amino-5-(trifluoromethyl)pyrrolo[2,1-f][1,2,4]triazin-7-yl) benzonitrile (643); (R)-2-(4-acetyl-3,3,6-trimethyl-2-oxopiperazin-1-yl)-4-(4-amino-5-(trifluoromethyl) pyrrolo [2,1-f][1,2,4]triazin-7-yl)benzonitrile (644); (S)-4-acetyl-1-(5-(4-amino-5-chloropyrrolo[2,1-f][1,2,4]triazin-7-yl)-2-methoxyphenyl)-3,3,6-trimethylpiperazin-2-one (645); 2-((3R,6R)-4-acetyl-3,6-dimethyl-2-oxopiperazin-1-yl)-4-(4-amino-5-(trifluoromethyl)pyrrolo[2,1-f][1,2,4]triazin-7-yl)benzonitrile (646); 4-(4-amino-5-(trifluoromethyl)pyrrolo[2,1-f][1,2,4]triazin-7-yl)-2-(4-(2-hydroxyacetyl)-3,3-dimethyl-2-oxopiperazin-1-yl)benzonitrile (647); 1-(5-(4-amino-5-chloropyrrolo[2,1-f][1,2,4]triazin-7-yl)-2-fluorophenyl)-4-(2-hydroxyacetyl)-3,3-dimethylpiperazin-2-one (648); (S)-4-(4-amino-5-(trifluoromethyl)pyrrolo[2,1-f][1,2,4]triazin-7-yl)-2-(4-(2-hydroxypropanoyl)-3,3-dimethyl-2-oxopiperazin-1-yl)benzonitrile (649); 4-(4-amino-5-chloropyrrolo[2,1-f][1,2,4]triazin-7-yl)-2-(3,3-dimethyl-2-oxo-4-propionylpiperazin-1-yl)benzonitrile (651); 4-(4-amino-5-(trifluoromethyl)pyrrolo[2,1-f][1,2,4]triazin-7-yl)-2-(3,3-dimethyl-2-oxo-4-propionylpiperazin-1-yl)benzonitrile (652); (R)-4-(4-amino-5-chloropyrrolo[2,1-f][1,2,4]triazin-7-yl)-2-(2,2,6-trimethyl-3-oxomorpholino)benzonitrile (653); (S)-4-(4-amino-5-(trifluoromethyl)pyrrolo[2,1-f][1,2,4]triazin-7-yl)-2-(2,2,5-trimethyl-3-oxomorpholino) benzonitrile (654); (S)-7-(3-(4-acetyl-3,3,6-trimethyl-2-oxopiperazin-1-yl)-4-methoxyphenyl)-4-aminopyrrolo[2,1-f][1,2,4]triazine-5-carbonitrile (658); 7-(3-(4-acetyl-3,3-dimethyl-2-oxo-5,5,6,6-tetradeutero-piperazin-1-yl)phenyl)-4-aminopyrrolo[2,1-f][1,2,4]triazine-5-carbonitrile (659); 4-(4-amino-5-chloropyrrolo[2,1-f][1,2,4]triazin-7-yl)-2-(3,3-dimethyl-4-(2-(methylsulfonyl)acetyl)-2-oxopiperazin-1-yl) benzonitrile (660); and 2-((3S,6S)-4-acetyl-3,6-dimethyl-2-oxopiperazin-1-yl)-4-(4-amino-5-(trifluoromethyl)pyrrolo [2,1-f][1,2,4]triazin-7-yl)benzonitrile (663).

One embodiment provides a compound of Formula (I) or a salt thereof, wherein X is N; $Q_1$ is Cl, Br, or I; and $R_1$, $R_2$, $R_3$, $R_4$, $R_5$, and $R_6$ are defined in the first aspect. Included in this embodiment are compounds in which $R_3$ is piperazinyl substituted with zero to 8 substituents independently selected from D, —$CH_3$, —C(O)$CH_3$, —C(O)$CH_2$ $CH_3$, =O, —C(O)$CH_2$OH, —C(O)$CH_2$S(O)$_2$$CH_3$, and —S(O)$_2$$CH_3$; —C(O)N(cyclopropyl)(acetyl piperidinyl), —C(O)N(cyclopropyl)(methylpiperidinyl), —C(O)N(cyclopropyl) (tetrahydropyran), —$CH_2$N($CH_3$)(tetrahydropyranyl), —O(piperidinyl), —O(acetyl piperidinyl), trimethyl morpholinonyl, or 1H,2H,3H,4H,6H-pyrido[1,2-a]piperazinone-1,6-dionyl; and $R_1$, $R_2$, $R_4$, $R_5$, and $R_6$ are defined in the first aspect. Also included are compounds in which $R_1$ is H; $R_2$ is H or F; $R_4$ is H, F, —CN, —$CH_3$, —$CHF_2$, —$CF_3$, —$OCH_3$, —CH($CH_3$)OH, or —C(O)$OCH_3$; $R_5$ is H or F; and $R_6$ is H or F.

One embodiment provides a compound of Formula (I) or a salt thereof, wherein X is N; $Q_1$ is —CN; and $R_1$, $R_2$, $R_3$, $R_4$, $R_5$, and $R_6$ are defined in the first aspect. Included in this embodiment are compounds in which $R_3$ is piperazinyl substituted with zero to 8 substituents independently selected from D, —$CH_3$, —C(O)$CH_3$, =O, —C(O)$CH_2$S(O)$_2$$CH_3$, and —S(O)$_2$$CH_3$; and $R_1$, $R_2$, $R_4$, $R_5$, and $R_6$ are defined in the first aspect. Also included are compounds in which $R_1$ is H; $R_2$ is H; $R_4$ is H, F, Cl, —CN, —$CH_3$, —$CF_3$, and —$OCH_3$; $R_5$ is H; and $R_6$ is H.

One embodiment provides a compound of Formula (I) or a salt thereof, wherein X is N; $Q_1$ is —$CH_3$; and $R_1$, $R_2$, $R_3$, $R_4$, $R_5$, and $R_6$ are defined in the first aspect. Included in this embodiment are compounds in which $R_3$ is piperazinyl substituted with two methyl groups and —C(O)$CH_3$; and $R_1$, $R_2$, $R_4$, $R_5$, and $R_6$ are defined in the first aspect. Also included are compounds in which $R_1$ is H; $R_2$ is H or F; $R_4$ is H, F, —CN, and —$OCH_3$; $R_5$ is H or F; and $R_6$ is H.

One embodiment provides a compound of Formula (I) or a salt thereof, wherein X is N; $Q_1$ is —$CF_3$; and $R_1$, $R_2$, $R_3$, $R_4$, $R_5$, and $R_6$ are defined in the first aspect. Included in this embodiment are compounds in which $R_3$ is trimethyl morpholinonyl or piperazinyl substituted with 3 to 8 substituents independently selected from D, —$CH_3$, —C(O)$CH_3$, =O, —C(O)$CH_2$$CH_3$, —C(O)$CH_2$OH, —C(O)CH($CH_3$)OH, —C(O)$CH_2$S(O)$_2$$CH_3$, and —S(O)$_2$$CH_3$; and $R_1$, $R_2$, $R_4$, $R_5$, and $R_6$ are defined in the first aspect. Also included are compounds in which $R_1$ is H; $R_2$ is H; $R_4$ is H, F, —CN, —$CH_3$, —$CHF_2$, —$CF_3$, —$OCH_3$, —CH($CH_3$)OH, —C($CH_3$)$_2$OH, or —S(O)$_2$$CH_3$; $R_5$ is H or F; and $R_6$ is H.

One embodiment provides a compound of Formula (I) or a salt thereof, wherein X is N; $Q_1$ is: (i) a 5-membered heteroaryl selected from pyrrolyl, pyrazolyl, imidazolyl, isoxazolyl, thiazolyl, triazolyl, oxadiazolyl, and thiadiazolyl; (ii) a 6-membered heteroaryl selected from pyridinyl, pyridazinyl, and pyrimidinyl; (iii) a bicyclic heteroaryl selected from indolyl, imidazopyridinyl, pyrrolopyridinyl, pyrazolopyridinyl and benzo[d]oxazolyl; wherein each of said 5-membered, 6-membered, and bicyclic heteroaryls is substituted with zero to 1 $R_a$ and zero to 1 $R_b$; and $R_a$, $R_b$, $R_1$, $R_2$, $R_3$, $R_4$, $R_5$, and $R_6$ are defined in the first aspect. Included in this embodiment are compounds in which $R_3$ is:
(i) —$CH_2$OH, —$CH_2$$NH_2$, —$CH_2$N($CH_3$)$_2$, —$CH_2$NHS(O)$_2$$CH_3$, —$CH_2$N($CH_3$)$CH_2$$CH_2$$OCH_3$, —$CH_2$CH($CH_3$)$NHCH_2$$CH_2$$OCH_3$, —C($CH_3$)$_2$N($CH_3$)$_2$, —C($CH_3$)$_2$N($CH_2$$CH_3$)$_2$, —$CH_2$CH($CH_3$)NH(tetrahydropyranyl), —C($CH_3$)$_2$N($CH_3$)(tetrahydropyran), —$CH_2$CH($CH_3$)N($CH_3$)$_2$, —C($CH_3$)$_2$$CH_2$N($CH_3$)$_2$, —$CH_2$(morpholinyl), —$CH_2$(morpholinonyl), —$CH_2$(oxazinanonyl), —$CH_2$(pyrrolidinonyl), —$CH_2$(hydroxypyrrolidinyl), —$CH_2$(t-butyl oxazolidinonyl), —$CH_2$(dimethyl oxazolidinonyl), —$CH_2$(i-propyl oxazolidinonyl), —$CH_2$(acetyl piperazinyl), —$CH_2$(methyl piperazinonyl), —$CH_2$(methyl pyrrolidinonyl), —$CH_2$(8-oxa-3-azabicyclo[3.2.1]octanyl), —$CH_2$N(tetrahydropyranyl)$_2$, —$CH_2$NHC(O)(methoxyphenyl), —$CH_2$N(cyclopropyl) (methylsulfonyl azetidinyl), —$CH_2$N($CH_3$)(tetrahydropyranyl), —$CH_2$N($CH_3$)(oxetanyl), —$CH_2$N(C(O)$CH_3$) (morpholinyl), —$CH_2$CH($CH_3$)(morpholinyl), —$CH_2$CH ($CH_3$)(pyrrolidinyl), —CH($CH_3$)(morpholinyl), —CH ($CH_3$)(dimethylazetidinyl), —CH($CH_3$) (dimethylmorpholinyl), —CH($CH_3$)(hydroxy pyrrolidinyl), —CH($CH_3$)(methoxypyrrolidinyl), —CH ($CH_3$)(methyl hydroxyazetidinyl), —CH($CH_3$)(acetopiperazinyl), —CH($CH_3$)NH(tetrahydropyranyl), —CH ($CF_3$)(morpholinyl), —$CH_2$C(O) (dioxidothiomorpholinyl), —$CH_2$CH($CH_3$)N($CH_3$) (tetrahydropyranyl), —C($CH_3$)$_2$(pyrrolidinyl), —C($CH_3$)$_2$(morpholinyl), —C($CH_3$)$_2$(oxazolidinonyl), —C($CH_3$)$_2$(methyl pyrrolidinium), —C($CH_3$)$_2$NHC(O)$CH_2$C($CH_3$)$_2$OH, or —$CH_2$O(pyridinyl);
(ii) —C(O)OH, —C(O)$NH_2$, —C(O)$NHCH_3$, —C(O)NHC($CH_3$)$_2$C(O)$NHCH_3$, —C(O)(cyanoazetidinyl), —C(O)(methyl, hydroxyazetidinyl), —C(O)(morpholinyl), —C(O)(dioxidothiomorpholinyl), —C(O)(piperazinyl) wherein said piperazinyl is substituted with —C(O)$CH_3$, —C(O)$CH_2$$CH_3$, —C(O)C($CH_3$)$_2$H, —C(O)$OCH_3$, or —C(O)tetrahydrofuranyl; —C(O)(methyl piperazinonyl), —C(O)(piperidinyl) wherein said piperidinyl is substituted with 1 to 2 substituents independently selected from —OH, —$CH_2$OH, —C($CH_3$)$_2$OH, —C(O)$NH_2$—C(O)$NHCH_3$, —N($CH_3$)$_2$, and —NHC(O)$CH_3$; —C(O)(pyrrolidinyl), —C(O)(8-oxa-3-azabicyclo[3.2.1]octanyl), —C(O)NHCH$_3$, —C(O)NH(oxopiperidinyl), —C(O)NH (oxopyrrolidinyl), —C(O)NH(benzamide), —C(O)NH (carbamoyl thiazolyl), —C(O)NH(acetyl piperidinyl), —C(O)NH(methyl piperidinyl), —C(O)NH(methyl, cyclopropyl-pyrazolyl), —C(O)NH(tetrahydropyranyl), —C(O)NH(hydroxymethyl tetrahydropyranyl), —C(O)N(CH$_3$)(methyl pyrrolidinyl), —C(O)N(CH$_3$)(oxetanyl), —C(O)N(CH$_3$)(tetrahydropyran), —C(O)N(CH$_3$)$_2$, —C(O)N(CH$_3$)C(O)CH$_2$NH$_2$, —C(O)N(CH$_3$)CH$_2$(dimethylisoxazolyl), —C(O)N(CH$_3$)CH$_2$(methyl pyrrolidinyl), —C(O)N(CH$_3$)CH$_2$C(CH$_3$)$_2$CH$_2$OH, —C(O)N(CH$_3$)CH$_2$CF$_2$H, —C(O)N(CH$_2$CH$_3$)$_2$, —C(O)N(cyclopropyl)(methyl piperidinyl), —C(O)N(cyclopropyl)(methyl pyrazolyl), —C(O)N(cyclopropyl)(acetyl piperidinyl), —C(O)N(cyclopropyl)(methyl piperidinyl), —C(O)N(cyclopropyl)(tetrahydropyranyl), —C(O)N(cyclopropyl)(thiazolyl), —C(O)N(cyclopropyl)$_2$, —C(O)N(cyclopropyl)(CH$_2$(methyl pyrazolyl)), and —C(O)N(cyclopropyl)(CH$_2$-thiazolyl);

(iii) —O(tetrahydropyranyl), —O(dimethyltetrahydropyranyl), —O(dioxotetrahydrothiopyranyl), —O(piperidinyl) wherein said piperidinyl is substituted with zero to 1 substituent selected from —CH$_3$, —C(O)CH$_3$, and —C(O)CH(CH$_3$)$_2$; —O(dimethylpyridinonyl), or —O(methyl pyridinonyl);

(iv) —NHC(O)CH$_3$ or —NHS(O)$_2$CH$_3$;

(v) cyclopropyl substituted with —C(O)NH(CH$_2$CH$_3$), —C(O)NH(CH(CH$_3$)$_2$), —C(O)NH(cyclopropyl), —C(O)NH(oxetanyl), —C(O)NH(difluorocyclobutyl), or —CH$_2$NH(tetrahydropyranyl); or cyclobutyl substituted with 1 to 3 substituents independently selected from F, —OH, —CH$_3$, —CF$_3$, —OCH$_3$, —OCHF$_2$, —C(O)NH(CH$_3$), —C(O)NH(CH$_2$CH$_3$), —C(O)NH(CH(CH$_3$)$_2$), —C(O)NH(CH$_2$CF$_3$), —C(O)NH(cyclopropyl), —C(O)NH(difluorocyclobutyl), —C(O)N(CH$_3$)(oxetanyl), —C(O)(morpholinyl), —C(O)(methoxypyrrolidinyl), and —C(O)(difluoroazetidinyl); or (vi) azetidinyl substituted with 1 to 2 substituents independently selected from fluorobenzoyl, dioxothiomorpholinyl, and —C(O)(hydroxypropyl phenyl); octahydropyrrolo[3,4-c]pyrrole substituted with zero to 1 substituent selected from —CH$_3$, —C(O)CH$_3$, —CH(CH$_3$)$_2$), —CH(CH$_3$)C(CH$_3$)$_2$OH, —CH(CH$_3$)CH$_2$OCH$_3$, —S(O)$_2$CH$_3$, and cyclobutyl; 1,2-dihydropyridinonyl substituted with 1 to 3 substituents independently selected from —CH$_3$, —CD$_3$, —CH$_2$CH$_3$, =O, and —CH$_2$CHF$_2$; 4,7-diazaspiro[2.5]octanyl substituted with zero to 1 substituent selected from —C(O)CH$_3$, —C(O)OCH$_3$, cyclobutyl, and oxetanyl; tetrahydropyranyl substituted with —OH, —CN, —OCH$_3$, —C(O)NH$_2$, or —NHC(O)CH$_3$; oxetanyl substituted with —N(CH$_3$)$_2$, —NHC(O)C(CH$_3$)$_3$, —NHS(O)C(CH$_3$)$_3$, —N(CH$_3$)S(O)C(CH$_3$)$_3$, —N(CH$_3$)(acetyl piperidinyl), piperidinonyl, hydroxypiperidinyl, hydroxypyrrolidinyl, morpholinyl, or dioxothiomorpholinyl; piperazinyl substituted with 1 to 8 substituents independently selected from D, —OH, —CH$_3$, —CH(CH$_3$)$_2$, —CF$_3$, =O, —C(O)(cyclopropyl), —C(O)(cyclobutyl), —S(O)$_2$CH$_3$, —C(O)CH$_2$S(O)$_2$CH$_3$, —C(O)CH$_3$, —C(O)CH(CH$_3$)$_2$, —C(O)OCH$_3$, —C(O)CH$_2$CN, —C(O)CH$_2$OH, —C(O)CH(CH$_3$)OH, —C(O)C(CH$_3$)$_2$OH, —C(O)(phenyl), —N(CH$_3$)C(O)CH$_3$, cyclopropyl, cyclobutyl, oxetanyl, phenyl, fluorophenyl, chlorophenyl, pyridinyl, pyrimidinyl, and methyloxadiazolyl; pyrrolidinyl substituted with 1 to 2 substituents independently selected from —OH, —CH$_3$, —C(CH$_3$)$_2$OH, —C(O)CH$_3$, —C(O)CH(CH$_3$)$_2$, —C(O)C(CH$_3$)$_3$, —NHC(O)CH$_3$, —N(CH$_3$)C(O)CH$_3$, —N(CH$_3$)C(O)C(CH$_3$)$_2$OH, —N(CH$_3$)C(O)CH$_2$(pyrazinyl), —C(O)(phenyl), —C(O)(fluorophenyl), —C(O)(methyl phenyl), —C(O)(cyclopropyl), —C(O)(difluorocyclopropyl), —C(O)(oxazolyl), —C(O)(pyrazolyl), —C(O)(pyridazinyl), —C(O)(pyridinyl), —C(O)(tetrahydropyranyl), —C(O)(thiazolyl), —C(O)(methyl thiazolyl), —C(O)(methyl pyrazolyl), and morpholinyl; piperidinyl substituted with zero to 4 substituents independently selected from —OH, —CH$_3$, —CN, —OCH$_3$, =O, —C(O)CH$_3$, —C(O)CH$_2$CN, —C(O)(morpholinyl), —C(O)NH$_2$, —NHC(O)CH$_3$, —N(CH$_3$)S(O)$_2$CH$_3$, —N(CH$_3$)C(O)NH(CH(CH$_3$)$_2$), —N(CH$_3$)C(O)CH$_2$(pyrazinyl), —N(CH$_3$)C(O)(furanyl), —N(CH$_3$)C(O)(cyanocyclopropyl), oxetanyl, morpholinyl, and piperidinonyl; phenyl substituted with 1 to 2 substituents independently selected from F and —C(O)NH$_2$; quinazolinyl substituted with zero to 4 substituents independently selected from F, —CH$_3$, and =O; carbamoyl azepanyl, imidazolyl, dimethyloxazolindinonyl, methyl imidazol[1,2a]pyridinyl, morpholinyl, carbamoyl-morpholinyl, morpholinonyl, methyl pyridinonyl, dimethyl morpholinonyl, dioxothiomorpholinyl, methyl[1,2,4]triazolo[4,3-a]pyridinyl], dimethyl[1,2,4]triazolo[4,3-a]pyridinyl), 1-(3,4-dihydroquinoxalin-1 (2H)-yl)ethanone, 2,3-dihydroquinazolin-4(1H)-one, 1,3-oxazinan-2-one, 1H,2H,3H,4H,6H-pyrido[1,2-a]piperazinone-1,6-dionyl, 1H-pyrido[1,2-c]pyrimidine-1,3(2H)-dione, or 3,8-diazabicyclo[3.2.1]octanyl ethanone.

Also included in this embodiment are compounds in which R$_a$ is —CH$_3$, —CD$_3$, —CHF$_2$, —CF$_3$, —CH$_2$CHF$_2$, —CH$_2$CF$_3$, —CD$_2$CD$_3$, —CH$_2$CF$_2$H, —CH$_2$CH$_2$CH$_3$, —CH(CH$_3$)$_2$, —CH(CD$_3$)$_2$, —CH(CH$_2$F)$_2$, —CH(CH$_3$)(CF$_3$), —CD(CD$_3$)$_2$, —CH$_2$CH(CH$_3$)$_2$, —C(CH$_3$)$_3$, —CH(CH$_3$)CH$_2$CH$_3$, —CH$_2$C(CH$_3$)$_3$, —CH$_2$(C(CH$_3$)$_2$OH, —CH$_2$CH(OH)CF$_3$, —NH$_2$, —CH$_2$CH$_2$OCH$_3$, —S(O)$_2$CH$_3$, —S(O)$_2$CH(CH$_3$)$_2$, —CH$_2$(cyclopropyl), —CH$_2$(cyclobutyl), —CH$_2$(oxetanyl), —CH$_2$(methyloxetanyl), —S(O)$_2$(cyclopropyl), cyclopropyl, difluorocyclopropyl, cyclobutyl, cyclohexyl, difluorocyclohexyl, oxetanyl, tetrahydropyranyl, phenyl, fluorophenyl, pyridinyl, pyrimidinyl, or pyridazinyl; R$_1$ is H; R$_2$ is H or F; R$_4$ is H, F, Cl, —CN, —CH$_3$, —CF$_3$, —OCH$_3$, —C(O)N(CH$_3$)$_2$, or —C≡C(CH$_2$)$_3$CH$_3$; R$_5$ is H, F, Cl, —CH$_3$, or —OCH$_3$; and R$_6$ is H or F.

One embodiment provides a compound of Formula (I) or a salt thereof, wherein X is CH; and Q$_1$, R$_1$, R$_2$, R$_3$, R$_4$, R$_5$, and R$_6$ are defined in the first aspect.

One embodiment provides a compound of Formula (I) or a salt thereof, wherein X is CH; Q$_1$ is Cl, Br, I, —CN, —CH$_3$, or —CF$_3$; and R$_1$, R$_2$, R$_3$, R$_4$, R$_5$, and R$_6$ are defined in the first aspect.

One embodiment provides a compound of Formula (I) or a salt thereof, wherein X is CH; Q$_1$ is: (i) a 5-membered heteroaryl selected from pyrrolyl, pyrazolyl, imidazolyl, isoxazolyl, thiazolyl, triazolyl, oxadiazolyl, and thiadiazolyl; (ii) a 6-membered heteroaryl selected from pyridinyl, pyridazinyl, and pyrimidinyl; (iii) a bicyclic heteroaryl selected from indolyl, imidazopyridinyl, pyrrolopyridinyl, pyrazolopyridinyl and benzo[d]oxazolyl; wherein each of said 5-membered, 6-membered, and bicyclic heteroaryls is substituted with zero to 1 R$_a$ and zero to 1 R$_b$; and R$_a$, R$_b$, R$_1$, R$_2$, R$_3$, R$_4$, R$_5$, and R$_6$ are defined in the first aspect.

One embodiment provides a compound of Formula (I) or a salt thereof, wherein X is CH; Q$_1$ is pyrazolyl substituted with tetrahydropyran; R$_1$ is H; R$_2$ is H; R$_3$ is benzamide, piperazinonyl substituted with two methyl groups and —C(O)CH$_3$, or oxetan-3-yl-1λ6,4-thiomorpholine-1,1-dionyl; R$_4$ is H; R$_5$ is H; and R$_6$ is H. Included in this embodiment are the compounds selected from 4-acetyl-1-(3-(1-amino-8-(1-(tetrahydro-2H-pyran-4-yl)-1H-pyrazol-5-yl)pyrrolo[1,2-a]pyrazin-6-yl)phenyl)-3,3-dimethylpiperazin-2-one (619); 4-[3-(3-{1-amino-8-[1-(oxan-4-yl)-1H-pyrazol-5-yl]pyrrolo[1,2-a]pyrazin-6-yl}phenyl)oxetan-3-yl]-1$\lambda^6$,4-thiomorpholine-1,1-dione (620); and 2-(3-{1-amino-8-[1-(oxan-4-yl)-1H-pyrazol-5-yl]pyrrolo[1,2-a]pyrazin-6-yl}phenyl)benzamide; or salts thereof.

One embodiment provides a compound of Formula (I) or a salt thereof, wherein $Q_1$ is a 5-membered heteroaryl selected from pyrrolyl, pyrazolyl, imidazolyl, isoxazolyl, thiazolyl, triazolyl, oxadiazolyl, and thiadiazolyl, wherein each of said 5-membered heteroaryls is substituted with zero to 1 $R_a$ and zero to 1 $R_b$; and X, $R_a$, $R_b$, $R_1$, $R_2$, $R_3$, $R_4$, $R_5$, and $R_6$ are defined in the first aspect. Included in this embodiment are compounds in which $R_a$ is —CH$_3$, —CD$_3$, —CF$_2$H, —CF$_3$, —CD$_2$CD$_3$, —CH$_2$CF$_2$H, —CH$_2$CF$_3$, —CH$_2$CH$_2$CH$_3$, —CH(CH$_3$)$_2$, —CH(CD$_3$)$_2$, —CH(CH$_3$)(CF$_3$), —CH(CH$_2$F)$_2$, —CH(CF$_3$)$_2$, —C(CH$_3$)$_3$, —CD(CD$_3$)$_2$, —CH$_2$C(CH$_3$)$_3$, —CH$_2$CH(CH$_3$)$_2$, —CH$_2$CH(OH)CF$_3$, —CH(CH$_3$)CH$_2$CH$_3$, —CH$_2$(C(CH$_3$)$_2$OH, —CH$_2$CH$_2$OCH$_3$, —CH$_2$(cyclopropyl), —CH$_2$(cyclobutyl), —CH$_2$(oxetanyl), —CH$_2$(methyloxetanyl), —S(O)$_2$CH$_3$, —S(O)$_2$CH(CH$_3$)$_2$, —S(O)$_2$(cyclopropyl), cyclopropyl, difluorocyclopropyl, cyclobutyl, cyclohexyl, difluorocyclohexyl, oxetanyl, tetrahydropyranyl, phenyl, fluorophenyl, pyridinyl, or pyridazinyl. Also included in this embodiment are compounds in which $R_3$ is:

(i) —CH$_2$OH, —CH$_2$NH$_2$, —CH$_2$N(CH$_3$)$_2$, —CH$_2$NHS(O)$_2$CH$_3$, —CH$_2$N(CH$_3$)CH$_2$CH$_2$OCH$_3$, —CH$_2$CH(CH$_3$)NHCH$_2$CH$_2$OCH$_3$, —C(CH$_3$)$_2$N(CH$_3$)$_2$, —C(CH$_3$)$_2$N(CH$_2$CH$_3$)$_2$, —CH$_2$CH(CH$_3$)NH(tetrahydropyranyl), —C(CH$_3$)$_2$N(CH$_3$)(tetrahydropyran), —CH$_2$CH(CH$_3$)N(CH$_3$)$_2$, —C(CH$_3$)$_2$CH$_2$N(CH$_3$)$_2$, —CH$_2$(morpholinyl), —CH$_2$(morpholinonyl), —CH$_2$(oxazinanonyl), —CH$_2$(pyrrolidinonyl), —CH$_2$(hydroxypyrrolidinyl), —CH$_2$(t-butyl oxazolidinonyl), —CH$_2$(dimethyl oxazolidinonyl), —CH$_2$(i-propyl oxazolidinonyl), —CH$_2$(acetyl piperazinyl), —CH$_2$(methyl piperazinonyl), —CH$_2$(methyl pyrrolidinonyl), —CH$_2$(8-oxa-3-azabicyclo[3.2.1]octanyl), —CH$_2$N(tetrahydropyranyl)$_2$, —CH$_2$NHC(O)(methoxyphenyl), —CH$_2$N(cyclopropyl)(methylsulfonyl azetidinyl), —CH$_2$N(CH$_3$)(tetrahydropyranyl), —CH$_2$N(CH$_3$)(oxetanyl), —CH$_2$N(C(O)CH$_3$)(morpholinyl), —CH$_2$CH(CH$_3$)(morpholinyl), —CH$_2$CH(CH$_3$)(pyrrolidinyl), —CH(CH$_3$)(morpholinyl), —CH(CH$_3$)(dimethylazetidinyl), —CH(CH$_3$)(dimethylmorpholinyl), —CH(CH$_3$)(hydroxy pyrrolidinyl), —CH(CH$_3$)(methoxypyrrolidinyl), —CH(CH$_3$)(methyl hydroxyazetidinyl), —CH(CH$_3$)(acetopiperazinyl), —CH(CH$_3$)NH(tetrahydropyranyl), —CH(CF$_3$)(morpholinyl), —CH$_2$C(O)(dioxidothiomorpholinyl), —CH$_2$CH(CH$_3$)N(CH$_3$)(tetrahydropyranyl), —C(CH$_3$)$_2$(pyrrolidinyl), —C(CH$_3$)$_2$(morpholinyl), —C(CH$_3$)$_2$(oxazolidinonyl), —C(CH$_3$)$_2$(methyl pyrrolidinium), —C(CH$_3$)$_2$NHC(O)CH$_2$C(CH$_3$)$_2$OH, or —CH$_2$O(pyridinyl);

(ii) —C(O)OH, —C(O)NH$_2$, —C(O)NHCH$_3$, —C(O)NHC(CH$_3$)$_2$C(O)NHCH$_3$, —C(O)(cyanoazetidinyl), —C(O)(methyl, hydroxyazetidinyl), —C(O)(morpholinyl), —C(O)(dioxidothiomorpholinyl), —C(O)(piperazinyl) wherein said piperazinyl is substituted with —C(O)CH$_3$, —C(O)CH$_2$CH$_3$, —C(O)C(CH$_3$)$_2$H, —C(O)OCH$_3$, or —C(O)tetrahydrofuranyl; —C(O)(methyl piperazinonyl), —C(O)(piperidinyl) wherein said piperidinyl is substituted with 1 to 2 substituents independently selected from —OH, —CH$_2$OH, —C(CH$_3$)$_2$OH, —C(O)NH$_2$—C(O)NHCH$_3$, —N(CH$_3$)$_2$, and —NHC(O)CH$_3$; —C(O)(pyrrolidinyl), —C(O)(8-oxa-3-azabicyclo[3.2.1]octanyl), —C(O)NHCH$_3$, —C(O)NH(oxopiperidinyl), —C(O)NH(oxopyrrolidinyl), —C(O)NH(benzamide), —C(O)NH(carbamoyl thiazolyl), —C(O)NH(acetyl piperidinyl), —C(O)NH(methyl piperidinyl), —C(O)NH(methyl, cyclopropyl-pyrazolyl), —C(O)NH(tetrahydropyranyl), —C(O)NH(hydroxymethyl tetrahydropyranyl), —C(O)N(CH$_3$)(methyl pyrrolidinyl), —C(O)N(CH$_3$)(oxetanyl), —C(O)N(CH$_3$)(tetrahydropyran), —C(O)N(CH$_3$)$_2$, —C(O)N(CH$_3$)C(O)CH$_2$NH$_2$, —C(O)N(CH$_3$)CH$_2$(dimethylisoxazolyl), —C(O)N(CH$_3$)CH$_2$(methyl pyrrolidinyl), —C(O)N(CH$_3$)CH$_2$C(CH$_3$)$_2$CH$_2$OH, —C(O)N(CH$_3$)CH$_2$CF$_2$H, —C(O)N(CH$_2$CH$_3$)$_2$, —C(O)N(cyclopropyl)(methyl piperidinyl), —C(O)N(cyclopropyl)(methyl pyrazolyl), —C(O)N(cyclopropyl)(acetyl piperidinyl), —C(O)N(cyclopropyl)(methyl piperidinyl), —C(O)N(cyclopropyl)(tetrahydropyranyl), —C(O)N(cyclopropyl)(thiazolyl), —C(O)N(cyclopropyl)$_2$, —C(O)N(cyclopropyl)(CH$_2$(methyl pyrazolyl)), and —C(O)N(cyclopropyl)(CH$_2$-thiazolyl);

(iii) —O(tetrahydropyranyl), —O(dimethyltetrahydropyranyl), —O(dioxotetrahydrothiopyranyl), —O(piperidinyl) wherein said piperidinyl is substituted with zero to 1 substituent selected from —CH$_3$, —C(O)CH$_3$, and —C(O)CH(CH$_3$)$_2$; —O(dimethylpyridinonyl), or —O(methyl pyridinonyl);

(iv) —NHC(O)CH$_3$ or —NHS(O)$_2$CH$_3$;

(v) cyclopropyl substituted with —C(O)NH(CH$_2$CH$_3$), —C(O)NH(CH(CH$_3$)$_2$), —C(O)NH(cyclopropyl), —C(O)NH(oxetanyl), —C(O)NH(difluorocyclobutyl), or —CH$_2$NH(tetrahydropyranyl); or cyclobutyl substituted with 1 to 3 substituents independently selected from F, —OH, —CH$_3$, —CF$_3$, —OCH$_3$, —OCHF$_2$, —C(O)NH(CH$_3$), —C(O)NH(CH$_2$CH$_3$), —C(O)NH(CH(CH$_3$)$_2$), —C(O)NH(CH$_2$CF$_3$), —C(O)NH(cyclopropyl), —C(O)NH(difluorocyclobutyl), —C(O)N(CH$_3$)(oxetanyl), —C(O)(morpholinyl), —C(O)(methoxypyrrolidinyl), and —C(O)(difluoroazetidinyl); or (vi) azetidinyl substituted with 1 to 2 substituents independently selected from fluorobenzoyl, dioxothiomorpholinyl, and —C(O)(hydroxypropyl phenyl); octahydropyrrolo[3,4-c]pyrrole substituted with zero to 1 substituent selected from —CH$_3$, —C(O)CH$_3$, —CH(CH$_3$)$_2$), —CH(CH$_3$)C(CH$_3$)$_2$OH, —CH(CH$_3$)CH$_2$OCH$_3$, —S(O)$_2$CH$_3$, and cyclobutyl; 1,2-dihydropyridinonyl substituted with 1 to 3 substituents independently selected from —CH$_3$, —CD$_3$, —CH$_2$CH$_3$, =O, and —CH$_2$CHF$_2$; 4,7-diazaspiro[2.5]octanyl substituted with zero to 1 substituent selected from —C(O)CH$_3$, —C(O)OCH$_3$, cyclobutyl, and oxetanyl; tetrahydropyranyl substituted with —OH, —CN, —OCH$_3$, —C(O)NH$_2$, or —NHC(O)CH$_3$; oxetanyl substituted with —N(CH$_3$)$_2$, —NHC(O)C(CH$_3$)$_3$, —NHS(O)C(CH$_3$)$_3$, —N(CH$_3$)S(O)C(CH$_3$)$_3$, —N(CH$_3$)(acetyl piperidinyl), piperidinonyl, hydroxypiperidinyl, hydroxypyrrolidinyl, morpholinyl, or dioxothiomorpholinyl; piperazinyl substituted with 1 to 8 substituents independently selected from D, —OH, —CH$_3$, —CH(CH$_3$)$_2$, —CF$_3$, =O, —C(O)(cyclopropyl), —C(O)(cyclobutyl), —S(O)$_2$CH$_3$, —C(O)CH$_2$S(O)$_2$CH$_3$, —C(O)CH$_3$, —C(O)CH(CH$_3$)$_2$, —C(O)OCH$_3$, —C(O)CH$_2$CN, —C(O)CH$_2$OH, —C(O)CH(CH$_3$)OH, —C(O)C(CH$_3$)$_2$OH, —C(O)(phenyl), —N(CH$_3$)C(O)CH$_3$, cyclopropyl, cyclobutyl, oxetanyl, phenyl, fluorophenyl, chlorophenyl, pyridinyl, pyrimidinyl, and methyloxadiazolyl; pyrrolidinyl substituted with 1 to 2 substituents independently selected from —OH, —CH$_3$, —C(CH$_3$)$_2$OH, —C(O)CH$_3$, —C(O)CH(CH$_3$)$_2$, —C(O)

C(CH₃)₃, —NHC(O)CH₃, —N(CH₃)C(O)CH₃, —N(CH₃)C(O)C(CH₃)₂OH, —N(CH₃)C(O)CH₂(pyrazinyl), —C(O)(phenyl), —C(O)(fluorophenyl), —C(O)(methyl phenyl), —C(O)(cyclopropyl), —C(O)(difluorocyclopropyl), —C(O)(oxazolyl), —C(O)(pyrazolyl), —C(O)(pyridazinyl), —C(O)(pyridinyl), —C(O)(tetrahydropyranyl), —C(O)(thiazolyl), —C(O)(methyl thiazolyl), —C(O)(methyl pyrazolyl), and morpholinyl; piperidinyl substituted with zero to 4 substituents independently selected from —OH, —CH₃, —CN, —OCH₃, =O, —C(O)CH₃, —C(O)CH₂CN, —C(O)(morpholinyl), —C(O)NH₂, —NHC(O)CH₃, —N(CH₃)S(O)₂CH₃, —N(CH₃)C(O)NH(CH(CH₃)₂), —N(CH₃)C(O)CH₂(pyrazinyl), —N(CH₃)C(O)(furanyl), —N(CH₃)C(O)(cyanocyclopropyl), oxetanyl, morpholinyl, and piperidinonyl; phenyl substituted with 1 to 2 substituents independently selected from F and —C(O)NH₂; quinazolinyl substituted with zero to 4 substituents independently selected from F, —CH₃, and =O; carbamoyl azepanyl, imidazolyl, dimethyloxazolindinonyl, methyl imidazol[1,2a]pyridinyl, morpholinyl, carbamoyl-morpholinyl, morpholinonyl, methyl pyridinonyl, dimethyl morpholinonyl, dioxothiomorpholinyl, methyl[1,2,4]triazolo[4,3-a]pyridinyl), dimethyl[1,2,4]triazolo[4,3-a]pyridinyl), 1-(3,4-dihydroquinoxalin-1 (2H)-yl)ethanone, 2,3-dihydroquinazolin-4(1H)-one, 1,3-oxazinan-2-one, 1H,2H,3H,4H,6H-pyrido[1,2-a]piperazinone-1,6-dionyl, 1H-pyrido[1,2-c]pyrimidine-1,3(2H)-dione, or 3,8-diazabicyclo[3.2.1]octanyl ethanone.

One embodiment provides a compound of Formula (I) or a salt thereof, wherein $Q_1$ is a 6-membered heteroaryl selected from pyridinyl, pyridazinyl, and pyrimidinyl, wherein each of said 6-membered heteroaryls is substituted with zero to 1 $R_a$ and zero to 1 $R_b$; and X, $R_a$, $R_b$, $R_1$, $R_2$, $R_3$, $R_4$, $R_5$, and $R_6$ are defined in the first aspect. Included in this embodiment are compounds in which $R_a$ is —CH₃, —NH₂, or pyrimidinyl. Also included in this embodiment are compounds in which $R_3$ is piperazinonyl substituted with two methyl groups and —C(O)CH₃.

One embodiment provides a compound of Formula (I) or a salt thereof, wherein $Q_1$ is a bicyclic heteroaryl selected from indolyl, imidazopyridinyl, pyrrolopyridinyl, pyrazolopyridinyl and benzo[d]oxazolyl, wherein each of said bicyclic heteroaryls is substituted with zero to 1 $R_a$ and zero to 1 $R_b$; and X, $R_a$, $R_b$, $R_1$, $R_2$, $R_3$, $R_4$, $R_5$, and $R_6$ are defined in the first aspect. Included in this embodiment are compounds in which $R_a$ is —CH₃ or CHF₂. Also included in this embodiment are compounds in which $R_3$ is dimethyl morpholinonyl or piperazinonyl substituted with two methyl groups and —C(O)CH₃. This embodiment also includes compounds in which $R_2$ is H or F; and $R_4$ is H, F, or —OCH₃.

One embodiment provides a compound of Formula (I) or a salt thereof, wherein $R_4$ is —CHR$_c$OH, —S(O)$_{0-2}$(C$_{1-4}$ alkyl), or —S(O)$_{0-2}$(C$_{3-6}$ cycloalkyl); and X, $Q_1$, $R_1$, $R_2$, $R_3$, $R_5$, $R_6$, and $R_c$ are defined in the first aspect.

One embodiment provides a compound of Formula (I) or a salt thereof, wherein $R_4$ is —CHR$_c$OH; and X, $Q_1$, $R_1$, $R_2$, $R_3$, $R_5$, $R_6$, and $R_c$ are defined in the first aspect.

One embodiment provides a compound of Formula (I) or a salt thereof, wherein $R_4$ is —S(O)$_{0-2}$(C$_{1-4}$ alkyl) or —S(O)$_{0-2}$(C$_{3-6}$ cycloalkyl); and X, $Q_1$, $R_1$, $R_2$, $R_3$, $R_5$, and $R_6$ are defined in the first aspect.

One embodiment provides a compound of Formula (I) or a salt thereof, wherein $R_4$ is —S(O)$_{0-2}$(C$_{1-4}$ alkyl); and X, $Q_1$, $R_1$, $R_2$, $R_3$, $R_5$, and $R_6$ are defined in the first aspect.

One embodiment provides a compound of Formula (I) or a salt thereof, wherein $R_4$ is —S(O)$_{0-2}$(C$_{3-6}$ cycloalkyl); and X, $Q_1$, $R_1$, $R_2$, $R_3$, $R_5$, and $R_6$ are defined in the first aspect.

One embodiment provides a compound of any one of Formula (I), Formula (II-B), and Formula (II-C), or a salt thereof, wherein $R_a$ is —CH₂CHF₂, —CH₂CF₃, —CH(CH₃)₂, —CD(CD₃)₂, —CH(CF₃)₂, —CH(CH₂F)₂, —CH(CH₃)(CF₃), cyclopropyl, cyclobutyl, cyclohexyl, difluorocyclohexyl, oxetanyl, phenyl, fluorophenyl, or tetrahydropyranyl.

One embodiment provides a compound of any one of Formula (I), Formula (II-A), Formula (II-B), Formula (II-C), Formula (II-D), Formula (II-E), Formula (II-F), Formula (II-G), Formula (II-H), Formula (II-I), Formula (II-J), Formula (II-K), Formula (III-A), Formula (III-B), Formula (III-C), Formula (IV-A), Formula (IV-B), Formula (IV-C), Formula (IV-D), Formula (IV-E), and Formula (IV-F), or a salt thereof, wherein $R_a$ is tetrahydropyranyl, cyclopropyl, or cyclohexyl. Included in this embodiment are compounds in which $R_3$ is tetrahydropyranyl.

One embodiment provides a compound of any one of Formula (I), Formula (II-A), Formula (II-B), Formula (II-C), Formula (II-D), Formula (II-E), Formula (II-F), Formula (II-G), Formula (II-H), Formula (II-I), Formula (II-J), Formula (II-K), Formula (III-A), Formula (III-B), Formula (III-C), Formula (IV-A), Formula (IV-B), Formula (IV-C), Formula (IV-D), Formula (IV-E), and Formula (IV-F), or a salt thereof, wherein $R_a$ is —CH₃, —CH₂CF₃, or —CH(CH₃)₂.

One embodiment provides a compound of any one of Formula (I), Formula (II-A), Formula (II-B), Formula (II-C), Formula (II-D), Formula (II-E), Formula (II-F), Formula (II-G), Formula (II-H), Formula (II-I), Formula (II-J), Formula (II-K), Formula (III-A), Formula (III-B), Formula (III-C), Formula (IV-A), Formula (IV-B), Formula (IV-C), Formula (IV-D), Formula (IV-E), and Formula (IV-F), or a salt thereof, wherein $R_3$ is:

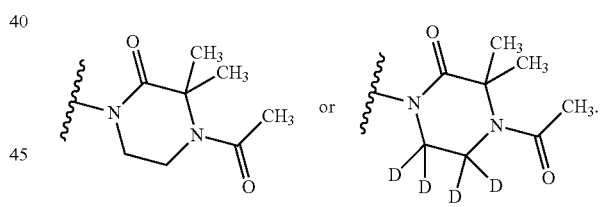

Included in this embodiment are compounds in which $Q_1$ is Cl, Br, I, —CN, or —CF₃.

One embodiment provides a compound of Formula (I) or a salt thereof, wherein $R_3$ is H; and $R_4$ is —CH₂NH₂; and X, $Q_1$, $R_1$, $R_2$, $R_5$, and $R_6$ are defined in the first aspect.

One embodiment provides a compound of Formula (I) or a salt thereof, wherein said compound is selected from Examples 1 to 618 and 622-663; or a salt thereof.

One embodiment provides a compound of Formula (I) or a salt thereof, wherein said compound is selected from 5-(4-amino-5-(1-cyclohexyl-1H-pyrazol-5-yl)pyrrolo [2,1-f][1,2,4]triazin-7-yl)-2-fluorobenzamide (1); 7-(3-(aminomethyl)phenyl)-5-(1-cyclohexyl-1H-pyrazol-5-yl)pyrrolo[2,1-f][1,2,4]triazin-4-amine (2); 5-(1-cyclohexyl-1H-pyrazol-5-yl)-7-(3-((dimethylamino)methyl)phenyl)pyrrolo[2,1-f][1,2,4]triazin-4-amine (3); (3-(4-amino-5-(1-(tetrahydro-2H-pyran-4-yl)-1H-pyrazol-5-yl)pyrrolo[2,1-f][1,2,4]triazin-7-yl)phenyl)(pyrrolidin-1-yl)methanone (4); N-(3-(4-amino-5-(1-cyclohexyl-1H-pyrazol-5-yl)pyrrolo[2,1-f]

[1,2,4]triazin-7-yl)benzyl)methanesulfonamide (5); 5-(1-cyclohexyl-1H-pyrazol-5-yl)-7-(3-(morpholinomethyl)phenyl)pyrrolo[2,1-f][1,2,4]triazin-4-amine (6); (5-(4-amino-5-(1-cyclohexyl-1H-pyrazol-5-yl)pyrrolo[2,1-f][1,2,4]triazin-7-yl)-2-fluorophenyl)methanol (7); N-(3-(4-amino-5-(1-cyclohexyl-1H-pyrazol-5-yl)pyrrolo[2,1-f][1,2,4]triazin-7-yl)phenyl)acetamide (8); N-(3-(4-amino-5-(1-cyclohexyl-1H-pyrazol-5-yl)pyrrolo[2,1-f][1,2,4]triazin-7-yl)phenyl)methanesulfonamide (9); 3-(4-amino-5-(1-cyclohexyl-1H-pyrazol-5-yl)pyrrolo[2,1-f][1,2,4]triazin-7-yl)-N-methylbenzamide (10); 3-(4-amino-5-(1-cyclohexyl-1H-pyrazol-5-yl)pyrrolo[2,1-f][1,2,4]triazin-7-yl)-N,N-dimethylbenzamide (11); 4-(4-amino-5-(1-cyclohexyl-1H-pyrazol-5-yl)pyrrolo[2,1-f][1,2,4]triazin-7-yl)-N,N-dimethylbenzamide (12); 3-(4-amino-5-(1-cyclohexyl-1H-pyrazol-5-yl)pyrrolo[2,1-f][1,2,4]triazin-7-yl)benzoic acid (13); 7-(3-(morpholinomethyl)phenyl)-5-(1-(tetrahydro-2H-pyran-4-yl)-1H-pyrazol-5-yl)pyrrolo [2,1-f][1,2,4]triazin-4-amine (14); (3-(4-amino-5-(1-(tetrahydro-2H-pyran-4-yl)-1H-pyrazol-5-yl)pyrrolo[2,1-f][1,2,4]triazin-7-yl)phenyl)(pyrrolidin-1-yl)methanone (15); 7-(3-((dimethylamino)methyl)phenyl)-5-(1-(tetrahydro-2H-pyran-4-yl)-1H-pyrazol-5-yl)pyrrolo[2,1-f][1,2,4]triazin-4-amine (16); 7-(3-(2-(dimethylamino)propan-2-yl)phenyl)-5-(1-(tetrahydro-2H-pyran-4-yl)-1H-pyrazol-5-yl)pyrrolo[2,1-f][1,2,4]triazin-4-amine (17); N-(3-(4-amino-5-(1-(tetrahydro-2H-pyran-4-yl)-1H-pyrazol-5-yl)pyrrolo[2,1-f][1,2,4]triazin-7-yl)benzyl)methanesulfonamide (18); (3-(4-amino-5-(1-cyclohexyl-1H-pyrazol-5-yl)pyrrolo[2,1-f][1,2,4]triazin-7-yl)phenyl)(morpholino) methanone (19); (3-(4-amino-5-(1-cyclohexyl-1H-pyrazol-5-yl)pyrrolo[2,1-f][1,2,4]triazin-7-yl)phenyl)(4-(2-hydroxypropan-2-yl)piperidin-1-yl) methanone 20); 2-(3-(4-amino-5-(1-cyclohexyl-1H-pyrazol-5-yl)pyrrolo[2,1-f][1,2,4]triazin-7-yl)benzamido) thiazole-5-carboxamide (21); N-(1-acetylpiperidin-4-yl)-3-(4-amino-5-(1-cyclohexyl-1H-pyrazol-5-yl)pyrrolo[2,1-f][1,2,4]triazin-7-yl)benzamide (22); 3-(4-amino-5-(1-cyclohexyl-1H-pyrazol-5-yl)pyrrolo[2,1-f][1,2,4]triazin-7-yl)-N-(1-methylpiperidin-3-yl)benzamide (23); 1-(4-(3-(4-amino-5-(1-cyclohexyl-1H-pyrazol-5-yl)pyrrolo[2,1-f][1,2,4]triazin-7-yl)benzoyl)piperazin-1-yl)-2-methylpropan-1-one (24); (S)-1-(3-(4-amino-5-(1-cyclohexyl-1H-pyrazol-5-yl)pyrrolo[2,1-f][1,2,4]triazin-7-yl)benzoyl) piperidine-2-carboxamide (25); 1-(3-(4-amino-5-(1-cyclohexyl-1H-pyrazol-5-yl)pyrrolo [2,1-f][1,2,4]triazin-7-yl)benzoyl)azetidine-3-carbonitrile (26); 4-(3-(4-amino-5-(1-cyclohexyl-1H-pyrazol-5-yl)pyrrolo[2,1-f][1,2,4]triazin-7-yl)benzoyl)-1-methylpiperazin-2-one (27); 3-(4-amino-5-(1-cyclohexyl-1H-pyrazol-5-yl)pyrrolo[2,1-f][1,2,4]triazin-7-yl)-N-(2-oxopiperidin-4-yl)benzamide (28); 1-(4-(3-(4-amino-5-(1-cyclohexyl-1H-pyrazol-5-yl)pyrrolo[2,1-f][1,2,4]triazin-7-yl)benzoyl)piperazin-1-yl)propan-1-one (29); N-(1-(3-(4-amino-5-(1-cyclohexyl-1H-pyrazol-5-yl)pyrrolo[2,1-f][1,2,4]triazin-7-yl)benzoyl)piperidin-4-yl)acetamide (30); (4-(3-(4-amino-5-(1-cyclohexyl-1H-pyrazol-5-yl)pyrrolo[2,1-f][1,2,4]triazin-7-yl)benzoyl)piperazin-1-yl)(tetrahydrofuran-2-yl)methanone (31); (3-(4-amino-5-(1-cyclohexyl-1H-pyrazol-5-yl)pyrrolo[2,1-f][1,2,4]triazin-7-yl)phenyl)(3-(dimethylamino)piperidin-1-yl)methanone (32); 1-(3-(4-amino-5-(1-cyclohexyl-1H-pyrazol-5-yl)pyrrolo[2,1-f][1,2,4]triazin-7-yl)benzoyl)piperidine-4-carboxamide (33); (3-(4-amino-5-(1-cyclohexyl-1H-pyrazol-5-yl)pyrrolo[2,1-f][1,2,4]triazin-7-yl)phenyl)(3-hydroxy-3-methylazetidin-1-yl)methanone (34); 1-(4-(3-(4-amino-5-(1-cyclohexyl-1H-pyrazol-5-yl)pyrrolo[2,1-f][1,2,4]triazin-7-yl)benzoyl)piperazin-1-yl)ethanone (35); 3-(4-amino-5-(1-cyclohexyl-1H-pyrazol-5-yl)pyrrolo[2,1-f][1,2,4]triazin-7-yl)-N-(3-carbamoylphenyl)benzamide (36); 3-(4-amino-5-(1-cyclohexyl-H-pyrazol-5-yl)pyrrolo[2,1-f][1,2,4]triazin-7-yl)-N-(tetrahydro-2H-pyran-4-yl)benzamide (37); 1-(3-(4-amino-5-(1-cyclohexyl-1H-pyrazol-5-yl)pyrrolo[2,1-f][1,2,4]triazin-7-yl)benzoyl)-N-methylpiperidine-4-carboxamide (38); (3-(4-amino-5-(1-cyclohexyl-1H-pyrazol-5-yl)pyrrolo[2,1-f][1,2,4]triazin-7-yl)phenyl)(4-hydroxy-4-(hydroxymethyl) piperidin-1-yl)methanone (39); 3-(4-amino-5-(1-cyclohexyl-1H-pyrazol-5-yl)pyrrolo[2,1-f][1,2,4]triazin-7-yl)-N-(3-cyclopropyl-1-methyl-1H-pyrazol-5-yl)benzamide (40); methyl 4-(3-(4-amino-5-(1-cyclohexyl-1H-pyrazol-5-yl)pyrrolo[2,1-f][1,2,4]triazin-7-yl)benzoyl)piperazine-1-carboxylate (41); 3-(4-amino-5-(1-cyclohexyl-1H-pyrazol-5-yl)pyrrolo[2,1-f][1,2,4]triazin-7-yl)-N-(2-oxopyrrolidin-3-yl)benzamide (42); 3-(4-amino-5-(1-cyclohexyl-1H-pyrazol-5-yl)pyrrolo[2,1-f][1,2,4]triazin-7-yl)-N-(2-methyl-1-(methylamino)-1-oxopropan-2-yl)benzamide (43); 3-(4-amino-5-(1-cyclohexyl-1H-pyrazol-5-yl)pyrrolo[2,1-f][1,2,4]triazin-7-yl)-N-(4-(hydroxymethyl)tetrahydro-2H-pyran-4-yl)benzamide (44); 3-(4-amino-5-(1-cyclohexyl-1H-pyrazol-5-yl)pyrrolo[2,1-f][1,2,4]triazin-7-yl)-N-cyclopropyl-N-(tetrahydro-2H-pyran-4-yl)benzamide (45); (3-(4-amino-5-(1-cyclohexyl-1H-pyrazol-5-yl)pyrrolo[2,1-f][1,2,4]triazin-7-yl)phenyl)(1,1-dioxidothiomorpholino) methanone (46); 3-(4-amino-5-(1-cyclohexyl-1H-pyrazol-5-yl)pyrrolo[2,1-f][1,2,4]triazin-7-yl)-N-(2H-tetrazol-5-yl)benzamide (47); 5-(1-(4,4-difluorocyclohexyl)-1H-pyrazol-5-yl)-7-(3-((dimethylamino)methyl)phenyl)pyrrolo[2,1-f][1,2,4]triazin-4-amine (48); 5-(1-(4,4-difluorocyclohexyl)-1H-pyrazol-5-yl)-7-(3-(2-(dimethylamino)propan-2-yl)phenyl)pyrrolo[2,1-f][1,2,4]triazin-4-amine (49); 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-fluoro-N-(tetrahydro-2H-pyran-4-yl)benzamide (50); 5-(4-amino-5-(1-(tetrahydro-2H-pyran-4-yl)-1H-pyrazol-5-yl)pyrrolo[2,1-f][1,2,4]triazin-7-yl)-N-((3,5-dimethylisoxazol-4-yl)methyl)-2-fluoro-N-methylbenzamide (51); 5-(4-amino-5-(1-(tetrahydro-2H-pyran-4-yl)-1H-pyrazol-5-yl)pyrrolo[2,1-f][1,2,4]triazin-7-yl)-N,N-dicyclopropyl-2-fluorobenzamide (52); (5-(4-amino-5-(1-(tetrahydro-2H-pyran-4-yl)-1H-pyrazol-5-yl)pyrrolo[2,1-f][1,2,4]triazin-7-yl)-2-fluorophenyl)((1R,5R)-8-oxa-3-azabicyclo[3.2.1]octan-3-yl)methanone (53); 5-(4-amino-5-(1-(tetrahydro-2H-pyran-4-yl)-1H-pyrazol-5-yl)pyrrolo[2,1-f][1,2,4]triazin-7-yl)-2-fluoro-N-methyl-N-((1-methylpyrrolidin-2-yl)methyl)benzamide (54); N-(1-acetylpiperidin-4-yl)-5-(4-amino-5-(1-(tetrahydro-2H-pyran-4-yl)-1H-pyrazol-5-yl)pyrrolo[2,1-f][1,2,4]triazin-7-yl)-N-cyclopropyl-2-fluorobenzamide (55); 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-methoxy-N-(tetrahydro-2H-pyran-4-yl)benzamide (56); 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-methyl-N-(tetrahydro-2H-pyran-4-yl) benzamide (57); 5-(4-amino-5-(1-(tetrahydro-2H-pyran-4-yl)-1H-pyrazol-5-yl)pyrrolo[2,1-f][1,2,4]triazin-7-yl)-2-chlorobenzoic acid (58); 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-(tetrahydro-2H-pyran-4-yl) benzamide (59); 5-(4-amino-5-(1-(tetrahydro-2H-pyran-4-yl)-1H-pyrazol-5-yl)pyrrolo[2,1-f][1,2,4]triazin-7-yl)-2-chloro-N-(2,2-difluoroethyl)-N-methylbenzamide (60); 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-((1-methyl-1H-pyrazol-4-yl)methyl)benzamide (61); 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-(thiazol-2-ylmethyl)benzamide (62); 5-(4-amino-5-(1-(tetrahydro-2H-pyran-4-yl)-1H-pyrazol-5-yl)pyrrolo[2,1-f][1,2,4]triazin-7-yl)-2-chloro-N-methyl-N-(tetrahydro-2H-pyran-4-yl)benzamide (63); N-(1-acetylpiperidin-4-yl)-5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropylbenzamide (64); 5-(4-amino-5-(1-(tetrahydro-2H-pyran-4-yl)-1H-pyrazol-5-yl)pyrrolo[2,1-f][1,2,4]triazin-7-yl)-2-chloro-N-(3-hydroxy-2,2-dimethylpropyl)-N-methylbenzamide (65); 5-(4-amino-5-(1-(tetrahydro-2H-pyran-4-yl)-1H-pyrazol-5-yl)pyrrolo[2,1-f][1,2,4]triazin-7-yl)-2-chloro-N,N-diethylbenzamide (66); 3-(4-amino-5-(1-methyl-1H-pyrrol-2-yl)pyrrolo[2,1-f][1,2,4]triazin-7-yl)-N-cyclopropyl-N-(tetrahydro-2H-pyran-4-yl)benzamide (67); 3-(4-amino-5-(1-phenyl-1H-pyrrol-2-yl)pyrrolo[2,1-f][1,2,4]triazin-7-yl)-N-cyclopropyl-N-(tetrahydro-2H-pyran-4-yl)benzamide (68); 3-(4-amino-5-(1-(tetrahydro-2H-pyran-4-yl)-1H-pyrazol-5-yl)pyrrolo[2,1-f][1,2,4]triazin-7-yl)-N,N-dicyclopropylbenzamide (69); 3-(4-amino-5-(1-(tetrahydro-2H-pyran-4-yl)-1H-pyrazol-5-yl)pyrrolo[2,1-f][1,2,4]triazin-7-yl)-N-cyclopropyl-N-((1-methyl-1H-pyrazol-5-yl)methyl)benzamide (70); 3-(4-amino-5-(1-(tetrahydro-2H-pyran-4-yl)-1H-pyrazol-5-yl)pyrrolo[2,1-f][1,2,4]triazin-7-yl)-N-(3-hydroxy-2,2-dimethylpropyl)-N-methylbenzamide (71); 3-(4-amino-5-(1-(tetrahydro-2H-pyran-4-yl)-1H-pyrazol-5-yl)pyrrolo[2,1-f][1,2,4]triazin-7-yl)-N-cyclopropyl-N-(thiazol-2-ylmethyl)benzamide (72); 3-(4-amino-5-(1-(tetrahydro-2H-pyran-4-yl)-1H-pyrazol-5-yl)pyrrolo[2,1-f][1,2,4]triazin-7-yl)-N-methyl-N-((1-methylpyrrolidin-2-yl)methyl)benzamide (73); 3-(4-amino-5-(1-(tetrahydro-2H-pyran-4-yl)-1H-pyrazol-5-yl)pyrrolo[2,1-f][1,2,4]triazin-7-yl)-N,N-diethylbenzamide (74); N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-N-cyclopropylbenzamide (75); 3-(4-amino-5-(1-(tetrahydro-2H-pyran-4-yl)-1H-pyrazol-5-yl)pyrrolo[2,1-f][1,2,4]triazin-7-yl)-N-((3,5-dimethylisoxazol-4-yl)methyl)-N-methylbenzamide (76); 3-(4-amino-5-(1-(tetrahydro-2H-pyran-4-yl)-1H-pyrazol-5-yl)pyrrolo[2,1-f][1,2,4]triazin-7-yl)-5-chloro-N-(3-hydroxy-2,2-dimethylpropyl)-N-methylbenzamide (77); 3-(4-amino-5-(1-(tetrahydro-2H-pyran-4-yl)-1H-pyrazol-5-yl)pyrrolo[2,1-f][1,2,4]triazin-7-yl)-5-chloro-N-cyclopropyl-N-(1-methylpiperidin-4-yl)benzamide (78); 3-(4-amino-5-(1-(tetrahydro-2H-pyran-4-yl)-1H-pyrazol-5-yl)pyrrolo[2,1-f][1,2,4]triazin-7-yl)-5-chloro-N-(tetrahydro-2H-pyran-4-yl)benzamide (79); N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-5-chloro-N-cyclopropylbenzamide (80); 3-(4-amino-5-(1-(tetrahydro-2H-pyran-4-yl)-1H-pyrazol-5-yl)pyrrolo[2,1-f][1,2,4]triazin-7-yl)-5-chloro-N-methyl-N-(oxetan-3-yl)benzamide (81); 3-(4-amino-5-(1-(tetrahydro-2H-pyran-4-yl)-1H-pyrazol-5-yl)pyrrolo [2,1-f][1,2,4]triazin-7-yl)-5-chloro-N-methyl-N-((1-methylpyrrolidin-2-yl)methyl)benzamide (82); 3-(4-amino-5-(1-(tetrahydro-2H-pyran-4-yl)-1H-pyrazol-5-yl)pyrrolo [2,1-f][1,2,4]triazin-7-yl)-5-fluoro-N-(3-hydroxy-2,2-dimethylpropyl)-N-methylbenzamide (83); 3-(4-amino-5-(1-(tetrahydro-2H-pyran-4-yl)-1H-pyrazol-5-yl)pyrrolo[2,1-f][1,2,4]triazin-7-yl)-N-cyclopropyl-5-fluoro-N-(thiazol-2-ylmethyl) benzamide (84); N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-N-cyclopropyl-5-fluorobenzamide (85); 3-(4-amino-5-(1-(tetrahydro-2H-pyran-4-yl)-1H-pyrazol-5-yl)pyrrolo[2,1-f][1,2,4]triazin-7-yl)-5-fluoro-N-methyl-N-((1-methylpyrrolidin-2-yl)methyl)benzamide (86); 5-(4-amino-5-(1-(tetrahydro-2H-pyran-4-yl)-1H-pyrazol-5-yl) pyrrolo[2,1-f][1,2,4]triazin-7-yl)-N-(2,2-difluoroethyl)-2-fluoro-N-methylbenzamide (87); 5-(4-amino-5-(1-(tetrahydro-2H-pyran-4-yl)-1H-pyrazol-5-yl)pyrrolo[2,1-f][1,2,4]triazin-7-yl)-2-fluoro-N-methyl-N-(tetrahydro-2H-pyran-4-yl)benzamide (88); 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-fluoro-N-(thiazol-2-ylmethyl)benzamide (89); 7-(3-(3-(dimethylamino)oxetan-3-yl)phenyl)-5-(1-(tetrahydro-2H-pyran-4-yl)-1H-pyrazol-5-yl)pyrrolo[2,1-f][1,2,4]triazin-4-amine (90); N-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)-2-methylpropane-2-sulfinamide (91); 1-[3-(3-{amino-5-[1-(oxan-4-yl)-1H-pyrazol-5-yl]pyrrolo[2,1-f][1,2,4]triazin-7-yl}phenyl)oxetan-3-yl]piperidin-4-one (92); 1-(3-(3-(4-amino-5-(1-(tetrahydro-2H-pyran-4-yl)-1H-1,2,3-triazol-5-yl)pyrrolo[2,1-f][1,2,4]triazin-7-yl)phenyl)oxetan-3-yl) piperidin-4-one (93); 1-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)pyrrolidin-3-ol (94); 1-[3-(3-{4-amino-5-[1-(oxan-4-yl)-1H-1,2,3-triazol-5-yl]pyrrolo[2,1-f][1,2,4]triazin-7-yl}phenyl)oxetan-3-yl]piperidin-4-ol (95); 4-(3-(3-(4-amino-5-(1-(tetrahydro-2H-pyran-4-yl)-1H-pyrazol-5-yl)pyrrolo[2,1-f][1,2,4]triazin-7-yl)phenyl) oxetan-3-yl)thiomorpholine 1,1-dioxide (96); 4-(3-(3-(4-amino-5-(1-(2,2,2-trifluoroethyl)-1H-pyrazol-5-yl)pyrrolo [2,1-f][1,2,4]triazin-7-yl)phenyl)oxetan-3-yl) thiomorpholine 1,1-dioxide (97); 7-(3-(3-morpholinooxetan-3-yl)phenyl)-5-(1-(tetrahydro-2H-pyran-4-yl)-1H-pyrazol-5-yl)pyrrolo[2,1-f][1,2,4]triazin-4-amine (98); 1-(3-(3-(4-amino-5-(1-(tetrahydro-2H-pyran-4-yl)-1H-pyrazol-5-yl)pyrrolo [2,1-f][1,2,4]triazin-7-yl)phenyl) oxetan-3-yl)pyrrolidin-3-ol (99); 1-(3-(3-(4-amino-5-(1-isopropyl-1H-1,2,3-triazol-5-yl)pyrrolo[2,1-f][1,2,4]triazin-7-yl)phenyl)oxetan-3-yl)pyrrolidin-3-ol (100); 1-(4-((3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)(methyl)amino) piperidin-1-yl)ethanone (101); N-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)-N,2-dimethylpropane-2-sulfinamide (102); N-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)pivalamide (103); (cis)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-methylcyclobutanecarboxamide (104); (trans)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-methylcyclobutanecarboxamide (105); (trans)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-(trifluoromethyl)cyclobutanecarboxamide (106); (cis)-1-(3-(4-amino-5-(1-cyclobutyl-1H-pyrazol-5-yl)pyrrolo[2,1-f][1,2,4]triazin-7-yl)phenyl)-3-hydroxy-N,3-dimethylcyclobutanecarboxamide (107); (cis)-1-(3-(4-amino-5-(1-isopropyl-1H-pyrazol-5-yl)pyrrolo[2,1-f][1,2,4]triazin-7-yl)phenyl)-3-hydroxy-N,3-dimethylcyclobutanecarboxamide (108); 1-(3-(4-amino-5-(1-cyclopropyl-1H-pyrazol-5-yl)pyrrolo[2,1-f][1,2,4]triazin-7-yl)phenyl)-N-(3,3-difluorocyclobutyl)-3,3-difluorocyclobutanecarboxamide (109); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropyl-3-methoxycyclobutanecarboxamide (110); (cis)-1-(3-(4-amino-5-(1-cyclopropyl-1H-pyrazol-5-yl)pyrrolo[2,1-f][1,2,4]triazin-7-yl)phenyl)-N-cyclopropyl-3-methoxycyclobutanecarboxamide (111); (cis)-1-(3-(4- amino-5-(1-(tetrahydro-2H-pyran-4-yl)-1H-pyrazol-5-yl)pyrrolo[2,1-f][1,2,4]triazin-7-yl)phenyl)-3-(difluoromethoxy)-N-methylcyclobutanecarboxamide (112); ((cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutyl) (morpholino)methanone (113); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-methyl-N-(oxetan-3-yl)cyclobutanecarboxamide (114); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-methylcyclobutanecarboxamide (115); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropyl-3-hydroxycyclobutanecarboxamide (116); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-isopropylcyclobutanecarboxamide (117); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-N-ethyl-3-hydroxycyclobutanecarboxamide (118); ((1s,3s)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutyl)(3-methoxypyrrolidin-1-yl)methanone (119); ((cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutyl)(3,3-difluoroazetidin-1-yl)methanone (120); (cis)-1-(3-(4-amino-5-(1-cyclopropyl-1H-pyrazol-5-yl)pyrrolo[2,1-f][1,2,4]triazin-7-yl)phenyl)-N-ethyl-3-hydroxycyclobutanecarboxamide (121); (cis)-1-(3-(4-amino-5-(1-cyclopropyl-1H-pyrazol-5-yl)pyrrolo[2,1-f][1,2,4]triazin-7-yl)phenyl)-3-hydroxy-N-isopropylcyclobutanecarboxamide (122); (cis)-1-(3-(4-amino-5-(1-cyclopropyl-1H-pyrazol-5-yl)pyrrolo[2,1-f][1,2,4]triazin-7-yl)phenyl)-3-hydroxy-N-(2,2,2-trifluoroethyl)cyclobutanecarboxamide (123); (cis)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxycyclobutanecarboxamide (124); 1-(3-(4-amino-5-(1-(tetrahydro-2H-pyran-4-yl)-1H-pyrazol-5-yl)pyrrolo[2,1-f][1,2,4]triazin-7-yl)phenyl)-N-(3,3-difluorocyclobutyl) cyclopropanecarboxamide (125); 1-(3-(4-amino-5-(1-(tetrahydro-2H-pyran-4-yl)-1H-pyrazol-5-yl)pyrrolo[2,1-f][1,2,4]triazin-7-yl)phenyl)-N-ethylcyclopropanecarboxamide (126); 1-(3-(4-amino-5-(1-(tetrahydro-2H-pyran-4-yl)-1H-pyrazol-5-yl)pyrrolo[2,1-f][1,2,4]triazin-7-yl)phenyl)-N-isopropylcyclopropanecarboxamide (127); 1-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropylcyclopropanecarboxamide (128); 1-(3-(4-amino-5-(1-cyclopropyl-1H-pyrazol-5-yl)pyrrolo[2,1-f][1,2,4]triazin-7-yl)phenyl)-N-(oxetan-3-yl)cyclopropanecarboxamide (129); 1-(3-(4-amino-5-(1-cyclopropyl-1H-pyrazol-5-yl)pyrrolo[2,1-f][1,2,4]triazin-7-yl)phenyl)-N-ethylcyclopropanecarboxamide (130); 1-(3-(4-amino-5-(1-cyclopropyl-1H-pyrazol-5-yl)pyrrolo[2,1-f][1,2,4]triazin-7-yl)phenyl)-N-isopropylcyclopropanecarboxamide (131); 4-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethyloxazolidin-2-one (132); (3R,5S)-5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyrrolidin-3-ol (133); (3S,5R)-5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyrrolidin-3-ol (134); (3R,5R)-5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyrrolidin-3-ol (135); 1-((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)ethanone (136); 1-((2S,4S)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)ethanone (137); 1-((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)-2,2-dimethylpropan-1-one (138); 1-((2S,4R)-2-(3-(4-amino-5-(1-cyclopropyl-1H-pyrazol-5-yl)pyrrolo[2,1-f][1,2,4]triazin-7-yl)phenyl)-4-hydroxypyrrolidin-1-yl)ethanone (139); (2S,4R)-tert-butyl 2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidine-1-carboxylate (140); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(cyclopropyl)methanone (141); 1-((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)-2-methylpropan-1-one (142); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(2,2-difluorocyclopropyl) methanone (143); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(tetrahydro-2H-pyran-4-yl)methanone (144); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(phenyl)methanone (145); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(4-methylthiazol-5-yl)methanone (146); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(oxazol-4-yl)methanone (147); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(thiazol-5-yl)methanone (148); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridin-4-yl)methanone (149); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridin-3-yl)methanone (150); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(o-tolyl)methanone (151); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(1H-pyrazol-3-yl)methanone (152); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(3-fluorophenyl)methanone (153); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(1-methyl-1H-pyrazol-5-yl) methanone (154); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridazin-4-yl)methanone (155); (S)-3-(3-(4-amino-5-(1-(tetrahydro-2H-pyran-4-yl)-1H-pyrazol-5-yl)pyrrolo[2,1-f][1,2,4]triazin-7-yl)benzyl)-4-(tert-butyl)oxazolidin-2-one (156); 3-(3-(4-amino-5-(1-(tetrahydro-2H-pyran-4-yl)-1H-pyrazol-5-yl)pyrrolo[2,1-f][1,2,4]triazin-7-yl)benzyl)-1,3-oxazinan-2-one (157); (S)-3-(3-(4-amino-5-(1-(tetrahydro-2H-pyran-4-yl)-1H-pyrazol-5-yl)pyrrolo[2,1-f][1,2,4]triazin-7-yl)benzyl)-4-isopropyloxazolidin-2-one (158); 1-(3-(4-amino-5-(1-(tetrahydro-2H-pyran-4-yl)-1H-pyrazol-5-yl)pyrrolo[2,1-f][1,2,4]triazin-7-yl)benzyl)pyrrolidin-2-one (159); N-(3-(4-amino-5-(1-(tetrahydro-2H-pyran-4-yl)-1H-pyrazol-5-yl)pyrrolo[2,1-f][1,2,4]triazin-7-yl)benzyl)-N-(tetrahydro-2H-pyran-4-yl)acetamide (160); 1-(3-(4-amino-5-(1-(tetrahydro-2H-pyran-4-yl)-1H-pyrazol-5-yl)pyrrolo[2,1-f][1,2,4]triazin-7-yl)benzyl)-3-methylpyrrolidin-2-one (161); 3-(3-(4-amino-5-(1-(tetrahydro-2H-pyran-4-yl)-1H-pyrazol-5-yl)pyrrolo[2,1-f][1,2,4]triazin-7-yl)benzyl)-5,5-dimethyloxazolidin-2-one (162); 3-(2-(3-(4-amino-5-(1-(tetrahydro-2H-pyran-4-yl)-1H-pyrazol-5-yl)pyrrolo[2,1-f][1,2,4]triazin-7-yl)phenyl)propan-2-yl)oxazolidin-2-one (163); 7-(3-((1S,5S)-8-oxa-3-azabicyclo[3.2.1]octan-3-ylmethyl)phenyl)-5-(1-(tetrahydro-2H-pyran-4-yl)-1H-pyrazol-5-yl)pyrrolo[2,1-f][1,2,4]triazin-4-amine (164); N-(3-(4-amino-5-(1-(tetrahydro-2H-pyran-4-yl)-1H-pyrazol-5-yl)pyrrolo[2,1-f][1,2,4]triazin-7-yl)benzyl)-4-methoxybenzamide (165); N-(2-(3-(4-amino-5-(1-(tetrahydro-2H-pyran-4-yl)-1H-pyrazol-5-yl)pyrrolo[2,1-f][1,2,4]triazin-7-yl)phenyl)propan-2-yl)-3-hydroxy-3-methylbutanamide (166); 1-(4-(3-(4-amino-5-(1-(tetrahydro-2H-pyran-4-yl)-1H-pyrazol-5-yl)pyrrolo[2,1-f][1,2,4]triazin-7-yl)benzyl)piperazin-1-yl)ethanone (167); 4-(3-(4-amino-5-(1-(tetrahydro-2H-pyran-4-yl)-1H-pyrazol-5-yl)pyrrolo[2,1-f][1,2,4]triazin-7-yl)benzyl)-1-methylpiperazin-2-one (168); 7-(3-((methyl(tetrahydro-2H-pyran-4-yl)amino)methyl)phenyl)-5-(1-(tetrahydro-2H-pyran-4-yl)-1H-pyrazol-5-yl)pyrrolo[2,1-f][1,2,4]triazin-4-amine (169); 7-(3-(((2-methoxyethyl)(methyl)amino)methyl)phenyl)-5-(1-(tetrahydro-2H-pyran-4-yl)-1H-pyrazol-5-yl)pyrrolo[2,1-f][1,2,4]triazin-4-amine (170); (3R)-1-(1-(3-(4-amino-5-(1-(tetrahydro-2H-pyran-4-yl)-1H-pyrazol-5-yl)pyrrolo [2,1-f][1,2,4]triazin-7-yl)phenyl)ethyl)pyrrolidin-3-ol (171); 7-(3-(1-(3,3-dimethylmorpholino)ethyl)phenyl)-5-(1-(tetrahydro-2H-pyran-4-yl)-1H-pyrazol-5-yl)pyrrolo[2,1-f][1,2,4]triazin-4-amine (172); 1-(4-(1-(3-(4-amino-5-(1-(tetrahydro-2H-pyran-4-yl)-1H-pyrazol-5-yl)pyrrolo[2,1-f][1,2,4]triazin-7-yl)phenyl)ethyl)piperazin-1-yl)ethanone (173); 7-(3-(1-(3-methoxypyrrolidin-1-yl)ethyl)phenyl)-5-(1-(tetrahydro-2H-pyran-4-yl)-1H-pyrazol-5-yl)pyrrolo[2,1-f][1,2,4]triazin-4-amine (174); 7-(3-(1-morpholinoethyl)phenyl)-5-(1-(tetrahydro-2H-pyran-4-yl)-1H-pyrazol-5-yl)pyrrolo[2,1-f][1,2,4]triazin-4-amine (175); 7-(3-(1-((cis)-2,6-dimethylmorpholino)ethyl)phenyl)-5-(1-(tetrahydro-2H-pyran-4-yl)-1H-pyrazol-5-yl)pyrrolo[2,1-f][1,2,4]triazin-4-amine (176); 7-(3-(1-(methyl(tetrahydro-2H-pyran-4-yl)amino)ethyl)phenyl)-5-(1-(tetrahydro-2H-pyran-4-yl)-1H-pyrazol-5-yl)pyrrolo[2,1-f][1,2,4]triazin-4-amine (177); 7-(3-(1-(3,3-dimethylazetidin-1-yl)ethyl)phenyl)-5-(1-(tetrahydro-2H-pyran-4-yl)-1H-pyrazol-5-yl)pyrrolo[2,1-f][1,2,4]triazin-4-amine (178); 1-(1-(3-(4-amino-5-(1-(tetrahydro-2H-pyran-4-yl)-1H-pyrazol-5-yl)pyrrolo[2,1-f][1,2,4]triazin-7-yl)phenyl)ethyl)-3-methylazetidin-3-ol (179); 7-(3-(2-morpholinopropan-2-yl)phenyl)-5-(1-(tetrahydro-2H-pyran-4-yl)-1H-pyrazol-5-yl)pyrrolo[2,1-f][1,2,4]triazin-4-amine (180); 5-(1-(tetrahydro-2H-pyran-4-yl)-1H-pyrazol-5-yl)-7-(3-(2,2,2-trifluoro-1-morpholinoethyl)phenyl)pyrrolo [2,1-f][1,2,4]triazin-4-amine (181); 7-(3-(2-(dimethylamino)propan-2-yl)phenyl)-5-(1-(tetrahydro-2H-pyran-4-yl)-1H-1,2,3-triazol-5-yl)pyrrolo[2,1-f][1,2,4]triazin-4-amine (182); 7-(3-(2-(diethylamino)propan-2-yl)phenyl)-5-(1-(tetrahydro-2H-pyran-4-yl)-1H-1,2,3-triazol-5-yl)pyrrolo[2,1-f][1,2,4]triazin-4-amine (183); 1-((2S,4R)-2-(3-(4-amino-5-(1-isopropyl-1H-1,2,3-triazol-5-yl)pyrrolo[2,1-f][1,2,4]triazin-7-yl)phenyl)-4-hydroxypyrrolidin-1-yl)ethanone (184); 7-(3-(piperidin-4-yl)phenyl)-5-(1-(tetrahydro-2H-pyran-4-yl)-1H-1,2,3-triazol-5-yl)pyrrolo[2,1-f][1,2,4]triazin-4-amine (185); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-1-yl)ethanone (186); 7-(3-(1-methylpiperidin-4-yl)phenyl)-5-(1-(tetrahydro-2H-pyran-4-yl)-1H-1,2,3-triazol-5-yl)pyrrolo[2,1-f][1,2,4]triazin-4-amine (187); 5-(1-isopropyl-1H-1,2,3-triazol-5-yl)-7-(3-(1-methylpiperidin-4-yl)phenyl) pyrrolo[2,1-f][1,2,4]triazin-4-amine (188); 4-(3-(4-amino-5-(1-(tetrahydro-2H-pyran-4-yl)-1H-1,2,3-triazol-5-yl)pyrrolo[2,1-f][1,2,4]triazin-7-yl)benzyl)morpholin-3-one (189); 7-(3-((methyl(tetrahydro-2H-pyran-4-yl)amino)methyl)phenyl)-5-(1-(tetrahydro-2H-pyran-4-yl)-1H-1,2,3-triazol-5-yl)pyrrolo[2,1-f][1,2,4]triazin-4-amine (190); 7-(3-((methyl(oxetan-3-yl)amino)methyl)phenyl)-5-(1-(tetrahydro-2H-pyran-4-yl)-1H-pyrazol-5-yl)pyrrolo[2,1-f][1,2,4]triazin-4-amine (191); 7-(3-((cyclopropyl(1-(methylsulfonyl)azetidin-3-yl)amino)methyl)phenyl)-5-(1-(tetrahydro-2H-pyran-4-yl)-1H-1,2,3-triazol-5-yl)pyrrolo[2,1-f][1,2,4]triazin-4-amine (192); 7-(3-((bis(tetrahydro-2H-pyran-4-yl)amino)methyl)phenyl)-5-(1-(tetrahydro-2H-pyran-4-yl)-1H-pyrazol-5-yl)pyrrolo[2,1-f][1,2,4]triazin-4-amine (193); 7-(3-(morpholinomethyl)phenyl)-5-(1-(tetrahydro-2H-pyran-4-yl)-1H-1,2,3-triazol-5-yl)pyrrolo[2,1-f][1,2,4]triazin-4-amine (194); (R)-1-(3-(4-amino-5-(1-isopropyl-1H-1,2,3-triazol-5-yl)pyrrolo[2,1-f][1,2,4]triazin-7-yl)benzyl)pyrrolidin-3-ol (195); 4-(3-(4-amino-5-(1-(tetrahydro-2H-pyran-4-yl)-1H-pyrazol-5-yl)pyrrolo[2,1-f][1,2,4]triazin-7-yl)phenoxy)tetrahydro-2H-thiopyran 1,1-dioxide (196); 5-(1-(tetrahydro-2H-pyran-4-yl)-1H-pyrazol-5-yl)-7-(3-((tetrahydro-2H-pyran-4-yl)oxy)phenyl)pyrrolo[2,1-f][1,2,4]triazin-4-amine (197); 7-(1-(2,6-dimethyltetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine (198); 7-(3-(piperidin-4-yloxy) phenyl)-5-(1-(tetrahydro-2H-pyran-4-yl)-1H-1,2,3-triazol-5-yl)pyrrolo[2,1-f][1,2,4]triazin-4-amine (199); 7-(3-(piperidin-4-yloxy)phenyl)-5-(1-(tetrahydro-2H-pyran-4-yl)-1H-pyrazol-5-yl)pyrrolo[2,1-f][1,2,4]triazin-4-amine (200); 7-(3-((1-methylpiperidin-4-yl)oxy)phenyl)-5-(1-(tetrahydro-2H-pyran-4-yl)-1H-1,2,3-triazol-5-yl)pyrrolo[2,1-f][1,2,4]triazin-4-amine (201); 7-(3-((1-methylpiperidin-4-yl)oxy)phenyl)-5-(1-(tetrahydro-2H-pyran-4-yl)-1H-pyrazol-5-yl)pyrrolo[2,1-f][1,2,4]triazin-4-amine (202); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenoxy)piperidin-1-yl)-2-methylpropan-1-one (203); 1-(4-(3-(4-amino-5-(1-isopropyl-1H-1,2,3-triazol-5-yl)pyrrolo[2,1-f][1,2,4]triazin-7-yl)phenoxy) piperidin-1-yl)-2-methylpropan-1-one (204); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenoxy)piperidin-1-yl)ethanone (205); 1-(4-(3-(4-amino-5-(1-isopropyl-1H-1,2,3-triazol-5-yl)pyrrolo[2,1-f][1,2,4]triazin-7-yl)phenoxy)piperidin-1-yl)ethanone (206); 5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyridin-2(1H)-one (207); 5-(3-(4-amino-5-(1-isopropyl-1H-1,2,3-triazol-5-yl)pyrrolo[2,1-f][1,2,4]triazin-7-yl)phenyl)-1-methylpyridin-2(1H)-one (208); 5-(3-(4-amino-5-(1-cyclopropyl-1H-pyrazol-5-yl)pyrrolo[2,1-f][1,2,4]triazin-7-yl)phenyl)-1-methylpyridin-2(1H)-one (209); 5-(3-(4-amino-5-(1-(tetrahydro-2H-pyran-4-yl)-1H-pyrazol-5-yl)pyrrolo[2,1-f][1,2,4]triazin-7-yl)phenyl)-1,4-dimethylpyridin-2 (1H)-one (210); 4-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyridin-2(1H)-one (211);

4-(3-(4-amino-5-(1-isopropyl-1H-1,2,3-triazol-5-yl)pyrrolo[2,1-f][1,2,4]triazin-7-yl)phenyl)-1-methylpyridin-2(1H)-one (212); 4-(3-(4-amino-5-(1-(tetrahydro-2H-pyran-4-yl)-1H-1,2,3-triazol-5-yl)pyrrolo[2,1-f][1,2,4]triazin-7-yl)phenyl)-1-methylpyridin-2(1H)-one (213); 4-(3-(4-amino-5-(1-isopropyl-1H-1,2,3-triazol-5-yl)pyrrolo[2,1-f][1,2,4]triazin-7-yl)phenyl)thiomorpholine 1,1-dioxide (214); 7-(3-morpholinophenyl)-5-(1-(tetrahydro-2H-pyran-4-yl)-1H-1,2,3-triazol-5-yl)pyrrolo[2,1-f][1,2,4]triazin-4-amine, TFA (215); 4-(3-(4-amino-5-(1-cyclohexyl-1H-1,2,3-triazol-5-yl)pyrrolo[2,1-f][1,2,4]triazin-7-yl)phenyl)thiomorpholine 1,1-dioxide (216); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-fluorophenyl)-2,6-dimethylpiperazin-1-yl)ethanone (217); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-fluorophenyl)-2,6-dimethylpiperazin-1-yl)ethanone (218); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-chlorophenyl)-2,6-dimethylpiperazin-1-yl)ethanone (219); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methylphenyl)-2,6-dimethylpiperazin-1-yl)ethanone (220); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-methylphenyl)-2,6-dimethylpiperazin-1-yl)ethanone (221); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methoxyphenyl)-2,6-dimethylpiperazin-1-yl)ethanone (222); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-methoxyphenyl)-2,6-dimethylpiperazin-1-yl)ethanone (223); 1-(4-(3-(4-amino-5-(1-isopropyl-1H-1,2,3-triazol-5-yl)pyrrolo[2,1-f][1,2,4]triazin-7-yl)phenyl)-3,5-dimethylpiperazin-1-yl)ethanone (224); 1-((cis)-4-(3-(4-amino-5-(1-(tetrahydro-2H-pyran-4-yl)-1H-pyrazol-5-yl)pyrrolo [2,1-f][1,2,4]triazin-7-yl)-5-fluorophenyl)-3,5-dimethylpiperazin-1-yl)ethanone (225); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-fluorophenyl)-3,5-dimethylpiperazin-1-yl)ethanone (226); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methylphenyl)-3,5-dimethylpiperazin-1-yl)ethanone (227); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-methylphenyl)-3,5-dimethylpiperazin-1-yl)ethanone (228); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methoxyphenyl)-3,5-dimethylpiperazin-1-yl)ethanone (229); 1-(4-(3-(4-amino-5-(1-isopropyl-1H-1,2,3-triazol-5-yl)pyrrolo[2,1-f][1,2,4]triazin-7-yl)phenyl)-3,3-dimethylpiperazin-1-yl)ethanone (230); 1-(4-(3-(4-amino-5-(thiazol-5-yl)pyrrolo[2,1-f][1,2,4]triazin-7-yl)phenoxy)piperidin-1-yl)ethanone (231); 3-(4-amino-5-(1-phenyl-1H-pyrrol-2-yl)pyrrolo[2,1-f][1,2,4]triazin-7-yl)-N-cyclopropyl-N-(tetrahydro-2H-pyran-4-yl)benzamide (232); N-(1-acetylpiperidin-4-yl)-3-(4-amino-5-(thiazol-5-yl)pyrrolo[2,1-f][1,2,4]triazin-7-yl)-N-cyclopropylbenzamide (233); 3-(4-amino-5-(1-(tetrahydro-2H-pyran-4-yl)-1H-1,2,3-triazol-5-yl)pyrrolo[2,1-f][1,2,4]triazin-7-yl)-N-cyclopropyl-N-(tetrahydro-2H-pyran-4-yl)benzamide (234); (3-(4-amino-5-(1-isopropyl-1H-1,2,3-triazol-5-yl)pyrrolo[2,1-f][1,2,4]triazin-7-yl)phenyl)(pyrrolidin-1-yl)methanone (235); (3-(4-amino-5-(1-(tetrahydro-2H-pyran-4-yl)-1H-1,2,3-triazol-5-yl)pyrrolo[2,1-f][1,2,4]triazin-7-yl)phenyl)(pyrrolidin-1-yl)methanone (236); 3-(4-amino-5-(1-(tetrahydro-2H-pyran-4-yl)-1H-1,2,3-triazol-5-yl)pyrrolo[2,1-f][1,2,4]triazin-7-yl)-N,N-dicyclopropylbenzamide (237); 2-(3-(4-amino-5-(1-(tetrahydro-2H-pyran-4-yl)-1H-1,2,3-triazol-5-yl)pyrrolo[2,1-f][1,2,4]triazin-7-yl)phenyl)-1-(1,1-dioxidothiomorpholino)ethanone (238); 2-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropylcyclopropane carboxamide (239); 1-(3-(4-amino-5-(1-(tetrahydro-2H-pyran-4-yl)-1H-pyrazol-5-yl)pyrrolo[2,1-f][1,2,4]triazin-7-yl)phenyl)-4-methylpiperidin-4-ol (240); 7-(3-morpholinophenyl)-5-(1-(tetrahydro-2H-pyran-4-yl)-1H-pyrazol-5-yl)pyrrolo[2,1-f][1,2,4]triazin-4-amine (241); 7-(3-(4-methoxypiperidin-1-yl)phenyl)-5-(1-(tetrahydro-2H-pyran-4-yl)-1H-pyrazol-5-yl)pyrrolo [2,1-f][1,2,4]triazin-4-amine (242); 4-(3-(4-amino-5-(1-(tetrahydro-2H-pyran-4-yl)-1H-pyrazol-5-yl)pyrrolo[2,1-f][1,2,4]triazin-7-yl)phenyl)thiomorpholine 1,1-dioxide (243); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(trifluoromethyl)piperazin-1-yl)ethanone (244); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(trifluoromethyl)piperazin-1-yl)ethanone (245); 1-((2S,6R)-4-(3-(4-amino-5-(1-(tetrahydro-2H-pyran-4-yl)-1H-pyrazol-5-yl)pyrrolo[2,1-f][1,2,4]triazin-7-yl)phenyl)-2,6-dimethylpiperazin-1-yl)ethanone (246); 1-((2S,6R)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,6-dimethylpiperazin-1-yl)ethanone (247); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2-cyclopropyl-6-isopropylpiperazin-1-yl)ethanone (248); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2,6-dicyclopropylpiperazin-1-yl)ethanone (249); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2-cyclopropyl-6-isopropylpiperazin-1-yl)ethanone (250); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2-phenylpiperazin-1-yl)ethanone (251); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2-(pyridin-3-yl)piperazin-1-yl)ethanone (252); 1-(4-(3-(4-amino-5-(1-(tetrahydro-2H-pyran-4-yl)-1H-1,2,3-triazol-5-yl)pyrrolo [2,1-f][1,2,4]triazin-7-yl)phenyl)-2-(pyridin-3-yl)piperazin-1-yl)ethanone (253); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(2-fluorophenyl)piperazin-1-yl)ethanone (254); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(2-fluorophenyl)piperazin-1-yl)ethanone (255); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(pyridin-3-yl)piperazin-1-yl)ethanone (256); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(pyridin-3-yl)piperazin-1-yl)ethanone (257); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2,3-dimethylpiperazin-1-yl)ethanone (258); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,3-dimethylpiperazin-1-yl)ethanone (259); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(4-chlorophenyl)piperazin-1-yl)ethanone (260); N-(1-(3-(4-amino-5-(1-(tetrahydro-2H-pyran-4-yl)-1H-pyrazol-5-yl)pyrrolo[2,1-f][1,2,4]triazin-7-yl)phenyl)-4-methylpiperidin-4-yl)

acetamide (261); 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)ethanone (262); 5-(1-(tetrahydro-2H-pyran-4-yl)-1H-pyrazol-5-yl)-7-(3-((cis)-2,4,6-trimethylpiperazin-1-yl)phenyl)pyrrolo[2,1-f][1,2,4]triazin-4-amine (263); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)ethanone (264); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)-2-hydroxyethanone (265); (cis)-methyl 4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazine-1-carboxylate (266); 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)-2-hydroxyethanone (267); 1-((cis)-4-(3-(4-amino-5-(1-isopropyl-1H-pyrazol-5-yl)pyrrolo[2,1-f][1,2,4]triazin-7-yl)phenyl)-3,5-dimethylpiperazin-1-yl)ethanone (268); 7-(3-((cis)-2,6-dimethyl-4-(methylsulfonyl) piperazin-1-yl)phenyl)-5-(1-(tetrahydro-2H-pyran-4-yl)-1H-pyrazol-5-yl)pyrrolo[2,1-f][1,2,4]triazin-4-amine (269); (cis)-methyl 4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazine-1-carboxylate (270); 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)-2-hydroxy-2-methylpropan-1-one (271); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)-2-hydroxy-2-methyl-propan-1-one (272); 1-((cis)-4-(3-(4-amino-5-(1-(2,2,2-trifluoroethyl)-1H-pyrazol-5-yl)pyrrolo[2,1-f][1,2,4]triazin-7-yl)phenyl)-3,5-dimethylpiperazin-1-yl)ethanone (273); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)ethanone (274); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,3-dimethylpiperazin-1-yl)ethanone (275); methyl 4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazine-1-carboxylate (276); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)-2-hydroxyethanone (277); 7-(3-(2,2-dimethyl-4-(methylsulfonyl)piperazin-1-yl)phenyl)-5-(1-(tetrahydro-2H-pyran-4-yl)-1H-pyrazol-5-yl)pyrrolo[2,1-f][1,2,4]triazin-4-amine (278); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-4,7-diazaspiro[2.5]octan-7-yl)ethanone (279); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-4,7-diazaspiro[2.5]octan-7-yl)ethanone (280); 1-(4-(3-(4-amino-5-(1-isopropyl-1H-1,2,3-triazol-5-yl)pyrrolo[2,1-f][1,2,4]triazin-7-yl)phenyl)-4,7-diazaspiro[2.5]octan-7-yl)ethanone (281); (S)-1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)-2-hydroxypropan-1-one (282); 1-(4-(3-(4-amino-5-(1-cyclohexyl-1H-1,2,3-triazol-5-yl)pyrrolo[2,1-f][1,2,4]triazin-7-yl)phenyl)-3,3-dimethylpiperazin-1-yl)-2-hydroxyethanone (283); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,4-dihydroquinoxalin-1(2H)-yl)ethanone (284); 7-(3-(piperidin-4-yl)phenyl)-5-(1-(tetrahydro-2H-pyran-4-yl)-1H-pyrazol-5-yl)pyrrolo[2,1-f][1,2,4]triazin-4-amine (285); 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperidin-1-yl)ethanone (286); 7-(3-(1-(oxetan-3-yl)piperidin-4-yl)phenyl)-5-(1-(tetrahydro-2H-pyran-4-yl)-1H-pyrazol-5-yl)pyrrolo[2,1-f][1,2,4]triazin-4-amine (287); 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)ethanone (288); 7-(3-(4-(oxetan-3-yl)piperazin-1-yl)phenyl)-5-(1-(tetrahydro-2H-pyran-4-yl)-1H-pyrazol-5-yl)pyrrolo[2,1-f][1,2,4]triazin-4-amine (289); 7-(3-(4-methylpiperazin-1-yl)phenyl)-5-(1-(tetrahydro-2H-pyran-4-yl)-1H-pyrazol-5-yl)pyrrolo[2,1-f][1,2,4]triazin-4-amine (290); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-phenylpiperazin-1-yl)ethanone (291); methyl 4-(3-(4-amino-5-(1-(tetrahydro-2H-pyran-4-yl)-1H-pyrazol-5-yl)pyrrolo[2,1-f][1,2,4]triazin-7-yl)phenyl)piperazine-1-carboxylate (292); methyl 4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperazine-1-carboxylate (293); 7-(3-(4-(methylsulfonyl)piperazin-1-yl)phenyl)-5-(1-(tetrahydro-2H-pyran-4-yl)-1H-pyrazol-5-yl)pyrrolo[2,1-f][1,2,4]triazin-4-amine (294); 7-(3-(4-(methylsulfonyl)piperazin-1-yl)phenyl)-5-(1-(tetrahydro-2H-pyran-4-yl)-1H-1,2,3-triazol-5-yl)pyrrolo[2,1-f][1,2,4]triazin-4-amine (295); 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)-2-methylpropan-1-one (296); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperazin-1-yl)-2-methylpropan-1-one (297); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperazin-1-yl)ethanone (298); (4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)(phenyl) methanone (299); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-phenylpiperazin-1-yl) ethanone (300); N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methylacetamide (301); 1-(4-(3-(4-amino-5-(1-isopropyl-1H-pyrazol-5-yl)pyrrolo[2,1-f][1,2,4]triazin-7-yl)phenyl)piperazin-1-yl)ethanone (302); 1-(4-(3-(4-amino-5-(1-cyclopropyl-1H-pyrazol-5-yl)pyrrolo[2,1-f][1,2,4]triazin-7-yl)phenyl)piperazin-1-yl)ethanone (303); 3-(3-(4-amino-5-(1-(tetrahydro-2H-pyran-4-yl)-1H-pyrazol-5-yl)pyrrolo[2,1-f][1,2,4]triazin-7-yl)phenyl)-1,3-oxazinan-2-one (304); 3-(3-(4-amino-5-(1-(tetrahydro-2H-pyran-4-yl)-1H-1,2,3-triazol-5-yl)pyrrolo[2,1-f][1,2,4]triazin-7-yl)phenyl)-1,3-oxazinan-2-one (305); 4-(3-(4-amino-5-(1H-indol-2-yl)pyrrolo[2,1-f][1,2,4]triazin-7-yl)phenyl)-2,2-dimethylmorpholin-3-one (306); 4-(3-(4-amino-5-(1-(tetrahydro-2H-pyran-4-yl)-1H-pyrazol-5-yl)pyrrolo[2,1-f][1,2,4]triazin-7-yl)phenyl)-2,2-dimethylmorpholin-3-one (307); 4-(3-(4-amino-5-(1-(4,4-difluorocyclohexyl)-1H-pyrazol-5-yl)pyrrolo[2,1-f][1,2,4]triazin-7-yl)phenyl)-2,2-dimethylmorpholin-3-one (308); 4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,2-dimethylmorpholin-3-one (309); 7-(3-(2-(methyl (tetrahydro-2H-pyran-4-yl)amino)propan-2-yl)phenyl)-5-(1-(tetrahydro-2H-pyran-4-yl)-1H-pyrazol-5-yl)pyrrolo[2,1-f][1,2,4]triazin-4-amine (310); 7-(3-(2-(methyl(tetrahydro-2H-pyran-4-yl)amino)propan-2-yl)phenyl)-5-(1-(tetrahydro-2H-pyran-4-yl)-1H-1,2,3-triazol-5-yl)pyrrolo[2,1-f][1,2,4]triazin-4-amine (311); 7-(3-(2-(pyrrolidin-1-yl)

propan-2-yl)phenyl)-5-(1-(tetrahydro-2H-pyran-4-yl)-1H-pyrazol-5-yl)pyrrolo[2,1-f][1,2,4]triazin-4-amine (312); 7-(3-(2-(pyrrolidin-1-yl)propan-2-yl)phenyl)-5-(1-(tetrahydro-2H-pyran-4-yl)-1H-1,2,3-triazol-5-yl)pyrrolo[2,1-f][1,2,4]triazin-4-amine (313); 1-(2-(3-(4-amino-5-(1-(tetrahydro-2H-pyran-4-yl)-1H-pyrazol-5-yl)pyrrolo[2,1-f][1,2,4]triazin-7-yl)phenyl)propan-2-yl)-1-methylpyrrolidin-1-ium (314); 4-(3-(4-amino-5-(1-(tetrahydro-2H-pyran-4-yl)-1H-pyrazol-5-yl)pyrrolo[2,1-f][1,2,4]triazin-7-yl)phenyl)-1-methylpiperidin-4-ol (315); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypiperidin-1-yl)ethanone (316); 4-(3-(4-amino-5-(1-(tetrahydro-2H-pyran-4-yl)-1H-1,2,3-triazol-5-yl)pyrrolo[2,1-f][1,2,4]triazin-7-yl)phenyl)tetrahydro-2H-pyran-4-ol (317); 7-(3-(4-methoxytetrahydro-2H-pyran-4-yl)phenyl)-5-(1-(tetrahydro-2H-pyran-4-yl)-1H-pyrazol-5-yl)pyrrolo[2,1-f][1,2,4]triazin-4-amine (318); 7-(3-(4-methoxytetrahydro-2H-pyran-4-yl)phenyl)-5-(1-(tetrahydro-2H-pyran-4-yl)-1H-1,2,3-triazol-5-yl)pyrrolo[2,1-f][1,2,4]triazin-4-amine (319); N-(4-(3-(4-amino-5-(1-(tetrahydro-2H-pyran-4-yl)-1H-pyrazol-5-yl)pyrrolo[2,1-f][1,2,4]triazin-7-yl)phenyl)tetrahydro-2H-pyran-4-yl)acetamide (320); N-(1-acetyl-4-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)acetamide (321); 4-(3-(4-amino-5-(1-(tetrahydro-2H-pyran-4-yl)-1H-pyrazol-5-yl)pyrrolo[2,1-f][1,2,4]triazin-7-yl)phenyl)tetrahydro-2H-pyran-4-carbonitrile (322); 4-(3-(4-amino-5-(1-(tetrahydro-2H-pyran-4-yl)-1H-pyrazol-5-yl)pyrrolo[2,1-f][1,2,4]triazin-7-yl)phenyl)tetrahydro-2H-pyran-4-carboxamide (323); 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-2-one (324); 4-acetyl-1-(3-(4-amino-5-(1-(4,4-difluorocyclohexyl)-1H-pyrazol-5-yl)pyrrolo[2,1-f][1,2,4]triazin-7-yl)phenyl)-3,3-dimethylpiperazin-2-one (325); 1-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-2-one (326); 4-acetyl-1-(3-(4-amino-5-(1H-indol-2-yl)pyrrolo[2,1-f][1,2,4]triazin-7-yl)phenyl)-3,3-dimethylpiperazin-2-one (327); 4-acetyl-1-(3-(4-amino-5-(1-cyclopropyl-1H-pyrazol-5-yl)pyrrolo[2,1-f][1,2,4]triazin-7-yl)phenyl)-3,3-dimethylpiperazin-2-one (328); 4-acetyl-1-(3-(4-amino-5-(1-(2,2,2-trifluoroethyl)-1H-pyrazol-5-yl)pyrrolo[2,1-f][1,2,4]triazin-7-yl)phenyl)-3,3-dimethylpiperazin-2-one (329); 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethylpiperazin-2-one (330); 4-acetyl-1-(3-(4-amino-5-(1-(4,4-difluorocyclohexyl)-1H-pyrazol-5-yl)pyrrolo[2,1-f][1,2,4]triazin-7-yl)phenyl)-6,6-dimethylpiperazin-2-one (331); 4-acetyl-1-(3-(4-amino-5-(1-isopropyl-1H-pyrazol-5-yl)pyrrolo[2,1-f][1,2,4]triazin-7-yl)phenyl)-6,6-dimethylpiperazin-2-one (332); 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-6,6-dimethylpiperazin-2-one (333); 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)piperazin-2-one (334); 4-acetyl-1-(3-(4-amino-5-(1-methyl-1H-pyrazol-4-yl)pyrrolo[2,1-f][1,2,4]triazin-7-yl)phenyl)-3,3-dimethylpiperazin-2-one (335); 4-acetyl-1-(3-(4-amino-5-(1-cyclopropyl-1H-pyrazol-5-yl)pyrrolo[2,1-f][1,2,4]triazin-7-yl)phenyl)-6,6-dimethylpiperazin-2-one (336); 1-(3-(4-amino-5-(1-(tetrahydro-2H-pyran-4-yl)-1H-pyrazol-5-yl)pyrrolo[2,1-f][1,2,4]triazin-7-yl)phenyl)-3,3,4-trimethylpiperazin-2-one (337); 4-acetyl-1-(3-(4-amino-5-(1-isopropyl-1H-pyrazol-4-yl)pyrrolo[2,1-f][1,2,4]triazin-7-yl)phenyl)-3,3-dimethylpiperazin-2-one (338); 4-acetyl-1-(3-(4-amino-5-(5-methyl-1-phenyl-1H-pyrazol-4-yl)pyrrolo[2,1-f][1,2,4]triazin-7-yl)phenyl)-3,3-dimethylpiperazin-2-one (339); 4-acetyl-1-(3-(4-amino-5-(1-phenyl-1H-pyrazol-4-yl)pyrrolo[2,1-f][1,2,4]triazin-7-yl)phenyl)-3,3-dimethylpiperazin-2-one (340); 4-acetyl-1-(3-(4-amino-5-(3-(trifluoromethyl)-1H-pyrazol-4-yl)pyrrolo[2,1-f][1,2,4]triazin-7-yl)phenyl)-3,3-dimethylpiperazin-2-one (341); 4-acetyl-1-(3-(4-amino-5-(1-methyl-1H-indol-2-yl)pyrrolo[2,1-f][1,2,4]triazin-7-yl)phenyl)-3,3-dimethylpiperazin-2-one (342); 4-acetyl-1-(3-(4-amino-5-(1-isobutyl-1H-pyrazol-4-yl)pyrrolo[2,1-f][1,2,4]triazin-7-yl)phenyl)-3,3-dimethylpiperazin-2-one (343); 4-acetyl-1-(3-(4-amino-5-(3-(trifluoromethyl)-1H-pyrazol-4-yl)pyrrolo[2,1-f][1,2,4]triazin-7-yl)phenyl)-6,6-dimethylpiperazin-2-one (344); 4-acetyl-1-(3-(4-amino-5-(1-methyl-3-(trifluoromethyl)-1H-pyrazol-4-yl)pyrrolo[2,1-f][1,2,4]triazin-7-yl)phenyl)-3,3-dimethylpiperazin-2-one (345); 4-acetyl-1-(3-(4-amino-5-(1H-indol-2-yl)pyrrolo[2,1-f][1,2,4]triazin-7-yl)phenyl)-6,6-dimethylpiperazin-2-one (346); 4-acetyl-1-(3-(4-amino-5-(1-(cyclopropylmethyl)-1H-pyrazol-4-yl)pyrrolo[2,1-f][1,2,4]triazin-7-yl)phenyl)-3,3-dimethylpiperazin-2-one (347); 4-acetyl-1-(3-(4-amino-5-(1-methyl-5-phenyl-1H-pyrazol-4-yl)pyrrolo[2,1-f][1,2,4]triazin-7-yl)phenyl)-3,3-dimethylpiperazin-2-one (348); 4-acetyl-1-(3-(4-amino-5-(1-cyclopropyl-1H-pyrazol-4-yl)pyrrolo[2,1-f][1,2,4]triazin-7-yl)phenyl)-3,3-dimethylpiperazin-2-one (349); 4-acetyl-1-(3-(4-amino-5-(1-(2-hydroxy-2-methylpropyl)-1H-pyrazol-4-yl)pyrrolo[2,1-f][1,2,4]triazin-7-yl)phenyl)-3,3-dimethylpiperazin-2-one (350); 1-(3-(4-amino-5-(1-(tetrahydro-2H-pyran-4-yl)-1H-pyrazol-5-yl)pyrrolo[2,1-f][1,2,4]triazin-7-yl)phenyl)-4-(4-fluorophenyl)-3,3-dimethylpiperazine-2,5-dione (351); 1-(3-(4-amino-5-(1-(tetrahydro-2H-pyran-4-yl)-1H-1,2,3-triazol-5-yl)pyrrolo[2,1-f][1,2,4]triazin-7-yl)phenyl)-4-(4-fluorophenyl)-3,3-dimethylpiperazine-2,5-dione (352); 4-acetyl-1-(3-(4-amino-5-(1-(tetrahydrofuran-3-yl)-1H-pyrazol-4-yl)pyrrolo[2,1-f][1,2,4]triazin-7-yl)phenyl)-3,3-dimethylpiperazin-2-one (353); 4-acetyl-1-(3-(4-amino-5-(1-(pyridin-3-yl)-1H-pyrazol-4-yl)pyrrolo[2,1-f][1,2,4]triazin-7-yl)phenyl)-3,3-dimethylpiperazin-2-one (354); 4-acetyl-1-(3-(4-amino-5-(1-(pyridin-2-yl)-1H-pyrazol-4-yl)pyrrolo[2,1-f][1,2,4]triazin-7-yl)phenyl)-3,3-dimethylpiperazin-2-one (355); 4-acetyl-1-(3-(4-amino-5-(1-(sec-butyl)-1H-pyrazol-4-yl)pyrrolo[2,1-f][1,2,4]triazin-7-yl)phenyl)-3,3-dimethylpiperazin-2-one (356); 1-(3-(4-amino-5-(1-(tetrahydro-2H-pyran-4-yl)-1H-pyrazol-5-yl)pyrrolo[2,1-f][1,2,4]triazin-7-yl)phenyl)-4-isopropyl-3,6-dimethylpiperazine-2,5-dione (357); 3-(3-(4-amino-5-(1-(tetrahydro-2H-pyran-4-yl)-1H-pyrazol-5-yl)pyrrolo[2,1-f][1,2,4]triazin-7-yl)phenyl)-8-fluoro-1-methylquinazoline-2,4(1H,3H)-dione (358); 3-(3-(4-amino-5-(1-(tetrahydro-2H-pyran-4-yl)-1H-pyrazol-5-yl)pyrrolo[2,1-f][1,2,4]triazin-7-yl)phenyl)-1-methylquinazoline-2,4(1H,3H)-dione (359); 3-(3-(4-amino-5-(1-(tetrahydro-2H-pyran-4-yl)-1H-pyrazol-5-yl)pyrrolo[2,1-f][1,2,4]triazin-7-yl)phenyl)quinazolin-4(3H)-one (360); 2-(3-(4-amino-5-(1-(tetrahydro-2H-pyran-4-yl)-1H-pyrazol-5-yl)pyrrolo[2,1-f][1,2,4]triazin-7-yl)phenyl)-1H-pyrido[1,2-c]pyrimidine-1,3(2H)-dione (361); 3-(3-(4-amino-5-(1-(tetrahydro-2H-pyran-4-yl)-1H-1,2,3-triazol-5-yl)pyrrolo[2,1-f][1,2,4]triazin-7-yl)phenyl)-1-methylquinazoline-2,4(1H,3H)-dione (362); 3-(3-(4-amino-5-(1-(tetrahydro-2H-pyran-4-yl)-1H-1,2,3-triazol-5-yl)pyrrolo[2,1-f][1,2,4]triazin-7-yl)phenyl)quinazolin-4(3H)-one (363); 3-(3-(4-amino-5-(1-(tetrahydro-2H-pyran-4-yl)-1H-1,2,3-triazol-5-yl)pyrrolo[2,1-f][1,2,4]triazin-7-yl)phenyl)-8-fluoro-1-methylquinazoline-2,4(1H,3H)-dione (364); 5-(1-isopropyl-1H-1,2,3-triazol-5-yl)-7-(3-(5-(methylsulfonyl) hexahydropyrrolo[3,4-c]pyrrol-2(1H)-yl)phenyl)pyrrolo[2,1-f][1,2,4]triazin-4-amine (365); 7-(3-(5-(methylsulfonyl)hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (366); 7-(3-(5-methylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (367); 1-(5-(3-(4-amino-5-(1-(tetrahydro-2H-pyran-4-yl)-1H-1,2,3-triazol-5-yl)pyrrolo[2,1-f][1,2,4]triazin-7-yl)phenyl)hexahydropyrrolo[3,4-c]pyrrol-2(1H)-yl)ethanone (368); 1-(5-(3-(4-amino-5-(1-(tetrahydro-2H-pyran-4-yl)-1H-pyrazol-5-yl)pyrrolo[2,1-f][1,2,4]triazin-7-yl)phenyl) hexahydropyrrolo[3,4-c]pyrrol-2(1H)-yl)ethanone (369); 7-(3-(hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (370); 7-(3-(5-isopropylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (371); 7-(3-(5-cyclobutylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (372); 3-(5-(3-(4-amino-5-(1-(tetrahydro-2H-pyran-4-yl)-1H-pyrazol-5-yl)pyrrolo[2,1-f][1,2,4]triazin-7-yl)phenyl)hexahydropyrrolo[3,4-c]pyrrol-2(1H)-yl)-2-methylbutan-2-ol (373); 7-(3-(5-(1-methoxypropan-2-yl)hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (374); N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methylmethanesulfonamide (375); N-(1-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-4-yl)-N-methylmethanesulfonamide (376); N-(1-(3-(4-amino-5-(1-isopropyl-1H-1,2,3-triazol-5-yl)pyrrolo[2,1-f][1,2,4]triazin-7-yl)phenyl)piperidin-4-yl)-N-methylmethanesulfonamide (377); 1'-(3-(4-amino-5-(1-(tetrahydro-2H-pyran-4-yl)-1H-1,2,3-triazol-5-yl)pyrrolo[2,1-f][1,2,4]triazin-7-yl)phenyl)-[1,4'-bipiperidin]-2-one (378); N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methylfuran-2-carboxamide (379); N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methyl-2-(pyrazin-2-yl)acetamide (380); 1-(1-(3-(4-amino-5-(1-(tetrahydro-2H-pyran-4-yl)-1H-pyrazol-5-yl)pyrrolo[2,1-f][1,2,4]triazin-7-yl)phenyl) piperidin-4-yl)-3-isopropyl-1-methylurea (381); N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-1-cyano-N-methylcyclopropanecarboxamide (382); 7-(3-(4-morpholinopiperidin-1-yl)phenyl)-5-(1-(tetrahydro-2H-pyran-4-yl)-1H-pyrazol-5-yl)pyrrolo[2,1-f][1,2,4]triazin-4-amine (383); 1-(3-(4-amino-5-(1-(tetrahydro-2H-pyran-4-yl)-1H-pyrazol-5-yl)pyrrolo [2,1-f][1,2,4]triazin-7-yl)phenyl)-3-(morpholine-4-carbonyl)piperidin-2-one (384); N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)-2-hydroxy-N,2-dimethylpropanamide (385); N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)-N-methyl-2-(pyrazin-2-yl)acetamide (386); N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)-N-methylacetamide (387); S)—N-(1-(3-(4-amino-5-(1-(tetrahydro-2H-pyran-4-yl)-1H-pyrazol-5-yl)pyrrolo[2,1-f][1,2,4]triazin-7-yl)phenyl) pyrrolidin-3-yl)acetamide (388); 7-(3-((pyridin-3-yloxy)methyl)phenyl)-5-(1-(tetrahydro-2H-pyran-4-yl)-1H-pyrazol-5-yl)pyrrolo[2,1-f][1,2,4]triazin-4-amine (389); 7-(3-((pyridin-2-yloxy)methyl)phenyl)-5-(1-(tetrahydro-2H-pyran-4-yl)-1H-pyrazol-5-yl)pyrrolo[2,1-f][1,2,4]triazin-4-amine (390); 7-(3-(2-morpholinopropyl)phenyl)-5-(1-(tetrahydro-2H-pyran-4-yl)-1H-pyrazol-5-yl)pyrrolo[2,1-f][1,2,4]triazin-4-amine (391); 7-(3-(2-(pyrrolidin-1-yl)propyl)phenyl)-5-(1-(tetrahydro-2H-pyran-4-yl)-1H-pyrazol-5-yl)pyrrolo[2,1-f][1,2,4]triazin-4-amine (392); 7-(3-(2-((2-methoxyethyl)amino)propyl) phenyl)-5-(1-(tetrahydro-2H-pyran-4-yl)-1H-pyrazol-5-yl)pyrrolo[2,1-f][1,2,4]triazin-4-amine (393); 5-(1-(tetrahydro-2H-pyran-4-yl)-1H-pyrazol-5-yl)-7-(3-(2-((tetrahydro-2H-pyran-4-yl)amino)propyl)phenyl)pyrrolo[2,1-f][1,2,4]triazin-4-amine (394); 7-(3-(2-(methyl(tetrahydro-2H-pyran-4-yl)amino)propyl)phenyl)-5-(1-(tetrahydro-2H-pyran-4-yl)-1H-pyrazol-5-yl)pyrrolo[2,1-f][1,2,4]triazin-4-amine (395); 7-(3-(2-(dimethylamino)propyl)phenyl)-5-(1-(tetrahydro-2H-pyran-4-yl)-1H-pyrazol-5-yl)pyrrolo[2,1-f][1,2,4]triazin-4-amine (396); 7-(3-(1-(dimethylamino)-2-methylpropan-2-yl)phenyl)-5-(1-(tetrahydro-2H-pyran-4-yl)-1H-pyrazol-5-yl)pyrrolo[2,1-f][1,2,4]triazin-4-amine (397); 5-(1-(tetrahydro-2H-pyran-4-yl)-1H-pyrazol-5-yl)-7-(3-(1-(((tetrahydro-2H-pyran-4-yl)amino)methyl)cyclopropyl)phenyl)pyrrolo[2,1-f][1,2,4]triazin-4-amine (398); 7-(3-(3-morpholinopyrrolidin-1-yl)phenyl)-5-(1-(tetrahydro-2H-pyran-4-yl)-1H-pyrazol-5-yl)pyrrolo[2,1-f][1,2,4]triazin-4-amine (399); 2-(1-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-4-yl) propan-2-ol (400); 7-(3-(1H-imidazol-2-yl)phenyl)-5-(1-(tetrahydro-2H-pyran-4-yl)-1H-pyrazol-5-yl)pyrrolo[2,1-f][1,2,4]triazin-4-amine (401); 4-(3-(4-amino-5-(1-(tetrahydro-2H-pyran-4-yl)-1H-pyrazol-5-yl)pyrrolo[2,1-f][1,2,4]triazin-7-yl)phenyl) morpholine-3-carboxamide (402); 3'-(4-amino-5-(2-methylthiazol-5-yl)pyrrolo[2,1-f][1,2,4]triazin-7-yl)-[1,1'-biphenyl]-2-carboxamide (403); 3'-(4-amino-5-(thiazol-5-yl)pyrrolo[2,1-f][1,2,4]triazin-7-yl)-[1,1'-biphenyl]-2-carboxamide (404); 3'-(4-amino-5-(1-(tetrahydro-2H-pyran-4-yl)-1H-pyrazol-5-yl)pyrrolo[2,1-f][1,2,4]triazin-7-yl)-3-fluoro-[1,1'-biphenyl]-2-carboxamide (405); 4-acetyl-1-(3-(4-amino-5-(2-propylthiazol-5-yl)pyrrolo[2,1-f][1,2,4]triazin-7-yl)phenyl)-3,3-dimethylpiperazin-2-one (406); 4-acetyl-1-(3-(4-amino-5-(1H-pyrazol-4-yl)pyrrolo[2,1-f][1,2,4]triazin-7-yl)phenyl)-3,3-dimethylpiperazin-2-one (407); 4-acetyl-1-(3-(4-amino-5-(1-(difluoromethyl)-1H-pyrazol-4-yl)pyrrolo[2,1-f][1,2,4]triazin-7-yl)phenyl)-3,3-dimethylpiperazin-2-one (408); 4-acetyl-1-(3-(4-amino-5-(thiazol-5-yl)pyrrolo[2,1-f][1,2,4]triazin-7-yl)phenyl)-3,3-dimethylpiperazin-2-one (409); 4-acetyl-1-(3-(4-amino-5-(2-methylthiazol-5-yl)pyrrolo[2,1-f][1,2,4]triazin-7-yl)phenyl)-3,3-dimethylpiperazin-2-one (410); 3'-(4-amino-5-(1-methyl-1H-pyrazol-4-yl)pyrrolo[2,1-f][1,2,4]triazin-7-yl)-[1,1'-biphenyl]-2-carboxamide (411); 4-acetyl-1-(3-(4-amino-5-(1-trideuteromethyl-1H-pyrazol-4-yl)pyrrolo[2,1-f][1,2,4]triazin-7-yl)phenyl)-3,3-dimethylpiperazin-2-one (412); 3'-(4-amino-5-(1-(tetrahydro-2H-pyran-4-yl)-1H-pyrazol-5-yl)pyrrolo[2,1-f][1,2,4]triazin-7-yl)-6-fluoro-[1,1'-biphenyl]-2-carboxamide (413); 1-(3-(4-amino-5-(1-(tetrahydro-2H-pyran-4-yl)-1H-pyrazol-5-yl)pyrrolo[2,1-f][1,2,4]triazin-7-yl)phenyl)piperidine-2-carboxamide (414); 4-acetyl-1-(3-(4-amino-5-(1-(2,2-difluoroethyl)-1H-pyrazol-4-yl)pyrrolo[2,1-f][1,2,4]triazin-7-yl)phenyl)-3,3-dimethylpiperazin-2-one (415); 4-acetyl-1-(3-(4-amino-5-(2-phenylthiazol-5-yl)pyrrolo[2,1-f][1,2,4]triazin-7-yl)phenyl)-3,3-dimethylpiperazin-2-one (416); 4-acetyl-1-(3-(4-amino-5-(2-isobutylthiazol-5-yl)

pyrrolo[2,1-f][1,2,4]triazin-7-yl)phenyl)-3,3-dimethylpiperazin-2-one (417); 4-acetyl-1-(3-(4-amino-5-(benzo[d]oxazol-2-yl)pyrrolo[2,1-f][1,2,4]triazin-7-yl)phenyl)-3,3-dimethylpiperazin-2-one (418); 4-acetyl-1-(3-(4-amino-5-(1-(cyclobutylmethyl)-1H-pyrazol-4-yl)pyrrolo[2,1-f][1,2,4]triazin-7-yl)phenyl)-3,3-dimethylpiperazin-2-one (419); 4-acetyl-1-(3-(4-amino-5-(thiazol-2-yl)pyrrolo[2,1-f][1,2,4]triazin-7-yl)phenyl)-3,3-dimethylpiperazin-2-one (420); 4-acetyl-1-(3-(4-amino-5-(1-neopentyl-1H-pyrazol-4-yl)pyrrolo[2,1-f][1,2,4]triazin-7-yl)phenyl)-3,3-dimethylpiperazin-2-one (421); 4-acetyl-1-(3-(4-amino-5-(1-(2-methoxyethyl)-1H-pyrazol-4-yl)pyrrolo[2,1-f][1,2,4]triazin-7-yl)phenyl)-3,3-dimethylpiperazin-2-one (422); 4-acetyl-1-(3-(4-amino-5-(1-(oxetan-3-ylmethyl)-1H-pyrazol-4-yl)pyrrolo[2,1-f][1,2,4]triazin-7-yl)phenyl)-3,3-dimethylpiperazin-2-one (423); 4-acetyl-1-(3-(4-amino-5-(1-((3-methyloxetan-3-yl)methyl)-1H-pyrazol-4-yl)pyrrolo[2,1-f][1,2,4]triazin-7-yl)phenyl)-3,3-dimethylpiperazin-2-one (424); 1-(3-(4-amino-5-(1-(tetrahydro-2H-pyran-4-yl)-1H-pyrazol-5-yl)pyrrolo[2,1-f][1,2,4]triazin-7-yl)phenyl) azepane-2-carboxamide (425); 4-acetyl-1-{3-[4-amino-6-fluoro-5-(1-methyl-1H-pyrazol-4-yl)pyrrolo[2,1-f][1,2,4]triazin-7-yl]phenyl}-3,3-dimethylpiperazin-2-one (426); 4-acetyl-1-(3-{4-amino-5-[1-(2,2-difluoroethyl)-1H-pyrazol-4-yl]-6-fluoropyrrolo[2,1-f][1,2,4]triazin-7-yl}phenyl)-3,3-dimethylpiperazin-2-one (427); 4-acetyl-1-{3-[4-amino-5-(1-methanesulfonyl-1H-pyrazol-4-yl)pyrrolo[2,1-f][1,2,4]triazin-7-yl]phenyl}-3,3-dimethylpiperazin-2-one (428); 4-acetyl-1-{5-[4-amino-5-(1-methanesulfonyl-1H-pyrazol-4-yl)pyrrolo[2,1-f][1,2,4]triazin-7-yl]-2-fluorophenyl}-3,3-dimethylpiperazin-2-one (429); 4-acetyl-1-(3-{4-amino-5-[1-(cyclopropanesulfonyl)-1H-pyrazol-4-yl]pyrrolo [2,1-f][1,2,4]triazin-7-yl} phenyl)-3,3-dimethylpiperazin-2-one (430); 4-acetyl-1-(5-{4-amino-5-[1-(cyclopropanesulfonyl)-1H-pyrazol-4-yl]pyrrolo[2,1-f][1,2,4]triazin-7-yl}-2-fluorophenyl)-3,3-dimethylpiperazin-2-one (431); 4-acetyl-1-(3-{4-amino-5-[1-(propane-2-sulfonyl)-1H-pyrazol-4-yl]pyrrolo[2,1-f][1,2,4]triazin-7-yl}phenyl)-3,3-dimethylpiperazin-2-one (432); 4-acetyl-1-(5-{4-amino-5-[1-(propane-2-sulfonyl)-1H-pyrazol-4-yl]pyrrolo[2,1-f][1,2,4]triazin-7-yl}-2-fluorophenyl)-3,3-dimethylpiperazin-2-one (433); 4-acetyl-1-(3-{4-amino-5-[1-(1,3-difluoropropan-2-yl)-1H-pyrazol-4-yl]pyrrolo[2,1-f][1,2,4]triazin-7-yl}phenyl)-3,3-dimethylpiperazin-2-one (434); 4-acetyl-1-[3-(4-amino-5-{1-[($^{2}H_7$)propan-2-yl]-1H-pyrazol-4-yl}pyrrolo[2,1-f][1,2,4]triazin-7-yl)phenyl]-3,3-dimethylpiperazin-2-one (435); 4-acetyl-1-{3-[4-amino-5-(1-cyclobutyl-1H-pyrazol-4-yl)pyrrolo[2,1-f][1,2,4]triazin-7-yl]phenyl}-3,3-dimethylpiperazin-2-one (436); 4-acetyl-1-(3-{4-amino-5-[1-($^{2}H_5$)ethyl-1H-pyrazol-4-yl]pyrrolo[2,1-f][1,2,4]triazin-7-yl}phenyl)-3,3-dimethylpiperazin-2-one (437); 4-acetyl-1-{3-[4-amino-5-(1-methyl-1H-pyrazol-4-yl)pyrrolo[2,1-f][1,2,4]triazin-7-yl]-5-fluorophenyl}-3,3-dimethylpiperazin-2-one (438); 4-acetyl-1-{5-[4-amino-5-(1-methyl-1H-pyrazol-4-yl)pyrrolo[2,1-f][1,2,4]triazin-7-yl]-2-fluorophenyl}-3,3-dimethylpiperazin-2-one (439); 4-acetyl-1-{3-[4-amino-5-(1-methyl-1H-pyrazol-4-yl)pyrrolo[2,1-f][1,2,4]triazin-7-yl]-4-fluorophenyl}-3,3-dimethylpiperazin-2-one (440); 4-acetyl-1-{3-[4-amino-5-(1-methyl-1H-pyrazol-4-yl)pyrrolo[2,1-f][1,2,4]triazin-7-yl]-2-fluorophenyl}-3,3-dimethylpiperazin-2-one (441); 1-{3-[4-amino-5-(1-methyl-1H-pyrazol-4-yl)pyrrolo[2,1-f][1,2,4]triazin-7-yl]phenyl}-4-cyclobutanecarbonyl-3,3-dimethylpiperazin-2-one (442); 1-{3-[4-amino-5-(1-methyl-1H-pyrazol-4-yl)pyrrolo[2,1-f][1,2,4]triazin-7-yl]phenyl}-4-cyclopropanecarbonyl-3,3-dimethylpiperazin-2-one (443); 3-(4-{3-[4-amino-5-(1-methyl-1H-pyrazol-4-yl)pyrrolo[2,1-f][1,2,4]triazin-7-yl]phenyl}-2,2-dimethyl-3-oxopiperazin-1-yl)-3-oxopropanenitrile (444); 4-acetyl-1-[3-(4-amino-5-{1-[(2S)-3,3,3-trifluoro-2-hydroxypropyl]-1H-pyrazol-4-yl}pyrrolo[2,1-f][1,2,4]triazin-7-yl)phenyl]-3,3-dimethylpiperazin-2-one (445); 4-acetyl-1-[3-(4-amino-5-{1-[(2R)-3,3,3-trifluoro-2-hydroxypropyl]-1H-pyrazol-4-yl}pyrrolo[2,1-f][1,2,4]triazin-7-yl)phenyl]-3,3-dimethylpiperazin-2-one (446); 4-acetyl-1-[3-(4-amino-5-{1-[(2S)-2-hydroxypropyl]-1H-pyrazol-4-yl}pyrrolo[2,1-f][1,2,4]triazin-7-yl)phenyl]-3,3-dimethylpiperazin-2-one (447); 4-acetyl-1-(3-{4-amino-5-[1-(2,2,2-trifluoroethyl)-1H-pyrazol-5-yl]pyrrolo[2,1-f][1,2,4]triazin-7-yl}-2-fluorophenyl)-3,3-dimethylpiperazin-2-one (448); 4-acetyl-1-(3-{4-amino-5-[1-(2,2,2-trifluoroethyl)-1H-pyrazol-5-yl]pyrrolo[2,1-f][1,2,4]triazin-7-yl]-4-fluorophenyl)-3,3-dimethylpiperazin-2-one (449); 4-acetyl-1-(3-{4-amino-5-[1-(2,2,2-trifluoroethyl)-1H-pyrazol-5-yl]pyrrolo[2,1-f][1,2,4]triazin-7-yl]-5-fluorophenyl)-3,3-dimethylpiperazin-2-one (450); 4-acetyl-1-(5-{4-amino-5-[1-(2,2,2-trifluoroethyl)-1H-pyrazol-5-yl]pyrrolo[2,1-f][1,2,4]triazin-7-yl]-2-fluorophenyl)-3,3-dimethylpiperazin-2-one (451); 4-acetyl-1-(3-{4-amino-5-[1-(1,3-difluoropropan-2-yl)-1H-pyrazol-5-yl]pyrrolo[2,1-f][1,2,4]triazin-7-yl}phenyl)-3,3-dimethylpiperazin-2-one (452); 4-acetyl-1-[3-(4-amino-5-{1-[(1,1,1,3,3,3-$^{2}H_6$)propan-2-yl]-1H-pyrazol-5-yl}pyrrolo[2,1-f][1,2,4]triazin-7-yl)phenyl]-3,3-dimethylpiperazin-2-one (453); 4-acetyl-1-[3-(4-amino-5-{1-[($^{2}H_7$)propan-2-yl]-1H-pyrazol-5-yl}pyrrolo[2,1-f][1,2,4]triazin-7-yl)phenyl]-3,3-dimethylpiperazin-2-one (454); 4-acetyl-1-(3-{4-amino-5-[1-(propan-2-yl)-1H-pyrazol-5-yl]pyrrolo[2,1-f][1,2,4]triazin-7-yl}phenyl)-3,3-dimethylpiperazin-2-one (455); 4-acetyl-1-(3-{4-amino-5-[1-(2,2-difluoroethyl)-1H-pyrazol-5-yl]pyrrolo[2,1-f][1,2,4]triazin-7-yl}phenyl)-3,3-dimethylpiperazin-2-one (456); 4-acetyl-1-(3-{4-amino-5-[1-(oxan-4-yl)-1H-pyrazol-5-yl]pyrrolo[2,1-f][1,2,4]triazin-7-yl}phenyl)-3-(propan-2-yl)piperazin-2-one (457); 4-acetyl-1-(3-{4-amino-5-[1-(oxan-4-yl)-1H-pyrazol-5-yl]pyrrolo[2,1-f][1,2,4]triazin-7-yl}phenyl)-3-(propan-2-yl)piperazin-2-one, chiral (458); 4-acetyl-1-(3-{4-amino-5-[1-(oxan-4-yl)-1H-pyrazol-5-yl]pyrrolo[2,1-f][1,2,4]triazin-7-yl}phenyl)-3-(propan-2-yl)piperazin-2-one, chiral (459); 4-acetyl-1-(3-{4-amino-5-[1-(2,2,2-trifluoroethyl)-1H-pyrazol-5-yl]pyrrolo[2,1-f][1,2,4]triazin-7-yl}phenyl)-3-(propan-2-yl)piperazin-2-one (460); 4-acetyl-1-(3-{4-amino-5-[1-(oxan-4-yl)-1H-pyrazol-5-yl]pyrrolo[2,1-f][1,2,4]triazin-7-yl}phenyl)-3-methylpiperazin-2-one (461); 4-acetyl-1-(3-{4-amino-5-[1-(propan-2-yl)-1H-pyrazol-5-yl]pyrrolo[2,1-f][1,2,4]triazin-7-yl}phenyl)-3-methylpiperazin-2-one (462); 1-(3-{4-amino-5-[1-(oxan-4-yl)-1H-pyrazol-5-yl]pyrrolo[2,1-f][1,2,4]triazin-7-yl}phenyl)-4-methanesulfonyl-3-methylpiperazin-2-one (463); 7-(3-{4-amino-5-[1-(oxan-4-yl)-1H-pyrazol-5-yl]pyrrolo[2,1-f][1,2,4]triazin-7-yl}phenyl)-4,7-diazaspiro[2.5]octan-8-one (464); 4-acetyl-7-(3-{4-amino-5-[1-(oxan-4-yl)-1H-pyrazol-5-yl]pyrrolo[2,1-f][1,2,4]triazin-7-yl}phenyl)-4,7-diazaspiro[2.5]octan-8-one (465); 7-(3-{4-amino-5-[1-(oxan-4-yl)-1H-pyrazol-5-yl]pyrrolo[2,1-f][1,2,4]triazin-7-yl}phenyl)-4-cyclobutyl-4,7-diazaspiro[2.5]octan-8-one (466); 4-acetyl-7-(3-{4-amino-5-[1-(propan-2-yl)-1H-pyrazol-5-yl]pyrrolo[2,1-f][1,2,4]triazin-7-yl}phenyl)-4,7-diazaspiro[2.5]octan-8-one (467); 7-(3-{4-amino-5-[1-(oxan-4-yl)-1H-pyrazol-5-yl]pyrrolo[2,1-f][1,2,4]triazin-7-yl}phenyl)-4-(oxetan-3-yl)-4,7-diazaspiro[2.5]octan-8-one (468); methyl 4-(3-{4-amino-5-[1-(2,2,2-trifluoroethyl)-1H-pyrazol-5-yl]pyrrolo[2,1-f][1,2,4]triazin-7-yl}phenyl)-2,2-dimethyl-3-oxopiperazine-1-carboxylate (469); 2-(3-{4-amino-5-[1-(oxan-4-yl)-1H-pyrazol-5-yl]pyrrolo[2,1-f][1,2, 4]triazin-7-yl}phenyl)-1H,2H,3H,4H,6H-pyrido[1,2-a]piperazine-1,6-dione (470); 1-[8-(3-{4-amino-5-[1-(oxan-4-yl)-1H-pyrazol-5-yl]pyrrolo[2,1-f][1,2,4]triazin-7-yl}phenyl)-3,8-diazabicyclo[3.2.1]octan-3-yl]ethan-1-one (471); 1-[3-(3-{4-amino-5-[1-(oxan-4-yl)-1H-pyrazol-5-yl]pyrrolo[2,1-f][1,2,4]triazin-7-yl}phenyl)-3,8-diazabicyclo[3.2.1]octan-8-yl]ethan-1-one (472); 4-[3-(3-{4-amino-5-[1-(oxan-4-yl)-1H-pyrazol-5-yl]pyrrolo[2,1-f][1,2,4]triazin-7-yl}phenyl)-1-(4-fluorobenzoyl)azetidin-3-yl]-1$\lambda^6$,4-thiomorpholine-1,1-dione (473); 1-(3-{4-amino-5-[1-(oxan-4-yl)-1H-pyrazol-5-yl]pyrrolo[2,1-f][1,2,4]triazin-7-yl}phenyl)-4-(pyrimidin-2-yl)piperazin-2-one (474); 5-(3-{4-amino-5-[1-(oxan-4-yl)-1H-pyrazol-5-yl]pyrrolo[2,1-f][1,2,4]triazin-7-yl}phenyl)-1-ethyl-4-methyl-1,2-dihydropyridin-2-one (475); 5-(3-{4-amino-5-[1-(oxan-4-yl)-1H-1,2,3-triazol-5-yl]pyrrolo[2,1-f][1,2,4]triazin-7-yl}phenyl)-1-ethyl-4-methyl-1,2-dihydropyridin-2-one (476); 4-acetyl-1-(3-{4-amino-5-[1-(propan-2-yl)-1H-1,2,3-triazol-5-yl]pyrrolo[2,1-f][1,2,4]triazin-7-yl}phenyl)-3,3-dimethylpiperazin-2-one (477); 4-acetyl-1-(3-{4-amino-5-[5-(propan-2-yl)-1,3,4-oxadiazol-2-yl]pyrrolo[2,1-f][1,2,4]triazin-7-yl}phenyl)-3,3-dimethylpiperazin-2-one (478); 4-acetyl-1-{3-[4-amino-5-(2-chloro-1-methyl-1H-imidazol-5-yl)pyrrolo[2,1-f][1,2,4]triazin-7-yl]phenyl}-3,3-dimethylpiperazin-2-one (479); 4-acetyl-1-{3-[4-amino-5-(1,3-thiazol-4-yl)pyrrolo[2,1-f][1,2,4]triazin-7-yl]phenyl}-3,3-dimethylpiperazin-2-one (480); 4-acetyl-1-{3-[4-amino-5-(5-methyl-1,3,4-thiadiazol-2-yl)pyrrolo[2,1-f][1,2,4]triazin-7-yl]phenyl}-3,3-dimethylpiperazin-2-one (481); 4-acetyl-1-{3-[4-amino-5-(3-methyl-1,2-oxazol-5-yl)pyrrolo[2,1-f][1,2,4]triazin-7-yl]phenyl}-3,3-dimethylpiperazin-2-one (482); 4-acetyl-1-(3-{4-amino-5-[1-(cyclopropylmethyl)-1H-1,2,3-triazol-4-yl]pyrrolo[2,1-f][1,2,4]triazin-7-yl}phenyl)-3,3-dimethylpiperazin-2-one (483); 4-acetyl-1-(3-{4-amino-5-[1-(propan-2-yl)-1H-1,2,3-triazol-4-yl]pyrrolo[2,1-f][1,2,4]triazin-7-yl}phenyl)-3,3-dimethylpiperazin-2-one (484); 4-acetyl-1-{3-[4-amino-5-(1-methyl-1H-1,2,3-triazol-4-yl)pyrrolo[2,1-f][1,2,4]triazin-7-yl]phenyl}-3,3-dimethylpiperazin-2-one (485); 4-acetyl-1-{3-[4-amino-5-(6-methylpyridazin-4-yl)pyrrolo[2,1-f][1,2,4]triazin-7-yl]phenyl}-3,3-dimethylpiperazin-2-one (486); 4-acetyl-1-{3-[4-amino-5-(6-aminopyridin-3-yl)pyrrolo[2,1-f][1,2,4]triazin-7-yl]phenyl}-3,3-dimethylpiperazin-2-one (487); 4-acetyl-1-{3-[4-amino-5-(2-amino-1,3-thiazol-5-yl)pyrrolo[2,1-f][1,2,4]triazin-7-yl]phenyl}-3,3-dimethylpiperazin-2-one (488); 4-acetyl-1-[3-(4-amino-5-{1-methyl-1H-pyrrolo[2,3-b]pyridin-5-yl}pyrrolo[2,1-f][1,2,4]triazin-7-yl)phenyl]-3,3-dimethylpiperazin-2-one (489); 4-acetyl-1-[3-(4-amino-5-{1H-pyrazolo[3,4-b]pyridin-5-yl}pyrrolo[2,1-f][1,2,4]triazin-7-yl)phenyl]-3,3-dimethylpiperazin-2-one (490); 4-acetyl-1-[3-(4-amino-5-{1H-pyrrolo[2,3-b]pyridin-5-yl}pyrrolo[2,1-f][1,2,4]triazin-7-yl)phenyl]-3,3-dimethylpiperazin-2-one (491); 4-acetyl-1-(3-{4-amino-5-[1-(difluoromethyl)-1H-pyrrolo[2,3-b]pyridin-5-yl]pyrrolo[2,1-f][1,2,4]triazin-7-yl}phenyl)-3,3-dimethylpiperazin-2-one (492); 4-acetyl-1-{3-[4-amino-5-(1-methyl-1H-pyrazol-4-yl)pyrrolo[2,1-f][1,2,4]triazin-7-yl]-2,6-difluorophenyl}-3,3-dimethylpiperazin-2-one (493); 4-acetyl-1-(3-{4-amino-5-[1-(2,2,2-trifluoroethyl)-1H-pyrazol-5-yl]pyrrolo[2,1-f][1,2,4]triazin-7-yl}-2,6-difluorophenyl)-3,3-dimethylpiperazin-2-one (494); 4-acetyl-1-(5-{4-amino-5-[1-(2,2,2-trifluoroethyl)-1H-pyrazol-5-yl]pyrrolo[2,1-f][1,2,4]triazin-7-yl}-2-(trifluoromethyl)phenyl)-3,3-dimethylpiperazin-2-one (495); 4-acetyl-1-(5-{4-amino-5-[1-(2,2,2-trifluoroethyl)-1H-pyrazol-5-yl]pyrrolo[2,1-f][1,2,4]triazin-7-yl}-2-methylphenyl)-3,3-dimethylpiperazin-2-one (496); 2-(5-{4-amino-5-[1-(oxan-4-yl)-1H-pyrazol-5-yl]pyrrolo[2,1-f][1,2,4]triazin-7-yl}-2-fluorophenyl)-1H,2H,3H,4H,6H-pyrido[1,2-a]piperazine-1,6-dione (497); 5-(3-{4-amino-5-[1-(oxan-4-yl)-1H-1,2,3-triazol-5-yl]pyrrolo[2,1-f][1,2,4]triazin-7-yl}phenyl)-1-(2,2-difluoroethyl)-4-methyl-1,2-dihydropyridin-2-one (498); 7-(3-{7-methyl-imidazo[1,2-a]pyridin-6-yl}phenyl)-5-[1-(oxan-4-yl)-1H-pyrazol-5-yl]pyrrolo[2,1-f][1,2,4]triazin-4-amine (499); 4-acetyl-1-(5-{4-amino-5-[1-(oxan-4-yl)-1H-pyrazol-5-yl]pyrrolo[2,1-f][1,2,4]triazin-7-yl}-2-fluorophenyl)-3,3-dimethylpiperazin-2-one (500); 2-(4-acetyl-3,3-dimethyl-2-oxopiperazin-1-yl)-4-[4-amino-5-(1-methyl-1H-pyrazol-4-yl)pyrrolo[2,1-f][1,2,4]triazin-7-yl]benzonitrile (501); 4-acetyl-1-(5-{4-amino-5-[1-(2,2,2-trifluoroethyl)-1H-pyrazol-5-yl]pyrrolo[2,1-f][1,2,4]triazin-7-yl}-2-methoxyphenyl)-3,3-dimethylpiperazin-2-one (502); 4-acetyl-1-{5-[4-amino-5-(1-methyl-1H-pyrazol-4-yl)pyrrolo[2,1-f][1,2,4]triazin-7-yl]-2-methoxyphenyl}-3,3-dimethylpiperazin-2-one (503); 4-acetyl-1-{5-[4-amino-5-(1-methyl-1H-pyrazol-4-yl)pyrrolo[2,1-f][1,2,4]triazin-7-yl]-2-methylphenyl}-3,3-dimethylpiperazin-2-one (504); 1-(3-{4-amino-5-[1-(2,2,2-trifluoroethyl)-1H-pyrazol-5-yl]pyrrolo[2,1-f][1,2,4]triazin-7-yl}-2-fluorophenyl)-4-methanesulfonyl-3,3-dimethylpiperazin-2-one (505); 2-(4-acetyl-3,3-dimethyl-2-oxopiperazin-1-yl)-4-{4-amino-5-[1-(2,2,2-trifluoroethyl)-1H-pyrazol-5-yl]pyrrolo[2,1-f][1,2,4]triazin-7-yl}benzonitrile (506); 2-{3-[4-amino-5-(1-methyl-H-pyrazol-4-yl)pyrrolo[2,1-f][1,2,4]triazin-7-yl]phenyl}-1H,2H,3H,4H,6H-pyrido[1,2-a]piperazine-1,6-dione (507); 5-(3-{4-amino-5-[1-(oxan-4-yl)-1H-pyrazol-5-yl]pyrrolo[2,1-f][1,2,4]triazin-7-yl}phenyl)-1-($^2$H$_3$)methyl-4-methyl-1,2-dihydropyridin-2-one (508); 4-[3-(3-{4-amino-5-[1-(oxan-4-yl)-1H-pyrazol-5-yl]pyrrolo[2,1-f][1,2,4]triazin-7-yl}phenyl)-1-[4-(2-hydroxypropan-2-yl)benzoyl]azetidin-3-yl]-1$\lambda^6$,4-thiomorpholine-1,1-dione (509); 1-(3-{4-amino-5-[1-(oxan-4-yl)-1H-1,2,3-triazol-5-yl]pyrrolo[2,1-f][1,2,4]triazin-7-yl}phenyl)-3,3-dimethyl-4-(5-methyl-1,2,4-oxadiazol-3-yl)piperazin-2-one (510); 4-acetyl-1-{3-[4-amino-5-(1-phenyl-1H-pyrazol-5-yl)pyrrolo[2,1-f][1,2,4]triazin-7-yl]phenyl}-3,3-dimethylpiperazin-2-one (511); 1-(3-{4-amino-5-[1-(oxan-4-yl)-1H-pyrazol-5-yl]pyrrolo[2,1-f][1,2,4]triazin-7-yl}phenyl)-3,3-dimethyl-4-(5-methyl-1,2,4-oxadiazol-3-yl)piperazin-2-one (512); 5-(3-{4-amino-5-[1-(oxan-4-yl)-1H-1,2,3-triazol-5-yl]pyrrolo[2,1-f][1,2,4]triazin-7-yl}phenyl)-1,4-dimethyl-1,2-dihydropyridin-2-one (513); 4-acetyl-1-(5-{4-amino-5-[1-(difluoromethyl)-1H-pyrazol-4-yl]pyrrolo[2,1-f][1,2,4]triazin-7-yl}-2-methylphenyl)-3,3-dimethylpiperazin-2-one (514); 4-acetyl-1-[5-(4-amino-5-{1-[($^2$H$_7$)propan-2-yl]-1H-pyrazol-4-yl}pyrrolo[2,1-f][1,2,4]triazin-7-yl)-2-fluorophenyl]-3,3-dimethylpiperazin-2-one (515); 4-acetyl-1-(5-{4-amino-5-[1-(difluoromethyl)-1H-pyrazol-4-yl]pyrrolo[2,1-f][1,2,4]triazin-7-yl}-2-fluorophenyl)-3,3-dimethylpiperazin-2-one (516); 4-acetyl-1-[3-(4-amino-5-{1-[($^2$H$_7$)propan-2-yl]-1H-pyrazol-4-yl}pyrrolo[2,1-f][1,2,4]triazin-7-yl)-5-fluorophenyl]-3,3-dimethylpiperazin-2-one (517); 7-(3-{7-methyl-[1,2,4]triazolo[4,3-a]pyridin-6-yl}phenyl)-5-[1-(oxan-4-yl)-1H-pyrazol-5-yl]pyrrolo[2,1-f][1,2,4]triazin-4-amine (518); 4-acetyl-1-(3-{4-amino-5-[1-(pyridazin-3-yl)-1H-pyrazol-4-yl]pyrrolo[2,1-f][1,2,4]triazin-7-yl}phenyl)-3,3-dimethylpiperazin-2-one (519); 4-(3-{4-amino-5-[1-(oxan-4-yl)-1H-pyrazol-5-yl]pyrrolo[2,1-f][1,2,4]triazin-7-yl}phenyl)-1-(2-cyanoacetyl)piperidine-4-carbonitrile (520); 4-acetyl-1-[5-(4-amino-5-{1-[($^2$H$_7$)propan-2-yl]-1H-pyrazol-4-yl}pyrrolo[2,1-f][1,2,4]triazin-7-yl)-2-methoxyphenyl]-3,3-dimethylpiperazin-2-one (521); 1-{5-[4-amino-5-(1-methyl-1H-pyrazol-4-yl)

pyrrolo[2,1-f][1,2,4]triazin-7-yl]-2-fluorophenyl}-4-cyclopropanecarbonyl-3,3-dimethylpiperazin-2-one (522); 4-acetyl-1-(5-{4-amino-5-[1-(difluoromethyl)-1H-pyrazol-4-yl]pyrrolo[2,1-f][1,2,4]triazin-7-yl}-2-methoxyphenyl)-3,3-dimethylpiperazin-2-one (523); 4-acetyl-1-[5-(4-amino-5-{1-[(²H₇)propan-2-yl]-1H-pyrazol-4-yl}pyrrolo[2,1-f][1,2,4]triazin-7-yl)-2-methylphenyl]-3,3-dimethylpiperazin-2-one (524); 7-(3-{7-methyl-[1,2,4]triazolo[4,3-a]pyridin-6-yl}phenyl)-5-[1-(oxan-4-yl)-1H-1,2,3-triazol-5-yl]pyrrolo[2,1-f][1,2,4]triazin-4-amine (525); 4-acetyl-1-(3-{4-amino-5-[1-(pyrimidin-2-yl)-1H-pyrazol-4-yl]pyrrolo[2,1-f][1,2,4]triazin-7-yl}phenyl)-3,3-dimethylpiperazin-2-one (526); 7-(3-{3,7-dimethyl-[1,2,4]triazolo[4,3-a]pyridin-6-yl}phenyl)-5-[1-(oxan-4-yl)-1H-pyrazol-5-yl]pyrrolo[2,1-f][1,2,4]triazin-4-amine (527); 1-[4-(3-{4-amino-5-[1-(propan-2-yl)-1H-pyrazol-5-yl]pyrrolo[2,1-f][1,2,4]triazin-7-yl}phenyl)-4-hydroxy-3,3-dimethylpiperidin-1-yl]ethan-1-one (528); 4-acetyl-1-{3-[4-amino-5-(1-cyclopropyl-1H-pyrazol-4-yl)-6-fluoropyrrolo[1,2-f][1,2,4]triazin-7-yl]phenyl}-3,3-dimethylpiperazin-2-one (529); 4-acetyl-1-(5-{4-amino-5-[1-(2-fluorophenyl)-1H-pyrazol-5-yl]pyrrolo[2,1-f][1,2,4]triazin-7-yl}-2-methylphenyl)-3,3-dimethylpiperazin-2-one (530); 4-(5-{4-amino-5-[1-(propan-2-yl)-1H-pyrazol-5-yl]pyrrolo[2,1-f][1,2,4]triazin-7-yl}-2-fluorophenyl)-1λ⁶,4-thiomorpholine-1,1-dione (531); 1-(5-{4-amino-5-[1-(2,2,2-trifluoroethyl)-1H-pyrazol-5-yl]pyrrolo[2,1-f][1,2,4]triazin-7-yl}-2-fluorophenyl)-4-methanesulfonyl-3,3-dimethylpiperazin-2-one (532); 4-acetyl-1-{5-[4-amino-5-(1-methyl-1H-pyrazol-4-yl)pyrrolo[2,1-f][1,2,4]triazin-7-yl]-2-(trifluoromethyl)phenyl}-3,3-dimethylpiperazin-2-one (533); 4-(3-{4-amino-5-[1-(oxan-4-yl)-1H-pyrazol-5-yl]pyrrolo[2,1-f][1,2,4]triazin-7-yl}-4-fluorophenyl)-1λ⁶,4-thiomorpholine-1,1-dione (534); 1-[4-(3-{4-amino-5-[1-(2,2,2-trifluoroethyl)-1H-pyrazol-5-yl]pyrrolo[2,1-f][1,2,4]triazin-7-yl}phenyl)piperazin-1-yl]ethan-1-one (535); 4-acetyl-1-(3-{4-amino-5-[5-(2,2-difluorocyclopropyl)-1,3,4-oxadiazol-2-yl]pyrrolo[2,1-f][1,2,4]triazin-7-yl}phenyl)-3,3-dimethylpiperazin-2-one (536); 4-(5-{4-amino-5-[1-(propan-2-yl)-1H-1,2,3-triazol-5-yl]pyrrolo[2,1-f][1,2,4]triazin-7-yl}-2-fluorophenyl)-1λ⁶,4-thiomorpholine-1,1-dione (537); 4-acetyl-1-(3-(4-amino-5-(1-(1,1,1-trifluoropropan-2-yl)-1H-pyrazol-5-yl)pyrrolo[2,1-f][1,2,4]triazin-7-yl)phenyl)-3,3-dimethylpiperazin-2-one (538); (R)- and (S)-4-acetyl-1-(3-(4-amino-5-(1-(1,1,1-trifluoropropan-2-yl)-1H-pyrazol-5-yl)pyrrolo[2,1-f][1,2,4]triazin-7-yl)phenyl)-3,3-dimethylpiperazin-2-one (539 and 540); 3-(4-amino-5-bromopyrrolo[2,1-f][1,2,4]triazin-7-yl)-N-cyclopropyl-N-(tetrahydro-2H-pyran-4-yl)benzamide (541); 1-(4-(3-(4-amino-5-bromopyrrolo[2,1-f][1,2,4]triazin-7-yl)phenoxy)piperidin-1-yl)ethanone (542); 1-(4-(3-(4-amino-5-bromopyrrolo[2,1-f][1,2,4]triazin-7-yl)phenoxy)piperidin-1-yl)ethanone (543); 5-bromo-7-(3-((methyl(tetrahydro-2H-pyran-4-yl)amino)methyl)phenyl)pyrrolo[2,1-f][1,2,4]triazin-4-amine (544); 3-(4-amino-5-iodopyrrolo[2,1-f][1,2,4]triazin-7-yl)-N-cyclopropyl-N-(tetrahydro-2H-pyran-4-yl)benzamide (545); N-(1-acetylpiperidin-4-yl)-3-(4-amino-5-bromopyrrolo[2,1-f][1,2,4]triazin-7-yl)-N-cyclopropylbenzamide (546); 3-(4-amino-5-bromopyrrolo[2,1-f][1,2,4]triazin-7-yl)-N-cyclopropyl-N-(1-methylpiperidin-4-yl)benzamide (547); 4-acetyl-1-(3-(4-amino-5-bromopyrrolo[1,2-f][1,2,4]triazin-7-yl)phenyl)-3,3-dimethylpiperazin-2-one (548); 4-acetyl-1-(3-(4-amino-5-bromopyrrolo[2,1-f][1,2,4]triazin-7-yl)phenyl)-6,6-dimethylpiperazin-2-one (549); 4-acetyl-1-(3-(4-amino-5-iodopyrrolo[2,1-f][1,2,4]triazin-7-yl)phenyl)-3,3-dimethylpiperazin-2-one (550); 4-acetyl-1-(5-(4-amino-5-iodopyrrolo[2,1-f][1,2,4]triazin-7-yl)-2-fluorophenyl)-3,3-dimethylpiperazin-2-one (551); 4-acetyl-1-(5-{4-amino-5-bromopyrrolo[2,1-f][1,2,4]triazin-7-yl}-2-methylphenyl)-3,3-dimethylpiperazin-2-one (552); 4-acetyl-1-(5-{4-amino-5-bromopyrrolo[2,1-f][1,2,4]triazin-7-yl}-2-fluorophenyl)-3,3-dimethylpiperazin-2-one (553); 4-acetyl-1-(3-{4-amino-5-bromopyrrolo[2,1-f][1,2,4]triazin-7-yl}-5-fluorophenyl)-3,3-dimethylpiperazin-2-one (554); 4-acetyl-1-(5-{4-amino-5-bromopyrrolo[2,1-f][1,2,4]triazin-7-yl}-2-methoxyphenyl)-3,3-dimethylpiperazin-2-one (555); 2-(4-acetyl-3,3-dimethyl-2-oxopiperazin-1-yl)-4-{4-amino-5-bromopyrrolo[2,1-f][1,2,4]triazin-7-yl}benzonitrile (556); 7-(3-(4-acetyl-3,3-dimethyl-2-oxopiperazin-1-yl)-4-fluorophenyl)-4-aminopyrrolo[2,1-f][1,2,4]triazine-5-carbonitrile (557); 7-(3-(4-acetyl-3,3-dimethyl-2-oxopiperazin-1-yl)phenyl)-4-aminopyrrolo[2,1-f][1,2,4]triazine-5-carbonitrile (558); 4-amino-7-[3-(4-methanesulfonyl-3,3-dimethyl-2-oxopiperazin-1-yl)-4-methylphenyl]pyrrolo[2,1-f][1,2,4]triazine-5-carbonitrile (559); 7-(3-(4-acetyl-3,3-dimethyl-2-oxopiperazin-1-yl)-4-cyanophenyl]-4-aminopyrrolo[2,1-f][1,2,4]triazine-5-carbonitrile (560); 7-[3-(4-acetyl-3,3-dimethyl-2-oxopiperazin-1-yl)-4-(trifluoromethyl)phenyl]-4-aminopyrrolo[2,1-f][1,2,4]triazine-5-carbonitrile (561); 7-[3-(4-acetyl-3,3-dimethyl-2-oxopiperazin-1-yl)-4-methylphenyl]-4-aminopyrrolo[2,1-f][1,2,4]triazine-5-carbonitrile (562); 7-[3-(4-acetyl-3,3-dimethyl-2-oxopiperazin-1-yl)-4-methoxyphenyl]-4-aminopyrrolo[2,1-f][1,2,4]triazine-5-carbonitrile (563); 4-acetyl-1-(3-(4-amino-5-(trifluoromethyl)pyrrolo[2,1-f][1,2,4]triazin-7-yl)phenyl)-3,3-dimethylpiperazin-2-one (564); 2-(4-acetyl-3,3-dimethyl-2-oxopiperazin-1-yl)-4-(4-amino-5-(trifluoromethyl)pyrrolo[1,2-f][1,2,4]triazin-7-yl)benzonitrile (565); 4-acetyl-1-{5-[4-amino-5-(trifluoromethyl) pyrrolo[2,1-f][1,2,4]triazin-7-yl]-2-fluorophenyl}-3,3-dimethylpiperazin-2-one (566); 4-acetyl-1-{3-[4-amino-5-(trifluoromethyl)pyrrolo[2,1-f][1,2,4]triazin-7-yl]-2,6-difluorophenyl}-3,3-dimethylpiperazin-2-one (567); 4-acetyl-1-{5-[4-amino-5-(trifluoromethyl)pyrrolo[2,1-f][1,2,4]triazin-7-yl]-2-methoxyphenyl}-3,3-dimethylpiperazin-2-one (568); 4-acetyl-1-{3-[4-amino-5-(trifluoromethyl)pyrrolo[2,1-f][1,2,4]triazin-7-yl]-2-fluorophenyl}-3,3-dimethylpiperazin-2-one (569); 4-acetyl-1-{3-[4-amino-5-(trifluoromethyl)pyrrolo[2,1-f][1,2,4]triazin-7-yl]-5-fluorophenyl}-3,3-dimethylpiperazin-2-one (570); 1-(4-{3-[4-amino-5-(trifluoromethyl)pyrrolo[2,1-f][1,2,4]triazin-7-yl]phenyl}-3,3-dimethylpiperazin-1-yl)ethan-1-one (571); 4-acetyl-1-{5-[4-amino-5-(trifluoromethyl)pyrrolo[2,1-f][1,2,4]triazin-7-yl]-2-methylphenyl}-3,3-dimethylpiperazin-2-one (572); 4-acetyl-1-{5-[4-amino-5-(trifluoromethyl)pyrrolo[2,1-f][1,2,4]triazin-7-yl]-2-(trifluoromethyl)phenyl}-3,3-dimethylpiperazin-2-one (573); 4-acetyl-1-(3-(4-amino-5-methylpyrrolo[2,1-f][1,2,4]triazin-7-yl)phenyl)-3,3-dimethylpiperazin-2-one (574); 2-(4-acetyl-3,3-dimethyl-2-oxopiperazin-1-yl)-4-{4-amino-5-methylpyrrolo[2,1-f][1,2,4]triazin-7-yl}benzonitrile (575); 4-acetyl-1-(5-{4-amino-5-methylpyrrolo[2,1-f][1,2,4]triazin-7-yl}-2-fluorophenyl)-3,3-dimethylpiperazin-2-one (576); 4-acetyl-1-(3-{4-amino-5-methylpyrrolo[2,1-f][1,2,4]triazin-7-yl}-2,6-difluorophenyl)-3,3-dimethylpiperazin-2-one (577); 4-acetyl-1-(3-{4-amino-5-methylpyrrolo[2,1-f][1,2,4]triazin-7-yl}-5-fluorophenyl)-3,3-dimethylpiperazin-2-one (578); 4-acetyl-1-(5-{4-amino-5-methylpyrrolo[2,1-f][1,2,4]triazin-7-yl}-2-methoxyphenyl)-3,3-dimethylpiperazin-2-one (579); 2-(4-acetyl-3,3-dimethyl-2-oxopiperazin-1-yl)-4-(4-amino-5-chloropyrrolo[1,2-f][1,2,4]triazin-7-yl)benzonitrile (580); 4-acetyl-1-(3-(4-amino-5-chloropyrrolo[1,2-f][1,2,4]triazin-7-yl)phenyl)-3,3-dimethylpiperazin-2-one (581); 4-acetyl-1-(3-{4-amino-5-chloropyrrolo[2,1-f][1, 2,4]triazin-7-yl}-2-fluorophenyl)-3,3-dimethylpiperazin-2-one (582); 4-acetyl-1-(5-{4-amino-5-chloropyrrolo[2,1-f][1,2,4]triazin-7-yl}-2-fluorophenyl)-3,3-dimethylpiperazin-2-one (583); 4-acetyl-1-(3-{4-amino-5-chloropyrrolo[2,1-f][1,2,4]triazin-7-yl}-5-fluorophenyl)-3,3-dimethylpiperazin-2-one (584); 4-acetyl-1-(5-{4-amino-5-chloropyrrolo[2,1-f][1,2,4]triazin-7-yl}-2-methylphenyl)-3,3-dimethylpiperazin-2-one (585); 4-acetyl-1-(3-{4-amino-5-chloropyrrolo[2,1-f][1,2,4]triazin-7-yl}-4-fluorophenyl)-3,3-dimethylpiperazin-2-one (586); 4-acetyl-1-(5-{4-amino-5-chloropyrrolo[2,1-f][1,2,4]triazin-7-yl}-2-(trifluoromethyl)phenyl)-3,3-dimethylpiperazin-2-one (587); 4-acetyl-1-(3-{4-amino-5-chloropyrrolo[2,1-f][1,2,4]triazin-7-yl}-2,6-difluorophenyl)-3,3-dimethylpiperazin-2-one (588); 2-(5-{4-amino-5-chloropyrrolo[2,1-f][1,2,4]triazin-7-yl}-2-fluorophenyl)-1H,2H,3H,4H,6H-pyrido[1,2-a]piperazine-1,6-dione (589); 1-(5-{4-amino-5-chloropyrrolo[2,1-f][1,2,4]triazin-7-yl}-2-(trifluoromethyl)phenyl)-4-methanesulfonyl-3,3-dimethylpiperazin-2-one (590); 1-(5-{4-amino-5-chloropyrrolo[2,1-f][1,2,4]triazin-7-yl}-2-fluorophenyl)-4-methanesulfonyl-3,3-dimethylpiperazin-2-one (591); 1-(5-{4-amino-5-chloropyrrolo[2,1-f][1,2,4]triazin-7-yl}-2-methoxyphenyl)-4-methanesulfonyl-3,3-dimethylpiperazin-2-one (592); 4-{4-amino-5-chloropyrrolo[2,1-f][1,2,4]triazin-7-yl}-2-(4-methanesulfonyl-3,3-dimethyl-2-oxopiperazin-1-yl)benzonitrile (593); 4-acetyl-1-(5-(4-amino-5-chloropyrrolo[1,2-f][1,2,4]triazin-7-yl)-2-methoxyphenyl)-3,3-dimethylpiperazin-2-one (594); 2-(4-acetyl-3,3,6-trimethyl-2-oxopiperazin-1-yl)-4-{4-amino-5-chloropyrrolo[2,1-f][1,2,4]triazin-7-yl}benzonitrile (595); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-methoxyphenyl)-3,3-dimethylpiperazin-2-one (596); 2-(4-acetyl-3,3,6-trimethyl-2-oxopiperazin-1-yl)-4-[4-amino-5-(trifluoromethyl)pyrrolo[2,1-f][1,2,4]triazin-7-yl]benzonitrile, racemic R,S (597); (R)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile (598); (S)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile (599); 4-acetyl-1-{3-[4-amino-5-(trifluoromethyl)pyrrolo[2,1-f][1,2,4]triazin-7-yl]phenyl}-3,3-dimethyl-5,5,6,6-tetradeuteropiperazin-2-one (600); 4-acetyl-1-(5-(4-amino-5-(1-(tetrahydro-2H-pyran-4-yl)-1H-pyrazol-5-yl)pyrrolo[2,1-f][1,2,4]triazin-7-yl)-2-chlorophenyl)-3,3-dimethylpiperazin-2-one (601); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one, racemate, R,S (602); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one (603); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one (604); 1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-4-cyclopropanecarbonyl-3,3-dimethylpiperazin-2-one (605); 4-acetyl-1-(3-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one (606); 2-(4-acetyl-3,3-dimethyl-2-oxopiperazin-1-yl)-4-{4-amino-5-[1-(1,1,1-trifluoropropan-2-yl)-1H-pyrazol-5-yl]pyrrolo[2,1-f][1,2,4]triazin-7-yl}benzonitrile (607); 4-acetyl-1-(3-{4-amino-5-[1-(oxetan-3-yl)-1H-pyrazol-5-yl]pyrrolo[2,1-f][1,2,4]triazin-7-yl}phenyl)-3,3-dimethylpiperazin-2-one (608); 4-acetyl-1-[3-(4-amino-5-{3-methyl-3H-imidazo[4,5-b]pyridin-6-yl}pyrrolo[2,1-f][1,2,4]triazin-7-yl)phenyl]-3,3-dimethylpiperazin-2-one (609); 4-acetyl-1-[5-(4-amino-5-{3-methyl-3H-imidazo[4,5-b]pyridin-6-yl}pyrrolo[2,1-f][1,2,4]triazin-7-yl)-2-fluorophenyl]-3,3-dimethylpiperazin-2-one (610); 4-acetyl-1-[5-(4-amino-5-{3-methyl-3H-imidazo[4,5-b]pyridin-6-yl}pyrrolo[2,1-f][1,2,4]triazin-7-yl)-2-methoxyphenyl]-3,3-dimethylpiperazin-2-one (611); 4-acetyl-1-[3-(4-amino-5-{3-methyl-3H-imidazo[4,5-b]pyridin-6-yl}pyrrolo[2,1-f][1,2,4]triazin-7-yl)-2-fluorophenyl]-3,3-dimethylpiperazin-2-one (612); 4-acetyl-1-(3-{4-amino-5-[3-(difluoromethyl)-3H-imidazo[4,5-b]pyridin-6-yl]pyrrolo[2,1-f][1,2,4]triazin-7-yl}phenyl)-3,3-dimethylpiperazin-2-one (613); 2-(4-acetyl-3,3-dimethyl-2-oxopiperazin-1-yl)-4-{4-amino-5-[1-(oxan-4-yl)-1H-pyrazol-5-yl]pyrrolo[2,1-f][1,2,4]triazin-7-yl}benzonitrile (614); 2-(4-acetyl-3,3-dimethyl-2-oxopiperazin-1-yl)-4-{4-amino-5-[1-(difluoromethyl)-1H-pyrazol-4-yl]pyrrolo[2,1-f][1,2,4]triazin-7-yl}benzonitrile (615); 4-acetyl-1-[3-(4-amino-5-{imidazo[1,2-a]pyridin-7-yl}pyrrolo[2,1-f][1,2,4]triazin-7-yl)phenyl]-3,3-dimethylpiperazin-2-one (616); 1-[(3S)-4-(3-{4-amino-5-[1-(propan-2-yl)-1H-pyrazol-5-yl]pyrrolo[2,1-f][1,2,4]triazin-7-yl}phenyl)-3-methylpiperazin-1-yl]ethan-1-one (617); 1-[(3S)-4-(3-{4-amino-5-[1-(oxan-4-yl)-1H-pyrazol-5-yl]pyrrolo[2,1-f][1,2,4]triazin-7-yl} phenyl)-3-methylpiperazin-1-yl]ethan-1-one (618); 4-acetyl-1-(3-(1-amino-8-(1-(tetrahydro-2H-pyran-4-yl)-1H-pyrazol-5-yl)pyrrolo[1,2-a]pyrazin-6-yl)phenyl)-3,3-dimethylpiperazin-2-one (619); 4-[3-(3-{1-amino-8-[1-(oxan-4-yl)-1H-pyrazol-5-yl]pyrrolo[1,2-a]pyrazin-6-yl}phenyl)oxetan-3-yl]-1λ$^6$,4-thiomorpholine-1,1-dione (620); 2-(3-{1-amino-8-[1-(oxan-4-yl)-1H-pyrazol-5-yl]pyrrolo[1,2-a]pyrazin-6-yl}phenyl)benzamide (621); 4-(4-amino-5-(1-(1,1,1-trifluoropropan-2-yl)-1H-pyrazol-5-yl)pyrrolo[2,1-f][1,2,4]triazin-7-yl)-2-(4-(cyclopropanecarbonyl)-3,3-dimethyl-2-oxopiperazin-1-yl)benzonitrile, (622); 4-acetyl-1-(5-(4-amino-5-(1-(tetrahydro-2H-pyran-4-yl)-1H-pyrazol-5-yl)pyrrolo[2,1-f][1,2,4]triazin-7-yl)-2-(hex-1-yn-1-yl)phenyl)-3,3-dimethylpiperazin-2-one (623); 4-acetyl-1-(5-(4-amino-5-(trifluoromethyl)pyrrolo[2,1-f][1,2,4]triazin-7-yl)-2-(difluoromethyl)phenyl)-3,3-dimethylpiperazin-2-one (624); 4-acetyl-1-(5-(4-amino-5-(trifluoromethyl)pyrrolo [2,1-f][1,2,4]triazin-7-yl)-2-(1-hydroxyethyl)phenyl)-3,3-dimethylpiperazin-2-one (625); 4-acetyl-1-(5-(4-amino-5-chloropyrrolo[2,1-f][1,2,4]triazin-7-yl)-2-(1-hydroxyethyl) phenyl)-3,3-dimethylpiperazin-2-one (626); methyl 2-(4-acetyl-3,3-dimethyl-2-oxopiperazin-1-yl)-4-(4-amino-5-chloropyrrolo[2,1-f][1,2,4]triazin-7-yl)benzoate (627); 7-(3-(4-acetyl-3,3-dimethyl-2-oxopiperazin-1-yl)-4-chlorophenyl)-4-aminopyrrolo[2,1-f][1,2,4]triazine-5-carbonitrile (628); 4-acetyl-1-(5-(4-amino-5-(trifluoromethyl)pyrrolo [2,1-f][1,2,4]triazin-7-yl)-2-(methylsulfonyl)phenyl)-3,3-dimethylpiperazin-2-one (629); 4-acetyl-1-(5-(4-amino-5-(trifluoromethyl)pyrrolo[2,1-f][1,2,4]triazin-7-yl)-2-(2-hydroxypropan-2-yl)phenyl)-3,3-dimethylpiperazin-2-one (630); 4-acetyl-1-(5-(4-amino-5-chloropyrrolo[2,1-f][1,2,4]triazin-7-yl)-2-(difluoromethyl)phenyl)-3,3-dimethylpiperazin-2-one (631); 4-acetyl-1-(5-(4-amino-5-(1-(tetrahydro-2H-pyran-4-yl)-1H-pyrazol-5-yl)-pyrrolo[2,1-f][1,2,4]triazin-7-yl)-2-fluorophenyl)-3,3-dimethyl-5,5,6,6-tetradeuteropiperazin-2-one (632); 4-acetyl-1-(5-(4-amino-5-(1-methyl-1H-pyrazol-4-yl)pyrrolo[2,1-f][1,2,4]triazin-7-yl)-2-fluorophenyl)-3,3-dimethyl-5,5,6,6-tetradeuteropiperazin-2-one (633); 4-acetyl-1-(5-(4-amino-5-(1-cyclopropyl-H-pyrazol-4-yl)pyrrolo[2,1-f][1,2,4]triazin-7-yl)-2-fluorophenyl)-3,3-dimethyl-5,5,6,6-tetradeuteropiperazin-2-one (634); 7-(3-(4-acetyl-3,3-dimethyl-2-oxo-5,5,6,6-tetradeuteropiperazin-1-yl)-4- fluorophenyl)-4-aminopyrrolo[2,1-f][1,2,4]triazine-5-carbonitrile (635); 4-acetyl-1-(5-(4-amino-5-chloropyrrolo[2,1-f][1,2,4]triazin-7-yl)-2-fluorophenyl)-3,3-dimethyl-5,5,6,6-tetradeuteropiperazin-2-one (636); 2-(4-acetyl-3,3-dimethyl-2-oxo-5,5,6,6-tetradeuteropiperazin-1-yl)-4-(4-amino-5-chloropyrrolo[2,1-f][1,2,4]triazin-7-yl)benzonitrile (637); 4-acetyl-1-(5-(4-amino-5-(trifluoromethyl)pyrrolo [2,1-f][1,2,4]triazin-7-yl)-2-methoxyphenyl)-3,3-dimethyl-5,5,6,6-tetradeuteropiperazin-2-one (638); 2-(4-acetyl-3,3-dimethyl-2-oxo-5,5,6,6-tetradeuteropiperazin-1-yl)-4-(4-amino-5-(trifluoromethyl)pyrrolo[2,1-f][1,2,4]triazin-7-yl)benzonitrile (639); 4-acetyl-1-(5-(4-amino-5-(trifluoromethyl)pyrrolo[2,1-f][1,2,4]triazin-7-yl)-2-fluorophenyl)-3,3-dimethyl-5,5,6,6-tetradeuteropiperazin-2-one (640); 4-acetyl-1-(5-(4-amino-5-(1-(2,2,2-trifluoroethyl)-1H-pyrazol-5-yl)pyrrolo[2,1-f][1,2,4]triazin-7-yl)-2-fluorophenyl)-3,3-dimethyl-5,5,6,6-tetradeuteropiperazin-2-one (641); (S)-2-(4-acetyl-3,3,6-trimethyl-2-oxopiperazin-1-yl)-4-(4-amino-5-chloropyrrolo[2,1-f][1,2,4]triazin-7-yl)benzonitrile (642); (S)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile (643); (R)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile (644); (S)-4-acetyl-1-(5-(4-amino-5-chloropyrrolo[2,1-f][1,2,4]triazin-7-yl)-2-methoxyphenyl)-3,3,6-trimethylpiperazin-2-one (645); 2-((3R,6R)-4-acetyl-3,6-dimethyl-2-oxopiperazin-1-yl)-4-(4-amino-5-(trifluoromethyl) pyrrolo[2,1-f][1,2,4]triazin-7-yl)benzonitrile (646); 4-(4-amino-5-(trifluoromethyl) pyrrolo[2,1-f][1,2,4]triazin-7-yl)-2-(4-(2-hydroxyacetyl)-3,3-dimethyl-2-oxopiperazin-1-yl)benzonitrile (647); 1-(5-(4-amino-5-chloropyrrolo[2,1-f][1,2,4]triazin-7-yl)-2-fluorophenyl)-4-(2-hydroxyacetyl)-3,3-dimethylpiperazin-2-one (648); (S)-4-(4-amino-5-(trifluoromethyl)pyrrolo[2,1-f][1,2,4]triazin-7-yl)-2-(4-(2-hydroxypropanoyl)-3,3-dimethyl-2-oxopiperazin-1-yl)benzonitrile (649); 1-(5-(4-amino-5-(1-(1,1,1-trifluoropropan-2-yl)-1H-pyrazol-5-yl)pyrrolo[2,1-f][1,2,4]triazin-7-yl)-2-fluorophenyl)-4-(cyclopropanecarbonyl)-3,3-dimethylpiperazin-2-one (650); 4-(4-amino-5-chloropyrrolo[2,1-f][1,2,4]triazin-7-yl)-2-(3,3-dimethyl-2-oxo-4-propionylpiperazin-1-yl)benzonitrile (651); 4-(4-amino-5-(trifluoromethyl)pyrrolo[2,1-f][1,2,4]triazin-7-yl)-2-(3,3-dimethyl-2-oxo-4-propionylpiperazin-1-yl)benzonitrile (652); (R)-4-(4-amino-5-chloropyrrolo[2,1-f][1,2,4]triazin-7-yl)-2-(2,2,6-trimethyl-3-oxomorpholino)benzonitrile (653); (S)-4-(4-amino-5-(trifluoromethyl)pyrrolo[2,1-f][1,2,4]triazin-7-yl)-2-(2,2,5-trimethyl-3-oxomorpholino)benzonitrile (654); 1-(3-(4-amino-5-(2-isopropyl-1-methyl-1H-imidazol-5-yl)pyrrolo[2,1-f][1,2,4]triazin-7-yl)phenyl)-4-(cyclopropanecarbonyl)-3,3-dimethylpiperazin-2-one (655); 4-acetyl-1-(3-(4-amino-5-(2-isopropyl-1-methyl-1H-imidazol-5-yl)pyrrolo[2,1-f][1,2,4]triazin-7-yl)phenyl)-3,3-dimethylpiperazin-2-one (656); 4-acetyl-1-(3-(4-amino-5-(1-(2,2,2-trifluoroethyl)-1H-pyrazol-5-yl)pyrrolo[2,1-f][1,2,4]triazin-7-yl)phenyl)-3,3-dimethyl-5,5,6,6-tetradeuteropiperazin-2-one (657); (S)-7-(3-(4-acetyl-3,3,6-trimethyl-2-oxopiperazin-1-yl)-4-methoxyphenyl)-4-aminopyrrolo [2,1-f][1,2,4]triazine-5-carbonitrile (658); 7-(3-(4-acetyl-3,3-dimethyl-2-oxo-5,5,6,6-tetradeutero-piperazin-1-yl)phenyl)-4-aminopyrrolo[2,1-f][1,2,4]triazine-5-carbonitrile (659); 4-(4-amino-5-chloropyrrolo[2,1-f][1,2,4]triazin-7-yl)-2-(3,3-dimethyl-4-(2-(methylsulfonyl)acetyl)-2-oxopiperazin-1-yl)benzonitrile (660); (S)-7-(3-(4-acetyl-3,3,6-trimethyl-2-oxopiperazin-1-yl)-4-chlorophenyl)-4-aminopyrrolo[2,1-f][1,2,4]triazine-5-carbonitrile (661); 4-acetyl-1-(3-(4-amino-5-(1-(1,1,1-trifluoropropan-2-yl)-1H-pyrazol-5-yl)pyrrolo[2,1-f][1,2,4]triazin-7-yl)-2-fluorophenyl)-3,3-dimethyl-5,5,6,6-tetradeuteropiperazin-2-one (chiral)(662); 2-((3S,6S)-4-acetyl-3,6-dimethyl-2-oxopiperazin-1-yl)-4-(4-amino-5-(trifluoromethyl)pyrrolo[2,1-f][1,2,4]triazin-7-yl)benzonitrile (663); (4-acetyl-1-(3-(4-amino-5-(trifluoromethyl)pyrrolo[2,1-f][1,2,4]triazin-7-yl)phenyl)-5,5-dimethyl-6-oxopiperazin-2-yl)methyl acetate (664); (4-acetyl-1-(3-(4-amino-5-(1-(2,2,2-trifluoroethyl)-1H-pyrazol-5-yl)pyrrolo[2,1-f][1,2,4]triazin-7-yl)phenyl)-5,5-dimethyl-6-oxopiperazin-2-yl)methyl acetate (665); (4-acetyl-1-(3-(4-amino-5-chloropyrrolo[2,1-f][1,2,4]triazin-7-yl)phenyl)-5,5-dimethyl-6-oxopiperazin-2-yl)methyl acetate (666); (4-acetyl-1-(3-(4-amino-5-(1-methyl-1H-pyrazol-4-yl)pyrrolo [2,1-f][1,2,4]triazin-7-yl)phenyl)-5,5-dimethyl-6-oxopiperazin-2-yl)methyl acetate (667); 4-acetyl-1-(3-(4-amino-5-chloropyrrolo[2,1-f][1,2,4]triazin-7-yl)phenyl)-6-(hydroxymethyl)-3,3-dimethylpiperazin-2-one (668); 4-acetyl-1-(3-(4-amino-5-(1-methyl-1H-pyrazol-4-yl)pyrrolo[2,1-f][1,2,4]triazin-7-yl)phenyl)-6-(hydroxymethyl)-3,3-dimethylpiperazin-2-one (669); 4-acetyl-1-(3-(4-amino-5-chloropyrrolo[2,1-f][1,2,4]triazin-7-yl)phenyl)-6-(methoxymethyl)-3,3-dimethylpiperazin-2-one (670); 4-acetyl-1-(3-(4-amino-5-(trifluoromethyl)pyrrolo[2,1-f][1,2,4]triazin-7-yl)phenyl)-6-(methoxymethyl)-3,3-dimethylpiperazin-2-one (671); (S)-7-(3-(4-acetyl-3,3,6-trimethyl-2-oxopiperazin-1-yl)-4-(methylsulfonyl)phenyl)-4-aminopyrrolo[2,1-f][1,2,4]triazine-5-carbonitrile (672); (S)-4-acetyl-1-(5-(4-amino-5-(trifluoromethyl)pyrrolo[2,1-f][1,2,4]triazin-7-yl)-2-(methylsulfonyl)phenyl)-3,3,6-trimethylpiperazin-2-one (673); (S)-4-acetyl-1-(5-(4-amino-5-(trifluoromethyl)pyrrolo[2,1-f][1,2,4]triazin-7-yl)-2-(methylsulfonyl)phenyl)-3,3,6-trimethylpiperazin-2-one (674); (S)-4-acetyl-1-(5-(4-amino-5-chloropyrrolo[2,1-f][1,2,4]triazin-7-yl)-2-(methylsulfonyl)phenyl)-3,3,6-trimethylpiperazin-2-one (675); (S)-4-acetyl-1-(5-(4-amino-5-chloropyrrolo[2,1-f][1,2,4]triazin-7-yl)-2-(methylsulfonyl)phenyl)-3,3,6-trimethylpiperazin-2-one (676); (S)-4-acetyl-1-(5-(4-amino-5-(trifluoromethyl)pyrrolo[2,1-f][1,2,4]triazin-7-yl)-2-fluorophenyl)-3,3,6-trimethylpiperazin-2-one (677); (S)-4-acetyl-1-(5-(4-amino-5-chloropyrrolo[2,1-f][1,2,4]triazin-7-yl)-2-fluorophenyl)-3,3,6-trimethylpiperazin-2-one (678); (S)-4-acetyl-1-(5-(4-amino-5-(1-(2,2,2-trifluoroethyl)-1H-pyrazol-5-yl)pyrrolo [2,1-f][1,2,4]triazin-7-yl)-2-fluorophenyl)-3,3,6-trimethylpiperazin-2-one (679); (S)-4-acetyl-1-(5-(4-amino-5-(1-((R)-1,1,1-trifluoropropan-2-yl)-1H-pyrazol-5-yl)pyrrolo[2,1-f][1,2,4]triazin-7-yl)-2-fluorophenyl)-3,3,6-trimethylpiperazin-2-one (680); (S)-4-acetyl-1-(5-(4-amino-5-(1-((S)-1,1,1-trifluoropropan-2-yl)-1H-pyrazol-5-yl)pyrrolo[2,1-f][1,2,4]triazin-7-yl)-2-fluorophenyl)-3,3,6-trimethylpiperazin-2-one (681); (S)-7-(3-(4-acetyl-3,3,6-trimethyl-2-oxopiperazin-1-yl)-4-fluorophenyl)-4-aminopyrrolo[2,1-f][1,2,4]triazine-5-carbonitrile (682); (S)-4-acetyl-1-(5-(4-amino-5-(1-methyl-1H-pyrazol-4-yl)pyrrolo[2,1-f][1,2,4]triazin-7-yl)-2-fluorophenyl)-3,3,6-trimethylpiperazin-2-one (683); (S)-4-acetyl-1-(5-(4-amino-5-(1-cyclopropyl-1H-pyrazol-4-yl)pyrrolo[2,1-f][1,2,4]triazin-7-yl)-2-fluorophenyl)-3,3,6-trimethylpiperazin-2-one (684); 2-(4-acetyl-3-ethyl-3-methyl-2-oxopiperazin-1-yl)-4-(4-amino-5-chloropyrrolo[2,1-f][1,2,4]triazin-7-yl)benzonitrile (685); 2-(4-acetyl-3-ethyl-3-methyl-2-oxopiperazin-1-yl)-4-(4-amino-5-(trifluoromethyl)pyrrolo[2,1-f][1,2,4]triazin-7-yl)benzonitrile (686); (R)-2-(4-acetyl-3-ethyl-3-methyl-2-oxopiperazin-1-yl)-4-(4-amino-5-chloropyrrolo[2,1-f][1,2, 4]triazin-7-yl)benzonitrile (687); (S)-2-(4-acetyl-3-ethyl-3-methyl-2-oxopiperazin-1-yl)-4-(4-amino-5-chloropyrrolo[2,1-f][1,2,4]triazin-7-yl)benzonitrile (689); (S)-2-(4-acetyl-3-ethyl-3-methyl-2-oxopiperazin-1-yl)-4-(4-amino-5-(trifluoromethyl)pyrrolo[2,1-f][1,2,4]triazin-7-yl) benzonitrile (690); (R)-2-(4-acetyl-3-ethyl-3-methyl-2-oxopiperazin-1-yl)-4-(4-amino-5-(trifluoromethyl)pyrrolo[2,1-f][1,2,4]triazin-7-yl)benzonitrile (691); 1-(3-(4-amino-5-chloropyrrolo[2,1-f][1,2,4]triazin-7-yl)phenyl)-3,3-dimethylpiperidin-2-one (692); 1-(3-(4-amino-5-(trifluoromethyl)pyrrolo[2,1-f][1,2,4]triazin-7-yl)phenyl)-3,3-dimethylpiperidin-2-one (693); 4-amino-7-(3-(3-oxomorpholino)phenyl)pyrrolo[2,1-f][1,2,4]triazine-5-carbonitrile (694); 4-amino-7-(3-(2,2-dimethyl-3-oxomorpholino) phenyl)pyrrolo[2,1-f][1,2,4]triazine-5-carbonitrile (695); (R)-4-(3-(4-amino-5-chloropyrrolo[2,1-f][1,2,4]triazin-7-yl)phenyl)-2,2,5-trimethylmorpholin-3-one (696); (R)-4-(3-(4-amino-5-(trifluoromethyl)pyrrolo[2,1-f][1,2,4]triazin-7-yl)phenyl)-2,2,5-trimethylmorpholin-3-one (697); (S)-4-(3-(4-amino-5-(trifluoromethyl)pyrrolo[2,1-f][1,2,4]triazin-7-yl)phenyl)-2,2,6-trimethylmorpholin-3-one (698); (S)-4-(3-(4-amino-5-chloropyrrolo[2,1-f][1,2,4]triazin-7-yl)phenyl)-2,2,6-trimethylmorpholin-3-one (699); (R)-4-(3-(4-amino-5-(1-(2,2,2-trifluoroethyl)-1H-pyrazol-5-yl)pyrrolo[2,1-f][1,2,4]triazin-7-yl)phenyl)-2,2,5-trimethylmorpholin-3-one (700); (R)-4-amino-7-(3-(2,2,5-trimethyl-3-oxomorpholino)phenyl)pyrrolo[2,1-f][1,2,4]triazine-5-carbonitrile (701); (S)-4-amino-7-(3-(2,2,6-trimethyl-3-oxomorpholino)phenyl)pyrrolo[2,1-f][1,2,4]triazine-5-carbonitrile (702); (R)-4-(3-(4-amino-5-(1-(2,2,2-trifluoroethyl)-1H-pyrazol-5-yl)pyrrolo[2,1-f][1,2,4]triazin-7-yl)phenyl)-2,2,5-trimethylmorpholin-3-one (703); 4-(4-amino-5-(trifluoromethyl)pyrrolo[2,1-f][1,2,4]triazin-7-yl)-2-(2,2-dimethyl-5-(methyl-d$_3$)-3-oxomorpholino-5,6,6-d$_3$)benzonitrile (704); 4-(4-amino-5-chloropyrrolo[2,1-f][1,2,4]triazin-7-yl)-2-(2,2-dimethyl-5-(methyl-d$_3$)-3-oxomorpholino-5,6,6-d$_3$)benzonitrile (705); 4-(4-amino-5-(trifluoromethyl)pyrrolo[2,1-f][1,2,4]triazin-7-yl)-2-(2,2-dimethyl-5-(methyl-d$_3$)-3-oxomorpholino-5,6,6-d$_3$) benzonitrile (706); 4-(4-amino-5-chloropyrrolo [2,1-f][1,2,4]triazin-7-yl)-2-(2,2-dimethyl-5-(methyl-d$_3$)-3-oxomorpholino-5,6,6-d$_3$)benzonitrile (707); (S)-4-(5-(4-amino-5-(trifluoromethyl)pyrrolo[2,1-f][1,2,4]triazin-7-yl)-2-(methylsulfonyl)phenyl)-2,2,5-trimethylmorpholin-3-one (708); 4-(4-amino-5-(trifluoromethyl)pyrrolo[2,1-f][1,2,4]triazin-7-yl)-2-((5S,6S)-2,2,5,6-tetramethyl-3-oxomorpholino)benzonitrile (709); (S)-4-(5-(4-amino-5-(1-(2,2,2-trifluoroethyl)-1H-pyrazol-5-yl)pyrrolo[2,1-f][1,2,4]triazin-7-yl)-2-(methylsulfonyl)phenyl)-2,2,5-trimethylmorpholin-3-one (710); (S)-4-(5-(4-amino-5-(1-(2,2,2-trifluoroethyl)-1H-pyrazol-5-yl)pyrrolo[2,1-f][1,2,4]triazin-7-yl)-2-(methylsulfonyl)phenyl)-2,2,5-trimethylmorpholin-3-one (711); (R)-4-(5-(4-amino-5-(1-(2,2,2-trifluoroethyl)-1H-pyrazol-5-yl)pyrrolo[2,1-f][1,2,4]triazin-7-yl)-2-(methylsulfonyl)phenyl)-2,2,6-trimethylmorpholin-3-one (712); (S)-4-amino-7-(4-cyano-3-(2,2,6-trimethyl-3-oxomorpholino)phenyl)pyrrolo[2,1-f][1,2,4]triazine-5-carbonitrile (713); 4-(4-amino-5-(1-(2,2,2-trifluoroethyl)-1H-pyrazol-5-yl)pyrrolo[2,1-f][1,2,4]triazin-7-yl)-2-((5S,6S)-2,2,5,6-tetramethyl-3-oxomorpholino)benzonitrile (714); 4-(4-amino-5-chloropyrrolo [2,1-f][1,2,4]triazin-7-yl)-2-((5S,6S)-2,2,5,6-tetramethyl-3-oxomorpholino)benzonitrile (715); (S)-4-(5-(4-amino-5-chloropyrrolo[2,1-f][1,2,4]triazin-7-yl)-2-(methylsulfonyl) phenyl)-2,2,5-trimethylmorpholin-3-one (716); (S)-4-(5-(4-amino-5-(trifluoromethyl) pyrrolo[2,1-f][1,2,4]triazin-7-yl)-2-(methylsulfonyl)phenyl)-2,2,5-trimethylmorpholin-3-one (717); (R)-4-(5-(4-amino-5-chloropyrrolo[2,1-f][1,2,4]triazin-7-yl)-2-(methylsulfonyl)phenyl)-2,2,6-trimethylmorpholin-3-one (718); (R)-4-(5-(4-amino-5-chloropyrrolo[2,1-f][1,2,4]triazin-7-yl)-2-fluorophenyl)-2,2,5-trimethylmorpholin-3-one (719); (S)-4-(5-(4-amino-5-chloropyrrolo[2,1-f][1,2,4]triazin-7-yl)-2-fluorophenyl)-2,2,6-trimethylmorpholin-3-one (720); (R)-4-(5-(4-amino-5-(trifluoromethyl)pyrrolo[2,1-f][1,2,4]triazin-7-yl)-2-fluorophenyl)-2,2,5-trimethylmorpholin-3-one (721); (S)-4-(5-(4-amino-5-(trifluoromethyl)pyrrolo[2,1-f][1,2,4]triazin-7-yl)-2-fluorophenyl)-2,2,6-trimethylmorpholin-3-one (722); 4-amino-7-(4-cyano-3-(2,2-dimethyl-3-oxomorpholino-5,5,6,6-d$_4$)phenyl)pyrrolo[2,1-f][1,2,4]triazine-5-carbonitrile (723); (R)-4-amino-7-(4-(methylsulfonyl)-3-(2,2,5-trimethyl-3-oxomorpholino)phenyl)pyrrolo[2,1-f][1,2,4]triazine-5-carbonitrile (724); 4-amino-7-(3-(2,2-dimethyl-3-oxomorpholino)-4-methoxyphenyl)pyrrolo[2,1-f][1,2,4]triazine-5-carbonitrile (725); (R)-4-(5-(4-amino-5-(1-(2,2,2-trifluoroethyl)-1H-pyrazol-5-yl)pyrrolo[2,1-f][1,2,4]triazin-7-yl)-2-fluorophenyl)-2,2,5-trimethylmorpholin-3-one (726); (S)-4-(5-(4-amino-5-(1-(2,2,2-trifluoroethyl)-1H-pyrazol-5-yl)pyrrolo[2,1-f][1,2,4]triazin-7-yl)-2-fluorophenyl)-2,2,6-trimethylmorpholin-3-one (727); (R)-4-(4-amino-5-chloropyrrolo[2,1-f][1,2,4]triazin-7-yl)-2-(2,2,5-trimethyl-3-oxomorpholino)benzamide (728); (R)-4-(4-amino-5-(trifluoromethyl)pyrrolo[2,1-f][1,2,4]triazin-7-yl)-2-(2,2,5-trimethyl-3-oxomorpholino) benzamide (729); (S)-4-(4-amino-5-chloropyrrolo[2,1-f][1,2,4]triazin-7-yl)-2-(5-ethyl-2,2-dimethyl-3-oxomorpholino)benzonitrile (730); (S)-4-(4-amino-5-chloropyrrolo[2,1-f][1,2,4]triazin-7-yl)-2-(5-ethyl-2,2-dimethyl-3-oxomorpholino)benzonitrile (731); (S)-4-(4-amino-5-(1-(2,2,2-trifluoroethyl)-1H-pyrazol-5-yl)pyrrolo[2,1-f][1,2,4]triazin-7-yl)-2-(5-ethyl-2,2-dimethyl-3-oxomorpholino)benzonitrile (732); (S)-4-(4-amino-5-(1-(2,2,2-trifluoroethyl)-1H-pyrazol-5-yl)pyrrolo[2,1-f][1,2,4]triazin-7-yl)-2-(5-ethyl-2,2-dimethyl-3-oxomorpholino) benzonitrile (733); (S)-4-(4-amino-5-(trifluoromethyl)pyrrolo[2,1-f][1,2,4]triazin-7-yl)-2-(5-ethyl-2,2-dimethyl-3-oxomorpholino)benzonitrile (734); (S)-4-(4-amino-5-(trifluoromethyl)pyrrolo[2,1-f][1,2,4]triazin-7-yl)-2-(5-ethyl-2,2-dimethyl-3-oxomorpholino)benzonitrile (735); 3-(2-(4-(3-(4-amino-5-(trifluoromethyl)pyrrolo[2,1-f][1,2,4]triazin-7-yl)phenyl)-2,2-dimethyl-3-oxopiperazin-1-yl)-2-oxoethyl)oxazolidin-2-one (736); (R)-4-(4-amino-5-(trifluoromethyl)pyrrolo[2,1-f][1,2,4]triazin-7-yl)-2-(4-(2-hydroxypropanoyl)-3,3-dimethyl-2-oxopiperazin-1-yl) benzonitrile (737); 3-(2-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl)oxazolidin-2-one (738); 3-(2-(4-(5-(4-amino-5-(trifluoromethyl)pyrrolo[2,1-f][1,2,4]triazin-7-yl)-2-fluorophenyl)-2,2-dimethyl-3-oxopiperazin-1-yl)-2-oxoethyl)oxazolidin-2-one (739); 3-(2-(4-(3-(4-amino-5-chloropyrrolo[2,1-f][1,2,4]triazin-7-yl)phenyl)-2,2-dimethyl-3-oxopiperazin-1-yl)-2-oxoethyl)oxazolidin-2-one (740); N-(3-(4-(5-(4-amino-5-chloropyrrolo[2,1-f][1,2,4]triazin-7-yl)-2-cyanophenyl)-2,2-dimethyl-3-oxopiperazin-1-yl)-3-oxopropyl)acetamide (741); 4-(4-amino-5-chloropyrrolo[2,1-f][1,2,4]triazin-7-yl)-2-(3,3-dimethyl-4-(3-(3-methyl-1H-pyrazol-1-yl)propanoyl)-2-oxopiperazin-1-yl)benzonitrile (742); 4-(4-amino-5-chloropyrrolo[2,1-f][1,2,4]triazin-7-yl)-2-(4-(2-(1,1-dioxido-1,2-thiazinan-2-yl)acetyl)-3,3-dimethyl-2-oxopiperazin-1-yl)benzonitrile (743); 1-(3-(4-amino-5-chloropyrrolo[2,1-f][1,2,4]triazin-7-yl)phenyl)-3,3-dimethyl-4-(2-(methylsulfonyl)acetyl)piperazin-2-one (744); N-(3-(4-(3-(4-amino-5-chloropyrrolo[2,1-f][1,2,4]triazin-7-yl)phenyl)-2,2-dimethyl-3-oxopiperazin-1-yl)-3-oxopropyl)acetamide (745); 1-(3-(4-amino-5-chloropyrrolo

[2,1-f][1,2,4]triazin-7-yl)phenyl)-3,3-dimethyl-4-(2-(2-oxopyrrolidin-1-yl)acetyl)piperazin-2-one (746); 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile (747); N-(3-(4-(3-(4-amino-5-(trifluoromethyl)pyrrolo[2,1-f][1,2,4]triazin-7-yl)phenyl)-2,2-dimethyl-3-oxopiperazin-1-yl)-3-oxopropyl) methanesulfonamide (748); N-(3-(4-(3-(4-amino-5-chloropyrrolo[2,1-f][1,2,4]triazin-7-yl)phenyl)-2,2-dimethyl-3-oxopiperazin-1-yl)-3-oxopropyl) methanesulfonamide (749); N-(3-(4-(3-(4-amino-5-cyanopyrrolo[2,1-f][1,2,4]triazin-7-yl)phenyl)-2,2-dimethyl-3-oxopiperazin-1-yl)-3-oxopropyl) methanesulfonamide (750); N-(3-(4-(5-(4-amino-5-(trifluoromethyl)pyrrolo[2,1-f][1,2,4]triazin-7-yl)-2-fluorophenyl)-2,2-dimethyl-3-oxopiperazin-1-yl)-3-oxopropyl) methanesulfonamide (751); 1-(5-(4-amino-5-chloropyrrolo[2,1-f][1,2,4]triazin-7-yl)-2-fluorophenyl)-3,3-dimethyl-4-(2-(methylsulfonyl)acetyl)piperazin-2-one (752); N-(3-(4-(5-(4-amino-5-chloropyrrolo[2,1-f][1,2,4]triazin-7-yl)-2-fluorophenyl)-2,2-dimethyl-3-oxopiperazin-1-yl)-3-oxopropyl)acetamide (753); N-(3-(4-(5-(4-amino-5-chloropyrrolo [2,1-f][1,2,4]triazin-7-yl)-2-fluorophenyl)-2,2-dimethyl-3-oxopiperazin-1-yl)-3-oxopropyl) methanesulfonamide (754); 1-(5-(4-amino-5-chloropyrrolo[2,1-f][1,2,4]triazin-7-yl)-2-fluorophenyl)-3,3-dimethyl-4-(2-(methylsulfonyl)propanoyl)piperazin-2-one (755); N-(2-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl)acetamide (756); 4-(4-amino-5-chloropyrrolo[2,1-f][1,2,4]triazin-7-yl)-2-(4-(3-hydroxy-3-methylbutanoyl)-3,3-dimethyl-2-oxopiperazin-1-yl)benzonitrile (757); 1-(5-(4-amino-5-chloropyrrolo[2,1-f][1,2,4]triazin-7-yl)-2-fluorophenyl)-4-(2-(1,1-dioxidothiomorpholino)acetyl)-3,3-dimethylpiperazin-2-one (758); 1-(5-(4-amino-5-chloropyrrolo[2,1-f][1,2,4]triazin-7-yl)-2-fluorophenyl)-4-(3-hydroxy-3-methylbutanoyl)-3,3-dimethylpiperazin-2-one (759); 1-(5-(4-amino-5-(trifluoromethyl)pyrrolo[2,1-f][1,2,4]triazin-7-yl)-2-fluorophenyl)-4-(3-hydroxy-3-methylbutanoyl)-3,3-dimethylpiperazin-2-one (760); 1-(3-(4-amino-5-(trifluoromethyl)pyrrolo[2,1-f][1,2,4]triazin-7-yl)phenyl)-4-(3-hydroxy-3-methylbutanoyl)-3,3-dimethylpiperazin-2-one (761); 1-(3-(4-amino-5-chloropyrrolo[2,1-f][1,2,4]triazin-7-yl)phenyl)-4-(3-hydroxy-3-methylbutanoyl)-3,3-dimethylpiperazin-2-one (762); (S)-4-(4-amino-5-chloropyrrolo[2,1-f][1,2,4]triazin-7-yl)-2-(3,3,6-trimethyl-4-(2-(methylsulfonyl)acetyl)-2-oxopiperazin-1-yl)benzonitrile (763); 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile (764); 4-(4-amino-5-(trifluoromethyl)pyrrolo[2,1-f][1,2,4]triazin-7-yl)-2-(4-(2-(4,4-dimethyl-2-oxopyrrolidin-1-yl)acetyl)-3,3-dimethyl-2-oxopiperazin-1-yl)benzonitrile (765); 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile (766); 1-(5-(4-amino-5-(trifluoromethyl)pyrrolo[2,1-f][1,2,4]triazin-7-yl)-2-methoxyphenyl)-3,3-dimethyl-4-(2-(methylsulfonyl)propanoyl)piperazin-2-one (767); N-(2-(4-(5-(4-amino-5-(trifluoromethyl)pyrrolo[2,1-f][1,2,4]triazin-7-yl)-2-cyanophenyl)-2,2-dimethyl-3-oxopiperazin-1-yl)-2-oxoethyl)methanesulfonamide (768); (S)-1-(5-(4-amino-5-chloropyrrolo[2,1-f][1,2,4]triazin-7-yl)-2-fluorophenyl)-3,3,6-trimethyl-4-(2-(methylsulfonyl)acetyl)piperazin-2-one (769); (S)-1-(5-(4-amino-5-(trifluoromethyl) pyrrolo[2,1-f][1,2,4]triazin-7-yl)-2-fluorophenyl)-3,3,6-trimethyl-4-(2-(methylsulfonyl) acetyl)piperazin-2-one (770); 4-(4-amino-5-chloropyrrolo[2,1-f][1,2,4]triazin-7-yl)-2-(4-(2-(4,4-dimethyl-2-oxopyrrolidin-1-yl)acetyl)-3,3-dimethyl-2-oxopiperazin-1-yl)benzonitrile (771); N-(2-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl) methanesulfonamide (772); N-(2-(4-(5-(4-amino-5-chloropyrrolo[2,1-f][1,2,4]triazin-7-yl)-2-cyanophenyl)-2,2-dimethyl-3-oxopiperazin-1-yl)-2-oxoethyl) methanesulfonamide (773); 4-(4-amino-5-(trifluoromethyl) pyrrolo[2,1-f][1,2,4]triazin-7-yl)-2-(4-(3-hydroxy-3-methylbutanoyl)-3,3-dimethyl-2-oxopiperazin-1-yl) benzonitrile (774); N-(1-(4-(5-(4-amino-5-chloropyrrolo[2,1-f][1,2,4]triazin-7-yl)-2-methoxyphenyl)-2,2-dimethyl-3-oxopiperazin-1-yl)-1-oxopropan-2-yl)methanesulfonamide (775); N-(2-(4-(5-(4-amino-5-(trifluoromethyl)pyrrolo[2,1-f][1,2,4]triazin-7-yl)-2-fluorophenyl)-2,2-dimethyl-3-oxopiperazin-1-yl)-2-oxoethyl)methanesulfonamide (776); 2-(4-acetyl-3,3-dimethylpiperazin-1-yl)-4-(4-amino-5-chloropyrrolo[2,1-f][1,2,4]triazin-7-yl)benzonitrile (777); 7-(3-(4-acetyl-3,3-dimethylpiperazin-1-yl)-4-cyanophenyl)-4-aminopyrrolo[2,1-f][1,2,4]triazine-5-carbonitrile (778); 2-(4-acetyl-3,3-dimethylpiperazin-1-yl)-4-(4-amino-5-(1-(methyl-d$_3$)-1H-pyrazol-4-yl)pyrrolo[2,1-f][1,2,4]triazin-7-yl)benzonitrile (779); 2-(4-acetyl-3,3-dimethylpiperazin-1-yl)-4-(4-amino-5-(1-(2,2,2-trifluoroethyl)-1H-pyrazol-5-yl)pyrrolo[2,1-f][1,2,4]triazin-7-yl)benzonitrile (780); 2-(4-acetyl-3,3-dimethylpiperazin-1-yl)-4-(4-amino-5-(trifluoromethyl)pyrrolo[2,1-f][1,2,4]triazin-7-yl) benzonitrile (781); 1-(4-(3-(4-amino-5-chloropyrrolo[2,1-f][1,2,4]triazin-7-yl)phenyl)-3-(pyrrolidine-1-carbonyl) piperazin-1-yl)ethan-1-one (782); 4-acetyl-1-(3-(4-amino-5-chloropyrrolo[2,1-f][1,2,4]triazin-7-yl)phenyl)-N,N-dimethylpiperazine-2-carboxamide (783); 4-(4-amino-5-(1-(2,2,2-trifluoroethyl)-1H-pyrazol-5-yl)pyrrolo[2,1-f][1,2,4] triazin-7-yl)-2-((4aR,8aS)-2,2-dimethyl-3-oxooctahydro-4H-benzo[b][1,4]oxazin-4-yl)benzonitrile (784); 4-(3-(4-amino-5-(trifluoromethyl)pyrrolo[2,1-f][1,2,4]triazin-7-yl) phenyl)-2,2-dimethyl-2H-benzo[b][1,4]oxazin-3(4H)-one (785); methyl 2-(4-acetyl-3,3-dimethyl-2-oxopiperazin-1-yl)-4-(4-amino-5-(trifluoromethyl)pyrrolo[2,1-f][1,2,4]triazin-7-yl)benzoate (786); 4-acetyl-1-(5-(4-amino-5-(trifluoromethyl)pyrrolo [2,1-f][1,2,4]triazin-7-yl)-2-(4-methylpiperazine-1-carbonyl)phenyl)-3,3-dimethylpiperazin-2-one (787); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(3-hydroxypropyl) benzamide (788); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-hydroxy-2-methylpropyl)-N-methylbenzamide (789); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-hydroxyethyl)-N-methylbenzamide (790); 2-(4-acetyl-3,3-dimethyl-2-oxopiperazin-1-yl)-4-(4-amino-5-(trifluoromethyl)pyrrolo[2,1-f][1,2,4]triazin-7-yl)-N-cyclopropylbenzamide (791); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-hydroxyethyl)benzamide (792); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(cyanomethyl)benzamide (793); 2-(4-acetyl-3,3-dimethyl-2-oxopiperazin-1-yl)-4-(4-amino-5-(trifluoromethyl) pyrrolo[2,1-f][1,2,4]triazin-7-yl)benzamide (794); 2-(4-acetyl-3,3-dimethyl-2-oxopiperazin-1-yl)-4-(4-amino-5-(trifluoromethyl)pyrrolo[2,1-f][1,2,4]triazin-7-yl)-N-methylbenzamide (795); 2-(4-acetyl-3,3-dimethyl-2-oxopiperazin-1-yl)-4-(4-amino-5-(trifluoromethyl)pyrrolo[2,1-f][1,2,4]triazin-7-yl)-N-ethylbenzamide (796); 2-(4- acetyl-3,3-dimethyl-2-oxopiperazin-1-yl)-4-(4-amino-5-(trifluoromethyl)pyrrolo [2,1-f][1,2,4]triazin-7-yl)-N,N-dimethylbenzamide (797); 2-(4-acetyl-3,3-dimethyl-2-oxopiperazin-1-yl)-4-(4-amino-5-(trifluoromethyl)pyrrolo [2,1-f][1,2,4]triazin-7-yl)-N-(2-fluoroethyl)benzamide (798); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(3-hydroxy-3-methylbutyl) benzamide (799); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-(methylsulfonyl)ethyl)benzamide (800); 4-acetyl-1-(5-(4-amino-5-(trifluoromethyl)pyrrolo[2,1-f][1,2,4]triazin-7-yl)-2-(morpholine-4-carbonyl)phenyl)-3,3-dimethylpiperazin-2-one (801); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2,2-difluoroethyl)benzamide (802); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-(dimethylamino)ethyl)-N-methylbenzamide (803); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-methoxyethyl)-N-methylbenzamide (804); 4-acetyl-1-(5-(4-amino-5-(trifluoromethyl) pyrrolo[2,1-f][1,2,4]triazin-7-yl)-2-(pyrrolidine-1-carbonyl)phenyl)-3,3-dimethylpiperazin-2-one (805); 2-(4-acetyl-3,3-dimethyl-2-oxopiperazin-1-yl)-4-(4-amino-5-(trifluoromethyl)pyrrolo[2,1-f][1,2,4]triazin-7-yl)-N-isopropylbenzamide (806); 2-(4-acetyl-3,3-dimethyl-2-oxopiperazin-1-yl)-4-(4-amino-5-(trifluoromethyl)pyrrolo [2,1-f][1,2,4]triazin-7-yl)-N-(2-methoxyethyl)benzamide (807); 2-(4-acetyl-3,3-dimethyl-2-oxopiperazin-1-yl)-4-(4-amino-5-(trifluoromethyl) pyrrolo[2,1-f][1,2,4]triazin-7-yl)-N-(pyridin-3-yl) benzamide (808); 2-(4-acetyl-3,3-dimethyl-2-oxopiperazin-1-yl)-4-(4-amino-5-(trifluoromethyl)pyrrolo[2,1-f][1,2,4] triazin-7-yl)-N-(2-(dimethylamino)ethyl) benzamide (809); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(methyl-d₃)benzamide (810); 7-(3-(4-acetyl-3,3-dimethyl-2-oxopiperazin-1-yl)-4-(1-methyl-1H-1,2,4-triazol-3-yl) phenyl)-4-aminopyrrolo[2,1-f][1,2,4]triazine-5-carbonitrile (811); (R)-4-acetyl-1-(5-(4-amino-5-(trifluoromethyl)pyrrolo[2,1-f][1,2,4]triazin-7-yl)-2-(1-hydroxyethyl)phenyl)-3,3-dimethylpiperazin-2-one (812); (S)-4-acetyl-1-(5-(4-amino-5-(trifluoromethyl)pyrrolo [2,1-f][1,2,4]triazin-7-yl)-2-(1-hydroxyethyl)phenyl)-3,3-dimethylpiperazin-2-one (813); 4-acetyl-1-(5-(4-amino-5-(trifluoromethyl)pyrrolo[2,1-f][1,2,4]triazin-7-yl)-2-(methoxymethyl)phenyl)-3,3-dimethylpiperazin-2-one (814); 4-acetyl-1-(5-(4-amino-5-chloropyrrolo[2,1-f][1,2,4]triazin-7-yl)-2-(methoxymethyl) phenyl)-3,3-dimethylpiperazin-2-one (815); (R)-4-acetyl-1-(5-(4-amino-5-(trifluoromethyl)pyrrolo [2,1-f][1,2,4]triazin-7-yl)-2-(1-hydroxypropyl)phenyl)-3,3-dimethylpiperazin-2-one (816); (S)-4-acetyl-1-(5-(4-amino-5-(trifluoromethyl) pyrrolo[2,1-f][1,2,4]triazin-7-yl)-2-(1-hydroxypropyl) phenyl)-3,3-dimethylpiperazin-2-one (817); (S)-4-acetyl-1-(5-(4-amino-5-chloropyrrolo[2,1-f][1,2,4]triazin-7-yl)-2-(1-hydroxypropyl)phenyl)-3,3-dimethylpiperazin-2-one (818); (R)-4-acetyl-1-(5-(4-amino-5-chloropyrrolo[2,1-f][1,2,4] triazin-7-yl)-2-(1-hydroxypropyl)phenyl)-3,3-dimethylpiperazin-2-one (819); 4-acetyl-1-(3-(4-amino-5-(2-methyl-1-(2,2,2-trifluoroethyl)-1H-imidazol-5-yl)pyrrolo[2,1-f][1,2,4]triazin-7-yl)phenyl)-3,3-dimethylpiperazin-2-one (820); (R)-4-(4-amino-5-(1,2-dimethyl-1H-imidazol-5-yl)pyrrolo [2,1-f][1,2,4]triazin-7-yl)-2-(2,2,6-trimethyl-3-oxomorpholino) benzonitrile (821); 4-acetyl-1-(3-(4-amino-5-(4-methyl-1H-pyrazol-1-yl)pyrrolo[2,1-f][1,2,4]triazin-7-yl) phenyl)-3,3-dimethylpiperazin-2-one (822); 2-(4-acetyl-3,3-dimethylpiperazin-1-yl)-4-(4-amino-5-chloro-6-fluoropyrrolo[2,1-f][1,2,4]triazin-7-yl)benzonitrile (823); (R)-4-(5-(4-amino-5-chloro-6-fluoropyrrolo[2,1-f][1,2,4] triazin-7-yl)-2-fluorophenyl)-2,2,5-trimethylmorpholin-3-one (824); (S)-4-(5-(4-amino-5-chloro-6-fluoropyrrolo[2,1-f][1,2,4]triazin-7-yl)-2-fluorophenyl)-2,2,6-trimethylmorpholin-3-one (825); 4-(3-(4-amino-5-chloro-6-fluoropyrrolo[2,1-f][1,2,4]triazin-7-yl)phenyl) morpholin-3-one (826); 4-(4-amino-5-chloro-6-fluoropyrrolo[2,1-f][1,2,4]triazin-7-yl)-2-(2,2-dimethyl-3-oxomorpholino) benzonitrile (827); 4-(3-(4-amino-5-chloro-6-fluoropyrrolo[2,1-f][1,2,4]triazin-7-yl)phenyl)morpholin-3-one (828); 4-(3-(4-amino-5-chloro-6-fluoropyrrolo[2,1-f][1,2,4]triazin-7-yl)phenyl)-2,2-dimethyl-3-oxopiperazine-1-carbonitrile (829); 4-(3-(4-amino-5-chloro-6-fluoropyrrolo[2,1-f] [1,2,4]triazin-7-yl)phenyl)-2,2-dimethylmorpholin-3-one (830); 4-(4-amino-5-chloro-6-fluoropyrrolo[2,1-f][1,2,4]triazin-7-yl)-2-(2,2-dimethyl-3-oxomorpholino-5,5,6,6-d₄) benzonitrile (831); 4-(5-(4-amino-5-chloro-6-fluoropyrrolo [2,1-f][1,2,4]triazin-7-yl)-2-methoxyphenyl)-2,2-dimethylmorpholin-3-one (832); 4-acetyl-1-(3-(4-amino-5-chloro-6-fluoropyrrolo[2,1-f][1,2,4]triazin-7-yl)-2-fluorophenyl)-3,3-dimethylpiperazin-2-one-5,5,6,6-d₄ (833); 4-acetyl-1-(5-(4-amino-5-chloro-6-fluoropyrrolo[2,1-f][1,2,4]triazin-7-yl)-2-fluorophenyl)-3,3-dimethylpiperazin-2-one (834); 4-acetyl-1-(3-(4-amino-5-chloro-6-fluoropyrrolo[2,1-f][1,2,4]triazin-7-yl)phenyl)-3,3-dimethylpiperazin-2-one-5,5,6,6-d₄ (835); 2-(4-acetyl-3,5-dimethylpiperazin-1-yl)-4-(4-amino-5-chloro-6-fluoropyrrolo[2,1-f][1,2,4]triazin-7-yl)benzonitrile (836); 2-(4-acetyl-3,3-dimethyl-2-oxopiperazin-1-yl)-4-(4-amino-5-chloro-6-fluoropyrrolo[2,1-f][1,2,4]triazin-7-yl)benzonitrile (837); and a salt thereof.

One embodiment provides a compound selected from any subset list of compounds within the scope of the first aspect or of any of the above embodiments.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art, ⊱ is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "deuteroalkyl" includes both branched and straight-chain saturated alkyl groups substituted with one or more deuterium atoms. Representative examples of deuteroalkyl groups include, but are not limited to, —$CD_3$ and —$CH_2CD_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include C1, C2, C3, and C4 alkyl groups substituted with one or more fluorine atoms. Representative examples of fluoroalkyl groups include, but are not limited to, —$CF_3$ and —$CH_2CF_3$.

The term "cyanoalkyl" includes both branched and straight-chain saturated alkyl groups substituted with one or more cyano groups. For example, "cyanoalkyl" includes —$CH_2CN$, —$CH_2CH_2CN$, and $C_{1-4}$ cyanoalkyl.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and $C_{1-4}$ hydroxyalkyl.

The term "hydroxyfluoroalkyl" includes both branched and straight-chain saturated alkyl groups substituted with one or more hydroxyl groups and one or more fluorine atoms. Representative examples of hydroxy-fluoroalkyl groups include, but are not limited to, —$CF_2OH$ and —$CF_2CH_2OH$.

The term "alkoxyalkoxy" as used herein, refers to an alkoxy group attached through an alkoxy group to the patent molecular moiety. For example, "($C_{1-3}$ alkoxy)-($C_{1-6}$ alkoxy)" denotes a $C_{1-3}$ alkoxy group attached through a $C_{1-6}$ alkoxy group to the parent molecular moiety.

The term "cyano" refers to the group —CN.

The term "oxo" refers to the group =O.

The term "cycloalkyl", as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" refers to a cycloalkyl group in which one or more hydrogen atoms are replaced by fluoro group(s).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", *A Textbook of Drug Design and Development*, pp. 113-191, Krogsgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to PI3K, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Utility

The compounds of the invention modulate kinase activity, including the modulation of PI3K.

Accordingly, compounds of Formula (I) have utility in treating conditions associated with the modulation of kinase activity, and particularly the selective inhibition of PI3K activity. Such conditions include B-cell mediated diseases in which cytokine levels are modulated as a consequence of intracellular signaling.

As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as selective inhibitors of PI3K, compounds of Formula (I) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, Kawasaki disease, chronic inflammatory demyelinating polyneuropathy (CIDP), dermatomyositis, uveitis, anti-factor-VIII disease, ankylosing spondylitis, myasthenia gravis, Goodpasture's disease, antiphospholipid syndrome, ANCA-associated vasculitis, dermatomyositis/polymyositis, cerebral malaria, chronic pulmonary inflammatory disease, silicosis, pulmonary sarcoidosis, bone resorption disease, allograft rejections, fever and myalgias due to infection, cachexia secondary to infection, myeloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the PI3K inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional PI3K-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "PI3K-associated condition" or "PI3K-associated disease or disorder" are used herein, each is intended to encompass all of the conditions identified above as if repeated at length, as well as any other condition that is affected by PI3K kinase activity.

"Therapeutically effective amount" is intended to include an amount of a compound of the present invention that is effective when administered alone or in combination to inhibit PI3K.

One embodiment provides methods for treating such PI3K kinase-associated conditions, comprising administering to a subject in need thereof at least one compound of Formula (I). A therapeutically-effective amount for treating such conditions may be administered. The methods of the present embodiment may be employed to treat PI3K kinase-associated conditions such as treatment of allergic disorders and/or autoimmune and/or inflammatory diseases including, but not limited to, SLE, rheumatoid arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

The methods of treating PI3K kinase-associated conditions may comprise administering at least one compound of Formula (I) alone or in combination with each other and/or other suitable therapeutic agents useful in treating such conditions. Therapeutically-effective amounts of at least one compound of Formula (I) and other suitable therapeutic agents for treating such conditions may be administered. Accordingly, "therapeutically effective amount" is also intended to include an amount of the combination of compounds claimed that is effective to treat PI3K kinase-associated conditions. The combination of compounds is preferably a synergistic combination. Synergy, as described, for example, by Chou et al., Adv. Enzyme Regul., 22:27-55 (1984), occurs when the effect (in this case, inhibition of PI3K) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-PI3K effect, or some other beneficial effect of the combination compared with the individual components.

Exemplary of such other therapeutic agents include corticosteroids, rolipram, calphostin, cytokine-suppressive anti-inflammatory drugs (CSAIDs), 4-substituted imidazo[1,2-a]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating PI3K kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Another embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment or prophylaxis of an allergic disorder and/or autoimmune and/or inflammatory disease. In the present embodiment, the use for the manufacture of a medicament may include the administration of a therapeutically-effective amount of a compound of Formula (I) for the treatment of prophylaxis of an allergic disorder and/or autoimmune and/or inflammatory disease.

The present invention also provides the use of the compounds of Formula (I) for the manufacture of a medicament for treatment of cancer. The present embodiment may include the use for the manufacture of a medicament includes the administration of a therapeutically-effective amount of a compound of Formula (I) for the treatment of prophylaxis of an allergic disorder and/or autoimmune and/or inflammatory disease.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula (I) may be administered by any means suitable for the condition to be treated, which may depend on the need for site-specific treatment or quantity of drug to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; buccally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of PI3K enzyme levels.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Examples of compounds of Formula (I) as specified in the "Examples" section below, have been tested in one or more of the assays described below.

In one embodiment, the compounds of Formula (I) inhibit PI3K enzymes with $IC_{50}$ values of 60 nM or less, for example, from 0.001 to 60 nM, as measured by the ADP-Glo Format PI3K assays. Preferably, the compounds of Formula (I) inhibit PI3K enzymes with $IC_{50}$ values of 20 nM and less, for example, from 0.001 to 20 nM. Other preferred compounds inhibit PI3K enzymes with $IC_{50}$ values of 10.0 nM and less, for example, from 0.001 to 10.0 nM.

In one embodiment, the compounds of Formula (I) have improved potency in the whole blood BCR-stimulated CD69 expression assay with $IC_{50}$ values of 4 mM or less, for example, from 0.1 to 4 mM. More preferably, the compounds of Formula (I) have potency in the whole blood BCR-stimulated CD69 expression assay with $IC_{50}$ values of 250 nM or less, for example, from 0.1 to 250 nM; and with $IC_{50}$ values of 100 nM or less, for example, from 0.1 to 100 nM.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples and intermediates section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary; and starting from chiral intermediates.

The compounds of Formula (I) may be prepared by the processes described herein in the following reaction schemes. Examples of suitable reagents and procedures for conducting these reactions appear hereinafter and in the working examples included therein. Protection and deprotection in the schemes herein may be carried out by procedures generally known in the art (See, for example, Greene T. W. et al., *Protecting Groups in Organic Synthesis*, 4th Edition, Wiley, (2007)).

Compounds of Formula (I) can be prepared using methods shown in Scheme 1. Compound 1 (for preparation see WO 2011/123493, Example 1F) can be converted to the corresponding acetylene compound 2 by reacting with ethynylsilane and base, such as n-butyl lithium. 1,5-Pyrazoles 3 can be prepared as the major isomer by reacting compounds 2 with hydrazines 4 with heating. The regio-isomeric 1,3-pyrazoles 5 can be obtained as a secondary product. Alternatively in Scheme 2, compound 1 is treated with dimethylamine to give the intermediate 6, which forms cleanly the pyrazoles 3 when reacted with hydrazines 4.

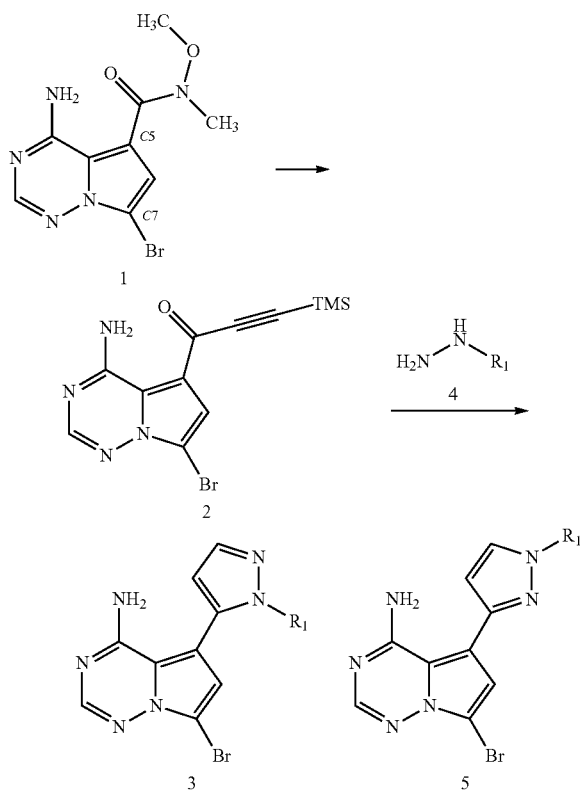

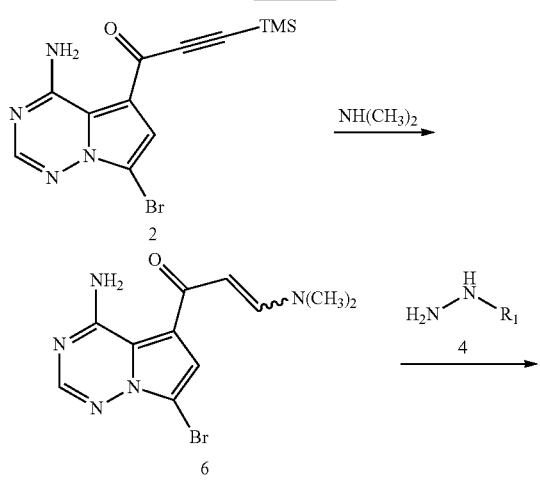

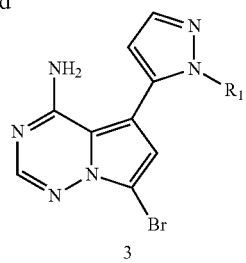

A synthesis of intermediate 12 for the preparation of compounds of Formula (I) is shown in Scheme 3. Compounds 7 can be transformed to nitriles 8 using aminooxysulfonic acid (B). Amino-pyrroles 9 can be prepared from 8 using chloramine, then transformed to the pyrrolotriazines 10 with formimidamide. The amino group in 10 can be protected, such as P being the Boc group, to give compounds 11. Bromination, with NBS for example, can give the bromos 12. In Scheme 3, X and Y can both be hydrogen, fluoro or one of X and Y are independently fluoro.

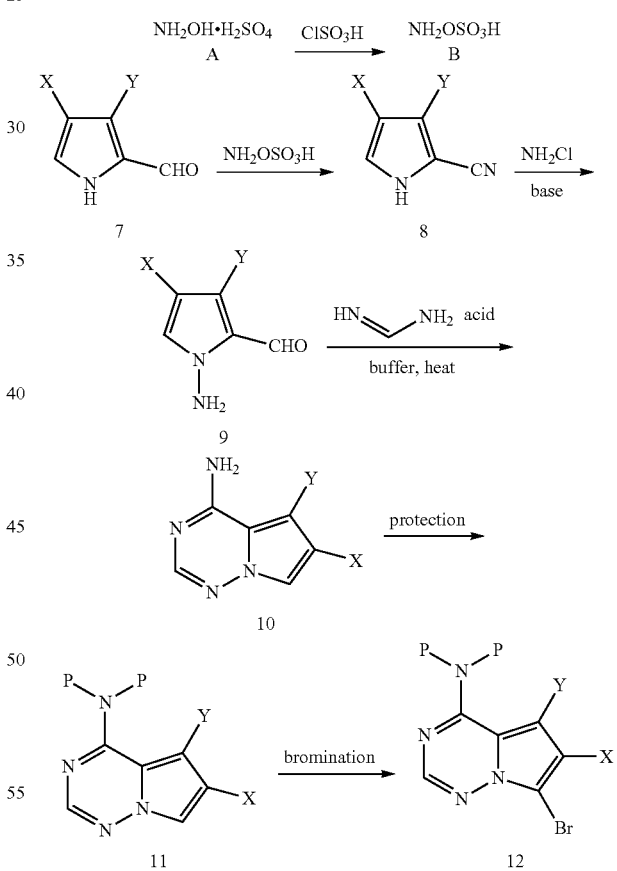

A synthesis of triazines from intermediate 12 is shown in Scheme 4. Deprotection of 12 (acid if P is Boc) followed by iodination (NIS) gives compounds 14. Reacting TMS-acetylene with 14 in the presence of metals, such as copper and palladium, followed by deprotection, gives compounds 16. Triazines 17 are prepared from 16 by reacting azides 18 using metal catalysis (ruthenium (II)). Acetylenes 16 can also give isoxazoles 19 from hydroxylamines.

Scheme 4

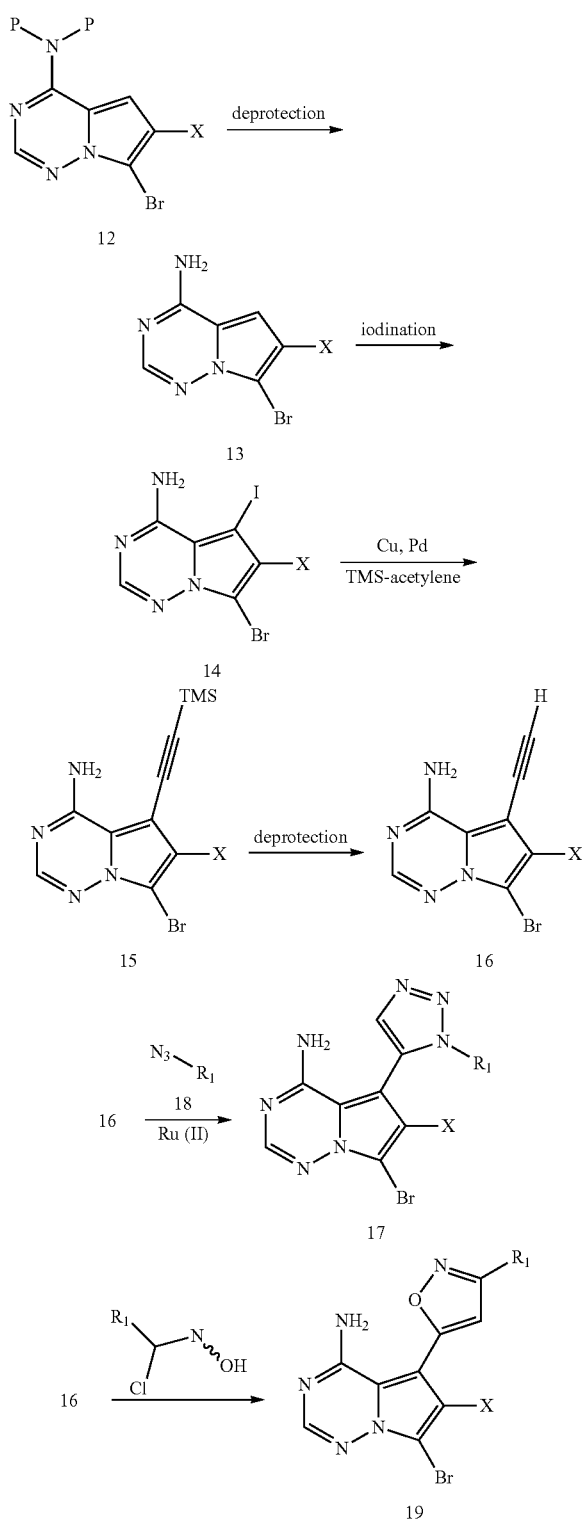

either commercially available or prepared via methods known in the art (see, for example, Ishiyama, T. et al., *Tetrahedron*, 57:9813 (2001), and references cited therein).

Scheme 5

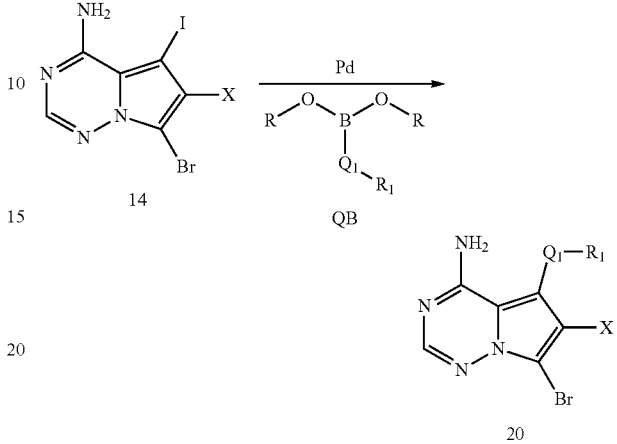

Analogs with a C-7 bromo (such as 3, 5, 17, and 19), represented by compounds 20, can be further transformed to compounds of Formula I by Scheme 6. This conversion may be achieved by using a suitable base such as potassium carbonate, cesium carbonate or tripotassium phosphate, and a suitable catalyst such as tetrakis(triphenylphosphine) palladium, 1,1'-bis(diphenylphosphino)ferrocene palladium(II) chloride, or 1,1'-bis(di-tert-butylphosphino)ferrocene palladium(II) chloride, in a suitable solvent such as dioxane or tetrahydrofuran, optionally with a suitable cosolvent such as water. Such coupling reactions are commonly known as Suzuki-Miyaura coupling reactions, and are well known in the chemical literature (see, for example, Heravi, M. M. et al., *Tetrahedron*, 68:9145 (2012), and references cited therein).

Reacting compounds 20 with aryl boronic esters or acids 21 will give C7 phenyl linked analogs 22 of Formula (I). The reagents 21 are either commercially available or prepared using methods well known in the chemical literature (see, for example, Ishiyama, T. et al., *Tetrahedron*, 57:9813 (2001), and references cited therein). One method called General Procedure 1 involves taking an appropriate halo (optimally bromo) analog 23 and forming the boronic ester intermediate 21 using palladium catalysis followed by a second palladium assisted coupling in the same reaction vessel with 20 to give compounds 22. This transformation can also be done step-wise by isolating 21.

Intermediates 14 can be used to react with boronic esters or acids of optimally substituted heteroaryls as shown in Scheme 5. Under metal assisted coupling conditions, such as palladium assisted Suzuki reactions, bromo intermediates 20 are formed from 14 using boronic esters or acids QB, selectively reacting at the C5 iodo. The reagents QB are

Scheme 6

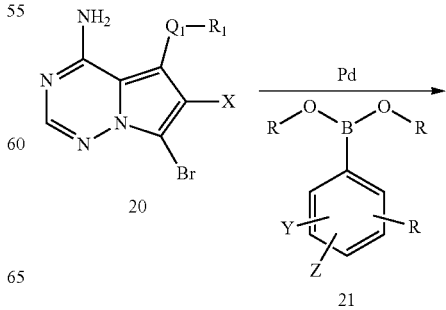

-continued

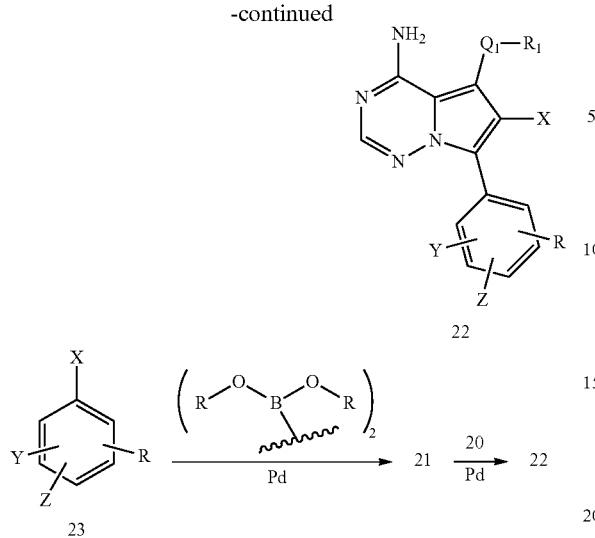

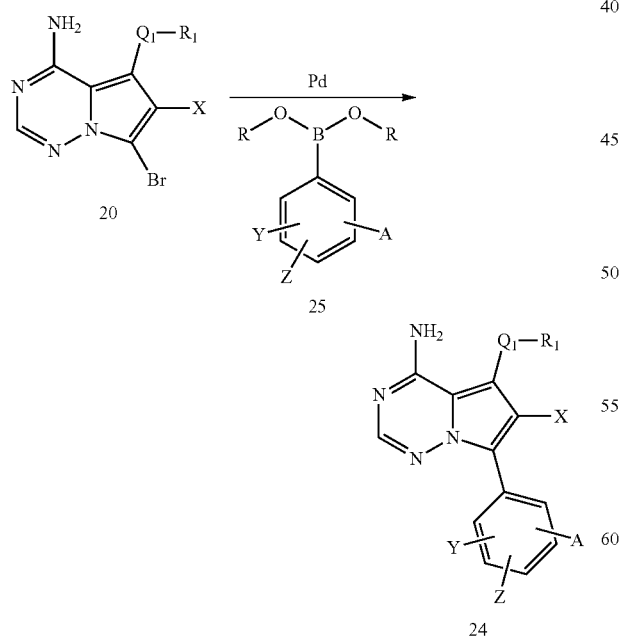

Bromos 13 can be coupled with aryl boronic esters or acids 21 or 25 to give compounds 26 or 27 as shown in Scheme 8. Halogenation under standard procedures would give final compounds 28 or 29 of Formula I where X1 is chloro, bromo or iodo. Compounds 28 or 29, optimally with X1 as iodo, can be further transformed to nitriles with a cyanide nucleophile, such as copper cyanide, to give xx and zz.

Scheme 8

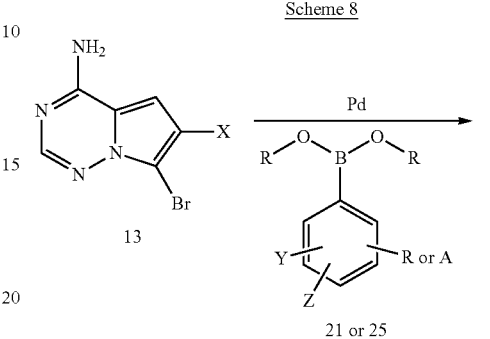

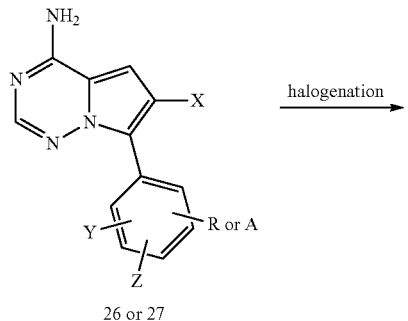

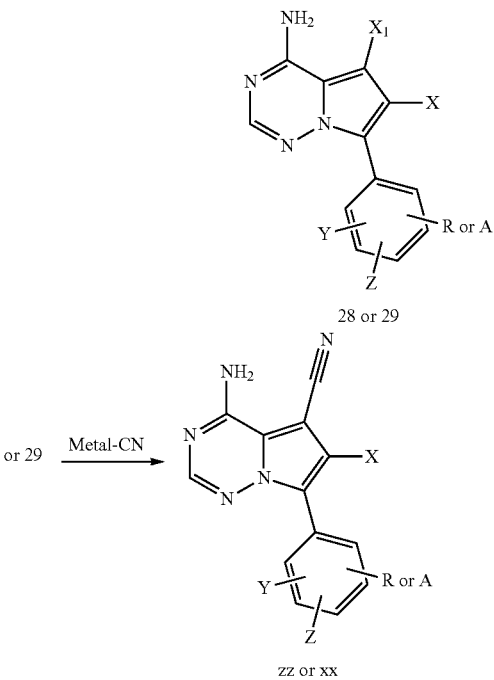

Alternatively, coupling of compounds 20 will provide compounds 24 that can be further transformed to new compounds of Formula I (Scheme 7). Standard coupling with compounds 25 with a group A that can be further modified gives 24. The group A can be halogens, such as bromo, that can be used in Suzuki couplings with boronic esters or acids or in Buchwald couplings with amines. The group A can also be a carboxylic acid for use in standard amide coupling reactions. Boronic esters can also be used as Group A, allowing Suzuki couplings with desired halogen intermediates. Benzylic amines can also be group A, allowing standard functionalization of amines (reductive aminations, Buchwald couplings, as well as amide, urea or carbamate formations).

Alternatively, intermediate 16 can be treated with TMS-azide and base (cesium carbonate) in air to give directly the bromo nitrile intermediate xyx, as shown in Scheme 9. Intermediates xyx can be transformed as described and shown in Schemes X and X1 to give compounds xyx2 or xyx3.

Scheme 9

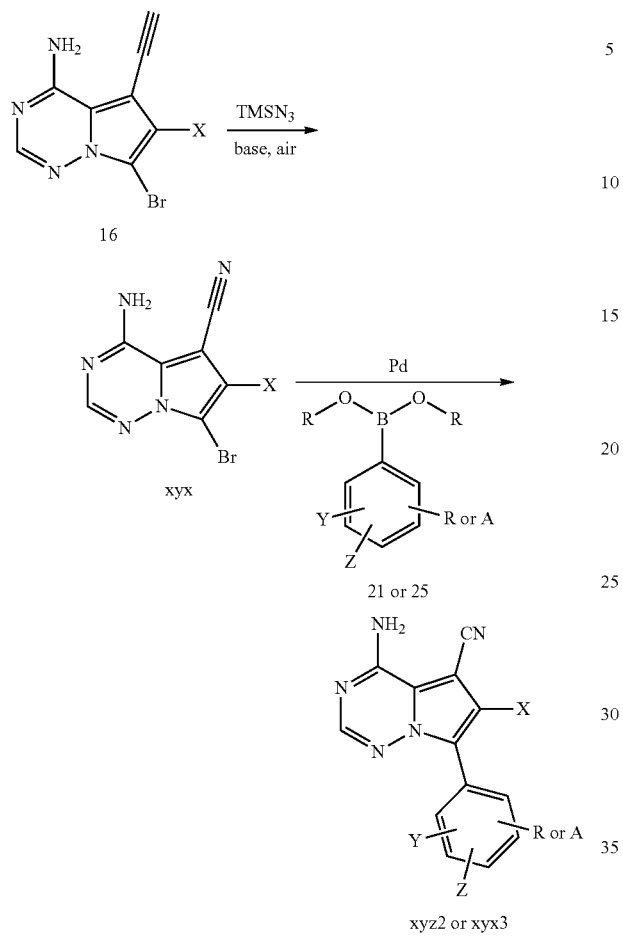

Compounds of Formula I where Q1 is a trifluoromethyl group can be prepared as shown in Scheme 10. The protected (optimally para-methoxybenzyl) amine 12 can be iodinated under standard conditions (NIS) to give xxx. Treatment of xxx with Cu(I)I and methyl 2,2-difluoro-2-(fluorosulfonyl)acetate with heating gives intermediate xxy after deprotection. Intermediates xxy can be transformed as described and shown in Schemes 6 and 7 to give compounds xxz or xxw. Alternatively, compounds 28 or 29 can be protected followed by reacting with copper iodide and methyl 2,2-difluoro-2-(fluorosulfonyl)acetate to give after deprotection xxz or xxw.

Scheme 10

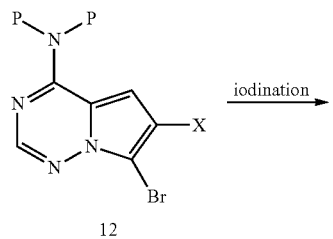

Alternately, compounds 28 or 29, optimally X1 is iodo or bromo, can be reacted with boronic esters or acids of optimally substituted heteroaryls QB to give compounds 22 or 24, as shown in Scheme 11. Some heteroaryls QC can be coupled directly with palladium to compounds 28 or 29 without requiring boronic ester or acid intermediates to give 22 or 24.

Scheme 11

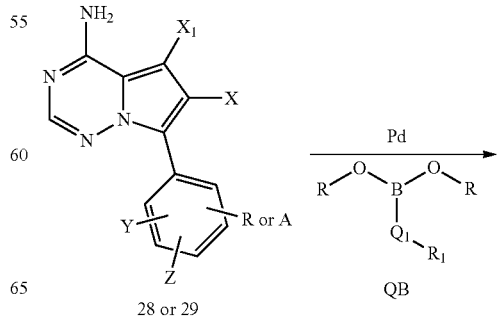

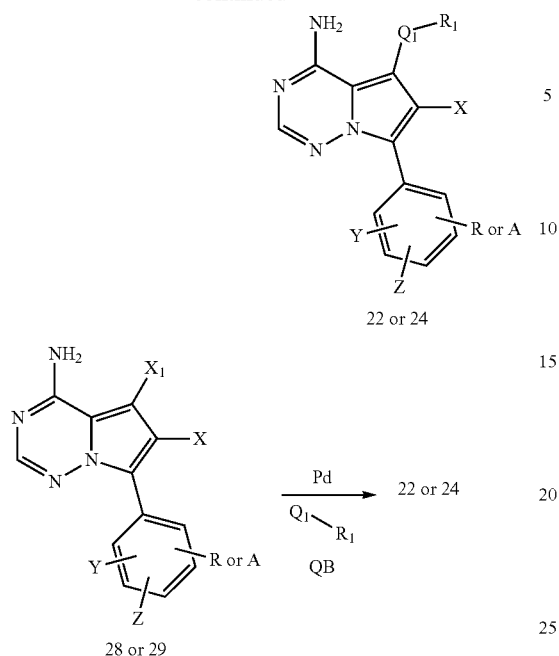

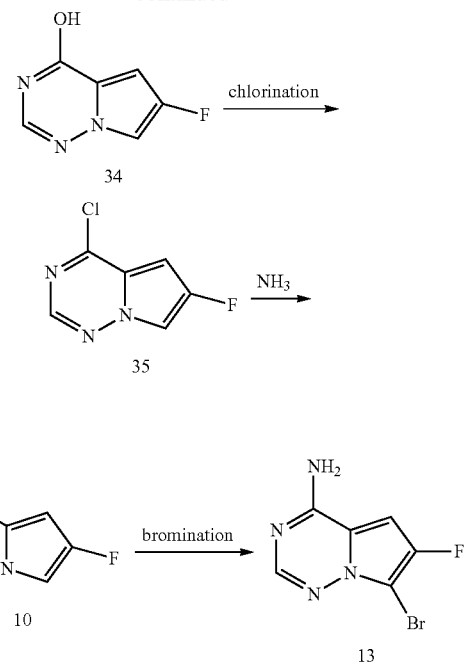

Alternatively, intermediate 12 where X is fluoro can be prepared as shown in Scheme 12. Compounds 30 can be deprotected and oxidized (MnO$_2$) to pyrroles 32. Aminopyrroles 33 can be prepared from 32 using chloramine, then transformed to the pyrrolotriazines 34 with formamide. Compound 34 can be chlorinate (POCl$_3$) followed by treatment with ammonia to give intermediate 10 (X=F). Bromination as in Scheme 3 can give directly compound 13. Alternatively, the amine can be protected before bromination.

Scheme 13 describes a general procedure to synthesize key intermediates leading to imidazoles of Formula I. Compound 36 (for preparation see WO 2011/123493, Example 1) can be treated with base to give the acids 37, followed by reduction to the aldehydes 38. Enamine formation with optimally substituted amines followed by reacting with TOSMIC (toluenesulfonylmethyl isocyanide) gives imidazoles 40. Intermediates 40 can be further transformed as in Schemes 6 or 7 using compounds 21 or 25.

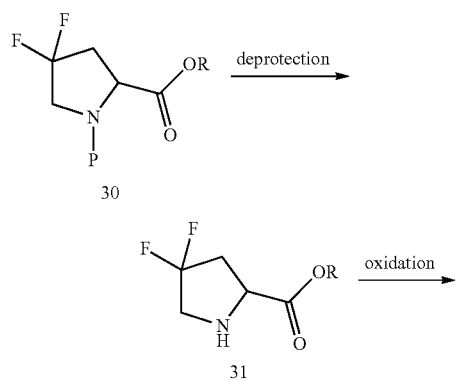

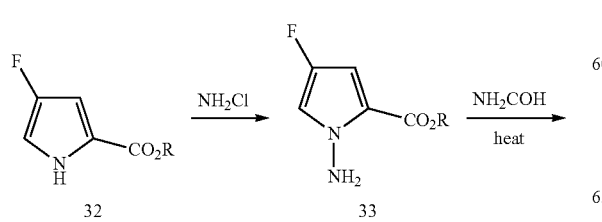

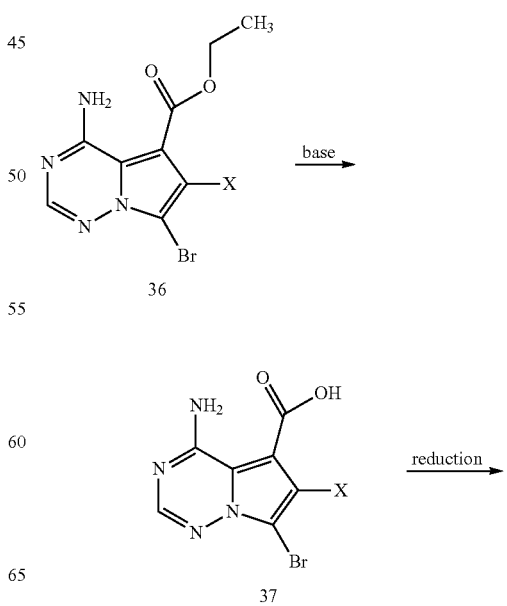

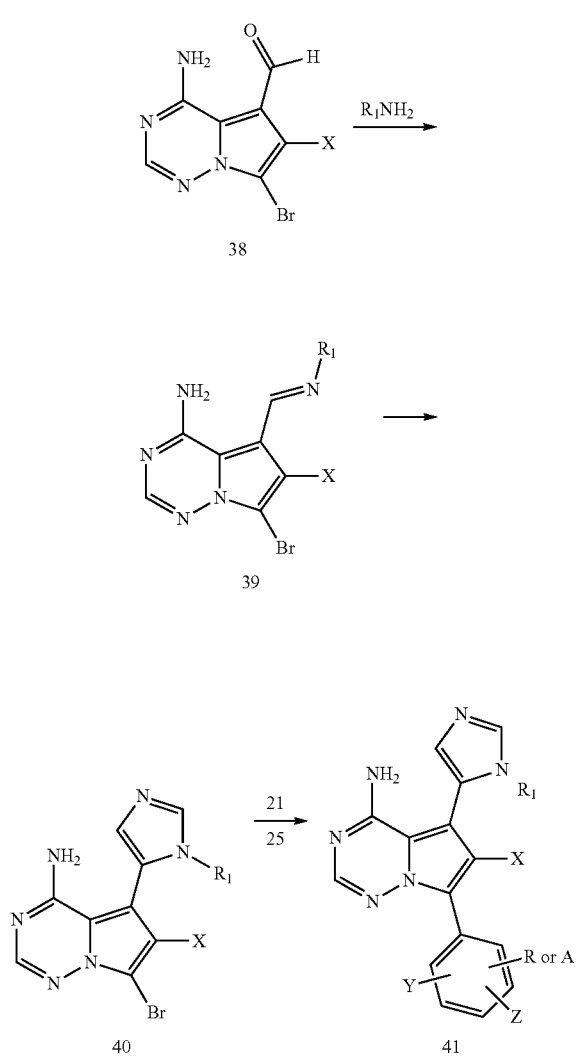
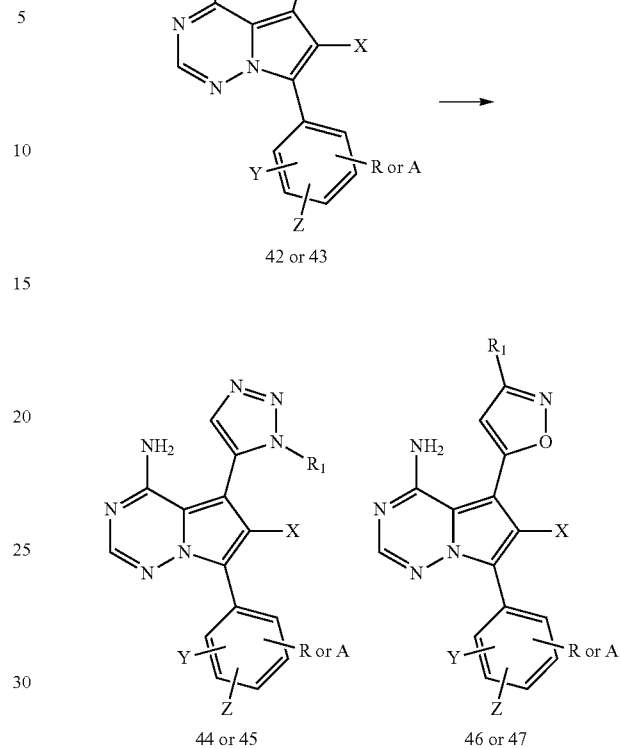
Alternatively, triazines 44 or 45 and isooxazoles 46 or 47 can be prepared as shown in Scheme 14 from intermediates 28 or 29 by similar methods described for Scheme 4.
Analogs 24 where A is a benzylic alcohol can be further transformed as shown in Scheme 15. Compound 49 can be activated in the benzylic position to give 50, which is further reacted with an amine to give compound 51.
Scheme 14
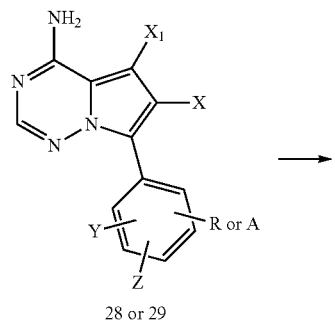
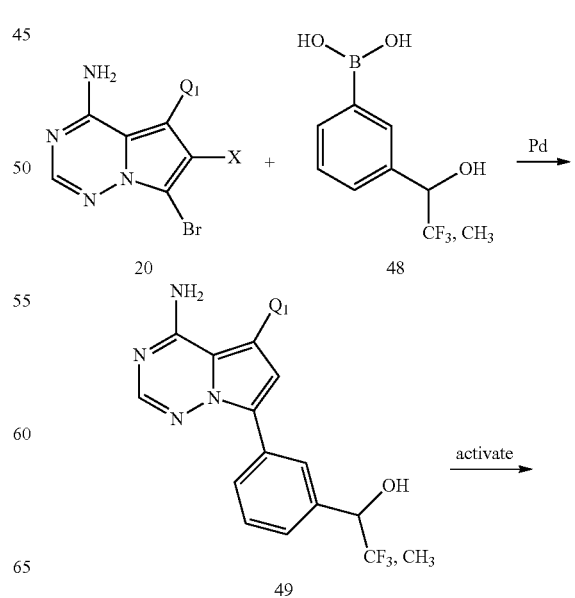

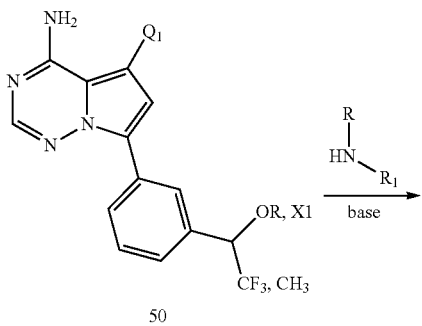

50

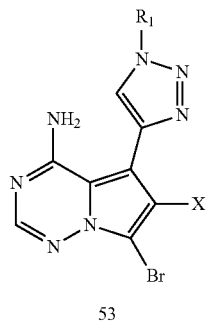

53

Alternately, triazines 53 of Formula I can be prepared as in Scheme 16. Intermediate 16 is doubly protected to give 52, followed by treatment with sodium azide and an alkyl iodide under copper catalysis to give, after deprotection, alkylated triazines 53.

Analogs of Formula I containing a piperazine analog can be prepared as shown in Scheme 17. Anilines xc1 (X=halo) are reacted with protected amino acids or activated acids to give amides xc2 under standard conditions. After the amine is deprotected (acid if P is Boc), the resulting amine is alkylated, for example using reductive amination, to give xc4. After deprotection, the resulting alcohol is cyclized using conditions known in the art, such as a Mitsunobu reaction, to give piperazine xc5. Alternatively, intermediate xc3 can be alkylated with a doubly activated ethylene unit to give directly xc5. The amine can be transformed further by methods known in the art, such as reacting with acids to give xc7 amides. The halo intermediates can be further transformed to boronic ester or acid intermediates 21 or 25 by methods know in the art (palladium coupling with pinacol borane). [reference from page 8.] Alternatively, xc1 can be coupled to an acid or activated acid (acid bromide, A=Br) with a suitably activated leaving group to give xc8. Treatment of xc8 with an amino alcohol and silver oxide would directly give xc5.

Scheme 16

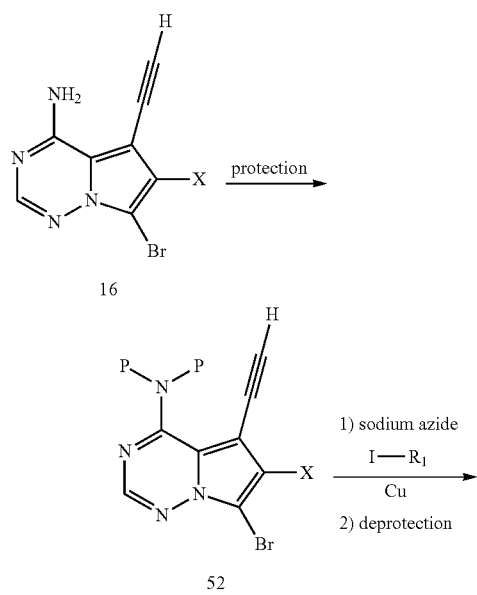

Scheme 17

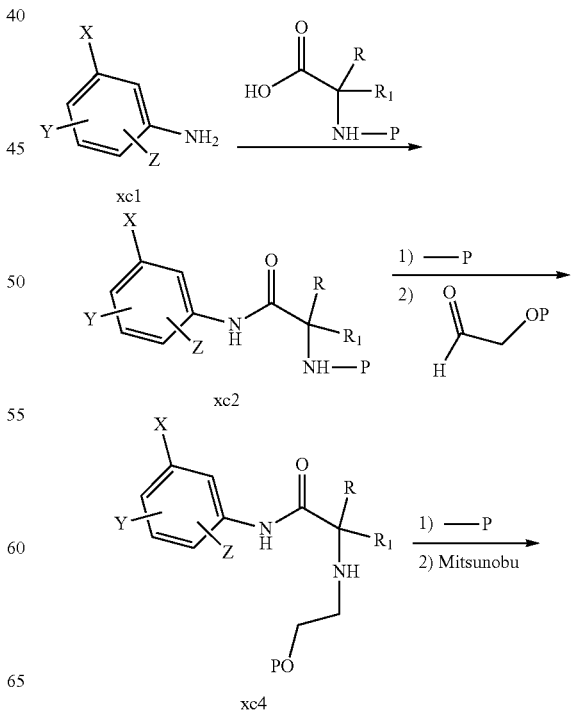

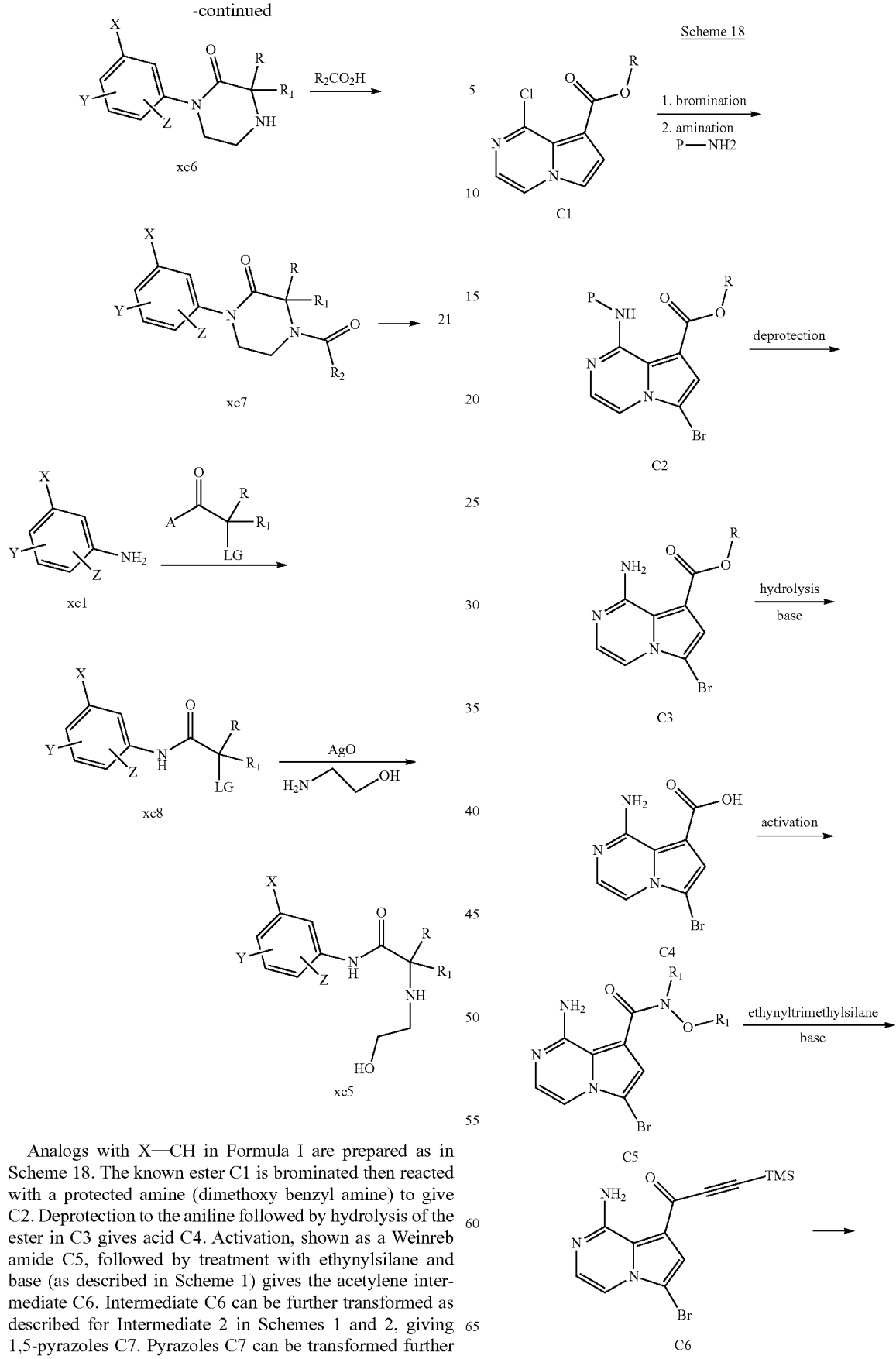

Scheme 18

Analogs with X=CH in Formula I are prepared as in Scheme 18. The known ester C1 is brominated then reacted with a protected amine (dimethoxy benzyl amine) to give C2. Deprotection to the aniline followed by hydrolysis of the ester in C3 gives acid C4. Activation, shown as a Weinreb amide C5, followed by treatment with ethynylsilane and base (as described in Scheme 1) gives the acetylene intermediate C6. Intermediate C6 can be further transformed as described for Intermediate 2 in Schemes 1 and 2, giving 1,5-pyrazoles C7. Pyrazoles C7 can be transformed further into final compounds as described in the Schemes above.

-continued

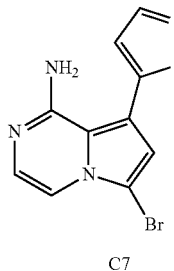

C7

Abbreviations

Ac acetyl
ACN acetonitrile
AcOH acetic acid
aq. aqueous
anhyd. anhydrous
BISPIN 4,4,4',4',5,5,5',5'-Octamethyl-2,2'-bi-1,3,2-dioxaborolane
Boc tert-butoxycarbonyl
BOP benzotriazole-1-yl-oxy-tris-(dimethylamino)-phosphonium hexafluorophosphate
Bu butyl
BuOH butyl alcohol
Cbz carbobenzyloxy
Conc. concentration
d day(s)
DCM dichloromethane
DIEA or DIPEA diisopropylethylamine
DMAP dimethylaminopyridine
DMA N,N-dimethylacetamide
DMF dimethylformamide
DMSO dimethylsulfoxide
DPPA diphenylphosphorylazide
% ee percent enantiomeric excess
(+/−) or (±) racemic
eq. or Eq. or equiv. equivalent(s)
EtOAc or EA ethyl acetate
Et ethyl
EtOH ethanol
HATU N,N,N,N-tetramethyl-O-(7-azabenzotriazol-1-yl) uronium hexafluorophosphate
Hex hexanes
h or hr hour(s)
i iso
Hz hertz
HPLC high pressure liquid chromatography
RP-HPLC reverse-phase high pressure liquid chromatography
KOAc potassium acetate
LC liquid chromatography
LCMS or LC/MS liquid chromatograph mass spectrometry
MHz megahertz
Me methyl
MeOH methanol
min. minute(s)
$M^+$ $(M+H)^+$
$M^{+1}$ $(M+H)^+$
MS mass spectrometry
m/z mass to charge ratio
N Normal
NBS N-bromosuccinimide
NCS N-chlorosuccinimide
NIS N-iodosuccinimide
NMR nuclear magnetic resonance
$PdCl_2$(dppf) [1,1-bis(diphenylphosphino)ferrocene]dichloropalladium(II)
Ph phenyl
$Ph_3PO$ triphenylphosphine oxide
Pr propyl
ppm parts per million
PSI or psi pounds per square inch
quant. quantitative
Ret Time or Rt retention time
sat. or sat'd. saturated
sec seconds
SFC super critical fluid
SCX clean up extraction column
TEA triethylamine
TFA trifluoroacetic acid
THF tetrahydrofuran
TOSMIC toluenesulfonylmethyl isocyanide
t triplet
m multiplet
s singlet
d doublet
br. s. broad singlet
dd doublet of doublets
tt triplet of triplets
ddd doublet of doublet of doublets
q quartet
quin. quintet
UV ultraviolet
W/V or w/v weight to volume
X-Phos dicyclohexyl(2',4',6'-triisopropylbiphenyl-2-yl)phosphine Preparative HPLC Conditions:

Method A: Column: Luna 5 μm C18 30×100 mm; Flow rate=40 mL/min; Solvent A=10% MeOH-90% $H_2O$-0.1% TFA; Solvent B=90% MeOH-10% $H_2O$-0.1% TFA, Start % B=30, Final % B=100, linear gradient time=10 min; Products detected at 220 nm wavelength.

Method B: Column: Waters XBridge C18, 19×250 mm, 5-μm particles; Mobile Phase A: 5:95 acetonitrile:water with 10 mM ammonium acetate; Mobile Phase B: 95:5 acetonitrile:water with 10 mM ammonium acetate; Flow: 20 mL/min. Products detected by mass spectrometry. Fractions containing the desired product were combined and dried via centrifugal evaporation.

Method C: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; 5-100% B over 25 minutes, then 5-minute hold at 100% B; Flow: 20 mL/min. Products detected by mass spectrometry. Fractions containing the desired product were combined and dried via centrifugal evaporation.

Method D: Column: SunFire 5 μm C18 19×150 mm; Mobile Phase A: 90% $H_2O$-10% ACN-0.1% TFA; Mobile Phase B: 10% $H_2O$-90% ACN-0.1% TFA; Gradient: 0-100% B over 10 min then 4 minute hold at 100% B. Amount of mobile phases A and B were adjusted appropriately for the isolate of each title compound. Flow: 20 mL/min. Products detected by UV. Fractions containing the desired product were combined and dried via under reduced pressure and then partitioned between 1.5 M aqueous $KH_2PO_4$ and either DCM or ethyl acetate to remove residual TFA. The organic portion was dried over either $MgSO_4$ or $Na_2SO_4$ and the solvents were removed in vacuo providing title compound.

Analytical LCMS Conditions:

Method A: Column: PHENOMENEX® Luna 5 µm C18 30×4.6 mm; Linear gradient of 0-100% Solvent B over 2 min, then 0.5 min hold at 100% B; Flow rate: 4 mL/min; Solvent A: 10% MeOH-90% $H_2O$-0.1% TFA; Solvent B: 90% MeOH-10% $H_2O$-0.1% TFA; Products detected at 220 nm wavelength w/ positive or negative ionization mode.

Method B: Column: BEH C18 2.1×50 mm 1.7 µm; Linear gradient of 0-100% Solvent B over 2 min, then 0.5 min hold at 100% B; Flow rate: 1 mL/min; Solvent A: 100% water w/ 0.05% TFA; Solvent B: 100% acetonitrile w/ 0.05% TFA; Products detected at 220 nm wavelength w/ positive ionization mode.

Method C: Column: XBridge (150×4.6 mm), 3.5 µm SC/840; Flow rate: 1 mL/min; Solvent A: 10 mM $NH_4HCO_3$ in water pH=9.5 adjusted using dil. ammonia; Solvent B: MeOH; Products detected by positive or negative ionization.

Method D: Column-Ascentis Waters SunFire C18 2.1×50 mm 5 m; Mobile Phase A: 10% MeOH-90% $H_2O$-0.1% TFA; Mobile Phase B—90% MeOH-10% $H_2O$-0.1% TFA; Gradient Time=4 min; Flow: 1 mL/min.; Oven Temp.=40° C.; Products detected at 220 nm wavelength w/ positive ionization mode.

Method E: Column: SunFire C18, (150×4.6 mm), 3.5 µm, SC/862; Linear gradient of 0 to 100% Solvent B over 12 min, then 3 min hold at 100% B; Flow rate: 1 mL/min; Buffer: 0.5% TFA, in water with pH adjusted to 2.5 using dilute ammonia; Solvent A: Buffer: acetonitrile (95:5); Solvent B: acetonitrile; Products detected at 220 nm.

Method F: Column: Waters Acquity UPLC BEH C18, 2.1×50 mm, 1.7-µm particles; Linear gradient of 0 to 100% Solvent B over 3 min, with 0.75 min hold at 100% B; Flow rate: 1.1 mL/min; Solvent A: 5:95 acetonitrile:water with 0.05% TFA; Solvent B: 95:5 acetonitrile:water with 0.05% TFA; Temperature: 50° C.; Products detected at 220 nm, positive ionization mode.

Method G: Column: XBridge Phenyl (4.6×150 mm); Linear gradient of 0 to 100% Solvent B over 12 min, then 3 min hold at 100% B; Flow rate: 1 mL/min; Solvent A: 5% acetonitrile −95% $H_2O$-0.05% TFA; Solvent B: 95% acetonitrile-5% $H_2O$-0.05% TFA; Products detected at 220 nm.

Method H: Column: Waters Acquity BEH C18 2.1×50 mm 1.7 µm; Linear gradient of 0-100% Solvent B over 3 min, then 0.75 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Temperature=50° C.; Products detected at 220 nm wavelength w/ positive ionization mode.

Method I: Column: Waters Acquity BEH C18 2.1×50 mm 1.7 µm; Linear gradient of 0-100% Solvent B over 3 min, then 0.75 min hold at 100% B; Flow rate: 1.11 mL/min; Solvent A: 5:95 acetonitrile:water with 0.05% TFA; Solvent B: 95:5 acetonitrile:water with 0.05% TFA; Temperature=50° C.; Products detected at 220 nm wavelength w/ positive ionization mode.

Method J: Column: PHENOMENEX®, 2.5µ, 2.0×30 mm; Mobile phase: 10-90% aq $CH_3OH$/0.1% TFA; Gradient=4.0 min. linear with 1.0 min. hold; Flow rate: 1 ml/min detected at 220 nm or 254 nm detection wavelength.

Method K: Column: Waters XBridge C18 4.6×50 mm 5µ; Linear gradient of 0-100% Solvent B over 4.0 min; Flow rate: 4 mL/min; Solvent A: 5:95 acetonitrile:$H_2O$ with 0.05% TFA; Solvent B: 5:95 $H_2O$:acetonitrile with 0.05% TFA; Products detected at 220 nm wavelength w/ positive ionization mode.

Method L (Shimadzu HPLC): Column: Waters Acquity BEH C18 2.0×50 mm, 1.7µ; Linear gradient of 0-100% Solvent B over 1.5 min; Flow rate: 1 mL/min; Solvent A: 90:10 water:acetonitrile with 0.1% TFA; Solvent B: 90:10 acetonitrile: Water with 0.1% TFA; Products detected at 220 wavelength w/ positive ionization mode;

Method M: (Waters HPLC); Column: Waters Acquity BEH C18 2.1×50 mm, 1.7µ; Linear gradient of 2-98% Solvent B over 1.0 min, hold at 98% B for 0.5 min; Flow rate: 0.8 mL/min; Solvent A: $H_2O$ with 0.05% TFA; Solvent B: Acetonitrile with 0.05% TFA; Products detected at 220 nm wavelength w/ positive ionization mode.

Method N: Column: Waters XBridge C18 4.6×50 mm 5µ; Linear gradient of 0-100% Solvent B over 4.0 min; Flow rate: 4 mL/min; Solvent A: 5:95 ACN:$H_2O$ with 10 mM $NH_4OAc$; Solvent B: 5:95 $H_2O$:ACN with 10 mM $NH_4OAc$; Products detected at 220 nm wavelength w/ positive ionization mode.

Method P: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Intermediate N1

7-Bromo-5-(1-(tetrahydro-2H-pyran-4-yl)-1H-pyrazol-5-yl)pyrrolo[2,1-f][1,2,4]triazin-4-amine

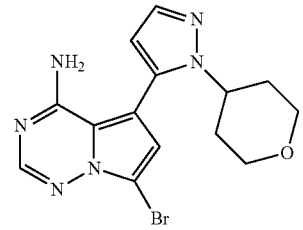

Intermediate N1-A: 1-(4-Amino-7-bromopyrrolo[2,1-f][1,2,4]triazin-5-yl)-3-(trimethylsilyl)prop-2-yn-1-one

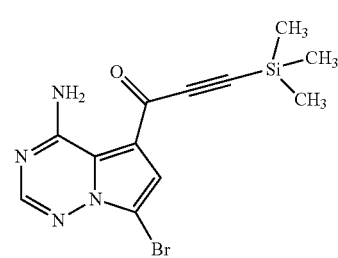

To a solution of ethynyltrimethylsilane (0.83 mL, 5.9 mmol) in THF (15 mL) at −78° C. was added n-butyllithium (2.27 mL, 5.68 mmol) dropwise. After stirring for 5 min at −78° C., 4-amino-7-bromo-N-methoxy-N-methylpyrrolo[2,1-f][1,2,4]triazine-5-carboxamide (0.59 g, 1.96 mmol, for preparation see WO 2011/123493) as a solution in THF (3 mL). After 30 min, AcOH (0.3 mL) was added to give a bright yellow solution. The mixture was partitioned between ethyl acetate (20 mL) and water (10 mL). The organic layer was washed with brine, dried over sodium sulfate and concentrated to afford Intermediate N1-A (0.66 g) as a yellow solid. The material was used without further purification.

Intermediate N1

Intermediate N1-A (3.2 g, 9.49 mmol) was suspended in ethanol (123 mL) and (tetrahydro-2H-pyran-4-yl)hydrazine, HCl salt (2.90 g, 18.98 mmol) was added. The suspension was stirred vigorously for 2 min and triethylamine (6.61 ml, 47.4 mmol) was added. The mixture was refluxed for 18 h, cooled to room temperature and water (50 mL) was added. The mixture was concentrated to 50 mL and the solid formed was filtered, dried in vacuo providing 7-bromo-5-(1-(tetrahydro-2H-pyran-4-yl)-1H-pyrazol-5-yl)pyrrolo[2,1-f][1,2,4]triazin-4-amine (N1) (3.24 g, 94% yield) as a white solid. $^1$H NMR (400 MHz, DMSO-$d_6$) δ 8.06 (s, 1H), 7.65 (d, J=1.5 Hz, 1H), 7.04 (s, 1H), 6.42 (d, J=1.8 Hz, 1H), 4.33-4.23 (m, 1H), 3.87 (dd, J=11.2, 3.5 Hz, 2H), 3.37-3.31 (m, 2H), 2.06 (qd, J=12.2, 4.7 Hz, 2H), 1.84-1.68 (m, 2H). LC/MS: Rt=0.69 min; [M+I]$^+$=363, 365 (Method M).

Intermediate N2

7-Bromo-5-(1-isopropyl-1H-pyrazol-5-yl)pyrrolo[2,1-f][1,2,4]triazin-4-amine

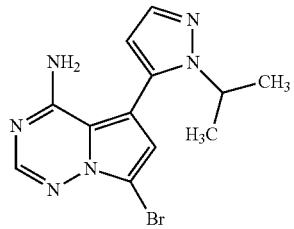

(N2)

Intermediate N1-A, 1-(4-amino-7-bromopyrrolo[2,1-f][1,2,4]triazin-5-yl)-3-(trimethylsilyl)prop-2-yn-1-one, (607 mg, 1.800 mmol) was suspended in ethanol (9 mL) and treated with dimethylamine (304 mg, 2.70 mmol 40% solution in water). The mixture was heated at 90° C. for 2 h. The mixture was cooled to room temperature and followed by the addition of acetic acid (515 µl, 9.00 mmol). The mixture was stirred for 10 min at room temperature and then isopropylhydrazine (200 mg, 2.70 mmol) was added dropwise. The resulting mixture was heated at 90° C. for 1 h. The mixture was cooled to room temperature and the precipitated product was collected by filtration and washed with ethanol and ethyl acetate. The filtrate was concentrated and the residue was purified by silica gel chromatography eluting with dichloromethane and methanol providing additional desired product. The product isolated from filtration and purification were combined providing Intermediate N2 (389 mg, 1.211 mmol, 67.3% yield) as a white solid. $^1$H NMR (400 MHz, DMSO-$d_6$) δ 10.18 (br. s., 1H), 8.13-8.04 (m, 1H), 7.89-7.83 (m, 2H), 7.30-7.22 (m, 1H), 6.75 (d, J=2.2 Hz, 1H), 4.58-4.48 (m, 1H), 1.50-1.41 (m, 6H) LC/MS: [M+1]$^+$=320.9, 322.9 (Method M).

Intermediate N3

7-Bromo-5-(1-methyl-1H-pyrazol-5-yl)pyrrolo[2,1-f][1,2,4]triazin-4-amine

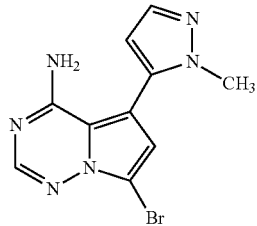

(N3)

Intermediate N3-A: (E)-1-(4-Amino-7-bromopyrrolo[2,1-f][1,2,4]triazin-5-yl)-3-(dimethylamino)prop-2-en-1-one

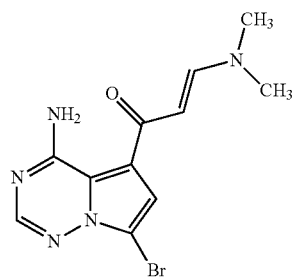

(N3-A)

Intermediate N1-A (1.1 g, 3.26 mmol) was suspended in ethanol (16.31 ml) and dimethylamine ((0.620 ml, 4.89 mmol, 40% solution in water) was added. The mixture was heated at 80° C. for 0.5 h and then cooled to room temperature and filtered. The collected solid was washed with ethanol, ethyl acetate and hexanes and volatiles were removed in vacuo providing (E)-1-(4-amino-7-bromopyrrolo[2,1-f][1,2,4]triazin-5-yl)-3-(dimethylamino)prop-2-en-1-one (904 mg, 2.91 mmol, 89% yield) as a yellow/green solid. $^1$H NMR (400 MHz, DMSO-$d_6$) δ 10.86 (br. s., 1H), 8.17 (br. s., 1H), 8.03-7.93 (m, 1H), 7.78 (d, J=12.1 Hz, 1H), 7.64-7.56 (m, 1H), 5.92 (d, J=12.1 Hz, 1H), 3.17 (s, 3H), 2.97 (s, 3H) LC/MS: [M+1]$^+$=310.2.

Intermediate N-3

Intermediate N3-A (150 mg, 0.484 mmol) was suspended in ethanol (2418 µl) and trifluoroacetic acid (55.9 µl, 0.725 mmol) was added. The resulting suspension was stirred vigorously for 5 min and then methylhydrazine (63.7 µl, 1.209 mmol) was added and the mixture was heated at 80° C. for 1.5 h. The reaction mixture was cooled to room temperature and the desired product was collected via filtration providing a white solid. The solid was dried under vacuum providing 7-bromo-5-(1-methyl-1H-pyrazol-5-yl)pyrrolo[2,1-f][1,2,4]triazin-4-amine (100 mg, 0.375 mmol, 78% yield) as a white solid. $^1$H NMR (400 MHz, DMSO-$d_6$) δ 8.06 (s, 1H), 7.55 (d, J=1.8 Hz, 1H), 7.09 (s, 1H), 6.41 (d, J=1.8 Hz, 1H), 3.78-3.73 (m, 3H) LC/MS: [M+1]$^+$=293.1 (Method L)

The following Intermediates were prepared using the procedure described for the synthesis of Intermediate N3 using an appropriate hydrazine reagent. .

TABLE N1

| Intermediate | R | Name | LC/MS [M + 1] Method |
|---|---|---|---|
| N4 | cyclopropyl | 7-bromo-5-(1-cyclopropyl-1H-pyrazol-5-yl)pyrrolo[2,1-f][1,2,4]triazin-4-amine | 319.0, 321.0 (Method M) |
| N5 | -CH$_2$-CF$_3$ | 7-bromo-5-(1-(2,2,2-trifluoroethyl)-1H-pyrazol-5-yl)pyrrolo[2,1-f][1,2,4]triazin-4-amine | 361.0, 363.0 (Method M) |
| N6 | cyclobutyl | 7-bromo-5-(1-cyclobutyl-1H-pyrazol-5-yl)pyrrolo[2,1-f][1,2,4]triazin-4-amine | 333.0, 335.0 (Method M) |
| N7 | isobutyl (H$_3$C-CH(CH$_3$)-CH$_2$-) | 7-bromo-5-(1-isobutyl-1H-pyrazol-5-yl)pyrrolo[2,1-f][1,2,4]triazin-4-amine | 335.0, 337.0 (Method N) |

Intermediate N8

3-(3-Bromophenyl)oxetan-3-amine hydrochloride

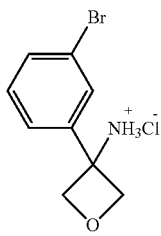

(N8)

Intermediate N8-A:
2-Methyl-N-(oxetan-3-ylidene)propane-2-sulfinamide

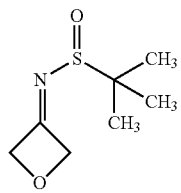

(N8-A)

Oxetan-3-one (0.81 mL, 13.88 mmol) and 2-methylpropane-2-sulfinamide (1.85 g, 15.26 mmol) were combined in DCM (34 mL). While the mixture was stirred vigorously, titanium(IV) isopropoxide (7.2 mL, 27.8 mmol) was added dropwise. The resulting mixture was then heated at 50° C. for 5 h, cooled and then stirred at room temperature for 18 h. The reaction mixture was poured into 20 mL of NaHCO$_3$ solution and stirred vigorously. After 20 min, the resulting heterogeneous mixture was filtered through a pad of CELITE®, the filtrate was washed with brine, dried over magnesium sulfate, filtered and concentrated. The crude product was dissolved in a small amount of DCM and purified by 12 g silica gel cartridge eluting with a 14 min gradient from 0-50% hexane/ethyl acetate to obtain 2-methyl-N-(oxetan-3-ylidene)propane-2-sulfinamide (557 mg, 3.18 mmol, 22.90% yield) as a yellow oil. $^1$H NMR (400 MHz, CDCl$_3$) δ 5.84-5.76 (m, 1H), 5.71-5.61 (m, 1H), 5.55-5.39 (m, 2H), 1.29-1.25 (m, 9H). LC/MS: Rt=0.62 min, [M+1]$^+$=176 (Method M).

Intermediate N8-B: N-(3-(3-Bromophenyl)oxetan-3-yl)-2-methylpropane-2-sulfinamide

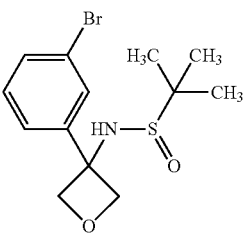

(N8-B)

To a solution of 1,3-dibromobenzene (5.76 mL, 4.77 mmol) in THF (28.9 mL) at −78° C. was added N-butyllithium (1.78 mL, 4.45 mmol, 2.5M solution in THF) dropwise and the mixture. After 1 h, Intermediate N8-A (557 mg, 3.18 mmol) was added dropwise as a solution in 2 mL of THF, the cooling bath was removed and the reaction mixture was allowed to warm to room temperature. The reaction was quenched by the addition of water (10 mL) and the organic volatiles were removed in vacuo. The resulting aqueous suspension was extracted with 2×20 mL of ethyl acetate and the organic layer was washed with brine, dried over MgSO$_4$ and concentrated. The crude residue was purified by silica gel chromatography eluting with a gradient of ethyl acetate in hexanes providing N-(3-(3-bromophenyl)oxetan-3-yl)-2-methylpropane-2-sulfinamide (650 mg, 1.866 mmol, 58.7% yield) as a pale yellow oil. $^1$H NMR (400 MHz, CDCl$_3$) δ 7.57-7.52 (m, 1H), 7.50 (dt, J=7.7, 1.7 Hz, 1H), 7.39-7.28 (m, 2H), 5.17 (d, J=7.0 Hz, 1H), 5.07 (d, J=7.0 Hz, 1H), 5.03 (d, J=7.0 Hz, 1H), 4.95 (d, J=6.8 Hz, 1H), 1.24 (s, 9H).

Intermediate N8

A solution of crude Intermediate N8-B in anhydrous methanol (2 mL) was cooled to 0° C. in an ice bath. HCl (4N solution in dioxane, 4.86 mL, 19.43 mmol) was added dropwise and the mixture was stirred briefly (1 min) at 0° C. and then concentrated to dryness. The solid residue was suspended in Et$_2$O and filtered providing the title compound as a tan solid (2.31 g, 8.73 mmol, 67% yield) $^1$H NMR (400 MHz, methanol-d$_4$) δ 7.72-7.61 (m, 2H), 7.54-7.43 (m, 2H), 5.10 (d, J=7.9 Hz, 2H), 4.96 (d, J=7.9 Hz, 2H). LC/MS: [M+1]$^+$=227.8, 229.8 (Method M).

Intermediate N9

1-(3-(3-Bromophenyl)oxetan-3-yl)piperidin-4-one

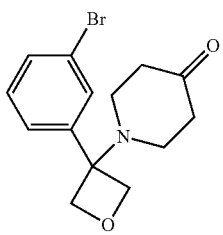

(N9)

To a suspension of 3-(3-bromophenyl)oxetan-3-amine hydrochloride (150 mg, 0.567 mmol) in ethanol (1.5 mL) was added K$_2$CO$_3$ (86 mg, 0.624 mmol) and the mixture was heated to 80° C. To this solution was added dropwise a solution of 1-ethyl-1-methyl-4-oxopiperidin-1-ium, iodide salt (183 mg, 0.680 mmol) in water (3 mL). After heating the mixture at 100° C. for 2 h, more of a solution of 1-ethyl-1-methyl-4-oxopiperidin-1-ium, iodide salt (183 mg, 0.680 mmol) in water (5 mL) was added. The resulting mixture was heated at 100° C. for 1 h, cooled to room temperature and extracted with ethyl acetate (3×10 mL). The organic layer was separated, washed with brine, dried over MgSO$_4$ and concentrated in vacuo. The crude residue was purified by silica gel chromatography eluting with a gradient of ethyl acetate in hexanes containing 1% TEA to obtain the Intermediate N9 (77 mg, 0.248 mmol, 43.8% yield) as a white solid. $^1$H NMR (400 MHz, DMSO-d$_6$) δ 7.54 (d, J=7.9 Hz, 1H), 7.44 (s, 1H), 7.36 (t, J=7.8 Hz, 1H), 7.22 (d, J=7.9 Hz, 1H), 4.84-4.77 (m, 4H), 2.54-2.48 (m, 8H). LC/MS: [M+1]=310.05, 312.05. Method L.

Intermediate N10

1-(3-(3-Bromophenyl)oxetan-3-yl)piperidin-4-ol

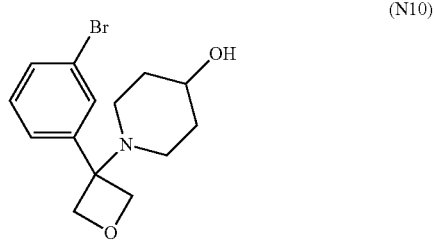 [SMILES: OC1CCN(C2(c3cccc(Br)c3)COC2)CC1]

1-(3-(3-Bromophenyl)oxetan-3-yl)piperidin-4-one (100 mg, 0.322 mmol) was dissolved in methanol (3.22 mL) and the mixture was cooled to 0° C. in an ice bath. Sodium borohydride (14.64 mg, 0.387 mmol) was added, the ice bath was removed and the mixture was allowed to warm to room temperature. After 18 h, the mixture was diluted with water (5 mL) and extracted with ethyl acetate (3×10 mL). The organic portion was separated, washed with brine, dried over MgSO$_4$ and concentrated in vacuo providing 1-(3-(3-bromophenyl)oxetan-3-yl)piperidin-4-ol (101 mg, 0.324 mmol, 100% yield) as a colorless oil. $^1$H NMR (400 MHz, CDCl$_3$) δ 7.46 (ddd, J=8.0, 1.9, 0.9 Hz, 1H), 7.21 (t, J=1.9 Hz, 1H), 7.02-6.96 (m, 1H), 4.89-4.84 (m, 4H), 3.57 (d, J=3.5 Hz, 1H), 2.65-2.49 (m, 2H), 2.00-1.84 (m, 4H), 1.70-1.58 (m, 2H), 1.32-1.27 (m, 1H). LC/MS [M+1]$^+$=311.9, 313.9 (Method M).

Intermediate N11

4-(3-(3-Bromophenyl)oxetan-3-yl)thiomorpholine 1,1-dioxide

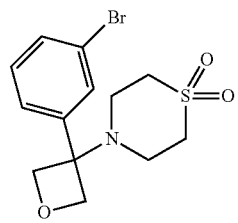

(N11)

To a solution of Intermediate N8 (100 mg, 0.378 mmol) in ethanol (1.5 mL) is added triethylamine (0.211 mL, 1.51 mmol) followed by (vinylsulfonyl)ethene (0.076 mL, 0.756 mmol). The reaction mixture was heated at 85° C. for overnight. The mixture was cooled to room temperature and concentrated. The crude product was purified by silica gel chromatography eluting with a gradient of ethyl acetate in hexanes (0-50% EtOAc) to obtain 4-(3-(3-bromophenyl) oxetan-3-yl) thiomorpholine 1,1-dioxide (131 mg, 99% yield) as a tan colored solid. $^1$H NMR (400 MHz, CDCl$_3$) δ 7.54-7.49 (m, 1H), 7.33-7.28 (m, 1H), 7.21 (t, J=1.8 Hz, 1H), 7.02-6.98 (m, 1H), 4.93 (d, J=6.2 Hz, 2H), 4.82 (d, J=6.4 Hz, 2H), 3.17-3.10 (m, 4H), 2.81-2.74 (m, 4H). LC/MS: Rt=0.77 min [M+1]$^+$=346, 348 (Method M).

Intermediate N12

N-(3-(3-Bromophenyl)oxetan-3-yl)-2-methylpropane-2-sulfonamide

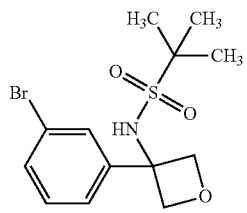

(N12)

To a solution of Intermediate N8-B (100 mg, 0.3 mmol) in DCM (3 mL) was added mCPBA (81 mg, 0.36 mmol) and the mixture was stirred at room temperature overnight. The mixture was diluted with 5 mL DCM and washed with water (2×5 mL). The organic layer was separated, dried over MgSO$_4$, filtered and concentrated in vacuo. The crude product was purified by silica gel chromatography eluting with a gradient of ethyl acetate in hexanes to obtain N-(3-(3-bromophenyl)oxetan-3-yl)-2-methylpropane-2-sulfonamide (67 mg, 0.192 mmol, 64% yield) LC/MS: Rt=0.85 min [M-C$_4$H$_9$]$^+$=292, 294 (Method M).

Intermediate N13

3-(3-Bromophenyl)-N,N-dimethyloxetan-3-amine

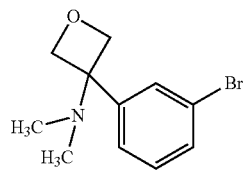

(N13)

To a solution of Intermediate N8 (25 mg, 0.110 mmol) in a mixture of DCM (0.275 mL) and THF (0.275 mL) was added formaldehyde (37% aqueous solution (0.474 g, 5.84 mmol)) and the mixture was cooled to 0° C. Sodium triacetoxyborohydride (62.7 mg, 0.296 mmol) was added and the mixture was stirred for 30 min at 0° C. The reaction was quenched by the addition of 1N aqueous NaOH solution (1 mL) and allowed to warm to room temperature. The mixture was partitioned between DCM (10 mL) and water (5 mL) and the organic layer was dried with MgSO$_4$, filtered and concentrated in vacuo to obtain 3-(3-bromophenyl)-N,N-dimethyloxetan-3-amine (27 mg, 0.105 mmol, 96% yield) as a yellow oil. LC/MS: M+1=256.0, 258.0.

Intermediate N14

4-(3-(3-Bromophenyl)oxetan-3-yl)morpholine

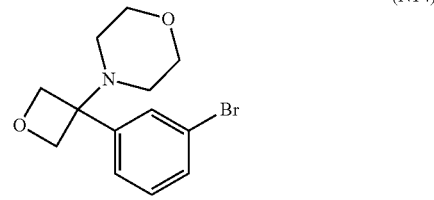

(N14)

Intermediate N8 (80 mg, 0.302 mmol) was dissolved in N,N-dimethylacetamide (1.51 mL) and 1-bromo-2-(2-bromoethoxy)ethane (50.8 µL, 0.363 mmol) followed by DIPEA (185 µL, 1.058 mmol) were added. After heating, the reaction mixture in a sealed vessel at 100° C. for 10 h, additional portions of both 1-bromo-2-(2-bromoethoxy) ethane (50.8 µL, 0.363 mmol) and DIPEA (185 µL, 1.058 mmol) were added to the reaction mixture. After stirring for 20 h at 100° C., the reaction mixture was cooled, diluted with EA (5 mL), and washed with 10 mL of 10% LiCl followed by brine. The organic layer was dried over MgSO$_4$, filtered and concentrated to give a brown oil. The crude product was purified by silica gel chromatography eluting with a gradient of ethyl acetate in hexanes to obtain 4-(3-(3-bromophenyl)oxetan-3-yl)morpholine (49 mg, 0.164 mmol, 54.3% yield) (LC/MS: 0.62 min [M+1]=298, 300. Method M).

Intermediate N15

1-(3-(3-Bromophenyl)oxetan-3-yl)pyrrolidin-3-ol

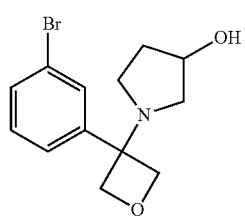

(N15)

A partial suspension of Intermediate N8 (60 mg, 0.227 mmol), 1,4-dibromobutan-2-ol (93 mg, 0.340 mmol) and K$_2$CO$_3$ (62.7 mg, 0.454 mmol) in water (2.27 mL) was sealed and heated in a microwave reactor for 20 min at 120° C. Additional portions of both 1,4-dibromobutan-2-ol (93 mg, 0.340 mmol) and K$_2$CO$_3$ (62.7 mg, 0.454 mmol) were added and the mixture was heated in a microwave reactor for 20 min at 120° C. Additional portions of 1,4-dibromobutan-2-ol (181 mg, 0.663 mmol) and K$_2$CO$_3$ (122 mg, 0.885 mmol) were added and the mixture was heated in a microwave reactor for 20 min at 120° C.

The final reaction mixture was diluted with 1 mL of saturated NaHCO$_3$ and extracted with 2×5 mL of ethyl acetate. The organic portion was dried over Na$_2$SO$_4$ and concentrated in vacuo. The crude product was purified by silica gel chromatography eluting with dichloromethane containing methanol to obtain 1-(3-(3-bromophenyl)oxetan- 3-yl)pyrrolidin-3-ol (40 mg, 0.134 mmol, 59.1% yield)) as a colorless oil. ¹H NMR (400 MHz, CDCl₃) δ 7.46 (ddd, J=7.9, 1.9, 1.0 Hz, 1H), 7.37 (t, J=1.8 Hz, 1H), 7.31-7.24 (m, 1H), 7.18-7.13 (m, 1H), 4.99-4.90 (m, 4H), 4.40-4.31 (m, 1H), 2.86 (td, J=8.5, 5.9 Hz, 1H), 2.73-2.63 (m, 2H), 2.46 (td, J=8.8, 5.5 Hz, 1H), 2.21-2.08 (m, 1H), 1.90 (d, J=6.8 Hz, 1H), 1.83-1.73 (m, 1H). LC/MS: 0.56 min [M+1]: 298, 300. Method M.

Intermediate N16

1-(4-((3-(3-Bromophenyl)oxetan-3-yl)(methyl)amino)piperidin-1-yl)ethanone

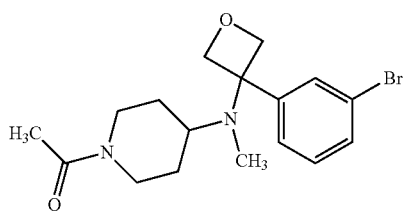

To a solution of Intermediate N8 (50 mg, 0.169 mmol) and 1-acetylpiperidin-4-one (53.4 mg, 0.378 mmol) in methanol (1 mL) was added acetic acid (10.82 µl, 0.189 mmol) and the mixture was stirred at room temperature for 40 h. Sodium cyanoborohydride (17.82 mg, 0.284 mmol) was added to the mixture and was stirred at room temperature for 6 h. The reaction mixture was placed in an ice bath and formaldehyde (0.070 mL, 0.945 mmol, 37% aqueous solution) was added followed by sodium cyanoborohydride (17.82 mg, 0.284 mmol). The ice bath was removed and the reaction mixture was allowed to room temperature, then diluted with ethyl acetate (3 mL) and washed with 2×1 mL of saturated NaHCO₃. The organic layer was dried over MgSO₄, filtered and concentrated to provide 1-(4-((3-(3-bromophenyl)oxetan-3-yl)(methyl)amino)piperidin-1-yl)ethanone (66 mg, 95% yield) as a yellow solid. LC/MS: Rt=0.57 min; [M+1]⁺: 367, 369 Method M).

Intermediate N17

N-(3-(3-Bromophenyl)oxetan-3-yl)-N,2-dimethylpropane-2-sulfonamide

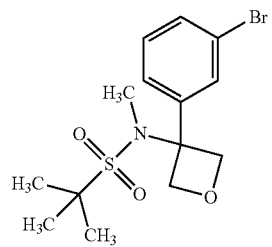

Intermediate N12, (52.4 mg, 0.15 mmol) was dissolved in DMF (0.75 mL) and sodium hydride (5.42 mg, 0.23 mmol) was added. After 30 min, methyl iodide (14.11 µl, 0.226 mmol) was added and the mixture was stirred for 18 h. Next, 10% LiCl (3 mL) was added carefully to the mixture and extracted with 1 mL of ethyl acetate. The organic layer was washed with an additional 3 mL of 10% LiCl, dried over MgSO₄, filtered and concentrated in vacuo to provide N-(3-(3-bromophenyl)oxetan-3-yl)-N,2-dimethylpropane-2-sulfonamide (29 mg, 0.080 mmol, 53.2% yield) as a white solid. LC/MS: Rt=0.94 min; [M-C₄H₉]⁺=306 (Method M).

Intermediate N18

N-(3-(3-Bromophenyl)oxetan-3-yl)-N,2-dimethylpropane-2-sulfinamide

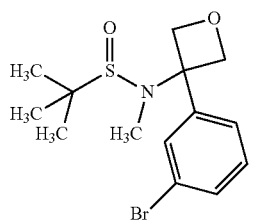

N-(3-(3-Bromophenyl)oxetan-3-yl)-N,2-dimethylpropane-2-sulfinamide (Intermediate N8-B) (50 mg, 0.150 mmol) was dissolved in DMF (0.75 mL) and sodium hydride (5.42 mg, 0.23 mmol) was added. After stirring the reaction mixture for 30 min, methyl iodide (14.11 µl, 0.226 mmol) was added. After 1 h, the mixture was diluted with 10% LiCl (3 mL) and extracted with ethyl acetate (1 mL). The organic layer was washed with an additional 10% LiCl (3 mL), dried over MgSO₄, filtered and concentrated in vacuo to obtain N-(3-(3-bromophenyl)oxetan-3-yl)-N,2-dimethylpropane-2-sulfinamide (30 mg, 0.087 mmol, 57.6% yield) as a white solid. LC/MS: Rt=0.87 min [M+1]⁺=346, 348.

Intermediate N19

N-(3-(3-Bromophenyl)oxetan-3-yl)pivalamide

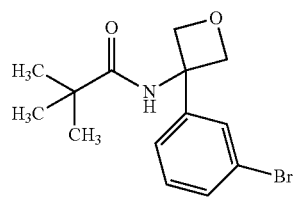

To a solution of Intermediate N8 (40 mg, 0.151 mmol) and DIPEA (39.6 µl, 0.227 mmol) in DCM (1.5 mL) was added pivaloyl chloride (27.9 µl, 0.227 mmol) and the mixture was stirred at room temperature for 30 min. The solvent was removed in vacuo and the residue was partitioned between ethyl acetate and saturated sodium bicarbonate. The organic portion was separated, dried over MgSO₄, filtered and concentrated in vacuo to provide N-(3-(3-bromophenyl)oxetan-3-yl)pivalamide (33 mg, 0.106 mmol, 70% yield) as a white solid. LC/MS: Rt=0.85 min [M+1]=312, 314, Method M.

Intermediate N20-A and Intermediate N20-B (Cis) and (trans)-methyl 1-(3-bromophenyl)-3-hydroxy-3-methylcyclobutanecarboxylate

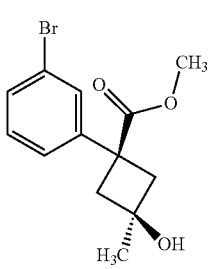
(N20-A)

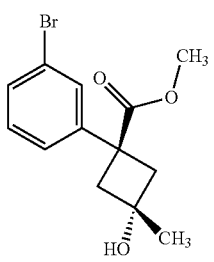
(N20-B)

Intermediate N20-A and Intermediate N20-B

To a cold (−5° C.) solution of methyl 1-(3-bromophenyl)-3-oxocyclobutanecarboxylate (330 mg, 1.17 mmol, *Org. Process Res. Dev.*, 16:1069-1081 (2012)) in toluene (14.6 mL) was added methylmagnesium bromide (0.47 mL, 1.4 mmol, 3M solution in $Et_2O$) was added dropwise while maintaining the internal temperature below 0° C. After stirring at 0° C. for 40 min, 2 mL of 1N HCl was added carefully to the mixture and extracted with ethyl acetate (2×20 mL). The organic layer was washed with brine, dried over $Na_2SO_4$ and the solvent was removed in vacuo. The crude product was purified by silica gel chromatography eluting with a gradient of ethyl acetate and hexanes to provide (cis)-methyl 1-(3-bromophenyl)-3-hydroxy-3-methylcyclobutanecarboxylate (N20-A) (117 mg, 0.391 mmol, 33.6% yield). $^1$H NMR (400 MHz, $CDCl_3$) δ 7.44-7.38 (m, 2H), 7.23-7.20 (m, 2H), 3.67 (s, 3H), 2.99-2.92 (m, 2H), 2.67-2.60 (m, 2H), 1.26 (s, 3H) (LC/MS: Rt=0.95 min; $[M+H_2O]^+$=281, 283. Method M; and (trans)-methyl 1-(3-bromophenyl)-3-hydroxy-3-methylcyclobutanecarboxylate (N20-B) as pale yellow solids (141 mg, 0.471 mmol, 40.4% yield). $^1$H NMR (400 MHz, $CDCl_3$) δ 7.44 (t, J=1.5 Hz, 1H), 7.38 (dt, J=7.1, 2.0 Hz, 1H), 7.22-7.17 (m, 2H), 3.67 (s, 3H), 3.11-3.04 (m, 2H), 2.63-2.56 (m, 2H), 1.42 (s, 3H) (LC/MS: Rt=0.94 min; $[M+H_2O]^+$=281, 283, Method M. Cis- and trans-isomers structures were confirmed by comparison of $^1$H NMR spectra obtained and $^1$H NMR spectral data for these products provided in *Org. Process Res. Dev.*, 16:1069-1081 (2012).

Intermediate N21-A and Intermediate N21-B 1-(3-Bromophenyl)-3-hydroxy-3-(trifluoromethyl)cyclobutanecarboxylic acid

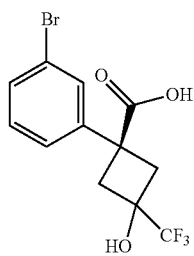
(N21-A)

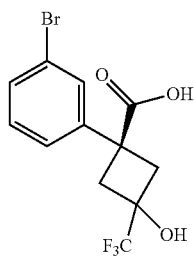
(N21-B)

1-(3-Bromophenyl)-3-oxocyclobutanecarboxylic acid (200 mg, 0.74 mmol) was dissolved in THF (7.4 mL) and (trifluoromethyl)trimethylsilane (0.24 mL, 1.64 mmol) was added. The solution was cooled to −10° C. and tetrabutylammonium fluoride (74.3 μl, 0.074 mmol, 1M solution in THF) was added and the resulting mixture was warmed to room temperature and stirred for 5 h. An additional 0.12 mL (0.82 mmol) of (trifluoromethyl)trimethylsilane was added and the reaction mixture was stirred at room temperature for 18 h. Additional (trifluoromethyl)trimethylsilane (241 μl, 1.64 mmol) and tetrabutylammonium fluoride (74.3 μl, 0.074 mmol) were added and the mixture was stirred further for 2.5 h at room temperature. Next, 4N HCl (4.5 mL) was added to the mixture and stirred for 30 min at room temperature. The mixture was partitioned between ethyl acetate and water, and the organic portion was washed with brine, dried over sodium sulfate and concentrated in vacuo. The crude product was purified by silica gel chromatography to provide Isomer A, 1-(3-bromophenyl)-3-hydroxy-3-(trifluoromethyl)cyclobutanecarboxylic acid (24 mg, 0.071 mmol, 9.52% yield) (N21-A) $^1$H NMR (400 MHz, DMSO-$d_6$) δ 7.54-7.47 (m, 2H), 7.38-7.33 (m, 2H), 6.61 (s, 1H), 3.24 (d, J=14.7 Hz, 2H), 2.64 (d, J=13.9 Hz, 2H), and Isomer B, 1-(3-bromophenyl)-3-hydroxy-3-(trifluoromethyl)cyclobutanecarboxylic acid (72 mg, 0.21 mmol, 28.6% yield) (N21-B) $^1$H NMR (400 MHz, DMSO-$d_6$) δ 7.49-7.45 (m, 1H), 7.34-7.30 (m, 1H), 6.67 (s, 1H), 2.95-2.88 (m, 2H), 2.85-2.77 (m, 2H).

Intermediate N22

(Cis)-1-(3-bromophenyl)-3-hydroxy-N,3-dimethyl-cyclobutanecarboxamide

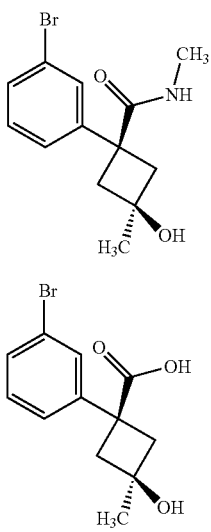

(N22)

(N22-A)

Intermediate N22-A: (Cis)-1-(3-bromophenyl)-3-hydroxy-3-methylcyclobutanecarboxylic acid (Cis)-methyl-1-(3-bromophenyl)-3-hydroxy-3-methylcyclobutanecarboxylate (242 mg, 0.809 mmol) (Intermediate N20-A) was dissolved in a mixture of THF (2.7 mL) and water (1.35 mL). Lithium hydroxide (97 mg, 4.04 mmol) was added and the mixture was stirred at room temperature overnight. The mixture was adjusted to pH=4 and extracted with 10% MeOH/DCM. The solvent was removed in vacuo to provide (cis)-1-(3-bromophenyl)-3-hydroxy-3-methylcyclobutanecarboxylic acid (170 mg, 0.596 mmol) (LC/MS: Rt=0.78 min, $[M-H_2O]^+$=266.8, 268.8, Method M).

Intermediate N22: (Cis)-1-(3-bromophenyl)-3-hydroxy-N,3-dimethylcyclobutanecarboxamide To a solution of (cis)-1-(3-bromophenyl)-3-hydroxy-3-methylcyclobutanecarboxylic acid 170 (mg, 0.596 mmol) in DMF (4 mL), methylamine hydrochloride (52.3 mg, 0.775 mmol), HBTU (452 mg, 1.192 mmol) and DIPEA (0.260 mL, 1.491 mmol) were added. After 30 min, the mixture was diluted with ethyl acetate (5 mL) and washed with 10% LiCl (2×10 mL). The organic layer was washed with brine, dried over $MgSO_4$, filtered and concentrated to obtain a yellow oil that was purified by silica gel chromatography eluting with a gradient of ethyl acetate and hexanes to afford (cis)-1-(3-bromophenyl)-3-hydroxy-N,3-dimethylcyclobutanecarboxamide (137 mg, 0.459 mmol, 77% yield). $^1$H NMR (400 MHz, $CDCl_3$) δ 7.47 (ddd, J=8.0, 1.9, 0.9 Hz, 1H), 7.35 (t, J=1.8 Hz, 1H), 7.32-7.28 (m, 1H), 7.17-7.11 (m, 1H), 5.09 (br. s., 1H), 2.90-2.87 (m, 1H), 2.87-2.84 (m, 1H), 2.81 (s, 1H), 2.74 (d, J=4.8 Hz, 3H), 2.62-2.56 (m, 2H), 1.31 (d, J=0.9 Hz, 3H). LC/MS: Rt=0.80 min, $[M+1]^+$=298.1, 300.1, Method M.

The following Intermediates were prepared according to the general process for the preparation of Intermediate N22 by employing the appropriate reagents.

TABLE N6

| Intermediate | Structure | Name | LC/MS [M + 1] Method |
|---|---|---|---|
| N23 | 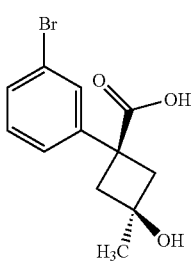 | (cis)-1-(3-bromophenyl)-N-cyclopropyl-3-hydroxy-3-methylcyclobutanecarboxamide | 0.99 min 324.1 Method L |
| N24 | 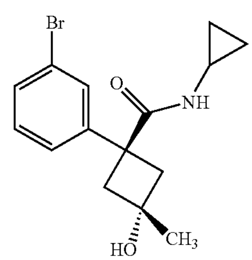 [SMILES: C[C@]1(O)C[C@@](C(=O)NC2CC2)(c2cccc(Br)c2)C1] | (trans)-1-(3-bromophenyl)-N-cyclopropyl-3-hydroxy-3-methylcyclobutanecarboxamide | 0.96 min 324.1 Method L |

TABLE N6-continued

| Intermediate | Structure | Name | LC/MS [M + 1] Method |
|---|---|---|---|
| N25 | 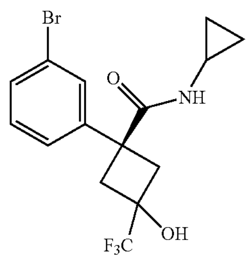 | 1-(3-bromophenyl)-N-cyclopropyl-3-hydroxy-3-(trifluoromethyl)cyclobutanecarboxamide, Isomer A | 1.11 min 378.1 Method L |
| N26 | 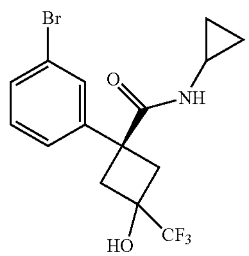 | (cis)-1-(3-bromophenyl)-N-cyclopropyl-3-hydroxy-3-(trifluoromethyl)cyclobutanecarboxamide, Isomer B | 1.03 min 378.1 Method L |

Intermediate N27

1-(3-(4-Amino-5-(1-cyclopropyl-1H-pyrazol-5-yl)pyrrolo[2,1-f][1,2,4]triazin-7-yl)phenyl)-3,3-difluorocyclobutanecarboxylic acid

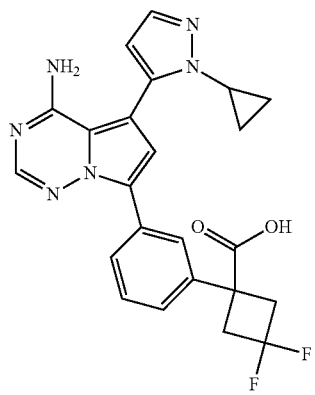

(N27)

Intermediate N27-A: 1-(3-Bromophenyl)-3,3-difluorocyclobutanecarboxylic acid

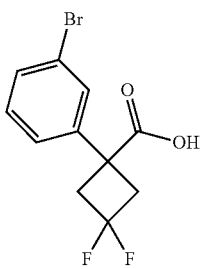

(N27-A)

Methyl 1-(3-bromophenyl)-3-oxocyclobutanecarboxylate (75 mg, 0.265 mmol) was dissolved in DCM (1.5 mL). DEOXO-FLUOR® (0.244 mL, 0.662 mmol, 50% solution in toluene) was added dropwise and the reaction mixture was stirred at room temperature for 18 h. Next, 2 mL of saturated aqueous NaHCO$_3$ was added and the mixture was stirred at room temperature overnight. The organic layer was removed and then aqueous portion was extracted with an addition 2 mL of DCM. The combined organic extracts were dried over MgSO$_4$, filtered and the solvent was removed in vacuo. The crude product was purified by silica gel chromatography eluting with ethyl acetate in hexanes providing methyl 1-(3-bromophenyl)-3,3-difluorocyclobutanecarboxylate. This product was dissolved in a mixture of THF (2 mL) and H$_2$O (1 mL). Lithium hydroxide (31.7 mg, 1.325 mmol) was added and the mixture was stirred at room temperature for 30 min and then heated at 35° C. for 1.5 h. The pH of the solution was adjusted to 3 by adding 1N HCl and the mixture was extracted with of ethyl acetate (3×5 mL). The combined organic extracts were washed with brine, dried over Na$_2$SO$_4$ and concentrated to provide 1-(3-bromophenyl)-3,3-difluorocyclobutanecarboxylic acid (71 mg, 0.244 mmol, 92% yield) (LC/MS: Rt=1.00 min, [M−1]$^-$=289, 291, Method O).

Intermediate N27

Intermediate N27-A, 1-(3-Bromophenyl)-3,3-difluorocyclobutanecarboxylic acid (136 mg, 0.467 mmol) 4,4,4',4',5,5,5',5'-octamethyl-2,2'-bi(1,3,2-dioxaborolane) (131 mg, 0.514 mmol) and potassium acetate (183 mg, 1.869 mmol) were combined in a vial. Dioxane (2.34 mL) was added and the resulting mixture was degassed by bubbling nitrogen gas into the solution while sonicating. PdCl$_2$(dppf)-CH$_2$Cl$_2$ adduct (38.2 mg, 0.047 mmol) was added and the mixture was heated at 80° C. overnight. Water (2336 µl), 7-bromo-5-(1-cyclopropyl-1H-pyrazol-5-yl)pyrrolo[2,1-f][1,2,4]triazin-4-amine (119 mg, 0.374 mmol) and sodium carbonate (149 mg, 1.402 mmol) were added. The degassing procedure above was repeated, PdCl$_2$(dppf)-CH$_2$Cl$_2$ adduct (38.2 mg, 0.047 mmol) was added and the mixture was heated at 85° C. for 1.5 h. The mixture was diluted with 1N HCl (10 mL) and filtered. The aqueous portion of the filtrate liquid was washed with 2×10 mL of ethyl acetate and then the pH was adjusted to 12. The aqueous was washed with ethyl acetate (2×10 mL) and then the pH was adjusted to pH 5 by adding concentrated HCl. The mixture was extracted with 3×20 mL of a 10% MeOH/DCM solution. The organic portion was dried over MgSO₄ filtered and the solvent were removed in vacuo providing 1-(3-(4-amino-5-(1-cyclopropyl-1H-pyrazol-5-yl)pyrrolo [2,1-f][1,2,4]triazin-7-yl)phenyl)-3,3-difluorocyclobutanecarboxylic acid (68 mg, 0.151 mmol, 32.3% yield). Analytical LCMS, Method L, Rt=1.00 min, [M+H]⁺=451.2).

Intermediate N28

(1s,3s)-1-(3-Bromophenyl)-N-cyclopropyl-3-methoxycyclobutanecarboxamide

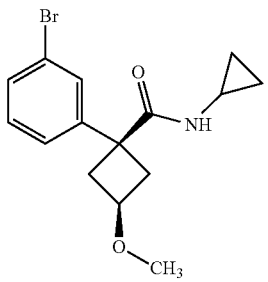

(N28)

Intermediate N28-A: (Cis)-methyl 1-(3-bromophenyl)-3-methoxycyclobutanecarboxylate

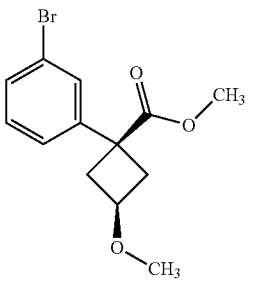

(N28-A)

A solution of (cis)-methyl 1-(3-bromophenyl)-3-hydroxycyclobutanecarboxylate (500 mg, 1.754 mmol) (prepared as described in *Org. Process Res. Dev.*, 16:1069-1081 (2012)) in DMF (10 mL) was treated with sodium hydride (105 mg, 2.63 mmol, 60% dispersion in mineral oil) and the mixture was stirred for 30 min at room temperature. Methyl iodide (0.164 mL, 2.63 mmol) was added and the resulting mixture was stirred at room temperature for 18 h after which an additional 2 eq each of sodium hydride and methyl iodide were added. The resulting mixture was stirred at room temperature for 18 h and then diluted with water and extracted with ethyl acetate. The organic portion was dried over MgSO₄, filtered and concentrated. The crude product was purified by silica gel chromatography eluting with a gradient of ethyl acetate in hexanes to provide (cis)-methyl 1-(3-bromophenyl)-3-methoxycyclobutanecarboxylate.

Intermediate N28-B: (Cis)-methyl 1-(3-bromophenyl)-3-methoxycyclobutanecarboxylate

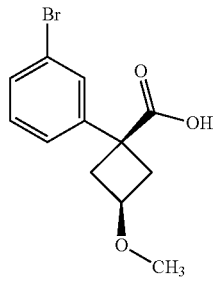

(N28-B)

All of the purified product obtained above was dissolved in a mixture of THF (10 mL) and water (3 mL), and lithium hydroxide (210 mg, 8.77 mmol) was added. The mixture was stirred at room temperature for 18 h. The pH of the mixture was adjusted to 4 and then extracted with ethyl acetate (3×20 mL). The organic portion was dried over MgSO₄, filtered, and the solvent removed in vacuo to afford (cis)-1-(3-bromophenyl)-3-methoxycyclobutanecarboxylic acid (286 mg, 1.003 mmol, 57.2% yield). LC/MS: Rt=1.07, [M+1]⁺=285, 287, Method L).

Intermediate N28

Intermediate N28 was prepared by amidation according to the general procedure used in the synthesis of Example 165 employing the appropriate reagents. (LC/MS: Rt=0.89 min, [M+1]⁺=324.0, 326.0, Method M).

Intermediate N29

(1s,3s)-1-(3-Bromophenyl)-3-(difluoromethoxy)-N-methylcyclobutanecarboxamide

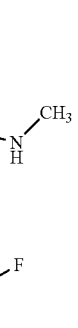

(N29)

Intermediate N29-A: (Cis)-methyl 1-(3-bromophenyl)-3-(difluoromethoxy) cyclobutanecarboxylate

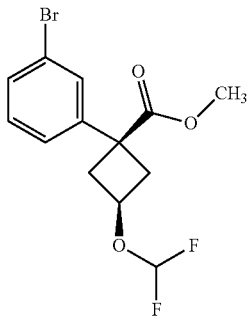

(N29-A)

Under anhydrous conditions, a solution of (cis)-methyl 1-(3-bromophenyl)-3-hydroxycyclobutanecarboxylate (100 mg, 0.351 mmol) in acetonitrile (1.2 mL) was treated with copper(I) iodide (6.68 mg, 0.035 mmol). The mixture was heated, with stirring, to 45° C., and 2-(fluorosulfonyl)difluoroacetic acid (36.2 µl, 0.351 mmol) was added. After 80 min at 45° C., the mixture was cooled to room temperature and quenched by diluting with 1.5 M aqueous $K_2HPO_4$ solution. The resulting mixture was extracted with ethyl acetate, the organic portion was dried over $MgSO_4$ and concentrated and the residue was purified by silica gel chromatography providing (cis)-methyl 1-(3-bromophenyl)-3-(difluoromethoxy)cyclobutanecarboxylate (38 mg, 0.113 mmol, 32.3% yield). $^1$H NMR (400 MHz, $CDCl_3$) δ 7.53 (t, J=1.8 Hz, 1H), 7.46-7.42 (m, 1H), 7.40-7.37 (m, 1H), 7.34-7.30 (m, 1H), 7.27-7.22 (m, 1H), 6.36-5.97 (m, 1H), 4.51 (quin, J=7.3 Hz, 1H), 3.67 (s, 3H), 2.98-2.92 (m, 4H). LC/MS: Rt=1.07, [M+1]$^+$=285, 287, Method L).

Intermediate N29-B: (Cis)-1-(3-bromophenyl)-3-(difluoromethoxy) cyclobutanecarboxylic acid

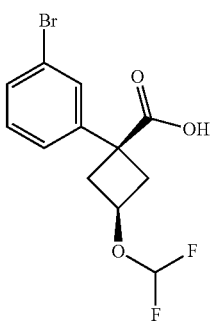

(N29-B)

A solution of (cis)-methyl 1-(3-bromophenyl)-3-(difluoromethoxy) cyclobutanecarboxylate (188 mg, 0.561 mmol) in THF (3.7 mL) and water (1.9 mL) was treated with lithium hydroxide (67.2 mg, 2.80 mmol) and the mixture was stirred at room temperature for 18 h. The mixture was diluted with water (3 mL), the pH of the mixture was adjusted to 3, and extracted with 10% MeOH solution in DCM (3×10 mL). The organic portion was dried over $MgSO_4$, filtered and concentrated to provide (cis)-1-(3-bromophenyl)-3-(difluoromethoxy)cyclobutanecarboxylic acid (167 mg, 0.520 mmol, 93% yield) as a pale yellow oil. LCMS=1.06 min [M–1]$^-$=319, 321.

Intermediate N29

Intermediate N29 was prepared by amidation according to the general procedure used in the synthesis of Example 165 employing the appropriate reagents. LC/MS: Rt=0.88 min, [M+1]$^+$=334.1, 336.1, Method M.

Intermediate N30

(Cis)1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutanecarboxylic acid

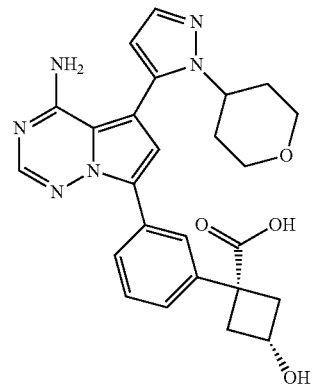

(N30)

(Cis)-1-(3-bromophenyl)-3-hydroxycyclobutanecarboxylic acid (0.515 g, 1.844 mmol) (prepared according to *Org. Process Res. Dev.,* 16:1069-1081 (2012)), 4,4,4',4',5,5,5',5'-octamethyl-2,2'-bi(1,3,2-dioxaborolane) (0.515 g, 2.029 mmol) and potassium acetate (0.724 g, 7.38 mmol) were combined in dioxane (8 mL). The mixture was degassed by bubbling nitrogen gas into the solution while being sonicated and $PdCl_2$(dppf)-$CH_2Cl_2$ adduct (0.151 g, 0.184 mmol) was added. The resulting mixture was heated at 90° C. for 1.5 h, cooled to room temperature and 7-bromo-5-(1-(tetrahydro-2H-pyran-4-yl)-1H-pyrazol-5-yl)pyrrolo[2,1-f][1,2,4]triazin-4-amine (N-1) (0.536 g, 1.475 mmol), sodium carbonate (0.586 g, 5.53 mmol) and water (7 mL) were added. The above degassing procedure was repeated, $PdCl_2$(dppf)-$CH_2Cl_2$ adduct (0.151 g, 0.184 mmol) was added and the mixture was heated at 100° C. for 1 h. After cooling to room temperature, water (5 mL) and ethyl acetate (20 mL) were added and the pH of the aqueous layer was adjusted to 5 with HCl. The organic portion was removed, dried over $MgSO_4$, filtered and concentrated. The crude product was suspended in 10 mL of toluene and then filtered. The collected solid was dried in vacuo providing (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutanecarboxylic acid (508 mg, 1.071 mmol, 58% yield) as a white solid. $^1$H NMR (400 MHz, DMSO-$d_6$) δ 8.16-8.06 (m, 2H), 7.95 (d, J=7.9 Hz, 1H), 7.68 (d, J=1.8 Hz, 1H), 7.51-7.45 (m, 1H), 7.43-7.31 (m, 2H), 7.30-7.21 (m, 1H), 6.46 (d, J=1.8 Hz, 1H), 4.42-4.30 (m, 1H), 4.00-3.80 (m, 3H), 3.33 (t, J=11.4 Hz, 2H), 2.84 (ddd, J=9.7, 7.0, 2.4 Hz, 2H), 2.60-2.53 (m, 1H), 2.18-2.03 (m, 2H), 1.92-1.71 (m, 2H), [M+1]$^+$=475.1.

Intermediate N34

(3R,5S)-5-(3-Bromophenyl) pyrrolidin-3-ol

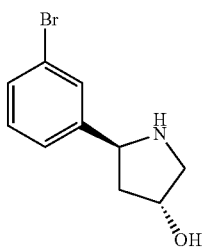

(N34)

(3R,5S)-5-(3-Bromophenyl)-1-(tert-butylsulfonyl)pyrrolidin-3-ol (240 mg, 0.662 mmol) (prepared according to *J. Org. Chem.*, 74:7859-7865 (2009)) was treated with hydrochloric acid (6N in H$_2$O) (1.32 mL). The mixture was heated at 100° C. for 3 h and then cooled to room temperature and lyophilized providing (3R,5S)-5-(3-bromophenyl) pyrrolidin-3-ol, HCl salt (181 mg, 0.650 mmol, 98% yield) as a white solid.

The following were prepared according to the general synthesis procedure for Intermediate N34.

Intermediate N38

(3R,5S)-5-(3-Bromophenyl)-1-methylpyrrolidin-3-ol

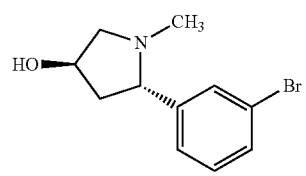

(N38)

(3R,5S)-5-(3-Bromophenyl)pyrrolidin-3-ol (30 mg, 0.124 mmol) was dissolved in a mixture of DCM (0.5 mL) and THF (0.5 mL). Formaldehyde 37% aqueous solution (46.1 µL, 0.620 mmol) was added and the mixture was cooled to 0° C. Sodium triacetoxyborohydride (131 mg, 0.620 mmol) was added and the mixture was stirred at 0° C. for 30 min. The reaction mixture was concentrated to dryness, diluted with 1 mL of 1N NaOH and extracted with DCM (3×3 mL). The combined organic portions were dried over MgSO$_4$, filtered and concentrated to obtain (3R,5S)-5-(3-bromophe-

TABLE N15

| Intermediate | Structure | Name | LC/MS [M + 1] Method |
|---|---|---|---|
| N34 | ![structure] | (3S,5S)-5-(3-bromophenyl)pyrrolidin-3-ol HCl salt | 0.53 min 243.9 Method I |
| N35 | ![structure] | (3S,5R)-5-(3-bromophenyl)-1-pyrrolidin-3-ol, HCl salt | 0.54 min 244.0 Method I |
| N36 | ![structure] | (3R,5R)-5-(3-bromophenyl)-1-pyrrolidin-3-ol, HCl salt | 0.54 min 244.0 Method I | nyl)-1-methylpyrrolidin-3-ol (30 mg, 0.117 mmol, 95% yield) as a colorless oil. LC/MS: 0.54 min, [M+1]⁺=256, 258 Method M.

Intermediate N42

1-(3-(4-Amino-5-(1-(tetrahydro-2H-pyran-4-yl)-1H-pyrazol-5-yl)pyrrolo[2,1-f][1,2,4]triazin-7-yl)phenyl)ethanol

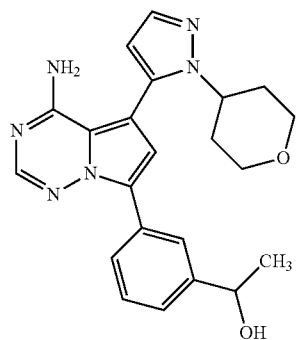

(N42)

7-Bromo-5-(1-(tetrahydro-2H-pyran-4-yl)-1H-pyrazol-5-yl)pyrrolo[2,1-f][1,2,4]triazin-4-amine (N-1) (0.3 g, 0.83 mmol), (3-(1-hydroxyethyl)phenyl)boronic acid (0.14 g, 0.826 mmol) and phosphoric acid, potassium salt (0.7 g, 3.30 mmol) were combined in a 20 mL microwave reactor vial and dioxane (2.75 mL) and water (2.75 mL) were added. The resulting suspension was degassed by bubbling N₂ with sonication. Tetrakis triphenylphosphine (0.143 g, 0.124 mmol) was added, the degassing process was repeated and the mixture was heated at 120° C. for 40 min. The reaction mixture was cooled, diluted with water (5 mL), extracted with ethyl acetate (20 mL) and the organic portion was dried over MgSO₄. The solvent removed in vacuo, and the residue was purified by silica gel chromatography eluting with gradient of methanol in DCM to afford 1-(3-(4-amino-5-(1-(tetrahydro-2H-pyran-4-yl)-1H-pyrazol-5-yl)pyrrolo[2,1-f][1,2,4]triazin-7-yl)phenyl)ethanol (0.293 g, 88% yield) as a yellow solid.

Intermediate R1

7-Bromo-5-(1-(tetrahydro-2H-pyran-4-yl)-1H-1,2,3-triazol-5-yl)pyrrolo[2,1-f][1,2,4]triazin-4-amine

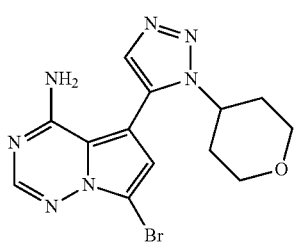

(R1)

Intermediate R1-A: 7-Bromo-5-iodopyrrolo[2,1-f][1,2,4]triazin-4-amine

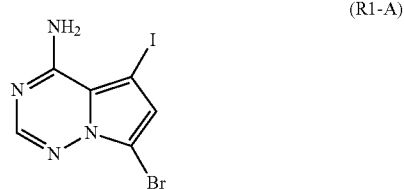 [SMILES: Nc1ncnn2c(Br)cc(I)c12]

(R1-A)

To a solution of 7-bromopyrrolo[2,1-f][1,2,4]triazin-4-amine (4 g, 18.78 mmol) in anhydrous DMF (200 mL) was added NIS (4.65 g, 20.65 mmol) and the mixture was stirred in the dark at room temperature for 10 h. The precipitate formed was filtered and washed with DCM (3×), and dried to provide white solid, 7-bromo-5-iodopyrrolo[2,1-f][1,2,4]triazin-4-amine (5 g, 79% yield). LC-MS m/z (M+H)⁺=339.95. ¹H NMR (500 MHz, DMSO-d₆) δ 7.10 (S, 1H), 7.98 (s, 1H).

Intermediate R1-B: 7-Bromo-5-((trimethylsilyl)ethynyl)pyrrolo[2,1-f][1,2,4]triazin-4-amine

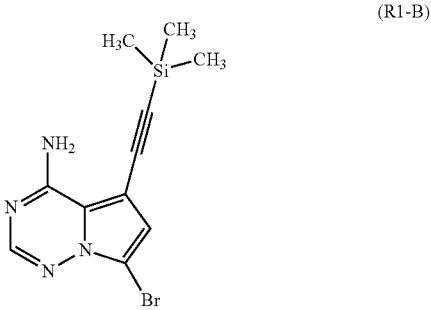 [SMILES: C[Si](C)(C)C#Cc1cc(Br)n2ncnc(N)c12]

(R1-B)

7-Bromo-5-iodopyrrolo[2,1-f][1,2,4]triazin-4-amine (2.4 g, 7.08 mmol) was suspended in anhydrous DMF (40 mL), and then triethylamine (3 mL, 21.24 mmol), copper(I) iodide (0.3 g, 1.56 mmol), bis(triphenylphosphine)palladium(II) chloride (0.5 g, 0.71 mmol) were added. Nitrogen gas was bubbled through the mixture for a 3 min and ethynyltrimethylsilane (1 mL, 7.1 mmol) was added. After stirring for 1 h, the reaction mixture was poured into ice water (200 mL) and the precipitate which formed was filtered. The solid was dissolved in ether (150 mL), washed with water (100 mL) followed by brine (100 mL). The crude solid was then suspended in MeOH (50 mL), stirred for an hour and then filtered and dried in vacuo to provide 7-bromo-5-((trimethylsilyl)ethynyl)pyrrolo[2,1-f][1,2,4]triazin-4-amine (90% yield). LC-MS m/z (M+H)⁺=309.10. ¹H NMR (500 MHz, DMSO-d₆) δ 2.50 (s, 9H), 7.05 (S, 1H), 8.03 (s, 1H).

Intermediate R1-C: 7-Bromo-5-ethynylpyrrolo[2,1-f][1,2,4]triazin-4-amine

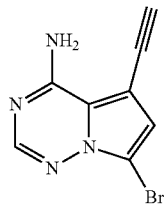

(R1-C)

To a suspension of 7-bromo-5-((trimethylsilyl)ethynyl)pyrrolo[2,1-f][1,2,4]triazin-4-amine (7.3 g, 23.61 mmol) in MeOH (100 mL) was added $K_2CO_3$ (16.31 g, 118 mmol) and the reaction mixture was stirred for 2 h at room temperature. Suspension was filtered, washed with water and DCM. The light yellow solid was dried in vacuo. The combined filtrate was concentrated and the solid was washed with DCM to provide more of yellow solid which was combined with the previous solid to provide 7-bromo-5-ethynylpyrrolo[2,1-f][1,2,4]triazin-4-amine (5.3 g, 95% yield). LCMS $(M+H)^+$=237.05. $^1$H NMR (500 MHz, DMSO-$d_6$) δ 4.48 (s, 1H), 7.05 (S, 1H), 8.01 (s, 1H).

Intermediate R1

To a solution of 7-bromo-5-ethynylpyrrolo[2,1-f][1,2,4]triazin-4-amine (200 mg, 0.844 mmol) in toluene (8 mL) was added 4-azidotetrahydro-2H-pyran (215 mg, 1.7 mmol) and then chloro(pentamethylcyclopentadienyl)ruthenium (II) tetramer (27 mg, 0.025 mmol). Nitrogen was bubbled through the mixture for 1 min, and the mixture was heated in a sealed tube at 100° C. for 50 min in a microwave instrument. The mixture was cooled, diluted with hexane (8 mL) and the precipitate formed was filtered, washed with hexane, and MeOH and dried in vacuo to provide 7-bromo-5-(1-(tetrahydro-2H-pyran-4-yl)-1H-1,2,3-triazol-5-yl)pyrrolo[2,1-f][1,2,4]triazin-4-amine (250 mg, 81% yield). LC/MS $(M+H)^+$=364.1. $^1$H NMR (500 MHz, DMSO-$d_6$) δ 1.95 (m, 2H), 2.14 (m, 2H), 3.40 (m, 2H), 3.92 (m, 2H), 4.51 (m, 1H), 7.08 (S, 1H), 7.83 (S, 1H), 8.10 (s, 1H).

Intermediate R1B

7-Bromo-5-(1-(cyclopropylmethyl)-1H-1,2,3-triazol-4-yl)pyrrolo[1,2-f][1,2,4]triazin-4-amine

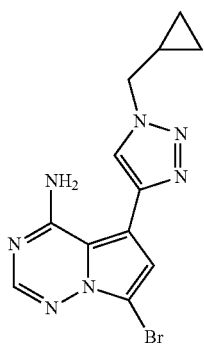

(R1B)

A mixture of tert-butyl (7-bromo-5-ethynylpyrrolo[2,1-f][1,2,4]triazin-4-yl) carbamate (320 mg, 0.949 mmol) and bis-tert-butyl (7-bromo-5-ethynylpyrrolo[2,1-f][1,2,4]triazin-4-yl)carbamate (104 mg, 0.237 mmol), sodium azide (61.7 mg, 0.949 mmol), sodium ascorbate (188 mg, 0.949 mmol), (bromomethyl)cyclopropane (128 mg, 0.949 mmol) suspended in DMSO (2 mL), DMF (1 mL) and water (2 mL) in a crimp-cap pressure vial was stirred at 100° C. After 1.5 h, the mixture was cooled to room temperature, diluted with water (100 mL) and filtered to collect the insoluble material. The solid was washed with water and dried in vacuo overnight. The resulting solid was washed with acetone and filtered. The combined filtrates were set aside. The solid was washed with acetone (>150 mL) and the combined filtrate concentrated under reduced pressure to give 7-bromo-5-(1-(cyclopropylmethyl)-1H-1,2,3-triazol-4-yl)pyrrolo[2,1-f][1,2,4]triazin-4-amine (300 mg, 0.898 mmol, 95% yield) as a yellow solid (isolate, 100 mg, isolate –04). LC/MS $(M+H)^+$=333.9 and 335.9 (Method I).

The following Intermediates and other triazines disclosed herein were prepared according to the general synthesis procedure for Intermediate R1 using appropriate azides in the last step.

TABLE R1

| Intermediate | C5 | Name |
|---|---|---|
| R2 | | 7-bromo-5-(1-isopropyl-1H-1,2,3-triazol-5-yl)pyrrolo[2,1-f][1,2,4]triazin-4-amine |
| R3 | | 7-bromo-5-(1-cyclohexyl-1H-1,2,3-triazol-5-yl)pyrrolo[2,1-f][1,2,4]triazin-4-amine |

Intermediate R4

7-Bromo-5-(1-(tetrahydro-2H-pyran-4-yl)-1H-imidazol-5-yl)pyrrolo[2,1-f][1,2,4]triazin-4-amine

(R4)

Intermediate R4-A: (4-Amino-7-bromopyrrolo[2,1-f][1,2,4]triazin-5-yl)methanol

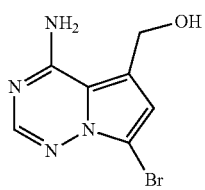
(R4-A)

To a solution of 4-amino-7-bromopyrrolo[2,1-f][1,2,4]triazine-5-carboxylic acid (2 g, 7.78 mmol) in THF was added boranedimethylsulfide complex (11.7 mL, 11.67 mmol). After stirring the mixture was at room temperature for 18 h, it was diluted with 20 mL of water and stirred for 30 min. The mixture was extracted with EtOAc (25 mL×3) and the combined organic layer was washed with brine, dried over $Na_2SO_4$ and concentrated to provide intermediate R4-A (1.64 g, 87% yield). LC-MS m/z $(M+H)^+=245.1$.

Intermediate R4-B: 4-Amino-7-bromopyrrolo[2,1-f][1,2,4]triazine-5-carbaldehyde

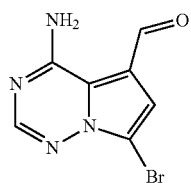
(R4-B)

To a suspension of (4-amino-7-bromopyrrolo[2,1-f][1,2,4]triazin-5-yl)methanol (100 mg, 0.411 mmol) in DCM (10 mL) was added $MnO_2$ (179 mg, 2.06 mmol) and stirred vigorously for 2 h. Additional $MnO_2$ (179 mg, 2.057 mmol) was added and the mixture was stirred overnight. Additional 5 eq of $MnO_2$ was added and stirred for 1.5 h. The mixture was diluted with DCM/MeOH and adsorbed directly on to silica gel and purified by ISCO column chromatography on a 12 g column, eluting with 0-10% MeOH/DCM to obtain a pale yellow solid (81 mg, 82% yield). LC-MS m/z $(M+H)^+=243.05$. $^1$H NMR (500 MHz, DMSO-$d_6$) δ 5.76 (s, 1H), 7.63 (s, 1H), 8.22 (s, 1H), 9.75 (s, 1H).

Intermediate R4

Tetrahydro-2H-pyran-4-amine (37.4 mg, 0.370 mmol) was stirred with a mixture of $MgSO_4$ (101 mg, 0.84 mmol) in $Et_3N$ (1.5 ml, 10.76 mmol) at room temperature for 10 min. Next, 4-amino-7-bromopyrrolo[2,1-f][1,2,4]triazine-5-carbaldehyde (81 mg, 0.336 mmol) was added and the mixture was refluxed for 2 h. The mixture was cooled, filtered and concentrated. The residue was dissolved in anhydrous MeOH (4 mL) and TOSMIC (85 mg, 0.437 mmol) and $K_2CO_3$ (139 mg, 1.01 mmol) were added. The resulting mixture was heated 100° C. for 10 h, cooled to room temperature, was filtered and the solid was washed with water. The filtrate was extracted with ethyl acetate (10 mL×3). The organic layers were mixed, dried and concentrated. The residue was purified by preparative LCMS (PHENOMENEX® Luna Axia, C18, 5μ, 21.20×100 mm column; gradient elution 0-100% B/A over 18 min (Solvent A=10% MeCN/$H_2O$ containing 0.1% TFA, Solvent B=90% MeCN/$H_2O$ containing 0.1% TFA, flow rate 20 mL/min, UV detection at 220 nm) to obtain 7-bromo-5-(1-(tetrahydro-2H-pyran-4-yl)-1H-imidazol-5-yl)pyrrolo[2,1-f][1,2,4]triazin-4-amine (10 mg, 0.028 mmol, 8.2% yield). LC-MS m/z $(M+H)^+=363.15, 365.15$.

Intermediate RX

7-Bromo-5-(1-methyl-1H-pyrazol-4-yl)pyrrolo[1,2-f][1,2,4]triazin-4-amine

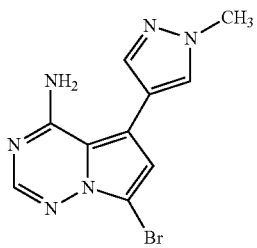
(RX)

A mixture of 7-bromo-5-iodopyrrolo[2,1-f][1,2,4]triazin-4-amine (462 mg, 1.2 mmol) (Intermediate R1-A), 1-methyl-4-(4,4,5,5-tetramethyl-1,3,2-dioxaborolan-2-yl)-1H-pyrazole (250 mg, 1.200 mmol), sodium carbonate (2.400 mL, 4.80 mmol), water (0.5 mL) and DMF (1.5 mL) was placed in a capped microwave pressure reaction vial. The mixture was sparged with nitrogen via hypodermic needles for 5 min and then heated at 90° C. for 5 min. A solution of 1,1'-bis(diphenylphosphino)ferrocene-palladium (II) dichloride dichloromethane complex (196 mg, 0.240 mmol) in DMF (0.2 mL) was added and the mixture stirred at 90° C. for 10 min. Flash chromatography using a 24 g ISCO silica gel cartridge eluted with EtOAc/hexanes gave 7-bromo-5-(1-methyl-1H-pyrazol-4-yl)pyrrolo[2,1-f][1,2,4]triazin-4-amine (205 mg, 0.699 mmol, 58% yield) as a light yellow solid. Mass spectrum m/z 293 $(M+H)^+$. $^1$H NMR (400 MHz, DMSO-$d_6$) δ 7.96 (s, 1H), 7.88 (s, 1H), 7.58 (d, J=0.9 Hz, 1H), 6.80 (s, 1H), 3.89 (s, 3H).

Intermediate RXA

7-Bromo-5-(1-(difluoromethyl)-1H-pyrazol-4-yl)pyrrolo[2,1-f][1,2,4]triazin-4-amine

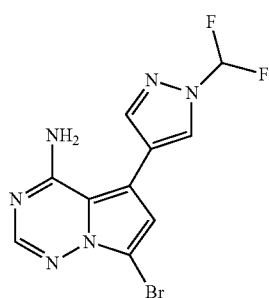

(RXA)

A mixture of 4-(4,4,5,5-tetramethyl-1,3,2-dioxaborolan-2-yl)-1H-pyrazole (300 mg, 1.546 mmol), Cs$_2$CO$_3$ (1007 mg, 3.09 mmol) and sodium chlorodifluoroacetate (471 mg, 3.09 mmol) in DMF (1 mL) was heated at 110° C. for 16 h. To the reaction mixture was added 7-bromo-5-iodopyrrolo[2,1-f][1,2,4] triazin-4-amine (Intermediate R1-A) (524 mg, 1.546 mmol), 2 M aqueous tripotassium phosphate (1.546 mL, 3.09 mmol) and PdCl$_2$(dppf)-CH$_2$Cl$_2$ adduct (63.1 mg, 0.077 mmol). The mixture was degassed by vacuum then back-filled with nitrogen, repeating twice. The reaction mixture was heated at 90° C. for 4 h, cooled to room temperature and water was added. The resulting precipitate was filtered and the filter cake washed with water twice. The filter cake was washed with DCM and methanol and the filtrate was concentrated to a black material containing 7-bromo-5-(1-(difluoromethyl)-1H-pyrazol-4-yl)pyrrolo[2,1-f][1,2,4]triazin-4-amine (412 mg, 92% purity, 1.14 mmol, 74% yield). The intermediate was used without further purification. Mass spectrum m/z 329, 331 (M+H)$^+$.

Intermediate RXB

7-Bromo-5-(1-isopropyl(heptadeutero)-1H-pyrazol-4-yl)pyrrolo[1,2-f][1,2,4]triazin-4-amine

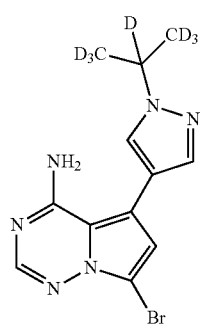

(RXB)

A mixture of 2-iodopropane-D7 (274 mg, 1.546 mmol), 4-(4,4,5,5-tetramethyl-1,3,2-dioxaborolan-2-yl)-1H-pyrazole (300 mg, 1.546 mmol) and Cs$_2$CO$_3$ (1007 mg, 3.09 mmol) in DMF (2 mL) was heated at 110° C. for 16 h. To the reaction mixture was added 7-bromo-5-iodopyrrolo[2,1-f][1,2,4]triazin-4-amine (524 mg, 1.546 mmol) (Intermediate R1-A), PdCl$_2$(dppf))-CH$_2$Cl$_2$ adduct (56.6 mg, 0.077 mmol) and 2 M aqueous tripotassium phosphate (1.546 mL, 3.09 mmol). The resulting mixture was degassed by vacuum then back-filled with nitrogen, repeating twice. The mixture was heated at 90° C. for 4 h, cooled to room temperature and water was added. The precipitate was filtered and the filter cake was washed with water twice. To the filter funnel containing the filter cake was added a 1:1 mixture of DCM and methanol until all soluble material was dissolved, filtered and the filtrate was concentrated to a black material containing 7-bromo-5-(1-methyl-D3-1H-pyrazol-4-yl)pyrrolo[2,1-f][1,2,4]triazin-4-amine (312 mg, 38% purity, 0.36 mmol, 23% yield). The intermediate was used without further purification. Mass spectrum m/z 328, 330 (M+H)$^+$.

The Intermediates in Tables JATR1 and JATR2 were prepared by chemistry exemplified in RX, RXA and RXB from Intermediate R1-A and available boronic esters or boronic acids. Alternatively, the boronic esters can be prepared by methods known in the art.

TABLE JATR1

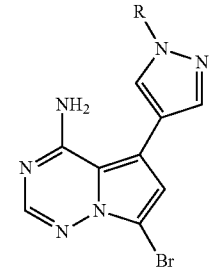

| Intermediate | R | Name | LCMS M + H |
|---|---|---|---|
| RXC | —CH(CH$_3$)$_2$ | 7-bromo-5-(1-isopropyl-1H-pyrazol-4-yl)pyrrolo[1,2-f][1,2,4]triazin-4-amine | 321 and 323 |
| RXD | —CD$_3$ | 7-bromo-5-(1-methyl(triduetero)-1H-pyrazol-4-yl)pyrrolo[1,2-f][1,2,4]triazin-4-amine | 296 and 298 |
| RXE | —cyclopropyl | 7-bromo-5-(1-cyclopropyl-1H-pyrazol-4-yl)pyrrolo[1,2-f][1,2,4]triazin-4-amine | 319 and 321 |
| RXF | —CH$_2$CHF$_2$ | 7-bromo-5-(1-(2,2-difluoroethyl)-1H-pyrazol-4-yl)pyrrolo[1,2-f][1,2,4]triazin-4-amine | 343 and 345 |
| RXG | —SO$_2$CH$_3$ | 7-bromo-5-(1-(methylsulfonyl)-1H-pyrazol-4-yl)pyrrolo[1,2-f][1,2,4]triazin-4-amine | 357 and 359 |
| RXH | —SO$_2$CH(CH$_3$)$_2$ | 7-bromo-5-(1-(isopropylsulfonyl)-1H-pyrazol-4-yl)pyrrolo[1,2-f][1,2,4]triazin-4-amine | 385 and 387 |
| RXI | —SO$_2$cyclopropyl | 7-bromo-5-(1-(cyclopropylsulfonyl)-1H-pyrazol-4-yl)pyrrolo[1,2-f][1,2,4]triazin-4-amine | 383 and 385 |

TABLE JATR2

| Intermediate | Structure | Name | LCMS M + H |
|---|---|---|---|
| RXJ | 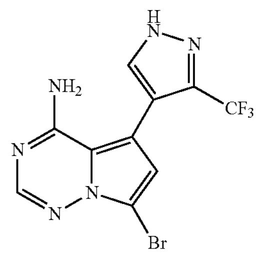 | 7-bromo-5-(4-(trifluoromethyl)-1H-pyrrol-3-yl)pyrrolo[1,2-f][1,2,4]triazin-4-amine | 346 and 348 |
| RXK | 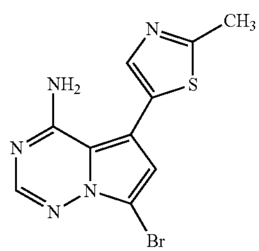 | 7-bromo-5-(2-methylthiazol-5-yl)pyrrolo[1,2-f][1,2,4]triazin-4-amine | 310 and 312 |
| RXL | 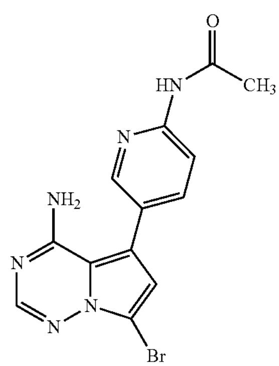 | N-(5-(4-amino-7-bromopyrrolo[1,2-f][1,2,4]triazin-5-yl)pyridin-2-yl)acetamide | 347 and 349 |

Intermediate R28

4-(3-Bromophenoxy)tetrahydro-2H-thiopyran 1,1-dioxide

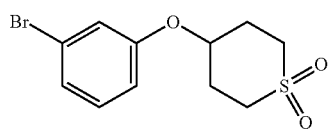
(R28)

Intermediate R28A:
4-(3-Bromophenoxy)tetrahydro-2H-thiopyran

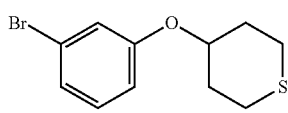
(R28-A)

To a solution of 3-bromophenol (250 mg, 1.445 mmol) in DMF (10 mL) was added tetrahydro-2H-thiopyran-4-yl methanesulfonate (425 mg, 2.168 mmol) and potassium carbonate (599 mg, 4.34 mmol). The mixture was heated with stirring at 115° C. for 10 h, then cooled to room temperature, diluted with EtOAc (20 mL), and washed with H$_2$O (20 mL). The orange organic layer was washed with brine, dried over with MgSO$_4$, and concentrated to give crude product, which was purified by flash chromatography on silica gel eluting with 0-100% EtOAc/hexane (12 g column, 16 min gradient) to provide 4-(3-bromophenoxy)tetrahydro-2H-thiopyran (301 mg, 76.2% yield). $^1$H NMR (500 MHz, CDCl$_3$) δ 2.05 (m, 2H), 2.20 (m, 2H), 2.59 (m, 2H), 2.94 (m, 2H), 4.36 (m, 1H), 6.85 (ddd, 1H), 7.09 (m, 2H), 7.11 (m, 1H), 7.16 (sc, 1H).

Intermediate R28

To a solution of 4-(3-bromophenoxy)tetrahydro-2H-thiopyran (301 mg, 1.1 mmol) in DCM (10 mL) was added mCPBA (380 mg, 2.2 mmol) at 0° C. The reaction mixture was stirred for 10 h, saturated NaHCO$_3$ (10 mL) was added and extracted with DCM (3×10 mL). The combined organic layers were washed with sodium metabisulfite, brine (10 mL), dried (MgSO$_4$) and concentrated. The residue was purified by ISCO silica gel chromatography (12 g column, 0-100% EtOAc/hexane solvent, 20 min gradient) to afford 4-(3-bromophenoxy)tetrahydro-2H-thiopyran 1,1-dioxide (250 mg, 0.819 mmol, 74.5% yield). $^1$H NMR (500 MHz, CDCl$_3$) δ 2.44 (m, 4H), 2.99 (m, 2H), 3.40 (m, 2H), 4.65 (m, 1H), 6.89 (m, 1H), 7.12 (s, 1H). 7.19 (m, 2H).

Intermediate R29

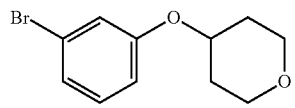
(R29)

Intermediate R29 was prepared according to the general synthesis procedure for Intermediate R28-A.

Intermediate R30

4-(3-Bromo-4-fluorophenyl)morpholine

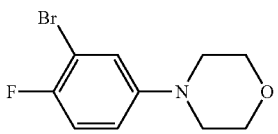
(R30)

To a solution of 3-bromo-4-fluoroaniline (300 mg, 1.579 mmol) and 1-iodo-2-(2-iodoethoxy)ethane (772 mg, 2.368 mmol) in acetonitrile (8 mL) was added K$_2$CO$_3$ (655 mg, 4.74 mmol). The mixture was heated to 80° C. for 36 h, cooled to room temperature, diluted with EtOAc (20 mL), and washed with H$_2$O (20 mL). The orange organic layer was washed with brine, dried over with MgSO$_4$, then concentrated to give crude product, which was purified by flash chromatography on silica gel eluting with 0-100% EtOAc/hexane (12 g column, 16 min gradient) to provide 4-(3-bromo-4-fluorophenyl) morpholine (308 mg, 1.184 mmol, 75% yield). LC/MS (M+H)$^+$=260.05, 262.05 (1:1 ratio).

Intermediate R32

1-((Cis)-4-(3-bromo-5-fluorophenyl)-3,5-dimethylpiperazin-1-yl)ethanone

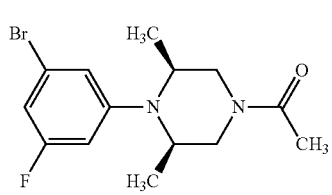
(R32)

Intermediate R32-A: 1-((Cis)-4-(3-bromo-5-fluorophenyl)-3,5-dimethylpiperazine

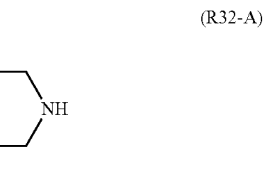
(R32-A)

To a 20 mL microwave reactor vial was added (3R,5S)-tert-butyl 3,5-dimethylpiperazine-1-carboxylate (250 mg, 1.167 mmol), 1,3-dibromo-5-fluorobenzene (592 mg, 2.333 mmol), Cs$_2$CO$_3$ (950 mg, 2.92 mmol) and toluene (4 mL). The vessel was purged and degassed with N$_2$, then 2,2'-bis(diphenylphosphino)-1,1'-binaphthalene (109 mg, 0.175 mmol) and palladium(II) acetate (52.4 mg, 0.233 mmol) were added. The reaction vessel was purged and degassed again. The reaction vessel was capped and the mixture was stirred at 110° C. overnight. The reaction mixture was filtered and washed with MeOH and then solvent was removed. The crude was diluted with EtOAc (20 mL), and washed with H$_2$O (20 mL). The orange organic layer was washed with brine, dried over with MgSO$_4$, then concentrated to give crude tert-butyl 4-(3-bromo-5-fluorophenyl)piperazine-1-carboxylate, which was then dissolved in 20% TFA in DCM. The mixture was stirred for 2 hours, concentrated, and then purified by SCX resin (CUBCX1-HL (Benzenesulfonyl, H.L. Resin, 5 g) to provide 1-((cis)-4-(3-bromo-5-fluorophenyl)-3,5-dimethylpiperazine, which used directly for next step. LCMS (M+H)$^+$=287.1, 289.1 (1:1 ratio).

Intermediate R32

To a solution of acetic acid (108 mg, 1.8 mmol) in DMF (6 mL) was added HATU (274 mg, 0.720 mmol). The mixture was stirred for 5 min. (Cis)-1-(3-bromo-5-methylphenyl)-2,6-dimethylpiperazine (170 mg, 0.6 mmol) and DIEPA (0.419 mL, 2.4 mmol) were added and the resulting reaction mixture was stirred for 1 h. The crude mixture was purified by preparative LC/MS method C to obtain 1-((cis)-4-(3-bromo-5-fluorophenyl)-3,5-dimethylpiperazin-1-yl)ethanone (86 mg, 43.5%). LCMS (M+H)$^+$=329.15, 331.20 (1:1 ratio).

The Intermediates in Table R4 were prepared according to the general synthesis procedures for the Intermediates described above, using the appropriate starting material.

TABLE R4

| Intermediate | Structure | Name |
| --- | --- | --- |
| R33 | 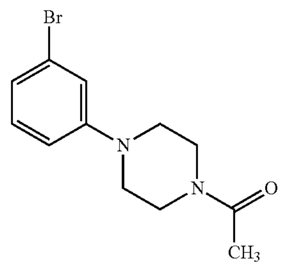 | 1-(4-(3-bromophenyl)piperazin-1-yl)ethanone |
| R35 | 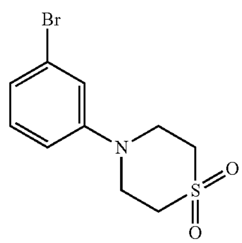 | 4-(3-bromophenyl)thiomorpholine 1,1-dioxide |
| R36 | 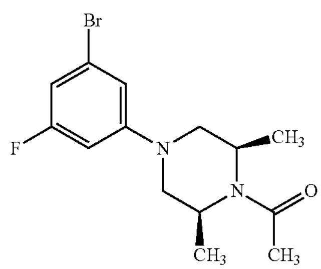 | 1-((cis)-4-(3-bromo-5-fluorophenyl)-2,6-dimethylpiperazin-1-yl)ethanone |
| R37 | 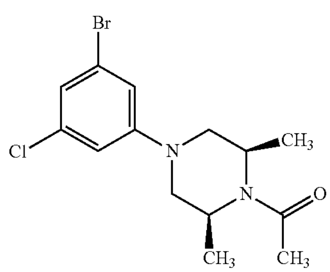 | 1-((cis)-4-(3-bromo-5-chlorophenyl)-2,6-dimethylpiperazin-1-yl)ethanone |
| R38 | 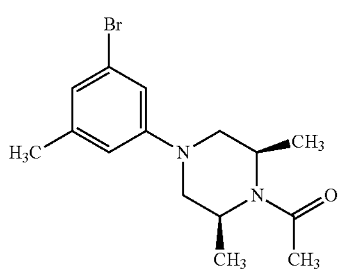 | 1-((cis)-4-(3-bromo-5-methylphenyl)-2,6-dimethylpiperazin-1-yl)ethanone |
| R39 | 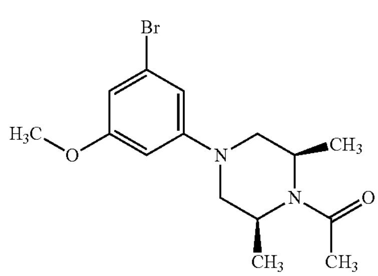 | 1-((cis)-4-(3-bromo-5-methoxyphenyl)-2,6-dimethylpiperazin-1-yl)ethanone |

TABLE R4-continued

| Intermediate | Structure | Name |
|---|---|---|
| R40 | 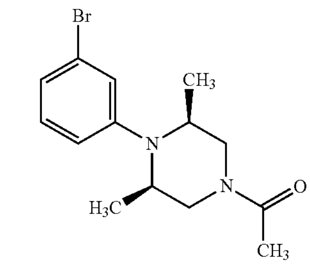 | 1-((cis)-4-(3-bromophenyl)-3,5-dimethylpiperazin-1-yl)ethanone |
| R41 | 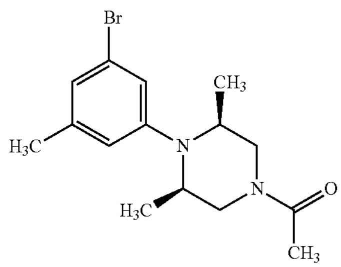 | 1-((cis)-4-(3-bromo-5-methylphenyl)-3,5-dimethylpiperazin-1-yl)ethanone |
| R42 | 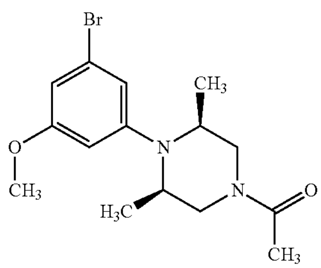 | 1-((cis)-4-(3-bromo-5-methoxyphenyl)-3,5-dimethylpiperazin-1-yl)ethanone |
| R43 | 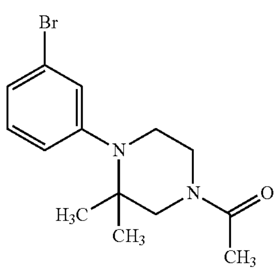 | 1-(4-(3-bromophenyl)-3,3-dimethylpiperazin-1-yl)ethanone |

Intermediate R46 tert-Butyl 3-(cyclopropylamino)azetidine-1-carboxylate

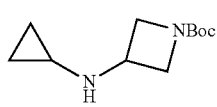

(R46)

To a solution of tert-butyl 3-oxoazetidine-1-carboxylate (1.8 g, 10.51 mmol) in DCE (40 mL) was added cyclopropanamine (500 mg, 8.76 mmol), then AcOH (1.5 mL, 26.3 mmol). The mixture was stirred for 5 min, sodium triacetoxyborohydride (2.78 g, 13.14 mmol) was added and the reaction mixture was stirred overnight at room temperature. The reaction mixture was quenched with water, adjusted pH to 10 using 1N NaOH, and the crude product was extracted with ether (3×). The organic extracts were combined, dried ($Na_2SO_4$) and concentrated. The residue was used for the next step without further purification. LC/MS: [2M+H]: 425.40.

Intermediate Q1

(Cis)-tert-butyl 4-(3-bromophenyl)-3,5-dimethylpiperazine-1-carboxylate

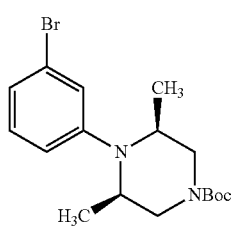

(Q1)

To a solution of 1,3-dibromobenzene (1.10 g, 4.67 mmol), (cis)-tert-butyl 3,5-dimethylpiperazine-1-carboxylate (0.5 g, 2.33 mmol) and 2-dicyclohexylphosphino-2',6'-dimethoxy-1,1'-biphenyl (47.9 mg, 0.117 mmol) in THF (15 mL) in a pressure reaction vial was purged with nitrogen. Tris(dibenzylideneacetone)dipalladium(0) (42.7 mg, 0.047 mmol) was added, followed by lithium bis(trimethylsilyl)amide (7.0 mL, 7.0 mmol, 1N in THF). The mixture was purged with nitrogen for several min and then capped and heated at 70° C. for 2.5 h. The reaction mixture was cooled and quenched with aq. NaHCO$_3$, then diluted with 75 mL of EtOAc, washed with H$_2$O, brine, dried and concentrated. The residue was purified on silica gel, with a linear gradient of 0-100% EtOAc/hexanes to give (cis)-tert-butyl 4-(3-bromophenyl)-3,5-dimethylpiperazine-1-carboxylate (0.505 g) as an oil. LCMS, M+H=369.2/371.2 Method G. Rt. 3.55 min.

The Intermediates in Table Q1 were synthesized according to the general synthetic procedure described in the preparation of Intermediate Q1.

and a solution of butyllithium in hexane (1.77 mL, 1.77 mmol, 1 M) was added dropwise while maintaining the internal temperature below −65° C. The mixture was stirred at −78° C. for 2 h, and then allowed to warm up to room temperature. The resulting solution was added dropwise to a solution of tert-butyl 4-oxopiperidine-1-carboxylate (282 mg, 1.414 mmol) in dry ethyl ether (10 mL) at −78° C. The mixture was stirred for additional 2 h at −78° C. and warmed up to room temperature. The mixture was quenched with saturated NH$_4$Cl (20 mL). The organic layer was separated, washed with water (3×20 mL), dried over NaSO$_4$, and concentrated. The residue was purified on silica gel with a linear gradient of 0-10% MEOH in DCM to obtain of tert-butyl 4-(3-bromophenyl)-4-hydroxypiperidine-1-carboxylate (378 mg, 60.0% yield). LCMS M+H=256.15/258.10. Method G. Retention time 3.447 min.

TABLE Q1

| Int. | Structure | Name | LCMS Retention Time(min)/Method | M + H |
|---|---|---|---|---|
| Q2 | ![structure] | tert-butyl 4-(3-bromophenyl)-3,3-dimethylpiperazine-1-carboxylate | 3.59/G | 369.20/371.20 |
| Q3 | ![structure] | tert-butyl 4-(3-bromophenyl)-4,7-diazaspiro[2.5]octane-7-carboxylate | 4.29/E | 367.20/369.20 |

Intermediate Q4 tert-Butyl 4-(3-bromophenyl)-4-hydroxypiperidine-1-carboxylate

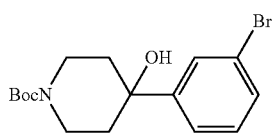

(Q4)

A solution of 1-bromo-3-iodobenzene (0.5 g, 1.77 mmol) in dry ethyl ether (10 mL) was cooled to −78° C. under N$_2$ Intermediate Q5

N-(4-(3-Bromophenyl)piperidin-4-yl)acetamide

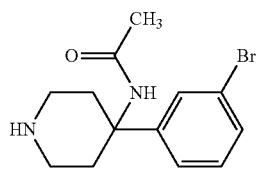

(Q5)

tert-Butyl 4-(3-bromophenyl)-4-hydroxypiperidine-1-carboxylate (88 mg, 0.247 mmol) (Intermediate Q4) in acetonitrile (0.2 mL) was cooled to 0° C., then concentrated sulfuric acid (2 mL) was slowly added. The mixture was allowed to warm to room temperature and stirred overnight. Next, 5 g of ice was added to the reaction mixture, and stirred for 15 min. The mixture was extracted with ethyl acetate (10 mL×3). The combined organic layers were dried and concentrated to give N-(4-(3-bromophenyl) piperidin-4-yl)acetamide (56 mg, 76% yield) as a solid. LCMS M$^+$=297.10/299.10. Method G. Rt 1.5 min.

The Intermediates in Table Q3 were synthesized according to the general synthetic procedures described in the preparation of Intermediates Q4 and Q5.

TABLE Q3

| Intermediate | Structure | Name | M + H Rt(min) Method |
|---|---|---|---|
| Q6 | 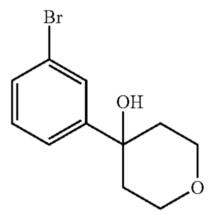 [SMILES: OC1(c2cccc(Br)c2)CCOCC1] | 4-(3-bromophenyl)tetrahydro-2H-pyran-4-ol | 2.46 257.1, 259.1 G |
| Q7 | 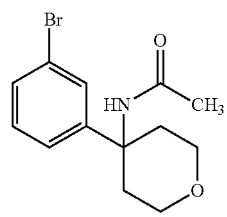 [SMILES: CC(=O)NC1(c2cccc(Br)c2)CCOCC1] | N-(4-(3-bromophenyl)tetrahydro-2H-pyran-4-yl)acetamide | 2.220 298.15/300.15 G |

Intermediate Q8

4-(3-Bromophenyl)-4-methoxytetrahydro-2H-pyran

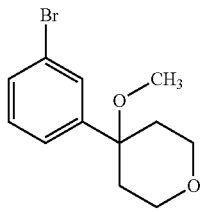
(Q8)

To a solution of 4-(3-bromophenyl)tetrahydro-2H-pyran-4-ol (Q6) (50 mg, 0.194 mmol) in DMF (2 mL) at 0° C. was added sodium hydride (9.3 mg, 0.389 mmol) and stirred for 10 minutes. Next, iodomethane (27.6 mg, 0.194 mmol) was added and stirred for 2 h, then MEOH (2 mL) was added and stirred overnight. Water (5 mL) was added to the mixture and extracted with EtOAc (8 mL×2). The combined organic layer was dried and concentrated to afford 4-(3-bromophenyl)-4-methoxytetrahydro-2H-pyran (43 mg, 87% yield). LC/MS M+Na+1=293.10/295.10. Method G. Rt 3.16 min. $^1$H NMR (400 MHz, chloroform-d) δ 7.56 (t, J=1.8 Hz, 1H), 7.49-7.41 (m, 1H), 7.38-7.33 (m, 1H), 7.30-7.24 (m, 1H), 3.92-3.74 (m, 4H), 3.01 (s, 3H), 2.09-1.88 (m, 4H).

Intermediate Q9

4-(3-Bromophenyl)tetrahydro-2H-pyran

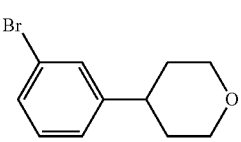
(Q9)

To a solution of 4-(3-bromophenyl)tetrahydro-2H-pyran-4-ol (Q6) (48 mg, 0.187 mmol) in toluene (2 mL) was added (methoxycarbonylsulfamoyl)triethylammonium hydroxide, inner salt (44.5 mg, 0.187 mmol). The resulting mixture was stirred at room temperature overnight, diluted with of EtOAc (10 mL), washed with water, brine, dried and concentrated. The residue was dissolved in MeOH (20 mL) and the solution was added to Pd/C (9 mg, 20% wt, wetted with MeOH) in a Parr bottle. The mixture was hydrogenated under 25 psi overnight. The bottle was evacuate and filled with nitrogen and mixture was filtered through CELITE® and concentrated to afford 4-(3-bromophenyl)tetrahydro-2H-pyran. $^1$H NMR (400 MHz, chloroform-d) δ 7.67 (t, J=1.8 Hz, 1H), 7.54-7.45 (m, 1H), 7.44-7.34 (m, 1H), 7.27-7.16 (m, 1H), 4.05 (dd, J=11.1, 2.8 Hz, 2H), 3.58-3.43 (m, 2H), 2.19-2.01 (m, 1H), 1.84-1.71 (m, 2H), 1.67 (d, J=12.1 Hz, 2H).

Intermediate Q10

4-(3-Bromophenyl)tetrahydro-2H-pyran-4-carbonitrile

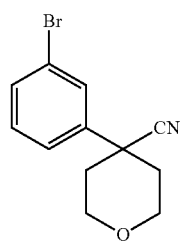

(Q10)

NaH (306 mg, 7.65 mmol) was washed with hexanes, DMF was added and the mixture was cooled to 0° C. A solution of 2-(3-bromophenyl)acetonitrile (0.5 g, 2.55 mmol) in DMF was added dropwise using an addition funnel. After stirring for 15 min at 0° C., a solution of 1-bromo-2-(2-bromoethoxy)ethane (0.62 g, 2.68 mmol) in DMF was added slowly. The reaction mixture was allowed to warm up to room temperature and stirred for 4 h, NH$_4$Cl solution was added carefully. The mixture was extracted (3×) with EA, the organic layer was isolated, dried and concentrated to give 4-(3-bromophenyl)tetrahydro-2H-pyran-4-carbonitrile (0.63 g, 93% yield) white solid. $^1$H NMR (400 MHz, chloroform-d) δ 7.65 (t, J=1.9 Hz, 1H), 7.52 (ddd, J=7.9, 1.9, 1.0 Hz, 1H), 7.46 (ddd, J=8.0, 1.9, 0.9 Hz, 1H), 7.33 (t, J=7.9 Hz, 1H), 4.16-4.07 (m, 2H), 3.92 (td, J=12.0, 2.4 Hz, 2H), 2.24-1.98 (m, 4H).

Intermediate Q11

4-(3-Bromophenyl)tetrahydro-2H-pyran-4-carbonitrile

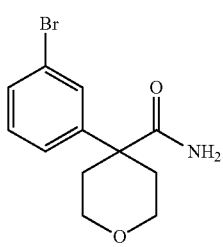

(Q11)

To a suspension of 4-(3-bromophenyl)tetrahydro-2H-pyran-4-carbonitrile (0.3 g, 1.13 mmol) in water (3 mL) was added sodium hydroxide (0.41 g, 11.27 mmol) in water (2 mL) and the mixture was refluxed for 6 h. The mixture was cooled to room temperature, extracted with EtOAc (3×), the organic layers were dried, and concentrated in vacuum to give 4-(3-bromophenyl)tetrahydro-2H-pyran-4-carbonitrile (0.3 g 94% yield). LCMS M$^+$=284.10/286.10. Method G. Retention time 2.253 min.

Intermediate Q12

N-(2-(3-Bromophenyl)propan-2-yl)-N-methyltetrahydro-2H-pyran-4-amine

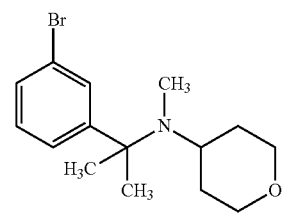

(Q12)

Intermediate Q12-A: 3-Bromo-N-methyl-N-(tetrahydro-2H-pyran-4-yl)benzamide (Q12-A)

To a solution of N-methyltetrahydro-2H-pyran-4-amine (80 mg, 0.695 mmol) in DCM (10 mL) and pyridine (0.5 mL) was added 3-bromobenzoyl chloride (0.101 mL, 0.764 mmol) in DCM (3 mL). The mixture was stirred at room temperature for 30 min, then 50 mL of DCM was added and the mixture was washed with water, 1N HCl, saturated NaHCO$_3$, brine, and concentrated to give 3-bromo-N-methyl-N-(tetrahydro-2H-pyran-4-yl)benzamide (160 mg, 77% yield). LCMS M$^+$=298.15/300.15. Method G. Rt 2.554 min.

Intermediate Q12

To a refluxing mixture of magnesium (21.9 mg, 0.901 mmol) in t-butyl-methylether (1 mL) under N$_2$ was added a solution of iodomethane (0.061 mL, 0.977 mmol) in t-butyl-methylether (1 mL). After 30 min, a solution of 3-bromo-N-methyl-N-(tetrahydro-2H-pyran-4-yl)benzamide (56 mg, 0.188 mmol) in toluene (2 mL) was added slowly, and then t-butyl-methylether (1 mL) was contemporaneously removed by distillation. The mixture was heated to reflux at 110° C. for 5 h, cooled to room temperature, and 15 mL of ether was added. The mixture was filtered through CELITE®, concentrated and the residue was purified by preparative HPLC using Method C to afford N-(2-(3-bromophenyl)propan-2-yl)-N-methyltetrahydro-2H-pyran-4-amine (40 mg, 68.2% yield). LCMS M$^+$=312.15/314.20. Method G. Retention time 1.748 min.

The Intermediates in Table Q4 were synthesized according to the general synthetic procedure described in the preparation of Intermediates Q12.

TABLE Q4

| Intermediate | Structure | Name | M+ Rt (min) Method |
|---|---|---|---|
| Q13 | 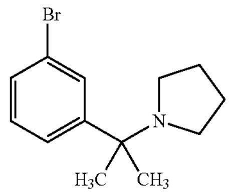 | 1-(2-(3-bromophenyl)propan-2-yl)pyrrolidine | 268.15/270.15 1.749 G |
| Q14 | 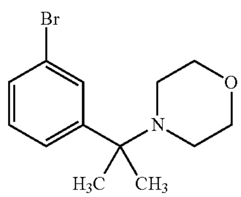 [SMILES: CC(C)(c1cccc(Br)c1)N1CCOCC1] | 4-(2-(3-bromophenyl)propan-2-yl)morpholine | 284.15/286.15 1.6 G |
| Q15 | 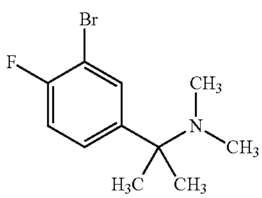 | 2-(3-bromo-4-fluorophenyl)-N,N-dimethylpropan-2-amine | 260.10/262.10 1.753 G |
| Q16 | 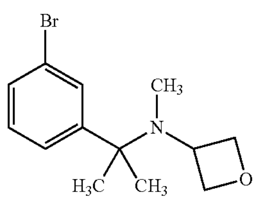 [SMILES: CN(C1COC1)C(C)(C)c1cccc(Br)c1] | N-(2-(3-bromophenyl)propan-2-yl)-N-methyloxetan-3-amine | 284.15/286.15 1.461 G |

Intermediate Q17 tert-Butyl 4-(3-bromophenyl)-3,4-dihydroquinoxaline-1(2H)-carboxylate

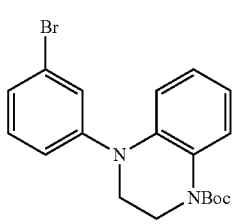

(Q17)

A partial solution of tert-butyl 3,4-dihydroquinoxaline-1(2H)-carboxylate (100 mg, 0.467 mmol), 1,3-dibromobenzene (220 mg, 0.933 mmol), $Cs_2CO_3$ (608 mg, 1.867 mmol) in toluene (1 mL), was purged and degassed with $N_2$, then 2,2'-bis(diphenylphosphino)-1,1'-binaphthalene (58.1 mg, 0.093 mmol) and palladium(II) acetate (20.95 mg, 0.093 mmol) were added, and the vessel was purged and degassed again. The reaction flask was capped and stirred at 110° C. overnight. The mixture was cooled, water (15 mL) was added and extracted with ethyl acetate (15 mL×3). The combined organic layers were washed with brine, dried over $Na_2SO_4$, and concentrated. The residue was purified on silica gel with a gradient of 0-100% EtOAc in hexanes to give tert-butyl 4-(3-bromophenyl)-3,4-dihydroquinoxaline-1 (2H)-carboxylate (120 mg 66.1% yield) as a white solid. LCMS M+=389.10/391.15. Method G. Retention time 4.175 min.

The Intermediates in Table Q5 were synthesized according to the general synthetic procedure described in the preparation of Intermediates Q17.

TABLE Q5
| Intermediate | Structure | Name | M+ LCMS Rt(min) Method |
|---|---|---|---|
| Q18 | 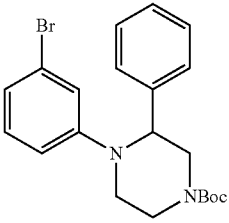 [SMILES: CC(C)(C)OC(=O)N1CCN(c2cccc(Br)c2)C(c2ccccc2)C1] | tert-butyl 4-(3-bromophenyl)-3-phenylpiperazine-1-carboxylate | 417.20/419.20 4.04 G |
| Q19 | 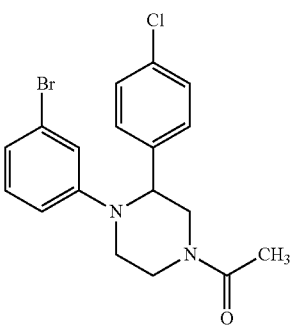 [SMILES: CC(=O)N1CCN(c2cccc(Br)c2)C(c2ccc(Cl)cc2)C1] | tert-butyl 4-(3-bromophenyl)-3-(4-chlorophenyl)piperazine-1-carboxylate | 451.20/453.20 4.2 G |
| Q20 | 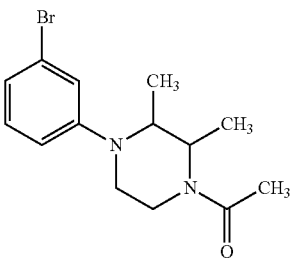 [SMILES: CC(=O)N1CCN(c2cccc(Br)c2)C(C)C1C] | 1-(3-bromophenyl)-2,3-dimethylpiperazine dimethylpropan-2-amine | 269.15/271.15 2.23 G |
| Q21 | 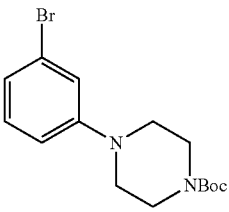 [SMILES: CC(C)(C)OC(=O)N1CCN(c2cccc(Br)c2)CC1] | tert-butyl 4-(3-bromophenyl)piperazine-1-carboxylate | 341.20/343.20 4.1 G |
| Q22 | 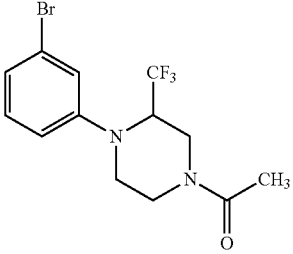 [SMILES: CC(=O)N1CCN(c2cccc(Br)c2)C(C(F)(F)F)C1] | 1-(4-(3-bromophenyl)-3-(trifluoromethyl)piperazin-1-yl)ethanone | 351.15/353.15 3.2 G |

TABLE Q5-continued

| Intermediate | Structure | Name | M+ LCMS Rt(min) Method |
|---|---|---|---|
| Q23 | 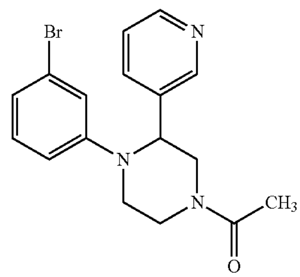 [SMILES: CC(=O)N1CCN(c2cccc(Br)c2)C(c2cccnc2)C1] | tert-butyl 4-(3-bromophenyl)-3-(pyridin-3-yl)piperazine-1-carboxylate | 418.20/420.20 2.83 G |
| Q24 | 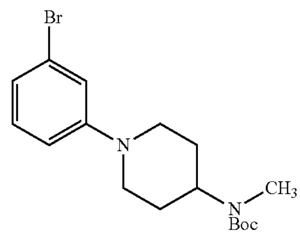 [SMILES: CN(C(=O)OC(C)(C)C)C1CCN(c2cccc(Br)c2)CC1] | tert-butyl (1-(3-bromophenyl)piperidin-4-yl)(methyl)carbamate | 369.25/371.2 3.59 G |
| Q25 | 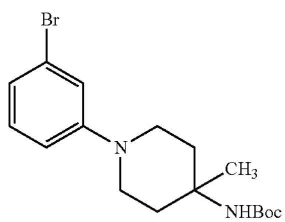 [SMILES: CC1(NC(=O)OC(C)(C)C)CCN(c2cccc(Br)c2)CC1] | tert-butyl (1-(3-bromophenyl)-4-methylpiperidin-4-yl)carbamate | 369.20/371.20 3.18 G |
| Q26 | 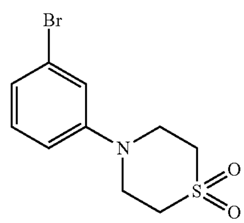 [SMILES: O=S1(=O)CCN(c2cccc(Br)c2)CC1] | 4-(3-bromophenyl)thiomorpholine 1,1-dioxide | 290.05/292.00 2.36 G |
| Q27 | 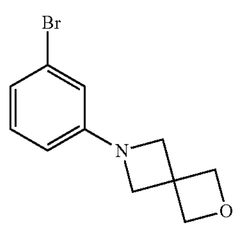 [SMILES: Brc1cccc(N2CC3(COC3)C2)c1] | 6-(3-bromophenyl)-2-oxa-6-azaspiro[3.3]heptane | 254.10/256.10 2.83 G |
| Q28 | 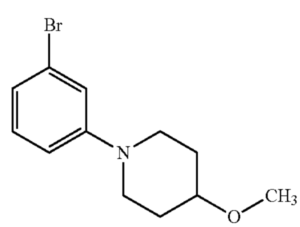 | 1-(3-bromophenyl)-4-methoxypiperidine | 270.15/272.15 2.1 E |

TABLE Q5-continued

| Intermediate | Structure | Name | M+ LCMS Rt(min) Method |
|---|---|---|---|
| Q29 | 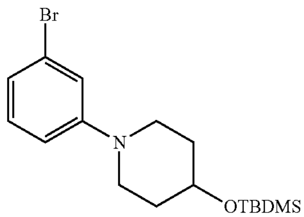 [SMILES: CC(C)(C)[Si](C)(C)OC1CCN(c2cccc(Br)c2)CC1] | 1-(3-bromophenyl)-4-((tert-butyldimethylsilyl)oxy)piperidine | 370.25/372.25 4.23 E |
| Q30 | 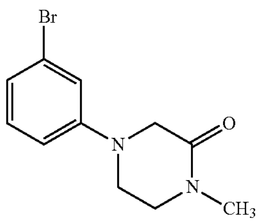 | 4-(3-bromophenyl)-1-methylpiperazin-2-one | 269.10/271.10 2.5 E |
| Q31 | 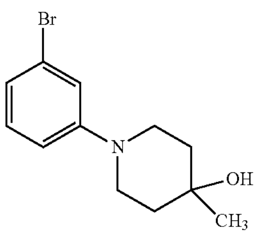 | 1-(3-bromophenyl)-4-methylpiperidin-4-ol | 270.15/272.15 1.52 E |
| Q32 | 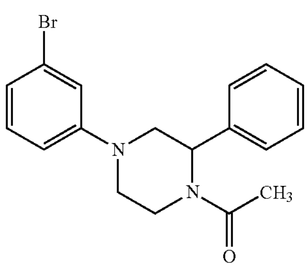 [SMILES: CC(=O)N1CCN(c2cccc(Br)c2)CC1c1ccccc1] | 1-(4-(3-bromophenyl)-2-phenylpiperazin-1-yl)ethanone | 359.15/361.10 3.88 G |
| Q33 | 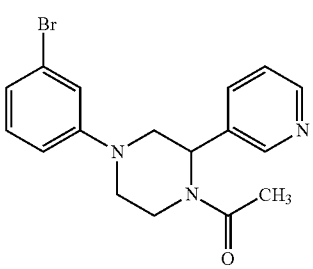 [SMILES: CC(=O)N1CCN(c2cccc(Br)c2)CC1c1cccnc1] | 1-(4-(3-bromophenyl)-2-(pyridin-3-yl)piperazin-1-yl)ethanone | 360.15/362.15 2.6 G |
| Q34 | 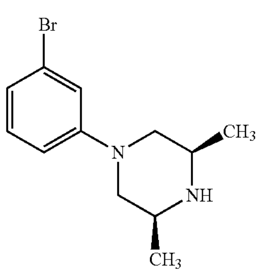 | (cis)-1-(3-bromophenyl)-3,5-dimethylpiperazine | 269.15/271.15 2.86 G |

TABLE Q5-continued

| Intermediate | Structure | Name | M+ LCMS Rt(min) Method |
|---|---|---|---|
| Q35 | 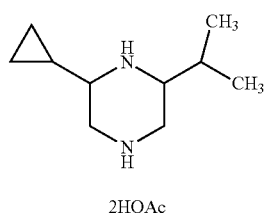 | 1-((cis)-4-(3-bromophenyl)-2,6-dimethylpiperazin-1-yl)ethanone | 311.15/313.15 3.81 G |

Intermediates Q36 and Q37

1-(4-(3-Bromophenyl)-2,6-dicyclopropylpiperazin-1-yl)ethanone (Q36), and 1-(4-(3-Bromophenyl)-2-cyclopropyl-6-isopropylpiperazin-1-yl)ethanone (Q37)

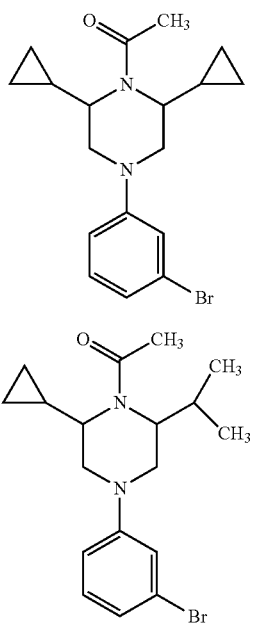

Intermediates Q36-A and Q37-A: 2,6-Dicyclopropylpiperazine (Q36-A) and 2-Cyclopropyl-6-isopropylpiperazine (Q37-A)

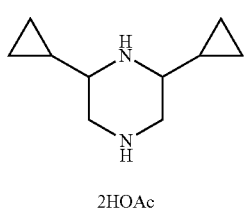

To a solution of 2,6-dicyclopropylpyrazine (411 mg, 2.57 mmol, see WO 2004/024720) in AcOH (5 mL) was added platinum(IV) oxide (29.1 mg, 0.128 mmol) and the reaction mixture was hydrogenated at room temperature under 30 psi overnight. The mixture was filtered through CELITE®, and the filter cake was washed with MeOH (10 mL) and DCM (10 mL). The combined filtrate was concentrated to give a mixture of 2,6-dicyclopropylpiperazine and 2-cyclopropyl-6-isoppropylpiperazine as AcOH salts (651 mg, 7:3 ratio, 90% pure). LCMS M+=167.3 and 169.3 Method G. Retention time 0.2 min.

Intermediates Q36 and Q37

The mixture of Intermediates Q36-A and Q37-A was converted to Intermediates Q36 and Q37 according to the general preparation of the intermediate tert-butyl 4-(3-bromophenyl)-3,4-dihydroquinoxaline-1(2H)-carboxylate (Q17) to afford a crude mixture. The crude mixture was dissolved in DCM and 2 eq. of acetic anhydride was added. Volatiles were removed. Chromatography: silica gel, 0-60% EtOAc/hexane to give a mixture of an oil of the compounds in quantitative yield. Intermediate Q36: LCMS M+=363.2/365.2 Method G. Retention time 4.20 min. Intermediate Q37: LCMS M+=365.25/367.25 Method G. Retention time 4.29 min. The mixture was used without additional purification or separation.

Intermediate Q38

1-(4-(3-Bromophenyl)-3-(2-fluorophenyl)piperazin-1-yl)ethanone

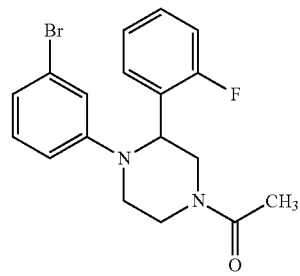
(Q38)

Intermediate Q38-A: tert-Butyl (2-((2-(2-fluorophenyl)-2-oxoethyl)(4-methoxybenzyl) amino)ethyl) carbamate

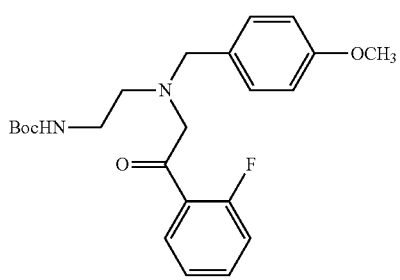
(Q38-A)

To a solution of tert-butyl (2-((4-methoxybenzyl)amino)ethyl)carbamate (258 mg, 0.922 mmol) in THF (5 mL) were added 2-bromo-1-(2-fluorophenyl)ethanone (0.2 g, 0.92 mmol) and N-ethyl-N-isopropylpropan-2-amine (0.247 mL, 1.382 mmol). After stirring the mixture overnight at room temperature, the reaction mixture was filtered, and the filtrate was concentrated. The residue was purified on silica gel eluting with a gradient of 0-100% EtOAc in hexanes to afford of tert-butyl (2-((2-(2-fluorophenyl)-2-oxoethyl)(4-methoxybenzyl)amino)ethyl)carbamate (275 mg, 71.7%). LCMS M$^+$=417.35. Method G. Retention time 3.24 min.

Intermediate Q38-B: 3-(2-Fluorophenyl)-1-(4-methoxybenzyl)piperazine

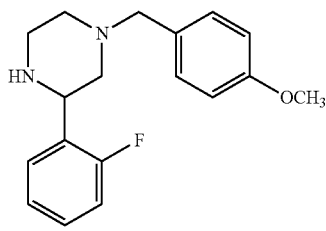
(Q38-B)

tert-Butyl (2-((2-(2-fluorophenyl)-2-oxoethyl)(4-methoxybenzyl)amino)ethyl) carbamate (275 mg, 0.660 mmol) was treated with TFA/DCM (1:1, 3 mL) for 30 min, and the volatiles were removed in vacuum. The residue was dissolved in DCE, sodium triacetoxyborohydride (140 mg, 0.66 mmol) was added, and stirred at room temperature for 30 min. The mixture was diluted with of DCM (20 mL), washed with saturated sodium bicarbonate, brine, concentrated to give 3-(2-fluorophenyl)-1-(4-methoxybenzyl) piperazine as a white solid in quantitatively yield. LCMS M$^+$=301.25. Method G. Retention time 2.24 min. The compound was used for the next step without further purification.

Intermediate Q38-C: 1-(3-Bromophenyl)-2-(2-fluorophenyl)-4-(4-methoxybenzyl) piperazine

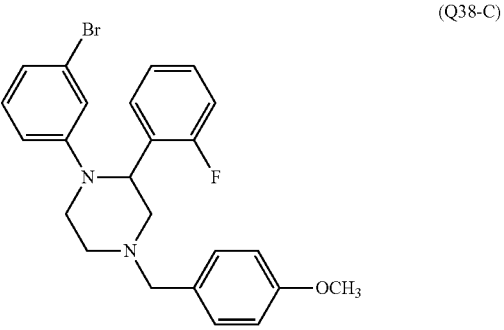 [SMILES: COc1ccc(CN2CCN(c3cccc(Br)c3)C(c3ccccc3F)C2)cc1]
(Q38-C)

Intermediate Q38-B (257 mg) was coupled with 1,3-dibromobenzene in a manner similar as described for Intermediate Q17 to give 1-(3-bromophenyl)-2-(2-fluorophenyl)-4-(4-methoxybenzyl) piperazine (160 mg, 41.1% yield). LCMS, M$^+$=455.15/457.2. Method G. Retention time 3.42 min.

Intermediate Q38

1-(3-Bromophenyl)-2-(2-fluorophenyl)-4-(4-methoxybenzyl)piperazine (160 mg, 0.351 mmol) and 4 mL of TFA in a sealed vial, was heated to 100° C. over night. The mixture was cooled and the volatiles were removed in vacuum. The residue was dissolved in DCM and washed with NaHCO$_3$, brine, and concentrated. The residue was redissolved in DCM, treated with 1.5 eq of acetic anhydride for 1 h, and the reaction mixture was washed with aqueous NaHCO$_3$, brine, dried over Na$_2$SO$_4$, and concentrated to give 1-(4-(3-bromophenyl)-3-(2-fluorophenyl)piperazin-1-yl)ethanone (102 mg, 77% yield). LCMS M$^+$=377.15/379.15. Method G. Retention time 3.816 min.

Intermediate Q39

3-(3-Bromophenyl)-1,3-oxazinan-2-one

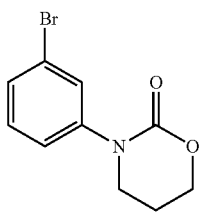

(Q39)

To a solution of 1,3-dibromobenzene (933 mg, 3.96 mmol) in toluene (2 mL), 1,3-oxazinan-2-one (200 mg, 1.978 mmol), potassium carbonate (547 mg, 3.96 mmol) and (1R,2R)—N1,N2-dimethylcyclohexane-1,2-diamine (56.3 mg, 0.396 mmol) were added. The mixture was purged with nitrogen and copper(I) iodide (75 mg, 0.396 mmol) was added and the resulting mixture was heated at 110° C. overnight. The reaction mixture was filtered, the filter cake was washed with 20 mL of DCM, and the combined filtrate was concentrated and residue was purified on silica gel eluting with a gradient of 0-10% MeOH/DCM to give 3-(3-bromophenyl)-1,3-oxazinan-2-one (342 mg, 67.5% yield). LCMS M+=256.05/258.05. Method G. Retention time 2.444 min.

The Intermediates in Table Q6 were synthesized according to the general synthetic procedure described in the preparation of Intermediates Q39.

TABLE Q6

| Intermediate | Structure | Name | LCMS M+ Retention Time(min)/ Method |
|---|---|---|---|
| Q40 | 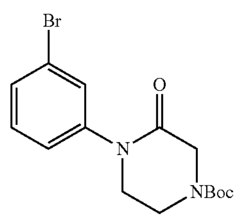 [SMILES: CC(C)(C)OC(=O)N1CCN(c2cccc(Br)c2)C(=O)C1] | tert-butyl 4-(3-bromophenyl)-3-oxopiperazine-1-carboxylate | 299.10/301.10 2.883 G |
| Q41 | 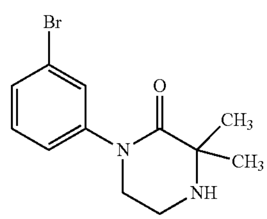 [SMILES: CC1(C)NCCN(c2cccc(Br)c2)C1=O] | 1-(3-bromophenyl)-3,3-dimethylpiperazin-2-one | 283.15/285.15 2.014 G |
| Q42 | 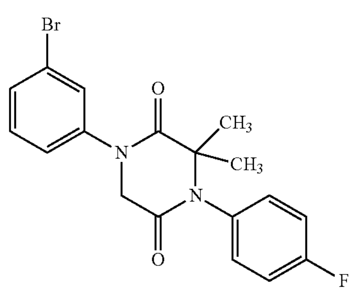 [SMILES: CC1(C)C(=O)N(c2cccc(Br)c2)CC(=O)N1c1ccc(F)cc1] | 1-(3-bromophenyl)-4-(4-fluorophenyl)-3,3-dimethylpiperazine-2,5-dione | 391.1/393.1 2.97 G |
| Q43 | 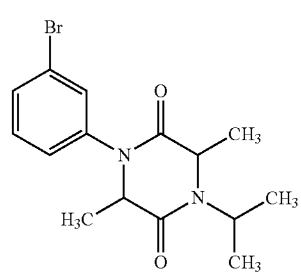 [SMILES: CC1C(=O)N(C(C)C)C(C)C(=O)N1c1cccc(Br)c1] | 1-(3-bromophenyl)-4-isopropyl-3,6-dimethylpiperazine-2,5-dione | 339.2/341.2 2.52 G |

An alternative route to the synthesis of Intermediate Q41 is as follows.

Intermediate Q41-A:
2-Bromo-N-(3-bromophenyl)-2-methylpropanamide

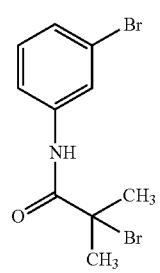

(Q41-A)

To a mixture of 3-bromoaniline (2.0 g, 11.63 mmol) and N-ethyl-N-isopropylpropan-2-amine (4.0 mL, 23.25 mmol) in DCM (100 mL) was cooled to 0° C. and 2-bromo-2-methylpropanoyl bromide (2.15 mL, 17.44 mmol) was dropwise added. The mixture was allowed to warm to room temperature over 2 h, diluted with DCM (100 mL), washed with water, 1N HCl, saturated NaHCO$_3$, brine, dried over Na$_2$SO$_4$, concentrated to give crude solid which was used without further purification.

Intermediate Q41-B: N-(3-Bromophenyl)-2-((2-hydroxyethyl)amino)-2-methylpropanamide

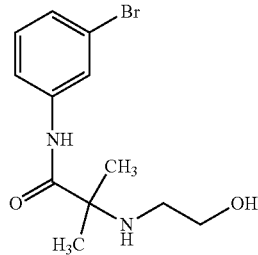

(Q41-B)

Intermediate Q41-A and 2-aminoethanol (1.42 g, 23.25 mmol) were dissolved in CH$_3$CN (95 mL) and water (5 mL), then silver oxide (5.39 g, 23.25 mmol) was added. The mixture was stirred at room temperature overnight, and then filtered. The filtrate was diluted with EtOAC (250 mL), washed with aqueous NaHCO$_3$, brine, and concentrated. The residue was purified on ISCO silica gel column eluting with a gradient of 0-100% EtOAC/hexanes to give N-(3-bromophenyl)-2-((2-hydroxyethyl)amino)-2-methylpropanamide (75% yield). LCMS M$^+$=301.10/303.10. Method G, Retention time 1.95 min.

Intermediate Q41

To a solution of DIAD (2.42 g, 11.95 mmol) in THF (50 mL) at room temperature was added triphenylphosphine (3.14 g, 11.95 mmol). After 10 min, a yellow solid formed. N-(3-Bromophenyl)-2-((2-hydroxyethyl)amino)-2-methyl-propanamide (1.2 g, 3.98 mmol) in of THF (50 mL) was added. After stirring overnight at room temperature, the mixture was diluted with 100 mL of EtOAc, washed with saturated NaHCO$_3$, brine, dried over Na$_2$SO$_4$, and concentrated. The residue was purified on silica gel eluting with a gradient of 0-100% EtOAC in hexanes to give 1-(3-bromophenyl)-3,3-dimethylpiperazin-2-one in 90% yield. LCMS M$^+$=283.15/285.10. Method X. Retention time 1.71 min.

Intermediate Q44

4-Acetyl-1-(3-bromophenyl)-5,5-dimethylpiperazin-2-one

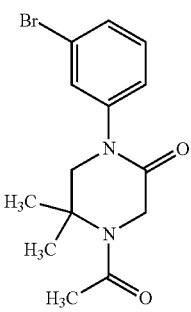

(Q44)

Intermediate Q44-A: tert-Butyl (1-((2,4-dimethoxybenzyl)amino)-2-methyl-1-oxopropan-2-yl)carbamate

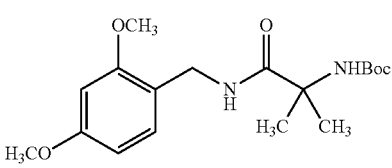

(Q44-A)

To a solution of 2-((tert-butoxycarbonyl)amino)-2-methylpropanoic acid (3 g, 14.76 mmol) in DCM (25 mL) was added 4-methylmorpholine (2.43 mL, 22.14 mmol), N1-((ethylimino)methylene)-N3,N3-dimethylpropane-1,3-diamine hydrochloride (4.24 g, 22.14 mmol), and 1H-benzo[d][1,2,3]triazol-1-ol hydrate (2.49 g, 16.24 mmol). The mixture was stirred for 5 min, then (2,4-dimethoxyphenyl)methanamine (2.71 g, 16.24 mmol) was added. After stirring the mixture at room temperature overnight, DCM was removed on rotovap, and the mixture was diluted with 100 mL of EtOAc, washed with water, 0.5N HCl, saturated NaHCO$_3$, brine, dried over Na$_2$SO$_4$, and concentrated to give a white solid. The white solid was washed with hexane 2×, dried in vacuum to afford tert-butyl (1-((2,4-dimethoxybenzyl)amino)-2-methyl-1-oxopropan-2-yl)carbamate (4.87 g, 94%). LCMS M$^+$=353.3. Method G. Retention time 3.32 min.

Intermediate Q44-B: tert-Butyl (1-((2,4-dimethoxybenzyl)amino)-2-methylpropan-2-yl) carbamate

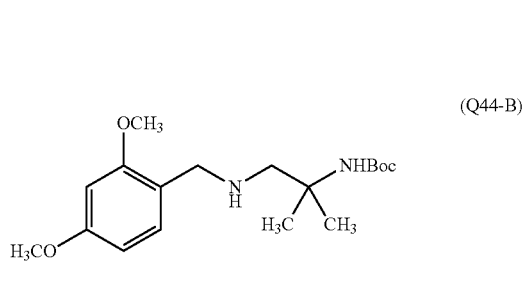 [SMILES: COc1ccc(CNCC(C)(C)NC(=O)OC(C)(C)C)c(OC)c1]
(Q44-B)

To a solution of tert-butyl (1-((2,4-dimethoxybenzyl)amino)-2-methyl-1-oxopropan-2-yl)carbamate (1.62 g, 4.60 mmol) in THF (25 mL), was added borane THF complex (1M, 13.79 mL) and the mixture was refluxed for 4 h. The reaction mixture was cooled to room temperature, saturated NH$_4$Cl was added carefully, and the mixture was extracted with 100 mL of ethyl acetate. The organic layer was separated, washed with saturated NaHCO$_3$, brine, dried over Na$_2$SO$_4$, and concentrated to give tert-butyl (1-((2,4-dimethoxybenzyl)amino)-2-methylpropan-2-yl)carbamate (0.552 g, 36%). LCMS M$^+$=339.3. Method G. Retention time 2.747 min.

Intermediate Q44-C: tert-Butyl (1-(2-bromo-N-(2,4-dimethoxybenzyl)acetamido)-2-methylpropan-2-yl) carbamate

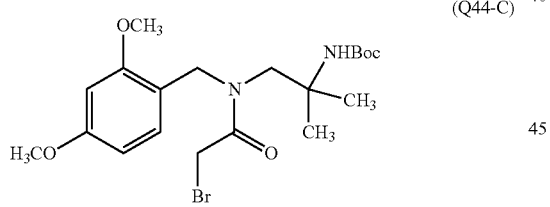
(Q44-C)

To a solution of 2-bromoacetic acid (197 mg, 1.418 mmol), HATU (539 mg, 1.418 mmol) in DCM (5 mL), was added DIPEA (0.371 mL, 2.127 mmol). After 5 min, tert-butyl (1-((2,4-dimethoxybenzyl)amino)-2-methylpropan-2-yl)carbamate (240 mg, 0.709 mmol) was added. The mixture was stirred at room temperature for 2 h and then diluted with 30 mL of DCM, washed with water, brine, dried over Na$_2$SO$_4$, and concentrated. The residue was purified on silica by ISCO (0-100% EtOAc/Hex) to give tert-butyl (1-(2-bromo-N-(2,4-dimethoxybenzyl)acetamido)-2-methylpropan-2-yl) carbamate (196 mg, 60.2%) LCMS M$^+$=no mass, Method G. Retention time 3.598 min. $^1$H NMR (400 MHz, CDCl$_3$) δ 6.93 (d, J=8.6 Hz, 1H), 6.54-6.41 (m, 2H), 5.23 (br. s., 1H), 4.61 (s, 2H), 3.93 (s, 2H), 3.82 (dd, J=5.2, 2.8 Hz, 6H), 3.62 (s, 2H), 1.44 (s, 9H), 1.36 (s, 6H).

Intermediate Q44-D: tert-Butyl 4-(2,4-dimethoxybenzyl)-2,2-dimethyl-5-oxopiperazine-1-carboxylate

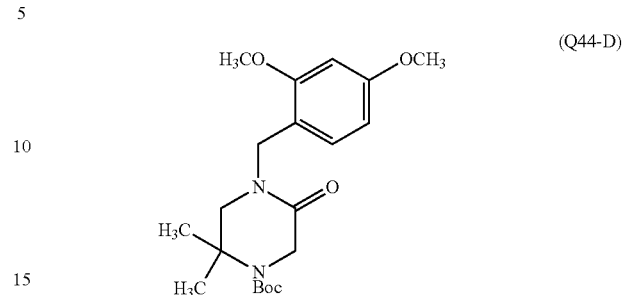
(Q44-D)

A solution of tert-butyl (1-(2-bromo-N-(2,4-dimethoxybenzyl)acetamido)-2-methylpropan-2-yl)carbamate (196 mg, 0.427 mmol) in dry DMF (5 mL) was cooled to −20° C. under nitrogen. Potassium t-butoxide (126 mg, 1.280 mmol) was added and the mixture was stirred overnight room temperature. Next, 5 mL of water was added to the mixture and extracted with EtOAc. The organic layer was washed with brine, dried, and concentrated. The crude product was purified by silica gel eluting with a gradient of 0-100% EtOAc/hexanes to afford tert-butyl 4-(2,4-dimethoxybenzyl)-2,2-dimethyl-5-oxopiperazine-1-carboxylate (106 mg, 65.6%) LCMS M$^+$=256.05/258.05. Method G. Retention time 2.444 min.

Intermediate Q44-E: 4-Acetyl-5,5-dimethylpiperazin-2-one

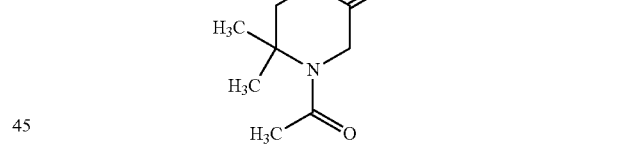
(Q44-E)

tert-Butyl 4-(2,4-dimethoxybenzyl)-2,2-dimethyl-5-oxopiperazine-1-carboxylate (140 mg, 0.370 mmol) in TFA was heated to reflux overnight. The volatiles were removed, and azeotroped several time with 1N HCl. To the residue was dissolved in DCM (2 mL) and triethyl amine (0.5 mL) followed by acetic anhydride (76 mg, 0.740 mmol) were added. The mixture was stirred for 2 h, washed with NaHCO$_3$, brine, dried and concentrated. The residue was dissolved in TFA heated to reflux. The mixture was cooled and concentrated in vacuum to give 4-acetyl-5,5-dimethylpiperazin-2-one (63.4% yield). LCMS M$^+$=171.2. Method G. Retention time 0.693 min.

Intermediate Q44

Intermediate Q44-E was converted to Intermediate Q44 by following the procedure described for Intermediate Q39. LCMS M$^+$=325.15/327.10. Method G. Retention time 2.808 min.

Intermediate Q45

4-Acetyl-1-(3-bromophenyl)-6,6-dimethylpiperazin-2-one

(Q45)

Intermediate Q45-A: 2-((3-Bromophenyl)amino)-N-(2,4-dimethoxybenzyl)-2-methylpropanamide

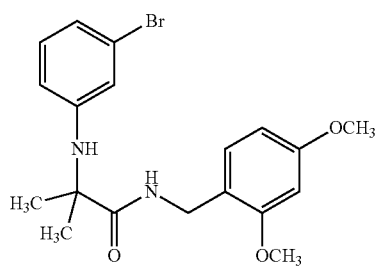

(Q45-A)

To a solution of 3-bromoaniline (1.415 g, 8.22 mmol) and 2-bromo-N-(2,4-dimethoxybenzyl)-2-methylpropanamide (1.3 g, 4.11 mmol) in acetonitrile (20 mL), was added water (1.5 mL) and the mixture was stirred vigorously. Silver oxide (1.9 g, 8.22 mmol) was added and the mixture was heated to 60° C. for 5 h. The reaction mixture was filtered and the filtrate was diluted with 250 mL of EtOAC. The mixture was washed with saturated NaHCO$_3$, brine, dried over Na$_2$SO$_4$, and concentrated. The residue was purified on silica gel eluting with a gradient of 0-100% EtOAC in hexanes to obtain 2-((3-bromophenyl)amino)-N-(2,4-dimethoxybenzyl)-2-methylpropanamide (83% yield). LCMS M$^+$=407.15/409.15. Method G. Retention time 3.569 min.

Intermediate Q45-B: N2-(3-Bromophenyl)-N1-(2,4-dimethoxybenzyl)-2-methylpropane-1,2-diamine

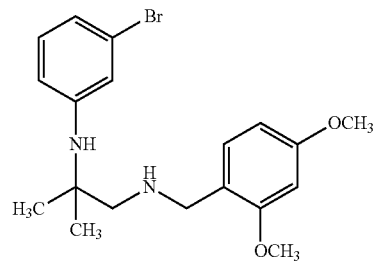

(Q45-B)

To a solution of 2-((3-bromophenyl)amino)-N-(2,4-dimethoxybenzyl)-2-methylpropanamide (250 mg, 0.614 mmol) in THF (20 mL) was added BH$_3$.S(CH$_3$)$_2$ complex in Et$_2$O (0.37 mL, 1.841 mmol) and the mixture was stirred at room temperature for 2 days, then heated at 60° C. for 1 h. The reaction mixture was cooled and diluted with 1N HCl, and 50 mL of EtOAC. The organic layer was separated, washed with NaHCO$_3$, brine, and concentrated to afford N2-(3-bromophenyl)-N1-(2,4-dimethoxybenzyl)-2-methylpropane-1,2-diamine (74.1% yield). LCMS M$^+$=393.20/395.15. Method G. Retention time 3.04 min.

Intermediate Q45-C: Methyl 2-((2-((3-bromophenyl)amino)-2-methylpropyl)(2,4-dimethoxybenzyl)amino)acetate

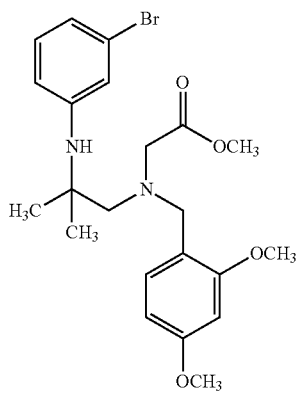

(Q45-C)

To a solution of N2-(3-bromophenyl)-N1-(2,4-dimethoxybenzyl)-2-methylpropane-1,2-diamine (0.5 g, 1.272 mmol) and DIPEA (0.44 mL, 2.542 mmol) in THF (20 mL) was added methyl 2-bromoacetate (195 mg, 1.272 mmol). The reaction mixture was stirred at room temperature overnight, then heated at 50° C. for 18 h. The mixture was diluted with 50 mL of EtOAC and washed with water and brine. The organic layer was dried over Na$_2$SO$_4$, and concentrated. The residue was purified on silica gel eluting with a gradient of 0-100% EtOAc in hexanes to give methyl 2-((2-((3-bromophenyl)amino)-2-methylpropyl)(2,4-dimethoxybenzyl)amino)acetate (95% yield). LCMS M$^+$=465.25/467.25. Method G. Retention time 3.13 min.

Intermediate Q45

A mixture of methyl 2-((2-((3-bromophenyl)amino)-2-methylpropyl)(2,4-dimethoxybenzyl)amino)acetate (175 mg, 0.376 mmol) and aqueous HCl (2N, 12 mL) was refluxed for 6 h. The volatiles were removed and the residue was dissolved in DCM (5 mL) and triethyl amine (1 mL) and acetic anhydride (3 eq) were added. The mixture was stirred at room temperature for 1 h, washed with water, NaHCO$_3$, brine, dried and concentrated to afford 4-acetyl-1-(3-bromophenyl)-6,6-dimethylpiperazin-2-one (85% yield). LCMS M$^+$=325.10/327.10. Method G. Retention time 2.616.

Intermediate Q46

4-(3-Bromophenyl)-2,2-dimethylmorpholin-3-one

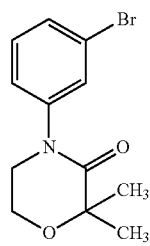
(Q46)

Intermediate Q46-A: N-(3-Bromophenyl)-2-(2-hydroxyethoxy)-2-methylpropanamide

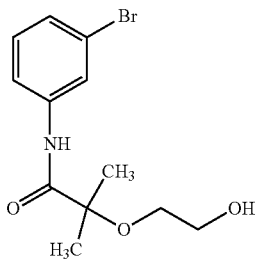
(Q46-A)

2-Bromo-N-(3-bromophenyl)-2-methylpropanamide (920 mg, 2.87 mmol) and ethane-1,2-diol (356 mg, 5.73 mmol) were dissolved in MeCN (20 mL), water (1.053 mL) was added and the mixture was stirred vigorously. Then silver oxide (1.33 g, 5.73 mmol) was added, and the mixture was heated to 60° C. for 1 h. The mixture was cooled, filtered and 150 mL of EtOAC was added. The mixture was washed with saturated NaHCO$_3$, brine, dried over Na$_2$SO$_4$, and concentrated. The residue was purified on silica gel eluting with a gradient of 0-100% EtOAc in hexanes to afford N-(3-bromophenyl)-2-(2-hydroxyethoxy)-2-methylpropanamide (65% yield). LCMS M$^+$=302.10/304.10. Method G. Retention time 3.08 min.

Intermediate Q46

Intermediate Q46-A was converted to Intermediate Q46 according to the general procedure described in the preparation of Intermediate Q41 to obtain 4-(3-bromophenyl)-2,2-dimethylmorpholin-3-one. LCMS M$^+$=284.15 and 286.05. Method G. Retention time 2.91 min.

Intermediate Q47

N-Cyclopropyloxetan-3-amine

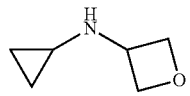
(Q47)

To a solution of cyclopropanamine (100 mg, 1.751 mmol) in 5 mL of DCE was added oxetan-3-one (151 mg, 2.102 mmol), and 0.05 mL of HOAc. The mixture was stirred for 2 min, sodium triacetoxyborohydride (742 mg, 3.50 mmol) was added and then stirred overnight. The mixture was diluted with water (5 mL), basified by sodium carbonate to pH 9, and extracted with ethyl ether (3×10 mL). The combined organic layer was washed with brine, dried over Na$_2$SO$_4$, and concentrated at low vacuum. For the structural determination, a small amount was reacted with benzoyl chloride in DCM and DIEA for 1 h, removed volatiles in vacuum, and checked by LCMS, which showed major peak is the desired benzoylated product. LCMS M$^+$=218.25. Method G. Retention time 2.018 min.

The Intermediates in Table Q7 were prepared according to the general procedure for the synthesis of Intermediate Q47.

TABLE Q7

| Intermediate | Structure | Name | LCMS M$^+$ Retention Time (min) Method |
|---|---|---|---|
| Q48 | 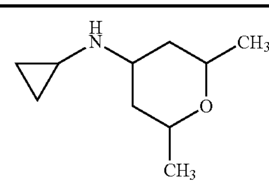 | N-cyclopropyl-2,6-dimethyltetrahydro-2H-pyran-4-amine | 170.25 0.662 G |
| Q49 | 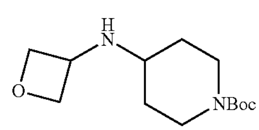 [SMILES: CC(C)(C)OC(=O)N1CCC(NC2COC2)CC1] | tert-butyl 4-(oxetan-3-ylamino)piperidine-1-carboxylate | 257.25 1.432 G |
| Q50 | 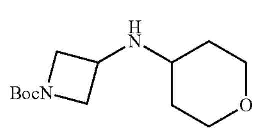 [SMILES: CC(C)(C)OC(=O)N1CC(NC2CCOCC2)C1] | tert-butyl 3-((tetrahydro-2H-pyran-4-yl)amino)azetidine-1-carboxylate | 257.20 1.279 G |

TABLE Q7-continued

| Intermediate | Structure | Name | LCMS M+ Retention Time (min) Method |
|---|---|---|---|
| Q51 | BocN-piperidine-NH-tetrahydropyran | tert-butyl 4-((tetrahydro-2H-pyran-4-yl)amino)piperidine-1-carboxylate | 285.25 1.537 G |
| Q52 | cyclopropyl-NH-4,4-difluorocyclohexane | N-cyclopropyl-4,4-difluorocyclohexanamine | 176.20 0.723 G |

Intermediate Q53

4-Acetyl-1-(3-bromophenyl)-3,3-dimethylpiperazin-2-one

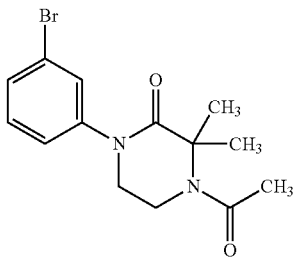

(Q53)

To 1-(3-bromophenyl)-3,3-dimethylpiperazin-2-one (Intermediate Q41) (0.82 g, 2.69 mmol) in dichloromethane (10 mL) and triethylamine (1 mL) was added acetic anhydride (0.33 g, 3.23 mmol) and the resulting mixture stirred for 2 hr. The reaction was diluted with dichloromethane (20 mL), washed with water, saturated sodium bicarbonate, brine, the organics dried and concentrated. The crude mixture was purified by silica gel chromatography (ISCO, 0-100% EtOAc/hexanes) to give 4-acetyl-1-(3-bromophenyl)-3,3-dimethylpiperazin-2-one (Q53) (0.9 g, 93% pure). LCMS M+H=325.1 and 327.1, Method J.

Intermediate Q53CN4

2-(4-Acetyl-3,3-dimethyl-2-oxopiperazin-1-yl)-4-bromobenzonitrile

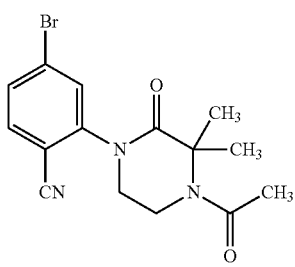

(Q53CN4)

Intermediate Q53CN4-A: 2-Bromo-N-(5-bromo-2-cyanophenyl)-2-methylpropanamide

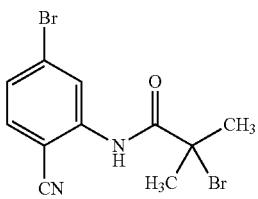

(Q53CN4-A)

To a solution of 2-amino-4-bromobenzonitrile (1.02 g, 5.18 mmol) and N-ethyl-N-isopropylpropan-2-amine (1.353 ml, 7.77 mmol) in DCM (24.65 ml), cooled to 0° C., was added 2-bromo-2-methylpropanoyl bromide (0.832 ml, 6.73 mmol) slowly. The reaction mixture was stirred at 0° C. for 5 min, then at room temperature for 1 h. The reaction was monitored by LCMS. The reaction mixture was diluted with DCM and washed with 1N HCl. The organic phase was washed with 1.5M $K_2HPO_4$, brine, dried by $Na_2SO_4$. The solvent was removed under reduced pressure affording 2-bromo-N-(5-bromo-2-cyanophenyl)-2-methylpropanamide (2.19 g) as a pale solid in quantitative yield. LCMS M+H=344.9, 346.9, and 348.9.

Intermediate Q53CN4-B: N-(5-Bromo-2-cyanophenyl)-2-((2-hydroxyethyl)amino)-2-methylpropanamide

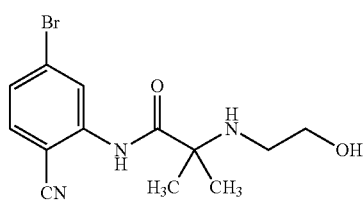

(Q53CN4-B)

To a solution of 2-bromo-N-(5-bromo-2-cyanophenyl)-2-methylpropanamide (2.19 g, 5.19 mmol) and 2-aminoethanol (0.627 ml, 10.38 mmol) in MeCN (25.9 ml), cooled at 0° C., was added silver oxide (2.285 g, 9.86 mmol) in portions. The cooling bath was removed and reaction mixture was stirred at room temperature. After 2 hrs, the clear solution was decanted out and the black residue was washed with EtOAc. The combined organic solutions were then concentrated, partitioned between EtOAc and 1N HCl, and it became a milky suspension, which was filtered through CELITE®. The CELITE® pad was washed with 1N HCl and EtOAc. The acidic aqueous phase was separated and set aside and the organic phase was washed with 1N HCl again. Both acidic phases were combined, basified with NaOH pellet and sodium bicarbonate to pH~9-10, extracted with EtOAc. The organic phase was washed with brine, dried by $Na_2SO_4$, filtered, concentrated to afford N-(5-bromo-2-cyanophenyl)-2-((2-hydroxyethyl)amino)-2-methylpropanamide (1.229 g) as a pale solid in 73% yield. LCMS M+H=325.9 and 327.9.

Intermediate Q53CN4-C: 4-Bromo-2-(3,3-dimethyl-2-oxopiperazin-1-yl)benzonitrile

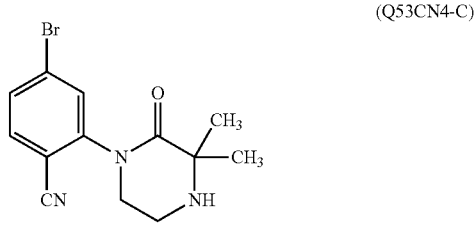 [SMILES: CC1(C)NCCN(c2cc(Br)ccc2C#N)C1=O]

(Q53CN4-C)

To a solution of triphenylphosphine (1.482 g, 5.65 mmol) and DIAD (1.099 ml, 5.65 mmol) in THF (29.9 ml) at room temperature, was added a solution of N-(5-bromo-2-cyanophenyl)-2-((2-hydroxyethyl)amino)-2-methylpropanamide (1.229 g, 3.77 mmol) in THF (29.9 ml). The reaction mixture was stirred overnight. After 17 hrs, the reaction mixture was concentrated under reduced pressure, then partitioned between EtOAc and 1N HCl. The aqueous layer was separated and kept aside. The organic layer was washed with 1N HCl again. Both aqueous phases were combined, basified using NaOH and $Na_2CO_3$ until pH is around 10, extracted with EtOAc. The EtOAc organic layer was washed with brine, dried by $Na_2SO_4$, filtered, and concentrated under reduced pressure to afford 4-bromo-2-(3,3-dimethyl-2-oxopiperazin-1-yl)benzonitrile (0.926 g, 90% pure) as a pale solid in 72% yield. LCMS M+H=307.9 and 309.9.

Intermediate Q53CN4

To a solution of 4-bromo-2-(3,3-dimethyl-2-oxopiperazin-1-yl)benzonitrile (0.65 g, 1.898 mmol) and triethylamine (0.529 ml, 3.80 mmol) in DCM (18.98 ml), at 0° C., was added acetyl chloride (0.202 ml, 2.85 mmol) slowly. The reaction mixture was then stirred at room temperature. After 1 hr, the reaction mixture was diluted with DCM, washed with 1N HCl, 1.5N $K_2HPO_4$, brine, and dried over $Na_2SO_4$. The solvent was removed under reduced pressure affording 2-(4-acetyl-3,3-dimethyl-2-oxopiperazin-1-yl)-4-bromobenzonitrile (0.69 g) as a yellow solid in 99% yield. LCMS M+H=349.9 and 351.9.

The Intermediates in Table JAT1 were made from available substituted bromo-anilines and chemistry exemplified in Intermediates Q41, Q53, Q53F4, Q53OMe4, and Q53CN4. Alternatively, the silver oxide bromide displacements similar to Intermediate Q41-B can be accomplished without the addition of water.

TABLE JAT1

| Intermediate | Structure | Name | LCMS M+ |
| --- | --- | --- | --- |
| Q53F2 | 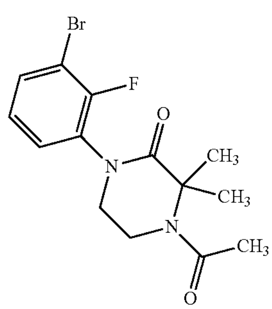 [SMILES: CC(=O)N1CCN(c2cccc(Br)c2F)C(=O)C1(C)C] | 4-acetyl-1-(3-bromo-2-fluorophenyl)-3,3-dimethylpiperazin-2-one | 343 and 345 |
| Q53F24 | 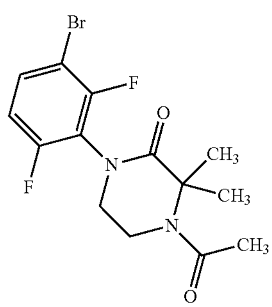 [SMILES: CC(=O)N1CCN(c2c(F)ccc(Br)c2F)C(=O)C1(C)C] | 4-acetyl-1-(3-bromo-2,6-difluorophenyl)-3,3-dimethylpiperazin-2-one | 361 and 363 |

TABLE JAT1-continued

| Intermediate | Structure | Name | LCMS M+ |
|---|---|---|---|
| Q53F5 | 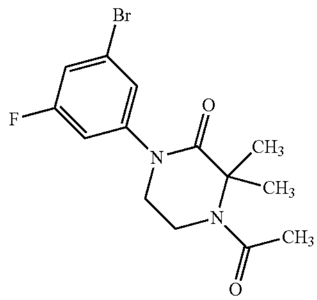 [SMILES: CC(=O)N1CCN(c2cc(F)cc(Br)c2)C(=O)C1(C)C] | 4-acetyl-1-(3-bromo-5-fluorophenyl)-3,3-dimethylpiperazin-2-one | 343 and 345 |
| Q53F6 | 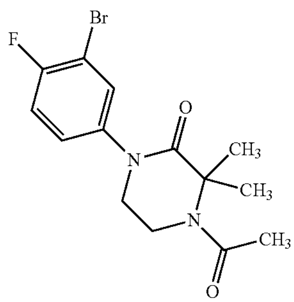 [SMILES: CC(=O)N1CCN(c2ccc(F)c(Br)c2)C(=O)C1(C)C] | 4-acetyl-1-(3-bromo-4-fluorophenyl)-3,3-dimethylpiperazin-2-one | 343 and 345 |
| Q53Me4 | 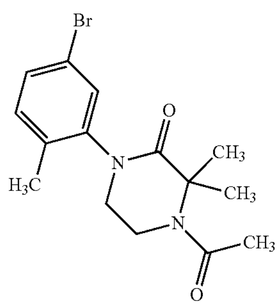 [SMILES: CC(=O)N1CCN(c2cc(Br)ccc2C)C(=O)C1(C)C] | 4-acetyl-1-(5-bromo-2-methylphenyl)-3,3-dimethylpiperazin-2-one | 339 and 341 |
| Q53Cl4 | 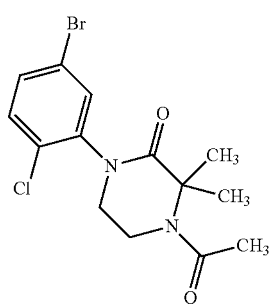 [SMILES: CC(=O)N1CCN(c2cc(Br)ccc2Cl)C(=O)C1(C)C] | 4-acetyl-1-(5-bromo-2-chlorophenyl)-3,3-dimethylpiperazin-2-one | 359 and 361 |
| Q53CF34 | 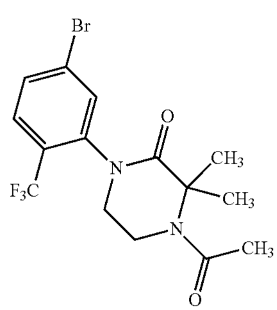 [SMILES: CC(=O)N1CCN(c2cc(Br)ccc2C(F)(F)F)C(=O)C1(C)C] | 4-acetyl-1-(5-bromo-2-(trifluoromethyl)phenyl)-3,3-dimethylpiperazin-2-one | 393 and 395 |

TABLE JAT1-continued

| Intermediate | Structure | Name | LCMS M+ |
|---|---|---|---|
| Q53F4 | 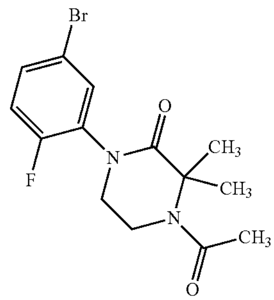 [SMILES: CC(=O)N1CCN(c2cc(Br)ccc2F)C(=O)C1(C)C] | 4-acetyl-1-(5-bromo-2-fluorophenyl)-3,3-dimethylpiperazin-2-one | 343 and 345 |
| Q53OMe4 | 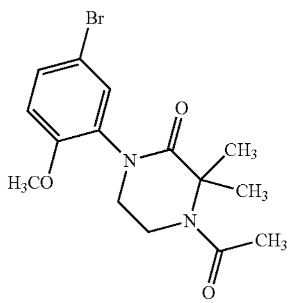 [SMILES: COc1ccc(Br)cc1N1CCN(C(C)=O)C(C)(C)C1=O] | 4-acetyl-1-(5-bromo-2-methoxyphenyl)-3,3-dimethylpiperazin-2-one | 355 and 357 |

Intermediate Q53A

4-Acetyl-3,3-dimethyl-1-(3-(4,4,5,5-tetramethyl-1,3,2-dioxaborolan-2-yl)phenyl)piperazin-2-one

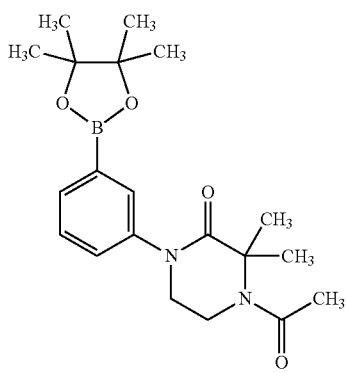

(Q53A)

A mixture of 4-acetyl-1-(3-bromophenyl)-3,3-dimethylpiperazin-2-one (1.95 g, 6.00 mmol, Intermediate Q53), 4,4,4',4',5,5,5',5'-octamethyl-2,2'-bi(1,3,2-dioxaborolane) (1.675 g, 6.60 mmol), PdCl₂(dppf)-CH₂Cl₂ adduct (0.147 g, 0.180 mmol) and potassium acetate (1.177 g, 11.99 mmol) in dioxane (15 mL) in a capped pressure reaction vial was degassed by vacuum then filled in nitrogen, repeating twice. The reaction mixture was placed in a 90° C. heating block and heated for 2.5 h. The reaction mixture was filtered through CELITE®, the filtrate concentrated onto CELITE® and was purified by MPLC (ISCO, 0-100% ethyl acetate/hexane, 40 g silica gel column) affording 4-acetyl-3,3-dimethyl-1-(3-(4,4,5,5-tetramethyl-1,3,2-dioxaborolan-2-yl)phenyl)piperazin-2-one (1.75 g, 4.7 mmol, 68% yield) as a white solid. LCMS M+=373.3. Method G. Retention time 0.94 min. ¹H NMR (400 MHz, chloroform-d) δ 7.77-7.73 (m, 1H), 7.68 (d, J=1.5 Hz, 1H), 7.45-7.42 (m, 2H), 3.84-3.74 (m, 4H), 2.20 (s, 3H), 1.86 (s, 6H), 1.37 (s, 12H).

Intermediate Q54

4-Acetyl-1-(3-(4-aminopyrrolo[2,1-f][1,2,4]triazin-7-yl)phenyl)-3,3-dimethylpiperazin-2-one

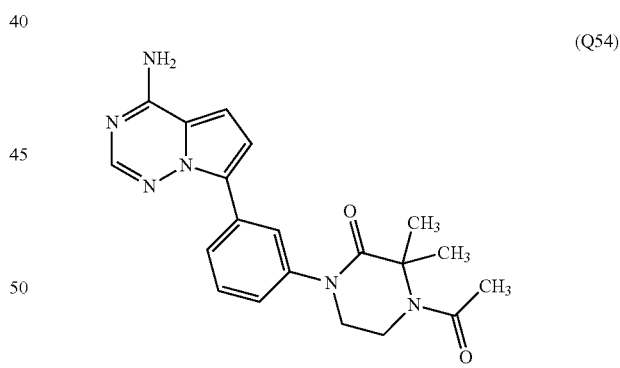

(Q54)

In a microwave vial 4-acetyl-1-(3-bromophenyl)-3,3-dimethylpiperazin-2-one (Q53) (500 mg, 1.54 mmol) was combined with 4,4,4',4',5,5,5',5'-octamethyl-2,2'-bi(1,3,2-dioxaborolane) (586 mg, 2.31 mmol), potassium acetate (453 mg, 4.61 mmol), PdCl₂(dppf)-CH₂Cl₂ adduct (251 mg, 0.308 mmol) and dioxane (12 mL). The mixture was purged with nitrogen and then the vessel was sealed and reacted in the microwave for 30 min at 120° C. The reaction mixture was cooled. Next, water (3 mL), 7-bromopyrrolo [2,1-f][1,2,4]triazin-4-amine (328 mg, 1.54 mmol), sodium carbonate (489 mg, 4.61), and PdCl₂(dppf)-CH₂Cl₂ adduct (251 mg, 0.308 mmol) were added and purged with nitrogen. The mixture was reacted in the microwave for 40 min at 110° C., diluted with 15 mL of water, extracted with EtOAc (30 mL×3). The combined organic layers were washed with brine, dried and concentrated. The residue was purified on silica to obtain the title compound 4-acetyl-1-(3-(4-aminopyrrolo[2,1-f][1,2,4]triazin-7-yl)phenyl)-3,3-dimethylpiperazin-2-one in (60.2% yield). LCMS M+=379.25. Method G. Retention time 1.90 min.

Alternative Synthesis of Intermediate Q54

Alternatively, a mixture of 7-bromopyrrolo[2,1-f][1,2,4]triazin-4-amine (0.436 g, 2.047 mmol), 4-acetyl-3,3-dimethyl-1-(3-(4,4,5,5-tetramethyl-1,3,2-dioxaborolan-2-yl)phenyl)piperazin-2-one (0.8 g, 2.149 mmol), PdCl$_2$(dppf))-CH$_2$Cl$_2$ adduct (0.084 g, 0.102 mmol) and 2M tripotassium phosphate aqueous solution (2.047 mL, 4.09 mmol) in dioxane (10 mL) in a closed pressure reaction vial was degassed by vacuum then back-filled with nitrogen. The degassing process was repeated twice. The reaction mixture was heated at 90° C. for 3 h and then cooled to room temperature. The organic phase of the reaction mixture was separated and concentrated. The residue was chromatographed on an ISCO Companion 24 g silica gel column and eluted with MeOH/DCM gradient (0-20%). The product containing fractions were collected and concentrated to give 4-acetyl-1-(3-(4-aminopyrrolo[2,1-f][1,2,4]triazin-7-yl)phenyl)-3,3-dimethylpiperazin-2-one (0.79 g, 89% purity, 1.86 mmol, 91% yield) as a light brown solid. Mass spectrum m/z 379.4 (M+H)+. $^1$H NMR (400 MHz, chloroform-d) δ 8.02-7.99 (m, 2H), 7.94-7.88 (m, 1H), 7.54-7.48 (m, 1H), 7.31-7.27 (m, 1H), 6.92 (d, J=4.6 Hz, 1H), 6.73 (d, J=4.6 Hz, 1H), 3.92-3.87 (m, 2H), 3.85-3.79 (m, 2H), 2.21 (s, 3H), 1.90 (s, 6H).

Intermediate M1

7-Iodo-5-methylpyrrolo[2,1-f][1,2,4]triazin-4-amine

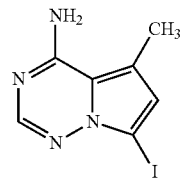

(M1)

Intermediate M1-A: 4-Chloro-7-iodo-5-methylpyrrolo[2,1-f][1,2,4]triazine

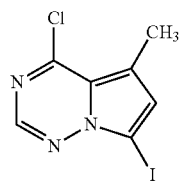

(M1-A)

A mixture of 1-iodopyrrolidine-2,5-dione (NIS) (671 mg, 2.98 mmol) and 4-chloro-5-methylpyrrolo[2,1-f][1,2,4]triazine (500 mg, 2.98 mmol) in DCM (3 mL) and THF (3 mL) was stirred at room temperature for 16 h. Additional NIS (340 mg, 0.5 eq) and DMF (5 mL) were added and stirring continued at room temperature for 16 h. The reaction mixture was diluted with ethyl acetate, washed with water, and the resulting solid collected by filtration of both layers. The resulting organic phase was separated, washed with 10% LiCl, water, and combined with the above insoluble filter cake and concentrated. The residue was loaded on CELITE® and chromatographed on an ISCO Companion 40 g silica gel column and eluted with EtOAc/hexane gradient (0-100%). The product containing fractions were collected and concentrated to give 4-chloro-7-iodo-5-methylpyrrolo[2,1-f][1,2,4]triazine (590 mg, 2.01 mmol, 67% yield). Mass spectrum m/z 293.7, 295.6 (M+H)+. $^1$H NMR (400 MHz, DMSO-d$_6$) δ 8.40 (s, 1H), 7.20 (s, 1H), 2.57 (d, J=0.7 Hz, 3H).

Intermediate M1

To a solution of 4-chloro-7-iodo-5-methylpyrrolo[2,1-f][1,2,4]triazine (60 mg, 0.204 mmol) in THF (2 mL) was added ammonia (0.511 mL, 1.022 mmol, 2M solution in isopropanol). After stirring at room temperature for 2 h, the reaction mixture was heated at 50° C. for 64 h. The reaction mixture was filtered and the filtrate was concentrated to give 60 mg of the title compound as a yellow solid, suitable for use without further purification. Mass spectrum m/z 274.6 (M+H)+. $^1$H NMR (400 MHz, chloroform-d) δ 7.96 (s, 1H), 6.70 (s, 1H), 2.58 (s, 3H).

Intermediate M2

7-Bromo-5-(trifluoromethyl)pyrrolo[1,2-f][1,2,4]triazin-4-amine

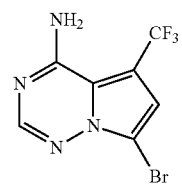

(M2)

Intermediate M2-A: 7-Bromo-N,N-bis(4-methoxybenzyl)pyrrolo[1,2-f][1,2,4]triazin-4-amine

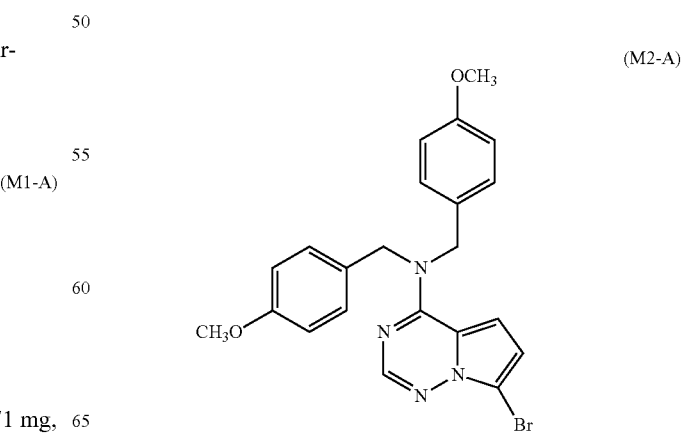

(M2-A)

A solution of 7-bromopyrrolo[2,1-f][1,2,4]triazin-4-amine (120 mg, 0.563 mmol) in N,N-dimethylformamide (2.5 mL) was treated with 4-methoxybenzyl chloride (0.168 mL, 1.239 mmol), then with cesium carbonate (459 mg, 1.408 mmol), added in one portion. The mixture was stirred at room temperature for 22 h. The mixture was diluted with water and extracted twice with ethyl acetate. The combined organic layers were washed with brine, dried over sodium sulfate and concentrated to provide a yellow semi-solid. The material was chromatographed on an ISCO Companion 4 g silica gel column and eluted with EtOAc/hexane gradient (5-30%). The product containing fractions were collected and concentrated to give 7-bromo-N,N-bis(4-methoxybenzyl)pyrrolo[2,1-f][1,2,4]triazin-4-amine (147.8 mg, 97% purity, 0.316 mmol, 56% yield). Mass spectrum m/z 453, 455 (M+H)+. 1H NMR (400 MHz, chloroform-d) δ 8.14 (s, 1H), 7.23 (d, J=8.6 Hz, 4H), 6.93-6.88 (m, 4H), 6.61 (d, J=1.3 Hz, 2H), 4.94 (s, 4H), 3.83 (s, 6H).

Alternatively sodium hydride can be used instead of cesium carbonate.

Intermediate M2-B: 7-Bromo-5-iodo-N,N-bis(4-methoxybenzyl)pyrrolo[1,2-f][1,2,4]triazin-4-amine

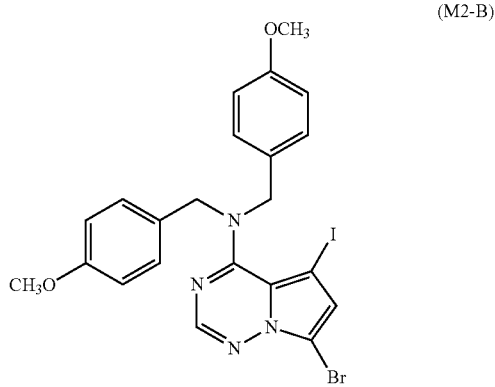

(M2-B)

A solution of 7-bromo-N,N-bis(4-methoxybenzyl)pyrrolo[2,1-f][1,2,4]triazin-4-amine (4.3 g, 9.49 mmol), NIS (2.134 g, 9.49 mmol) in DMF (20 mL) and 10 drops of TFA was stirred at room temperature for 16 h. Additional NIS (130 mg, 0.05 eq) was added and the mixture was stirred at room temperature for 1 h. The reaction mixture was poured into an ice-water and 1.5M K2HPO4 (~1:1) mixture to afford yellow precipitate. The precipitate was filtered. The filter cake was washed with water twice. The filter cake was triturated with ethyl acetate to give 2.98 g white solid as clean product. The mother liquor was concentrated and triturated with MeOH to give another 1.43 g crystalline white solid as clean product. Total yield of 7-bromo-5-iodo-N,N-bis(4-methoxybenzyl)pyrrolo[2,1-f][1,2,4]triazin-4-amine (4.41 g, 7.60 mmol, 80% yield). Mass spectrum m/z 579, 581 (M+H)+; 1H NMR (400 MHz, chloroform-d) δ 8.13 (s, 1H), 7.29 (s, 1H), 7.07-7.03 (m, 4H), 6.89-6.85 (m, 4H), 4.64 (s, 4H), 3.83 (s, 6H).

Intermediate M2-C: 7-Bromo-N,N-bis(4-methoxybenzyl)-5-(trifluoromethyl)pyrrolo [1,2-f][1,2,4]triazin-4-amine

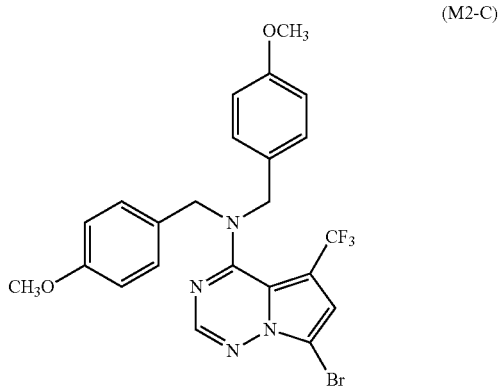

(M2-C)

A mixture of 7-bromo-5-iodo-N,N-bis(4-methoxybenzyl)pyrrolo[2,1-f][1,2,4]triazin-4-amine (0.2 g, 0.345 mmol) and copper(I) iodide (0.072 g, 0.380 mmol) in a capped pressure reaction vial was vacuum then filled in with nitrogen. The degassing process was repeated twice. To the above solid mixture was added DMF (3 mL). The resulting suspension was degassed three times. To the above suspension was added methyl 2,2-difluoro-2-(fluorosulfonyl)acetate (0.265 g, 1.381 mmol). The reaction vial was placed in a 80° C. heating block and heated for 3 h. The reaction mixture was cooled to room temperature then filtered through CELITE®. The filter cake was washed with ethyl acetate three times. The combined filtrate was washed with 5% ammonia twice, 10% LiCl once, water once, brine once, then concentrated to give 7-bromo-N,N-bis(4-methoxybenzyl)-5-(trifluoromethyl)pyrrolo[2,1-f][1,2,4]triazin-4-amine (211 mg, 72% purity, 0.291 mmol, 84% yield). Mass spectrum m/z 521, 523 (M+H)+; 1H NMR (400 MHz, chloroform-d) δ 8.21 (s, 1H), 7.10 (s, 1H), 6.96-6.93 (m, 4H), 6.84-6.82 (m, 4H), 4.58 (s, 4H), 3.81-3.79 (m, 6H).

Intermediate M2

7-Bromo-N,N-bis(4-methoxybenzyl)-5-(trifluoromethyl)pyrrolo[2,1-f][1,2,4]triazin-4-amine (1.2 g, 2.302 mmol) in TFA (10 mL) in a pressure reaction vial was placed in a 110° C. heating block and heated for 4 h. The reaction mixture was concentrated. The residue was dissolved in dichloromethane and chromatographed on an ISCO Companion 24 g silica gel column and eluted with EtOAc/Hexane gradient (0-100%). The product containing fractions were collected and concentrated. The yellow oily residue was triturated with methanol to give 7-bromo-5-(trifluoromethyl)pyrrolo[2,1-f][1,2,4]triazin-4-amine (502 mg, 1.79 mmol, 78% yield). Mass spectrum m/z 281, 283 (M+H)+; 1H NMR (400 MHz, DMSO-d6) δ 8.18 (s, 1H), 7.38 (s, 1H).

Intermediate M3

4-Amino-7-bromopyrrolo[1,2-f][1,2,4]triazine-5-carbonitrile

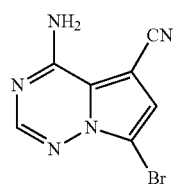

(M3)

4-Amino-7-bromopyrrolo[2,1-f][1,2,4]triazine-5-carbonitrile was prepared by nitrogenation of 7-bromo-5-ethynylpyrrolo[2,1-f][1,2,4]triazin-4-amine using the method described in *Angew. Chem. Int. Ed.,* 52:6677-6680 (2013). A mixture of 7-bromo-5-ethynylpyrrolo[2,1-f][1,2,4]triazin-4-amine (470 mg, 1.98 mmol) (Intermediate R1-C), azidotrimethylsilane (457 mg, 3.97 mmol), silver carbonate (54.7 mg, 0.198 mmol) and DMSO (10 mL) was placed in a pressure reaction vial, the vial flushed with nitrogen and the mixture stirred at 100° C. for 15 h. The mixture was cooled to room temperature, and diluted with water (100 mL) under vigorous stirring. The mixture was filtered to collect the product which was washed with water and ether and dried with suction to give crude 4-amino-7-bromopyrrolo[2,1-f][1,2,4]triazine-5-carbonitrile (400 mg). $^1$H NMR (400 MHz, DMSO-$d_6$) δ 8.19 (s, 1H), 7.50 (s, 1H).

An alternate preparation of M3:

Intermediate M3-A: 4-Amino-7-bromopyrrolo[2,1-f][1,2,4]triazine-5-carboxamide

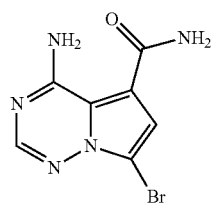

(M3-A)

A suspension of ethyl 4-amino-7-bromopyrrolo[2,1-f][1,2,4]triazine-5-carboxylate (5.3 g, 18.59 mmol), THF (40 mL), MeOH (20 mL) and lithium hydroxide monohydrate (4.68 g, 112 mmol) dissolved in water (20 mL) was stirred at room temperature for 15 h and 50° C. for 1 h. The mixture was cooled to room temperature made acidic (pH=2) by dropwise addition of concentrated HCl, diluted with water (200 mL) and the white precipitate collected by filtration. The product was washed with water and sucked dry and then dried further by rotovaping a suspension of the solid in 20% MeOH/toluene (2×100 mL).

The product from above was treated with DMF (40 mL) and DIPEA (19.48 mL, 112 mmol) and stirred for 5 min until most of the solid had dissolved. 1-hydroxy-7-azabenzotriazole (3.80 g, 27.9 mmol) and 1-(3-dimethylaminopropyl)-3-ethylcarbodiimide hydrochloride (5.35 g, 27.9 mmol) were added to the mixture, the resulting yellow mixture was stirred for 5 min and then treated with ammonium chloride (3.98 g, 74.4 mmol) and stirred at room temperature for 16 h. The mixture was diluted with water (20 mL), stirred for 5 min and filtered to collect the precipitate. The collected solid was washed with saturated NaHCO$_3$ (100 mL) and water (200 mL), dried under suction, and the dried further in vacuo to give 4-amino-7-bromopyrrolo[2,1-f][1,2,4]triazine-5-carboxamide as a white solid (4.5 g, 95%). LC-MS: m/z=255.8, (M+H)$^+$. $^1$H NMR (400 MHz, DMSO-$d_6$) δ 10.41 (br. s., 1H), 8.24 (br. s., 1H), 8.11 (br. s., 1H), 8.01 (s, 1H), 7.67 (br. s., 1H), 7.48 (s, 1H). LC-MS: m/z=255.8, (M+H)$^+$.

Intermediate M3

4-Amino-7-bromopyrrolo[2,1-f][1,2,4]triazine-5-carboxamide (1.0 g, 3.91 mmol) was placed in a 20 mL BIOTAGE® pressure reaction vial, treated with phosphorus oxychloride (7.28 ml, 78 mmol). The vial was capped and heated for 20 h in a 120° C. heating block. The resulting brown mixture was cooled to room temperature and poured slowly in 2 M NaOH (75 mL) cooled to 0° C. keeping the temperature below 35° C. The resulting was stirred for 10 min and then made basic to pH 7.5 with 5 M NaOH. The mixture was filtered to collect the yellow solid which was washed with water, dried under suction, and dried in vacuo. The filtrate was kept at room temperature overnight after which time more of the product predicated. The second crop was collected, washed with water, dried and combined with the first crop to give 4-amino-7-bromopyrrolo[2,1-f][1,2,4]triazine-5-carbonitrile (0.68 g, 73% yield). LC-MS: m/z=237.8, (M+H)$^+$. $^1$H NMR (400 MHz, DMSO-$d_6$) δ 8.19 (s, 1H), 7.50 (s, 2H); $^{13}$C NMR (125 MHz), DMSO-$d_6$) δ 154.4; 150.3; 119.2; 114.7; 102.5; 84.1.

Intermediate M4

7-Bromo-5-chloropyrrolo[1,2-f][1,2,4]triazin-4-amine

(M4)

To a solution of 7-bromopyrrolo[2,1-f][1,2,4]triazin-4-amine (0.48 g, 2.253 mmol) in DMF (11.27 ml) was added NCS (0.361 g, 2.70 mmol) and the reaction mixture was stirred at room temperature for 2 days. The reaction was monitored by LCMS. The reaction mixture was partitioned between 1.5M K$_2$HPO$_4$ and EtOAc. The organic phase was washed with 10% LiCl, brine, dried by Na$_2$SO$_4$, filtered, and concentrated to afford a white solid as the crude product. The crude product was then purified by ISCO column (24 g, 30-50-75% of EtOAc in hexane). The desired product was obtained as a white solid (0.48 g) in 86% yield. Mass spectrum m/z 246.8, 248.8, 250.8 (M+H)$^+$. $^1$H NMR (400 MHz, DMSO-$d_6$) δ 8.17 (d, J=8.4 Hz, 1H), 7.93 (s, 1H), 7.21-7.00 (m, 1H), 6.98 (s, 1H).

175

Intermediate M33

Di-tert-butyl (7-(3-(4-acetyl-3,3-dimethyl-2-oxopiperazin-1-yl)phenyl)-5-iodopyrrolo [2,1-f][1,2,4]triazin-4-yl)biscarbamate

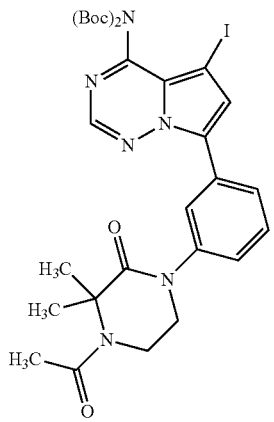
(M33)

A mixture of 4-acetyl-1-(3-(4-amino-5-iodopyrrolo[2,1-f][1,2,4]triazin-7-yl) phenyl)-3,3-dimethylpiperazin-2-one (60 mg, 0.119 mmol), di-tert-butyl dicarbonate (0.030 ml, 0.131 mmol), DIPEA (0.031 ml, 0.178 mmol), DMAP (2.91 mg, 0.024 mmol) and tetrahydrofuran (1 ml) was stirred at room temperature for 16 h. The reaction was not completed. Both mono- and bis-boc protected product formed. More di-tert-butyl dicarbonate (0.030 ml, 0.131 mmol) and DIPEA (0.031 ml, 0.178 mmol) were added. The reaction mixture was stirred at room temperature for 3 h. Reaction was completed. The reaction mixture was diluted with dichloromethane, washed with 1.5 M $K_2HPO_4$, water, and brine, and then concentrated to give 80 mg yellow solid as bis-boc protected product.

Intermediate C1

1-(1-Amino-6-bromopyrrolo[1,2-a]pyrazin-8-yl)-3-(trimethylsilyl)prop-2-yn-1-one

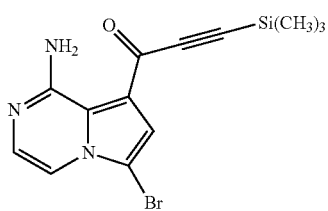
(C1)

176

Intermediate C1-A: Methyl 6-bromo-1-((2,4-dimethoxybenzyl)amino)pyrrolo[1,2-a]pyrazine-8-carboxylate

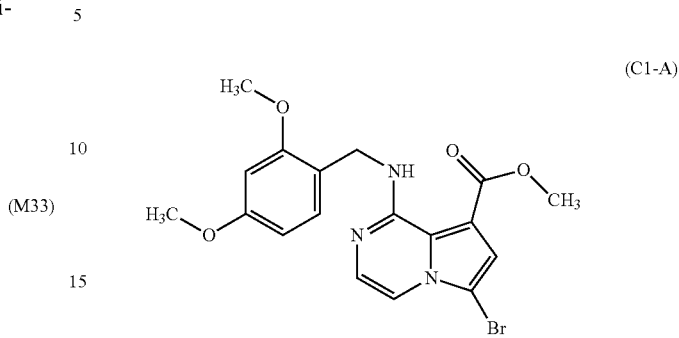
(C1-A)

A solution of methyl 1-chloropyrrolo[1,2-a]pyrazine-8-carboxylate (206 mg, 0.917 mmol) in acetic acid (5 mL) was treated with bromine (0.052 mL, 1.009 mmol). The mixture was stirred at room temperature for 10 min and then diluted with ethyl acetate (10 mL) and water (5 mL). The pH of the aqueous layer was adjusted to 5, and the layers were mixed and separated. The organic portion was washed with aqueous $K_2HPO_4$ and then brine, dried over $Na_2SO_4$ and concentrated. The crude residue was dissolved in THF (5 mL) and treated with DIPEA (0.272 mL, 1.559 mmol) and (2,4-dimethoxyphenyl)methanamine (0.207 mL, 1.376 mmol). This mixture was heated at 60° C. for 7 h and then cooled to room temperature, diluted with DCM and washed with water. The organic portion was dried over $MgSO_4$, filtered and concentrated. The residue was purified by silica gel chromatography eluting with 0-50% ethyl acetate/hexanes to provide methyl 6-bromo-1-((2,4-dimethoxybenzyl)amino)pyrrolo[1,2-a]pyrazine-8-carboxylate (284 mg, 0.523 mmol, 57.1% yield) as a tan solid. $^1$H NMR (400 MHz, chloroform-d) δ 9.68 (br. s., 1H), 7.41 (d, J=4.6 Hz, 1H), 7.34-7.28 (m, 2H), 7.18 (s, 1H), 6.49 (d, J=2.3 Hz, 1H), 6.47-6.43 (m, 2H), 4.72 (d, J=5.5 Hz, 2H), 4.32 (q, J=7.1 Hz, 2H), 3.88-3.84 (s, 3H), 3.82-3.79 (s, 3H), 1.37 (t, J=7.2 Hz, 3H). LC/MS: 0.83 min, [M+1]$^+$=245. Method F.

Intermediate C1-B: Methyl 1-amino-6-bromopyrrolo[1,2-a]pyrazine-8-carboxylate

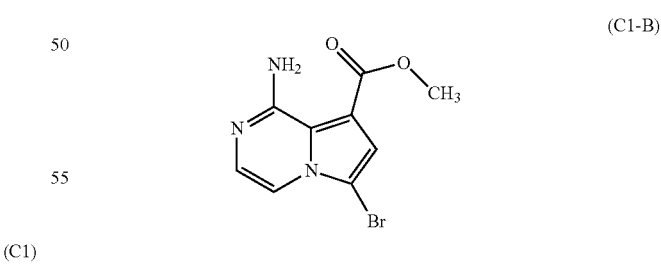
(C1-B)

A solution of methyl 6-bromo-1-((2,4-dimethoxybenzyl)amino)pyrrolo[1,2-a]pyrazine-8-carboxylate (207 mg, 0.493 mmol) in DCM (1 mL) was treated with trifluoroacetic acid (1.138 mL, 14.78 mmol) and then triethylsilane (0.393 mL, 2.463 mmol). The mixture was stirred at room temperature for 3 h, diluted with water (5 mL) and adjusted to pH 8 by the addition of concentrated NaOH. The mixture was extracted with 2×10 mL of a solution of 10% MeOH in DCM. The combined organic portion was dried over $MgSO_4$ and concentrated to provide methyl 1-amino-6-bromopyrrolo[1,2-a]pyrazine-8-carboxylate (105 mg, 0.389 mmol, 79% yield) as a crude solid, suitable for use in the next reaction. LC/MS: 0.59 min, [M+1]$^+$=270. Method F.

Intermediate C1-C: 1-Amino-6-bromopyrrolo[1,2-a]pyrazine-8-carboxylic acid

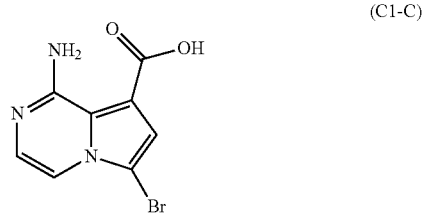 [SMILES: Nc1nccn2c(Br)cc(C(=O)O)c12]

(C1-C)

A solution of methyl 1-amino-6-bromopyrrolo[1,2-a]pyrazine-8-carboxylate (315 mg, 1.166 mmol) in a mixture of MeOH (5 mL), water (2.5 mL) and THF (2.5 mL) was treated with sodium hydroxide (233 mg, 5.83 mmol). The mixture was stirred at room temperature for 3 h and 40° C. for 1 h after which it was cooled to room temperature. The pH of the mixture was adjusted to 3. A suspension formed and was filtered. The collected solid was washed with water and ethyl acetate then dried under vacuum providing 1-amino-6-bromopyrrolo[1,2-a]pyrazine-8-carboxylic acid (255 mg, 1.00 mmol) as a white solid. LC/MS: 0.79 min, [M+1]$^+$=256. Method L.

Intermediate C1-D: 1-Amino-6-bromo-N-methoxy-N-methylpyrrolo[1,2-a]pyrazine-8-carboxamide

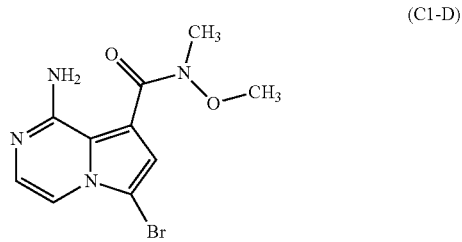 [SMILES: CON(C)C(=O)c1cc(Br)n2ccnc(N)c12]

(C1-D)

Under anhydrous conditions, a mixture of 1-amino-6-bromopyrrolo[1,2-a]pyrazine-8-carboxylic acid (1.75 g, 6.83 mmol) and N,O-dimethylhydroxylamine, HCl (1.000 g, 10.25 mmol) in THF (68.3 ml) was treated sequentially with 2,4,6-tripropyl-1,3,5,2,4,6-trioxatriphosphorinane-2,4,6-trioxide (50 wt % solution in ethyl acetate) (8.98 ml, 15.38 mmol) and DIPEA (4.18 ml, 23.92 mmol). The resulting mixture was stirred at room temperature for 1.5 h. THF was removed under reduced pressure and the resulting aqueous suspension was carefully treated with 100 mL of saturated NaHCO$_3$ and stirred at room temperature for 0.5 h. The suspension was filtered and the collected solid was washed with water followed by hexanes and dried under vacuum providing 1-amino-6-bromo-N-methoxy-N-methylpyrrolo[1,2-a]pyrazine-8-carboxamide (1.03 g, 3.44 mmol) as a pink solid. $^1$H NMR (400 MHz, DMSO-d$_6$) δ 7.56-7.42 (m, 3H), 7.32 (d, J=4.6 Hz, 1H), 7.29 (s, 1H), 3.63 (s, 1H), 3.33 (s, 1H). LC/MS: 0.84 min, [M+1]$^+$=299; Method L.

Intermediate C1

Under anhydrous conditions, a solution of ethynyltrimethylsilane (301 μl, 2.129 mmol) in THF (6653 μl) was cooled to −78° C. and treated with n-butyllithium (852 μl, 2.129 mmol, 2.5 M solution in hexanes). After stirring for 20 min, 1-amino-6-bromo-N-methoxy-N-methylpyrrolo[1,2-a]pyrazine-8-carboxamide (199 mg, 0.665 mmol) was added as a solution in THF (3 mL). The mixture was stirred at −78° C. for 30 min and then removed from the cooling bath and allowed to warm to room temperature over 45 min. The reaction was quenched by the addition of AcOH (1 mL) and water (10 mL) then extracted with ethyl acetate (2×20 mL). The organic portion was washed with brine, dried over sodium sulfate and concentrated to provide 1-(1-amino-6-bromopyrrolo[1,2-a]pyrazin-8-yl)-3-(trimethylsilyl)prop-2-yn-1-one (239 mg, 107% yield). $^1$H NMR (400 MHz, DMSO-d$_6$) δ 7.60 (d, J=4.6 Hz, 1H), 7.52 (d, J=4.4 Hz, 1H), 7.49 (s, 1H), 0.32 (s, 9H). LC/MS: 1.07 min, [M+1]$^+$=336. Method L.

Intermediate C2

6-Bromo-8-(1-(tetrahydro-2H-pyran-4-yl)-1H-pyrazol-5-yl)pyrrolo[1,2-a]pyrazin-1-amine

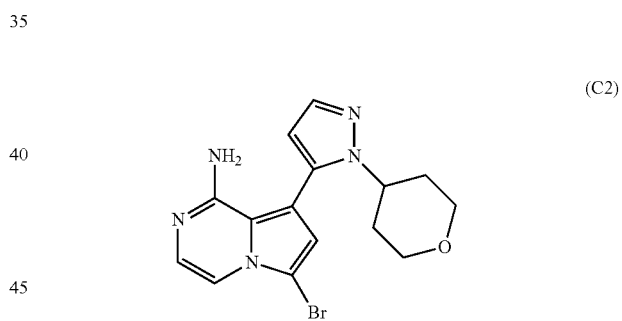

(C2)

A mixture of 1-(1-amino-6-bromopyrrolo[1,2-a]pyrazin-8-yl)-3-(trimethylsilyl) prop-2-yn-1-one (340 mg, 1.011 mmol, Intermediate C1) and (tetrahydro-2H-pyran-4-yl)hydrazine, HCl (386 mg, 2.53 mmol) was suspended in ethanol (11 mL) and treated with triethylamine (775 μl, 5.56 mmol). The resulting mixture was heated at 80° C. for 1.5 h and then concentrated under reduced pressure. The residue was suspended in ethyl acetate, filtered and the filtrate was concentrated under reduced pressure. The residue was purified by silica gel chromatography eluting with dichloromethane in methanol providing 6-bromo-8-(1-(tetrahydro-2H-pyran-4-yl)-1H-pyrazol-5-yl)pyrrolo[1,2-a]pyrazin-1-amine (235 mg, 0.65 mmol 64.2% yield) as a yellow solid. $^1$H NMR (400 MHz, DMSO-d$_6$) δ 7.66 (d, J=1.5 Hz, 1H), 7.56 (d, J=4.8 Hz, 1H), 7.23 (d, J=4.8 Hz, 1H), 7.02 (s, 1H), 6.41 (d, J=1.8 Hz, 1H), 5.73 (br. s., 2H), 4.23 (tt, J=11.4, 4.2 Hz, 1H), 3.95-3.81 (m, 2H), 3.38-3.24 (m, 2H), 2.08 (qd, J=12.2, 4.7 Hz, 2H), 1.86-1.65 (m, 2H). LC/MS: 0.65 min, [M+1]$^+$=362 Method F.

Example 1

5-(4-Amino-5-(1-cyclohexyl-1H-pyrazol-5-yl)pyrrolo[2,1-f][1,2,4]triazin-7-yl)-2-fluorobenzamide (1)

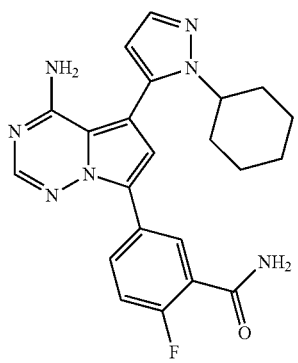

Intermediate 1A: 7-Bromo-5-(1-cyclohexyl-1H-pyrazol-5-yl)pyrrolo[2,1-f][1,2,4]triazin-4-amine (1A)

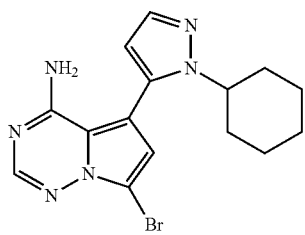

1-(4-Amino-7-bromopyrrolo[2,1-f][1,2,4]triazin-5-yl)-3-(trimethylsilyl)prop-2-yn-1-one (0.95 g, 6.7 mmol) was suspended in ethanol (24 mL) and cyclohexylhydrazine, HCl (1.01 g, 18.98 mmol) was added followed by triethylamine (1.5 mL, 10.7 mmol). The mixture was heated at 90° C. for 2 h, cooled to room temperature and added EtOAc (50 mL) and washed with water, brine, dried over $Na_2SO_4$, filtered and concentrated. The solid obtained was purified by silica gel chromatography eluting with a gradient of 0-10% Methanol in DCM to obtain the desire product (0.86 g) as a white solid. m/z 361, 363.

Example 1

Intermediate 1A (20 mg, 0.055 mmol), (3-carbamoyl-4-fluorophenyl)boronic acid (20.26 mg, 0.111 mmol) and potassium carbonate (30.6 mg, 0.221 mmol) were combined in a vial. DMA (1 mL) and water (0.25 mL) were added and the mixture was degassed by bubbling argon with sonication. Next, tetrakistriphenylphosphine (9.6 mg, 8.3 μmol) was added and the degassing procedure was repeated. The mixture was heated at 90° C. for 6 h. The reaction mixture was diluted with ACN containing 0.1% TFA and purified by reverse phase HPLC eluting with a gradient of 20-90% ACN/Water/0.1% TFA mixture. Concentration of the appropriate fraction afforded TFA salt of Example 1 (9.4 mg) as a pale yellow solid. LCMS $(M+H)^+=420.3$. HPLC, method E, Rt=6.48 min Following compounds were prepared following the general procedure for the synthesis of Example 1. In some examples $K_3PO_4$ was used in place of $K_2CO_3$. LCMS Method B was used for detection of product formation.

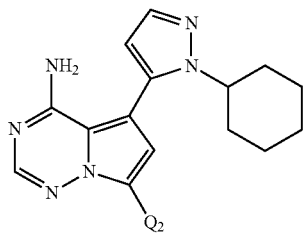

| Ex. No. | $Q_2$ | Name | LCMS $(M + H)^+$ |
|---|---|---|---|
| 2 | 3-(aminomethyl)phenyl | 7-(3-(aminomethyl)phenyl)-5-(1-cyclohexyl-1H-pyrazol-5-yl)pyrrolo[2,1-f][1,2,4]triazin-4-amine | 388.3 |
| 3 | 3-((dimethylamino)methyl)phenyl | 5-(1-cyclohexyl-1H-pyrazol-5-yl)-7-(3-((dimethylamino)methyl)phenyl)pyrrolo[2,1-f][1,2,4]triazin-4-amine | 416.3 |

-continued

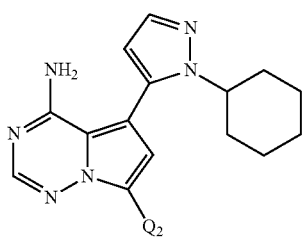

| Ex. No. | Q₂ | Name | LCMS (M + H)⁺ |
|---|---|---|---|
| 4 | [3-pyrrolidinyl-carbonyl-phenyl] | (3-(4-amino-5-(1-(tetrahydro-2H-pyran-4-yl)-1H-pyrazol-5-yl)pyrrolo[2,1-f][1,2,4]triazin-7-yl)phenyl)(pyrrolidin-1-yl)methanone | 455.4 |
| 5 | [3-(methanesulfonamidomethyl)phenyl] | N-(3-(4-amino-5-(1-cyclohexyl-1H-pyrazol-5-yl)pyrrolo[2,1-f][1,2,4]triazin-7-yl)benzyl)methanesulfonamide | 466.4 |
| 6 | [3-(morpholinomethyl)phenyl] | 5-(1-cyclohexyl-1H-pyrazol-5-yl)-7-(3-(morpholinomethyl)phenyl)pyrrolo[2,1-f][1,2,4]triazin-4-amine | 458.4 |
| 7 | [3-(hydroxymethyl)-4-fluorophenyl] | (5-(4-amino-5-(1-cyclohexyl-1H-pyrazol-5-yl)pyrrolo[2,1-f][1,2,4]triazin-7-yl)-2-fluorophenyl)methanol | 407.3 |
| 8 | [3-acetamidophenyl] | N-(3-(4-amino-5-(1-cyclohexyl-1H-pyrazol-5-yl)pyrrolo[2,1-f][1,2,4]triazin-7-yl)phenyl)acetamide | 416.3 |
| 9 | [3-(methanesulfonamido)phenyl] | N-(3-(4-amino-5-(1-cyclohexyl-1H-pyrazol-5-yl)pyrrolo[2,1-f][1,2,4]triazin-7-yl)phenyl)methanesulfonamide | 452.4 |
| 10 | [3-(N-methylcarbamoyl)phenyl] | 3-(4-amino-5-(1-cyclohexyl-1H-pyrazol-5-yl)pyrrolo[2,1-f][1,2,4]triazin-7-yl)-N-methylbenzamide | 416.3 |

183 184

-continued

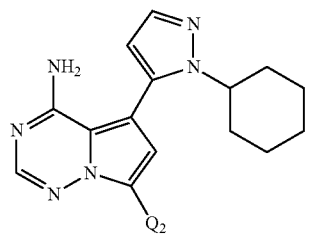

| Ex. No. | Q2 | Name | LCMS (M + H)+ |
|---|---|---|---|
| 11 | H3C-N(CH3)-C(=O)-phenyl- | 3-(4-amino-5-(1-cyclohexyl-1H-pyrazol-5-yl) pyrrolo[2,1-f][1,2,4]triazin-7-yl)-N,N-dimethylbenzamide | 430.4 |
| 12 | H3C-N(CH3)-C(=O)-phenyl- | 4-(4-amino-5-(1-cyclohexyl-1H-pyrazol-5-yl)pyrrolo[2,1-f][1,2,4]triazin-7-yl)-N,N-dimethylbenzamide | 430.4 |
| 13 | HOOC-phenyl- | 3-(4-amino-5-(1-cyclohexyl-1H-pyrazol-5-yl) pyrrolo[2,1-f][1,2,4]triazin-7-yl)benzoic acid | 403.3 |

Example 14

7-(3-(Morpholinomethyl)phenyl)-5-(1-(tetrahydro-2H-pyran-4-yl)-1H-pyrazol-5-yl) pyrrolo[2,1-f][1,2,4]triazin-4-amine (14)

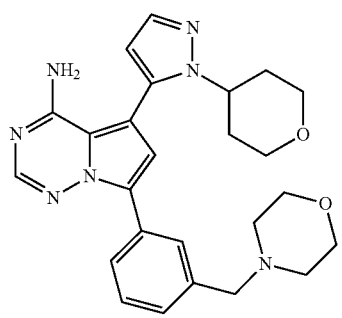

Intermediate 14A: Bis-(Boc)-7-bromo-5-(1-(tetrahydro-2H-pyran-4-yl)-1H-pyrazol-5-yl) pyrrolo[2,1-f][1,2,4]triazin-4-amine (14A)

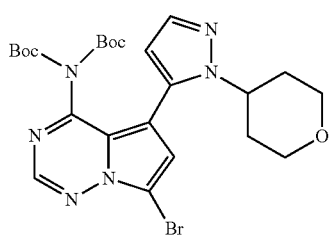

7-Bromo-5-(1-(tetrahydro-2H-pyran-4-yl)-1H-pyrazol-5-yl)pyrrolo[2,1-f][1,2,4]triazin-4-amine (1.97 g, 5.42 mmol) was suspended in THF (60 ml) and BOC-anhydride (3.55 g, 16.27 mmol) was added followed by DIPEA (2.84 ml, 16.27 mmol) and finally DMAP (0.133 g, 1.085 mmol). After stirring at room temperature for 18 h, the mixture was concentrated to dryness. The crude product was purified by silica gel chromatography (12 g silica gel cartridge) eluting with a gradient from 0-50% ethyl acetate in hexanes to obtain the desired product (2.42 g, 4.30 mmol, 79% yield) as a yellow solid.

Example 14

Intermediate 14A (60 mg, 0.106 mmol), (3-(morpholinomethyl)phenyl)boronic acid (35.3 mg, 0.160 mmol) and tripotassium phosphate (113 mg, 0.532 mmol) were combined in a vial. THF (1.5 mL) and water (0.2 mL) were added and the mixture was degassed by bubbling argon while sonicated. Tetrakistriphenylphosphine (12.31 mg, 10.65 µmol) was added and the degassing procedure was repeated. The mixture was heated at 85° C. for 2.5 h. The reaction mixture was cooled to room temperature, diluted with ethyl acetate (5 mL), water (2 mL) and the layers were mixed and then separated. The organic layer was dried over MgSO$_4$ and concentrated. The crude product was purified by silica gel chromatography eluting with a gradient of 0-10% MeOH in DCM (w/ 0.5% NH$_4$OAc added to each eluting solvent). The solid obtained was triturated with ethyl acetate to afford Example 14 (22.7 mg, 44.1% yield) as a white solid. LCMS (M+H)$^+$=460.26. Retention time 0.71 min. LCMS Method B.

Following Examples were prepared by using the general procedure for the synthesis of Example 14 by employing either Intermediate B or Intermediate N1 and the appropriate boronic acid.

Boronic acid for Example 17 was made as follows:

Intermediate 17A:
2-(3-Bromophenyl)-N,N-dimethylpropan-2-amine

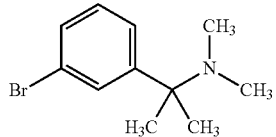

(17A)

To a solution of 2-(3-bromophenyl)propan-2-amine (0.25 g, 1.168 mmol) and formaldehyde 37% aqueous solution (0.474 g, 5.84 mmol) in DCM (3 mL) and THF (3 mL) was added sodium triacetoxyborohydride (1.23 g, 5.84 mmol) at 0° C. The mixture was stirred for 10 min and then the ice bath was removed and the reaction mixture was allowed to warm to room temperature. The reaction was quenched by adding saturated NaHCO$_3$ (5 m) and the resulting mixture was extracted with ethyl acetate (2×20 mL). The organic layer was separated, washed with brine and dried over MgSO$_4$. Concentration of mixture afforded 2-(3-bromophenyl)-N,N-dimethylpropan-2-amine (67 mg, 0.277 mmol, 23.70% yield) as an orange oil.

TABLE 2

| Ex. No. | R | Name | LCMS (M + H)$^+$ |
|---|---|---|---|
| 15 | pyrrolidin-1-yl-carbonyl | (3-(4-amino-5-(1-(tetrahydro-2H-pyran-4-yl)-1H-pyrazol-5-yl)pyrrolo[2,1-f][1,2,4]triazin-7-yl)phenyl)(pyrrolidin-1-yl)methanone | 403.3 |
| 16 | -CH$_2$-N(CH$_3$)$_2$ | 7-(3-((dimethylamino)methyl)phenyl)-5-(1-(tetrahydro-2H-pyran-4-yl)-1H-pyrazol-5-yl)pyrrolo[2,1-f][1,2,4]triazin-4-amine | 418.3 |
| 17 | -C(CH$_3$)$_2$-N(CH$_3$)$_2$ | 7-(3-(2-(dimethylamino)propan-2-yl)phenyl)-5-(1-(tetrahydro-2H-pyran-4-yl)-1H-pyrazol-5-yl)pyrrolo[2,1-f][1,2,4]triazin-4-amine | 445.3 |
| 18 | -CH$_2$-NH-S(O)$_2$-CH$_3$ | N-(3-(4-amino-5-(1-(tetrahydro-2H-pyran-4-yl)-1H-pyrazol-5-yl)pyrrolo[2,1-f][1,2,4]triazin-7-yl)benzyl)methanesulfonamide | 468.2 |

Intermediate 17B: N,N-Dimethyl-2-(3-(4,4,5,5-tetramethyl-1,3,2-dioxaborolan-2-yl) phenyl)propan-2-amine

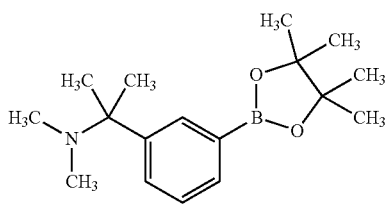

(17B)

To a solution of 2-(3-bromophenyl)-N,N-dimethylpropan-2-amine (0.097 g, 0.401 mmol) was dissolved in THF (4 mL) and the mixture was cooled to −78° C. N-Butyllithium (2.5M in hexanes) (0.208 mL, 0.52 mmol) was added dropwise to give a pale yellow solution. The resulting mixture was stirred for 10 min and then added 2-isopropoxy-4,4,5,5-tetramethyl-1,3,2-dioxaborolane (0.090 mL, 0.44 mmol) dropwise. After 10 min at −78° C., the cooling bath was removed to allow the mixture to warm to room temperature. The reaction was quenched by the addition of water (1 mL), the reaction mixture was diluted with ethyl acetate (10 mL) and water (5 mL) and the layers were separated. The organic layer was dried over and concentrated. Analysis of the crude material indicated the desired product N,N-dimethyl-2-(3-(4,4,5,5-tetramethyl-1,3,2-dioxaborolan-2-yl)phenyl)propan-2-amine (0.102 g) was isolated in high purity as a colorless oil.

Example 19

(3-(4-Amino-5-(1-cyclohexyl-1H-pyrazol-5-yl)pyrrolo[2,1-f][1,2,4]triazin-7-yl) phenyl)(morpholino)methanone

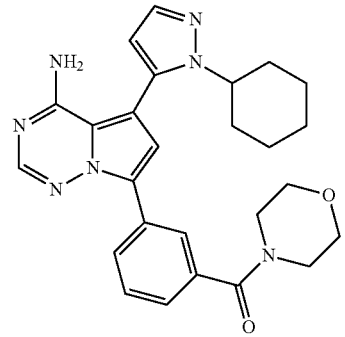

(19)

Example 13 (15 mg, 0.037 mmol) was dissolved in THF (2 mL), and morpholine (0.04 mL, 0.045 mmol) followed by DIPEA (0.013 mL, 0.075 mmol) and T3P®, 50 wt % in EA (0.033 mL, 0.056 mmol) were added. After 30 min, the mixture was concentrated, dissolved in EtOAc (5 mL) and washed with saturated aqueous NaHCO$_3$ solution. The organic layer was dried (Na$_2$SO$_4$) and concentrated. The crude solid was purified by RP HPLC on SunFire 5µ C18 19×150 mm column eluting with ACN/Water/0.1% TFA mobile phase to afford the desired product (4.54 mg) as a solid. HPLC, method E, Rt=6.97 min. Analytical LCMS, Method B, Rt=0.75, (M+H)$^+$=472.2.

Following compounds were prepared according to the general procedure for Example 19. In certain coupling reactions, HATU was used as a coupling reagent instead of T3P®.

TABLE 3

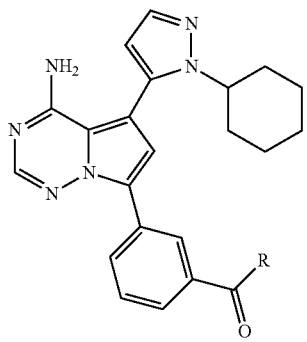

| Ex. No. | R | Name | LCMS (M + H)$^+$ |
|---|---|---|---|
| 20 | H$_3$C, OH, CH$_3$ (4-(2-hydroxypropan-2-yl)piperidin-1-yl) | (3-(4-amino-5-(1-cyclohexyl-1H-pyrazol-5-yl)pyrrolo[2,1-f][1,2,4]triazin-7-yl)phenyl)(4-(2-hydroxypropan-2-yl)piperidin-1-yl)methanone | 528.4 |

TABLE 3-continued

| Ex. No. | R | Name | LCMS (M + H)+ |
|---|---|---|---|
| 21 | [thiazole-CONH2 linked via NH] | 2-(3-(4-amino-5-(1-cyclohexyl-1H-pyrazol-5-yl)pyrrolo[2,1-f][1,2,4]triazin-7-yl)benzamido)thiazole-5-carboxamide | 528.4 |
| 22 | [1-acetylpiperidin-4-yl-NH] | N-(1-acetylpiperidin-4-yl)-3-(4-amino-5-(1-cyclohexyl-1H-pyrazol-5-yl)pyrrolo[2,1-f][1,2,4]triazin-7-yl)benzamide | 527.4 |
| 23 | [1-methylpiperidin-3-yl-NH] | 3-(4-amino-5-(1-cyclohexyl-1H-pyrazol-5-yl)pyrrolo[2,1-f][1,2,4]triazin-7-yl)-N-(1-methylpiperidin-3-yl)benzamide | 499.4 |
| 24 | [piperazine-isobutyryl] | 1-(4-(3-(4-amino-5-(1-cyclohexyl-1H-pyrazol-5-yl)pyrrolo[2,1-f][1,2,4]triazin-7-yl)benzoyl)piperazin-1-yl)-2-methylpropan-1-one | 541.4 |
| 25 | [piperidine-2-carboxamide] | (R,S)-1-(3-(4-amino-5-(1-cyclohexyl-1H-pyrazol-5-yl)pyrrolo[2,1-f][1,2,4]triazin-7-yl)benzoyl)piperidine-2-carboxamide | 513.4 |
| 26 | [3-cyanoazetidine] | 1-(3-(4-amino-5-(1-cyclohexyl-1H-pyrazol-5-yl)pyrrolo[2,1-f][1,2,4]triazin-7-yl)benzoyl)azetidine-3-carbonitrile | 467.3 |
| 27 | [4-methyl-3-oxopiperazine] | 4-(3-(4-amino-5-(1-cyclohexyl-1H-pyrazol-5-yl)pyrrolo[2,1-f][1,2,4]triazin-7-yl)benzoyl)-1-methylpiperazin-2-one | 499.4 |
| 28 | [2-oxopiperidin-4-yl-NH] | 3-(4-amino-5-(1-cyclohexyl-1H-pyrazol-5-yl)pyrrolo[2,1-f][1,2,4]triazin-7-yl)-N-(2-oxopiperidin-4-yl)benzamide | 499.4 |

TABLE 3-continued

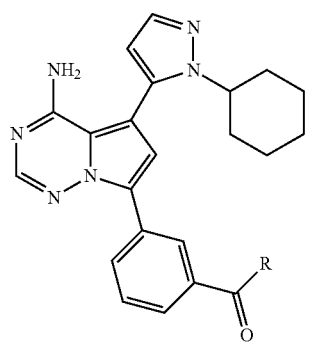

| Ex. No. | R | Name | LCMS (M + H)+ |
|---|---|---|---|
| 29 | piperazine-N-C(O)-CH2-CH3 | 1-(4-(3-(4-amino-5-(1-cyclohexyl-1H-pyrazol-5-yl)pyrrolo[2,1-f][1,2,4]triazin-7-yl)benzoyl)piperazin-1-yl)propan-1-one | 527.4 |
| 30 | piperidin-4-yl-NH-C(O)-CH3 | N-(1-(3-(4-amino-5-(1-cyclohexyl-1H-pyrazol-5-yl)pyrrolo[2,1-f][1,2,4]triazin-7-yl)benzoyl)piperidin-4-yl)acetamide | 527.4 |
| 31 | piperazine-N-C(O)-tetrahydrofuran-2-yl | (4-(3-(4-amino-5-(1-cyclohexyl-1H-pyrazol-5-yl)pyrrolo[2,1-f][1,2,4]triazin-7-yl)benzoyl)piperazin-1-yl)(tetrahydrofuran-2-yl)methanone | 569.4 |
| 32 | 3-(dimethylamino)piperidin-1-yl | (3-(4-amino-5-(1-cyclohexyl-1H-pyrazol-5-yl)pyrrolo[2,1-f][1,2,4]triazin-7-yl)phenyl)(3-(dimethylamino)piperidin-1-yl)methanone | 513.5 |
| 33 | piperidine-4-carboxamide | 1-(3-(4-amino-5-(1-cyclohexyl-1H-pyrazol-5-yl)pyrrolo[2,1-f][1,2,4]triazin-7-yl)benzoyl)piperidine-4-carboxamide | 513.4 |
| 34 | 3-hydroxy-3-methylazetidin-1-yl | (3-(4-amino-5-(1-cyclohexyl-1H-pyrazol-5-yl)pyrrolo[2,1-f][1,2,4]triazin-7-yl)phenyl)(3-hydroxy-3-methylazetidin-1-yl)methanone | 472.4 |
| 35 | piperazine-N-C(O)-CH3 | 1-(4-(3-(4-amino-5-(1-cyclohexyl-1H-pyrazol-5-yl)pyrrolo[2,1-f][1,2,4]triazin-7-yl)benzoyl)piperazin-1-yl)ethanone | 513.4 |
| 36 | NH-(3-carbamoylphenyl) | 3-(4-amino-5-(1-cyclohexyl-1H-pyrazol-5-yl)pyrrolo[2,1-f][1,2,4]triazin-7-yl)-N-(3-carbamoylphenyl)benzamide | 521.4 |

TABLE 3-continued

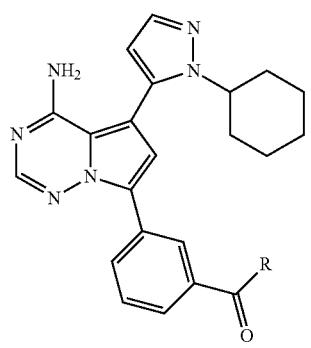

| Ex. No. | R | Name | LCMS (M + H)+ |
|---|---|---|---|
| 37 | [structure: NH-tetrahydropyran-4-yl] | 3-(4-amino-5-(1-cyclohexyl-1H-pyrazol-5-yl) pyrrolo[2,1-f][1,2,4]triazin-7-yl)-N-(tetrahydro-2H-pyran-4-yl)benzamide | 486.4 |
| 38 | [structure: piperidine with C(O)NHCH3] | 1-(3-(4-amino-5-(1-cyclohexyl-1H-pyrazol-5-yl) pyrrolo[2,1-f][1,2,4]triazin-7-yl)benzoyl)-N-methylpiperidine-4-carboxamide | 527.4 |
| 39 | [structure: 4-hydroxy-4-(hydroxymethyl)piperidine] | (3-(4-amino-5-(1-cyclohexyl-1H-pyrazol-5-yl) pyrrolo[2,1-f][1,2,4]triazin-7-yl)phenyl)(4-hydroxy-4-(hydroxymethyl)piperidin-1-yl)methanone | 516.4 |
| 40 | [structure: NH-(3-cyclopropyl-1-methyl-1H-pyrazol-5-yl)] | 3-(4-amino-5-(1-cyclohexyl-1H-pyrazol-5-yl) pyrrolo[2,1-f][1,2,4]triazin-7-yl)-N-(3-cyclopropyl-1-methyl-1H-pyrazol-5-yl)benzamide | 522.5 |
| 41 | [structure: piperazine-1-carboxylate methyl] | methyl 4-(3-(4-amino-5-(1-cyclohexyl-1H-pyrazol-5-yl)pyrrolo[2,1-f][1,2,4]triazin-7-yl) benzoyl)piperazine-1-carboxylate | 529.5 |
| 42 | [structure: NH-(2-oxopyrrolidin-3-yl)] | 3-(4-amino-5-(1-cyclohexyl-1H-pyrazol-5-yl) pyrrolo[2,1-f][1,2,4]triazin-7-yl)-N-(2-oxopyrrolidin-3-yl)benzamide | 484.4 |
| 43 | [structure: NH-C(CH3)2-C(O)NHCH3] | 3-(4-amino-5-(1-cyclohexyl-1H-pyrazol-5-yl) pyrrolo[2,1-f][1,2,4]triazin-7-yl)-N-(2-methyl-1-(methylamino)-1-oxopropan-2-yl)benzamide | 501.4 |
| 44 | [structure: NH-(4-(hydroxymethyl)tetrahydropyran-4-yl)] | 3-(4-amino-5-(1-cyclohexyl-1H-pyrazol-5-yl) pyrrolo[2,1-f][1,2,4]triazin-7-yl)-N-(4-(hydroxymethyl)tetrahydro-2H-pyran-4-yl)benzamide | 516.4 |

TABLE 3-continued

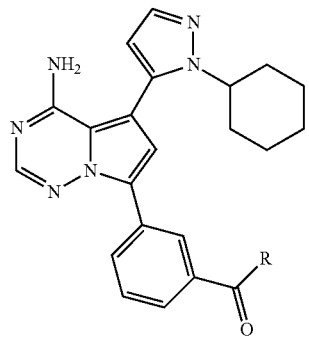

| Ex. No. | R | Name | LCMS (M + H)+ |
|---|---|---|---|
| 45 | (cyclopropyl-N-tetrahydropyran-4-yl group) | 3-(4-amino-5-(1-cyclohexyl-1H-pyrazol-5-yl) pyrrolo[2,1-f][1,2,4]triazin-7-yl)-N-cyclopropyl-N-(tetrahydro-2H-pyran-4-yl)benzamide | 525.4 |
| 46 | (1,1-dioxidothiomorpholino group) | (3-(4-amino-5-(1-cyclohexyl-1H-pyrazol-5-yl) pyrrolo[2,1-f][1,2,4]triazin-7-yl)phenyl)(1,1-dioxidothiomorpholino)methanone | 520.4 |
| 47 | (N-methyl glycinamide group) | 3-(4-amino-5-(1-cyclohexyl-1H-pyrazol-5-yl) pyrrolo[2,1-f][1,2,4]triazin-7-yl)-N-(2H-tetrazol-5-yl)benzamide | 473.3 |

Example 48

5-(1-(4,4-Difluorocyclohexyl)-1H-pyrazol-5-yl)-7-(3-((dimethylamino)methyl)phenyl)pyrrolo[2,1-f][1,2,4]triazin-4-amine

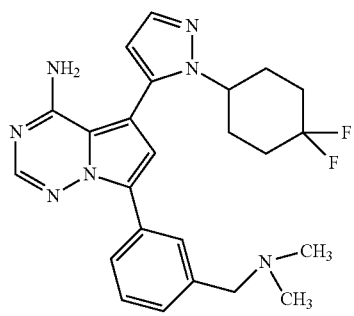

(48)

Intermediate 48A: tert-Butyl 2-(4,4-difluorocyclohexyl)hydrazinecarboxylate (48A)

4,4-Difluorocyclohexanone (0.5 g, 3.73 mmol), tert-butyl hydrazinecarboxylate (0.54 g, 4.10 mmol) and zinc chloride (7.46 mL, 3.73 mmol) were dissolved in methanol (10 mL) and AcOH (0.3 mL) was added. The reaction mixture was allowed to stir for 30 min at room temperature. Sodium cyanoborohydride (0.7 g, 11.18 mmol) was added and the mixture was stirred at room temperature for 16 h. The mixture was concentrated and the residue was partitioned between EA and saturated $NaHCO_3$. The organic layer was washed with brine, dried over $NaSO_4$ and concentrated. The residue, tert-butyl 2-(4,4-difluorocyclohexyl) hydrazinecarboxylate, was used in the next step without further purification.

Intermediate 48B: (4,4-Difluorocyclohexyl)hydrazine, 2 HCl

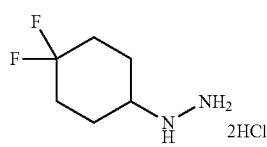

(48B)

Intermediate 48A (0.82 g, 3.27 mmol) was treated with HCl (4N, dioxane) (0.4 mL, 132 mmol) and stirred at room temperature. After 3 h, the mixture was concentrated to dryness and triturated with chloroform to obtain (4,4-difluorocyclohexyl)hydrazine, 2 HCl (0.71 mg, 3.19 mmol, 98% yield) as a white solid.

Intermediate 48C: 7-Bromo-5-(1-(4,4-difluorocyclohexyl)-1H-pyrazol-5-yl)pyrrolo[2,1-f][1,2,4]triazin-4-amine

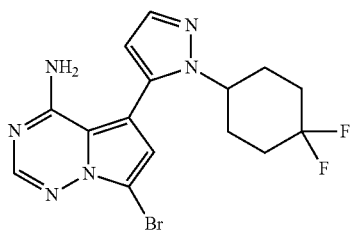

(48C)

1-(4-Amino-7-bromopyrrolo[2,1-f][1,2,4]triazin-5-yl)-3-(trimethylsilyl)prop-2-yn-1-one (0.1 g, 0.3 mmol) was suspended in ethanol (2.97 mL) and Intermediate 48B (0.165 g, 0.741 mmol) was added followed by triethylamine (0.25 mL, 1.78 mmol). The resulting mixture was heated at 80° C. for 2 h, then more of (4,4-difluorocyclohexyl) hydrazine, 2 HCl (0.17 g, 0.74 mmol) and triethylamine (0.25 mL, 1.78 mmol) and heated overnight at 80° C. The reaction mixture was concentrated, diluted with EA (10 mL) and water (5 mL) and the layers were mixed and then separated. The organic layer was dried and concentrated and the residue was purified on 12 g silica gel cartridge eluting with a 14 min gradient from 0-10% methanol in DCM, with 0.5% NH$_4$OH added. Intermediate 48C, 7-bromo-5-(1-(4,4-difluorocyclohexyl)-1H-pyrazol-5-yl)pyrrolo[2,1-f][1,2,4]triazin-4-amine (61 mg, 51.8% yield) was obtained as a pale yellow solid. LCMS=397.1 and 399.1 (1:1 ratio).

Example 48

Intermediate 48C (21 mg, 0.053 mmol), N,N-dimethyl-1-(3-(4,4,5,5-tetramethyl-1,3,2-dioxaborolan-2-yl)phenyl)methanamine (21 mg, 0.079 mmol) and K$_3$PO$_4$ (44.9 mg, 0.21 mmol) were combined in a 1 dram vial. THF (1.5 mL) and water (0.2 mL) were added and the mixture was degassed by bubbling argon while the vial was immersed in a sonicator. Tetrakis triphenylphosphine palladium (6.1 mg, 5.29 µmol) was added and the degassing procedure was repeated. The mixture was subjected to the microwave irradiation for 30 min at 120° C. The reaction mixture was diluted with ethyl acetate (5 mL) and water (2 mL) and the layers were mixed and then separated. The organic layer was separated, dried and concentrated and the residue was purified by RP HPLC eluting with CH$_3$CN/water/0.1% TFA mixture to afford Example 48 (18.2 mg, 0.040 mmol, 74.7% yield). LC/MS=451.2.

Example 49

5-(1-(4,4-Difluorocyclohexyl)-1H-pyrazol-5-yl)-7-(3-(2-(dimethylamino)propan-2-yl)phenyl)pyrrolo[2,1-f][1,2,4]triazin-4-amine

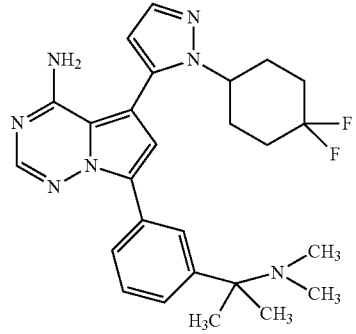

(49)

Example 49 was prepared from Intermediate 48C according to the general procedure for the conversion of Intermediate 48C to Example 48. M+H$^+$=480.3.

Example 50

5-(4-Amino-5-(1-(tetrahydro-2H-pyran-4-yl)-1H-pyrazol-5-yl)pyrrolo[2,1-f][1,2,4]triazin-7-yl)-N-cyclopropyl-2-fluoro-N-(tetrahydro-2H-pyran-4-yl)benzamide

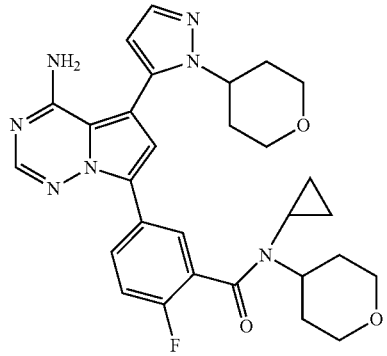

(50)

Intermediate 50A: 5-(4-Amino-5-(1-(tetrahydro-2H-pyran-4-yl)-1H-pyrazol-5-yl)pyrrolo[2,1-f][1,2,4]triazin-7-yl)-2-fluorobenzoic acid

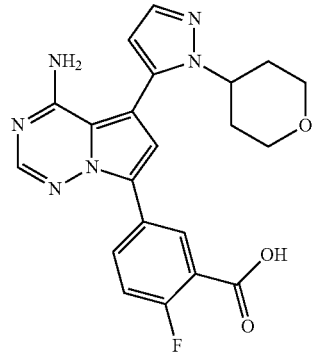

(50A)

A solution of 7-bromo-5-(1-(tetrahydro-2H-pyran-4-yl)-1H-pyrazol-5-yl) pyrrolo[2,1-f][1,2,4]triazin-4-amine (77 mg, 0.21 mmol), (4-fluoro-3-(methoxycarbonyl) phenyl) boronic acid (42.0 mg, 0.212 mmol) and K₃PO₄ (180 mg, 0.85 mmol) in a mixture of dioxane (1 mL) and water (1 mL) in a 5 mL microwave reactor vial was evacuated, backfilled with N₂ gas and then degassed by bubbling N₂ gas while the vial was sonicated. Tetrakistriphenylphosphine palladium (36.7 mg, 0.032 mmol) was added and the degassing process was repeated. The mixture was heated in microwave oven at 100° C. for 30 min. LCMS analysis showed the methylester was hydrolyzed to acid. The mixture was diluted with water (5 mL) and stirred vigorously, the resulting cloudy aqueous layer was extracted three times with EtOAc. Organic layers were combined, dried and concentrated to afford crude 5-(4-amino-5-(1-(tetrahydro-2H-pyran-4-yl)-1H-pyrazol-5-yl)pyrrolo[2,1-f][1,2,4]triazin-7-yl)-2-fluorobenzoic acid (106 mg) which was used in the next step without further purification.

Example 50

To a solution of the crude acid, Intermediate 50A (25 mg) and HATU (45 mg) in DMF (1 mL) at room temperature, were added morpholine (10.3 µL) and DIPEA (31 µL). After 2 h, water (2 mL) was added and the mixture was extracted with DCM (3×2 mL). The combined organic layers were dried and concentrated and purified by preparative HPLC condition (Method C). Fractions containing the desired product were combined and dried via centrifugal evaporation to afford Example 50. LCMS M⁺=546.15/547.25. Method I. Retention time 1.325 min. ¹H NMR (500 MHz, DMSO): δ 8.26 (d, J=5.4 Hz, 1H), 8.19 (dd, J=6.7, 2.2 Hz, 1H), 8.11 (s, 1H), 7.68 (d, J=1.5 Hz, 1H), 7.41 (t, J=9.2 Hz, 1H), 7.34 (s, 1H), 6.46 (d, J=1.5 Hz, 1H), 4.42-4.18 (m, 2H), 4.01-3.83 (m, 4H), 3.46-3.26 (m, 5H), 2.68 (m, 1H), 2.21-2.02 (m, 4H), 1.80 (m, 1H), 1.75 (d, J=10.4 Hz, 2H), 0.68-0.44 (m, 4H).

The compounds in Table 4 were obtained by reacting 5-(4-amino-5-(1-(tetrahydro-2H-pyran-4-yl)-1H-pyrazol-5-yl)pyrrolo[2,1-f][1,2,4]triazin-7-yl)-2-fluorobenzoic acid with various amines according to the general procedure for Example 50.

TABLE 4

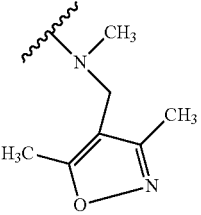

| Ex. No. | R | Name | M + H⁺ HPLC method |
|---|---|---|---|
| 51 | 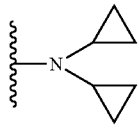 [SMILES: *N(C1CC1)C1CC1] | 5-(4-amino-5-(1-(tetrahydro-2H-pyran-4-yl)-1H-pyrazol-5-yl)pyrrolo[2,1-f][1,2,4]triazin-7-yl)-N-((3,5-dimethylisoxazol-4-yl)methyl)-2-fluoro-N-methylbenzamide | 545.2 P |
| 52 | 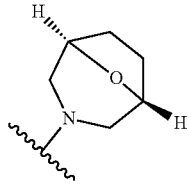 [SMILES: *N1C[C@H]2CC[C@H](C1)O2] | 5-(4-amino-5-(1-(tetrahydro-2H-pyran-4-yl)-1H-pyrazol-5-yl)pyrrolo[2,1-f][1,2,4]triazin-7-yl)-N,N-dicyclopropyl-2-fluorobenzamide | 502.2 P |
| 53 | 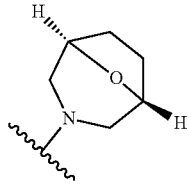 [SMILES: *N1C[C@H]2CC[C@H](C1)O2] | 5-(4-amino-5-(1-(tetrahydro-2H-pyran-4-yl)-1H-pyrazol-5-yl)pyrrolo[2,1-f][1,2,4]triazin-7-yl)-2-fluorophenyl)((1R,5R)-8-oxa-3-azabicyclo[3.2.1]octan-3-yl)methanone | 518.2 P |

TABLE 4-continued

| Ex. No. | R | Name | M + H⁺ HPLC method |
|---|---|---|---|
| 54 | (N-methyl-N-((1-methylpyrrolidin-2-yl)methyl)amino) | 5-(4-amino-5-(1-(tetrahydro-2H-pyran-4-yl)-1H-pyrazol-5-yl)pyrrolo[2,1-f][1,2,4]triazin-7-yl)-2-fluoro-N-methyl-N-((1-methylpyrrolidin-2-yl)methyl)benzamide | 533.3 P |
| 55 | (N-cyclopropyl-N-(1-acetylpiperidin-4-yl)amino) | N-(1-acetylpiperidin-4-yl)-5-(4-amino-5-(1-(tetrahydro-2H-pyran-4-yl)-1H-pyrazol-5-yl)pyrrolo[2,1-f][1,2,4]triazin-7-yl)-N-cyclopropyl-2-fluorobenzamide | 587.3 P |

Example 56

5-(4-Amino-5-(1-(tetrahydro-2H-pyran-4-yl)-1H-pyrazol-5-yl)pyrrolo[2,1-f][1,2,4]triazin-7-yl)-N-cyclopropyl-2-methoxy-N-(tetrahydro-2H-pyran-4-yl)benzamide

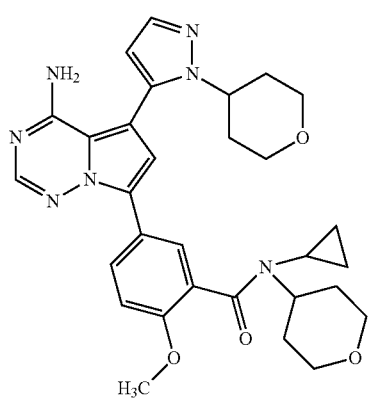

(56)

Intermediate 56A: 5-(4-Amino-5-(1-(tetrahydro-2H-pyran-4-yl)-1H-pyrazol-5-yl)pyrrolo [2,1-f][1,2,4]triazin-7-yl)-2-methoxybenzoic acid

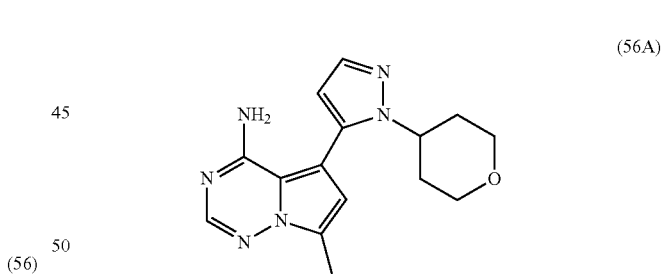

(56A)

A solution of 7-bromo-5-(1-(tetrahydro-2H-pyran-4-yl)-1H-pyrazol-5-yl)pyrrolo [2,1-f][1,2,4]triazin-4-amine (50 mg, 0.14 mmol), (4-methoxy-3-(methoxycarbonyl) phenyl) boronic acid (43.4 mg, 0.21 mmol) and K₃PO₄ (102 mg, 0.48 mmol) in THF (1 mL) and water (0.1 mL) in a 2 mL vial was degassed by bubbling argon while the vial was sonicated. Tetrakistriphenylphosphine palladium (16 mg, 0.014 mmol) was added and the degassing process was repeated. The mixture was heated in at 83° C. for 3 h. The mixture was cooled, purified by preparative HPLC using Method B. The desired fraction was concentrated to remove acetonitrile and aqueous suspension was adjusted to pH 6 and stirred vigorously. The white precipitate was filtered and washed with water, dried in vacuo. The crude product was hydrolyzed using aqueous 15% NaOH and methanol/THF mixture. The reaction mixture was worked up when all the ester was consumed. The crude acid, 5-(4-amino-5-(1-(tetrahydro-2H-pyran-4-yl)-1H-pyrazol-5-yl)pyrrolo[2,1-f][1,2,4]triazin-7-yl)-2-methoxybenzoic acid (26 mg), was used in the next step without further purification.

Example 56

Intermediate 56A was converted to Example 56 according to the general method described for the preparation of Example 50 from the corresponding acid. (M+H)$^+$=558.3.

Example 57

5-(4-Amino-5-(1-(tetrahydro-2H-pyran-4-yl)-1H-pyrazol-5-yl)pyrrolo[2,1-f][1,2,4]triazin-7-yl)-N-cyclopropyl-2-methyl-N-(tetrahydro-2H-pyran-4-yl)benzamide

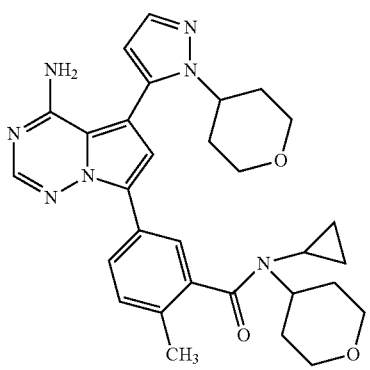

(57)

This compound was prepared from bis-(Boc)-7-bromo-5-(1-(tetrahydro-2H-pyran-4-yl)-1H-pyrazol-5-yl)pyrrolo[2,1-f][1,2,4]triazin-4-amine according to the general method described for the preparation of Example 14. The bis-boc group was removed after the Suzuki coupling step by treatment with TFA/DCM mixture. (M+H)$^+$=542.3.

Example 58

5-(4-Amino-5-(1-(tetrahydro-2H-pyran-4-yl)-1H-pyrazol-5-yl)pyrrolo[2,1-f][1,2,4]triazin-7-yl)-2-chlorobenzoic acid

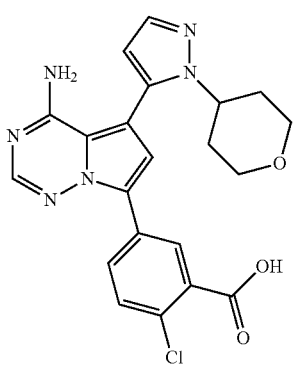

(58)

Intermediate 58A: Methyl 5-(4-amino-5-(1-(tetrahydro-2H-pyran-4-yl)-1H-pyrazol-5-yl) pyrrolo[2,1-f][1,2,4]triazin-7-yl)-2-chlorobenzoate

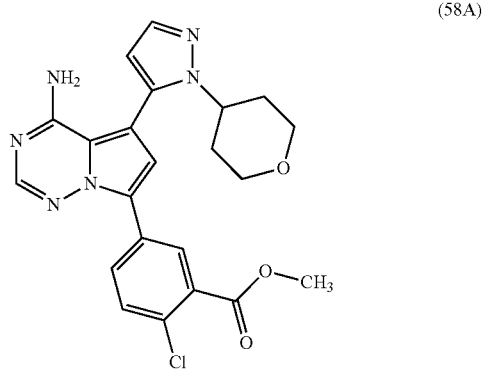 [SMILES: COC(=O)c1cc(-c2cc(-c3ccnn3C3CCOCC3)c3c(N)ncnn23)ccc1Cl]

(58A)

Intermediate N1, 7-bromo-5-(1-(tetrahydro-2H-pyran-4-yl)-1H-pyrazol-5-yl)pyrrolo[2,1-f][1,2,4]triazin-4-amine, (0.325 g, 0.895 mmol), (4-chloro-3-(methoxycarbonyl)phenyl)boronic acid (0.326 g, 1.52 mmol) and K$_3$PO$_4$ (0.76 mg, 3.58 mmol) were combined in a 20 mL vial fitted with a septum and dissolved in a mixture of THF (6.51 mL) and water (0.65 mL). Argon was bubbled through the mixture while the vial was sonicated. Tetrakistriphenylphosphine palladium (0.1 g, 0.09 mmol) was added and the mixture was heated at 85° C. After 1.5 h, the reaction mixture was diluted with ethyl acetate (20 mL) and water (5 mL) and the layers were mixed and then separated (3 times). The organic layers were mixed, dried over and concentrated. The residue was triturated with DCM, to obtain a white solid as the pure desired product (120 mg). The filtrate was concentrated and submitted for purification by silica gel column to obtain methyl 5-(4-amino-5-(1-(tetrahydro-2H-pyran-4-yl)-1H-pyrazol-5-yl)pyrrolo[2,1-f][1,2,4]triazin-7-yl)-2-chlorobenzoate (323 mg, 0.713 mmol, 80% yield) as a pale yellow solid.

Example 58

Intermediate 58A (0.323 g, 0.713 mmol) was suspended in a mixture of THF (9 mL) and water (2 mL). Lithium hydroxide (0.085 g, 3.57 mmol) was added and the mixture was stirred at room temperature. After 18 h, the mixture was concentrated to remove THF and then the resulting aqueous solution was adjusted to pH 4 using 1N HCl. The resulting suspension was filtered affording 5-(4-amino-5-(1-(tetrahydro-2H-pyran-4-yl)-1H-pyrazol-5-yl)pyrrolo[2,1-f][1,2,4]triazin-7-yl)-2-chlorobenzoic acid (0.27 g, 0.617 mmol, 87% yield) as a white solid. (M+H)$^+$=439.1, 441.1 (3:1 ratio).

Example 58 was reacted with various amines according to the general procedure for preparing Example 50 from corresponding acid to obtain following compounds.

TABLE 5

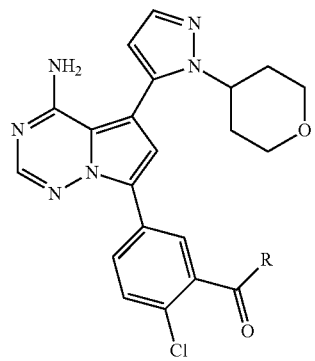

| Ex. No. | R | Name | M + H+ |
|---|---|---|---|
| 59 | (N-cyclopropyl, N-(tetrahydro-2H-pyran-4-yl)) | 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-(tetrahydro-2H-pyran-4-yl)benzamide | 562.10 |
| 60 | (N-methyl, N-(2,2-difluoroethyl)) | 5-(4-amino-5-(1-(tetrahydro-2H-pyran-4-yl)-1H-pyrazol-5-yl)pyrrolo[2,1-f][1,2,4]triazin-7-yl)-2-chloro-N-(2,2-difluoroethyl)-N-methylbenzamide | 516.1 |
| 61 | (N-cyclopropyl, N-((1-methyl-1H-pyrazol-4-yl)methyl)) | 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-((1-methyl-1H-pyrazol-4-yl)methyl)benzamide | 572.2 |
| 62 | (N-cyclopropyl, N-(thiazol-2-ylmethyl)) | 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-(thiazol-2-ylmethyl)benzamide | 574.2 |
| 63 | (N-methyl, N-(tetrahydro-2H-pyran-4-yl)) | 5-(4-amino-5-(1-(tetrahydro-2H-pyran-4-yl)-1H-pyrazol-5-yl)pyrrolo[2,1-f][1,2,4]triazin-7-yl)-2-chloro-N-methyl-N-(tetrahydro-2H-pyran-4-yl)benzamide | 536.2 |
| 64 | (N-cyclopropyl, N-(1-acetylpiperidin-4-yl)) | N-(1-acetylpiperidin-4-yl)-5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropylbenzamide | 603.3 |

TABLE 5-continued

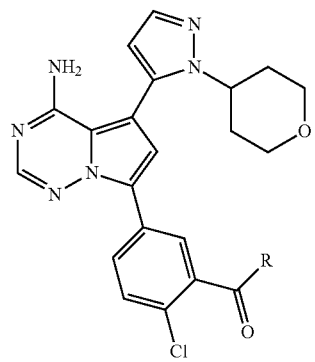

| Ex. No. | R | Name | M + H⁺ |
|---|---|---|---|
| 65 | (structure: CH₃-N-CH₂-C(CH₃)(CH₂OH)-C(CH₃)-, connected via N) | 5-(4-amino-5-(1-(tetrahydro-2H-pyran-4-yl)-1H-pyrazol-5-yl)pyrrolo[2,1-f][1,2,4]triazin-7-yl)-2-chloro-N-(3-hydroxy-2,2-dimethylpropyl)-N-methylbenzamide | 538.2 |
| 66 | (structure: N(CH₂CH₃)₂) | 5-(4-amino-5-(1-(tetrahydro-2H-pyran-4-yl)-1H-pyrazol-5-yl)pyrrolo[2,1-f][1,2,4]triazin-7-yl)-2-chloro-N,N-diethylbenzamide | 494.2 |

Example 67

3-(4-Amino-5-(1-methyl-1H-pyrrol-2-yl)pyrrolo[2,1-f][1,2,4]triazin-7-yl)-N-cyclopropyl-N-(tetrahydro-2H-pyran-4-yl)benzamide (67)

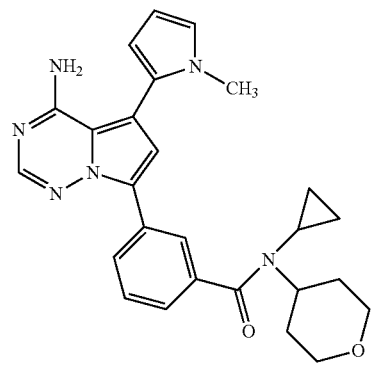

To a mixture of Example 541 (50 mg, 0.11 mmol), 1-methyl-2-(4,4,5,5-tetramethyl-1,3,2-dioxaborolan-2-yl)-1H-pyrrole (27.2 mg, 0.13 mmol) and tripotassium phosphate (69.8 mg, 0.33 mmol) in a vial were added dioxane (2 mL) and water (1 mL). Nitrogen was bubbled through the mixture and tetrakistriphenyl phosphine (12.66 mg, 0.011 mmol) was added and the mixture was heated to 100° C. for 40 min. The mixture was cooled, water was added and precipitate formed was filtered and purified by preparative HPLC condition C to afford Example 67. M⁺=457.3.

Example 68

3-(4-Amino-5-(1-phenyl-1H-pyrrol-2-yl)pyrrolo[2,1-f][1,2,4]triazin-7-yl)-N-cyclopropyl-N-(tetrahydro-2H-pyran-4-yl)benzamide (68)

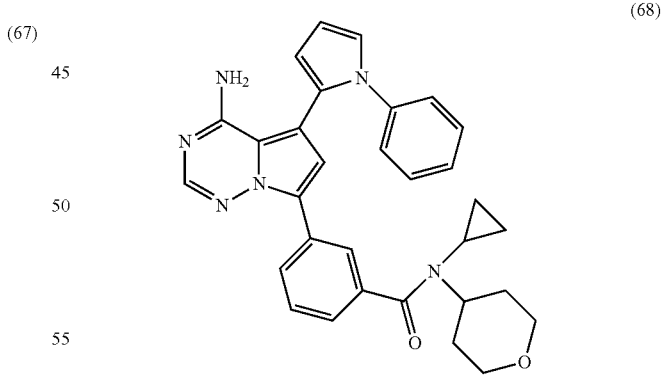

Example 68 was synthesized according to the general procedure for the preparation of Example 67, employing the appropriate boronic acid.

The Examples in the Table 6 were prepared as follows: To each vial containing carboxylic acid (1 eq) was added an amine (2 to 3 eq) dissolved in DMF, followed with HATU (2 eq) dissolved in DMF and DIPEA (5 eq). The reaction mixtures were stirred at room temperature for 3 h. Upon completion of reaction (by LCMS), DMF was added to each vial and the mixtures were purified by reverse-phase HPLC.

TABLE 6

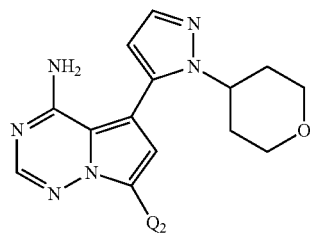

| Ex. No. | Q₂ | Name | LC/MS [M + 1] Method Rt |
|---|---|---|---|
| 69 | (3-substituted phenyl)-C(O)-N(cyclopropyl)₂ | 3-(4-amino-5-(1-(tetrahydro-2H-pyran-4-yl)-1H-pyrazol-5-yl)pyrrolo[2,1-f][1,2,4]triazin-7-yl)-N,N-dicyclopropylbenzamide | 484.28 F 1.39 |
| 70 | (3-substituted phenyl)-C(O)-N(cyclopropyl)-CH₂-(1-methyl-1H-pyrazol-5-yl) | 3-(4-amino-5-(1-(tetrahydro-2H-pyran-4-yl)-1H-pyrazol-5-yl)pyrrolo[2,1-f][1,2,4]triazin-7-yl)-N-cyclopropyl-N-((1-methyl-1H-pyrazol-5-yl)methyl)benzamide | 538.35 P 1.20 |
| 71 | (3-substituted phenyl)-C(O)-N(CH₃)-CH₂-C(CH₃)₂-CH₂OH | 3-(4-amino-5-(1-(tetrahydro-2H-pyran-4-yl)-1H-pyrazol-5-yl)pyrrolo[2,1-f][1,2,4]triazin-7-yl)-N-(3-hydroxy-2,2-dimethylpropyl)-N-methylbenzamide | 504.2 P 1.21 |
| 72 | (3-substituted phenyl)-C(O)-N(cyclopropyl)-CH₂-(thiazol-2-yl) | 3-(4-amino-5-(1-(tetrahydro-2H-pyran-4-yl)-1H-pyrazol-5-yl)pyrrolo[2,1-f][1,2,4]triazin-7-yl)-N-cyclopropyl-N-(thiazol-2-ylmethyl)benzamide | 541.24 F 1.36 |
| 73 | (3-substituted phenyl)-C(O)-N(CH₃)-CH₂-(1-methylpyrrolidin-2-yl) | 3-(4-amino-5-(1-(tetrahydro-2H-pyran-4-yl)-1H-pyrazol-5-yl)pyrrolo[2,1-f][1,2,4]triazin-7-yl)-N-methyl-N-((1-methylpyrrolidin-2-yl)methyl)benzamide | 514.83 F 0.71 |

TABLE 6-continued

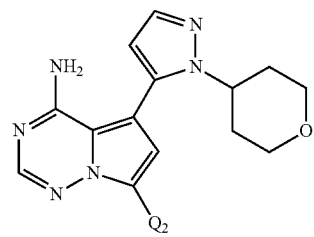

| Ex. No. | Q₂ | Name | LC/MS [M + 1] Method Rt |
|---|---|---|---|
| 74 | 3-carbamoyl-N,N-diethylbenzamide group | 3-(4-amino-5-(1-(tetrahydro-2H-pyran-4-yl)-1H-pyrazol-5-yl)pyrrolo[2,1-f][1,2,4]triazin-7-yl)-N,N-diethylbenzamide | 460.29 P 1.34 |
| 75 | N-cyclopropyl-N-(1-acetylpiperidin-4-yl)benzamide group | N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-N-cyclopropylbenzamide | 569.2 P 1.18 |
| 76 | N-((3,5-dimethylisoxazol-4-yl)methyl)-N-methylbenzamide group | 3-(4-amino-5-(1-(tetrahydro-2H-pyran-4-yl)-1H-pyrazol-5-yl)pyrrolo[2,1-f][1,2,4]triazin-7-yl)-N-((3,5-dimethylisoxazol-4-yl)methyl)-N-methylbenzamide | 527.2 F 1.13 |
| 77 | 5-chloro-N-(3-hydroxy-2,2-dimethylpropyl)-N-methylbenzamide group | 3-(4-amino-5-(1-(tetrahydro-2H-pyran-4-yl)-1H-pyrazol-5-yl)pyrrolo[2,1-f][1,2,4]triazin-7-yl)-5-chloro-N-(3-hydroxy-2,2-dimethylpropyl)-N-methylbenzamide | 538.15 P 1.37 |

TABLE 6-continued

| Ex. No. | Q₂ | Name | LC/MS [M + 1] Method Rt |
|---|---|---|---|
| 78 | 3-chloro-5-[N-cyclopropyl-N-(1-methylpiperidin-4-yl)carbamoyl]phenyl | 3-(4-amino-5-(1-(tetrahydro-2H-pyran-4-yl)-1H-pyrazol-5-yl)pyrrolo[2,1-f][1,2,4]triazin-7-yl)-5-chloro-N-cyclopropyl-N-(1-methylpiperidin-4-yl)benzamide | 575.15 F 1.10 |
| 79 | 3-chloro-5-[(tetrahydro-2H-pyran-4-yl)carbamoyl]phenyl | 3-(4-amino-5-(1-(tetrahydro-2H-pyran-4-yl)-1H-pyrazol-5-yl)pyrrolo[2,1-f][1,2,4]triazin-7-yl)-5-chloro-N-(tetrahydro-2H-pyran-4-yl)benzamide | 522.1 F 1.20 |
| 80 | 3-chloro-5-[N-(1-acetylpiperidin-4-yl)-N-cyclopropylcarbamoyl]phenyl | N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-5-chloro-N-cyclopropylbenzamide | 603.15 F 1.24 |
| 81 | 3-chloro-5-[N-methyl-N-(oxetan-3-yl)carbamoyl]phenyl | 3-(4-amino-5-(1-(tetrahydro-2H-pyran-4-yl)-1H-pyrazol-5-yl)pyrrolo[2,1-f][1,2,4]triazin-7-yl)-5-chloro-N-methyl-N-(oxetan-3-yl)benzamide | 508.1 F 1.16 |

TABLE 6-continued

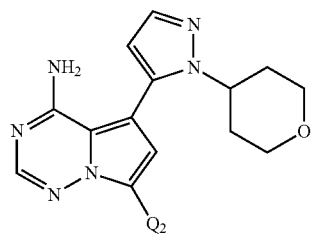

| Ex. No. | Q₂ | Name | LC/MS [M + 1] Method Rt |
|---|---|---|---|
| 82 | 3-chloro-5-... benzamide with N-methyl-N-((1-methylpyrrolidin-2-yl)methyl) group | 3-(4-amino-5-(1-(tetrahydro-2H-pyran-4-yl)-1H-pyrazol-5-yl)pyrrolo[2,1-f][1,2,4]triazin-7-yl)-5-chloro-N-methyl-N-((1-methylpyrrolidin-2-yl)methyl)benzamide | 549.15 F 1.06 |
| 83 | 3-fluoro-5-... benzamide with N-ethyl-N-(3-hydroxy-2,2-dimethylpropyl) group | 3-(4-amino-5-(1-(tetrahydro-2H-pyran-4-yl)-1H-pyrazol-5-yl)pyrrolo[2,1-f][1,2,4]triazin-7-yl)-5-fluoro-N-(3-hydroxy-2,2-dimethylpropyl)-N-methylbenzamide | 522.2 F 1.33 |
| 84 | 3-fluoro-5-... benzamide with N-cyclopropyl-N-(thiazol-2-ylmethyl) group | 3-(4-amino-5-(1-(tetrahydro-2H-pyran-4-yl)-1H-pyrazol-5-yl)pyrrolo[2,1-f][1,2,4]triazin-7-yl)-N-cyclopropyl-5-fluoro-N-(thiazol-2-ylmethyl)benzamide | 559.15 P 1.57 |
| 85 | 3-fluoro-5-... benzamide with N-(1-acetylpiperidin-4-yl)-N-cyclopropyl group | N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-N-cyclopropyl-5-fluorobenzamide | 587.2 P 1.42 |

TABLE 6-continued

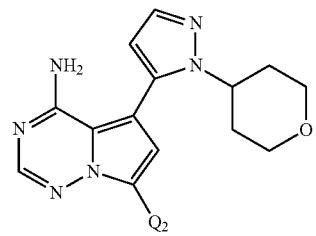

| Ex. No. | Q₂ | Name | LC/MS [M + 1] Method Rt |
|---|---|---|---|
| 86 | (3-fluoro-5-benzamide with N-methyl-N-((1-methylpyrrolidin-2-yl)methyl)) | 3-(4-amino-5-(1-(tetrahydro-2H-pyran-4-yl)-1H-pyrazol-5-yl)pyrrolo[2,1-f][1,2,4]triazin-7-yl)-5-fluoro-N-methyl-N-((1-methylpyrrolidin-2-yl)methyl)benzamide | 533.2 F 1.05 |
| 87 | (2-fluoro-benzamide with N-(2,2-difluoroethyl)-N-methyl) | 5-(4-amino-5-(1-(tetrahydro-2H-pyran-4-yl)-1H-pyrazol-5-yl)pyrrolo[2,1-f][1,2,4]triazin-7-yl)-N-(2,2-difluoroethyl)-2-fluoro-N-methylbenzamide | 500.15 P 1.46 |
| 88 | (2-fluoro-benzamide with N-methyl-N-(tetrahydro-2H-pyran-4-yl)) | 5-(4-amino-5-(1-(tetrahydro-2H-pyran-4-yl)-1H-pyrazol-5-yl)pyrrolo[2,1-f][1,2,4]triazin-7-yl)-2-fluoro-N-methyl-N-(tetrahydro-2H-pyran-4-yl)benzamide | 520.2 P 1.35 |
| 89 | (2-fluoro-benzamide with N-cyclopropyl-N-(thiazol-2-ylmethyl)) | 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-fluoro-N-(thiazol-2-ylmethyl)benzamide | 559.1 F 1.38 |

General Procedure 1: One-Pot Boronate Ester Formation/Suzuki Coupling.

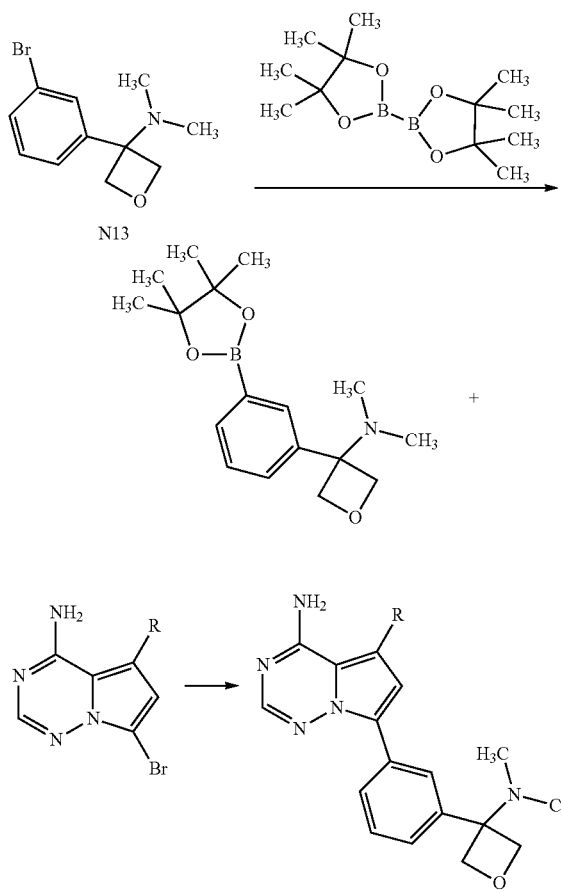

Example 90

7-(3-(3-(Dimethylamino)oxetan-3-yl)phenyl)-5-(1-(tetrahydro-2H-pyran-4-yl)-1H-pyrazol-5-yl)pyrrolo[2,1-f][1,2,4]triazin-4-amine

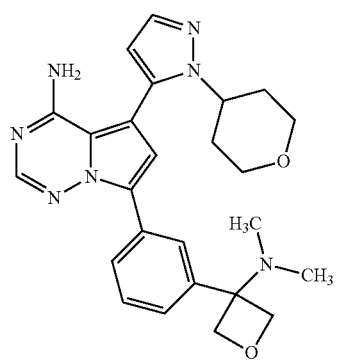

(90)

A suspension of Intermediate N13 (25 mg, 0.098 mmol), KOAc (38.3 mg, 0.390 mmol), 4,4,4',4',5,5,5',5'-octamethyl-2,2'-bi(1,3,2-dioxaborolane) (27.3 mg, 0.017 mmol) in THF (0.5 mL) was degassed by bubbling nitrogen while the flask was sonicated. PdCl$_2$(dppf)-CH$_2$Cl$_2$ adduct (15.94 mg, 0.020 mmol) was added and the mixture was heated at 80° C. until complete formation of the desired boronate ester was observed by LC/MS analysis. The reaction mixture was cooled to room temperature and treated with water (0.5 mL), 7-bromo-5-(1-(tetrahydro-2H-pyran-4-yl)-1H-pyrazol-5-yl)pyrrolo[2,1-f][1,2,4]triazin-4-amine (Intermediate N1) (17.73 mg, 0.049 mmol) and Na$_2$CO$_3$ (31.0 mg, 0.293 mmol). The resulting mixture was degassed as described above, PdCl$_2$(dppf)-CH$_2$Cl$_2$ adduct (15.94 mg, 0.020 mmol) was added and the resulting mixture was heated at 80° C. until consumption of the boronate ester was observed by LC/MS. The reaction mixture was cooled to room temperature, diluted with 1 mL of DMSO, filtered and purified by preparative HPLC to obtain 7-(3-(3-(dimethylamino)oxetan-3-yl)phenyl)-5-(1-(tetrahydro-2H-pyran-4-yl)-1H-pyrazol-5-yl)pyrrolo[2,1-f][1,2,4]triazin-4-amine (10.0 mg, 0.021 mmol, 21.40% yield). LC/MS Method I: 0.95 min [M+1]=460.

Example 91

N-(3-(3-(4-Amino-5-(1-(tetrahydro-2H-pyran-4-yl)-1H-pyrazol-5-yl)pyrrolo[2,1-f][1,2,4]triazin-7-yl)phenyl)oxetan-3-yl)-2-methylpropane-2-sulfinamide

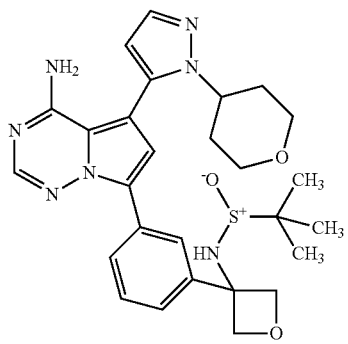

(91)

Intermediates N8-B and N1 were reacted according to General Procedure 1 for the preparation of Example 91 (LC/MS: Rt=1.21 min [M+1]=536.1).

The following analogs were prepared according to General Procedure 1 for the preparation of Example 90, but using Intermediate N9 and the appropriate bromide coupling partner, either Intermediate N1 or R1.

TABLE 7

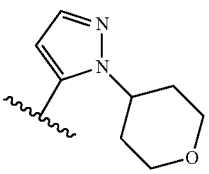 [SMILES: *c1ccnn1C1CCOCC1]

| Ex. No. | Q₁ | Name | LC/MS Retention time; [M + H₂O]⁺ Method |
|---|---|---|---|
| 92 | 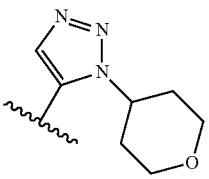 [SMILES: *c1cnnn1C1CCOCC1] | 1-[3-(3-{4-amino-5-[1-(oxan-4-yl)-1H-pyrazol-5-yl]pyrrolo[2,1-f][1,2,4]triazin-7-yl}phenyl)oxetan-3-yl]piperidin-4-one | 0.82 min; 532 (Method H) |
| 93 | 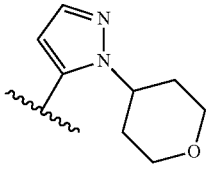 [SMILES: *c1ccnn1C1CCOCC1] | 1-(3-(3-(4-amino-5-(1-(tetrahydro-2H-pyran-4-yl)-1H-1,2,3-triazol-5-yl)pyrrolo[2,1-f][1,2,4]triazin-7-yl)phenyl)oxetan-3-yl)piperidin-4-one | 0.71 min; 533 (Method H) |

The following analogs were prepared according to General Procedure 1 for the preparation of Example 90, using Intermediate N10 and the appropriate bromide coupling partner, Intermediate N1 or R1.

TABLE 8

| Ex. No. | Q₁ | Name | LC/MS Retention time; [M + 1] Method |
|---|---|---|---|
| 94 |  | 1-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)pyrrolidin-3-ol | 0.76 min; 516 (Method I) |

TABLE 8-continued

| 95 | 1-[3-(3-{4-amino-5-[1-(oxan-4-yl)-1H-1,2,3-triazol-5-yl]pyrrolo[2,1-f][1,2,4]triazin-7-yl}phenyl)oxetan-3-yl]piperidin-4-ol | 0.69 min; 517 (Method I) |

The following analogs were prepared according to General Procedure 1 for the preparation of Example 90, but using Intermediate N11 or N12 and appropriate bromide intermediate described above as the coupling partner, Intermediates N1 and N5.

TABLE 9

| Ex. No. | Structure | Name | LC/MS Retention Time: [M + 1] Method |
|---|---|---|---|
| 96 | 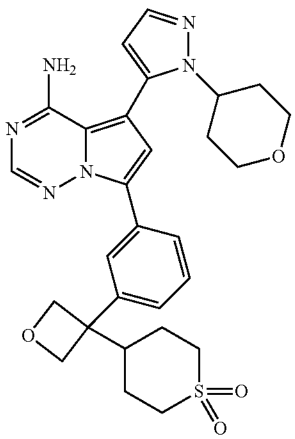 [SMILES: Nc1ncnn2c(-c3cccc(C4(C5CCS(=O)(=O)CC5)COC4)c3)cc(-c3ccnn3C3CCOCC3)c12] | 4-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)thiomorpholine 1,1-dioxide | 1.14 min; 550 (Method I) |
| 97 | 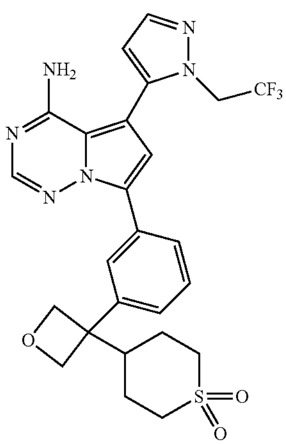 [SMILES: Nc1ncnn2c(-c3cccc(C4(C5CCS(=O)(=O)CC5)COC4)c3)cc(-c3ccnn3CC(F)(F)F)c12] | 4-(3-(3-(4-amino-5-(1-(2,2,2-trifluoroethyl)-1H-pyrazol-5-yl)pyrrolo[2,1-f][1,2,4]triazin-7-yl)phenyl)oxetan-3-yl)thiomorpholine 1,1-dioxide | 0.93 min; 548 (Method M) |

Example 98

7-(3-(3-Morpholinooxetan-3-yl)phenyl)-5-(1-(tetrahydro-2H-pyran-4-yl)-1H-pyrazol-5-yl)pyrrolo[2,1-f][1,2,4]triazin-4-amine

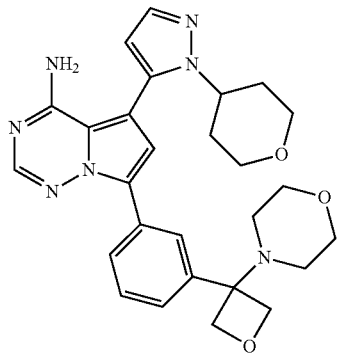

(98)

Example 98 was prepared according to the general procedure described for the preparation and coupling of Intermediate N13 in Example 90, but using Intermediate N14 and Intermediate N1 as the coupling partners. $^1$H NMR (400 MHz, CDCl$_3$) δ 8.04 (s, 1H), 7.94-7.87 (m, 1H), 7.82-7.77 (m, 1H), 7.69 (d, J=1.8 Hz, 1H), 7.53 (t, J=7.8 Hz, 1H), 7.11 (d, J=8.1 Hz, 1H), 6.88 (s, 1H), 6.41 (d, J=1.8 Hz, 1H), 5.36 (s, 2H), 5.05-4.91 (m, 4H), 4.32 (tt, J=11.5, 4.1 Hz, 1H), 4.11-4.00 (m, 2H), 3.80-3.71 (m, 4H), 3.40 (t, J=11.8 Hz, 2H), 2.48-2.30 (m, 6H), 1.84 (d, J=19.1 Hz, 2H). LC/MS: 0.59 min [M+1]=502.3, Method M.

The following analogs were prepared according to General Procedure 1, using Intermediate N15 and the appropriate bromide coupling partner.

TABLE 10

| Ex. No. | R | Name | LC/MS Retention Time: [M + 1] Method |
|---|---|---|---|
| 99 | | 1-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)pyrrolidin-3-ol | 1.21 min; 502 Method H |
| 100 | | 1-(3-(3-(4-amino-5-(1-isopropyl-1H-1,2,3-triazol-5-yl)pyrrolo[2,1-f][1,2,4]triazin-7-yl)phenyl)oxetan-3-yl)pyrrolidin-3-ol | 0.55 min; 502 Method I |

Example 101

1-(4-((3-(3-(4-Amino-5-(1-(tetrahydro-2H-pyran-4-yl)-1H-pyrazol-5-yl)pyrrolo[2,1-f][1,2,4]triazin-7-yl)phenyl)oxetan-3-yl)(methyl)amino)piperidin-1-yl)ethanone

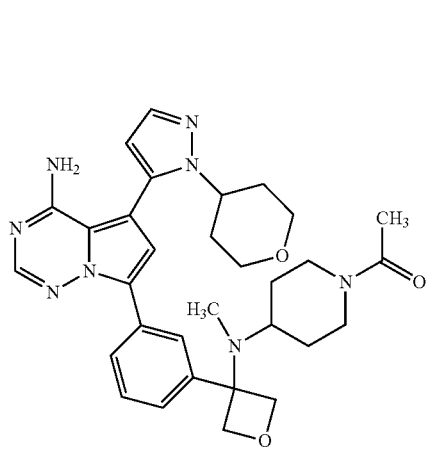

(101)

1-(4-((3-(3-(4-Amino-5-(1-(tetrahydro-2H-pyran-4-yl)-1H-pyrazol-5-yl)pyrrolo [2,1-f][1,2,4]triazin-7-yl)phenyl)oxetan-3-yl)(methyl)amino)piperidin-1-yl)ethanone was prepared employing General Procedure 1, using N16 and N1 as coupling partners. LC/MS: Rt=0.84 min; [M+1]⁺: 571. Method I.

Example 102

N-(3-(3-(4-Amino-5-(1-(tetrahydro-2H-pyran-4-yl)-1H-pyrazol-5-yl)pyrrolo[2,1-f][1,2,4]triazin-7-yl)phenyl)oxetan-3-yl)-N,2-dimethylpropane-2-sulfinamide

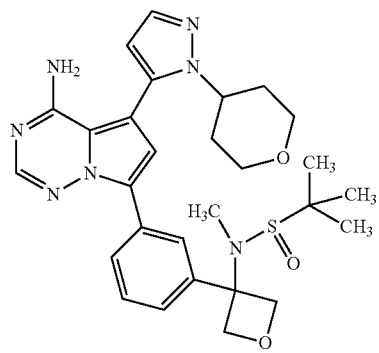

(102)

N-(3-(3-(4-Amino-5-(1-(tetrahydro-2H-pyran-4-yl)-1H-pyrazol-5-yl)pyrrolo[2,1-f][1,2,4]triazin-7-yl)phenyl)oxetan-3-yl)-N,2-dimethylpropane-2-sulfinamide was prepared according to General Procedure 1 using Intermediate N18 and Intermediate N1 as the coupling partners. LC/MS: Rt=1.24 min; [M+1]=550, Method I.

Example 103

N-(3-(3-(4-Amino-5-(1-(tetrahydro-2H-pyran-4-yl)-1H-pyrazol-5-yl)pyrrolo[2,1-f][1,2,4]triazin-7-yl)phenyl)oxetan-3-yl)pivalamide

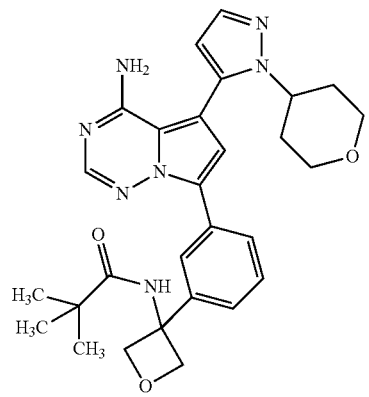

(103)

N-(3-(3-(4-Amino-5-(1-(tetrahydro-2H-pyran-4-yl)-1H-pyrazol-5-yl)pyrrolo[2,1-f][1,2,4]triazin-7-yl)phenyl)oxetan-3-yl)pivalamide was prepared according to General Procedure 1 using Intermediate N19 and Intermediate N1 as the coupling partners. LC/MS: Rt=1.14 min; [M+1]=516.2, Method I.

The following compounds were prepared following General Procedure 1 by employing the appropriate intermediates as starting materials.

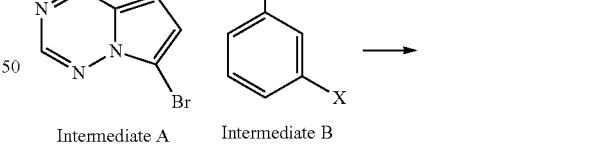

Intermediate A        Intermediate B

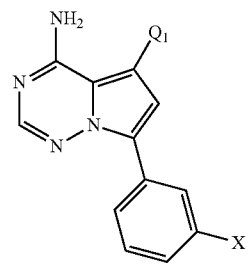

TABLE 11

| Ex. No. | Structure | Name | LC/MS Rt [M + 1] Method |
|---|---|---|---|
| 104 | 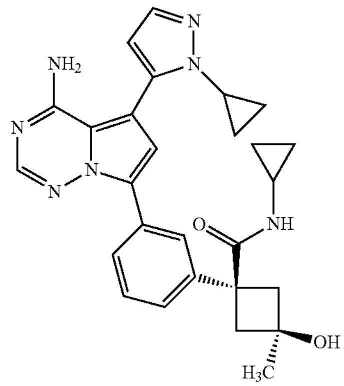 [SMILES: C[C@]1(O)C[C@](C(=O)NC2CC2)(c2cccc(-c3cc(-c4ccnn4C4CC4)c4c(N)ncnn34)c2)C1] | (cis)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-methylcyclobutanecarboxamide | 1.03 min 484.3 Method I |
| 105 | 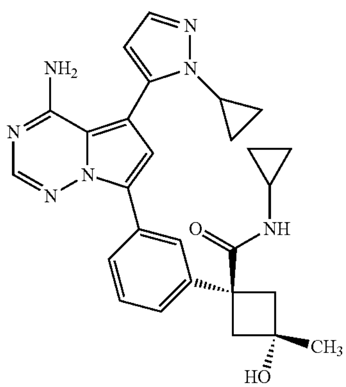 [SMILES: C[C@]1(O)C[C@@](C(=O)NC2CC2)(c2cccc(-c3cc(-c4ccnn4C4CC4)c4c(N)ncnn34)c2)C1] | (trans)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-methylcyclobutanecarboxamide | 0.99 min 484.1 Method I |
| 106 | 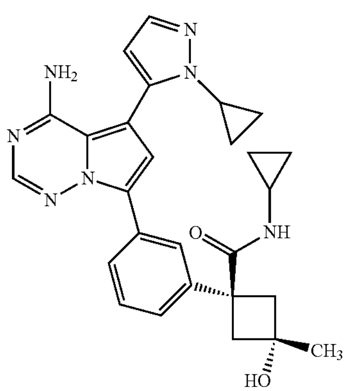 [SMILES: C[C@]1(O)C[C@@](C(=O)NC2CC2)(c2cccc(-c3cc(-c4ccnn4C4CC4)c4c(N)ncnn34)c2)C1] | (trans)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-(trifluoromethyl)cyclobutanecarboxamide | 1.33 min 538.3 Method H |
| 107 | 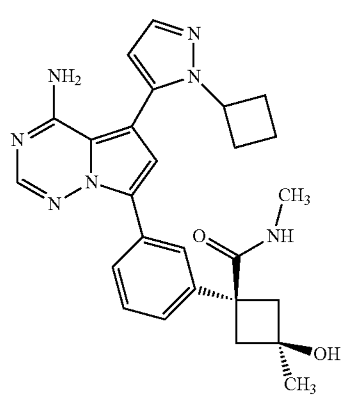 [SMILES: CNC(=O)[C@]1(c2cccc(-c3cc(-c4ccnn4C4CCC4)c4c(N)ncnn34)c2)C[C@](C)(O)C1] | (cis)-1-(3-(4-amino-5-(1-cyclobutyl-1H-pyrazol-5-yl)pyrrolo[2,1-f][1,2,4]triazin-7-yl)phenyl)-3-hydroxy-N,3-dimethylcyclobutanecarboxamide | 1.15 min 472.3 Method I |

TABLE 11-continued

| Ex. No. | Structure | Name | LC/MS Rt [M + 1] Method |
|---|---|---|---|
| 108 | 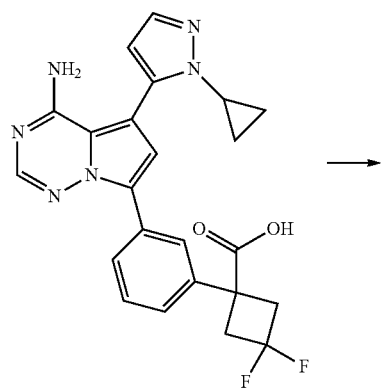 | (cis)-1-(3-(4-amino-5-(1-isopropyl-1H-pyrazol-5-yl)pyrrolo[2,1-f][1,2,4]triazin-7-yl)phenyl)-3-hydroxy-N,3-dimethylcyclobutanecarboxamide | 1.16 min 460.3 Method I |

Example 109

1-(3-(4-Amino-5-(1-cyclopropyl-1H-pyrazol-5-yl)pyrrolo[2,1-f][1,2,4]triazin-7-yl)phenyl)-N-(3,3-difluorocyclobutyl)-3,3-difluorocyclobutanecarboxamide

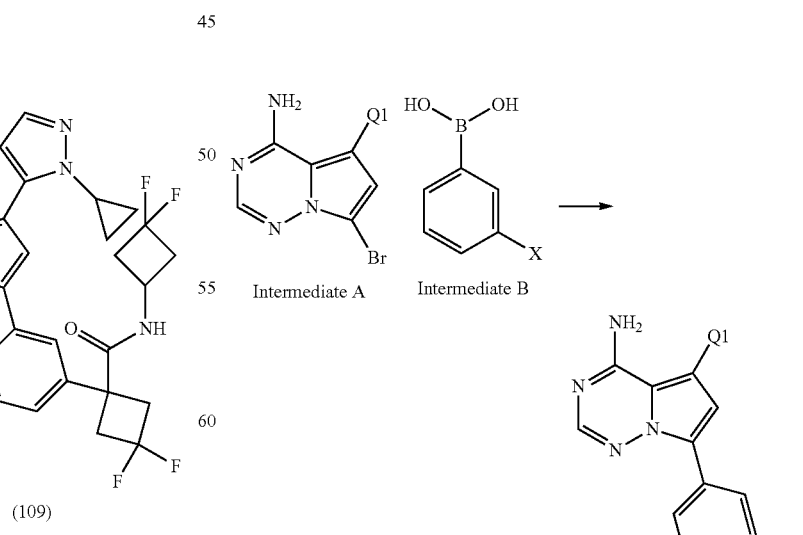

To 3,3-difluorocyclobutyl-1-amine (4.99 mg, 0.047 mmol) was added Intermediate N27 (14.5 mg, 0.039 mmol) in DMF (0.097 Molar solution), followed by HATU (17.73 mg, 0.047 mmol) and DIPEA (20.36 µl, 0.117 mmol). The mixture was stirred at room temperature overnight and diluted with DMF (2 mL). The resulting mixture was purified by preparative HPLC following Method B to provide 1-(3-(4-amino-5-(1-cyclopropyl-1H-pyrazol-5-yl)pyrrolo[1,2-f][1,2,4]triazin-7-yl)phenyl)-N-(3,3-difluorocyclobutyl)-3,3-difluorocyclobutanecarboxamide (3.52 mg). $^1$H NMR (500 MHz, DMSO-d$_6$) δ 8.38 (d, J=6.7 Hz, 1H), 8.08-8.02 (m, 3H), 7.96 (s, 1H), 7.56 (d, J=1.8 Hz, 1H), 7.50 (t, J=7.9 Hz, 1H), 7.40-7.36 (m, 2H), 6.46 (d, J=1.8 Hz, 1H), 4.05-3.96 (m, 1H), 3.71-3.65 (m, 1H), 3.20-3.09 (m, 2H), 2.87-2.78 (m, 2H), 2.62-2.53 (m, 2H), 1.09-1.03 (m, 2H), 0.89-0.83 (m, 2H). Analytical LCMS, Method F, Rt=1.55 min, [M+H]$^+$=540.20.

The following compounds were prepared following General Procedure 1 by employing the intermediates indicated as starting materials.

TABLE 13

| Ex. No. | Structure | Name | LC/MS [M + 1] RT Method |
|---|---|---|---|
| 110 | 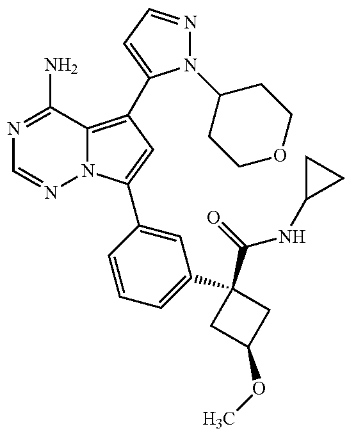 [SMILES: CO[C@H]1C[C@](C(=O)NC2CC2)(c2cccc(-c3cc(-c4ccnn4C4CCOCC4)c4c(N)ncnn34)c2)C1] | (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropyl-3-methoxycyclobutanecarboxamide | 528.2 1.14 Method I |
| 111 | 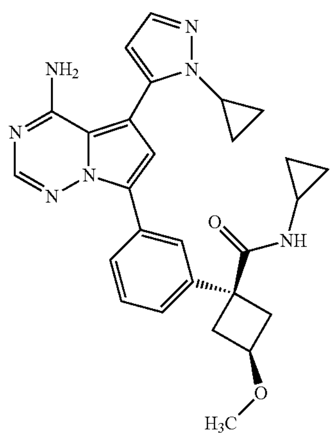 [SMILES: CO[C@H]1C[C@](C(=O)NC2CC2)(c2cccc(-c3cc(-c4ccnn4C4CC4)c4c(N)ncnn34)c2)C1] | (cis)-1-(3-(4-amino-5-(1-cyclopropyl-1H-pyrazol-5-yl)pyrrolo[2,1-f][1,2,4]triazin-7-yl)phenyl)-N-cyclopropyl-3-methoxycyclobutanecarboxamide | 484.3 1.15 Method I |
| 112 | 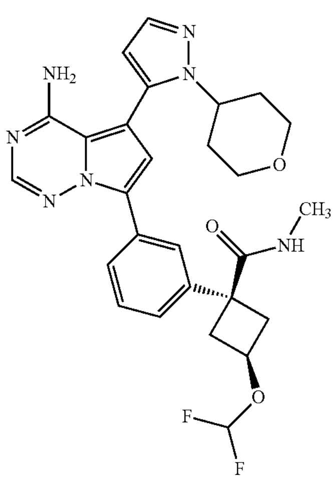 [SMILES: CNC(=O)[C@]1(c2cccc(-c3cc(-c4ccnn4C4CCOCC4)c4c(N)ncnn34)c2)C[C@H](OC(F)F)C1] | (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-(difluoromethoxy)-N-methylcyclobutanecarboxamide | 538.3 1.27 Method I |

Example 113

((Cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutyl)(morpholino)methanone

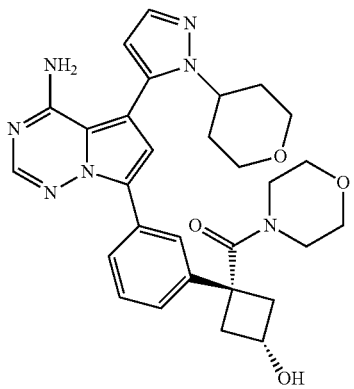

(113)

A mixture of (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutanecarboxylic acid, Intermediate N30 (13 mg, 0.027 mmol), HATU (16 mg, 0.041 mmol) and morpholine (4 µL, 0.041 mmol) in DMF (0.27 mL) was treated with DIPEA (19 µL, 0.11 mmol). The mixture was stirred at room temperature for 0.5 h, diluted with 1 mL DMF and purified by preparative HPLC using Method B to obtain ((cis)-1-(3-(4-amino-5-(1-(tetrahydro-2H-pyran-4-yl)-1H-pyrazol-5-yl)pyrrolo[2,1-f][1,2,4]triazin-7-yl)phenyl)hydroxycyclobutyl) (morpholino)methanone (7.4 mg, 0.014 mmol, 49.7% yield). LC/MS=0.95 min [M−1]⁻=543.8, Method I.

The following compounds were prepared according to the general synthesis procedure for Example 113 employing the appropriate starting materials.

TABLE 14

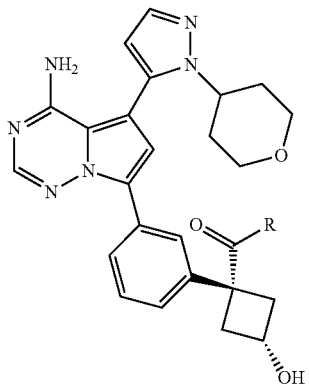

| Ex. No. | R | Name | LC/MS [M + 1] RT Method |
|---|---|---|---|
| 114 | ![N(CH3)-oxetanyl] | (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-methyl-N-(oxetan-3-yl)cyclobutanecarboxamide | 543.8 0.93 min Method I |
| 115 | ![NH-CH3] | (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-methylcyclobutanecarboxamide | 488.2 0.99 min Method I |
| 116 | ![NH-cyclopropyl] | (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropyl-3-hydroxycyclobutanecarboxamide | 514.3 0.93 min Method I |

TABLE 14-continued

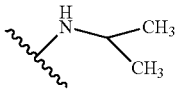

| Ex. No. | R | Name | LC/MS [M + 1] RT Method |
|---|---|---|---|
| 117 | 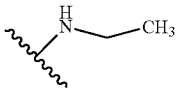 | (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-isopropylcyclobutanecarboxamide | 516.3 1.01 min Method I |
| 118 | 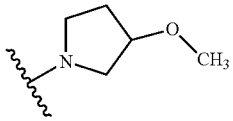 [SMILES: *N1CCC(OC)C1] | (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-N-ethyl-3-hydroxycyclobutane-carboxamide | 502.3 0.92 min Method I |
| 119 | 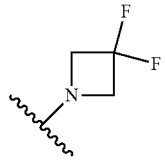 [SMILES: *N1CC(F)(F)C1] | ((1s,3s)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutyl)(3-methoxypyrrolidin-1-yl)methanone | 558.2 1.12 min Method I |
| 120 |  | ((cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutyl)(3,3-difluoroazetidin-1-yl)methanone | 550.2 1.24 min Method I |

The following compounds were prepared according to the general synthesis procedure for Example 113 employing the appropriate starting materials.

TABLE 15

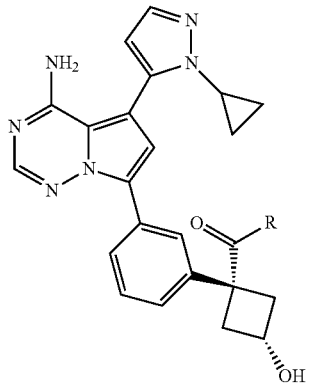

| Ex. No. | R | Name | LCMS (min) RT (M + H)+ Method |
|---|---|---|---|
| 121 | ![CH3-NH-] | (cis)-1-(3-(4-amino-5-(1-cyclopropyl-1H-pyrazol-5-yl)pyrrolo[2,1-f][1,2,4]triazin-7-yl)phenyl)-N-ethyl-3-hydroxycyclobutanecarboxamide | 1.01 457.2 Method I |
| 122 | ![H3C-CH(CH3)-NH-] | (cis)-1-(3-(4-amino-5-(1-cyclopropyl-1H-pyrazol-5-yl)pyrrolo[2,1-f][1,2,4]triazin-7-yl)phenyl)-3-hydroxy-N-isopropylcyclobutanecarboxamide | 1.05 472.2 Method I |
| 123 | ![CF3-CH2-NH-] | (cis)-1-(3-(4-amino-5-(1-cyclopropyl-1H-pyrazol-5-yl)pyrrolo[2,1-f][1,2,4]triazin-7-yl)phenyl)-3-hydroxy-N-(2,2,2-trifluoroethyl)cyclobutanecarboxamide | 1.11 486.1 Method I |
| 124 | ![cyclopropyl-NH-] | (cis)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxycyclobutanecarboxamide | 1.03 470.2 Method I |

The following compounds were prepared according to the general synthesis procedure for Example 113 employing the appropriate starting materials.

TABLE 16

| Ex. No. | R | Name | LCMS (min) RT (M + H)+ Method |
|---|---|---|---|
| 125 | 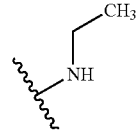 | 1-(3-(4-amino-5-(1-(tetrahydro-2H-pyran-4-yl)-1H-pyrazol-5-yl)pyrrolo[2,1-f][1,2,4]triazin-7-yl)phenyl)-N-(3,3-difluorocyclobutyl)cyclopropanecarboxamide | 1.56 min 534.3 Method H |
| 126 | 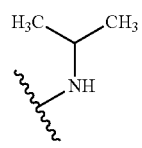 | 1-(3-(4-amino-5-(1-(tetrahydro-2H-pyran-4-yl)-1H-pyrazol-5-yl)pyrrolo[2,1-f][1,2,4]triazin-7-yl)phenyl)-N-ethylcyclopropanecarboxamide | 1.18 min 472.3 Method I |
| 127 | 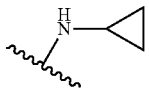 | 1-(3-(4-amino-5-(1-(tetrahydro-2H-pyran-4-yl)-1H-pyrazol-5-yl)pyrrolo[2,1-f][1,2,4]triazin-7-yl)phenyl)-N-isopropylcyclopropanecarboxamide | 1.29 min 486.3 Method I |
| 128 | | 1-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropylcyclopropanecarboxamide | 1.40 min 484.3 Method H |

The following compounds were prepared according to the general synthesis procedure for Example 113 employing the appropriate starting materials.

TABLE 17

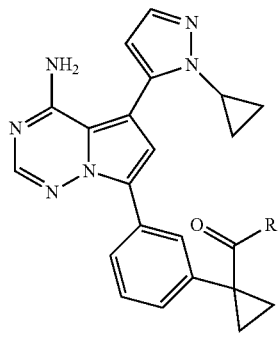

| Ex. No. | R | Name | LCMS (min) RT (M + H)+ Method |
|---|---|---|---|
| 129 | ![oxetan-3-yl-NH] | 1-(3-(4-amino-5-(1-cyclopropyl-1H-pyrazol-5-yl) pyrrolo[2,1-f][1,2,4]triazin-7-yl)phenyl)-N-(oxetan-3-yl)cyclopropanecarboxamide | 1.33 min 456.3 Method H |
| 130 | ![CH3-CH2-NH] | 1-(3-(4-amino-5-(1-cyclopropyl-1H-pyrazol-5-yl) pyrrolo[2,1-f][1,2,4]triazin-7-yl)phenyl)-N-ethylcyclopropanecarboxamide | 1.45 428.3 Method H |
| 131 | ![(CH3)2CH-NH] | 1-(3-(4-amino-5-(1-cyclopropyl-1H-pyrazol-5-yl) pyrrolo[2,1-f][1,2,4]triazin-7-yl)phenyl)-N-isopropylcyclopropanecarboxamide | 1.58 min 442.3 Method H |

Example 132

4-(3-(4-Amino-5-(1-(tetrahydro-2H-pyran-4-yl)-1H-pyrazol-5-yl)pyrrolo[2,1-f][1,2,4]triazin-7-yl)phenyl)-5,5-dimethyloxazolidin-2-one

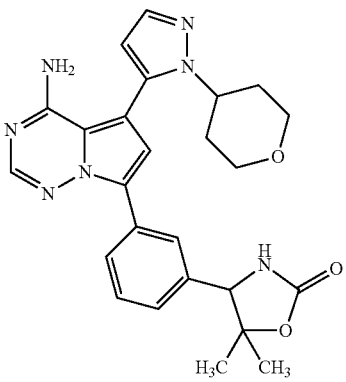
(132)

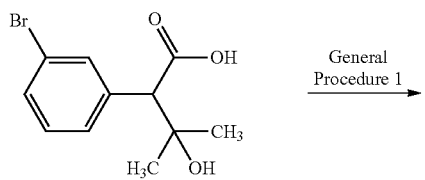
General Procedure 1 →

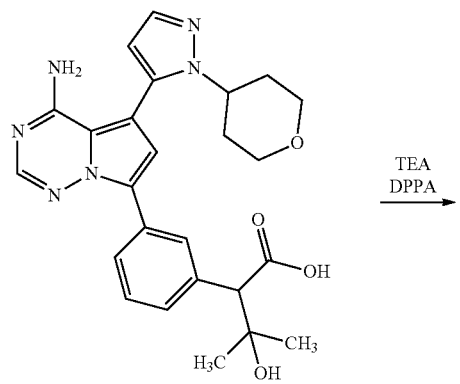
TEA DPPA →

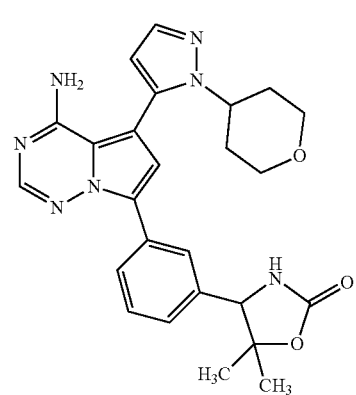

Intermediate 132A:
2-(3-Bromophenyl)-3-hydroxy-3-methylbutanoic acid

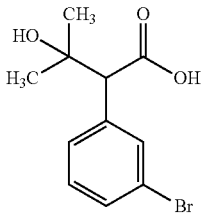
(132A)

A solution of LiHMDS (11.6 mL, 11.6 mmol, 1M in THF) in THF (10 mL) was cooled to −78° C. and a solution of 2-(3-bromophenyl)acetic acid (1 g, 4.65 mmol) in THF (4 mL) was added. The cooling bath was removed and the mixture was allowed to warm to room temperature and stirred at room temperature for 45 min. The mixture was then cooled again to −78° C., propan-2-one (0.51 mL, 6.98 mmol) was added dropwise as a solution in THF (2 mL) and the mixture was stirred at −78° C. for 30 min. The reaction mixture was warmed to room temperature, diluted with aqueous $NH_4Cl$, and the mixture was partitioned between water and ethyl acetate. The organic portion was washed with brine, dried over $Na_2SO_4$ and concentrated to obtain 2-(3-bromophenyl)-3-hydroxy-3-methylbutanoic acid (1.35 g) as a crude oil. $^1H$ NMR (400 MHz, $CDCl_3$) δ 7.57 (t, J=1.8 Hz, 1H), 7.46 (ddd, J=8.0, 1.9, 1.1 Hz, 1H), 7.35 (dt, J=7.8, 1.2 Hz, 1H), 7.24-7.17 (m, 1H), 3.59 (s, 2H), 3.50 (s, 3H), 1.40 (s, 3H), 1.11 (s, 3H).

Intermediate 133B: 2-(3-(4-Amino-5-(1-(tetrahydro-2H-pyran-4-yl)-1H-pyrazol-5-yl) pyrrolo[2,1-f][1,2,4]triazin-7-yl)phenyl)-3-hydroxy-3-methylbutanoic acid

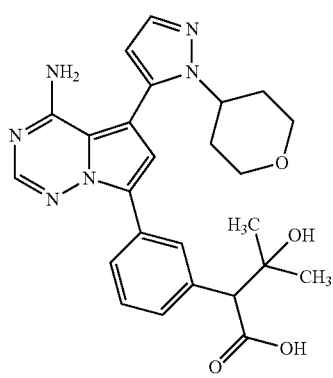
(133B)

Intermediate 133B (prepared using Intermediate N1 and Intermediate 132A as coupling partners following General Procedure 1):

Rac-4-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethyloxazolidin-2-one A suspension of 2-(3-(4-amino-5-(1-(tetrahydro-2H-pyran-4-yl)-1H-pyrazol-5-yl) pyrrolo[2,1-f][1,2,4]triazin-7- yl)phenyl)-3-hydroxy-3-methylbutanoic acid, TFA salt (161 mg, 0.273 mmol) in a mixture of dioxane (2 mL) and t-butanol (2 mL) was treated with triethylamine (76 µl, 0.54 mmol) and DPPA (59 µL, 0.276 mmol). The resulting mixture was heated at 80° C. for 18 h after which it was diluted with DMSO and the desired product was isolated by preparative HPLC (Column:YMC-Pack 5µ C18 30×250 mm, Mobile Phase A: 90% H$_2$O-10% ACN-0.1% TFA, mobile Phase B: 10% H$_2$O-90% ACN-0.1% TFA, 10-80% B over 10 min, 100% B for 4 min) providing rac-4-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethyloxazolidin-2-one (14.6 mg, 0.028 mmol, 45.5% yield). $^1$H NMR (500 MHz, DMSO-d$_6$) δ 8.11-8.01 (m, 4H), 7.94 (s, 2H), 7.67 (s, 1H), 7.52 (t, J=7.9 Hz, 1H), 7.29 (d, J=7.3 Hz, 1H), 7.23 (s, 1H), 6.45 (d, J=1.8 Hz, 1H), 4.72 (s, 1H), 4.40-4.27 (m, 1H), 3.93-3.82 (m, 2H), 3.31 (t, J=11.9 Hz, 2H), 2.09 (d, J=7.9 Hz, 2H), 1.55 (s, 3H), 0.87 (s, 3H). LC/MS: Rt=1.20 min [M+1]$^+$=474 (Method I).

The racemic compound was separated into two enantiomers by SFC chiral HPLC method. Enantiomer 1: (R)-4-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethyloxazolidin-2-one and Enantiomer 2: (S)-4-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethyloxazolidin-2-one Rac-4-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethyloxazolidin-2-one, TFA salt was further purified by SFC chromatography using the following method: Instrument: Berger SFC MGII, Column: Chiral OD-H 25×3 cl ID, 5µ, Flow Rate: 85.0 mL/min, Mobile Phase (73/27 CO$_2$/MeOH), Detector Wavelength: 220 nM. Enantiomer 1 and Enantiomer 2 were characterized by the following chiral analytical method: Instrument: Berger analytical SFC, Column: Chiral OD-H 250×4.6 mm ID, 5µ, Flow Rate: 2.0 mL/min, Mobile Phase: 70/30 CO$_2$/MeOH. (N32-enantiomer 1: Retention time=8.272 min, N32-enantiomer 2: Retention time: 9.233 min.

Enantiomer-1 LC/MS: Rt 0.904 min, [M+1]$^+$=474.4, Method L. Enantiomer-2 LC/MS: Rt 0.907 min, [M+1]$^+$=474.4, Method L.

Example 133

(3R,5S)-5-(3-(4-Amino-5-(1-(tetrahydro-2H-pyran-4-yl)-1H-pyrazol-5-yl) pyrrolo[2,1-f][1,2,4]triazin-7-yl)phenyl)-1-methylpyrrolidin-3-ol (133)

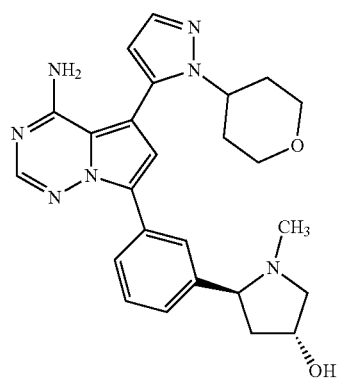

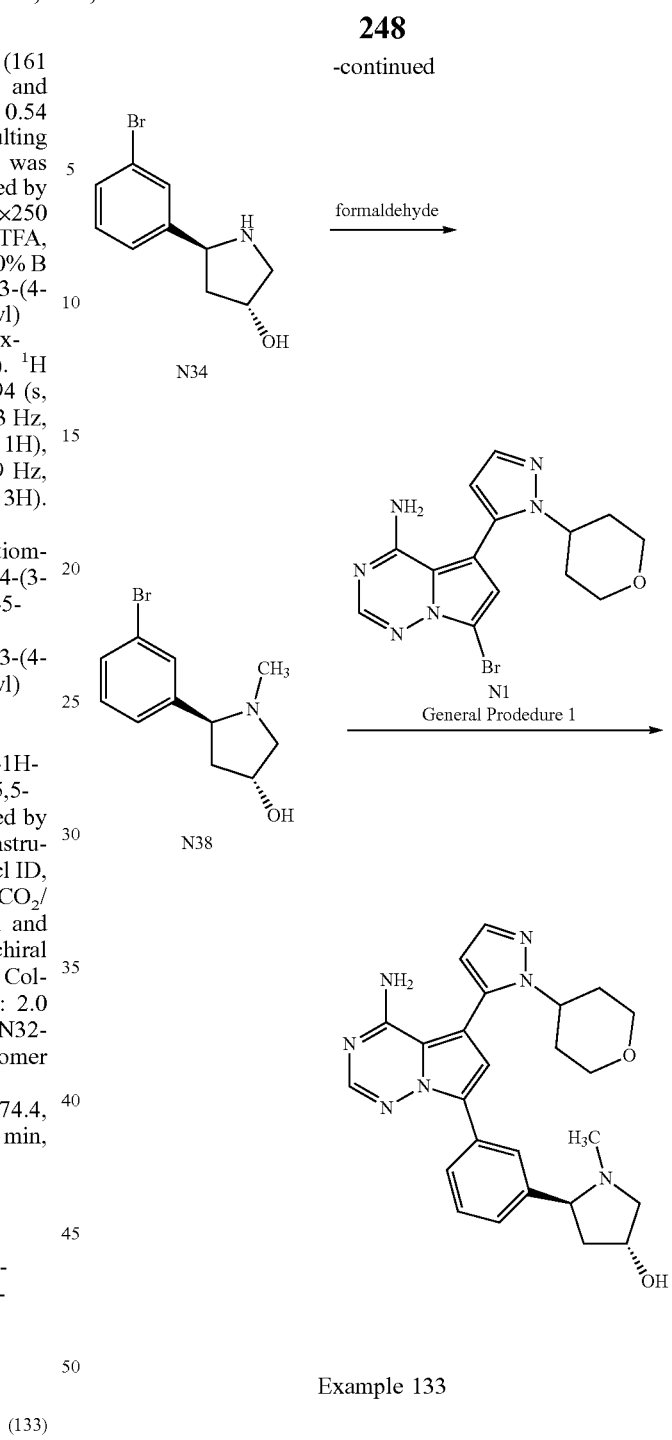

Example 133

The title compound was prepared according to the General Procedure 1 using N38 and N1 as starting materials. $^1$H NMR (500 MHz, DMSO-d$_6$) δ 8.04 (d, J=15.8 Hz, 2H), 7.98-7.91 (m, 2H), 7.67 (d, J=1.3 Hz, 1H), 7.43 (t, J=7.6 Hz, 1H), 7.32 (d, J=7.4 Hz, 1H), 7.21 (s, 1H), 6.45 (d, J=1.7 Hz, 1H), 4.40-4.25 (m, 2H), 3.87 (d, J=8.4 Hz, 1H), 2.18 (dd, J=9.4, 5.4 Hz, 1H), 2.14-2.04 (m, 5H), 2.02-1.93 (m, 1H), 1.93-1.85 (m, 2H), 1.79 (br. s., 1H). LC/MS: 0.74 min, [M+1]$^+$=460.2, Method I.

The following compounds were prepared according to the general synthesis procedure for Example 133 using Intermediate N1 and the appropriate intermediate as starting materials:

TABLE 18

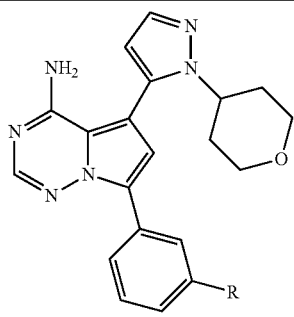

| Ex. No. | R | Name | LC/MS RT [M + 1] Method |
|---|---|---|---|
| 134 | ![CH3 pyrrolidine with OH] | (3S,5R)-5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyrrolidin-3-ol | 0.74 min 460.2 Method I |
| 135 | ![CH3 pyrrolidine with OH] | (3R,5R)-5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyrrolidin-3-ol | 0.87 min 460.2 Method I |

Example 136

1-((2S,4R)-2-(3-(4-Amino-5-(1-(tetrahydro-2H-pyran-4-yl)-1H-pyrazol-5-yl)pyrrolo [2,1-f][1,2,4]triazin-7-yl)phenyl)-4-hydroxypyrrolidin-1-yl)ethanone (136)

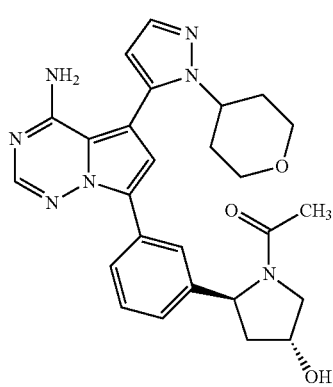

Intermediate 136A: 1-((2S,4R)-2-(3-Bromophenyl)-4-hydroxypyrrolidin-1-yl)ethanone

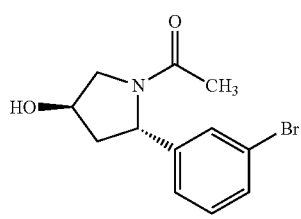

(136A)

(3R,5S)-5-(3-Bromophenyl)pyrrolidin-3-ol (74 mg, 0.306 mmol) was suspended in DCM (3 mL) and acetic anhydride (0.31 mL, 0.2 mmol, 10% solution in DCM) was added dropwise. The mixture was stirred at room temperature for 45 min and then filtered. The filtrate was concentrated in vacuo providing 1-((2S,4R)-2-(3-bromophenyl)-4-hydroxypyrrolidin-1-yl)ethanone (65 mg, 0.229 mmol, 74.8% yield) as an oil LC/MS: 0.90 min, [M+1]$^+$=284, 286, Method L.

Example 136

The title compound was prepared according to General Procedure 1 using the above compound and N1 as starting materials. LC/MS: 0.90 min, [M+1]$^+$=488 Method I. A mixture of rotamers was observed by $^1$H NMR (DMSO-d$_6$).

The following compounds were prepared according to the general synthesis procedure for Example 136 using appropriate intermediates.

TABLE 19

| Ex. No. | Structure | Name | LC/MS RT [M + 1] Method |
|---|---|---|---|
| 137 | 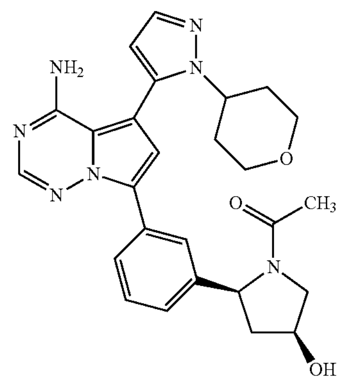 [SMILES: CC(=O)N1C[C@@H](O)C[C@H]1c1cccc(-c2cc(-c3ccnn3C3CCOCC3)c3c(N)ncnn23)c1] | 1-((2S,4S)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)ethanone | 0.86 min 487.8 Method I |
| 138 | 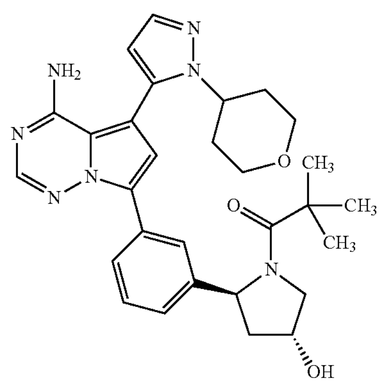 [SMILES: CC(C)(C)C(=O)N1C[C@H](O)C[C@H]1c1cccc(-c2cc(-c3ccnn3C3CCOCC3)c3c(N)ncnn23)c1] | 1-((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)-2,2-dimethylpropan-1-one | 1.25 min 530.3 Method I |
| 139 | 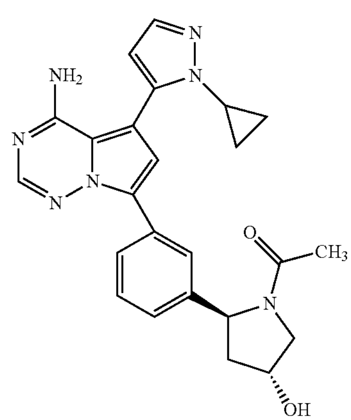 [SMILES: CC(=O)N1C[C@H](O)C[C@H]1c1cccc(-c2cc(-c3ccnn3C3CC3)c3c(N)ncnn23)c1] | 1-((2S,4R)-2-(3-(4-amino-5-(1-cyclopropyl-1H-pyrazol-5-yl)pyrrolo[2,1-f][1,2,4]triazin-7-yl)phenyl)-4-hydroxypyrrolidin-1-yl)ethanone | 0.84 min 444.3 Method L |

TABLE 19-continued

| Ex. No. | Structure | Name | LC/MS RT [M + 1] Method |
|---|---|---|---|
| 140 | 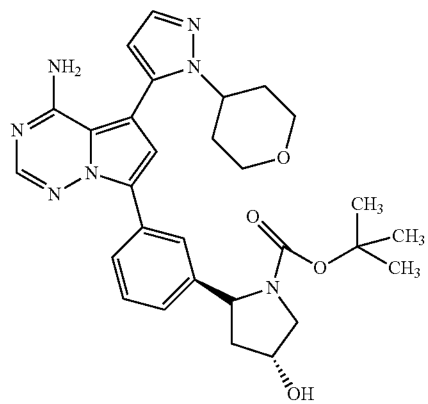 | (2S,4R)-tert-butyl 2-(3-(4-amino-5-(1-(tetrahydro-2H-pyran-4-yl)-1H-pyrazol-5-yl)pyrrolo[2,1-f][1,2,4]triazin-7-1)phenyl)-4-hydroxypyrrolidine-1-carboxylate | 0.80 min 546.2 Method M |

Example 140, (2S,4R)-tert-butyl 2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidine-1-carboxylate (319 mg, 0.585 mmol) was dissolved in DCM (5.8 mL) and HCl (4N solution in dioxane) (0.73 mL, 2.92 mmol) was added dropwise. The mixture was stirred at room temperature for 5 h and then the solvent was removed in vacuo to obtain (3R,5S)-5-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-ol, 2 HCl salt (301 mg, 0.581 mmol, 99% yield) as a tan solid LC/MS: 0.81 min, [M+1]$^+$=447 Method L.

Example 141

((2S,4R)-2-(3-(4-Amino-5-(1-(tetrahydro-2H-pyran-4-yl)-1H-pyrazol-5-yl) pyrrolo[2,1-f][1,2,4]triazin-7-yl)phenyl)-4-hydroxypyrrolidin-1-yl)(cyclopropyl)methanone

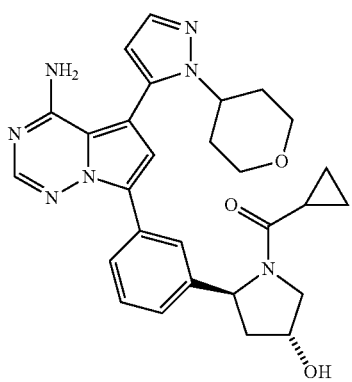

(141)

Intermediate 141A: (3R,5S)-5-(3-(4-Amino-5-(1-(tetrahydro-2H-pyran-4-yl)-1H-pyrazol-5-yl)pyrrolo[2,1-f][1,2,4]triazin-7-yl)phenyl)pyrrolidin-3-ol

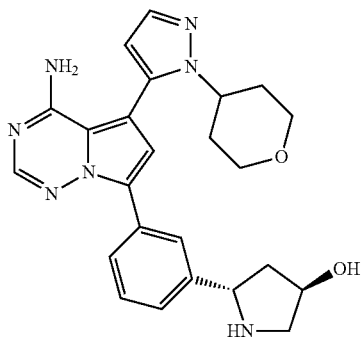

(141A)

Example 141

Intermediate 141A (15 mg, 0.029 mmol), HATU (16.50 mg, 0.043 mmol), and cyclopropanecarboxylic acid (2.74 mg, 0.032 mmol) were combined in DMA (0.5 mL) and DIPEA (0.02 mL, 0.116 mmol) was added. The reaction mixture was stirred at room temperature for 18 h, filtered and purified by preparative HPLC (Method B) to provide ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(cyclopropyl)methanone (5.7 mg, 10.54 μmol, 36.4% yield). LC/MS: 1.19 min, [M+1]$^+$=516.2 Method I.

The following compounds were prepared according to the general synthesis procedure for Example 141 using appropriate carboxylic acid as the starting material.

TABLE 20

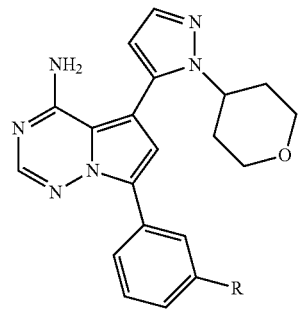

| Ex. No. | Structure | Name | LC/MS RT [M + 1] Method |
|---|---|---|---|
| 142 | 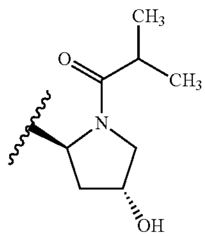 [SMILES: *[C@@H]1C[C@@H](O)CN1C(=O)C(C)C] | 1-((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)-2-methylpropan-1-one | 1.01 min 514.3 Method I |
| 143 | 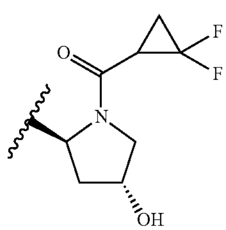 [SMILES: *[C@@H]1C[C@@H](O)CN1C(=O)C1CC1(F)F] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(2,2-difluorocyclopropyl)methanone | 1.20 min 516.2 Method I |
| 144 | 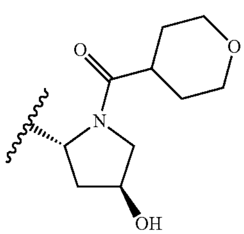 [SMILES: *[C@H]1C[C@H](O)CN1C(=O)C1CCOCC1] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(tetrahydro-2H-pyran-4-yl)methanone | 1.09 min 558.2 Method I |
| 145 | 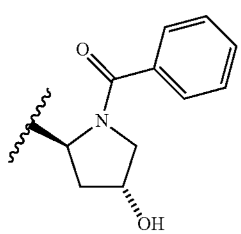 [SMILES: *[C@@H]1C[C@@H](O)CN1C(=O)c1ccccc1] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(phenyl)methanone | 1.24 min 550.2 Method I |
| 146 | 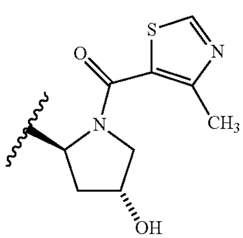 [SMILES: *[C@@H]1C[C@@H](O)CN1C(=O)c1scnc1C] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(4-methylthiazol-5-yl)methanone | 0.92 min 571.3 Method I |

TABLE 20-continued

| Ex. No. | Structure | Name | LC/MS RT [M + 1] Method |
|---|---|---|---|
| 147 | 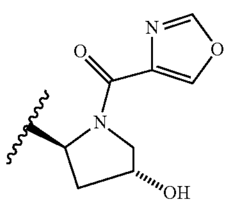 [SMILES: *[C@@H]1C[C@@H](O)CN1C(=O)c1cocn1] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(oxazol-4-yl)methanone | 0.90 min 541.3 Method I |
| 148 | 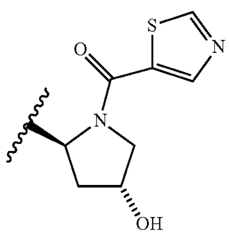 [SMILES: *[C@@H]1C[C@@H](O)CN1C(=O)c1cncs1] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(thiazol-5-yl)methanone | 1.09 min 557.3 Method H |
| 149 | 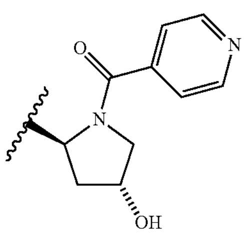 [SMILES: *[C@@H]1C[C@@H](O)CN1C(=O)c1ccncc1] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridin-4-yl)methanone | 1.05 min 551.3 Method H |
| 150 | 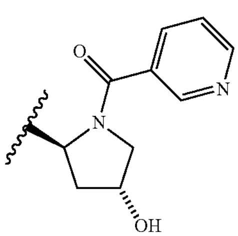 [SMILES: *[C@@H]1C[C@@H](O)CN1C(=O)c1cccnc1] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridin-3-yl)methanone | 1.05 min 550.2 Method H |
| 151 | 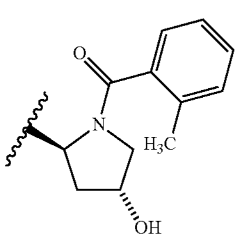 [SMILES: *[C@@H]1C[C@@H](O)CN1C(=O)c1ccccc1C] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(o-tolyl)methanone | 1.30 min 564.3 Method H |

TABLE 20-continued

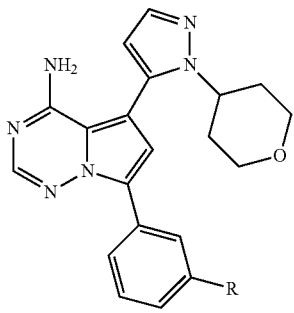

| Ex. No. | Structure | Name | LC/MS RT [M + 1] Method |
|---|---|---|---|
| 152 | 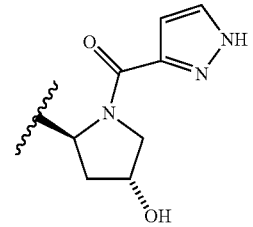 [SMILES: *[C@@H]1C[C@@H](O)CN1C(=O)c1cc[nH]n1] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(1H-pyrazol-3-yl)methanone | 1.03 min 540.3 Method H |
| 153 | 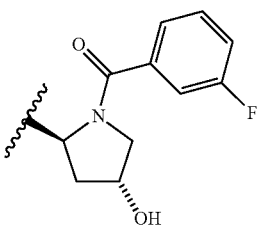 [SMILES: *[C@@H]1C[C@@H](O)CN1C(=O)c1cccc(F)c1] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(3-fluorophenyl)methanone | 1.34 min 568.2 Method H |
| 154 | 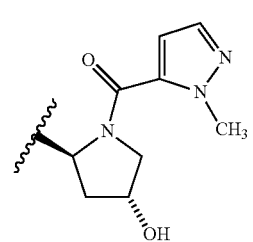 [SMILES: *[C@@H]1C[C@@H](O)CN1C(=O)c1ccnn1C] | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(1-methyl-1H-pyrazol-5-yl)methanone | 0.94 min 554.3 Method H |
| 155 | 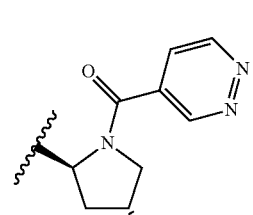 | ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridazin-4-yl)methanone | 1.00 min 552.3 Method H |

Example 156

(S)-3-(3-(4-Amino-5-(1-(tetrahydro-2H-pyran-4-yl)-1H-pyrazol-5-yl)pyrrolo[2,1-f][1,2,4]triazin-7-yl)benzyl)-4-(tert-butyl)oxazolidin-2-one

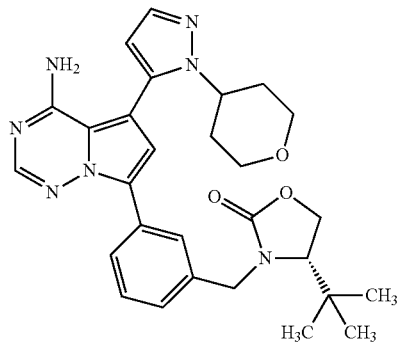

(156)

To a suspension of (S)-4-(tert-butyl)oxazolidin-2-one (29.6 mg, 0.206 mmol) in THF (0.75 mL) was added sodium hydride (5.78 mg, 0.241 mmol). The mixture was stirred briefly and then (3-(bromomethyl)phenyl)boronic acid (29.6 mg, 0.138 mmol) was added and the resulting mixture was stirred at room temperature for 18 h. Water (0.2 mL) was added followed by phosphoric acid, potassium salt (58.4 mg, 0.275 mmol) and 7-bromo-5-(1-(tetrahydro-2H-pyran-4-yl)-1H-pyrazol-5-yl)pyrrolo[2,1-f][1,2,4]triazin-4-amine (25 mg, 0.069 mmol) (Intermediate N1). The mixture was degassed by bubbling argon while sonicating and tetrakis triphenylphosphine (8.0 mg, 0.007 mmol) was added. The resulting mixture was heated at 85° C. until the reaction was judged to be complete by LC/MS to afford (S)-3-(3-(4-amino-5-(1-(tetrahydro-2H-pyran-4-yl)-1H-pyrazol-5-yl)pyrrolo[2,1-f][1,2,4]triazin-7-yl)benzyl)-4-(tert-butyl)oxazolidin-2-one (8.5 mg, 0.016 mmol, 23.71% yield). $^1$H NMR (500 MHz, DMSO-$d_6$) δ 8.04 (s, 1H), 8.02-7.97 (m, 2H), 7.67 (d, J=1.5 Hz, 1H), 7.49 (t, J=7.7 Hz, 1H), 7.26 (d, J=7.9 Hz, 1H), 7.22 (s, 1H), 6.46 (d, J=2.0 Hz, 1H), 4.78 (d, J=15.9 Hz, 1H), 4.42 (d, J=15.9 Hz, 1H), 4.39-4.32 (m, 1H), 4.31-4.26 (m, 1H), 4.26-4.22 (m, 1H), 3.88 (d, J=7.9 Hz, 2H), 3.50 (dd, J=8.7, 4.7 Hz, 1H), 2.15-2.03 (m, 2H), 0.89 (s, 9H). LC/MS: 1.48 min, [M+I]$^+$=516.2 Method I.

The following compounds were prepared according to the general synthesis procedure for Example 156 using the appropriate starting materials. Sodium hydride was not used in the synthesis of Example 164.

TABLE 21

| Ex. No. | Structure | Name | LC/MS RT [M + 1] Method |
|---|---|---|---|
| 157 | (structure) | 3-(3-(4-amino-5-(1-(tetrahydro-2H-pyran-4-yl)-1H-pyrazol-5-yl)pyrrolo[2,1-f][1,2,4]triazin-7-yl)benzyl)-1,3-oxazinan-2-one | 1.05 min 474.2 Method I |
| 158 | (structure) | (S)-3-(3-(4-amino-5-(1-(tetrahydro-2H-pyran-4-yl)-1H-pyrazol-5-yl)pyrrolo[2,1-f][1,2,4]triazin-7-yl)benzyl)-4-isopropyloxazolidin-2-one | 1.24 min 502.2 Method I |
| 159 | (structure) | 1-(3-(4-amino-5-(1-(tetrahydro-2H-pyran-4-yl)-1H-pyrazol-5-yl)pyrrolo[2,1-f][1,2,4]triazin-7-yl)benzyl)pyrrolidin-2-one | 1.09 min 458.2 Method I |

TABLE 21-continued

| Ex. No. | Structure | Name | LC/MS RT [M + 1] Method |
|---|---|---|---|
| 160 | 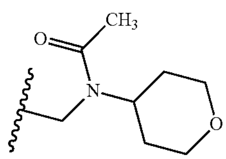 [SMILES: *CN(C(C)=O)C1CCOCC1] | N-(3-(4-amino-5-(1-(tetrahydro-2H-pyran-4-yl)-1H-pyrazol-5-yl)pyrrolo[2,1-f][1,2,4]triazin-7-yl)benzyl)-N-(tetrahydro-2H-pyran-4-yl)acetamide | 1.10 min 516.2 Method I |
| 161 | 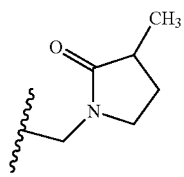 [SMILES: *CN1CCC(C)C1=O] | 1-(3-(4-amino-5-(1-(tetrahydro-2H-pyran-4-yl)-1H-pyrazol-5-yl)pyrrolo[2,1-f][1,2,4]triazin-7-yl)benzyl)-3-methylpyrrolidin-2-one | 1.16 min 472.2 Method I |
| 162 | 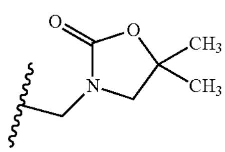 [SMILES: *CN1CC(C)(C)OC1=O] | 3-(3-(4-amino-5-(1-(tetrahydro-2H-pyran-4-yl)-1H-pyrazol-5-yl)pyrrolo[2,1-f][1,2,4]triazin-7-yl)benzyl)-5,5-dimethyloxazolidin-2-one | 1.18 min 488.2 Method I |
| 163 | 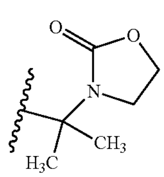 [SMILES: *C(C)(C)N1CCOC1=O] | 3-(2-(3-(4-amino-5-(1-(tetrahydro-2H-pyran-4-yl)-1H-pyrazol-5-yl)pyrrolo[2,1-f][1,2,4]triazin-7-yl)phenyl)propan-2-yl)oxazolidin-2-one | 1.26 min 488.2 Method I |
| 164 | 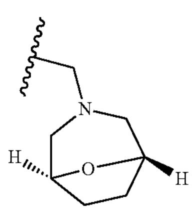 | 7-(3-((1S,5S)-8-oxa-3-azabicyclo[3.2.1]octan-3-ylmethyl)phenyl)-5-(1-(tetrahydro-2H-pyran-4-yl)-1H-pyrazol-5-yl)pyrrolo[2,1-f][1,2,4]triazin-4-amine | 0.84 468.0 F |

Example 165

N-(3-(4-Amino-5-(1-(tetrahydro-2H-pyran-4-yl)-1H-pyrazol-5-yl)pyrrolo[2,1-f][1,2,4]triazin-7-yl)benzyl)-4-methoxybenzamide

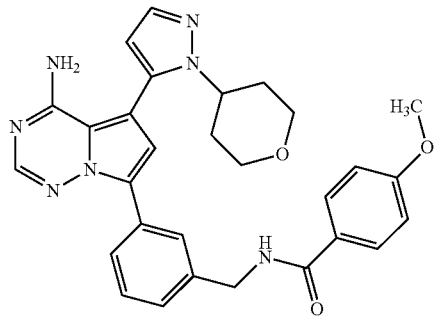

(165)

Intermediate 165A: 7-(3-(Aminomethyl)phenyl)-5-(1-(tetrahydro-2H-pyran-4-yl)-1H-pyrazol-5-yl)pyrrolo[2,1-f][1,2,4]triazin-4-amine

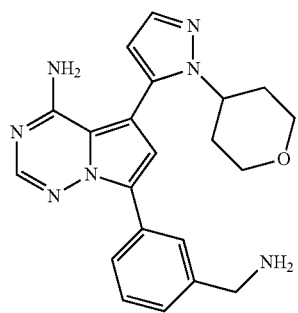

(165A)

(3-(((tert-Butoxycarbonyl)amino)methyl)phenyl)boronic acid (540 mg, 2.15 mmol), 7-bromo-5-(1-(tetrahydro-2H-pyran-4-yl)-1H-pyrazol-5-yl)pyrrolo[2,1-f][1,2,4]triazin-4-amine (651 mg, 1.79 mmol) (N1) and phosphoric acid, potassium salt (1.52 g, 7.17 mmol) were combined in a mixture of THF (10 mL) and water (2 mL). The mixture was degassed by bubbling argon into the mixture while sonicating, tetrakis triphenylphosphine (207 mg, 0.179 mmol) was added and the reaction mixture was heated at 85° C. for 18 h. The solvent was removed in vacuo and the crude residue was partitioned between ethyl acetate (20 mL) and water (5 mL). The organic portion was dried over $Na_2SO_4$, concentrated and purified by silica gel chromatography eluting with a gradient of ethyl acetate in hexanes to provide 7-(3-(aminomethyl)phenyl)-5-(1-(tetrahydro-2H-pyran-4-yl)-1H-pyrazol-5-yl)pyrrolo[2,1-f][1,2,4]triazin-4-amine. This product was treated with HCl (5 mL, 4N solution in 1,4-dioxane) and the mixture was stirred for 3 h at room temperature. The solvent was removed in vacuo providing 7-(3-(aminomethyl) phenyl)-5-(1-(tetrahydro-2H-pyran-4-yl)-1H-pyrazol-5-yl)pyrrolo[2,1-f][1,2,4]triazin-4-amine, 2 HCl (678 mg, 1.466 mmol, 82% yield) as a tan solid. LC/MS: 0.74 min, $[M+1]^+$=390 Method M.

Example 165

7-(3-(Aminomethyl)phenyl)-5-(1-(tetrahydro-2H-pyran-4-yl)-1H-pyrazol-5-yl) pyrrolo[2,1-f][1,2,4]triazin-4-amine, 2 HCl (15 mg, 0.032 mmol), 4-methoxybenzoic acid (7.4 mg, 0.049 mmol) and BOP (21.5 mg, 0.049 mmol) were combined in DMF (0.32 mL). DIPEA (17 μL, 0.097 mmol)) was added and the mixture was stirred at room temperature for 18 h, and purified by preparative HPLC according to Method B to obtain N-(3-(4-amino-5-(1-(tetrahydro-2H-pyran-4-yl)-1H-pyrazol-5-yl)pyrrolo[2,1-f][1,2,4]triazin-7-yl)benzyl)-4-methoxybenzamide (8.1 mg, 0.015 mmol, 46.7% yield). $^1$H NMR (500 MHz, DMSO-$d_6$) δ 8.98 (t, J=5.9 Hz, 1H), 8.07 (s, 1H), 8.00 (s, 1H), 7.96 (d, J=7.9 Hz, 1H), 7.92-7.87 (m, 2H), 7.67 (d, J=1.5 Hz, 1H), 7.45 (t, J=7.7 Hz, 1H), 7.32 (d, J=7.4 Hz, 1H), 7.17 (s, 1H), 7.06-6.98 (m, 2H), 6.46 (d, J=1.5 Hz, 1H), 4.55 (d, J=5.9 Hz, 2H), 4.41-4.29 (m, 1H), 3.89-3.78 (m, 5H), 3.34-3.23 (m, 2H), 2.09 (qd, J=12.2, 4.5 Hz, 2H), 1.78 (br, 2H). LC/MS: 1.33 min, $[M+1]^+$=524.2 Method I.

The following compounds were prepared according to the general synthesis procedure for Example 165 employing appropriate reagents. In the Examples where the final product is a benzylamine, potassium carbonate was used as a reagent instead of sodium hydride.

TABLE 22

| Ex. No. | Structure | Name | LC/MS RT [M + 1] Method |
|---|---|---|---|
| 166 | 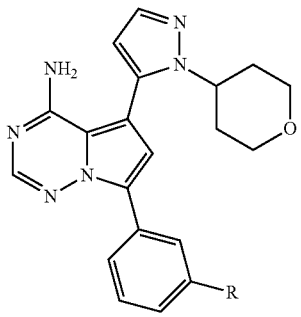 | N-(2-(3-(4-amino-5-(1-(tetrahydro-2H-pyran-4-yl)-1H-pyrazol-5-yl)pyrrolo[2,1-f][1,2,4]triazin-7-yl)phenyl)propan-2-yl)-3-hydroxy-3-methylbutanamide | 1.25 min 518.2 Method I |

TABLE 22-continued

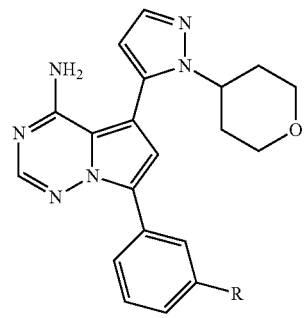

| Ex. No. | Structure | Name | LC/MS RT [M + 1] Method |
|---|---|---|---|
| 167 | ![structure] | 1-(4-(3-(4-amino-5-(1-(tetrahydro-2H-pyran-4-yl)-1H-pyrazol-5-yl)pyrrolo[2,1-f][1,2,4]triazin-7-yl)benzyl)piperazin-1-yl)ethanone | 0.14 501.2 Method I |
| 168 | ![structure] | 4-(3-(4-amino-5-(1-(tetrahydro-2H-pyran-4-yl)-1H-pyrazol-5-yl)pyrrolo[2,1-f][1,2,4]triazin-7-yl)benzyl)-1-methylpiperazin-2-one | 0.14 min 487.2 Method I |
| 169 | ![structure] | 7-(3-((methyl(tetrahydro-2H-pyran-4-yl)amino)methyl)phenyl)-5-(1-(tetrahydro-2H-pyran-4-yl)-1H-pyrazol-5-yl)pyrrolo[2,1-f][1,2,4]triazin-4-amine | 0.95 min 488.2 Method I |
| 170 | ![structure] | 7-(3-(((2-methoxyethyl)(methyl)amino)methyl)phenyl)-5-(1-(tetrahydro-2H-pyran-4-yl)-1H-pyrazol-5-yl)pyrrolo[2,1-f][1,2,4]triazin-4-amine | 0.97 min 447.3 Method I |

Example 171

(3R)-1-(1-(3-(4-Amino-5-(1-(tetrahydro-2H-pyran-4-yl)-1H-pyrazol-5-yl)pyrrolo[2,1-f][1,2,4]triazin-7-yl)phenyl)ethyl)pyrrolidin-3-ol

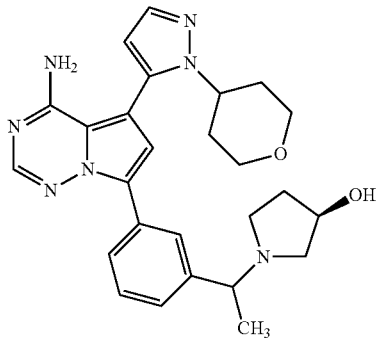

(171)

Intermediate 171A: 7-(3-(1-Chloroethyl)phenyl)-5-(1-(tetrahydro-2H-pyran-4-yl)-1H-pyrazol-5-yl)pyrrolo[2,1-f][1,2,4]triazin-4-amine

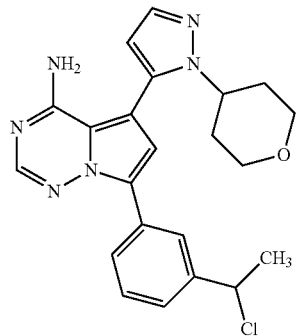

(171A)

A solution of Intermediate N42 (200 mg, 0.494 mmol) in DCM (5 mL) was cooled to 0° C. and thionyl chloride (39.7 μl, 0.544 mmol) was added. The mixture was stirred at room temperature for 1.5 h and then cooled to 0° C. Thionyl chloride (39.7 μl, 0.544 mmol) was added. The reaction mixture was stirred for 30 min at room temperature and then quenched by the dropwise addition of DIPEA (130 μl, 0.742 mmol). The mixture was concentrated to dryness providing 7-(3-(1-chloroethyl)phenyl)-5-(1-(tetrahydro-2H-pyran-4-yl)-1H-pyrazol-5-yl)pyrrolo[2,1-f][1,2,4]triazin-4-amine as a crude oil. LC/MS: 0.88 min, [M+1]$^+$=423.3, 425.2 Method M.

Example 171

(R)-Pyrrolidin-3-ol (16.5 mg, 0.189 mmol), 7-(3-(1-chloroethyl)phenyl)-5-(1-(tetrahydro-2H-pyran-4-yl)-1H-pyrazol-5-yl)pyrrolo[2,1-f][1,2,4]triazin-4-amine (40 mg, 0.095 mmol), and DIPEA (18.3 mg, 0.142 mmol) were combined in ACN (0.5 mL) and the mixture was heated at 80° C. for 18 h. The mixture was cooled to room temperature and purified by preparative HPLC (Method D). The appropriate fraction was concentrated, treated with saturated NaHCO$_3$ and extracted with ethyl acetate. The organic layer was dried, and concentrated to provide (3R)-1-(1-(3-(4-amino-5-(1-(tetrahydro-2H-pyran-4-yl)-1H-pyrazol-5-yl)pyrrolo[2,1-f][1,2,4]triazin-7-yl)phenyl) ethyl)pyrrolidin-3-ol (41 mg, 0.083 mmol, 88% yield) as a mixture of diastereomers, white solid as a free base. LC/MS: 0.59 min, [M+1]$^+$=474.3, Method M.

The following compounds were prepared according to the general synthesis procedure for Example 171.

TABLE 23

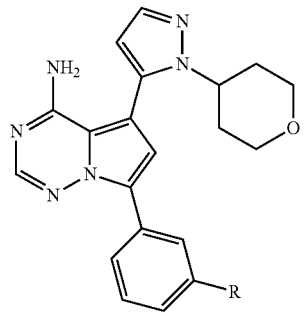

| Ex. No. | R | Name | LC/MS RT [M + 1] Method |
|---|---|---|---|
| 172 | ![morpholine with two CH3 groups and attachment via CH(CH3)] | 7-(3-(1-(3,3-dimethylmorpholino)ethyl)phenyl)-5-(1-(tetrahydro-2H-pyran-4-yl)-1H-pyrazol-5-yl)pyrrolo[2,1-f][1,2,4]triazin-4-amine | 1.64 min 500.2 Method H |

TABLE 23-continued

| Ex. No. | R | Name | LC/MS RT [M + 1] Method |
|---|---|---|---|
| 173 | 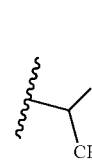 | 1-(4-(1-(3-(4-amino-5-(1-(tetrahydro-2H-pyran-4-yl)-1H-pyrazol-5-yl)pyrrolo[2,1-f][1,2,4]triazin-7-yl)phenyl)ethyl)piperazin-1-yl)ethanone | 1.35 min 515.2 Method H |
| 174 | 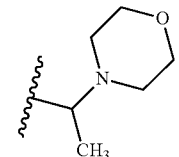 | 7-(3-(1-(3-methoxypyrrolidin-1-yl)ethyl)phenyl)-5-(1-(tetrahydro-2H-pyran-4-yl)-1H-pyrazol-5-yl)pyrrolo[2,1-f][1,2,4]triazin-4-amine | 1.24 min 588.4 Method H |
| 175 | 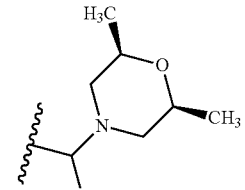 | 7-(3-(1-morpholinoethyl)phenyl)-5-(1-(tetrahydro-2H-pyran-4-yl)-1H-pyraozl-5-yl)pyrrolo[2,1-f][1,2,4]triazin-4-amine | 0.60 min 474.5 Method M |
| 176 | 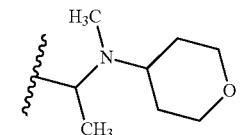 | 7-(3-(1-((cis)-2,6-dimethymorpholino)ethyl)phenyl)-5-(1-(tetrahydro-2H-pyran-4-yl)-1H-pyrazol-5-yl)pyrrolo[2,1-f][1,2,4]triazin-4-amine | 0.63 min 502.5 Method M |
| 177 | 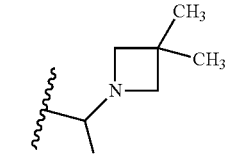 | 7-(3-(1-(methyl(tetrahydro-2H-pyran-4-yl)amino)ethyl)phenyl)-5-(1-(tetrahydro-2H-pyran-4-yl)-1H-pyrazol-5-yl)pyrrolo[2,1-f][1,2,4]triazin-4-amine | 1.02 min 502.3 Method I |
| 178 |  | 7-(3-(1-(3,3-dimethylazetidin-1-yl)ethyl)phenyl)-5-(1-(tetrahydro-2H-pyran-4-yl)-1H-pyrazol-5-yl)pyrrolo[2,1-f][1,2,4]triazin-4-amine | 1.10 min 472.3 Method I |

TABLE 23-continued

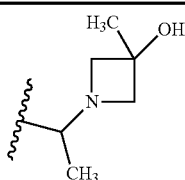

| Ex. No. | R | Name | LC/MS RT [M + 1] Method |
|---|---|---|---|
| 179 | H₃C, OH (on azetidine with N-CH(CH₃)- linker) | 1-(1-(3-(4-amino-5-(1-(tetrahydro-2H-pyran-4-yl)-1H-pyrazol-5-yl)pyrrolo[2,1-f][1,2,4]triazin-7-yl)phenyl)ethyl)-3-methylazetidin-3-ol | 0.86 min 474.3 Method I |

Example 180

7-(3-(2-Morpholinopropan-2-yl)phenyl)-5-(1-(tetrahydro-2H-pyran-4-yl)-1H-pyrazol-5-yl)pyrrolo[2,1-f][1,2,4]triazin-4-amine (180)

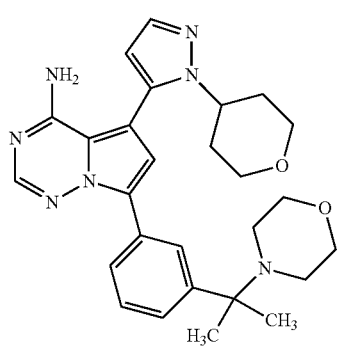

The title compound was prepared according to the general synthesis procedure for Example 98 employing 2-(3-bromophenyl)propan-2-amine as a starting material. ¹H NMR (400 MHz, CDCl₃) δ 8.20 (t, J=1.7 Hz, 1H), 8.06 (s, 1H), 7.87 (dt, J=7.9, 1.2 Hz, 1H), 7.70 (d, J=1.5 Hz, 1H), 7.58 (dt, J=8.1, 1.3 Hz, 1H), 7.50-7.42 (m, 1H), 6.87 (s, 1H), 6.41 (d, J=1.5 Hz, 1H), 5.33 (s, 2H), 4.34 (tt, J=11.5, 4.1 Hz, 1H), 4.06 (d, J=9.5 Hz, 2H), 3.75-3.68 (m, 4H), 3.45-3.33 (m, 2H), 2.61-2.52 (m, 4H), 2.45-2.32 (m, 2H), 1.42 (s, 6H), 1.25 (s, 4H). LC/MS: 0.58 min, [M+1]⁺=488.4, Method M.

Example 181

5-(1-(Tetrahydro-2H-pyran-4-yl)-1H-pyrazol-5-yl)-7-(3-(2,2,2-trifluoro-1-morpholinoethyl)phenyl)pyrrolo[2,1-f][1,2,4]triazin-4-amine (181)

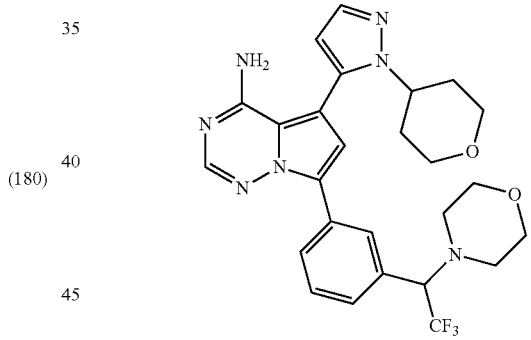

Intermediate 181A: Bis-(boc)-3-(4-amino-5-(1-(tetrahydro-2H-pyran-4-yl)-1H-pyrazol-5-yl)pyrrolo[2,1-f][1,2,4]triazin-7-yl)benzaldehyde (181A)

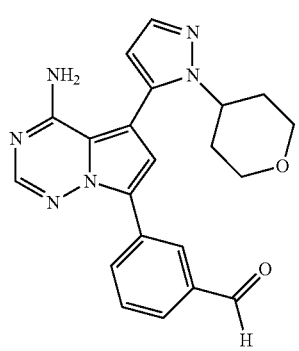

Intermediate 14-B (422 mg, 0.749 mmol), (3-formylphenyl)boronic acid (112 mg, 0.749 mmol) and phosphoric acid, potassium salt (636 mg, 3.00 mmol) were combined in a vial. THF (6809 µl) and water (681 µl) were added and the vessel was sealed, evacuated, backfilled with $N_2$ and then degassed by bubbling $N_2$ with sonication. Tetrakistriphenylphosphine (130 mg, 0.112 mmol) was added and the degassing process was repeated. The mixture was heated at 80° C. for 2 h and then the solvent was removed in vacuo. The residue was diluted with ethyl acetate (20 mL), washed with water (10 mL) and the organic portion was dried over magnesium sulfate and concentrated. The crude product was purified by silica gel chromatography eluting with 0-50% ethyl acetate in hexanes providing bis-(boc)-3-(4-amino-5-(1-(tetrahydro-2H-pyran-4-yl)-1H-pyrazol-5-yl)pyrrolo[2,1-f][1,2,4]triazin-7-yl)benzaldehyde (406 mg, 92% yield) as a yellow solid. $^1$H NMR (400 MHz, chloroform-d) δ 10.15 (s, 1H), 8.59-8.57 (m, 2H), 8.35 (dq, J=7.8, 1.0 Hz, 1H), 7.97 (dt, J=7.7, 1.3 Hz, 1H), 7.76-7.70 (m, 1H), 7.63 (d, J=1.8 Hz, 1H), 7.21 (s, 1H), 6.35 (d, J=1.8 Hz, 1H), 4.42 (tt, J=11.5, 4.1 Hz, 1H), 4.05 (dd, J=11.2, 3.7 Hz, 2H), 3.45-3.34 (m, 2H), 2.36 (qd, J=12.4, 4.7 Hz, 2H), 1.92-1.81 (m, 2H), 1.44 (s, 18H). LC/MS: 1.13 min, [M+1]$^+$=589 Method F.

Intermediate 181B: Bis-(Boc)-1-(3-(4-amino-5-(1-(tetrahydro-2H-pyran-4-yl)-1H-pyrazol-5-yl)pyrrolo[2,1-f][1,2,4]triazin-7-yl)phenyl)-2,2,2-trifluoroethanol

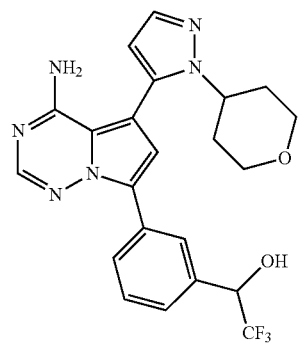

(181B)

Under anhydrous conditions a solution of bis-(Boc)-(7-(3-formylphenyl)-5-(1-(tetrahydro-2H-pyran-4-yl)-1H-pyrazol-5-yl)pyrrolo[2,1-f][1,2,4]triazin-4-yl)carbamate (106 mg, 0.180 mmol) in THF (1.8 mL) was cooled to 0° C. and treated with trimethyl (trifluoromethyl)silane (0.038 ml, 0.270 mmol). The mixture was stirred briefly at 0° C., treated with cesium fluoride (0.012 g, 0.082 mmol) and stirred at room temperature overnight. The reaction was quenched by the addition of saturated ammonium chloride (2 mL), diluted with water (5 mL) and extracted with 2x10 mL of ethyl acetate. The organic portion was dried over magnesium sulfate and concentrated providing crude bis-(Boc)-1-(3-(4-amino-5-(1-(tetrahydro-2H-pyran-4-yl)-1H-pyrazol-5-yl)pyrrolo[2,1-f][1,2,4]triazin-7-yl)phenyl)-2,2,2-trifluoroethanol (123 mg) as a crude oil. LC/MS: 1.12 min, [M+1]$^+$=659 Method F.

Intermediate 181C: Bis-(boc)-1-(3-(4-amino-5-(1-(tetrahydro-2H-pyran-4-yl)-1H-pyrazol-5-yl)pyrrolo[2,1-f][1,2,4]triazin-7-yl)phenyl)-2,2,2-trifluoroethyl trifluoromethanesulfonate

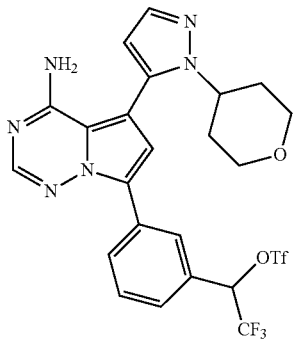

(181C)

Under anhydrous conditions a solution of bis-(Boc)-1-(3-(4-amino-5-(1-(tetrahydro-2H-pyran-4-yl)-1H-pyrazol-5-yl)pyrrolo[2,1-f][1,2,4]triazin-7-yl)phenyl)-2,2,2-trifluoroethanol (50 mg, 0.076 mmol) in DCM (1 mL) was cooled to 0° C. Triflic anhydride (0.114 mL, 0.114 mmol) was added dropwise followed by 2,6-lutidine (0.141 mL, 0.121 mmol). The resulting mixture was stirred for 45 min at 0° C. after which it was concentrated under reduced pressure providing crude bis-(Boc)1-(3-(4-amino-5-(1-(tetrahydro-2H-pyran-4-yl)-1H-pyrazol-5-yl)pyrrolo[2,1-f][1,2,4]triazin-7-yl)phenyl)-2,2,2-trifluoroethyl trifluoromethanesulfonate as a yellow oil.

Example 181

Under anhydrous conditions a solution of morpholine (0.250 mL, 2.87 mmol) in THF (1 mL)) was cooled to −78° C. N-butyllithium was added dropwise and the mixture was stirred at −78° C. for 30 min. A solution of bis-(Boc)1-(3-(4-amino-5-(1-(tetrahydro-2H-pyran-4-yl)-1H-pyrazol-5-yl)pyrrolo[2,1-f][1,2,4]triazin-7-yl)phenyl)-2,2,2-trifluoroethyl trifluoromethanesulfonate in THF (0.5 mL) was added dropwise and the mixture was stirred at −78° C. for 30 min and at room temperature overnight. The reaction mixture was quenched with water (2 mL) and extracted with ethyl acetate (5 mL). The organic portion was dried over magnesium sulfate and concentrated. The crude residue was treated with a solution of TFA (20% solution in DCM) and this mixture was stirred for 30 min at room temperature. The mixture was concentrated and the residue was purified by preparative HPLC (Method D) providing 5-(1-(tetrahydro-2H-pyran-4-yl)-1H-pyrazol-5-yl)-7-(3-(2,2,2-trifluoro-1-morpholinoethyl)phenyl)pyrrolo[2,1-f][1,2,4]triazin-4-amine (4.4 mg, 7.51 µmol). $^1$H NMR (500 MHz, chloroform-d) δ 8.13-8.04 (m, 3H), 7.71 (d, J=1.7 Hz, 1H), 7.56 (t, J=7.8 Hz, 1H), 7.45 (d, J=7.8 Hz, 1H), 6.95-6.88 (m, 1H), 6.46-6.39 (m, 1H), 5.43 (br. s., 2H), 4.34 (tt, J=11.5, 4.0 Hz, 1H), 4.13-4.00 (m, 3H), 3.79-3.69 (m, 4H), 3.42 (t, J=12.2 Hz, 2H), 2.78-2.63 (m, 4H), 2.40 (d, J=10.0 Hz, 2H), 1.83 (br. s., 2H). LC/MS: 0.86 min, [M+1]$^+$=528 Method F.

Example 182

7-(3-(2-(Dimethylamino)propan-2-yl)phenyl)-5-(1-(tetrahydro-2H-pyran-4-yl)-1H-1,2,3-triazol-5-yl)pyrrolo[2,1-f][1,2,4]triazin-4-amine

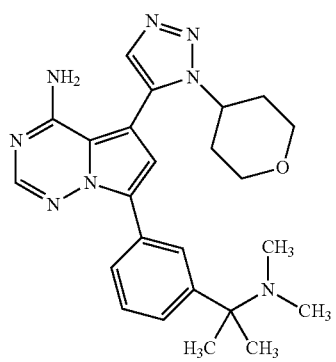

(182)

7-Bromo-5-(1-(tetrahydro-2H-pyran-4-yl)-1H-1,2,3-triazol-5-yl)pyrrolo[2,1-f][1,2,4]triazin-4-amine (Intermediate R1) (100 mg, 0.275 mmol), N,N-dimethyl-2-(3-(4,4,5,5-tetramethyl-1,3,2-dioxaborolan-2-yl)phenyl)propan-2-amine (119 mg, 0.412 mmol) and phosphoric acid, potassium salt (175 mg, 0.824 mmol) were dissolved in a mixture of dioxane (5 mL) and water (2.5 mL). The vessel was evacuated, backfilled with $N_2$ and then degassed by bubbling $N_2$ with sonication. Tetrakis triphenyl phosphine (47.6 mg, 0.041 mmol) was added and the degassing process was repeated. The reaction mixture was heated at 140° C. in a microwave for 1 hr. The reaction mixture was cooled, filtered, washed with water. The filtrate was extracted with ethyl acetate (20 mL×3). The organic layers were combined, dried and concentrated. The residue was purified by ISCO purification (12 g column, 0-10% MeOH/DCM solvent, 30 min gradient) to afford 7-(3-(2-(dimethylamino)propan-2-yl)phenyl)-5-(1-(tetrahydro-2H-pyran-4-yl)-1H-1,2,3-triazol-5-yl)pyrrolo[2,1-f][1,2,4]triazin-4-amine (100 mg, 77% yield). LCMS $(M+H)^+$=447.3. $^1$H NMR (500 MHz, $CDCl_3$) δ 1.45 (s, 9H), 1.95 (m, 2H), 2.25 (s, 9H), 2.47 (m, 2H), 3.46 (m, 2H), 4.10 (m, 2H), 4.53 (m, 1H), 6.93 (S, 1H), 7.48 (t, 1H), 7.57 (d, 1H), 7.83 (S, 1H), 7.93 (d, 1H), 8.08 (s, 1H), 8.13 (s, 1H).

The Examples in Table 24 were synthesized according to the general synthesis procedure for Example 182 by using appropriate starting materials or intermediates. Example 186 and Example 187 were respectively obtained by amide coupling and reductive amination with Example 185 by procedures known to those skilled in the art.

TABLE 24

| Ex. No. | Q₁ | Q₂ | Name | [M + H]⁺ | HPLC R₁ (min) [Method] |
|---|---|---|---|---|---|
| 183 | | | 7-(3-(2-(diethylamino)propan-2-yl)phenyl)-5-(1-(tetrahydro-2H-pyran-4-yl)-1H-1,2,3-triazol-5-yl)pyrrolo[2,1-f][1,2,4]triazin-4-amine | 475.20 | 1.242 [H] |
| 184 | | | 1-((2S,4R)-2-(3-(4-amino-5-(1-isopropyl-1H-1,2,3-triazol-5-yl)pyrrolo[2,1-f][1,2,4]triazin-7-yl)phenyl)-4-hydroxypyrrolidin-1-yl)ethanone | 447.10 | 1.13 [H] |
| 185 | | | 7-(3-(piperidin-4-yl)phenyl)-5-(1-(tetrahydro-2H-pyran-4-yl)-1H-1,2,3-triazol-5-yl)pyrrolo[2,1-f][1,2,4]triazin-4-amine | 445.30 | 0.91 [H] |

TABLE 24-continued

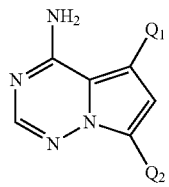

| Ex. No. | Q₁ | Q₂ | Name | [M + H]⁺ | HPLC R₁ (min) [Method] |
|---|---|---|---|---|---|
| 186 | (1-(tetrahydro-2H-pyran-4-yl)-1H-1,2,3-triazol-5-yl) | (3-(1-acetylpiperidin-4-yl)phenyl) | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-1-yl)ethanone | 517.20 | 1.363 [H] |
| 187 | (1-(tetrahydro-2H-pyran-4-yl)-1H-1,2,3-triazol-5-yl) | (3-(1-methylpiperidin-4-yl)phenyl) | 7-(3-(1-methylpiperidin-4-yl)phenyl)-5-(1-(tetrahydro-2H-pyran-4-yl)-1H-1,2,3-triazol-5-yl)pyrrolo[2,1-f][1,2,4]triazin-4-amine | 459.20 | 0.90 [H] |
| 188 | (1-isopropyl-1H-1,2,3-triazol-5-yl) | (3-(1-methylpiperidin-4-yl)phenyl) | 5-(1-isopropyl-1H-1,2,3-triazol-5-yl)-7-(3-(1-methylpiperidin-4-yl)phenyl)pyrrolo[2,1-f][1,2,4]triazin-4-amine | 417.20 | 0.97 [H] |

Example 189

4-(3-(4-Amino-5-(1-(tetrahydro-2H-pyran-4-yl)-1H-1,2,3-triazol-5-yl)pyrrolo[2,1-f][1,2,4]triazin-7-yl)benzyl)morpholin-3-one

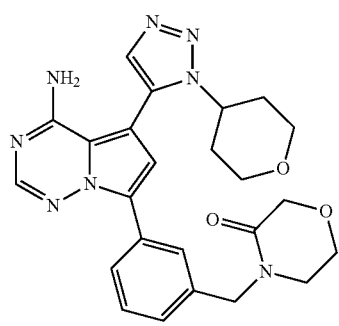

(189)

To a suspension of morpholin-3-one (29 mg, 0.288 mmol) in THF (2 mL) was added NaH (16.14 mg, 0.336 mmol). After stirring the mixture for 5 min, (3-(bromomethyl)phenyl)boronic acid (41.3 mg, 0.192 mmol) was added and the resulting mixture was stirred at room temperature for 2 h. Water (1 mL) was added, followed by phosphoric acid, potassium salt (61.2 mg, 0.288 mmol) and 7-bromo-5-(1-(tetrahydro-2H-pyran-4-yl)-1H-1,2,3-triazol-5-yl)pyrrolo[2,1-f][1,2,4]triazin-4-amine (35 mg, 0.096 mmol). The reaction vessel was evacuated, backfilled with $N_2$ and then degassed by bubbling $N_2$ while being sonicated. Tetrakis triphenylphosphine (11.11 mg, 9.61 µmol) was added and the degassing process was repeated. The reaction mixture was heated at 140° C. in a microwave for 1 h. The reaction mixture was cooled, filtered, washed with water and extracted with ethyl acetate (10 mL×3). The organic layers were combined, dried and concentrated. The residue purified by preparative LCMS method C to obtain 4-(3-(4-amino-5-(1-(tetrahydro-2H-pyran-4-yl)-1H-1,2,3-triazol-5-yl)pyrrolo[2,1-f][1,2,4] triazin-7-yl)benzyl)morpholin-3-one (5.3 mg, 11% yield). LC/MS (M+H)⁺=475.15. ¹H NMR (500 MHz, DMSO-d₆) δ 2.0 (m, 2H), 2.16 (m, 2H), 3.32 (t, 2H), 3.37 (m, 2H), 3.85 (t, 2H), 3.93 (m, 3H), 4.14 (s, 2H), 4.64 (s, 2H), 7.27 (m, 2H), 7.50 (t, 1H), 7.87 (s, 1H), 7.96 (m, 2H), 8.10 (m, 1H).

Example 190

7-(3-((Methyl(tetrahydro-2H-pyran-4-yl)amino)methyl)phenyl)-5-(1-(tetrahydro-2H-pyran-4-yl)-1H-1,2,3-triazol-5-yl)pyrrolo[2,1-f][1,2,4]triazin-4-amine

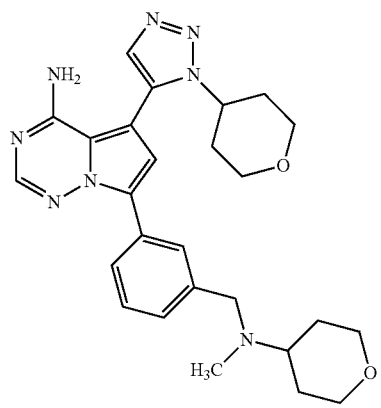

(190)

N-Methyltetrahydro-2H-pyran-4-amine (19 mg, 0.165 mmol) and (3-(bromomethyl)phenyl)boronic acid (23.60 mg, 0.111 mmol) were suspended in acetonitrile (2 mL). $K_2CO_3$ (37.9 mg, 0.275 mmol) was added, then the reaction mixture was stirred at room temperature for 10 h. The reaction mixture was concentrated, dioxane (1 mL) and water (0.5 mL), phosphoric acid, potassium salt (46.6 mg, 0.22 mmol) and 7-bromo-5-(1-(tetrahydro-2H-pyran-4-yl)-1H-1,2,3-triazol-5-yl)pyrrolo[2,1-f][1,2,4]triazin-4-amine (20 mg, 0.055 mmol) (Intermediate R1) were added to the residue. The reaction vessel was evacuated, backfilled with $N_2$ and then degassed by bubbling $N_2$ while being sonicated. Tetrakis triphenylphosphine (7 mg, 5.49 μmol) was added and the degassing process was repeated. The reaction mixture was heated at 140° C. in a microwave for 45 min. The reaction complex was filtered, washed with water and extracted with ethyl acetate (10 mL×3). The organic layers were combined, dried and concentrated. The crude mixture was purified by preparative LC method C to provide 7-(3-((methyl (tetrahydro-2H-pyran-4-yl)amino)methyl)phenyl)-5-(1-(tetrahydro-2H-pyran-4-yl)-1H-1,2,3-triazol-5-yl)pyrrolo[2,1-f][1,2,4]triazin-4-amine (8.2 mg, 41% yield). LC/MS $(M+H)^+=489.30$. $^1H$ NMR (500 MHz, MeOD) δ 1.72 (m, 2H), 1.85 (m, 2H), 2.01 (m, 2H), 2.29 (s, 3H), 2.42 (m, 2H), 2.75 (m, 1H), 3.42 (m, 2H), 3.47 (m, 2H), 3.73 (s, 2H), 4.06 (m, 4H), 4.56 (m, 1H), 6.97 (s, 1H), 7.37 (d, 2H), 7.47 (t, 1H), 7.84 (s, 1H), 7.95 (m, 2H), 8.01 (s, 1H).

The Examples in Table 25 were synthesized according to the general synthesis procedures for Example 189 or Example 190, using appropriate starting materials and intermediates. Example 192 was obtained by sulfonylation (sulfonyl chloride) with the corresponding intermediate obtained by removing the Boc group from Intermediate R46, 7-(3-((azetidin-3-yl(cyclopropyl)amino) methyl)phenyl)-5-(1-(tetrahydro-2H-pyran-4-yl)-1H-1,2,3-triazol-5-yl) pyrrolo[2,1-f][1,2,4]triazin-4-amine.

TABLE 25

| Ex. No. | $Q_1$ | $Q_2$ | Name | $[M + H]^+$ | HPLC $R_t$ (min) [Method] |
|---|---|---|---|---|---|
| 191 | ![pyrazole-THP] | ![benzyl-N-methyl-oxetanyl] | 7-(3-((methyl(oxetan-3-yl)amino)methyl)phenyl)-5-(1-(tetrahydro-2H-pyran-4-yl)-1H-pyrazol-5-yl)pyrrolo[2,1-f][1,2,4]triazin-4-amine | 460.15 | 0.930 [I] |

TABLE 25-continued

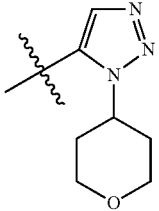

| Ex. No. | Q₁ | Q₂ | Name | [M + H]⁺ | HPLC R_t (min) [Method] |
|---|---|---|---|---|---|
| 192 | 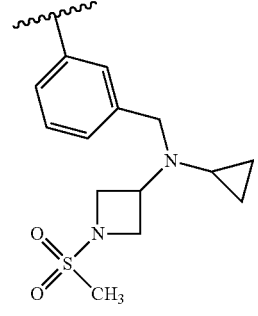 [SMILES: *c1cccc(CN(C2CC2)C2CN(S(C)(=O)=O)C2)c1] | 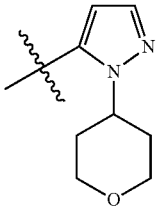 [SMILES: *c1ccnn1C1CCOCC1] | 7-(3-((cyclopropyl(1-(methylsulfonyl)azetidin-3-yl)amino)methyl)phenyl)-5-(1-(tetrahydro-2H-pyran-4-yl)-1H-1,2,3-triazol-5-yl)pyrrolo[2,1-f][1,2,4]triazin-4-amine | 564.15 | 1.58 [H] |
| 193 | 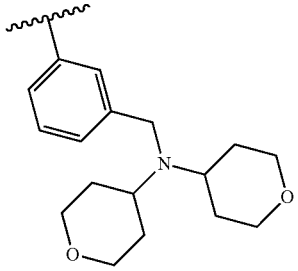 [SMILES: *c1cccc(CN(C2CCOCC2)C2CCOCC2)c1] | 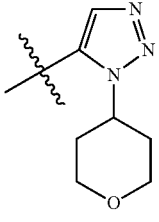 [SMILES: *c1cnnn1C1CCOCC1] | 7-(3-((bis(tetrahydro-2H-pyran-4-yl)amino)methyl)phenyl)-5-(1-(tetrahydro-2H-pyran-4-yl)-1H-pyrazol-5-yl)pyrrolo[2,1-f][1,2,4]triazin-4-amine | 558.25 | 1.621 [H] |
| 194 | 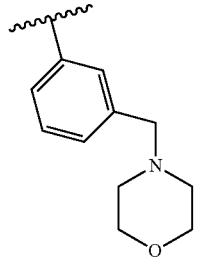 [SMILES: *c1cccc(CN2CCOCC2)c1] | 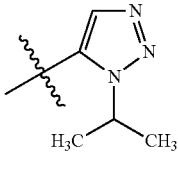 [SMILES: *c1cnnn1C(C)C] | 7-(3-(morpholinomethyl)phenyl)-5-(1-(tetrahydro-2H-pyran-4-yl)-1H-1,2,3-triazol-5-yl)pyrrolo[2,1-f][1,2,4]triazin-4-amine | 461.15 | 1.349 [H] |
| 195 | 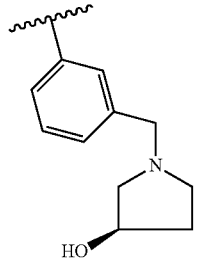 [SMILES: *c1cccc(CN2CC[C@@H](O)C2)c1] | | (R)-1-(3-(4-amino-5-(1-isopropyl-1H-1,2,3-triazol-5-yl)pyrrolo[2,1-f][1,2,4]triazin-7-yl)benzyl)pyrrolidin-3-ol | 419.10 | 1.039 [H] |

Example 196

4-(3-(4-Amino-5-(1-(tetrahydro-2H-pyran-4-yl)-1H-pyrazol-5-yl)pyrrolo[2,1-f][1,2,4]triazin-7-yl)phenoxy)tetrahydro-2H-thiopyran 1,1-dioxide

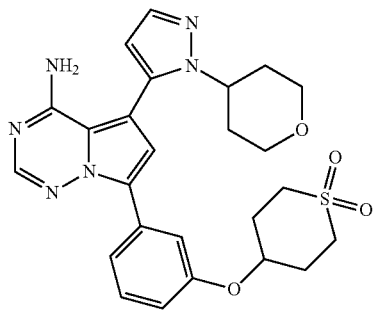

(196)

To a solution of 4-(3-bromophenoxy)tetrahydro-2H-thiopyran 1,1-dioxide (Intermediate R28) (30 mg, 0.098 mmol) in dioxane (2 mL) were added 4,4,4',4',5,5,5',5'-octamethyl-2,2'-bi(1,3,2-dioxaborolane) (31.8 mg, 0.125 mmol), potassium acetate (35.1 mg, 0.357 mmol), and PdCl$_2$(dppf)-CH$_2$Cl$_2$ adduct (10.95 mg, 0.013 mmol). The microwave reaction vessel was evacuated, backfilled with N$_2$ and then degassed by bubbling N$_2$ while being sonicated. The sealed reaction vessel was treated at 120° C. in a microwave for 30 min. The reaction mixture was cooled, water (1 mL), 7-bromo-5-(1-(tetrahydro-2H-pyran-4-yl)-1H-pyrazol-5-yl)pyrrolo[2,1-f][1,2,4]triazin-4-amine (32.5 mg, 0.089 mmol), Na$_2$CO$_3$ (0.134 mL, 0.134 mmol, 1M) and additional PdCl$_2$(dppf)-CH$_2$Cl$_2$ adduct (10.95 mg, 0.013 mmol) were added. The microwave reaction vessel was filled with N$_2$ and heated at 120° C. in a microwave for 40 min. The reaction mixture was filtered, washed with water, and extracted with ethyl acetate (10 mL×3). The organic layers were combined, dried and concentrated. The crude residue was purified by preparative LC method C to provide 4-(3-(4-amino-5-(1-(tetrahydro-2H-pyran-4-yl)-1H-pyrazol-5-yl)pyrrolo[2,1-f][1,2,4]triazin-7-yl)phenoxy)tetrahydro-2H-thiopyran 1,1-dioxide (24.3 mg, 0.047 mmol, 52.4% yield). LC/MS (M+H)$^+$=509.20. $^1$H NMR (500 MHz, DMSO-d$_6$) δ 1.80 (m, 2H), 2.09 (m, 2H), 2.25 (m, 2H), 3.18 (m, 4H), 3.32 (m, 1H), 3.43 (m, 1H), 3.90 (d, 2H), 4.35 (m, 1H), 4.80 (s, 1H), 6.45 (s, 1H), 7.06 (d, 1H), 7.43 (t, 1H), 7.68 (s, 1H), 7.77 (m, 2H), 7.95 (s, 1H), 8.107 (s, 1H).

Following Examples in Table 26 were synthesized in a manner similar to procedures described for the syntheses of Example 196, using appropriate starting materials or intermediates. Examples 201 to 203 and 205 were obtained by amide coupling or reductive-amination of Examples 199 and 200, respectively.

TABLE 26

| Ex. No. | R | Q$_1$ | Name | [M + H]$^+$ | HPLC R$_t$ (min) [Method] |
|---|---|---|---|---|---|
| 196 | (tetrahydro-2H-thiopyran 1,1-dioxide) | (1-(tetrahydro-2H-pyran-4-yl)-1H-pyrazol-5-yl) | 4-(3-(4-amino-5-(1-(tetrahydro-2H-pyran-4-yl)-1H-pyrazol-5-yl)pyrrolo[2,1-f][1,2,4]triazin-7-yl)phenoxy)tetrahydro-2H-thiopyran 1,1-dioxide | 509.20 | 1.19 [H] |
| 197 | (tetrahydro-2H-pyran-4-yl) | (1-(tetrahydro-2H-pyran-4-yl)-1H-pyrazol-5-yl) | 5-(1-(tetrahydro-2H-pyran-4-yl)-1H-pyrazol-5-yl)-7-(3-((tetrahydro-2H-pyran-4-yl)oxy)phenyl)pyrrolo[2,1-f][1,2,4]triazin-4-amine | 461.30 | 1.31 [H] |

TABLE 26-continued

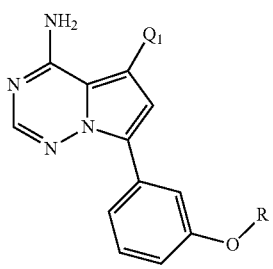

| Ex. No. | R | Q₁ | Name | [M + H]⁺ | HPLC R_t (min) [Method] |
|---|---|---|---|---|---|
| 198 | 2,6-dimethyltetrahydro-2H-pyran-4-yl | 1-(tetrahydro-2H-pyran-4-yl)-1H-pyrazol-5-yl | 7-(1-(2,6-dimethyltetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine | 513.30 | 1.44 [H] |
| 199 | piperidin-4-yl | 1-(tetrahydro-2H-pyran-4-yl)-1H-1,2,3-triazol-5-yl | 7-(3-(piperidin-4-yloxy)phenyl)-5-(1-(tetrahydro-2H-pyran-4-yl)-1H-1,2,3-triazol-5-yl)pyrrolo[2,1-f][1,2,4]triazin-4-amine | 461.30 | 0.90 [H] |
| 200 | piperidin-4-yl | 1-(tetrahydro-2H-pyran-4-yl)-1H-pyrazol-5-yl | 7-(3-(piperidin-4-yloxy)phenyl)-5-(1-(tetrahydro-2H-pyran-4-yl)-1H-pyrazol-5-yl)pyrrolo[2,1-f][1,2,4]triazin-4-amine | 460.20 | 1.00 [H] |
| 201 | 1-methylpiperidin-4-yl | 1-(tetrahydro-2H-pyran-4-yl)-1H-1,2,3-triazol-5-yl | 7-(3-((1-methylpiperidin-4-yl)oxy)phenyl)-5-(1-(tetrahydro-2H-pyran-4-yl)-1H-1,2,3-triazol-5-yl)pyrrolo[2,1-f][1,2,4]triazin-4-amine | 475.10 | 1.082 [H] |
| 202 | 1-methylpiperidin-4-yl | 1-(tetrahydro-2H-pyran-4-yl)-1H-pyrazol-5-yl | 7-(3-((1-methylpiperidin-4-yl)oxy)phenyl)-5-(1-(tetrahydro-2H-pyran-4-yl)-1H-pyrazol-5-yl)pyrrolo[2,1-f][1,2,4]triazin-4-amine | 474.15 | 1.176 [H] |

TABLE 26-continued

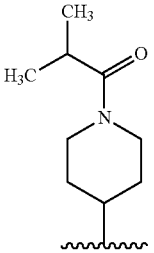

| Ex. No. | R | Q₁ | Name | [M + H]⁺ | HPLC R_t (min) [Method] |
|---|---|---|---|---|---|
| 203 | 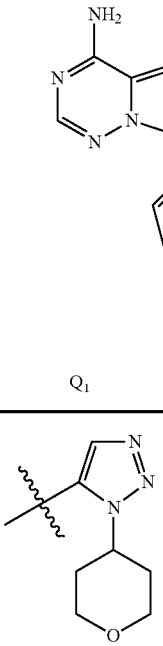 | 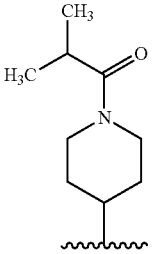 | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenoxy)piperidin-1-yl)-2-methylpropan-1-one | 531.30 | 1.51 [H] |
| 204 | 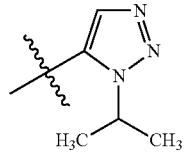 | 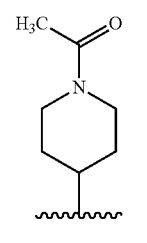 [SMILES: *C1CCN(C(C)=O)CC1] | 1-(4-(3-(4-amino-5-(1-isopropyl-1H-1,2,3-triazol-5-yl)pyrrolo[2,1-f][1,2,4]triazin-7-yl)phenoxy)piperidin-1-yl)-2-methylpropan-1-one | 489.30 | 1.73 [H] |
| 205 | 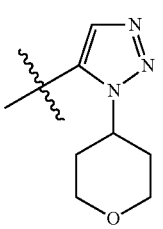 | 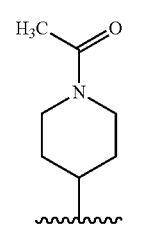 | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenoxy)piperidin-1-yl)ethanone | 503.20 | 1.37 [H] |
| 206 | 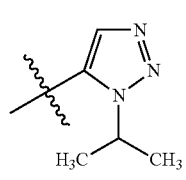 | | 1-(4-(3-(4-amino-5-(1-isopropyl-1H-1,2,3-triazol-5-yl)pyrrolo[2,1-f][1,2,4]triazin-7-yl)phenoxy)piperidin-1-yl)ethanone | 461.20 | 1.37 [H] |

Example 207

5-(3-(4-Amino-5-(1-(tetrahydro-2H-pyran-4-yl)-1H-pyrazol-5-yl)pyrrolo[2,1-f][1,2,4]triazin-7-yl)phenyl)-1-methylpyridin-2(1H)-one

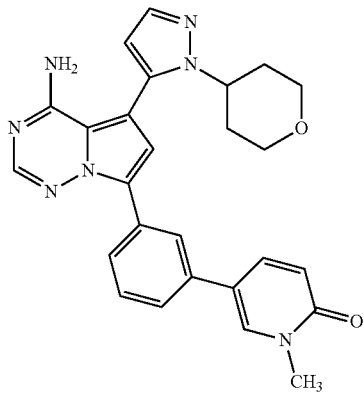

(207)

Intermediate 207A: 7-(3-Bromophenyl)-5-(1-(tetrahydro-2H-pyran-4-yl)-1H-pyrazol-5-yl)pyrrolo[2,1-f][1,2,4]triazin-4-amine

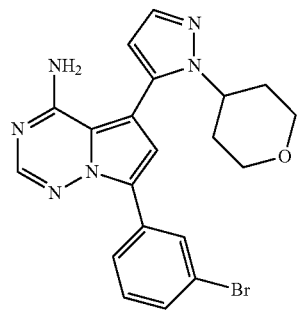

(207A)

A partial suspension of 7-bromo-5-(1-(tetrahydro-2H-pyran-4-yl)-1H-pyrazol-5-yl)pyrrolo[2,1-f][1,2,4]triazin-4-amine (Intermediate N1) (300 mg, 0.826 mmol), (3-bromophenyl)boronic acid (199 mg, 0.991 mmol), and phosphoric acid, potassium salt (701 mg, 3.30 mmol) in a mixture of dioxane (10 mL) and water (5 mL) was degassed with N₂ as described previously. Tetrakis triphenylphosphine (143 mg, 0.124 mmol) was added and the degassing process was repeated. The reaction mixture was heated at 120° C. in a microwave for 40 min. The reaction complex was filtered, washed with water, and extracted with ethyl acetate (20 mL×3). The organic layers were mixed, dried, concentrated and purified by ISCO silica gel column chromatography (12 g column, 0-100% EtOAc/hexane solvent, 20 min gradient) to obtain 7-(3-bromophenyl)-5-(1-(tetrahydro-2H-pyran-4-yl)-1H-pyrazol-5-yl)pyrrolo[2,1-f][1,2,4]triazin-4-amine (250 mg, 69% yield). LC/MS (M+H)⁺=439.2, 441.15 (1:1 ratio).

Example 207

7-(3-Bromophenyl)-5-(1-(tetrahydro-2H-pyran-4-yl)-1H-pyrazol-5-yl)pyrrolo [2,1-f][1,2,4]triazin-4-amine (20 mg, 0.046 mmol), 1-methyl-5-(4,4,5,5-tetramethyl-1,3,2-dioxaborolan-2-yl)pyridin-2(1H)-one (16.05 mg, 0.068 mmol), and Na₂CO₃ (0.068 mL, 0.068 mmol) were combined in a vial fitted with a septum. The mixture was dissolved in a mixture of dioxane (1.5 mL) and water (0.5 mL). The vessel was degassed with N₂ as described previously. PdCl₂(dppf)-CH₂Cl₂ adduct (5.58 mg, 6.83 μmol) was added and the degassing process was repeated. The reaction mixture was heated at 120° C. in a microwave for 30 min. The reaction complex was filtered, washed with water, and extracted with ethyl acetate (20 mL×3). The organic layers were mixed, dried, concentrated and purified by preparative LC method C to provide 5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyridin-2(1H)-one (6.5 mg, 29.6% yield). LCMS (M+H)⁺=468.15. ¹H NMR (500 MHz, DMSO-d₆) δ 1.81 (m, 2H), 2.10 (m, 2H), 3.32 (t, 2H), 3.49 (s, 3H), 3.88 (m, 2H), 4.36 (m, 1H), 6.47 (s, 1H), 6.53 (d, 1H), 7.35 (s, 1H), 7.57 (m, 2H), 7.69 (s, 1H), 7.92 (dd, 1H), 7.95 (s, 1H), 8.07 (s, 1H), 8.11 (d, 1H), 8.19 (s, 1H), 8.20 (s, 1H).

Example 208

5-(3-(4-Amino-5-(1-isopropyl-1H-1,2,3-triazol-5-yl)pyrrolo[2,1-f][1,2,4]triazin-7-yl) phenyl)-1-methylpyridin-2(1H)-one

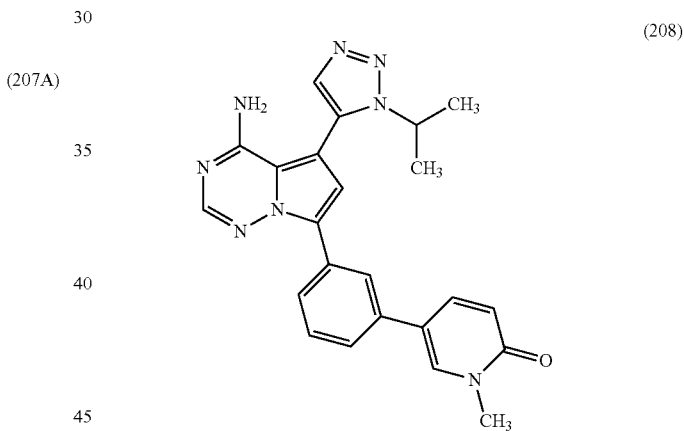

(208)

Intermediate 208A:
5-(3-Bromophenyl)-1-methylpyridin-2(1H)-one

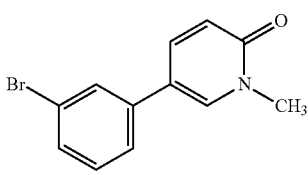

(208A)

To a solution of 5-bromo-1-methylpyridin-2(1H)-one (400 mg, 2.127 mmol) in dioxane (10 mL) was added 4,4,4',4',5,5,5',5'-octamethyl-2,2'-bi(1,3,2-dioxaborolane) (702 mg, 2.77 mmol), potassium acetate (626 mg, 6.38 mmol), and PdCl₂(dppf)-CH₂Cl₂ adduct (174 mg, 0.213 mmol). The microwave reaction vessel was degassed with N₂ as described previously. The sealed reaction vessel was heated at 120° C. in a microwave for 60 min. To the cooled reaction mixture were added 1,3-dibromobenzene (602 mg, 2.55 mmol), sodium carbonate (3.16 mL, 3.16 mmol, 1M) and additional PdCl₂(dppf)-CH₂Cl₂ adduct (174 mg, 0.213 mmol). The sealed reaction vessel was degassed and heated at 120° C. in a microwave for 60 min. The reaction mixture was filtered, washed with water, and extracted with ethyl acetate (20 mL×3). The organic layers were mixed, dried, concentrated and purified by ISCO purification (12 g column, 0-10% MeOH/DCM solvent, 15 min gradient) to provide 5-(3-bromophenyl)-1-methylpyridin-2(1H)-one (320 mg, 1.21 mmol, 57% yield). LC/MS (M+H)⁺=264.05, 266.05 (1:1 ratio).

Example 208

To a solution of 5-(3-bromophenyl)-1-methylpyridin-2 (1H)-one (25 mg, 0.095 mmol) in dioxane (1.5 mL) was added 4,4,4',4',5,5,5',5'-octamethyl-2,2'-bi(1,3,2-dioxaborolane) (33.7 mg, 0.133 mmol), potassium acetate (37.2 mg, 0.379 mmol), and PdCl₂(dppf)-CH₂Cl₂ adduct (11.59 mg, 0.014 mmol). The microwave reaction vessel was degassed with N₂ as described before. The sealed reaction vessel was heated at 120° C. in a microwave for 30 min. To the cooled reaction mixture were added, water (0.5 mL), 7-bromo-5-(1-isopropyl-1H-1,2,3-triazol-5-yl)pyrrolo[2,1-f][1,2,4]triazin-4-amine (34.5 mg, 0.095 mmol) (Intermediate R2), sodium carbonate (0.142 mL, 0.142 mmol, 1M) and additional PdCl₂(dppf)-CH₂Cl₂ adduct (11.59 mg, 0.014 mmol). The microwave reaction vessel was degassed again and was treated at 120° C. at microwave for 30 min. The reaction complex was filtered, washed with water, and extracted with ethyl acetate (20 mL×3). The organic layers were mixed, dried, concentrated and purified by preparative LC method C to provide 5-(3-(4-amino-5-(1-isopropyl-1H-1,2,3-triazol-5-yl)pyrrolo[2,1-f][1,2,4]triazin-7-yl)phenyl)-1-methylpyridin-2(1H)-one (5.4 mg, 12.7% yield). LCMS (M+H)⁺=427.25. ¹H NMR (500 MHz, DMSO-d) δ 1.49 (d, 6H), 3.50 (s, 3H), 4.65 (m, 1H), 6.53 (d, 1H), 7.35 (s, 1H), 7.58 (m, 2H), 7.88 (s, 1H), 7.92 (m, 1H), 8.09 (s, 1H), 8.16 (s, 1H), 8.20 (d, 1H).

The Examples in Table 27 were synthesized according to the general synthesis procedures for Example 207 and Example 208, using appropriate commercial materials and intermediates.

TABLE 27

| Ex. No. | R | Q₁ | Name | [M + H]⁺ | HPLC R₁ (min) [Method] |
|---|---|---|---|---|---|
| 209 | 3-(1-methylpyridin-2(1H)-one-5-yl) | 1-cyclopropyl-1H-pyrazol-5-yl | 5-(3-(4-amino-5-(1-cyclopropyl-1H-pyrazol-5-yl)pyrrolo[2,1-f][1,2,4]triazin-7-yl)phenyl)-1-methylpyridin-2(1H)-one | 424.30 | 1.04 [I] |
| 210 | 4-methyl-1-methylpyridin-2(1H)-one-5-yl | 1-(tetrahydro-2H-pyran-4-yl)-1H-pyrazol-5-yl | 5-(3-(4-amino-5-(1-(tetrahydro-2H-pyran-4-yl)-1H-pyrazol-5-yl)pyrrolo[2,1-f][1,2,4]triazin-7-yl)phenyl)-1,4-dimethylpyridin-2(1H)-one | 482.30 | 1.19 [I] |
| 211 | 1-methylpyridin-2(1H)-one-4-yl | 1-(tetrahydro-2H-pyran-4-yl)-1H-pyrazol-5-yl | 4-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyridin-2(1H)-one | 468.30 | 1.10 [I] |

TABLE 27-continued

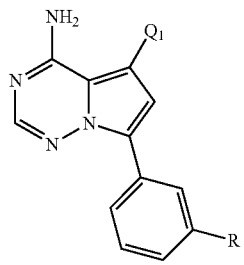

| Ex. No. | R | Q1 | Name | [M + H]+ | HPLC R1 (min) [Method] |
|---|---|---|---|---|---|
| 212 | ![pyridinone] | ![triazole-iPr] | 4-(3-(4-amino-5-(1-isopropyl-1H-1,2,3-triazol-5-yl)pyrrolo[2,1-f][1,2,4]triazin-7-yl)phenyl)-1-methylpyridin-2(1H)-one | 427.25 | 1.197 [I] |
| 213 | ![pyridinone] | ![triazole-THP] | 4-(3-(4-amino-5-(1-(tetrahydro-2H-pyran-4-yl)-1H-1,2,3-triazol-5-yl)pyrrolo[2,1-f][1,2,4]triazin-7-yl)phenyl)-1-methylpyridin-2(1H)-one | 469.25 | 1.130 [I] |

Example 214

4-(3-(4-Amino-5-(1-isopropyl-1H-1,2,3-triazol-5-yl)pyrrolo[2,1-f][1,2,4]triazin-7-yl) phenyl)thiomorpholine 1,1-dioxide (214)

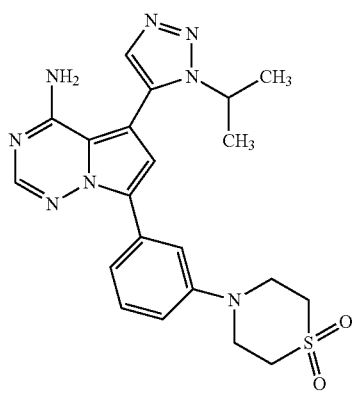

Intermediate R35 was reacted with Intermediate R2 using the procedure described in the synthesis of Example 196 to provide 4-(3-(4-amino-5-(1-isopropyl-1H-1,2,3-triazol-5-yl)pyrrolo[2,1-f][1,2,4]triazin-7-yl)phenyl)thiomorpholine 1,1-dioxide (17 mg, 23.5% yield). LCMS (M+H)+=453.25. $^1$H NMR (400 MHz, CDCl$_3$) δ 1.67 (d, 6H), 3.19 (m, 4H), 3.95 (m, 4H), 4.66 (m, 1H), 7.03 (s, 1H), 7.11 (d, 1H), 7.29 (s, 1H), 7.41 (d, 1H), 7.51 (m, 2H), 7.93 (s, 1H), 8.07 (s, 1H).

The Examples in Table 28 were synthesized according to the general synthetic procedure described for the synthesis of Example 196, using appropriate commercial materials and Intermediates R30 to R43.

TABLE 28

| Ex. No. | Q₁ | Q₂ | Name | [M + H]⁺ | HPLC Rt (min) [Method] |
|---|---|---|---|---|---|
| 215 | | | 7-(3-morpholinophenyl)-5-(1-(tetrahydro-2H-pyran-4-yl)-1H-1,2,3-triazol-5-yl)pyrrolo[2,1-f][1,2,4]triazin-4-amine, TFA | 477.15 | 1.336 [H] |
| 216 | | | 4-(3-(4-amino-5-(1-cyclohexyl-1H-1,2,3-triazol-5-yl)pyrrolo[2,1-f][1,2,4]triazin-7-yl)phenyl)thiomorpholine 1,1-dioxide | 493.40 | 1.37 [I] |
| 217 | | | 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-fluorophenyl)-2,6-dimethylpiperazin-1-yl)ethanone | 533.30 | 1.35 [I] |
| 218 | | | 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-fluorophenyl)-2,6-dimethylpiperazin-1-yl)ethanone | 534.30 | 1.29 [I] |
| 219 | | | 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-chlorophenyl)-2,6-dimethylpiperazin-1-yl)ethanone | 550.20 | 1.47 [I] |

TABLE 28-continued

| Ex. No. | Q₁ | Q₂ | Name | [M + H]⁺ | HPLC Rt (min) [Method] |
|---|---|---|---|---|---|
| 220 | 1,2,3-triazole-tetrahydropyran | 3,5-dimethylphenyl-cis-2,6-dimethylpiperazine-acetyl | 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methylphenyl)-2,6-dimethylpiperazin-1-yl)ethanone | 529.20 | 1.36 [I] |
| 221 | 1,2,3-triazole-tetrahydropyran | 3,5-dimethylphenyl-cis-2,6-dimethylpiperazine-acetyl | 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-methylphenyl)-2,6-dimethylpiperazin-1-yl)ethanone | 530.20 | 1.36 [I] |
| 222 | pyrazole-tetrahydropyran | 3-methoxyphenyl-cis-2,6-dimethylpiperazine-acetyl | 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methoxyphenyl)-2,6-dimethylpiperazin-1-yl)ethanone | 545.30 | 1.34 [I] |
| 223 | 1,2,3-triazole-tetrahydropyran | 3-methoxyphenyl-cis-2,6-dimethylpiperazine-acetyl | 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-methoxyphenyl)-2,6-dimethylpiperazin-1-yl)ethanone | 546.20 | 1.28 [I] |
| 224 | 1,2,3-triazole-isopropyl | phenyl-3,5-dimethylpiperazine-acetyl | 1-(4-(3-(4-amino-5-(1-isopropyl-1H-1,2,3-triazol-5-yl)pyrrolo[2,1-f][1,2,4]triazin-7-yl)phenyl)-3,5-dimethylpiperazin-1-yl)ethanone | 474.40 | 0.86 [I] |

TABLE 28-continued

| Ex. No. | Q₁ | Q₂ | Name | [M + H]⁺ | HPLC Rt (min) [Method] |
|---|---|---|---|---|---|
| 225 | | | 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-fluorophenyl)-3,5-dimethylpiperazin-1-yl)ethanone | 533.20 | 1.15 [I] |
| 226 | | | 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-fluorophenyl)-3,5-dimethylpiperazin-1-yl)ethanone | 534.20 | 1.07 [I] |
| 227 | | | 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methylphenyl)-3,5-dimethylpiperazin-1-yl)ethanone | 529.30 | 0.97 [I] |
| 228 | | | 1-((cis)-4-(3-(4-amino-5-(1-(tetrahydro-2H-pyran-4-yl)-1H-1,2,3-triazol-5-yl)pyrrolo[2,1-f][1,2,4]triazol-7-yl)-5-methylphenyl)-3,5-dimethylpiperazin-1-yl)ethanone | 530.30 | 0.85 [I] |

TABLE 28-continued

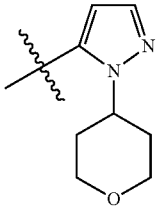 [SMILES: *c1ccnn1C1CCOCC1]

| Ex. No. | Q₁ | Q₂ | Name | [M + H]⁺ | HPLC Rt (min) [Method] |
|---|---|---|---|---|---|
| 229 | 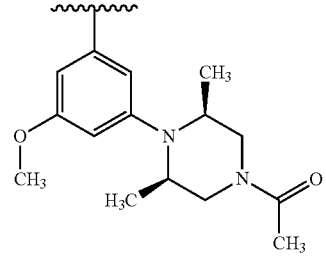 [SMILES: *c1cc(OC)cc(N2[C@H](C)CN(C(C)=O)C[C@@H]2C)c1] | 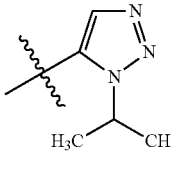 | 1-((cis)-4-(3-(4-amino-5-(1-tetrahydro-2H-pyran-4-yl)-1H-pyrazol-5-yl)pyrrolo[2,1-f][1,2,4]triazin-7-yl)-5-methoxyphenyl)-3,5-dimethylpiperazin-1-yl)ethanone | 545.20 | 0.98 [I] |
| 230 | 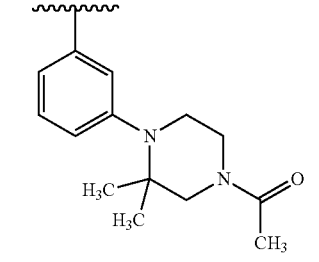 [SMILES: *c1cccc(N2CCN(C(C)=O)CC2(C)C)c1] | 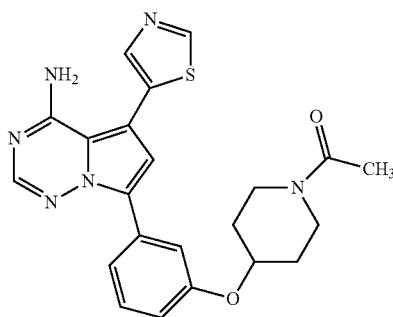 | 1-(4-(3-(4-amino-5-(1-isopropyl-1H-1,2,3-triazol-5-yl)pyrrolo[2,1-f][1,2,4]triazin-7-yl)phenyl)-3,3-dimethylpiperazin-1-yl)ethanone | 474.30 | 0.87 [I] |

Example 231

1-(4-(3-(4-Amino-5-(thiazol-5-yl)pyrrolo[2,1-f][1,2,4]triazin-7-yl)phenoxy)piperidin-1-yl)ethanone (231)

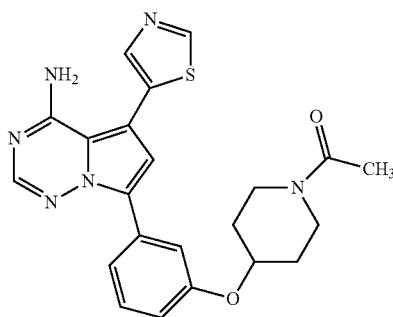

To a solution of 1-(4-(3-(4-amino-5-bromopyrrolo[2,1-f][1,2,4]triazin-7-yl) phenoxy)piperidin-1-yl)ethanone (40 mg, 0.093 mmol, Example 543) and 5-(4,4,5,5-tetramethyl-1,3,2-dioxaborolan-2-yl)thiazole (39.2 mg, 0.186 mmol) in DMA (2 mL) was added $CsF_2$ (42.4 mg, 0.279 mmol), copper(I) iodide (1.77 mg, 9.30 µmol) and $PdCl_2$(dppf)-$CH_2Cl_2$ adduct (7.59 mg, 9.30 µmol). The mixture was bubbled with $N_2$ and then heated in a microwave instrument at 140° C. for 60 min. The reaction mixture was filtered and washed with MeOH, filtrate concentrated and the residue purified by preparative LCMS method C to afford 1-(4-(3-(4-amino-5-(thiazol-5-yl)pyrrolo[2,1-f][1,2,4]triazin-7-yl)phenoxy) piperidin-1-yl)ethanone (10.3 mg, 0.024 mmol, 25.5% yield). LCMS (M+H)⁺=434.70. ¹H NMR (500 MHz, DMSO-d₆) δ 1.54 (m, 1H), 1.65 (m, 1H), 1.93 (m, 1H), 2.03 (m, 5H), 3.70 (m, 1H), 3.88 (m, 1H), 4.69 (m, 2H), 4.63 (m, 2H), 7.01 (d, 1H), 7.25 (s, 1H), 7.39 (t, 1H), 7.67 (d, 1H), 7.72 (s, 1H), 7.98 (s, 1H), 8.06 (s, 1H), 9.20 (s, 1H).

The Examples in Table 29 were synthesized according to the general synthetic procedure described for the synthesis of Example 231, using appropriate commercial materials and intermediates.

TABLE 29

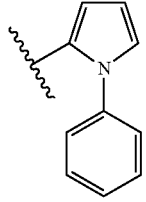 [SMILES: *c1cccn1-c1ccccc1]

| Ex. No. | Q₁ | Q₂ | Name | [M + H]⁺ | HPLC R$_t$ (min) [Method] |
|---|---|---|---|---|---|
| 232 | 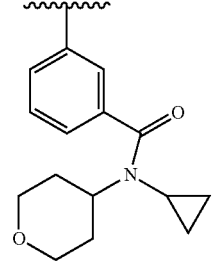 [SMILES: *c1cccc(C(=O)N(C2CCOCC2)C2CC2)c1] | 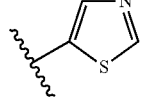 | 3-(4-amino-5-(1-phenyl-1H-pyrrol-2-yl)pyrrolo[2,1-f][1,2,4]triazin-7-yl)-N-cyclopropyl-N-(tetrahydro-2H-pyran-4-yl)benzoamide | 519.15 | 1.892 [H] |
| 233 | 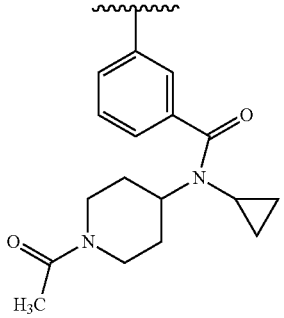 [SMILES: *c1cccc(C(=O)N(C2CC2)C2CCN(C(C)=O)CC2)c1] | | N-(1-acetylpiperidin-4-yl)-3-(4-amino-5-(thiazol-5-yl)pyrrolo[2,1-f][1,2,4]triazin-7-yl)-N-cyclopropylbenzamide | 502.10 | 1.34 [H] |

Example 234

3-(4-Amino-5-(1-(tetrahydro-2H-pyran-4-yl)-1H-1,2,3-triazol-5-yl)pyrrolo[2,1-f][1,2,4]triazin-7-yl)-N-cyclopropyl-N-(tetrahydro-2H-pyran-4-yl)benzamide (234)

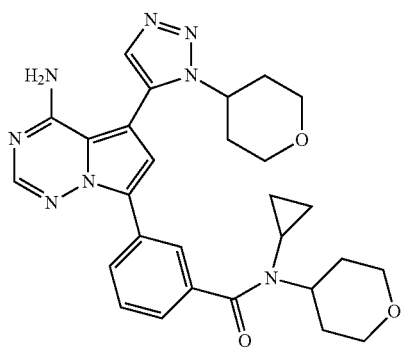

Intermediate 234A: 3-(4-Amino-5-((trimethylsilyl)ethynyl)pyrrolo[2,1-f][1,2,4]triazin-7-yl)-N-cyclopropyl-N-(tetrahydro-2H-pyran-4-yl)benzamide (234A)

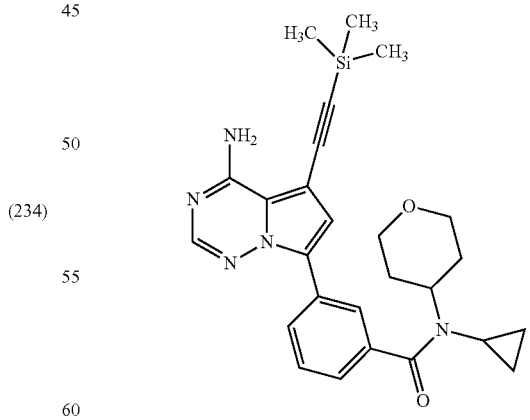

Example 545, 3-(4-amino-5-iodopyrrolo[2,1-f][1,2,4]triazin-7-yl)-N-cyclopropyl-N-(tetrahydro-2H-pyran-4-yl)benzamide (256 mg, 0.51 mmol), was suspended in anhydrous DMF (10 mL), then triethylamine (0.354 mL, 2.54 mmol), copper(I) iodide (19.37 mg, 0.102 mmol), bis(triphenylphosphine)palladium(II) chloride (53.5 mg, 0.076 mmol) were added. Nitrogen gas was bubbled for few min and then ethynyltrimethylsilane (0.216 mL, 1.5 mmol) was added. The mixture was stirred for 15 min, poured into ice water (200 mL) and the precipitate formed was filtered. The filtrate was concentrated and the residue was purified by flash chromatography on silica gel eluting with 0-100% EtOAc/hexane (12 g column, 16 min gradient) to obtain 3-(4-amino-5-((trimethylsilyl)ethynyl)pyrrolo[2,1-f][1,2,4]triazin-7-yl)-N-cyclopropyl-N-(tetrahydro-2H-pyran-4-yl)benzamide (~90% yield). LC-MS m/z (M+H)$^+$=474.35.

Intermediate 234B: 3-(4-Amino-5-ethynylpyrrolo[2,1-f][1,2,4]triazin-7-yl)-N-cyclopropyl-N-(tetrahydro-2H-pyran-4-yl)benzamide

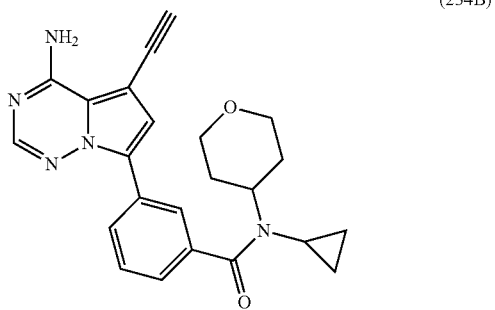

(234B)

To a solution of 3-(4-amino-5-((trimethylsilyl)ethynyl)pyrrolo[2,1-f][1,2,4]triazin-7-yl)-N-cyclopropyl-N-(tetrahydro-2H-pyran-4-yl)benzamide in MeOH (10 mL) was added K$_2$CO$_3$ (1 g). The reaction mixture was stirred for 2 hr at room temperature, filtered, and the filtrate was concentrated. The crude was purified by flash chromatography on silica gel eluting with 0-100% EtOAc/hexane (12 g column, 16 min gradient) to obtain 3-(4-amino-5-ethynylpyrrolo[2,1-f][1,2,4]triazin-7-yl)-N-cyclopropyl-N-(tetrahydro-2H-pyran-4-yl)benzamide, which was used in the next step without further purification (102 mg, 50% yield). LCMS (M+H)$^+$=402.25.

Example 234

To a solution of 3-(4-amino-5-ethynylpyrrolo[2,1-f][1,2,4]triazin-7-yl)-N-cyclopropyl-N-(tetrahydro-2H-pyran-4-yl)benzamide (25 mg, 0.062 mmol) in toluene (2 mL) was added 4-azidotetrahydro-2H-pyran (23.75 mg, 1.87 mmol) and then chloro (pentamethyl cyclopentadienyl)ruthenium (II) tetramer (2 mg, 1.8 μmol). Nitrogen was bubbled through the mixture for 1 min, and the sealed tube was heated to 100° C. for 60 min in a microwave instrument. The reaction mixture was cooled, concentrated and purified by preparative LC Method B to obtain 3-(4-amino-5-(1-(tetrahydro-2H-pyran-4-yl)-1H-1,2,3-triazol-5-yl)pyrrolo[2,1-f][1,2,4]triazin-7-yl)-N-cyclopropyl-N-(tetrahydro-2H-pyran-4-yl)benzamide (15.9 mg, 48.3% yield). LCMS (M+H)$^+$=529.20. $^1$H NMR (500 MHz, MeOD) δ 0.57 (m, 2H), 0.72 (m, 2H), 1.92 (m, 2H), 2.01 (m, 2H), 2.25 (m, 2H), 2.41 (m, 2H), 3.48 (m, 2H), 3.55 (m, 2H), 4.06 (m, 2H), 4.09 (m, 2H), 4.37 (m, 1H), 4.56 (m, 1H), 7.03 (S, 1H), 7.53 (m, 2H), 7.61 (s, 1H), 7.83 (s, 1H), 8.01 (s, 1H), 8.08 (d, 1H), 8.24 (s, 1H).

The Examples in Table 30 were synthesized according to the general synthetic procedures described in Example 234 and previous syntheses utilizing appropriate commercial materials and intermediates.

TABLE 30

| Ex. No. | Q$_1$ | Q$_2$ | Name | [M + H]$^+$ | HPLC R$_t$ (min) [Method] |
|---|---|---|---|---|---|
| 235 | triazole with N-CH(CH$_3$)$_2$ (isopropyl) | 3-benzoyl phenyl with pyrrolidine amide | (3-(4-amino-5-(1-isopropyl-1H-1,2,3-triazol-5-yl)pyrrolo[2,1-f][1,2,4]triazin-7-yl)phenyl)(pyrrolidin-1-yl)methanone | 415.05 | 1.32 [H] |
| 236 | triazole with N-(tetrahydro-2H-pyran-4-yl) | 3-benzoyl phenyl with pyrrolidine amide | (3-(4-amino-5-(1-(tetrahydro-2H-pyran-4-yl)-1H-1,2,3-triazol-5-yl)pyrrolo[2,1-f][1,2,4]triazin-7-yl)phenyl)(pyrrolidin-1-yl)methanone | 457.10 | 1.23 [H] |

TABLE 30-continued

| Ex. No. | Q₁ | Q₂ | Name | [M + H]⁺ | HPLC R$_t$ (min) [Method] |
|---|---|---|---|---|---|
| 237 | | | 3-(4-amino-5-(1-(tetrahydro-2H-pyran-4-yl)-1H-1,2,3-triazol-5-yl)pyrrolo[2,1-f][1,2,4]triazin-7-yl)-N,N-dicyclopropylbenzamide | 485.20 | 1.24 [H] |
| 238 | | | 2-(3-(4-amino-5-(1-(tetrahydro-2H-pyran-4-yl)-1H-1,2,3-triazol-5-yl)pyrrolo[2,1-f][1,2,4]triazin-7-yl)phenyl)-1-(1,1-dioxidothiomorpholino)ethanone | 537.20 | 0.95 [I] |
| 239 | | | 2-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropylcyclopropanecarboxamide | 484.20 | 1.19 [I] |

The analogs in Table 31 were prepared according to the general procedure for the synthesis of Example 90, General Procedure 1 using appropriate intermediates. Some appropriate bromo intermediates were prepared by methods known to those skilled in the arts (palladium couplings) from 1,3-dibromobenzene and the required amine. The synthesis was also performed under conventional heating at 100° C. overnight for boronic ester formation and subsequent Suzuki coupling. In some reactions tripotassium phosphate was used as base instead of sodium carbonate.

TABLE 31

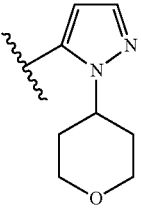 [SMILES: *c1ccnn1C1CCOCC1]

| Ex. No. | Q₁ | Q₂ | Name | LCMS M⁺ Retention Time (min) Method |
|---|---|---|---|---|
| 240 | 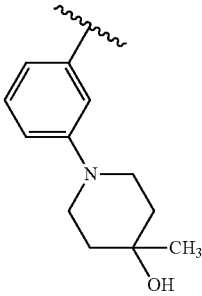 [SMILES: *c1cccc(N2CCC(C)(O)CC2)c1] | 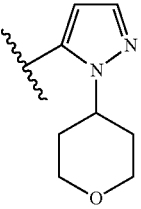 [SMILES: *c1ccnn1C1CCOCC1] | 1-(3-(4-amino-5-(1-(tetrahydro-2H-pyran-4-yl)-1H-pyrazol-5-yl)pyrrolo[2,1-f][1,2,4]triazin-7-yl)phenyl)-4-methylpiperidin-4-ol | 474.2 0.83 F |
| 241 | 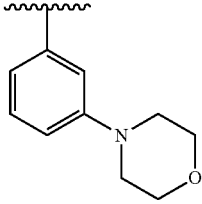 [SMILES: *c1cccc(N2CCOCC2)c1] | 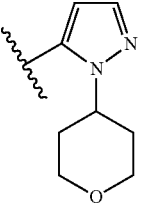 [SMILES: *c1ccnn1C1CCOCC1] | 7-(3-morpholinophenyl)-5-(1-(tetrahydro-2H-pyran-4-yl)-1H-pyrazol-5-yl)pyrrolo[2,1-f][1,2,4]triazin-4-amine | 446.10 1.21 F |
| 242 | 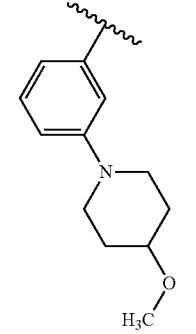 [SMILES: *c1cccc(N2CCC(OC)CC2)c1] | 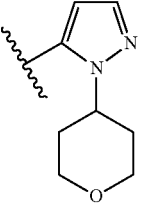 [SMILES: *c1ccnn1C1CCOCC1] | 7-(3-(4-methoxypiperidin-1-yl)phenyl)-5-(1-(tetrahydro-2H-pyran-4-yl)-1H-pyrazol-5-yl)pyrrolo[2,1-f][1,2,4]triazin-4-amine | 474.2 0.96 F |
| 243 | | 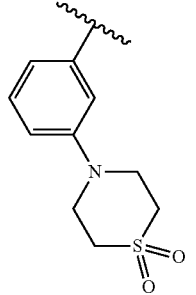 [SMILES: *c1cccc(N2CCS(=O)(=O)CC2)c1] | 4-(3-(4-amino-5-(1-(tetrahydro-2H-pyran-4-yl)-1H-pyrazol-5-yl)pyrrolo[2,1-f][1,2,4]triazin-7-yl)phenyl)thiomorpholine 1,1-dioxide | 494.1 1.04 F |

TABLE 31-continued

| Ex. No. | Q₁ | Q₂ | Name | LCMS M⁺ Retention Time (min) Method |
|---|---|---|---|---|
| 244 | pyrazole-N-tetrahydropyran | 3-(trifluoromethyl)piperazinyl-acetyl-phenyl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(trifluoromethyl)piperazin-1-yl)ethanone | 555.20 1.36 F |
| 245 | triazole-N-tetrahydropyran | 3-(trifluoromethyl)piperazinyl-acetyl-phenyl | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(trifluoromethyl)piperazin-1-yl)ethanone | 556.20 1.30 F |
| 246 | pyrazole-N-tetrahydropyran | (2S,6R)-2,6-dimethylpiperazinyl-acetyl-phenyl | 1-((2S,6R)-4-(3-(4-amino-5-(1-(tetrahydro-2H-pyran-4-yl)-1H-pyrazol-5-yl)pyrrolo[2,1-f][1,2,4]triazin-7-yl)phenyl)-2,6-dimethylpiperazin-1-yl)ethanone | 515.2 1.31 F |
| 247 | triazole-N-tetrahydropyran | (2S,6R)-2,6-dimethylpiperazinyl-acetyl-phenyl | 1-((2S,6R)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,6-dimethylpiperazin-1-yl)ethanone | 516.2 1.19 F |

TABLE 31-continued

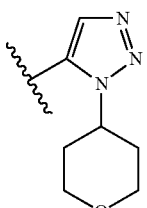

| Ex. No. | Q₁ | Q₂ | Name | LCMS M⁺ Retention Time (min) Method |
|---|---|---|---|---|
| 248 | 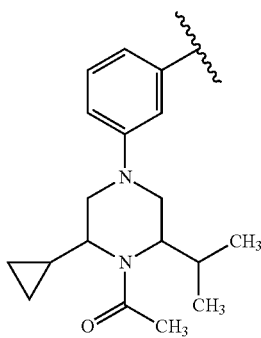 [SMILES: *c1cccc(N2CC(C(C)C)N(C(C)=O)C(C3CC3)C2)c1] | 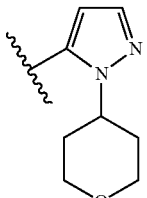 | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2-cyclopropyl-6-isopropylpiperazin-1-yl)ethanone | 570.25 1.51 F |
| 249 | 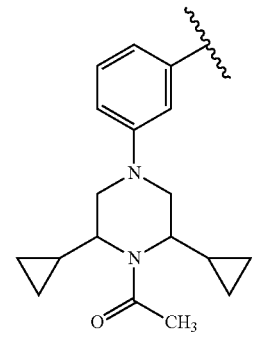 [SMILES: *c1cccc(N2CC(C3CC3)N(C(C)=O)C(C3CC3)C2)c1] | | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2,6-dicyclopropylpiperazin-1-yl)ethanone | 567.25 1.35 F |
| 250 | 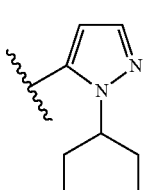 | 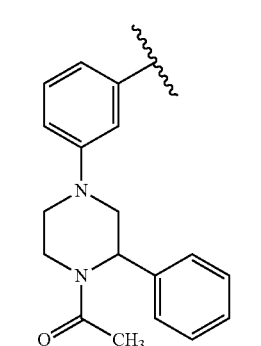 | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2-cyclopropyl-6-isopropylpiperazin-1-yl)ethanone | 563.3 1.44 F |

TABLE 31-continued

| Ex. No. | Q₁ | Q₂ | Name | LCMS M⁺ Retention Time (min) Method |
|---|---|---|---|---|
| 251 | 1-(tetrahydro-2H-pyran-4-yl)-1,2,3-triazol-5-yl | 3-phenyl (piperazine with N-acetyl, 3-phenyl) | 1-(4-(3-(4-amino-5-(1-(tetrahydro-2H-pyran-4-yl)-1H-1,2,3-triazol-5-yl) pyrrolo[2,1-f][1,2,4]triazin-7-yl) phenyl)-2-phenylpiperazin-1-yl) ethanone | 564.3 1.38 F |
| 252 | 1-(tetrahydro-2H-pyran-4-yl)-1H-pyrazol-5-yl | 3-(pyridin-3-yl) (piperazine with N-acetyl) | 1-(4-(3-(4-amino-5-(1-(tetrahydro-2H-pyran-4-yl)-1H-pyrazol-5-yl)pyrrolo [2,1-f][1,2,4]triazin-7-yl)phenyl)-2-(pyidirn-3-yl)piperazin-1-yl)ethanone | 564.3 0.91 F |
| 253 | 1-(tetrahydro-2H-pyran-4-yl)-1,2,3-triazol-5-yl | 3-(pyridin-3-yl) (piperazine with N-acetyl) | 1-(4-(3-(4-amino-5-(1-(tetrahydro-2H-pyran-4-yl)-1H-1,2,3-triazol-5-yl) pyrrolo[2,1-f][1,2,4]triazin-7-yl) phenyl)-2-(pyridin-3-yl)piperazin-1-yl)ethanone | 565.3 0.85 F |

TABLE 31-continued

| Ex. No. | Q₁ | Q₂ | Name | LCMS M⁺ Retention Time (min) Method |
|---|---|---|---|---|
| 254 | | | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(2-fluorophenyl)piperazin-1-yl)ethanone | 581.25 1.23 F |
| 255 | | | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(2-fluorophenyl)piperazin-1-yl)ethanone | 582.25 1.20 F |
| 256 | | | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(pyridin-3-yl)piperazin-1-yl)ethanone | 563.8 0.92 F |

TABLE 31-continued

| Ex. No. | Q₁ | Q₂ | Name | LCMS M⁺ Retention Time (min) Method |
|---|---|---|---|---|
| 257 | 1-(tetrahydro-2H-pyran-4-yl)-1H-1,2,3-triazol-5-yl | 3-(pyridin-3-yl)-4-acetylpiperazin-1-yl-phenyl | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(pyridin-3-yl)piperazin-1-yl)ethanone | 564.8 0.85 F |
| 258 | 1-(tetrahydro-2H-pyran-4-yl)-1H-pyrazol-5-yl | 3-(2,3-dimethyl-4-acetylpiperazin-1-yl)phenyl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2,3-dimethylpiperazin-1-yl)ethanone | 514.9 1.07 F |
| 259 | 1-(tetrahydro-2H-pyran-4-yl)-1H-1,2,3-triazol-5-yl | 3-(2,3-dimethyl-4-acetylpiperazin-1-yl)phenyl | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,3-dimethylpiperazin-1-yl)ethanone | 515.9 0.99 F |

TABLE 31-continued

| Ex. No. | Q₁ | Q₂ | Name | LCMS M⁺ Retention Time (min) Method |
|---|---|---|---|---|
| 260 |  | 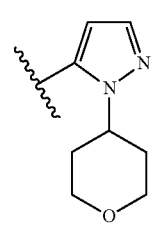 [SMILES: *c1ccnn1C1CCOCC1] | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(4-chlorophenyl)piperazin-1-yl)ethanone | 596.9<br>1.47<br>F |
| 261 |  | 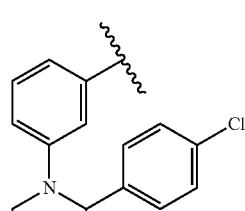 | N-(1-(3-(4-amino-5-(1-(tetrahydro-2H-pyran-4-yl)-1H-pyrazol-5-yl)pyrrolo[2,1-f][1,2,4]triazin-7-yl phenyl)-4-methylpiperidin-4-yl)acetamide | 515.0<br>0.89<br>F |

The analogs in Table 32 were prepared according to methods shown in previous Examples. In Table 32, the sulfonamide was formed using 1 eq. of methylsulfonic anhydride or alkylsufonyl chloride and DIPEA at room temperature for 2 h. The carbamate was formed using 1 eq. of chloroformate and DIPEA at room temperature for 30 min. Amide formation were performed by using appropriate acid and a coupling agent like HATU. Acetamides were formed by using 1 eq. of acetic anhydride for certain syntheses. Amine was formed via reductive amination with 3 eq. of an aldehyde or ketone, and 3 eq. of sodium cyanoborohydride at room temperature overnight.

TABLE 32

| Ex. No. | Q₁ | R | Name | LCMS Retention Time (min) Method | M⁺ |
|---|---|---|---|---|---|
| 262 | 5-(1-(tetrahydro-2H-pyran-4-yl)-1H-pyrazol-5-yl) | (cis)-3,5-dimethylpiperazine N-acetyl | 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)ethanone | 1.00 F | 515.20 |
| 263 | 5-(1-(tetrahydro-2H-pyran-4-yl)-1H-pyrazol-5-yl) | (cis)-1,3,5-trimethylpiperazine | 5-(1-(tetrahydro-2H-pyran-4-yl)-1H-pyrazol-5-yl)-7-(3-((cis)-2,4,6-trimethylpiperazin-1-yl)phenyl)pyrrolo[2,1-f][1,2,4]triazin-4-amine | 0.97 F | 487.3 |
| 264 | 5-(1-(tetrahydro-2H-pyran-4-yl)-1H-1,2,3-triazol-5-yl) | (cis)-3,5-dimethylpiperazine N-acetyl | 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)ethanone | 0.80 F | 515.9 |
| 265 | 5-(1-(tetrahydro-2H-pyran-4-yl)-1H-1,2,3-triazol-5-yl) | (cis)-3,5-dimethylpiperazine N-hydroxyacetyl | 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)-2-hydroxyethanone | 2.099 G | 532.40 |
| 266 | 5-(1-(tetrahydro-2H-pyran-4-yl)-1H-pyrazol-5-yl) | (cis)-3,5-dimethylpiperazine N-methoxycarbonyl | (cis)-methyl 4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazine-1-carboxylate | 1.12 F | 531.2 |

TABLE 32-continued

| Ex. No. | Q₁ | R | Name | LCMS Retention Time (min) Method | M⁺ |
|---|---|---|---|---|---|
| 267 | 5-(tetrahydro-2H-pyran-4-yl)-1H-pyrazol-1-yl | (cis)-3,5-dimethyl-4-(2-hydroxyacetyl)piperazin-1-yl | 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)-2-hydroxyethanone | 2.387 G | 531.40 |
| 268 | 1-isopropyl-1H-pyrazol-5-yl | (cis)-4-acetyl-3,5-dimethylpiperazin-1-yl | 1-((cis)-4-(3-(4-amino-5-(1-isopropyl-1H-pyrazol-5-yl)pyrrolo[2,1-f][1,2,4]triazin-7-yl)phenyl)-3,5-dimethylpiperazin-1-yl)ethanone | 1.09 F | 473.2 |
| 269 | 5-(tetrahydro-2H-pyran-4-yl)-1H-pyrazol-1-yl | (cis)-2,6-dimethyl-4-(methylsulfonyl)piperazin-1-yl | 7-(3-((cis)-2,6-dimethyl-4-(methylsulfonyl)piperazin-1-yl)phenyl)-5-(1-(tetrahydro-2H-pyran-4-yl)-1H-pyrazol-5-yl)pyrrolo[2,1-f][1,2,4]triazin-4-amine | 0.98 F | 551.2 |
| 270 | 5-(tetrahydro-2H-pyran-4-yl)-1H-1,2,3-triazol-1-yl | (cis)-4-(methoxycarbonyl)-3,5-dimethylpiperazin-1-yl | (cis)-methyl 4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazine-1-carboxylate | 0.95 F | 532.2 |
| 271 | 5-(tetrahydro-2H-pyran-4-yl)-1H-pyrazol-1-yl | (cis)-3,5-dimethyl-4-(2-hydroxy-2-methylpropanoyl)piperazin-1-yl | 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)-2-hydroxy-2-methylpropan-1-one | 0.90 F | 559.3 |

TABLE 32-continued

| Ex. No. | Q₁ | R | Name | LCMS Retention Time (min) Method | M⁺ |
|---|---|---|---|---|---|
| 272 | 1-(tetrahydro-2H-pyran-4-yl)-1H-1,2,3-triazol-5-yl | cis-3,5-dimethylpiperazine with 2-hydroxy-2-methylpropanoyl | 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)-2-hydroxy-2-methylpropan-1-one | 0.84 F | 560.3 |
| 273 | 1-(2,2,2-trifluoroethyl)-1H-pyrazol-5-yl | cis-3,5-dimethylpiperazine with acetyl | 1-((cis)-4-(3-(4-amino-5-(1-(2,2,2-trifluoroethyl)-1H-pyrazol-5-yl)pyrrolo[2,1-f][1,2,4]triazin-7-yl)phenyl)-3,5-dimethylpiperazin-1-yl)ethanone | 0.93 F | 513.4 |
| 274 | 1-(tetrahydro-2H-pyran-4-yl)-1H-pyrazol-5-yl | 3,3-dimethylpiperazin-1-yl phenyl with acetyl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)ethanone | 0.95 F | 514.9 |
| 275 | 1-(tetrahydro-2H-pyran-4-yl)-1H-1,2,3-triazol-5-yl | 3,3-dimethylpiperazin-1-yl phenyl with acetyl | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,3-dimethylpiperazin-1-yl)ethanone | 1.030 F | 516.2 |

TABLE 32-continued

| Ex. No. | Q₁ | R | Name | LCMS Retention Time (min) Method | M⁺ |
|---|---|---|---|---|---|
| 276 | 5-pyrazolyl with N-(tetrahydro-2H-pyran-4-yl) | 3-(3,3-dimethyl-4-(methoxycarbonyl)piperazin-1-yl)phenyl | methyl 4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazine-1-carboxylate | 1.19 F | 531.2 |
| 277 | 5-pyrazolyl with N-(tetrahydro-2H-pyran-4-yl) | 3-(3,3-dimethyl-4-(2-hydroxyacetyl)piperazin-1-yl)phenyl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)-2-hydroxyethanone | 1.02 F | 531.2 |
| 278 | 5-pyrazolyl with N-(tetrahydro-2H-pyran-4-yl) | 3-(3,3-dimethyl-4-(methylsulfonyl)piperazin-1-yl)phenyl | 7-(3-(2,2-dimethyl-4-(methylsulfonyl)piperazin-1-yl)phenyl)-5-(1-(tetrahydro-2H-pyran-4-yl)-1H-pyrazol-5-yl)pyrrolo[2,1-f][1,2,4]triazin-4-amine | 1.24 F | 551.20 |
| 279 | 5-(1,2,3-triazolyl) with N-(tetrahydro-2H-pyran-4-yl) | 3-(7-acetyl-4,7-diazaspiro[2.5]octan-4-yl)phenyl | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-4,7-diazaspiro[2.5]octan-7-yl)ethanone | 1.25 F | 514.20 |

TABLE 32-continued

| Ex. No. | Q₁ | R | Name | LCMS Retention Time (min) Method | M⁺ |
|---|---|---|---|---|---|
| 280 | 5-(tetrahydro-2H-pyran-4-yl)-1H-pyrazol-1-yl | 3-(4-acetyl-4,7-diazaspiro[2.5]octan-7-yl)phenyl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-4,7-diazaspiro[2.5]octan-7-yl)ethanone | 1.20 F | 513.3 |
| 281 | 1-isopropyl-1H-1,2,3-triazol-5-yl | 3-(4-acetyl-4,7-diazaspiro[2.5]octan-7-yl)phenyl | 1-(4-(3-(4-amino-5-(1-isopropyl-1H-1,2,3-triazol-5-yl)pyrrolo[2,1-f][1,2,4]triazin-7-yl)phenyl)-4,7-diazaspiro[2.5]octan-7-yl)ethanone | 1.22 F | 472.3 |
| 282 | 5-(tetrahydro-2H-pyran-4-yl)-1H-pyrazol-1-yl | 3-(3,3-dimethyl-4-((S)-2-hydroxypropanoyl)piperazin-1-yl)phenyl | (S)-1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)-2-hydroxypropan-1-one | 1.14 F | 530.5 |
| 283 | 1-(tetrahydro-2H-pyran-4-yl)-1H-1,2,3-triazol-5-yl | 3-(3,3-dimethyl-4-(2-hydroxyacetyl)piperazin-1-yl)phenyl | 1-(4-(3-(4-amino-5-(1-cyclohexyl-1H-1,2,3-triazol-5-yl)pyrrolo[2,1-f][1,2,4]triazin-7-yl)phenyl)-3,3-dimethylpiperazin-1-yl)-2-hydroxyethanone | 0.93 F | 545.3 |

Example 262

$^1$H NMR (500 MHz, MeOD:CDCl$_3$) δ 7.99 (s, 1H), 7.89 (s, 1H), 7.83 (d, J=7.9 Hz, 1H), 7.69 (d, J=1.5 Hz, 1H), 7.47 (t, J=7.9 Hz, 1H), 7.18 (d, J=7.9 Hz, 1H), 6.94 (s, 1H), 6.45 (d, J=1.5 Hz, 1H), 4.44-4.30 (m, 2H), 4.03 (m, 2H), 3.82 (d, J=9.4 Hz, 1H), 3.43 (t, J=11.1 Hz, 2H), 3.23-3.12 (m, 3H), 2.80 (dd, J=12.9, 9.9 Hz, 1H), 2.32 (d, J=11.4 Hz, 2H), 2.18 (s, 3H), 1.85 (dt, J=6.6, 3.4 Hz, 2H), 0.90 (d, J=6.4 Hz, 3H), 0.93 (d, J=5.4 Hz, 3H).

Example 284

1-(4-(3-(4-Amino-5-(1-(tetrahydro-2H-pyran-4-yl)-1H-pyrazol-5-yl)pyrrolo[2,1-f][1,2,4]triazin-7-yl)phenyl)-3,4-dihydroquinoxalin-1(2H)-yl)ethanone

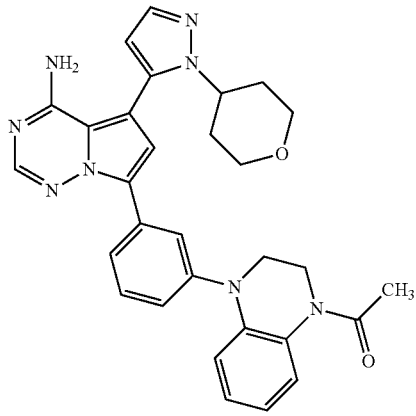

(284)

Intermediate 284A: 7-(3-(3,4-Dihydroquinoxalin-1(2H)-yl)phenyl)-5-(1-(tetrahydro-2H-pyran-4-yl)-1H-pyrazol-5-yl)pyrrolo[2,1-f][1,2,4]triazin-4-amine

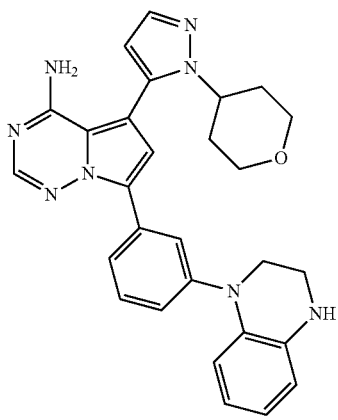

(284A)

Intermediate Q17, tert-butyl 4-(3-bromophenyl)-3,4-dihydroquinoxaline-1(2H)-carboxylate (43 mg, 0.110 mmol) was combined with 4,4,4',4',5,5,5',5'-octamethyl-2,2'-bi(1,3,2-dioxaborolane) (42.1 mg, 0.166 mmol), potassium acetate (43.4 mg, 0.442 mmol), PdCl$_2$(dppf)-CH$_2$Cl$_2$ adduct (18.04 mg, 0.022 mmol) and dioxane (2 mL) and the mixture was purged with nitrogen, the vessel was sealed and reacted in a microwave reactor for 30 min at 120° C. The reaction mixture was cooled to room temperature, water (0.5 mL), 7-bromo-5-(1-(tetrahydro-2H-pyran-4-yl)-1H-pyrazol-5-yl)pyrrolo[2,1-f][1,2,4]triazin-4-amine (40.1 mg, 0.110 mmol), sodium carbonate (35.1 mg, 0.331 mmol), and additional PdCl$_2$(dppf)-CH$_2$Cl$_2$ adduct (18.04 mg, 0.022 mmol) were added. The mixture was purged with nitrogen, then the vessel was sealed and reacted in the microwave for 40 min at 110° C. The mixture was cooled to room temperature, diluted with 5 mL of water, extracted with EtOAc (10 mL×2). The combined organic layers washed with brine, dried and concentrated. The residue, tert-butyl 4-(3-(4-amino-5-(1-(tetrahydro-2H-pyran-4-yl)-1H-pyrazol-5-yl)pyrrolo[2,1-f][1,2,4]triazin-7-yl)phenyl)-3,4-dihydroquinoxaline-1(2H)-carboxylate, was dissolved in DCM/TFA (1:1) for 15 min, the mixture was concentrated, residue was partitioned between DCM and aqueous NaHCO$_3$. The organic layer was washed with brine, dried over Na$_2$SO$_4$, and concentrated to afford 7-(3-(3,4-dihydroquinoxalin-1(2H)-yl)phenyl)-5-(1-(tetrahydro-2H-pyran-4-yl)-1H-pyrazol-5-yl)pyrrolo[2,1-f][1,2,4]triazin-4-amine. LCMS M$^+$=493.50. Method G. Retention time 2.51 min. The crude product was used without further purification in the next step.

Example 284

To Intermediate 284A, was added acetic anhydride (11.2 mg, 0.110 mmol) and DIPEA (38 μL, 0.22 mmol) and the mixture was stirred at room temperature for 2 h. The reaction mixture was concentrated and the residue was purified by preparative HPLC (Method B) to afford Example 504 (10.6 mg). LCMS M$^+$=534.8. Method F. Retention time 1.43 min. $^1$H NMR (500 MHz, DMSO-d$_6$) δ 8.08 (s, 1H), 8.05 (s, 1H), 7.88 (d, J=7.3 Hz, 1H), 7.68 (d, J=1.2 Hz, 1H), 7.53 (t, J=7.9 Hz, 1H), 7.31 (d, J=7.9 Hz, 2H), 7.28 (s, 1H), 7.00 (m, 1H), 6.87 (d, J=7.9 Hz, 1H), 6.77 (m, 1H), 6.46 (d, J=1.8 Hz, 1H), 4.44-4.27 (m, 1H), 3.95 (t, J=5.5 Hz, 2H), 3.84 (m, 2H), 3.79 (m, 2H), 3.31 (t, J=7.9 Hz, 2H), 2.23 (s, 3H), 2.16-2.00 (m, 2H), 1.80 (m, 2H).

The Examples in Table 33 were made according to the general preparation for Example 284 using intermediates prepared or commercial substituted 3-bromobenzene or commercial boronic acid or ester. For some examples, the synthesis also was performed under conventional heating for overnight at 100° C. In some reactions, tripotassium phosphate was used as a base instead sodium carbonate. Sulfonamide was formed using 1 eq. of methylsulfonic anhydride with DIPEA at room temperature for 2 h. Carbamate was formed using 1 eq. of chloroformate with DIPEA at room temperature for 30 min. Amides were formed using HATU coupling condition as described before. Tertiary amines were formed via reductive amination with 3 eq. of aldehyde or ketone and 3 eq. of sodium cyanoborohydride at room temperature overnight.

TABLE 33

| Ex. No. | Q₁ | Q₂ | Name | Retention Time (min) method | M⁺ |
|---|---|---|---|---|---|
| 285 | pyrazole-tetrahydropyran | phenyl-piperidine (NH) | 7-(3-(piperidin-4-yl)phenyl)-5-(1-(tetrahydro-2H-pyran-4-yl)-1H-pyrazol-5-yl)pyrrolo[2,1-f][1,2,4]triazin-4-amine | 0.98 F | 444.15 |
| 286 | pyrazole-tetrahydropyran | phenyl-piperazine-acetyl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperidin-1-yl)ethanone | .28 F | 585.45 |
| 287 | pyrazole-tetrahydropyran | phenyl-piperidine-oxetane | 7-(3-(1-(oxetan-3-yl)piperidin-4-yl)phenyl)-5-(1-(tetrahydro-2H-pyran-4-yl)-1H-pyrazol-5-yl)pyrrolo[2,1-f][1,2,4]triazin-4-amine | 0.98 F | 500.20 |
| 288 | pyrazole-tetrahydropyran | phenyl-piperazine-acetyl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)ethanone | 1.03 F | 487.3 |

TABLE 33-continued

| Ex. No. | Q₁ | Q₂ | Name | Retention Time (min) method | M⁺ |
|---|---|---|---|---|---|
| 289 | 1-(tetrahydro-2H-pyran-4-yl)-1H-pyrazol-5-yl | 3-(4-(oxetan-3-yl)piperazin-1-yl)phenyl | 7-(3-(4-(oxetan-3-yl)piperazin-1-yl)phenyl)-5-(1-(tetrahydro-2H-pyran-4-yl)-1H-pyrazol-5-yl)pyrrolo[2,1-f][1,2,4]triazin-4-amine | 0.95 F | 501.20 |
| 290 | 1-(tetrahydro-2H-pyran-4-yl)-1H-pyrazol-5-yl | 3-(4-methylpiperazin-1-yl)phenyl | 7-(3-(4-methylpiperazin-1-yl)phenyl)-5-(1-(tetrahydro-2H-pyran-4-yl)-1H-pyrazol-5-yl)pyrrolo[2,1-f][1,2,4]triazin-4-amine | 0.95 F | 459.15 |
| 291 | 1-(tetrahydro-2H-pyran-4-yl)-1H-pyrazol-5-yl | 3-(4-acetyl-2-phenylpiperazin-1-yl)phenyl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-phenylpiperazin-1-yl)ethanone | 1.50 F | 563.3 |

TABLE 33-continued

| Ex. No. | Q₁ | Q₂ | Name | Retention Time (min) method | M⁺ |
|---|---|---|---|---|---|
| 292 | [pyrazole with tetrahydropyran] | [phenyl-piperazine-N-C(O)OCH₃] | methyl 4-(3-(4-amino-5-(1-(tetrahydro-2H-pyran-4-yl)-1H-pyrazol-5-yl)pyrrolo[2,1-f][1,2,4]triazin-7-yl)phenyl)piperazine-1-carboxylate | 1.41 F | 503.2 |
| 293 | [triazole with tetrahydropyran] | [phenyl-piperazine-N-C(O)OCH₃] | methyl 4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperazine-1-carboxylate | 1.34 F | 504.2 |
| 294 | [pyrazole with tetrahydropyran] | [phenyl-piperazine-N-SO₂CH₃] | 7-(3-(4-(methylsulfonyl)piperazin-1-yl)phenyl)-5-(1-(tetrahydro-2H-pyran-4-yl)-1H-pyrazol-5-yl)pyrrolo[2,1-f][1,2,4]triazin-4-amine | 1.33 F | 523.2 |

TABLE 33-continued

| Ex. No. | Q₁ | Q₂ | Name | Retention Time (min) method | M⁺ |
|---|---|---|---|---|---|
| 295 | | | 7-(3-(4-(methylsulfonyl)piperazin-1-yl)phenyl)-5-(1-(tetrahydro-2H-pyran-4-yl)-1H-1,2,3-triazol-5-yl)pyrrolo[2,1-f][1,2,4]triazin-4-amine | 1.26 F | 524.2 |
| 296 | | | 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)-2-methylpropan-1-one | 1.42 F | 515.3 |
| 297 | | | 1-(4-(3-(4-amino-5-(1-tetrah-(1-(tetrahydro-2H-pyran-4-yl)-1H-1,2,3-triazol-5-yl)pyrrolo[2,1-f][1,2,4]triazin-7-yl)phenyl)piperazin-1-yl)-2-methylpropan-1-one | 1.35 F | 516.3 |

TABLE 33-continued
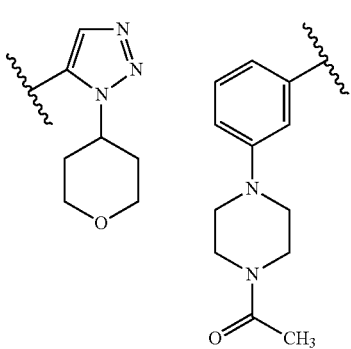
| Ex. No. | Q₁ | Q₂ | Name | Retention Time (min) method | M⁺ |
|---|---|---|---|---|---|
| 298 | 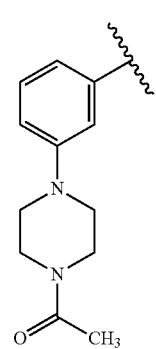 [SMILES: *c1cccc(N2CCN(C(C)=O)CC2)c1] | 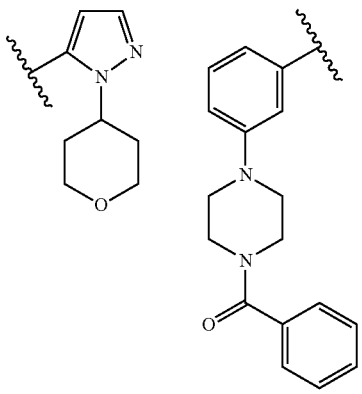 | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperazin-1-yl)ethanone | 1.12 F | 488.2 |
| 299 | 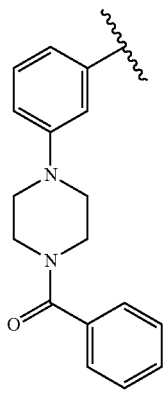 [SMILES: *c1cccc(N2CCN(C(=O)c3ccccc3)CC2)c1] | 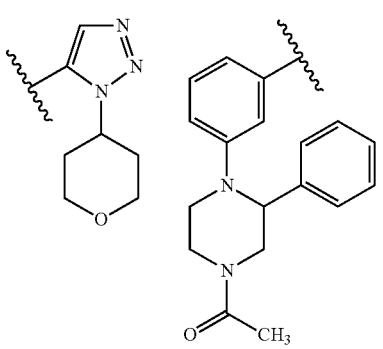 | (4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)(phenyl)methanone | 1.51 F | 549.2 |
| 300 | 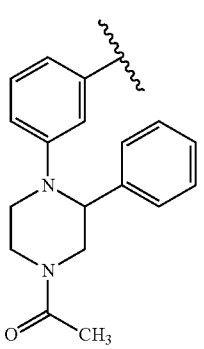 [SMILES: *c1cccc(N2CCN(C(C)=O)CC2c2ccccc2)c1] | | 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-phenylpiperazin-1-yl)ethanone | 1.30 F | 563.8 |

TABLE 33-continued

| Ex. No. | Q₁ | Q₂ | Name | Retention Time (min) method | M⁺ |
|---|---|---|---|---|---|
| 301 | 1-(tetrahydro-2H-pyran-4-yl)-1H-pyrazol-5-yl | 3-(piperidin-4-yl(N-methylacetamide))phenyl | N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methylacetamide | 1.08 F | 515.2 |
| 302 | 1-isopropyl-1H-pyrazol-5-yl | 3-(4-acetylpiperazin-1-yl)phenyl | 1-(4-(3-(4-amino-5-(1-isopropyl-1H-pyrazol-5-yl)pyrrolo[2,1-f][1,2,4]triazin-7-yl)phenyl)piperazin-1-yl)ethanone | 1.12 F | 445.3 |
| 303 | 1-cyclopropyl-1H-pyrazol-5-yl | 3-(4-acetylpiperazin-1-yl)phenyl | 1-(4-(3-(4-amino-5-(1-cyclopropyl-1H-pyrazol-5-yl)pyrrolo[2,1-f][1,2,4]triazin-7-yl)phenyl)piperazin-1-yl)ethanone | 1.08 F | 443.1 |

Example 304

3-(3-(4-Amino-5-(1-(tetrahydro-2H-pyran-4-yl)-1H-pyrazol-5-yl)pyrrolo[2,1-f][1,2,4]triazin-7-yl)phenyl)-1,3-oxazinan-2-one

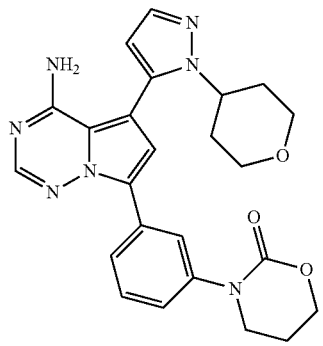

(304)

Example 304 was prepared according to the General Procedure 1 using Intermediate N1 and the appropriate bromide Intermediate Q39. LCMS M$^+$=460.4. Method F. Retention time 0.96 min. $^1$H NMR (500 MHz, DMSO-d$_6$) δ 8.11 (s, 1H), 8.08 (s, 1H), 8.02 (d, J=7.9 Hz, 1H), 7.72-7.65 (m, 1H), 7.51 (t, J=7.9 Hz, 1H), 7.36 (d, J=7.9 Hz, 1H), 7.26 (s, 1H), 6.46 (d, J=1.2 Hz, 1H), 4.43-4.31 (m, 3H), 3.92-3.82 (m, 2H), 3.73 (t, J=6.1 Hz, 2H), 3.32 (t, J=11.6 Hz, 2H), 2.19-2.02 (m, 4H), 1.80 (m, 2H).

The Examples in Table 34 were prepared according to the general procedure for the preparation of Example 304 using an appropriate intermediate. Some of the coupling reactions were performed under conventional heating overnight at 100° C. In some reactions, tripotassium phosphate was used as base instead of sodium carbonate.

TABLE 34

| Ex. No. | Q$_1$ | Q$_2$ | Name | LCMS Retention Time (min) Method | M+ |
|---|---|---|---|---|---|
| 305 | | | 3-(3-(4-amino-5-(1-(tetrahydro-2H-pyran-4-yl)-1H-1,2,3-triazol-5-yl)pyrrolo[2,1-f][1,2,4]triazin-7-yl)phenyl)-1,3-oxazinan-2-one | 0.88 F | 461.4 |
| 306 | | | 4-(3-(4-amino-5-(1H-indol-2-yl)pyrrolo[2,1-f][1,2,4]triazin-7-yl)phenyl)-2,2-dimethylmorpholin-3-one | 1.44 F | 453.3 |

TABLE 34-continued
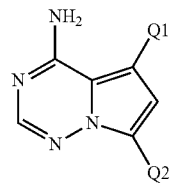
| Ex. No. | Q₁ | Q₂ | Name | LCMS Retention Time (min) Method | M+ |
|---|---|---|---|---|---|
| 307 | | | 4-(3-(4-amino-5-(1-(tetrahydro-2H-pyran-4-yl)-1H-pyrazol-5-yl)pyrrolo[2,1-f][1,2,4]triazin-7-yl)phenyl)-2,2-dimethylmorpholin-3-one | 1.15 F | 488.3 |
| 308 | | | 4-(3-(4-amino-5-(1-(4,4-difluorocyclohexyl)-1H-pyrazol-5-yl)pyrrolo[2,1-f][1,2,4]triazin-7-yl)phenyl)-2,2-dimethylmorpholin-3-one | 1.46 F | 522.3 |
| 309 | | | 4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,2-dimethylmorpholin-3-one | 1.09 F | 489.3 |

Example 310

7-(3-(2-(Methyl(tetrahydro-2H-pyran-4-yl)amino)propan-2-yl)phenyl)-5-(1-(tetrahydro-2H-pyran-4-yl)-1H-pyrazol-5-yl)pyrrolo[2,1-f][1,2,4]triazin-4-amine

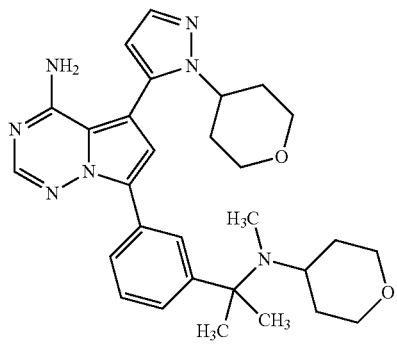

(310)

Example 310 was prepared according to the General Procedure 1 using Intermediate N1 and the required bromide intermediate Q12. The residue was purified by RP HPLC (Method B) to afford Example 310 (18.4 mg). LCMS M+=516.3. Method F. Retention time 0.96 min. $^1$H NMR (500 MHz, methanol-$d_4$) δ 8.20 (s, 1H), 7.96 (s, 1H), 7.87 (d, J=7.9 Hz, 1H), 7.69 (d, J=1.5 Hz, 1H), 7.59 (d, J=7.9 Hz, 1H), 7.48-7.42 (m, 1H), 6.91 (s, 1H), 6.46 (d, J=1.5 Hz, 1H), 4.46-4.34 (m, 1H), 4.04 (d, J=9.9 Hz, 2H), 3.87 (dd, J=11.4, 4.0 Hz, 2H), 3.42 (t, J=11.6 Hz, 2H), 3.25 (t, J=11.4 Hz, 2H), 2.84-2.68 (m, 1H), 2.39 (s, 3H), 2.36-2.23 (m, 2H), 1.90-1.80 (m., 2H), 1.80-1.69 (m, 2H), 1.57-1.48 (m, 2H), 1.49 (s, 6H).

The following compounds in Table 35 were prepared according to the General Procedure 1 using appropriate intermediates. Some of the coupling reactions were performed under conventional heating overnight at 100° C. In some reactions, tripotassium phosphate was used as base instead of sodium carbonate.

TABLE 35

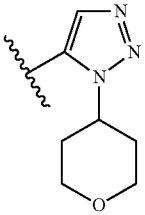 [SMILES: *c1cnnn1C1CCOCC1]

| Ex. No. | Q$_1$ | Q$_2$ | Name | LCMS retention Time (min) Method | M+ |
|---|---|---|---|---|---|
| 311 | 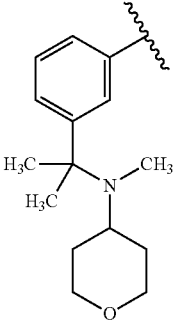 [SMILES: *c1cccc(C(C)(C)N(C)C2CCOCC2)c1] | 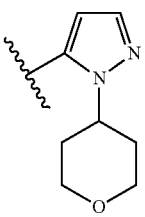 [SMILES: *c1ccnn1C1CCOCC1] | 7-(3-(2-(methyl(tetrahydro-2H-pyran-4-yl)amino)propan-2-yl)phenyl)-5-(1-(tetrahydro-2H-pyran-4-yl)-1H-1,2,3-triazol-5-yl)pyrrolo[2,1-f][1,2,4]triazin-4-amine | 0.89 F | 517.3 |
| 312 | 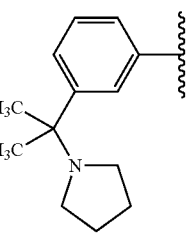 | | 7-(3-(2-(pyrrolidin-1-yl)propan-2-yl)phenyl)-5-(1-(tetrahydro-2H-pyran-4-yl)-1H-pyrazol-5-yl)pyrrolo[2,1-f][1,2,4]triazin-4-amine | 1.17 F | 472.3 |

TABLE 35-continued

| Ex. No. | Q₁ | Q₂ | Name | LCMS retention Time (min) Method | M+ |
|---|---|---|---|---|---|
| 313 | (2-(tetrahydro-2H-pyran-4-yl)-2H-1,2,3-triazol-5-yl) | 3-(2-(pyrrolidin-1-yl)propan-2-yl)phenyl | 7-(3-(2-(pyrrolidin-1-yl)propan-2-yl)phenyl)-5-(1-(tetrahydro-2H-pyran-4-yl)-1H-1,2,3-triazol-5-yl)pyrrolo[2,1-f][1,2,4]triazin-4-amine | 0.90 F | 473.3 |
| 314 | (1-(tetrahydro-2H-pyran-4-yl)-1H-pyrazol-5-yl) | 3-(2-(1-methylpyrrolidin-1-ium-1-yl)propan-2-yl)phenyl | 1-(2-(3-(4-amino-5-(1-(tetrahydro-2H-pyran-4-yl)-1H-pyrazol-5-yl)pyrrolo[2,1-f][1,2,4]triazin-7-yl)phenyl)propan-2-yl)-1-methylpyrrolidin-1-ium | 0.96 F | 486.3 |

The Examples in Table 36 were prepared according to the General Procedure 1 using appropriate intermediates. Some of the coupling reactions were performed under conventional heating overnight at 100° C. In some reactions, tripotassium phosphate was used as base instead sodium carbonate.

TABLE 36

| Ex. No. | Q₁ | Q₂ | Name | LCMS Retention Time(min) Method | M+ |
|---|---|---|---|---|---|
| 315 | (1-(tetrahydro-2H-pyran-4-yl)-1H-pyrazol-5-yl) | 3-(4-hydroxy-1-methylpiperidin-4-yl)phenyl | 4-(3-(4-amino-5-(1-(tetrahydro-2H-pyran-4-yl)-1H-pyrazol-5-yl)pyrrolo[2,1-f][1,2,4]triazin-7-yl)phenyl)-1-methylpiperidin-4-ol | 0.92 F | 474.15 |

TABLE 36-continued

| Ex. No. | Q₁ | Q₂ | Name | LCMS Retention Time(min) Method | M⁺ |
|---|---|---|---|---|---|
| 316 | pyrazole-N-(tetrahydropyran-4-yl) | phenyl-4-hydroxy-1-acetylpiperidin-4-yl | 1-(4-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypiperidin-1-yl)ethanone | 1.07 F | 502.15 |
| 317 | triazole-N-(tetrahydropyran-4-yl) | phenyl-4-hydroxytetrahydropyran-4-yl | 4-(3-(4-amino-5-(1-(tetrahydro-2H-pyran-4-yl)-1H-1,2,3-triazol-5-yl)pyrrolo[2,1-f][1,2,4]triazin-7-yl)phenyl)tetrahydro-2H-pyran-4-ol | 1.06 F | 462.10 |
| 318 | pyrazole-N-(tetrahydropyran-4-yl) | phenyl-4-methoxytetrahydropyran-4-yl | 7-(3-(4-methoxytetrahydro-2H-pyran-4-yl)phenyl)-5-(1-(tetrahydro-2H-pyran-4-yl)-1H-pyrazol-5-yl)pyrrolo[2,1-f][1,2,4]triazin-4-amine | 1.49 F | 474.9 |
| 319 | triazole-N-(tetrahydropyran-4-yl) | phenyl-4-methoxytetrahydropyran-4-yl | 7-(3-(4-methoxytetrahydro-2H-pyran-4-yl)phenyl)-5-(1-(tetrahydro-2H-pyran-4-yl)-1H-1,2,3-triazol-5-yl)pyrrolo[2,1-f][1,2,4]triazin-4-amine | 1.21 F | 475.8 |

TABLE 36-continued

| Ex. No. | Q₁ | Q₂ | Name | LCMS Retention Time(min) Method | M⁺ |
|---|---|---|---|---|---|
| 320 | pyrazole-tetrahydropyran | phenyl-tetrahydropyran-NHAc | N-(4-(3-(4-amino-5-(1-(tetrahydro-2H-pyran-4-yl)-1H-pyrazol-5-yl)pyrrolo[2,1-f][1,2,4]triazin-7-yl)phenyl)tetrahydro-2H-pyran-4-yl)acetamide | 1.04 F | 502.2 |
| 321 | pyrazole-tetrahydropyran | phenyl-piperidine(N-Ac)-NHAc | N-(1-acetyl-4-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)acetamide | 0.89 F | 543.2 |
| 322 | pyrazole-tetrahydropyran | phenyl-tetrahydropyran-CN | 4-(3-(4-amino-5-(1-(tetrahydro-2H-pyran-4-yl)-1H-pyrazol-5-yl)pyrrolo[2,1-f][1,2,4]triazin-7-yl)phenyl)tetrahydro-2H-pyran-4-carbonitrile | 1.24 F | 470.2 |
| 323 | pyrazole-tetrahydropyran | phenyl-tetrahydropyran-CONH₂ | 4-(3-(4-amino-5-(1-(tetrahydro-2H-pyran-4-yl)-1H-pyrazol-5-yl)pyrrolo[2,1-f][1,2,4]triazin-7-yl)phenyl)tetrahydro-2H-pyran-4-carboxamide | 1.07 F | 488.2 |

Example 324

4-Acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-2-one

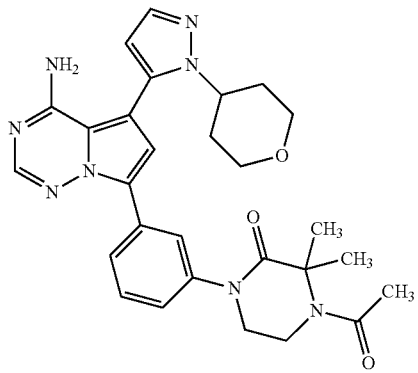

(324)

Example 324 was prepared according to the general procedure for the preparation of Example 304 using Intermediate N1 and Intermediate Q53. The residue was purified by RP HPLC (Method B) to afford Example 562 (22.0 mg). LCMS M$^+$=529.25. Method F. Retention time 1.06 min. $^1$H NMR (500 MHz, DMSO-d$_6$) δ 8.11-8.04 (m, 2H), 8.04 (s, 1H), 7.68 (s, 1H), 7.54 (t, J=7.9 Hz, 1H), 7.35 (d, J=8.4 Hz, 1H), 7.27 (s, 1H), 6.47 (s, 1H), 4.35 (m., 1H), 3.92-3.85 (m, 2H), 3.83 (m., 2H), 3.77 (m, 2H), 3.43-3.40 (m, 2H), 2.20-2.00 (m, 2H), 2.10 (s, 3H), 1.78 (m, 2H), 1.70 (s, 6H).

The Examples in Table 37 were prepared according to the General Procedure 1 using appropriate intermediates. Some of the coupling reactions were performed under conventional heating overnight at 100° C. In some reactions, tripotassium phosphate was used as the base instead of sodium carbonate.

TABLE 37

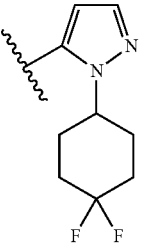 [SMILES: *c1ccnn1C1CCC(F)(F)CC1]

| Ex. No. | Q$_1$ | Q$_2$ | Name | LCMS Retention Time(min) Method | M$^+$ |
|---|---|---|---|---|---|
| 325 | 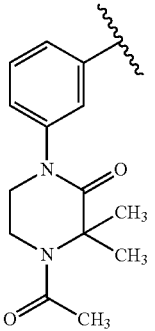 [SMILES: *c1cccc(N2CCN(C(C)=O)C(C)(C)C2=O)c1] | 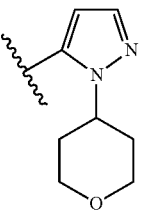 [SMILES: *c1ccnn1C1CCOCC1] | 4-acetyl-1-(3-(4-amino-5-(1-(4,4-difluorocyclohexyl)-1H-pyrazol-5-yl)pyrrolo[2,1-f][1,2,4]triazin-7-yl)phenyl)-3,3-dimethylpiperazin-2-one | 1.39 F | 563.4 |
| 326 | 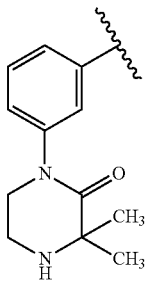 [SMILES: *c1cccc(N2CCNC(C)(C)C2=O)c1] | | 1-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-2-one | 0.71 F | 487.3 |

TABLE 37-continued

| Ex. No. | Q₁ | Q₂ | Name | LCMS Retention Time(min) Method | M⁺ |
|---|---|---|---|---|---|
| 327 | indol-2-yl | 3-(3,3-dimethyl-4-acetylpiperazin-2-on-1-yl)phenyl | 4-acetyl-1-(3-(4-amino-5-(1H-indol-2-yl)pyrrolo[2,1-f][1,2,4]triazin-7-yl)phenyl)-3,3-dimethylpiperazin-2-one | 1.37 F | 494.3 |
| 328 | 1-cyclopropyl-1H-pyrazol-5-yl | 3-(3,3-dimethyl-4-acetylpiperazin-2-on-1-yl)phenyl | 4-acetyl-1-(3-(4-amino-5-(1-cyclopropyl-1H-pyrazol-5-yl)pyrrolo[2,1-f][1,2,4]triazin-7-yl)phenyl)-3,3-dimethylpiperazin-2-one | 1.06 F | 485.1 |
| 329 | 1-(2,2,2-trifluoroethyl)-1H-pyrazol-5-yl | 3-(3,3-dimethyl-4-acetylpiperazin-2-on-1-yl)phenyl | 4-acetyl-1-(3-(4-amino-5-(1-(2,2,2-trifluoroethyl)-1H-pyrazol-5-yl)pyrrolo[2,1-f][1,2,4]triazin-7-yl)phenyl)-3,3-dimethylpiperazin-2-one | 1.12 F | 527.3 |
| 330 | 1-(tetrahydro-2H-pyran-4-yl)-1H-pyrazol-5-yl | 3-(5,5-dimethyl-4-acetylpiperazin-2-on-1-yl)phenyl | 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethylpiperazin-2-one | 1.07 F | 529.3 |

TABLE 37-continued
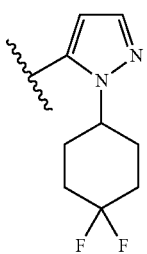 [SMILES: *c1ccnn1C1CCC(F)(F)CC1]
| Ex. No. | Q₁ | Q₂ | Name | LCMS Retention Time(min) Method | M⁺ |
|---|---|---|---|---|---|
| 331 | 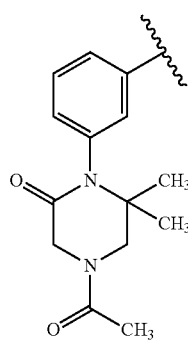 [SMILES: *c1cccc(N2C(=O)CN(C(C)=O)CC2(C)C)c1] | 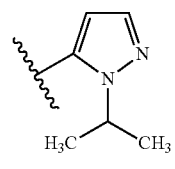 [SMILES: *c1ccnn1C(C)C] | 4-acetyl-1-(3-(4-amino-5-(1-(4,4-difluorocyclohexyl)-1H-pyrazol-5-yl)pyrrolo[2,1-f][1,2,4]triazin-7-yl)phenyl)-6,6-dimethylpiperazin-2-one | 1.33 F | 563.20 |
| 332 | 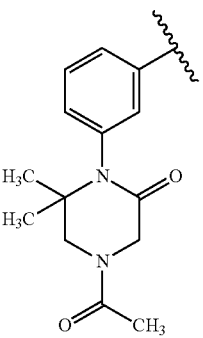 [SMILES: *c1cccc(N2C(=O)CN(C(C)=O)CC2(C)C)c1] | 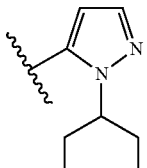 | 4-acetyl-1-(3-(4-amino-5-(1-isopropyl-1H-pyrazol-5-yl)pyrrolo[2,1-f][1,2,4]triazin-7-yl)phenyl)-6,6-dimethylpiperazin-2-one | 1.17 F | 487.20 |
| 333 | 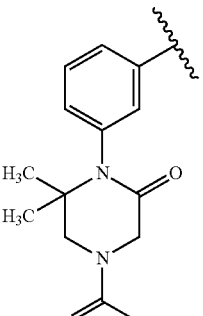 | | 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-6,6-dimethylpiperazin-2-one | 1.11 F | 529.25 |

TABLE 37-continued

| Ex. No. | Q₁ | Q₂ | Name | LCMS Retention Time(min) Method | M⁺ |
|---|---|---|---|---|---|
| 334 | 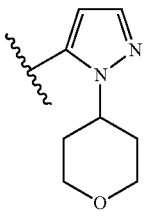 [SMILES: *c1ccnn1C1CCOCC1] | 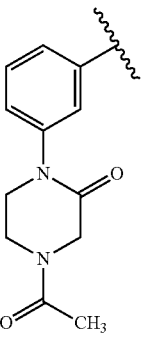 [SMILES: *c1cccc(N2CCN(C(C)=O)CC2=O)c1] | 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)piperazin-2-one | 0.86 F | 501.2 |
| 335 | 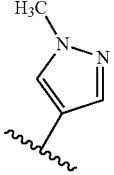 | 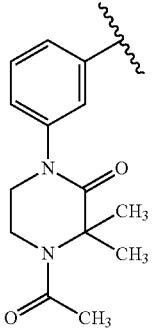 [SMILES: *c1cccc(N2CCN(C(C)=O)C(C)(C)C2=O)c1] | 4-acetyl-1-(3-(4-amino-5-(1-methyl-1H-pyrazol-4-yl)pyrrolo[2,1-f][1,2,4]triazin-7-yl)phenyl)-3,3-dimethylpiperazin-2-one | 0.93 F | 459.2 |
| 336 | 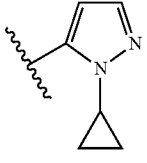 [SMILES: *c1ccnn1C1CC1] | 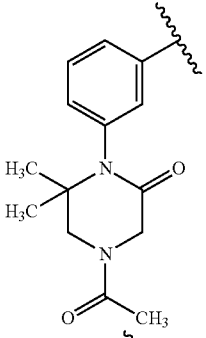 | 4-acetyl-1-(3-(4-amino-5-(1-cyclopropyl-1H-pyrazol-5-yl)pyrrolo[2,1-f][1,2,4]triazin-7-yl)phenyl)-6,6-dimethylpiperazin-2-one | 1.00 F | 485.3 |
| 337 | 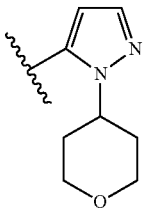 [SMILES: *c1ccnn1C1CCOCC1] | 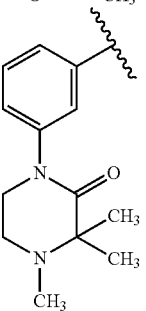 | 1-(3-(4-amino-5-(1-(tetrahydro-2H-pyran-4-yl)-1H-pyrazol-5-yl)pyrrolo[2,1-f][1,2,4]triazin-7-yl)phenyl)-3,3,4-trimethylpiperazin-2-one | 0.83 F | 501.4 |

Example 338

4-Acetyl-1-(3-(4-amino-5-(1-isopropyl-1H-pyrazol-4-yl)pyrrolo[2,1-f][1,2,4]triazin-7-yl)phenyl)-3,3-dimethylpiperazin-2-one

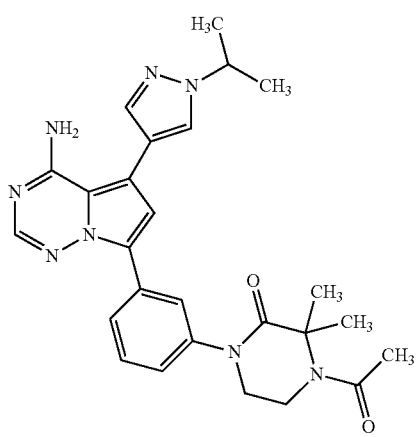

(338)

In a sealable pressure vial, 1-isopropyl-4-(4,4,5,5-tetramethyl-1,3,2-dioxaborolan-2-yl)-1H-pyrazole (7.74 mg, 0.033 mmol), 4-acetyl-1-(3-(4-amino-5-bromopyrrolo[2,1-f][1,2,4]triazin-7-yl)phenyl)-3,3-dimethylpiperazin-2-one (15 mg, 0.033 mmol, Example 548) and PdCl$_2$(dppf)-CH$_2$Cl$_2$ adduct (5.36 mg, 6.56 μmol) were dissolved in DMF (1 mL), followed by addition of tripotassium phosphate (0.049 mL, 0.098 mmol). The mixture was purged with nitrogen and stirred at 100° C. overnight. The mixture was cooled, diluted with 5 mL of water, and extracted with EtOAc (10 mL×2). The organic layers were combined, dried, concentrated and the residue was purified by preparative HPLC (Method B) to afford Example 338 (10.8 mg). LCMS M$^+$=487.4. Method F. Retention time 1.05 min. $^1$H NMR (500 MHz, DMSO-d$_6$) δ 8.06 (d, J=8.1 Hz, 1H), 8.01 (s, 1H), 8.00-7.93 (m, 2H), 7.65 (s, 1H), 7.51 (t, J=7.9 Hz, 1H), 7.31 (d, J=7.7 Hz, 1H), 7.10 (s, 1H), 4.63-4.50 (m, 1H), 3.82 (m, 2H), 3.76 (m, 2H), 2.10 (s, 3H), 1.70 (s, 6H), 1.48 (d, J=6.4 Hz, 6H).

The Examples in Table 38 were prepared according to the general procedure for the preparation of Example 338 using Examples 548, 549 and other intermediates prepared in a similar manner with an appropriate boronic ester or boronic acid.

TABLE 38

| Ex. No. | Q$_1$ | Q$_2$ | Name | LCMS Retention Time(min) Method | M+ |
|---|---|---|---|---|---|
| 339 | [pyrazole structure with H$_3$C and phenyl] | [phenyl-piperazinone with acetyl] | 4-acetyl-1-(3-(4-amino-5-(5-methyl-1-phenyl-1H-pyrazol-4-yl)pyrrolo[2,1-f][1,2,4]triazin-7-yl)phenyl)-3,3-dimethylpiperazin-2-one | 1.24 F | 535.3 |

TABLE 38-continued

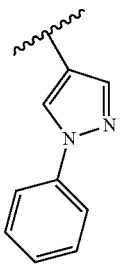 [SMILES: *c1cnn(-c2ccccc2)c1]

| Ex. No. | Q₁ | Q₂ | Name | LCMS Retention Time(min) Method | M+ |
|---|---|---|---|---|---|
| 340 | 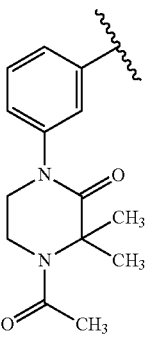 | 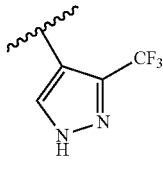 [SMILES: *c1c[nH]nc1C(F)(F)F] | 4-acetyl-1-(3-(4-amino-5-(1-phenyl-1H-pyrazol-4-yl)pyrrolo[2,1-f][1,2,4]triazin-7-yl)phenyl)-3,3-dimethylpiperazin-2-one | 1.26 F | 521.3 |
| 341 | 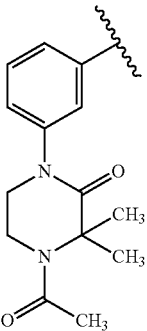 | 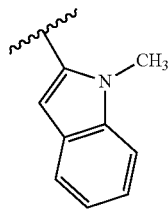 [SMILES: *c1cc2ccccc2n1C] | 4-acetyl-1-(3-(4-amino-5-(3-(trifluoromethyl)-1H-pyrazol-4-yl)pyrrolo[2,1-f][1,2,4]triazin-7-yl)phenyl)-3,3-dimethylpiperazin-2-one | 1.10 F | 513.3 |
| 342 | 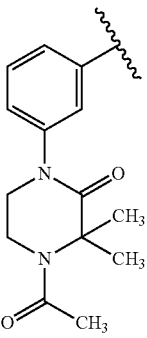 [SMILES: *c1cccc(N2CCN(C(C)=O)C(C)(C)C2=O)c1] | | 4-acetyl-1-(3-(4-amino-5-(1-methyl-1H-indol-2-yl)pyrrolo[2,1-f][1,2,4]triazin-7-yl)phenyl)-3,3-dimethylpiperazin-2-one | 1.46 F | 508.3 |
| 343 | 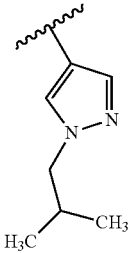 | 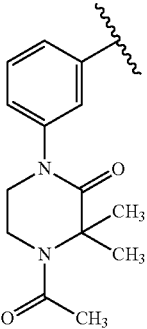 | 4-acetyl-1-(3-(4-amino-5-(1-isobutyl-1H-pyrazol-4-yl)pyrrolo[2,1-f][1,2,4]triazin-7-yl)phenyl)-3,3-dimethylpiperazin-2-one | 1.26 F | 501.4 |

TABLE 38-continued
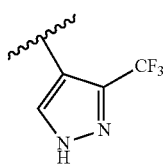 [SMILES: *c1c[nH]nc1C(F)(F)F]
| Ex. No. | Q₁ | Q₂ | Name | LCMS Retention Time(min) Method | M+ |
|---|---|---|---|---|---|
| 344 | 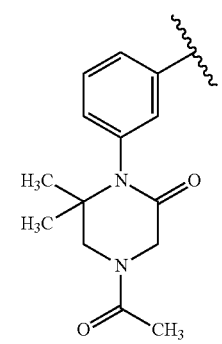 [SMILES: *c1cccc(N2C(=O)CN(C(C)=O)CC2(C)C)c1] | 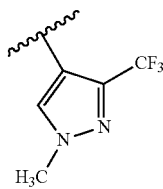 [SMILES: *c1cn(C)nc1C(F)(F)F] | 4-acetyl-1-(3-(4-amino-5-(3-(trifluoromethyl)-1H-pyrazol-4-yl)pyrrolo[2,1-f][1,2,4]triazin-7-yl)phenyl)-6,6-dimethylpiperazin-2-one | 1.04 F | 513.2 |
| 345 | 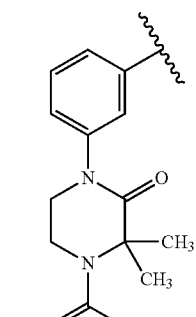 | 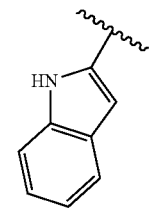 [SMILES: *c1cc2ccccc2[nH]1] | 4-acetyl-1-(3-(4-amino-5-(1-methyl-3-(trifluoromethyl)-1H-pyrazol-4-yl)pyrrolo[2,1-f][1,2,4]triazin-7-yl)phenyl)-3,3-dimethylpiperazin-2-one | 1.23 F | 527.3 |
| 346 | 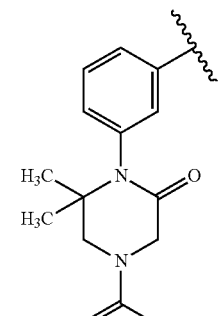 | 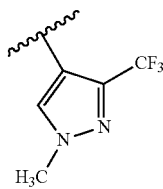 [SMILES: *c1cn(C)nc1C(F)(F)F] | 4-acetyl-1-(3-(4-amino-5-(1H-indol-2-yl)pyrrolo[2,1-f][1,2,4]triazin-7-yl)phenyl)-6,6-dimethylpiperazin-2-one | 1.25 F | 494.3 |

TABLE 38-continued

| Ex. No. | Q₁ | Q₂ | Name | LCMS Retention Time(min) Method | M+ |
|---|---|---|---|---|---|
| 347 | | | 4-acetyl-1-(3-(4-amino-5-(1-(cyclopropylmethyl)-1H-pyrazol-4-yl)pyrrolo[2,1-f][1,2,4]triazin-7-yl)phenyl)-3,3-dimethylpiperazin-2-one | 1.19 F | 499.4 |
| 348 | | | 4-acetyl-1-(3-(4-amino-5-(1-methyl-5-phenyl-1H-pyrazol-4-yl)pyrrolo[2,1-f][1,2,4]triazin-7-yl)phenyl)-3,3-dimethylpiperazin-2-one | 1.25 F | 535.3 |
| 349 | | | 4-acetyl-1-(3-(4-amino-5-(1-cyclopropyl-1H-pyrazol-4-yl)pyrrolo[2,1-f][1,2,4]triazin-7-yl)phenyl)-3,3-dimethylpiperazin-2-one | 1.09 F | 485.3 |
| 350 | | | 4-acetyl-1-(3-(4-amino-5-(1-(2-hydroxy-2-methylpropyl)-1H-pyrazol-4-yl)pyrrolo[2,1-f][1,2,4]triazin-7-yl)phenyl)-3,3-dimethylpiperazin-2-one | 1.01 F | 517.4 |

TABLE 38-continued

| Ex. No. | Q₁ | Q₂ | Name | LCMS Retention Time(min) Method | M+ |
|---|---|---|---|---|---|
| 351 | | | 1-(3-(4-amino-5-(1-(tetrahydro-2H-pyran-4-yl)-1H-pyrazol-5-yl)pyrrolo[2,1-f][1,2,4]triazin-7-yl)phenyl)-4-(4-fluorophenyl)-3,3-dimethylpiperazine-2,5-dione | 1.31 F | 595.3 |
| 352 | | | 1-(3-(4-amino-5-(1-(tetrahydro-2H-pyran-4-yl)-1H-1,2,3-triazol-5-yl)pyrrolo[2,1-f][1,2,4]triazin-7-yl)phenyl)-4-(4-fluorophenyl)-3,3-dimethylpiperazine-2,5-dione | 1.32 F | 596.4 |
| 353 | | | 4-acetyl-1-(3-(4-amino-5-(1-(tetrahydrofuran-3-yl)-1H-pyrazol-4-yl)pyrrolo[2,1-f][1,2,4]triazin-7-yl)phenyl)-3,3-dimethylpiperazin-2-one | 0.99 F | 515.4 |

TABLE 38-continued

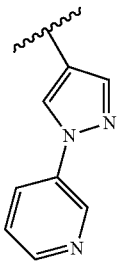 [SMILES: *c1cnn(-c2cccnc2)c1]

| Ex. No. | Q₁ | Q₂ | Name | LCMS Retention Time(min) Method | M+ |
|---|---|---|---|---|---|
| 354 | 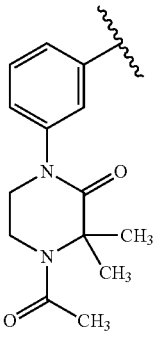 [SMILES: *c1cccc(N2CCN(C(C)=O)C(C)(C)C2=O)c1] | 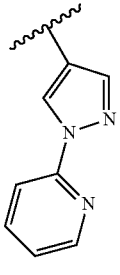 [SMILES: *c1cnn(-c2ccccn2)c1] | 4-acetyl-1-(3-(4-amino-5-(1-(pyridin-3-yl)-1H-pyrazol-4-yl)pyrrolo[2,1-f][1,2,4]triazin-7-yl)phenyl)-3,3-dimethylpiperazin-2-one | 0.93 F | 522.3 |
| 355 | 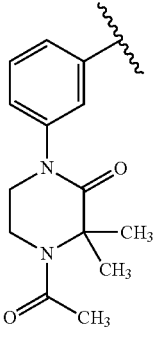 | 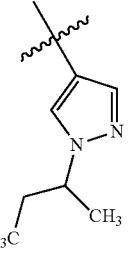 | 4-acetyl-1-(3-(4-amino-5-(1-(pyridin-2-yl)-1H-pyrazol-4-yl)pyrrolo[2,1-f][1,2,4]triazin-7-yl)phenyl)-3,3-dimethylpiperazin-2-one | 1.19 F | 522.3 |
| 356 | 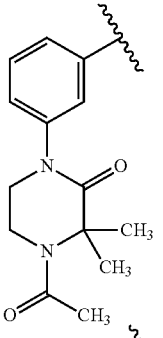 | 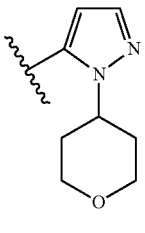 [SMILES: *c1ccnn1C1CCOCC1] | 4-acetyl-1-(3-(4-amino-5-(1-(sec-butyl)-1H-pyrazol-4-yl)pyrrolo[2,1-f][1,2,4]triazin-7-yl)phenyl)-3,3-dimethylpiperazin-2-one | 1.21 F | 501.4 |
| 357 | 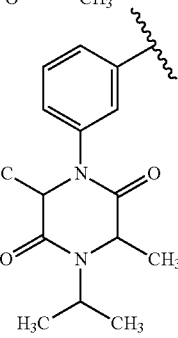 | | 1-(3-(4-amino-5-(1-(tetrahydro-2H-pyran-4-yl)-1H-pyrazol-5-yl)pyrrolo[2,1-f][1,2,4]triazin-7-yl)phenyl)-4-isopropyl-3,6-dimethylpiperazine-2,5-dione | 1.18 F | 543.4 |

The following Examples were prepared by employing the methodology exemplified above.

TABLE 39

| Ex. No. | Q₁ | Q₂ | Name | H + M⁺ Rt (min.) Method |
|---|---|---|---|---|
| 358 | 1-(tetrahydro-2H-pyran-4-yl)-1H-pyrazol-5-yl | 3-(8-fluoro-1-methyl-2,4-dioxo-1,2,3,4-tetrahydroquinazolin-3-yl)phenyl | 3-(3-(4-amino-5-(1-(tetrahydro-2H-pyran-4-yl)-1H-pyrazol-5-yl)pyrrolo[2,1-f][1,2,4]triazin-7-yl)phenyl)-8-fluoro-1-methylquinazoline-2,4(1H,3H)-dione | 553.13 2.848 D |
| 359 | 1-(tetrahydro-2H-pyran-4-yl)-1H-pyrazol-5-yl | 3-(1-methyl-2,4-dioxo-1,2,3,4-tetrahydroquinazolin-3-yl)phenyl | 3-(3-(4-amino-5-(1-(tetrahydro-2H-pyran-4-yl)-1H-pyrazol-5-yl)pyrrolo[2,1-f][1,2,4]triazin-7-yl)phenyl)-1-methylquinazoline-2,4(1H,3H)-dione | 535.11 2.661 D |
| 360 | 1-(tetrahydro-2H-pyran-4-yl)-1H-pyrazol-5-yl | 3-(4-oxoquinazolin-3(4H)-yl)phenyl | 3-(3-(4-amino-5-(1-(tetrahydro-2H-pyran-4-yl)-1H-pyrazol-5-yl)pyrrolo[2,1-f][1,2,4]triazin-7-yl)phenyl)quinazolin-4(3H)-one | 505.3 2.985 D |
| 361 | 1-(tetrahydro-2H-pyran-4-yl)-1H-pyrazol-5-yl | 3-(1,3-dioxo-1H-pyrido[1,2-c]pyrimidin-2(3H)-yl)phenyl | 2-(3-(4-amino-5-(1-(tetrahydro-2H-pyran-4-yl)-1H-pyrazol-5-yl)pyrrolo[2,1-f][1,2,4]triazin-7-yl)phenyl)-1H-pyrido[1,2-c]pyrimidine-1,3(2H)-dione | 521.3 2.535 D |
| 362 | 1-(tetrahydro-2H-pyran-4-yl)-1H-1,2,3-triazol-5-yl | 3-(1-methyl-2,4-dioxo-1,2,3,4-tetrahydroquinazolin-3-yl)phenyl | 3-(3-(4-amino-5-(1-(tetrahydro-2H-pyran-4-yl)-1H-1,2,3-triazol-5-yl)pyrrolo[2,1-f][1,2,4]triazin-7-yl)phenyl)-1-methylquinazoline-2,4(1H,3H)-dione | 536.2 1.18 F |

TABLE 39-continued

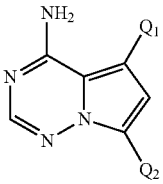

| Ex. No. | Q₁ | Q₂ | Name | H + M⁺ Rt (min.) Method |
|---|---|---|---|---|
| 363 | 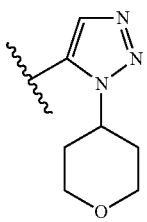 [SMILES: *c1cnnn1C1CCOCC1] | 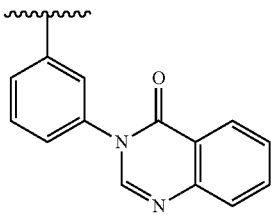 [SMILES: *c1cccc(-n2cnc3ccccc3c2=O)c1] | 3-(3-(4-amino-5-(1-(tetrahydro-2H-pyran-4-yl)-1H-1,2,3-triazol-5-yl) pyrrolo[2,1-f][1,2,4]triazin-7-yl) phenyl)quinazolin-4(3H)-one | 506.2 1.15 F |
| 364 | 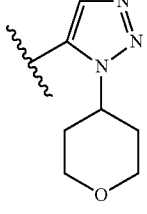 | 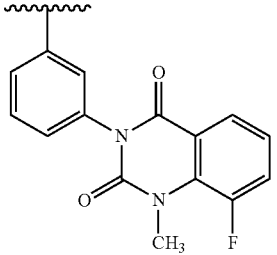 [SMILES: *c1cccc(-n2c(=O)c3cccc(F)c3n(C)c2=O)c1] | 3-(3-(4-amino-5-(1-(tetrahydro-2H-pyran-4-yl)-1H-1,2,3-triazol-5-yl) pyrrolo[2,1-f][1,2,4]triazin-7-yl) phenyl)-8-fluoro-1-methylquinazoline-2,4(1H,3H)-dione | 554.2 1.29 F |
| 365 | 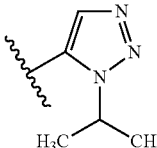 | 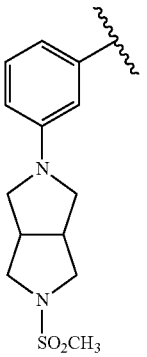 [SMILES: *c1cccc(N2CC3CN(S(C)(=O)=O)CC3C2)c1] | 5-(1-isopropyl-1H-1,2,3-triazol-5-yl)-7-(3-(5-(methylsulfonyl) hexahydropyrrolo[3,4-c]pyrrol-2(1H)-yl)phenyl)pyrrolo[2,1-f][1,2,4]triazin-4-amine | 508.3 1.24 F |
| 366 | 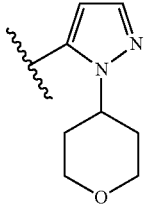 [SMILES: *c1ccnn1C1CCOCC1] | 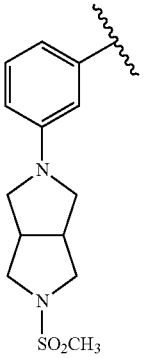 [SMILES: *c1cccc(N2CC3CN(S(C)(=O)=O)CC3C2)c1] | 7-(3-(5-(methylsulfonyl) hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine | 549.3 1.24 F |

TABLE 39-continued

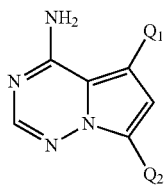

| Ex. No. | Q₁ | Q₂ | Name | H + M⁺ Rt (min.) Method |
|---|---|---|---|---|
| 367 | 5-(1-(tetrahydro-2H-pyran-4-yl)-1H-pyrazol-5-yl) | 3-(5-methylhexahydropyrrolo[3,4-c]pyrrol-2(1H)-yl)phenyl | 7-(3-(5-methylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine | 485.4 2.437 D |
| 368 | 1-(tetrahydro-2H-pyran-4-yl)-1H-1,2,3-triazol-5-yl | 3-(5-acetylhexahydropyrrolo[3,4-c]pyrrol-2(1H)-yl)phenyl | 1-(5-(3-(4-amino-5-(1-(tetrahydro-2H-pyran-4-yl)-1H-1,2,3-triazol-5-yl)pyrrolo[2,1-f][1,2,4]triazin-7-yl)phenyl)hexahydropyrrolo[3,4-c]pyrrol-2(1H)-yl)ethanone | 514.4 2.237 D |
| 369 | 1-(tetrahydro-2H-pyran-4-yl)-1H-pyrazol-5-yl | 3-(5-acetylhexahydropyrrolo[3,4-c]pyrrol-2(1H)-yl)phenyl | 1-(5-(3-(4-amino-5-(1-(tetrahydro-2H-pyran-4-yl)-1H-pyrazol-5-yl)pyrrolo[2,1-f][1,2,4]triazin-7-yl)phenyl)hexahydropyrrolo[3,4-c]pyrrol-2(1H)-yl)ethanone | 513.4 2.73 D |

TABLE 39-continued

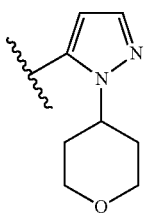 [SMILES: *c1ccnn1C1CCOCC1]

| Ex. No. | Q₁ | Q₂ | Name | H + M⁺ Rt (min.) Method |
|---|---|---|---|---|
| 370 | 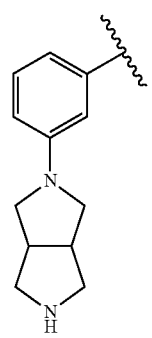 [SMILES: *c1cccc(N2CC3CNCC3C2)c1] | 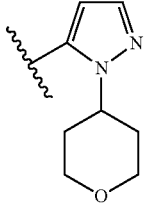 [SMILES: *c1ccnn1C1CCOCC1] | 7-(3-(hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine | 471.3 0.95 F |
| 371 | 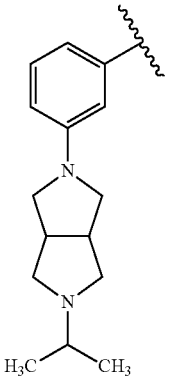 [SMILES: *c1cccc(N2CC3CN(C(C)C)CC3C2)c1] | 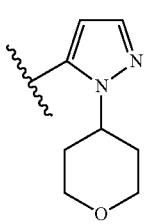 [SMILES: *c1ccnn1C1CCOCC1] | 7-(3-(5-isopropylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine | 513.3 0.98 F |
| 372 | 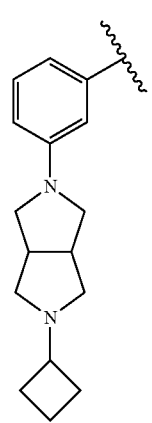 [SMILES: *c1cccc(N2CC3CN(C4CCC4)CC3C2)c1] | | 7-(3-(5-cyclobutylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine | 525.3 1.31 P |

TABLE 39-continued

| Ex. No. | Q₁ | Q₂ | Name | H + M⁺ Rt (min.) Method |
|---|---|---|---|---|
| 373 | pyrazole-N-(tetrahydro-2H-pyran-4-yl) | 3-phenyl-N-substituted hexahydropyrrolo[3,4-c]pyrrole with 3-methylbutan-2-ol substituent | 3-(5-(3-(4-amino-5-(1-(tetrahydro-2H-pyran-4-yl)-1H-pyrazol-5-yl)pyrrolo[2,1-f][1,2,4]triazin-7-yl)phenyl)hexahydropyrrolo[3,4-c]pyrrol-2(1H)-yl)-2-methylbutan-2-ol | 557.4 1.00 F |
| 374 | pyrazole-N-(tetrahydro-2H-pyran-4-yl) | 3-phenyl-N-substituted hexahydropyrrolo[3,4-c]pyrrole with 1-methoxypropan-2-yl substituent | 7-(3-(5-(1-methoxypropan-2-yl)hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine | 543.5 1.07 F |
| 375 | pyrazole-N-(tetrahydro-2H-pyran-4-yl) | 3-phenyl-N-(piperidin-4-yl)-N-methylmethanesulfonamide | N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methylmethanesulfonamide | 551.3 1.02 F |

TABLE 39-continued
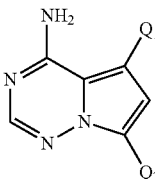
| Ex. No. | Q₁ | Q₂ | Name | H + M⁺ Rt (min.) Method |
|---|---|---|---|---|
| 376 | 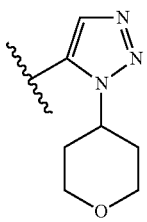 [SMILES: *c1cnnn1C1CCOCC1] | 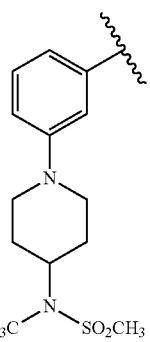 | N-(1-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-4-yl)-N-methylmethanesulfonamide | 552.3 0.94 F |
| 377 | 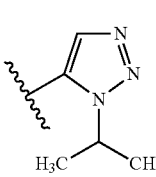 | 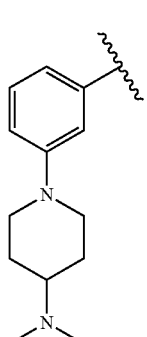 | N-(1-(3-(4-amino-5-(1-isopropyl-1H-1,2,3-triazol-5-yl)pyrrolo[2,1-f][1,2,4]triazin-7-yl)phenyl)piperidin-4-yl)-N-methylmethanesulfonamide | 510.3 1.02 F |
| 378 | 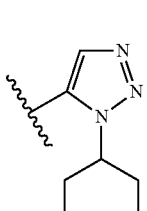 | 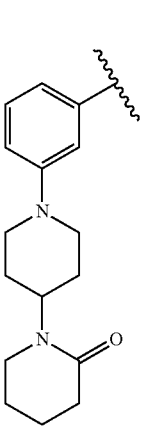 [SMILES: *c1cccc(N2CCC(N3CCCCC3=O)CC2)c1] | 1'-(3-(4-amino-5-(1-(tetrahydro-2H-pyran-4-yl)-1H-1,2,3-triazol-5-yl)pyrrolo[2,1-f][1,2,4]triazin-7-yl)phenyl)-[1,4'-bipiperidin]-2-one | 542.4 1.32 P |

TABLE 39-continued

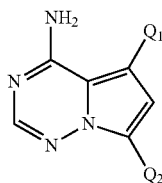

| Ex. No. | Q₁ | Q₂ | Name | H + M⁺ Rt (min.) Method |
|---|---|---|---|---|
| 379 | 5-(1-(tetrahydro-2H-pyran-4-yl)-1H-pyrazol-5-yl) | 3-(1-(4-(N-methylfuran-2-carboxamido)piperidin-1-yl)phenyl) | N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methylfuran-2-carboxamide | 567.4 1.18 F |
| 380 | 5-(1-(tetrahydro-2H-pyran-4-yl)-1H-pyrazol-5-yl) | 3-(4-(N-methyl-2-(pyrazin-2-yl)acetamido)piperidin-1-yl)phenyl | N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methyl-2-(pyrazin-2-yl)acetamide | 593.4 0.97 F |
| 381 | 5-(1-(tetrahydro-2H-pyran-4-yl)-1H-pyrazol-5-yl) | 3-(4-(3-isopropyl-1-methylureido)piperidin-1-yl)phenyl | 1-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-3-isopropyl-1-methylurea | 558.4 1.05 F |

TABLE 39-continued

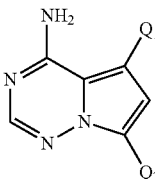

| Ex. No. | Q₁ | Q₂ | Name | H + M⁺ Rt (min.) Method |
|---|---|---|---|---|
| 382 | 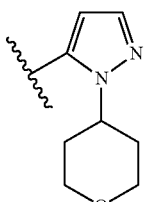 | 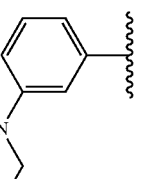 | N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-1-cyano-N-methylcyclopropanecarboxamide | 566.4 1.63 P |
| 383 | 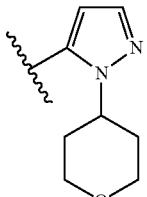 | 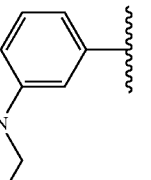 | 7-(3-(4-morpholinopiperidin-1-yl)phenyl)-5-(1-(tetrahydro-2H-pyran-4-yl)-1H-pyrazol-5-yl)pyrrolo[2,1-f][1,2,4]triazin-4-amine | 529.3 0.9 F |
| 384 | 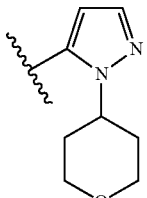 | 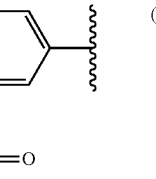 | 1-(3-(4-amino-5-(1-(tetrahydro-2H-pyran-4-yl)-1H-pyrazol-5-yl)pyrrolo[2,1-f][1,2,4]triazin-7-yl)phenyl)-3-(morpholine-4-carbonyl)piperidin-2-one | 571.3 0.97 F |

TABLE 39-continued

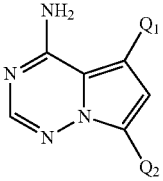

| Ex. No. | Q₁ | Q₂ | Name | H + M⁺ Rt (min.) Method |
|---|---|---|---|---|
| 385 | 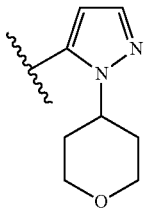 [SMILES: *c1ccnn1C1CCOCC1] | 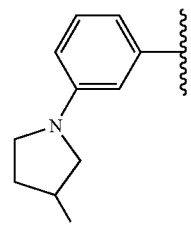 | N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)-2-hydroxy-N,2-dimethylpropanamide | 545.5 1.31 F |
| 386 | 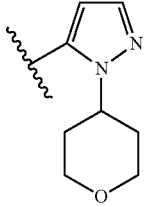 [SMILES: *c1ccnn1C1CCOCC1] | 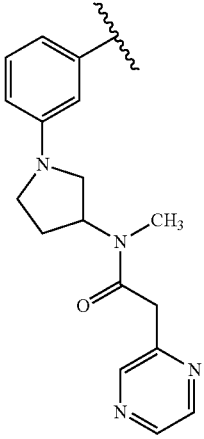 [SMILES: *c1cccc(N2CCC(N(C)C(=O)Cc3cnccn3)C2)c1] | N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)-N-methyl-2-(pyrazin-2-yl)acetamide | 579.4 1.25 F |
| 387 | 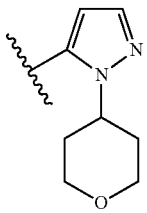 [SMILES: *c1ccnn1C1CCOCC1] | 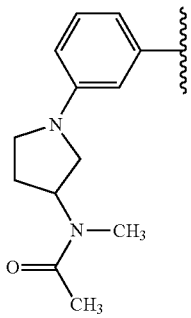 [SMILES: *c1cccc(N2CCC(N(C)C(C)=O)C2)c1] | N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)-N-methylacetamide | 501.4 1.48 P |

TABLE 39-continued

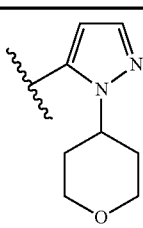

| Ex. No. | Q₁ | Q₂ | Name | H + M⁺ Rt (min.) Method |
|---|---|---|---|---|
| 388 | 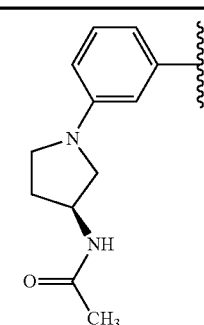 | 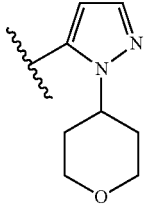 | S)-N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)acetamide | 487.4 D |
| 389 | 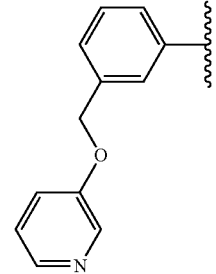 [SMILES: *c1cccc(COc2cccnc2)c1] | 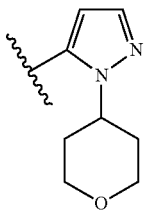 [SMILES: *c1ccnn1C1CCOCC1] | 7-(3-((pyridin-3-yloxy)methyl)phenyl)-5-(1-(tetrahydro-2H-pyran-4-yl)-1H-pyrazol-5-yl)pyrrolo[2,1-f][1,2,4]triazin-4-amine | 468.1 2.253 D |
| 390 | 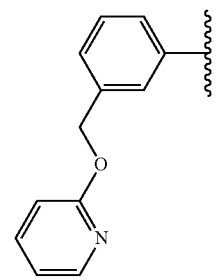 [SMILES: *c1cccc(COc2ccccn2)c1] | 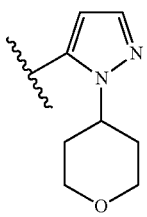 | 7-(3-((pyridin-2-yloxy)methyl)phenyl)-5-(1-(tetrahydro-2H-pyran-4-yl)-1H-pyrazol-5-yl)pyrrolo[2,1-f][1,2,4]triazin-4-amine | 468.1 2.463 D |
| 391 | 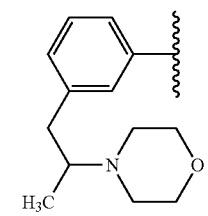 | 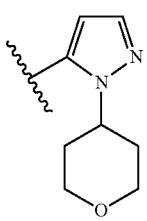 [SMILES: *c1ccnn1C1CCOCC1] | 7-(3-(2-morpholinopropyl)phenyl)-5-(1-(tetrahydro-2H-pyran-4-yl)-1H-pyrazol-5-yl)pyrrolo[2,1-f][1,2,4]triazin-4-amine | 488.3 084 F |
| 392 | 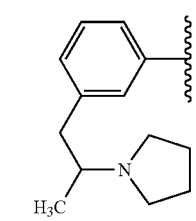 | | 7-(3-(2-(pyrrolidin-1-yl)propyl)phenyl)-5-(1-(tetrahydro-2H-pyran-4-yl)-1H-pyrazol-5-yl)pyrrolo[2,1-f][1,2,4]triazin-4-amine | 472.3 0.9 F |

TABLE 39-continued

| Ex. No. | Q₁ | Q₂ | Name | H + M⁺ Rt (min.) Method |
|---|---|---|---|---|
| 393 | pyrazole-tetrahydropyran | 3-(2-((2-methoxyethyl)amino)propyl)phenyl | 7-(3-(2-((2-methoxyethyl)amino)propyl)phenyl)-5-(1-(tetrahydro-2H-pyran-4-yl)-1H-pyrazol-5-yl)pyrrolo[2,1-f][1,2,4]triazin-4-amine | 476.2 1.23 P |
| 394 | pyrazole-tetrahydropyran | 3-(2-((tetrahydro-2H-pyran-4-yl)amino)propyl)phenyl | 5-(1-(tetrahydro-2H-pyran-4-yl)-1H-pyrazol-5-yl)-7-(3-(2-((tetrahydro-2H-pyran-4-yl)amino)propyl)phenyl)pyrrolo[2,1-f][1,2,4]triazin-4-amine | 502.3 1.04 P |
| 395 | pyrazole-tetrahydropyran | 3-(2-(methyl(tetrahydro-2H-pyran-4-yl)amino)propyl)phenyl | 7-(3-(2-(methyl(tetrahydro-2H-pyran-4-yl)amino)propyl)phenyl)-5-(1-(tetrahydro-2H-pyran-4-yl)-1H-pyrazol-5-yl)pyrrolo[2,1-f][1,2,4]triazin-4-amine | 516.3 0.91 F |
| 396 | pyrazole-tetrahydropyran | 3-(2-(dimethylamino)propyl)phenyl | 7-(3-(2-(dimethylamino)propyl)phenyl)-5-(1-(tetrahydro-2H-pyran-4-yl)-1H-pyrazol-5-yl)pyrrolo[2,1-f][1,2,4]triazin-4-amine | 446.14 1.958 D |

TABLE 39-continued

| Ex. No. | Q₁ | Q₂ | Name | H + M⁺ Rt (min.) Method |
|---|---|---|---|---|
| 397 | 1-(tetrahydro-2H-pyran-4-yl)-1H-pyrazol-5-yl | 3-(1-(dimethylamino)-2-methylpropan-2-yl)phenyl | 7-(3-(1-(dimethylamino)-2-methylpropan-2-yl)phenyl)-5-(1-(tetrahydro-2H-pyran-4-yl)-1H-pyrazol-5-yl)pyrrolo[2,1-f][1,2,4]triazin-4-amine | 460.17 2.227 D |
| 398 | 1-(tetrahydro-2H-pyran-4-yl)-1H-pyrazol-5-yl | 3-(1-(((tetrahydro-2H-pyran-4-yl)amino)methyl)cyclopropyl)phenyl | 5-(1-(tetrahydro-2H-pyran-4-yl)-1H-pyrazol-5-yl)-7-(3-(1-(((tetrahydro-2H-pyran-4-yl)amino)methyl)cyclopropyl)phenyl)pyrrolo[2,1-f][1,2,4]triazin-4-amine | 514.16 2.257 D |
| 399 | 1-(tetrahydro-2H-pyran-4-yl)-1H-pyrazol-5-yl | 3-(3-morpholinopyrrolidin-1-yl)phenyl | 7-(3-(3-morpholinopyrrolidin-1-yl)phenyl)-5-(1-(tetrahydro-2H-pyran-4-yl)-1H-pyrazol-5-yl)pyrrolo[2,1-f][1,2,4]triazin-4-amine | 515.4 0.9 F |
| 400 | 1-(tetrahydro-2H-pyran-4-yl)-1H-1,2,3-triazol-5-yl | 3-(4-(2-hydroxypropan-2-yl)piperidin-1-yl)phenyl | 2-(1-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-4-yl)propan-2-ol | 503.4 0.78 F |

Example 401

7-(3-(1H-Imidazol-2-yl)phenyl)-5-(1-(tetrahydro-2H-pyran-4-yl)-1H-pyrazol-5-yl) pyrrolo[2,1-f][1,2,4]triazin-4-amine

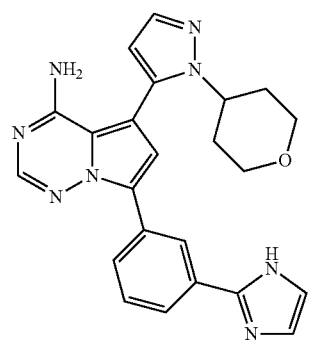

(401)

Intermediate 401A: 3-(4-Amino-5-(1-(tetrahydro-2H-pyran-4-yl)-1H-pyrazol-5-yl) pyrrolo[2,1-f][1,2,4]triazin-7-yl)benzonitrile

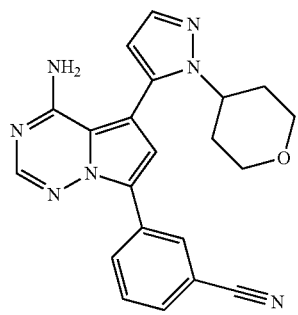

(401A)

A solution of 7-bromo-5-(1-(tetrahydro-2H-pyran-4-yl)-1H-pyrazol-5-yl)pyrrolo [2,1-f][1,2,4]triazin-4-amine (200 mg, 0.551 mmol), (3-cyanophenyl)boronic acid (121 mg, 0.826 mmol) and tripotassium phosphate (468 mg, 2.203 mmol) in a mixture of dioxane (1 mL) and water (1 mL) in a 2-5 mL microwave reactor vial was purged with nitrogen while the vial was sonicated. Tetrakis triphenylphosphine (95 mg, 0.083 mmol), the mixture was purged with nitrogen again, and the vial was heated in a microwave at 120° C. for 45 min. The reaction mixture was cooled to room temperature, diluted with 5 mL of water, and extracted with EtOAc (10 mL×3). The combined organic layers were washed with brine, dried and concentrated. The residue was purified on silica gel eluting with a gradient of 0-10% MeOH/DCM to obtain of 3-(4-amino-5-(1-(tetrahydro-2H-pyran-4-yl)-1H-pyrazol-5-yl)pyrrolo[2,1-f][1,2,4]triazin-7-yl)benzonitrile (76 mg). LCMS M$^+$=386.2. Method G. Retention time 2.68 min.

Intermediate 401B: 3-(4-Amino-5-(1-(tetrahydro-2H-pyran-4-yl)-1H-pyrazol-5-yl) pyrrolo[2,1-f][1,2,4]triazin-7-yl)benzimidamide

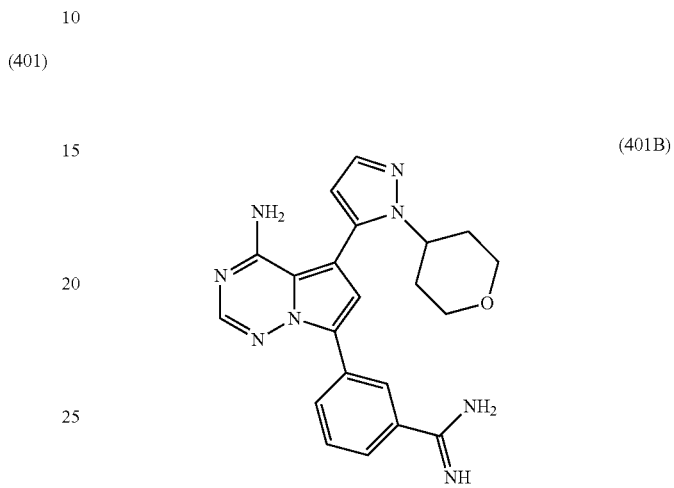

(401B)

To a solution of 3-(4-amino-5-(1-(tetrahydro-2H-pyran-4-yl)-1H-pyrazol-5-yl) pyrrolo[2,1-f][1,2,4]triazin-7-yl)benzonitrile (50 mg, 0.130 mmol) in dry THF (2 mL) in a pressure reaction vial, was added lithium bis(trimethylsilyl)amide (0.324 mL, 0.324 mmol). The vial was sealed and the orange solution was heated to reflux for 16 h. The solution was cooled to 5° C., and 3M aq. HCl (0.3 mL) was added carefully. After stirring for 15 min, 3M aq. NaOH (0.1 mL) followed by Na$_2$CO$_3$ were added until pH of ~11 was reached. The yellow solid formed was filtered and washed with water, hexane, dried in vacuo to obtain 3-(4-amino-5-(1-(tetrahydro-2H-pyran-4-yl)-1H-pyrazol-5-yl) pyrrolo[2,1-f][1,2,4]triazin-7-yl)benzimidamide (54 mg). LCMS M$^+$=403.2. Method G. Retention time 1.54 min.

Example 401

To a solution of 3-(4-amino-5-(1-(tetrahydro-2H-pyran-4-yl)-1H-pyrazol-5-yl) pyrrolo[2,1-f][1,2,4]triazin-7-yl)benzimidamide (30 mg, 0.075 mmol) in BuOH (1 mL), was added 2-chloroacetaldehyde (5.85 mg, 0.075 mmol) and potassium carbonate (20.60 mg, 0.149 mmol). The solution in a sealed tube was refluxed for 18 h, cooled to room temperature and 2 mL of water was added. The mixture was extracted with EtOAc (3 mL×3), the combined organic layers were dried, concentrated and the residue was purified by preparative HPLC, Method B to yield Example 401. LCMS M$^+$=427.10. Method I. Retention time 0.88 min. $^1$H NMR (500 MHz, (1:1) CDCl$_3$:methanol-d$_4$) δ 8.47 (t, J=1.5 Hz, 1H), 8.19-8.11 (m, 1H), 8.00 (s, 1H), 7.90-7.84 (m, 1H), 7.70 (d, J=2.0 Hz, 1H), 7.62-7.53 (m, 2H), 7.13 (s, 1H), 7.05 (s, 1H), 6.46 (d, J=1.5 Hz, 1H), 4.47-4.36 (m, 1H), 4.29 (m, 2H), 4.10-3.97 (m, 2H), 3.44 (m, 2H), 2.33 (d, J=9.4 Hz, 2H).

Example 402

4-(3-(4-Amino-5-(1-(tetrahydro-2H-pyran-4-yl)-1H-pyrazol-5-yl)pyrrolo[2,1-f][1,2,4]triazin-7-yl)phenyl)morpholine-3-carboxamide

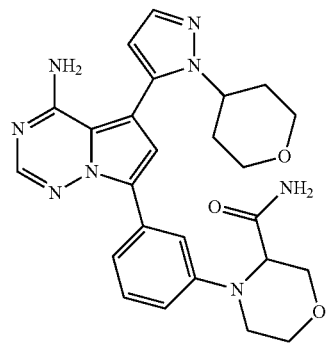
(402)

Intermediate 402A:
4-(3-Bromophenyl)morpholine-3-carboxylic acid

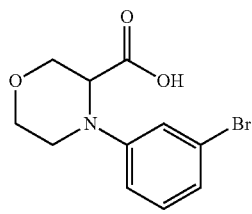
(402A)

A suspension of 1,3-dibromobenzene (1.408 g, 5.97 mmol), morpholine-3-carboxylic acid hydrochloride (500 mg, 2.98 mmol) and potassium carbonate (1.649 g, 11.93 mmol) in DMSO (20 mL) in a capped pressure reaction vial was degassed by vacuum then filled in with nitrogen. The cap was removed and to the reaction mixture was added copper iodide (4.55 mg, 0.024 mmol). The cap was closed again and the reaction mixture was degassed again. The reaction vial was then placed in a 90° C. heating block and heated overnight. The reaction mixture was cooled to room temperature and filtered. The filtrate was extracted between ethyl acetate and saturated aqueous ammonium chloride solution. Water was added to dissolve the insoluble salt. The two phases were separated. The aqueous phase was back-extracted with ethyl acetate. The combined organic phases was washed with water, then brine and concentrated. The residue was chromatographed on an ISCO Companion 12 g silica gel column and eluted with EtOAc/hexane gradient (0-70%) to give 4-(3-bromophenyl) morpholine-3-carboxylic acid (210 mg, 0.74 mmol) as a glassy material. Yield 24%. m/z (M+H)$^+$=285.8, 287.8.

Intermediate 402B:
4-(3-Bromophenyl)morpholine-3-carboxamide

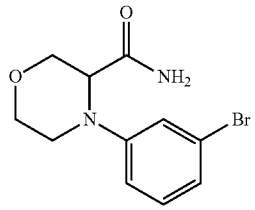
(402B)

A suspension of 4-(3-bromophenyl)morpholine-3-carboxylic acid (210 mg, 0.734 mmol), 1H-benzo[d][1,2,3]triazol-1-ol (119 mg, 0.881 mmol) and 1-ethyl-3-(3-dimethylaminopropyl)carbodiimide (211 mg, 1.101 mmol) in THF (5 mL) was stirred at room temperature for 1 h. Aqueous ammonia (0.367 mL, 3.67 mmol) was added to the above reaction mixture and the resulting mixture was allowed to stir at room temperature for 0.5 h. The reaction mixture was diluted with ethyl acetate and washed with water twice. The organic phase was separated and concentrated to give 4-(3-bromophenyl) morpholine-3-carboxamide (250 mg, 0.88 mmol) as a colorless film. Yield 120%. m/z (M+H)$^+$=284.8, 286.8 (M-CONH$_2$)$^+$=239.7, 241.7.

Intermediate 402C: 4-(3-(4,4,5,5-Tetramethyl-1,3,2-dioxaborolan-2-yl)phenyl) morpholine-3-carboxamide

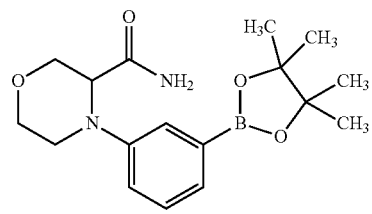
(402C)

A mixture of 4-(3-bromophenyl)morpholine-3-carboxamide (210 mg, 0.736 mmol), 4,4,4',4',5,5,5',5'-octamethyl-2,2'-bi(1,3,2-dioxaborolane) (224 mg, 0.884 mmol), potassium acetate (217 mg, 2.209 mmol) and PdCl$_2$(dppf)-CH$_2$Cl$_2$ adduct (30.1 mg, 0.037 mmol) in dioxane (4 mL) in a capped pressure reaction vial was degassed by vacuum then filled in with nitrogen. The degassing process was repeated twice. The reaction vial was placed in a 90° C. heating block and heated for 3 h. The reaction mixture was filtered and concentrated. The residue was chromatographed on an ISCO Companion 12 g silica gel column and eluted with EtOAc/hexane gradient (0-100%) to give 4-(3-(4,4,5,5-tetramethyl-1,3,2-dioxaborolan-2-yl)phenyl)morpholine-3-carboxamide (133 mg, 0.40 mmol) as a glassy material. Yield 54%. m/z (M+H)$^+$=332.9 (M-CONH$_2$)$^+$=287.8.

Example 402

A mixture of 7-bromo-5-(1-(tetrahydro-2H-pyran-4-yl)-1H-pyrazol-5-yl)pyrrolo [2,1-f][1,2,4]triazin-4-amine (30 mg, 0.083 mmol), 4-(3-(4,4,5,5-tetramethyl-1,3,2-dioxaborolan-2-yl)phenyl)morpholine-3-carboxamide (27.4 mg, 0.083 mmol), PdCl$_2$(dppf) (3.37 mg, 4.13 µmol) and 2M tripotassium phosphate aqueous solution (0.083 mL, 0.165 mmol) in DMF (1 mL) in a capped pressure reaction vial was degassed by vacuum then filled in with nitrogen. The degassing process was repeated twice. The reaction vial was placed in a 90° C. heating block and heated for 2 h. The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-45% B over 25 minutes, then a 10-minute hold at 45% B; Flow: 20 mL/min. Fractions containing the desired product were combined and dried via centrifugal evaporation to give the title compound (15 mg, 0.031 mmol). Yield 37%. m/z (M+H)$^+$=489.2. $^1$H NMR (500 MHz, DMSO-d$_6$) δ 8.04 (s, 1H), 7.68 (s, 1H), 7.56 (br. s., 1H), 7.51 (d, J=7.7 Hz, 1H), 7.37-7.28 (m, 2H), 7.18 (s, 1H), 7.08 (br. s., 1H), 6.85 (d, J=7.4 Hz, 1H), 6.46 (s, 1H), 4.35 (t, J=11.3 Hz, 1H), 4.25 (br. s., 1H), 4.16 (d, J=11.4 Hz, 1H), 3.95 (d, J=7.7 Hz, 1H), 3.92-3.84 (m, 2H), 3.81 (dd, J=11.4, 3.4 Hz, 1H), 3.66-3.55 (m, 2H), 3.50-3.38 (m, 2H), 3.32 (t, J=11.6 Hz, 1H), 2.10 (d, J=11.8 Hz, 2H).

Example 403

3'-(4-Amino-5-(2-methylthiazol-5-yl)pyrrolo[2,1-f][1,2,4]triazin-7-yl)-[1,1'-biphenyl]-2-carboxamide

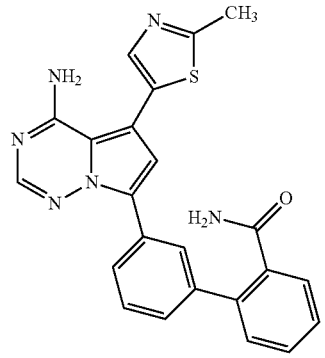

(403)

Intermediate 403A: 7-Bromo-5-(2-methylthiazol-5-yl)pyrrolo[2,1-f][1,2,4]triazin-4-amine

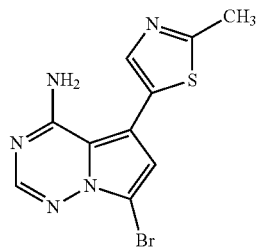

(403A)

A mixture of 7-bromo-5-iodopyrrolo[2,1-f][1,2,4]triazin-4-amine (200 mg, 0.590 mmol, Intermediate R1-A), 2-methyl-5-(4,4,5,5-tetramethyl-1,3,2-dioxaborolan-2-yl)thiazole (133 mg, 0.590 mmol), PdCl$_2$(dppf)-CH$_2$Cl$_2$ adduct (24.09 mg, 0.030 mmol) and 2M tripotassium phosphate aqueous solution (0.89 mL, 1.77 mmol) in dioxane (5 mL) in a capped pressure reaction vial was degassed by vacuum then filled in with nitrogen. The degassing process was repeated twice. The reaction vial was placed in a 90° C. heating block and heated at 90° C. for 15 h. The organic phase of the reaction mixture was separated and concentrated. The residue was chromatographed on an ISCO Companion 24 g silica gel column and eluted with methanol/dichloromethane gradient (0-20%) to give 7-bromo-5-(2-methylthiazol-5-yl)pyrrolo[2,1-f][1,2,4]triazin-4-amine (60 mg, 0.19 mmol). Yield 33%. m/z (M+H)$^+$=309.9, 311.9.

Intermediate 403B: 3'-(4,4,5,5-Tetramethyl-1,3,2-dioxaborolan-2-yl)-[1,1'-biphenyl]-2-carboxamide

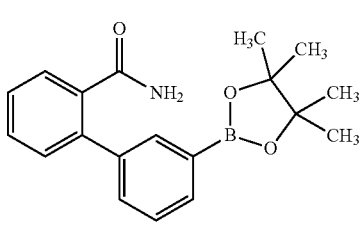

(403B)

A mixture of 2-bromobenzamide (0.5 g, 2.500 mmol), 1,3-bis(4,4,5,5-tetramethyl-1,3,2-dioxaborolan-2-yl)benzene (0.990 g, 3.00 mmol), PdCl$_2$(dppf)-CH$_2$Cl$_2$ adduct (0.102 g, 0.125 mmol) and tripotassium phosphate (1.500 mL, 3.00 mmol) in dioxane (8 mL) in a capped pressure reaction vial was degassed by vacuum then filled in with nitrogen. The degassing process was repeated twice. The vial was placed in a 90° C. heating block and heated for 4 h. The organic phase of the reaction mixture was separated and concentrated. The residue was chromatographed on an ISCO Companion 40 g silica gel column and eluted with ethyl acetate/hexane gradient (0-100%) to give 3'-(4,4,5,5-tetramethyl-1,3,2-dioxaborolan-2-yl)-[1,1'-biphenyl]-2-carboxamide (600 mg, 1.85 mmol). Yield 74%. m/z (M+H)$^+$=324.2.

Example 403

A mixture of 7-bromo-5-(2-methylthiazol-5-yl)pyrrolo[2,1-f][1,2,4]triazin-4-amine (20 mg, 0.064 mmol), 3'-(4,4,5,5-tetramethyl-1,3,2-dioxaborolan-2-yl)-[1,1'-biphenyl]-2-carboxamide (27.1 mg, 0.084 mmol), PdCl$_2$(dppf)-CH$_2$Cl$_2$ adduct (2.63 mg, 3.22 µmol) and tripotassium phosphate (0.064 mL, 0.129 mmol) in dioxane (8 mL) in a capped pressure reaction vial was degassed by vacuum then filled in with nitrogen. The degassing process was repeated twice. The vial was placed in a 90° C. heating block and heated for 4 h. The organic phase of the reaction mixture was separated and concentrated. The crude material was purified via preparative LC/MS with the following conditions: Column: Waters XBridge C18, 19×250 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-100% B over 25 minutes, then a 5-minute hold at 100% B; Flow: 20 mL/min. Fractions containing the desired product were combined and dried via centrifugal evaporation to give Example 403 (2.1 mg, 0.0049 mmol). Yield 8%. m/z (M+H)$^+$=427.2. $^1$H NMR (500 MHz, DMSO-d$_6$) δ 8.12 (s, 1H), 8.06-8.01 (m, 2H), 7.72 (br. s., 1H), 7.68 (s, 1H), 7.55-7.40 (m, 8H), 7.34 (br. s., 1H), 7.15 (s, 1H), 2.71 (s, 3H).

The Examples in Table 40 were prepared according to the general procedure for the preparation of Example 403, and other Examples exemplified above, using appropriate intermediates.

TABLE 40
| Ex. No. | Structure | Name | [M + 1] |
|---|---|---|---|
| 404 | 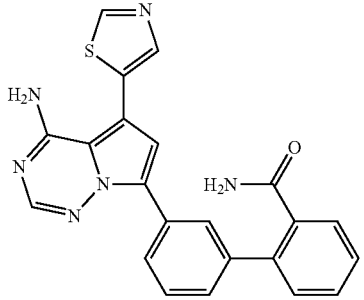 [SMILES: NC(=O)c1ccccc1-c1cccc(-c2cc(-c3cncs3)c3c(N)ncnn23)c1] | 3'-(4-amino-5-(thiazol-5-yl)pyrrolo[2,1-f][1,2,4]triazin-7-yl)-[1,1'-biphenyl]-2-carboxamide | 413 |
| 405 | 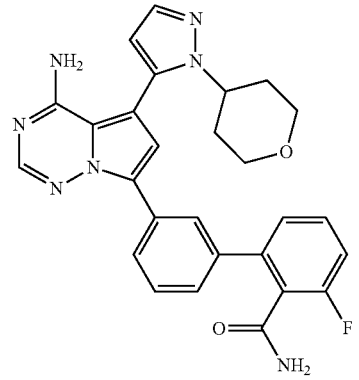 [SMILES: NC(=O)c1c(F)cccc1-c1cccc(-c2cc(-c3ccnn3C3CCOCC3)c3c(N)ncnn23)c1] | 3'-(4-amino-5-(1-(tetrahydro-2H-pyran-4-yl)-1H-pyrazol-5-yl)pyrrolo[2,1-f][1,2,4]triazin-7-yl)-3-fluoro-[1,1'-biphenyl]-2-carboxamide | 498 |
| 406 | 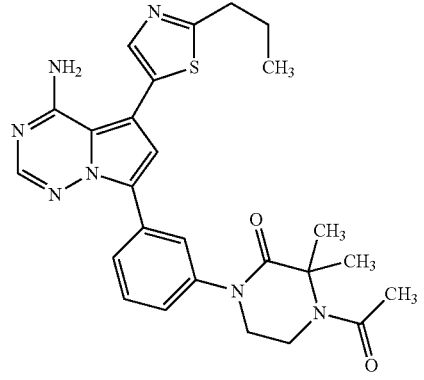 [SMILES: CCCc1ncc(-c2cc(-c3cccc(N4CCN(C(C)=O)C(C)(C)C4=O)c3)n3ncnc(N)c23)s1] | 4-acetyl-1-(3-(4-amino-5-(2-propylthiazol-5-yl)pyrrolo[2,1-f][1,2,4]triazin-7-yl)phenyl)-3,3-dimethylpiperazin-2-one | 504 |
| 407 | 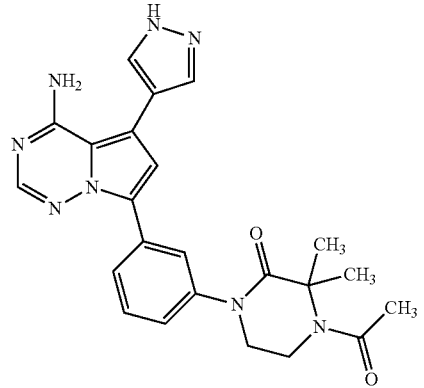 [SMILES: CC(=O)N1CCN(c2cccc(-c3cc(-c4cn[nH]c4)c4c(N)ncnn34)c2)C(=O)C1(C)C] | 4-acetyl-1-(3-(4-amino-5-(1H-pyrazol-4-yl)pyrrolo[2,1-f][1,2,4]triazin-7-yl)phenyl)-3,3-dimethylpiperazin-2-one | 445 |

TABLE 40-continued

| Ex. No. | Structure | Name | [M + 1] |
|---|---|---|---|
| 408 | 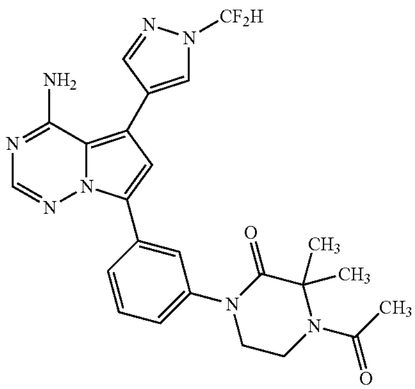 [SMILES: CC(=O)N1CCN(c2cccc(-c3cc(-c4cnn(C(F)F)c4)c4c(N)ncnn34)c2)C(=O)C1(C)C] | 4-acetyl-1-(3-(4-amino-5-(1-(difluoromethyl)-1H-pyrazol-4-yl)pyrrolo[2,1-f][1,2,4]triazin-7-yl)phenyl)-3,3-dimethylpiperazin-2-one | 495 |
| 409 | 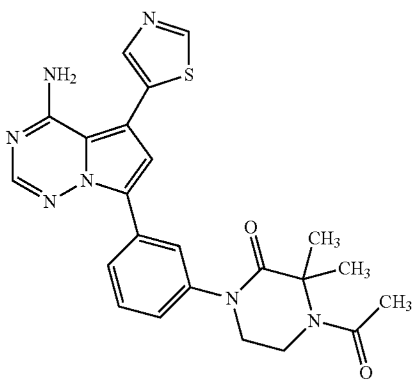 [SMILES: CC(=O)N1CCN(c2cccc(-c3cc(-c4cncs4)c4c(N)ncnn34)c2)C(=O)C1(C)C] | 4-acetyl-1-(3-(4-amino-5-(thiazol-5-yl)pyrrolo[2,1-f][1,2,4]triazin-7-yl)phenyl)-3,3-dimethylpiperazin-2-one | 462 |
| 410 | 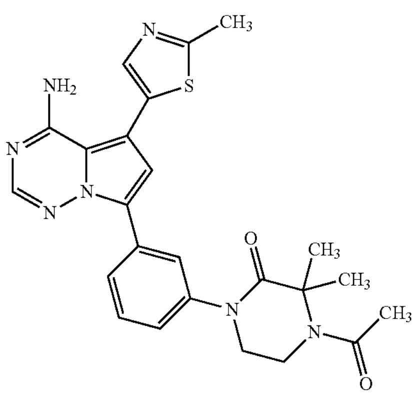 [SMILES: CC(=O)N1CCN(c2cccc(-c3cc(-c4cnc(C)s4)c4c(N)ncnn34)c2)C(=O)C1(C)C] | 4-acetyl-1-(3-(4-amino-5-(2-methylthiazol-5-yl)pyrrolo[2,1-f][1,2,4]triazin-7-yl)phenyl)-3,3-dimethylpiperazin-2-one | 476 |
| 411 | 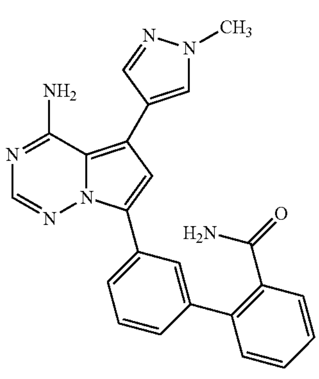 [SMILES: Cn1cc(-c2cc(-c3cccc(-c4ccccc4C(N)=O)c3)n3ncnc(N)c23)cn1] | 3'-(4-amino-5-(1-methyl-1H-pyrazol-4-yl)pyrrolo[2,1-f][1,2,4]triazin-7-yl)-[1,1'-biphenyl]-2-carboxamide | 410 |

TABLE 40-continued

| Ex. No. | Structure | Name | [M + 1] |
|---|---|---|---|
| 412 | 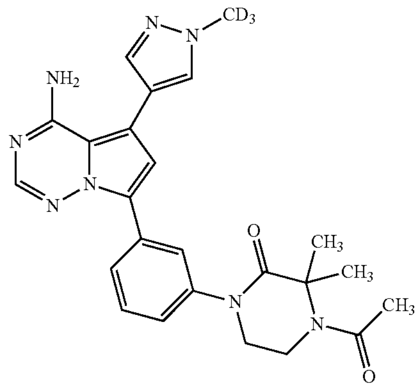 [SMILES: [2H]C([2H])([2H])n1cc(-c2cc(-c3cccc(N4CCN(C(C)=O)C(C)(C)C4=O)c3)n3ncnc(N)c23)cn1] | 4-acetyl-1-(3-(4-amino-5-(1-trideuteromethyl-1H-pyrazol-4-yl)pyrrolo[2,1-f][1,2,4]triazin-7-yl)phenyl)-3,3-dimethylpiperazin-2-one | 462 |
| 413 | 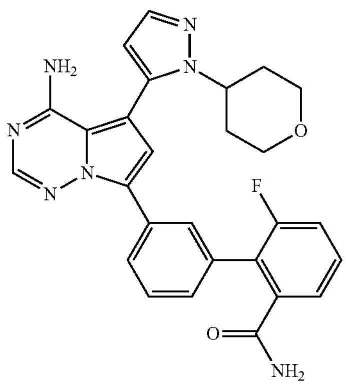 [SMILES: NC(=O)c1cccc(F)c1-c1cccc(-c2cc(-c3ccnn3C3CCOCC3)c3c(N)ncnn23)c1] | 3'-(4-amino-5-(1-(tetrahydro-2H-pyran-4-yl)-1H-pyrazol-5-yl)pyrrolo[2,1-f][1,2,4]triazin-7-yl)-6-fluoro-[1,1'-biphenyl]-2-carboxamide | 498 |
| 414 | 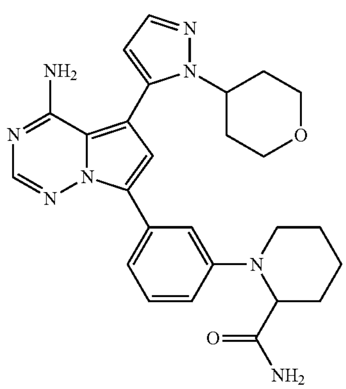 [SMILES: NC(=O)C1CCCCN1c1cccc(-c2cc(-c3ccnn3C3CCOCC3)c3c(N)ncnn23)c1] | 1-(3-(4-amino-5-(1-(tetrahydro-2H-pyran-4-yl)-1H-pyrazol-5-yl)pyrrolo[2,1-f][1,2,4]triazin-7-yl)phenyl)piperidine-2-carboxamide | 487 |
| 415 | 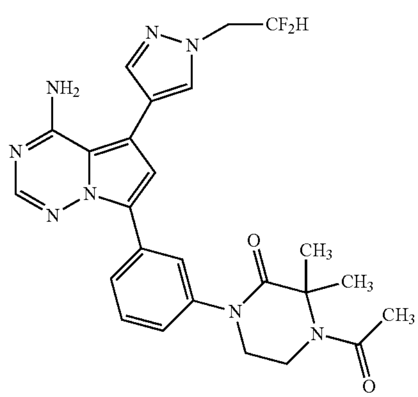 [SMILES: CC(=O)N1CCN(c2cccc(-c3cc(-c4cnn(CC(F)F)c4)c4c(N)ncnn34)c2)C(=O)C1(C)C] | 4-acetyl-1-(3-(4-amino-5-(1-(2,2-difluoroethyl)-1H-pyrazol-4-yl)pyrrolo[2,1-f][1,2,4]triazin-7-yl)phenyl)-3,3-dimethylpiperazin-2-one | 509 |

TABLE 40-continued
| Ex. No. | Structure | Name | [M + 1] |
|---|---|---|---|
| 416 | 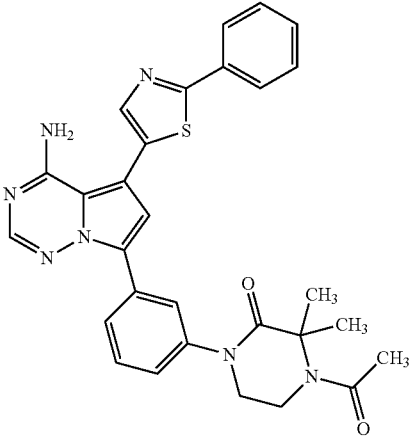 [SMILES: CC(=O)N1CCN(c2cccc(-c3cc(-c4cnc(-c5ccccc5)s4)c4c(N)ncnn34)c2)C(=O)C1(C)C] | 4-acetyl-1-(3-(4-amino-5-(2-phenylthiazol-5-yl)pyrrolo[2,1-f][1,2,4]triazin-7-yl)phenyl)-3,3-dimethylpiperazin-2-one | 538 |
| 417 | 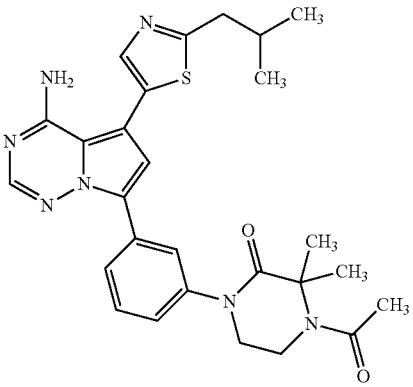 [SMILES: CC(=O)N1CCN(c2cccc(-c3cc(-c4cnc(CC(C)C)s4)c4c(N)ncnn34)c2)C(=O)C1(C)C] | 4-acetyl-1-(3-(4-amino-5-(2-isobutylthiazol-5-yl)pyrrolo[2,1-f][1,2,4]triazin-7-yl)phenyl)-3,3-dimethylpiperazin-2-one | 518 |
| 418 | 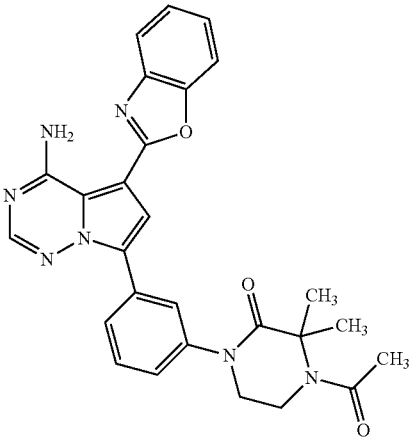 [SMILES: CC(=O)N1CCN(c2cccc(-c3cc(-c4nc5ccccc5o4)c4c(N)ncnn34)c2)C(=O)C1(C)C] | 4-acetyl-1-(3-(4-amino-5-(benzo[d]oxazol-2-yl)pyrrolo[2,1-f][1,2,4]triazin-7-yl)phenyl)-3,3-dimethylpiperazin-2-one | 496 |

TABLE 40-continued

| Ex. No. | Structure | Name | [M + 1] |
|---|---|---|---|
| 419 | 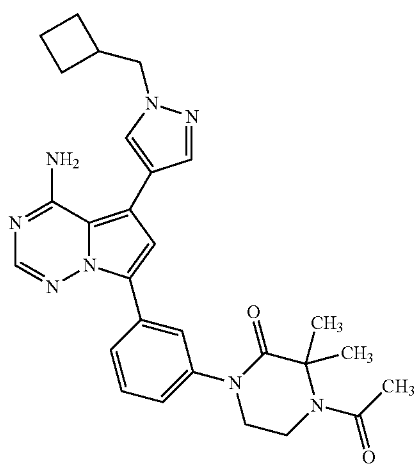 [SMILES: CC(=O)N1CCN(c2cccc(-c3cc(-c4cnn(CC5CCC5)c4)c4c(N)ncnn34)c2)C(=O)C1(C)C] | 4-acetyl-1-(3-(4-amino-5-(1-(cyclobutylmethyl)-1H-pyrazol-4-yl)pyrrolo[2,1-f][1,2,4]triazin-7-yl)phenyl)-3,3-dimethylpiperazin-2-one | 513 |
| 420 | 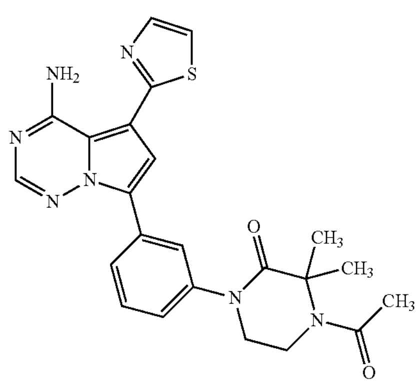 [SMILES: CC(=O)N1CCN(c2cccc(-c3cc(-c4nccs4)c4c(N)ncnn34)c2)C(=O)C1(C)C] | 4-acetyl-1-(3-(4-amino-5-(thiazol-2-yl)pyrrolo[2,1-f][1,2,4]triazin-7-yl)phenyl)-3,3-dimethylpiperazin-2-one | 462 |
| 421 | 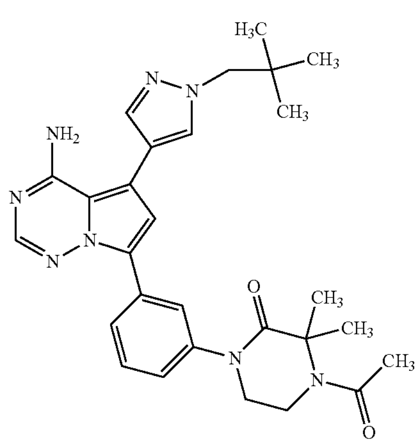 [SMILES: CC(=O)N1CCN(c2cccc(-c3cc(-c4cnn(CC(C)(C)C)c4)c4c(N)ncnn34)c2)C(=O)C1(C)C] | 4-acetyl-1-(3-(4-amino-5-(1-neopentyl-1H-pyrazol-4-yl)pyrrolo[2,1-f][1,2,4]triazin-7-yl)phenyl)-3,3-dimethylpiperazin-2-one | 515 |

TABLE 40-continued

| Ex. No. | Structure | Name | [M + 1] |
|---|---|---|---|
| 422 | 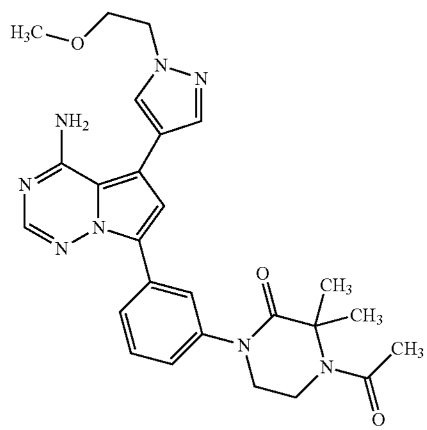 [SMILES: COCCn1cc(-c2cc(-c3cccc(N4CCN(C(C)=O)C(C)(C)C4=O)c3)n3ncnc(N)c23)cn1] | 4-acetyl-1-(3-(4-amino-5-(1-(2-methoxyethyl)-1H-pyrazol-4-yl)pyrrolo[2,1-f][1,2,4]triazin-7-yl)phenyl)-3,3-dimethylpiperazin-2-one | 503 |
| 423 | 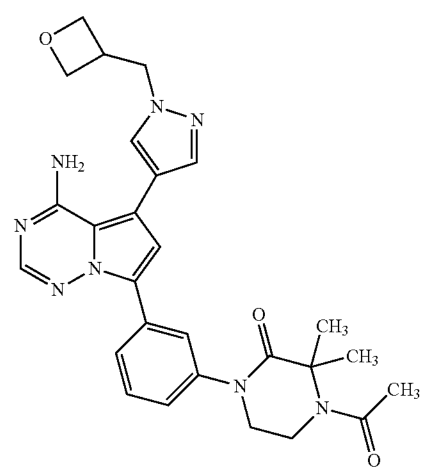 [SMILES: CC(=O)N1CCN(c2cccc(-c3cc(-c4cnn(CC5COC5)c4)c4c(N)ncnn34)c2)C(=O)C1(C)C] | 4-acetyl-1-(3-(4-amino-5-(1-(oxetan-3-ylmethyl)-1H-pyrazol-4-yl)pyrrolo[2,1-f][1,2,4]triazin-7-yl)phenyl)-3,3-dimethylpiperazin-2-one | 515 |
| 424 | 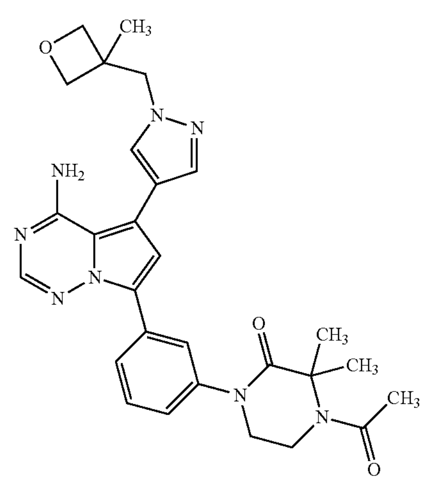 [SMILES: CC(=O)N1CCN(c2cccc(-c3cc(-c4cnn(CC5(C)COC5)c4)c4c(N)ncnn34)c2)C(=O)C1(C)C] | 4-acetyl-1-(3-(4-amino-5-(1-((3-methyloxetan-3-yl)methyl)-1H-pyrazol-4-yl)pyrrolo[2,1-f][1,2,4]triazin-7-yl)phenyl)-3,3-dimethylpiperazin-2-one | 529 |

TABLE 40-continued

| Ex. No. | Structure | Name | [M + 1] |
|---|---|---|---|
| 425 | 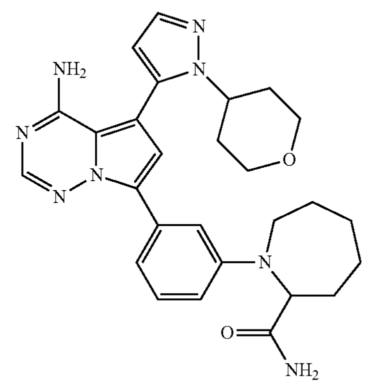 [SMILES: NC(=O)C1CCCCCN1c1cccc(-c2cc(-c3ccnn3C3CCOCC3)c3c(N)ncnn23)c1] | 1-(3-(4-amino-5-(1-(tetrahydro-2H-pyran-4-yl)-1H-pyrazol-5-yl)pyrrolo[2,1-f][1,2,4]triazin-7-yl)phenyl)azepane-2-carboxamide | 501 |
| 426 | 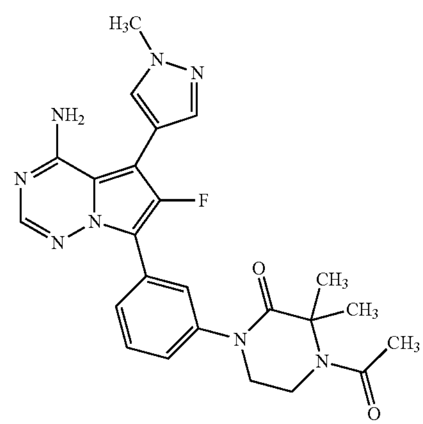 [SMILES: CC(=O)N1CCN(c2cccc(-c3c(F)c(-c4cnn(C)c4)c4c(N)ncnn34)c2)C(=O)C1(C)C] | 4-acetyl-1-{3-[4-amino-6-fluoro-5-(1-methyl-1H-pyrazol-4-yl)pyrrolo[2,1-f][1,2,4]triazin-7-yl]phenyl}-3,3-dimethylpiperazin-2-one | 478 |
| 427 | 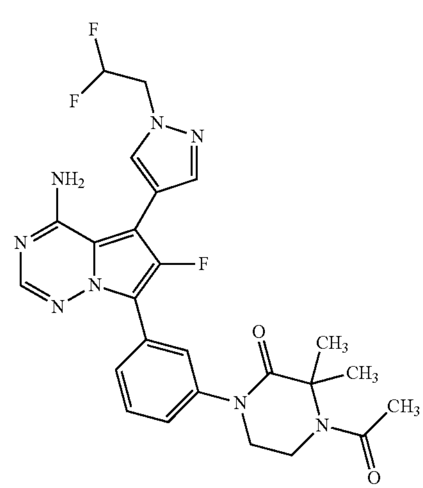 [SMILES: CC(=O)N1CCN(c2cccc(-c3c(F)c(-c4cnn(CC(F)F)c4)c4c(N)ncnn34)c2)C(=O)C1(C)C] | 4-acetyl-1-(3-{4-amino-5-[1-(2,2-difluoroethyl)-1H-pyrazol-4-yl]-6-fluoropyrrolo[2,1-f][1,2,4]triazin-7-yl}phenyl)-3,3-dimethylpiperazin-2-one | 528 |

TABLE 40-continued

| Ex. No. | Structure | Name | [M + 1] |
|---|---|---|---|
| 428 | 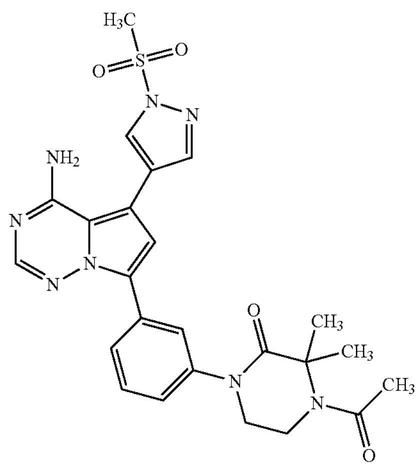 [SMILES: CC(=O)N1CCN(c2cccc(-c3cc(-c4cnn(S(C)(=O)=O)c4)c4c(N)ncnn34)c2)C(=O)C1(C)C] | 4-acetyl-1-{3-[4-amino-5-(1-methanesulfonyl-1H-pyrazol-4-yl)pyrrolo[2,1-f][1,2,4]triazin-7-yl]phenyl}-3,3-dimethylpiperazin-2-one | 524 |
| 429 | 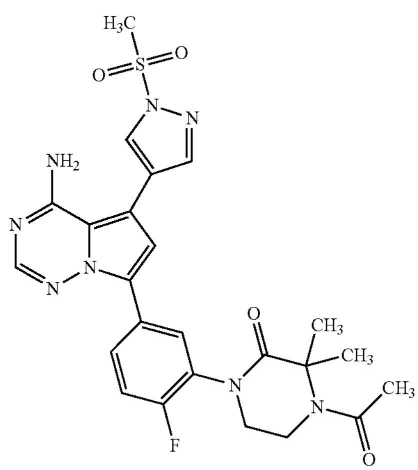 [SMILES: CC(=O)N1CCN(c2cc(-c3cc(-c4cnn(S(C)(=O)=O)c4)c4c(N)ncnn34)ccc2F)C(=O)C1(C)C] | 4-acetyl-1-{5-[4-amino-5-(1-methanesulfonyl-1H-pyrazol-4-yl)pyrrolo[2,1-f][1,2,4]triazin-7-yl]-2-fluorophenyl}-3,3-dimethylpiperazin-2-one | 542 |
| 430 | 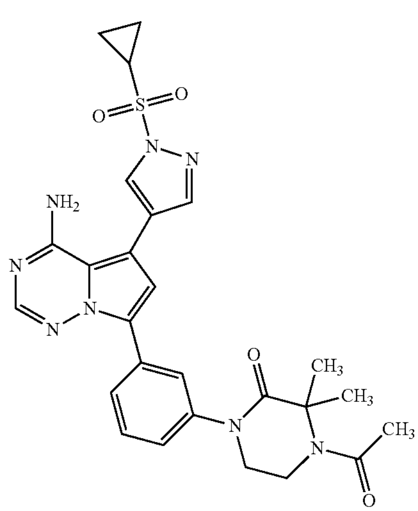 [SMILES: CC(=O)N1CCN(c2cccc(-c3cc(-c4cnn(S(=O)(=O)C5CC5)c4)c4c(N)ncnn34)c2)C(=O)C1(C)C] | 4-acetyl-1-(3-{4-amino-5-[1-(cyclopropanesulfonyl)-1H-pyrazol-4-yl]pyrrolo[2,1-f][1,2,4]triazin-7-yl}phenyl)-3,3-dimethylpiperazin-2-one | 550 |

TABLE 40-continued

| Ex. No. | Structure | Name | [M + 1] |
|---|---|---|---|
| 431 | 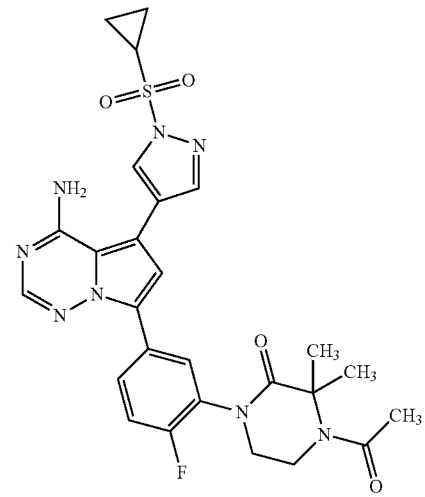 [SMILES: CC(=O)N1CCN(c2cc(-c3cc(-c4cnn(S(=O)(=O)C5CC5)c4)c4c(N)ncnn34)ccc2F)C(=O)C1(C)C] | 4-acetyl-1-(5-{4-amino-5-[1-(cyclopropanesulfonyl)-1H-pyrazol-4-yl]pyrrolo[2,1-f][1,2,4]triazin-7-yl}-2-fluorophenyl)-3,3-dimethylpiperazin-2-one | 568 |
| 432 | 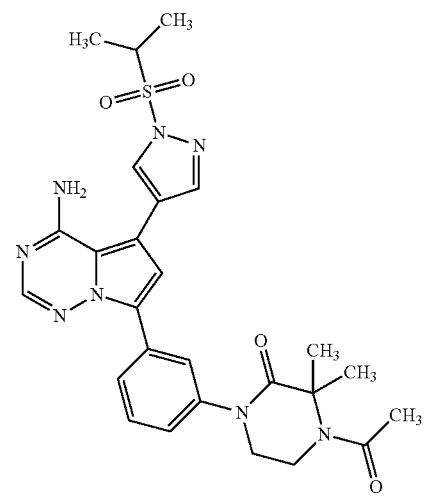 [SMILES: CC(=O)N1CCN(c2cccc(-c3cc(-c4cnn(S(=O)(=O)C(C)C)c4)c4c(N)ncnn34)c2)C(=O)C1(C)C] | 4-acetyl-1-(3-{4-amino-5-[1-(propane-2-sulfonyl)-1H-pyrazol-4-yl]pyrrolo[2,1-f][1,2,4]triazin-7-yl}phenyl)-3,3-dimethylpiperazin-2-one | 552 |
| 433 | 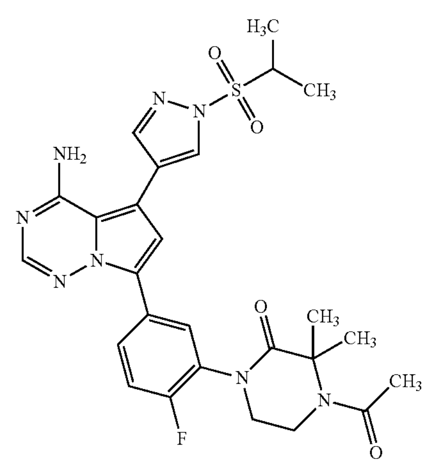 [SMILES: CC(=O)N1CCN(c2cc(-c3cc(-c4cnn(S(=O)(=O)C(C)C)c4)c4c(N)ncnn34)ccc2F)C(=O)C1(C)C] | 4-acetyl-1-(5-{4-amino-5-[1-(propane-2-sulfonyl)-1H-pyrazol-4-yl]pyrrolo[2,1-f][1,2,4]triazin-7-yl}-2-fluorophenyl)-3,3-dimethylpiperazin-2-one | 570 |

TABLE 40-continued

| Ex. No. | Structure | Name | [M + 1] |
|---|---|---|---|
| 434 | 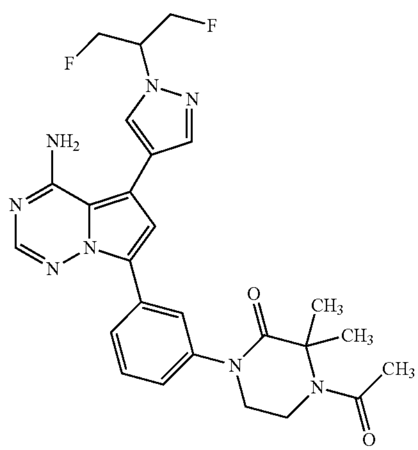 [SMILES: CC(=O)N1CCN(c2cccc(-c3cc(-c4cnn(C(CF)CF)c4)c4c(N)ncnn34)c2)C(=O)C1(C)C] | 4-acetyl-1-(3-{4-amino-5-[1-(1,3-difluoropropan-2-yl)-1H-pyrazol-4-yl]pyrrolo[2,1-f][1,2,4]triazin-7-yl}phenyl)-3,3-dimethylpiperazin-2-one | 524 |
| 435 | 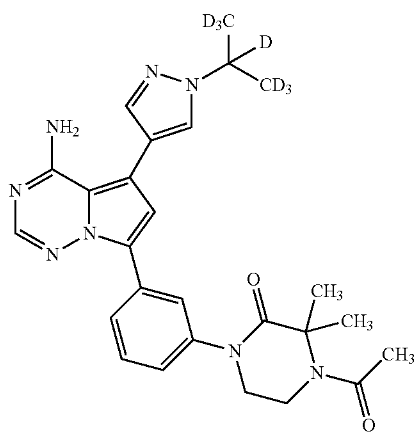 [SMILES: [2H]C([2H])([2H])C([2H])(n1cc(-c2cc(-c3cccc(N4CCN(C(C)=O)C(C)(C)C4=O)c3)n3ncnc(N)c23)cn1)C([2H])([2H])[2H]] | 4-acetyl-1-[3-(4-amino-5-{1-[($^2$H$_7$)propan-2-yl]-1H-pyrazol-4-yl}pyrrolo[2,1-f][1,2,4]triazin-7-yl)phenyl]-3,3-dimethylpiperazin-2-one | 495 |
| 436 | 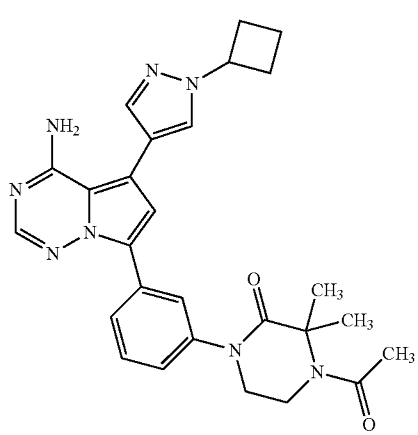 [SMILES: CC(=O)N1CCN(c2cccc(-c3cc(-c4cnn(C5CCC5)c4)c4c(N)ncnn34)c2)C(=O)C1(C)C] | 4-acetyl-1-{3-[4-amino-5-(1-cyclobutyl-1H-pyrazol-4-yl)pyrrolo[2,1-f][1,2,4]triazin-7-yl]phenyl}-3,3-dimethylpiperazin-2-one | 500 |

TABLE 40-continued

| Ex. No. | Structure | Name | [M + 1] |
|---|---|---|---|
| 437 | 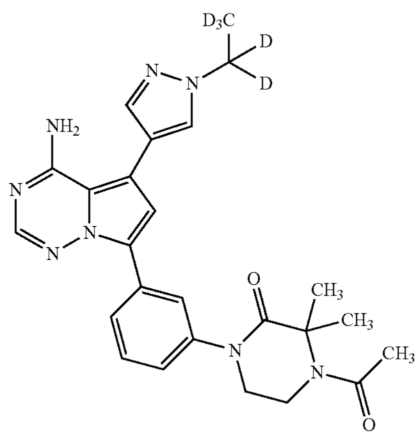 [SMILES: [2H]C([2H])([2H])C([2H])([2H])n1cc(-c2cc(-c3cccc(N4CCN(C(C)=O)C(C)(C)C4=O)c3)n3ncnc(N)c23)cn1] | 4-acetyl-1-(3-{4-amino-5-[1-($^2$H$_5$)ethyl-1H-pyrazol-4-yl]pyrrolo[2,1-f][1,2,4]triazin-7-yl}phenyl)-3,3-dimethylpiperazin-2-one | 479 |
| 438 | 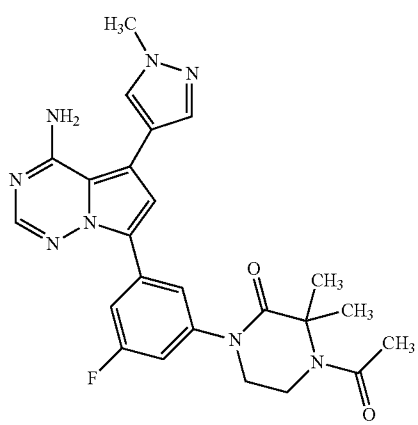 [SMILES: CC(=O)N1CCN(c2cc(F)cc(-c3cc(-c4cnn(C)c4)c4c(N)ncnn34)c2)C(=O)C1(C)C] | 4-acetyl-1-{3-[4-amino-5-(1-methyl-1H-pyrazol-4-yl)pyrrolo[2,1-f][1,2,4]triazin-7-yl]-5-fluorophenyl}-3,3-dimethylpiperazin-2-one | 478 |
| 439 | 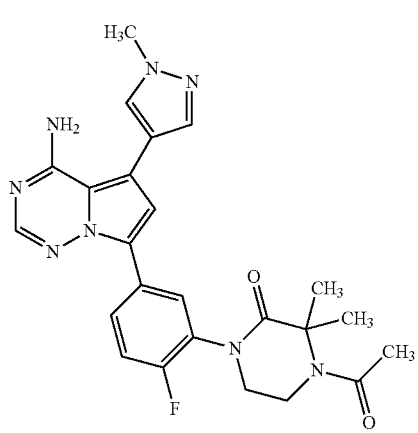 [SMILES: CC(=O)N1CCN(c2cc(-c3cc(-c4cnn(C)c4)c4c(N)ncnn34)ccc2F)C(=O)C1(C)C] | 4-acetyl-1-{5-[4-amino-5-(1-methyl-1H-pyrazol-4-yl)pyrrolo[2,1-f][1,2,4]triazin-7-yl]-2-fluorophenyl}-3,3-dimethylpiperazin-2-one | 478 |

TABLE 40-continued

| Ex. No. | Structure | Name | [M + 1] |
|---|---|---|---|
| 440 | 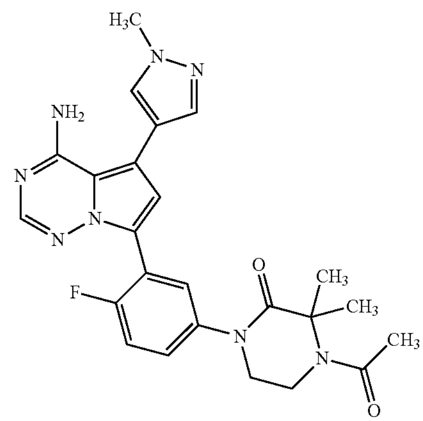 [SMILES: CC(=O)N1CCN(c2ccc(F)c(-c3cc(-c4cnn(C)c4)c4c(N)ncnn34)c2)C(=O)C1(C)C] | 4-acetyl-1-{3-[4-amino-5-(1-methyl-1H-pyrazol-4-yl)pyrrolo[2,1-f][1,2,4]triazin-7-yl]-4-fluorophenyl}-3,3-dimethylpiperazin-2-one | 478 |
| 441 | 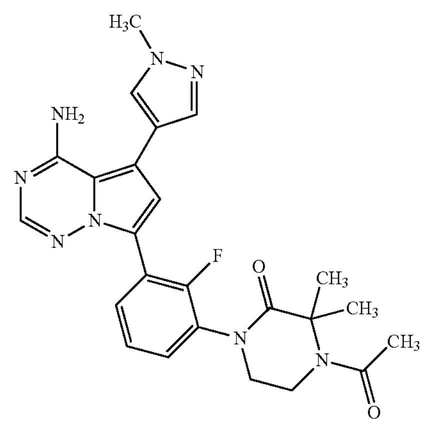 [SMILES: CC(=O)N1CCN(c2cccc(-c3cc(-c4cnn(C)c4)c4c(N)ncnn34)c2F)C(=O)C1(C)C] | 4-acetyl-1-{3-[4-amino-5-(1-methyl-1H-pyrazol-4-yl)pyrrolo[2,1-f][1,2,4]triazin-7-yl]-2-fluorophenyl}-3,3-dimethylpiperazin-2-one | 478 |
| 442 | 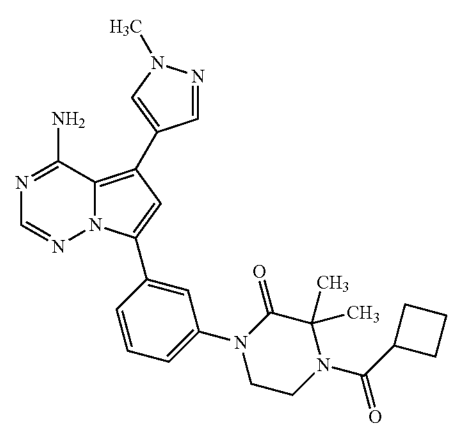 [SMILES: Cn1cc(-c2cc(-c3cccc(N4CCN(C(=O)C5CCC5)C(C)(C)C4=O)c3)n3ncnc(N)c23)cn1] | 1-{3-[4-amino-5-(1-methyl-1H-pyrazol-4-yl)pyrrolo[2,1-f][1,2,4]triazin-7-yl]phenyl}-4-cyclobutanecarbonyl-3,3-dimethylpiperazin-2-one | 500 |

TABLE 40-continued

| Ex. No. | Structure | Name | [M + 1] |
|---|---|---|---|
| 443 | 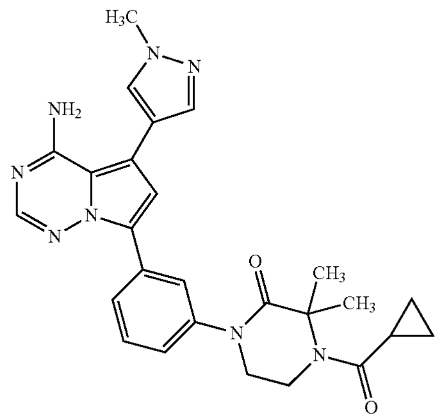 [SMILES: Cn1cc(-c2cc(-c3cccc(N4CCN(C(=O)C5CC5)C(C)(C)C4=O)c3)n3ncnc(N)c23)cn1] | 1-{3-[4-amino-5-(1-methyl-1H-pyrazol-4-yl)pyrrolo[2,1-f][1,2,4]triazin-7-yl]phenyl}-4-cyclopropanecarbonyl-3,3-dimethylpiperazin-2-one | 486 |
| 444 | 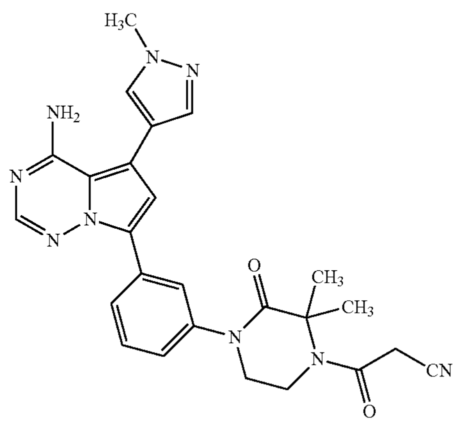 [SMILES: Cn1cc(-c2cc(-c3cccc(N4CCN(C(=O)CC#N)C(C)(C)C4=O)c3)n3ncnc(N)c23)cn1] | 3-(4-{3-[4-amino-5-(1-methyl-1H-pyrazol-4-yl)pyrrolo[2,1-f][1,2,4]triazin-7-yl]phenyl}-2,2-dimethyl-3-oxopiperazin-1-yl)-3-oxopropanenitrile | 485 |
| 445 | 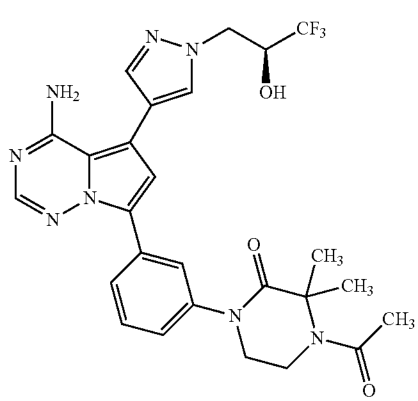 [SMILES: CC(=O)N1CCN(c2cccc(-c3cc(-c4cnn(C[C@H](O)C(F)(F)F)c4)c4c(N)ncnn34)c2)C(=O)C1(C)C] | 4-acetyl-1-[3-(4-amino-5-{1-[(2S)-3,3,3-trifluoro-2-hydroxypropyl]-1H-pyrazol-4-yl}pyrrolo[2,1-f][1,2,4]triazin-7-yl)phenyl]-3,3-dimethylpiperazin-2-one | 558 |

TABLE 40-continued

| Ex. No. | Structure | Name | [M + 1] |
|---|---|---|---|
| 446 | 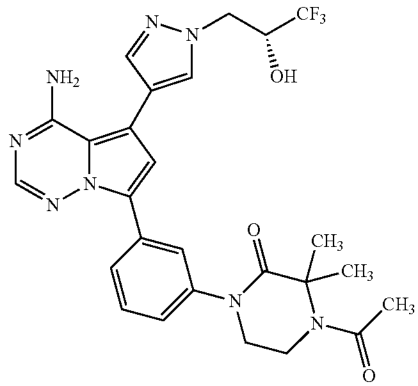 [SMILES: CC(=O)N1CCN(c2cccc(-c3cc(-c4cnn(C[C@@H](O)C(F)(F)F)c4)c4c(N)ncnn34)c2)C(=O)C1(C)C] | 4-acetyl-1-[3-(4-amino-5-{1-[(2R)-3,3,3-trifluoro-2-hydroxypropyl]-1H-pyrazol-4-yl}pyrrolo[2,1-f][1,2,4]triazin-7-yl)phenyl]-3,3-dimethylpiperazin-2-one | 558 |
| 447 | 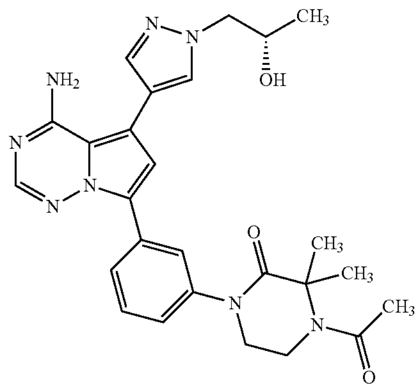 [SMILES: CC(=O)N1CCN(c2cccc(-c3cc(-c4cnn(C[C@H](C)O)c4)c4c(N)ncnn34)c2)C(=O)C1(C)C] | 4-acetyl-1-[3-(4-amino-5-{1-[(2S)-2-hydroxypropyl]-1H-pyrazol-4-yl}pyrrolo[2,1-f][1,2,4]triazin-7-yl)phenyl]-3,3-dimethylpiperazin-2-one | 504 |
| 448 | 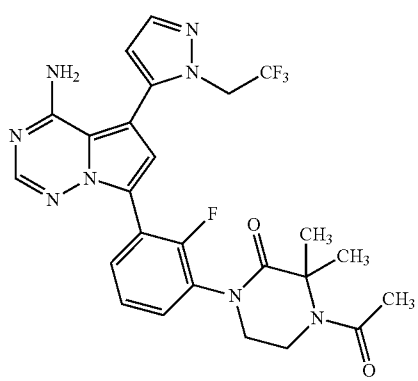 [SMILES: CC(=O)N1CCN(c2cccc(-c3cc(-c4ccnn4CC(F)(F)F)c4c(N)ncnn34)c2F)C(=O)C1(C)C] | 4-acetyl-1-(3-{4-amino-5-[1-(2,2,2-trifluoroethyl)-1H-pyrazol-5-yl]pyrrolo[2,1-f][1,2,4]triazin-7-yl}-2-fluorophenyl)-3,3-dimethylpiperazin-2-one | 546 |
| 449 | 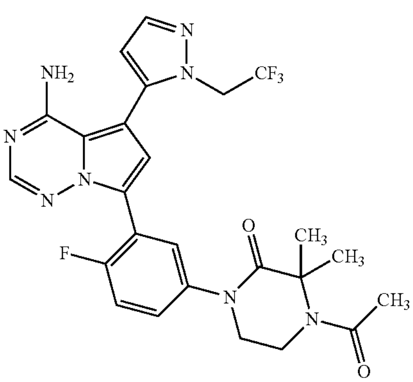 [SMILES: CC(=O)N1CCN(c2ccc(F)c(-c3cc(-c4ccnn4CC(F)(F)F)c4c(N)ncnn34)c2)C(=O)C1(C)C] | 4-acetyl-1-(3-{4-amino-5-[1-(2,2,2-trifluoroethyl)-1H-pyrazol-5-yl]pyrrolo[2,1-f][1,2,4]triazin-7-yl}-4-fluorophenyl)-3,3-dimethylpiperazin-2-one | 546 |

TABLE 40-continued

| Ex. No. | Structure | Name | [M + 1] |
|---|---|---|---|
| 450 | 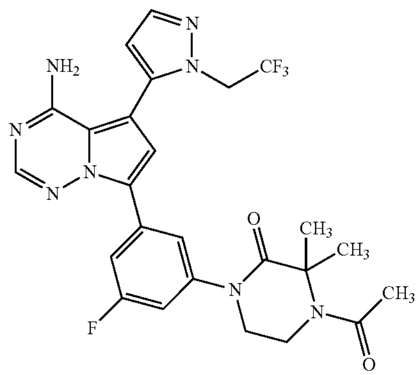 [SMILES: CC(=O)N1CCN(c2cc(F)cc(-c3cc(-c4ccnn4CC(F)(F)F)c4c(N)ncnn34)c2)C(=O)C1(C)C] | 4-acetyl-1-(3-{4-amino-5-[1-(2,2,2-trifluoroethyl)-1H-pyrazol-5-yl]pyrrolo[2,1-f][1,2,4]triazin-7-yl}-5-fluorophenyl)-3,3-dimethylpiperazin-2-one | 546 |
| 451 | 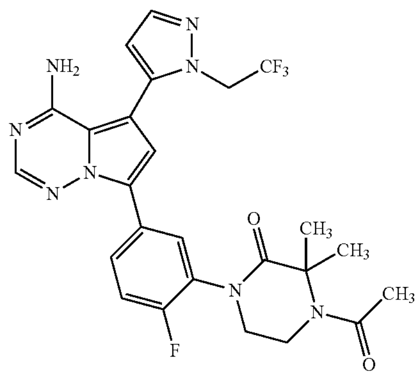 [SMILES: CC(=O)N1CCN(c2cc(-c3cc(-c4ccnn4CC(F)(F)F)c4c(N)ncnn34)ccc2F)C(=O)C1(C)C] | 4-acetyl-1-(5-{4-amino-5-[1-(2,2,2-trifluoroethyl)-1H-pyrazol-5-yl]pyrrolo[2,1-f][1,2,4]triazin-7-yl}-2-fluorophenyl)-3,3-dimethylpiperazin-2-one | 546 |
| 452 | 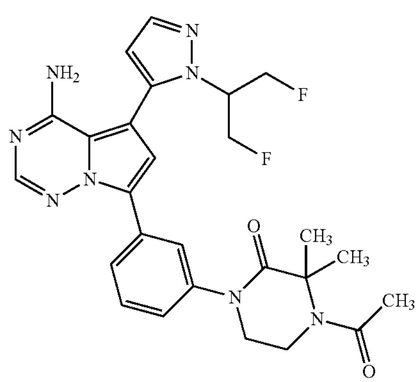 [SMILES: CC(=O)N1CCN(c2cccc(-c3cc(-c4ccnn4C(CF)CF)c4c(N)ncnn34)c2)C(=O)C1(C)C] | 4-acetyl-1-(3-{4-amino-5-[1-(1,3-difluoropropan-2-yl)-1H-pyrazol-5-yl]pyrrolo[2,1-f][1,2,4]triazin-7-yl}phenyl)-3,3-dimethylpiperazin-2-one | 524 |
| 453 | 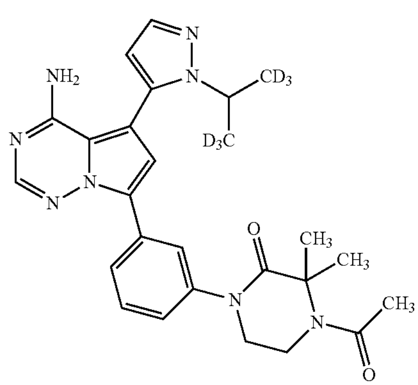 [SMILES: [2H]C([2H])([2H])C(n1nccc1-c1cc(-c2cccc(N3CCN(C(C)=O)C(C)(C)C3=O)c2)n2ncnc(N)c12)C([2H])([2H])[2H]] | 4-acetyl-1-[3-(4-amino-5-{1-[(1,1,1,3,3,3-$^2$H$_6$)propan-2-yl]-1H-pyrazol-5-yl}pyrrolo[2,1-f][1,2,4]triazin-7-yl)phenyl]-3,3-dimethylpiperazin-2-one | 494 |

TABLE 40-continued

| Ex. No. | Structure | Name | [M + 1] |
|---|---|---|---|
| 454 | 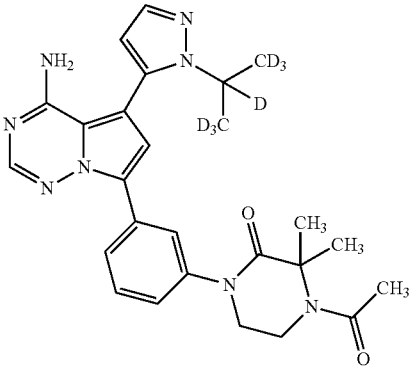 [SMILES: [2H]C([2H])([2H])C([2H])(n1nccc1-c1cc(-c2cccc(N3CCN(C(C)=O)C(C)(C)C3=O)c2)n2ncnc(N)c12)C([2H])([2H])[2H]] | 4-acetyl-1-[3-(4-amino-5-{1-[($^2$H$_7$)propan-2-yl]-1H-pyrazol-5-yl}pyrrolo[2,1-f][1,2,4]triazin-7-yl)phenyl]-3,3-dimethylpiperazin-2-one | 495 |
| 455 | 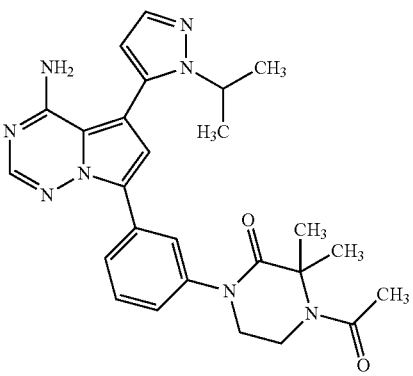 [SMILES: CC(=O)N1CCN(c2cccc(-c3cc(-c4ccnn4C(C)C)c4c(N)ncnn34)c2)C(=O)C1(C)C] | 4-acetyl-1-(3-{4-amino-5-[1-(propan-2-yl)-1H-pyrazol-5-yl]pyrrolo[2,1-f][1,2,4]triazin-7-yl}phenyl)-3,3-dimethylpiperazin-2-one | 488 |
| 456 | 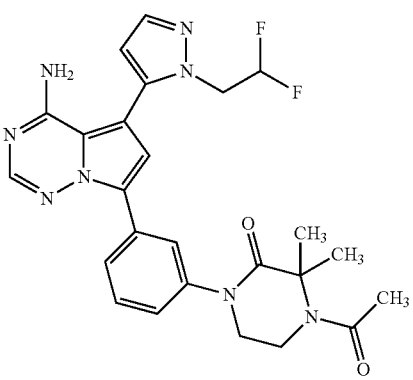 [SMILES: CC(=O)N1CCN(c2cccc(-c3cc(-c4ccnn4CC(F)F)c4c(N)ncnn34)c2)C(=O)C1(C)C] | 4-acetyl-1-(3-{4-amino-5-[1-(2,2-difluoroethyl)-1H-pyrazol-5-yl]pyrrolo[2,1-f][1,2,4]triazin-7-yl}phenyl)-3,3-dimethylpiperazin-2-one | 510 |
| 457 | 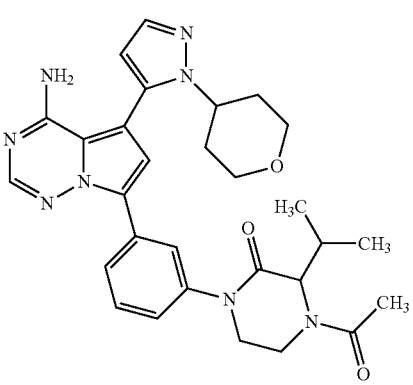 [SMILES: CC(=O)N1CCN(c2cccc(-c3cc(-c4ccnn4C4CCOCC4)c4c(N)ncnn34)c2)C(=O)C1C(C)C] | 4-acetyl-1-(3-{4-amino-5-[1-(oxan-4-yl)-1H-pyrazol-5-yl]pyrrolo[2,1-f][1,2,4]triazin-7-yl}phenyl)-3-(propan-2-yl)piperazin-2-one | 544 |

TABLE 40-continued

| Ex. No. | Structure | Name | [M + 1] |
|---|---|---|---|
| 458 | 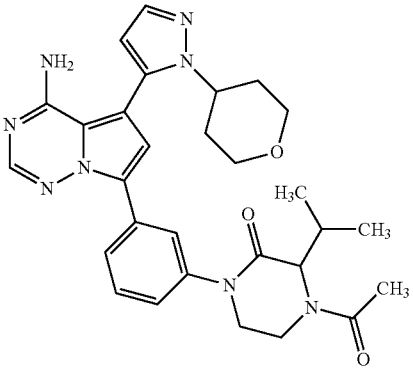 [SMILES: CC(=O)N1CCN(c2cccc(-c3cc(-c4ccnn4C4CCOCC4)c4c(N)ncnn34)c2)C(=O)C1C(C)C] | 4-acetyl-1-(3-{4-amino-5-[1-(oxan-4-yl)-1H-pyrazol-5-yl]pyrrolo[2,1-f][1,2,4]triazin-7-yl}phenyl)-3-(propan-2-yl)piperazin-2-one; chiral | 544 |
| 459 | 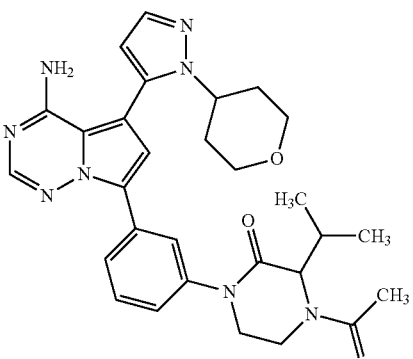 | 4-acetyl-1-(3-{4-amino-5-[1-(oxan-4-yl)-1H-pyrazol-5-yl]pyrrolo[2,1-f][1,2,4]triazin-7-yl}phenyl)-3-(propan-2-yl)piperazin-2-one; chiral | 544 |
| 460 | 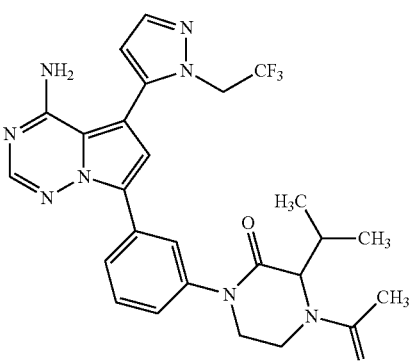 | 4-acetyl-1-(3-{4-amino-5-[1-(2,2,2-trifluoroethyl)-1H-pyrazol-5-yl]pyrrolo[2,1-f][1,2,4]triazin-7-yl}phenyl)-3-(propan-2-yl)piperazin-2-one | 542 |
| 461 | 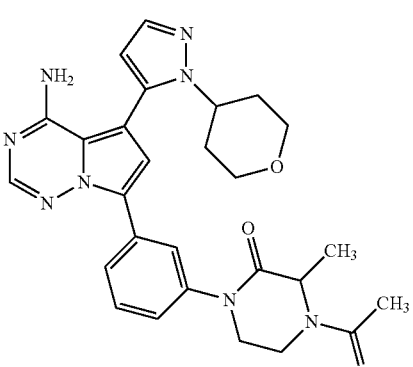 | 4-acetyl-1-(3-{4-amino-5-[1-(oxan-4-yl)-1H-pyrazol-5-yl]pyrrolo[2,1-f][1,2,4]triazin-7-yl}phenyl)-3-methylpiperazin-2-one | 516 |

TABLE 40-continued

| Ex. No. | Structure | Name | [M + 1] |
|---|---|---|---|
| 462 | 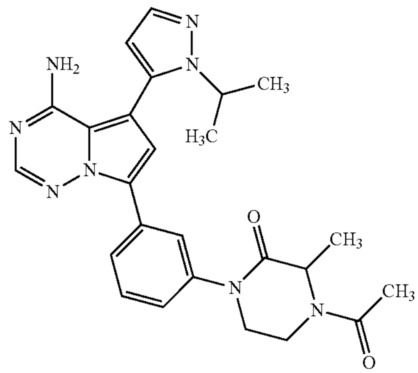 [SMILES: CC(=O)N1CCN(c2cccc(-c3cc(-c4ccnn4C(C)C)c4c(N)ncnn34)c2)C(=O)C1C] | 4-acetyl-1-(3-{4-amino-5-[1-(propan-2-yl)-1H-pyrazol-5-yl]pyrrolo[2,1-f][1,2,4]triazin-7-yl}phenyl)-3-methylpiperazin-2-one | 474 |
| 463 | 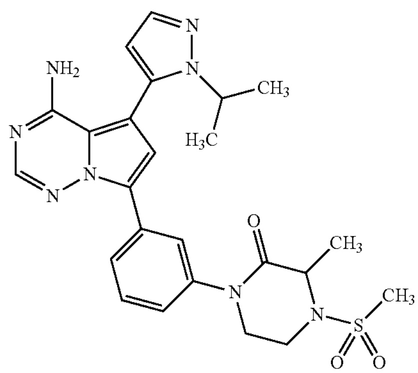 [SMILES: CC1C(=O)N(c2cccc(-c3cc(-c4ccnn4C(C)C)c4c(N)ncnn34)c2)CCN1S(C)(=O)=O] | 1-(3-{4-amino-5-[1-(oxan-4-yl)-1H-pyrazol-5-yl]pyrrolo[2,1-f][1,2,4]triazin-7-yl}phenyl)-4-methanesulfonyl-3-methylpiperazin-2-one | 552 |
| 464 | 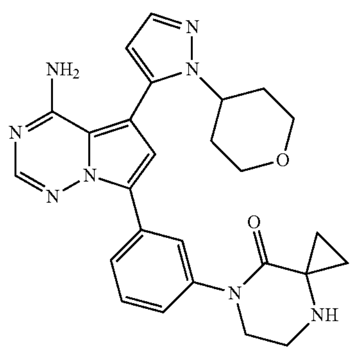 [SMILES: Nc1ncnn2c(-c3cccc(N4CCNC5(CC5)C4=O)c3)cc(-c3ccnn3C3CCOCC3)c12] | 7-(3-{4-amino-5-[1-(oxan-4-yl)-1H-pyrazol-5-yl]pyrrolo[2,1-f][1,2,4]triazin-7-yl}phenyl)-4,7-diazaspiro[2.5]octan-8-one | 486 |
| 465 | 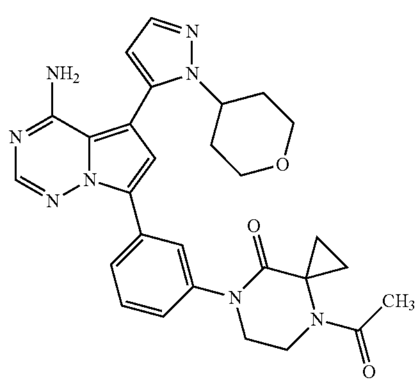 [SMILES: CC(=O)N1CCN(c2cccc(-c3cc(-c4ccnn4C4CCOCC4)c4c(N)ncnn34)c2)C(=O)C12CC2] | 4-acetyl-7-(3-{4-amino-5-[1-(oxan-4-yl)-1H-pyrazol-5-yl]pyrrolo[2,1-f][1,2,4]triazin-7-yl}phenyl)-4,7-diazaspiro[2.5]octan-8-one | 528 |

TABLE 40-continued

| Ex. No. | Structure | Name | [M + 1] |
|---|---|---|---|
| 466 | 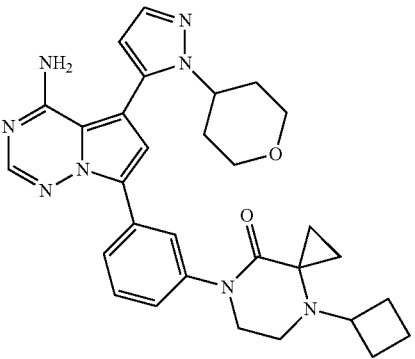 [SMILES: Nc1ncnn2c(-c3cccc(N4CCN(C5CCC5)C5(CC5)C4=O)c3)cc(-c3ccnn3C3CCOCC3)c12] | 7-(3-{4-amino-5-[1-(oxan-4-yl)-1H-pyrazol-5-yl]pyrrolo[2,1-f][1,2,4]triazin-7-yl}phenyl)-4-cyclobutyl-4,7-diazaspiro[2.5]octan-8-one | 540 |
| 467 | 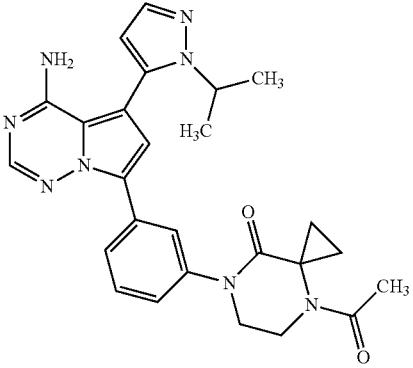 [SMILES: CC(=O)N1CCN(c2cccc(-c3cc(-c4ccnn4C(C)C)c4c(N)ncnn34)c2)C(=O)C12CC2] | 4-acetyl-7-(3-{4-amino-5-[1-(propan-2-yl)-1H-pyrazol-5-yl]pyrrolo[2,1-f][1,2,4]triazin-7-yl}phenyl)-4,7-diazaspiro[2.5]octan-8-one | 486 |
| 468 | 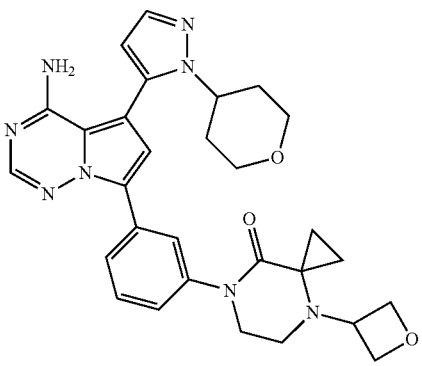 [SMILES: Nc1ncnn2c(-c3cccc(N4CCN(C5COC5)C5(CC5)C4=O)c3)cc(-c3ccnn3C3CCOCC3)c12] | 7-(3-{4-amino-5-[1-(oxan-4-yl)-1H-pyrazol-5-yl]pyrrolo[2,1-f][1,2,4]triazin-7-yl}phenyl)-4-(oxetan-3-yl)-4,7-diazaspiro[2.5]octan-8-one | 542 |
| 469 | 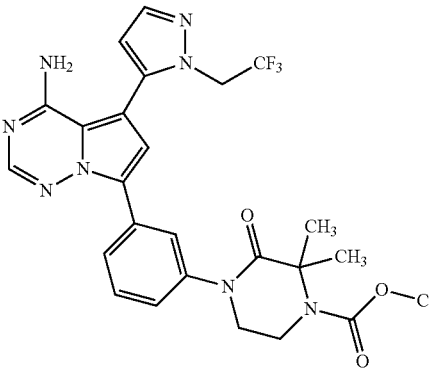 | methyl 4-(3-{4-amino-5-[1-(2,2,2-trifluoroethyl)-1H-pyrazol-5-yl]pyrrolo[2,1-f][1,2,4]triazin-7-yl}phenyl)-2,2-dimethyl-3-oxopiperazine-1-carboxylate | 544 |

TABLE 40-continued

| Ex. No. | Structure | Name | [M + 1] |
|---|---|---|---|
| 470 | 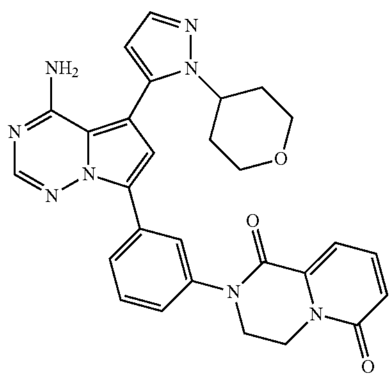 [SMILES: Nc1ncnn2c(-c3cccc(N4CCn5c(cccc5=O)C4=O)c3)cc(-c3ccnn3C3CCOCC3)c12] | 2-(3-{4-amino-5-[1-(oxan-4-yl)-1H-pyrazol-5-yl]pyrrolo[2,1-f][1,2,4]triazin-7-yl}phenyl)-1H,2H,3H,4H,6H-pyrido[1,2-a]piperazine-1,6-dione | 524 |
| 471 | 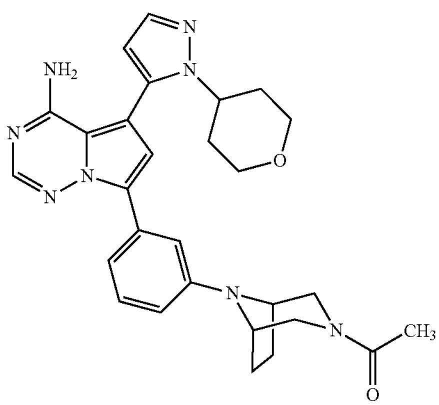 [SMILES: CC(=O)N1CC2CCC(C1)N2c1cccc(-c2cc(-c3ccnn3C3CCOCC3)c3c(N)ncnn23)c1] | 1-[8-(3-{4-amino-5-[1-(oxan-4-yl)-1H-pyrazol-5-yl]pyrrolo[2,1-f][1,2,4]triazin-7-yl}phenyl)-3,8-diazabicyclo[3.2.1]octan-3-yl]ethan-1-one | 514 |
| 472 | 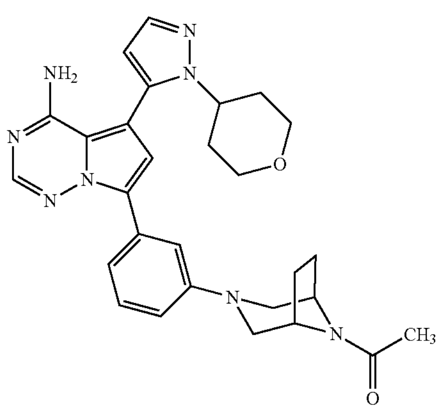 [SMILES: CC(=O)N1C2CCC1CN(c1cccc(-c3cc(-c4ccnn4C4CCOCC4)c4c(N)ncnn34)c1)C2] | 1-[3-(3-{4-amino-5-[1-(oxan-4-yl)-1H-pyrazol-5-yl]pyrrolo[2,1-f][1,2,4]triazin-7-yl}phenyl)-3,8-diazabicyclo[3.2.1]octan-8-yl]ethan-1-one | 514 |

TABLE 40-continued

| Ex. No. | Structure | Name | [M + 1] |
|---|---|---|---|
| 473 | 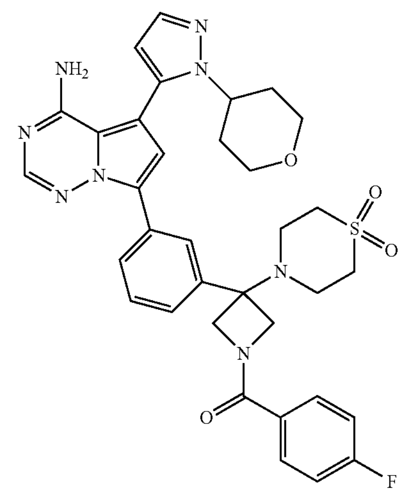 [SMILES: Nc1ncnn2c(-c3cccc(C4(N5CCS(=O)(=O)CC5)CN(C(=O)c5ccc(F)cc5)C4)c3)cc(-c3ccnn3C3CCOCC3)c12] | 4-[3-(3-{4-amino-5-[1-(oxan-4-yl)-1H-pyrazol-5-yl]pyrrolo[2,1-f][1,2,4]triazin-7-yl}phenyl)-1-(4-fluorobenzoyl)azetidin-3-yl]-1λ⁶,4-thiomorpholine-1,1-dione | 672 |
| 474 | 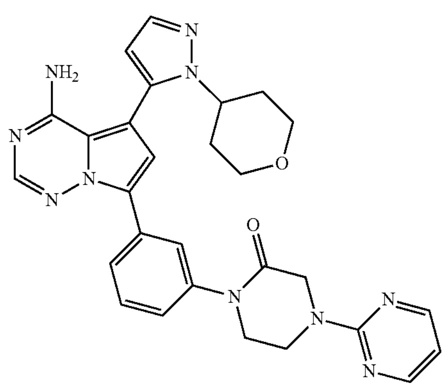 [SMILES: Nc1ncnn2c(-c3cccc(N4CCN(c5ncccn5)CC4=O)c3)cc(-c3ccnn3C3CCOCC3)c12] | 1-(3-{4-amino-5-[1-(oxan-4-yl)-1H-pyrazol-5-yl]pyrrolo[2,1-f][1,2,4]triazin-7-yl}phenyl)-4-(pyrimidin-2-yl)piperazin-2-one | 538 |
| 475 | 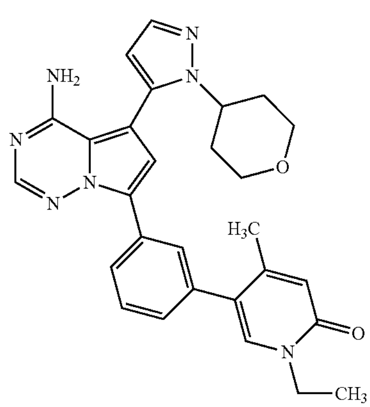 [SMILES: CCn1cc(-c2cccc(-c3cc(-c4ccnn4C4CCOCC4)c4c(N)ncnn34)c2)c(C)cc1=O] | 5-(3-{4-amino-5-[1-(oxan-4-yl)-1H-pyrazol-5-yl]pyrrolo[2,1-f][1,2,4]triazin-7-yl}phenyl)-1-ethyl-4-methyl-1,2-dihydropyridin-2-one | 497 |

TABLE 40-continued

| Ex. No. | Structure | Name | [M + 1] |
|---|---|---|---|
| 476 | 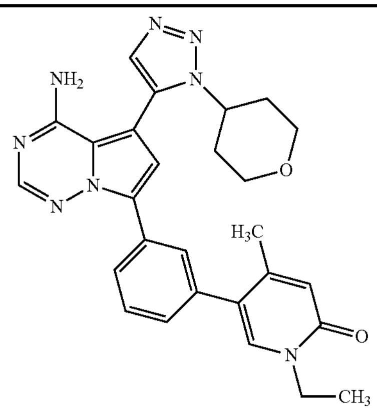 | 5-(3-{4-amino-5-[1-(oxan-4-yl)-1H-1,2,3-triazol-5-yl]pyrrolo[2,1-f][1,2,4]triazin-7-yl}phenyl)-1-ethyl-4-methyl-1,2-dihydropyridin-2-one | 498 |
| 477 | 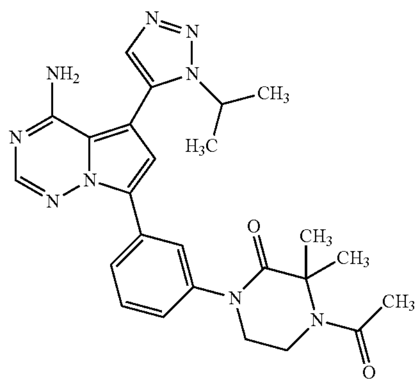 [SMILES: CC(=O)N1CCN(c2cccc(-c3cc(-c4cnnn4C(C)C)c4c(N)ncnn34)c2)C(=O)C1(C)C] | 4-acetyl-1-(3-{4-amino-5-[1-(propan-2-yl)-1H-1,2,3-triazol-5-yl]pyrrolo[2,1-f][1,2,4]triazin-7-yl}phenyl)-3,3-dimethylpiperazin-2-one | 489 |
| 478 | 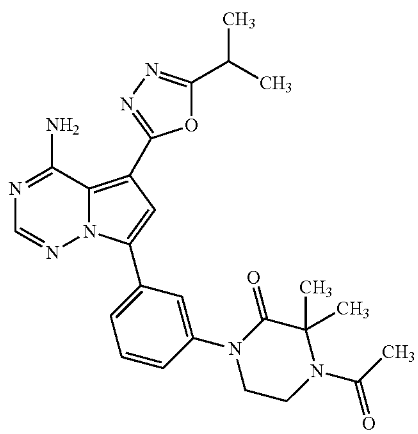 [SMILES: CC(=O)N1CCN(c2cccc(-c3cc(-c4nnc(C(C)C)o4)c4c(N)ncnn34)c2)C(=O)C1(C)C] | 4-acetyl-1-(3-{4-amino-5-[5-(propan-2-yl)-1,3,4-oxadiazol-2-yl]pyrrolo[2,1-f][1,2,4]triazin-7-yl}phenyl)-3,3-dimethylpiperazin-2-one | 490 |
| 479 | 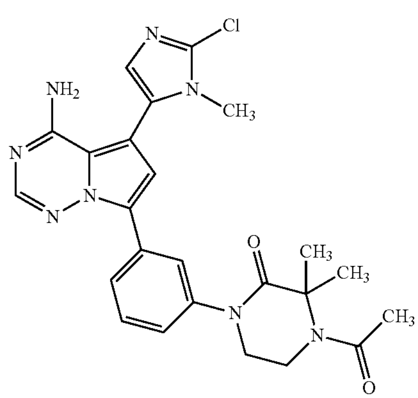 [SMILES: CC(=O)N1CCN(c2cccc(-c3cc(-c4cnc(Cl)n4C)c4c(N)ncnn34)c2)C(=O)C1(C)C] | 4-acetyl-1-{3-[4-amino-5-(2-chloro-1-methyl-1H-imidazol-5-yl)pyrrolo[2,1-f][1,2,4]triazin-7-yl]phenyl}-3,3-dimethylpiperazin-2-one | 494 |

TABLE 40-continued

| Ex. No. | Structure | Name | [M + 1] |
|---|---|---|---|
| 480 | 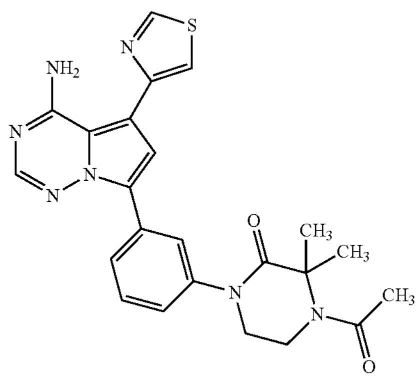 [SMILES: CC(=O)N1CCN(c2cccc(-c3cc(-c4cscn4)c4c(N)ncnn34)c2)C(=O)C1(C)C] | 4-acetyl-1-{3-[4-amino-5-(1,3-thiazol-4-yl)pyrrolo[2,1-f][1,2,4]triazin-7-yl]phenyl}-3,3-dimethylpiperazin-2-one | 463 |
| 481 | 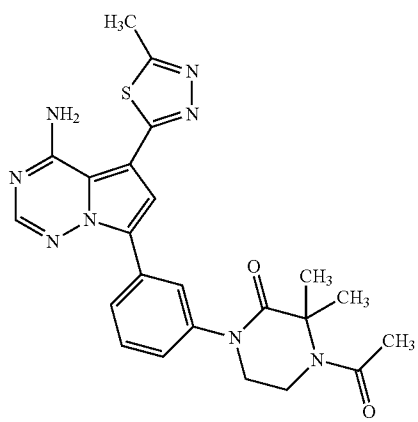 [SMILES: CC(=O)N1CCN(c2cccc(-c3cc(-c4nnc(C)s4)c4c(N)ncnn34)c2)C(=O)C1(C)C] | 4-acetyl-1-{3-[4-amino-5-(5-methyl-1,3,4-thiadiazol-2-yl)pyrrolo[2,1-f][1,2,4]triazin-7-yl]phenyl}-3,3-dimethylpiperazin-2-one | 478 |
| 482 | 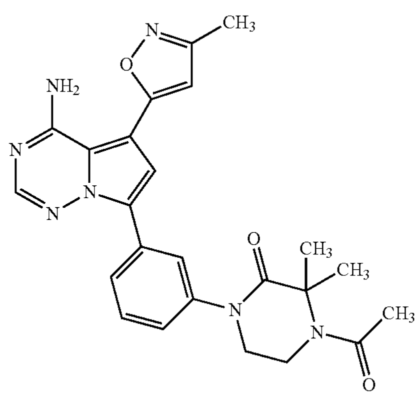 [SMILES: CC(=O)N1CCN(c2cccc(-c3cc(-c4cc(C)no4)c4c(N)ncnn34)c2)C(=O)C1(C)C] | 4-acetyl-1-{3-[4-amino-5-(3-methyl-1,2-oxazol-5-yl)pyrrolo[2,1-f][1,2,4]triazin-7-yl]phenyl}-3,3-dimethylpiperazin-2-one | 461 |

TABLE 40-continued

| Ex. No. | Structure | Name | [M + 1] |
|---|---|---|---|
| 483 | 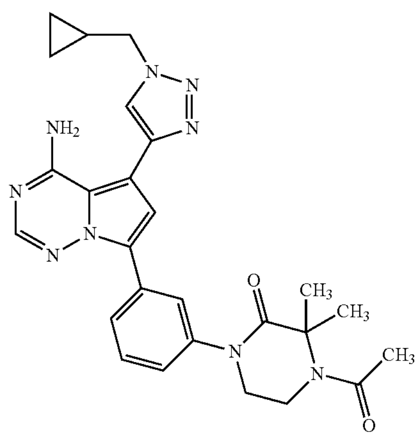 [SMILES: CC(=O)N1CCN(c2cccc(-c3cc(-c4cn(CC5CC5)nn4)c4c(N)ncnn34)c2)C(=O)C1(C)C] | 4-acetyl-1-(3-{4-amino-5-[1-(cyclopropylmethyl)-1H-1,2,3-triazol-4-yl]pyrrolo[2,1-f][1,2,4]triazin-7-yl}phenyl)-3,3-dimethylpiperazin-2-one | 501 |
| 484 | 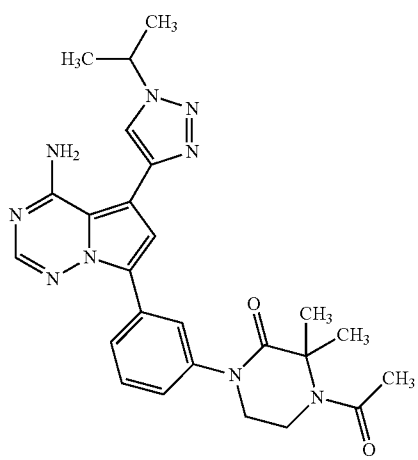 [SMILES: CC(=O)N1CCN(c2cccc(-c3cc(-c4cn(C(C)C)nn4)c4c(N)ncnn34)c2)C(=O)C1(C)C] | 4-acetyl-1-(3-{4-amino-5-[1-(propan-2-yl)-1H-1,2,3-triazol-4-yl]pyrrolo[2,1-f][1,2,4]triazin-7-yl}phenyl)-3,3-dimethylpiperazin-2-one | 489 |
| 485 | 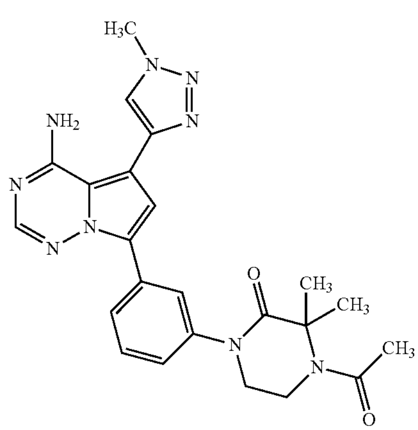 [SMILES: CC(=O)N1CCN(c2cccc(-c3cc(-c4cn(C)nn4)c4c(N)ncnn34)c2)C(=O)C1(C)C] | 4-acetyl-1-{3-[4-amino-5-(1-methyl-1H-1,2,3-triazol-4-yl)pyrrolo[2,1-f][1,2,4]triazin-7-yl]phenyl}-3,3-dimethylpiperazin-2-one | 461 |

TABLE 40-continued

| Ex. No. | Structure | Name | [M + 1] |
|---|---|---|---|
| 486 | 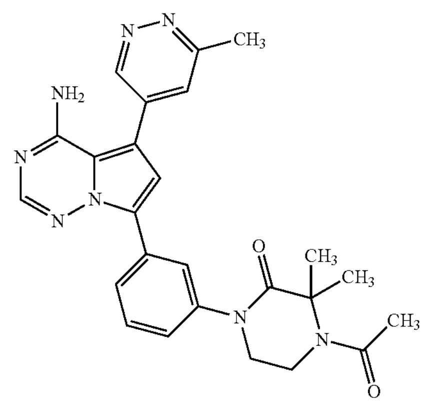 [SMILES: CC(=O)N1CCN(c2cccc(-c3cc(-c4cnnc(C)c4)c4c(N)ncnn34)c2)C(=O)C1(C)C] | 4-acetyl-1-{3-[4-amino-5-(6-methylpyridazin-4-yl)pyrrolo[2,1-f][1,2,4]triazin-7-yl]phenyl}-3,3-dimethylpiperazin-2-one | 472 |
| 487 | 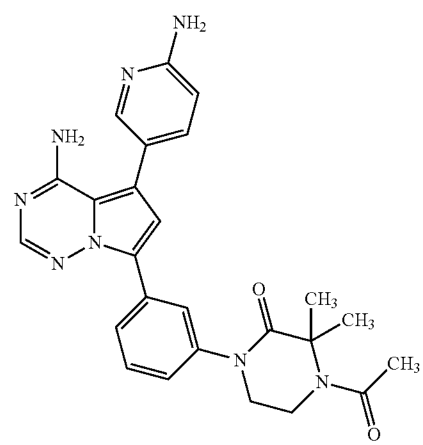 [SMILES: CC(=O)N1CCN(c2cccc(-c3cc(-c4ccc(N)nc4)c4c(N)ncnn34)c2)C(=O)C1(C)C] | 4-acetyl-1-{3-[4-amino-5-(6-aminopyridin-3-yl)pyrrolo[2,1-f][1,2,4]triazin-7-yl]phenyl}-3,3-dimethylpiperazin-2-one | 472 |
| 488 | 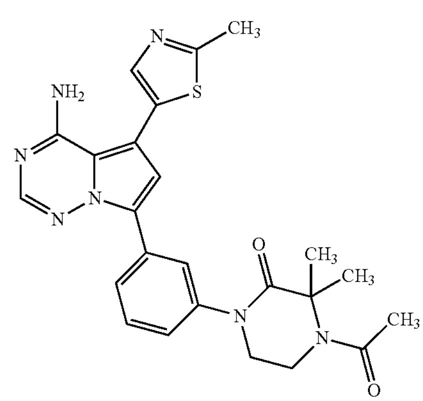 [SMILES: CC(=O)N1CCN(c2cccc(-c3cc(-c4cnc(C)s4)c4c(N)ncnn34)c2)C(=O)C1(C)C] | 4-acetyl-1-{3-[4-amino-5-(2-amino-1,3-thiazol-5-yl)pyrrolo[2,1-f][1,2,4]triazin-7-yl]phenyl}-3,3-dimethylpiperazin-2-one | 478 |

TABLE 40-continued
| Ex. No. | Structure | Name | [M + 1] |
|---|---|---|---|
| 489 | 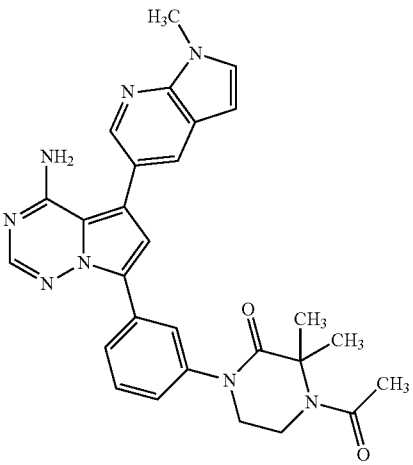 [SMILES: CC(=O)N1CCN(c2cccc(-c3cc(-c4cnc5c(ccn5C)c4)c4c(N)ncnn34)c2)C(=O)C1(C)C] | 4-acetyl-1-[3-(4-amino-5-{1-methyl-1H-pyrrolo[2,3-b]pyridin-5-yl}pyrrolo[2,1-f][1,2,4]triazin-7-yl)phenyl]-3,3-dimethylpiperazin-2-one | 510 |
| 490 | 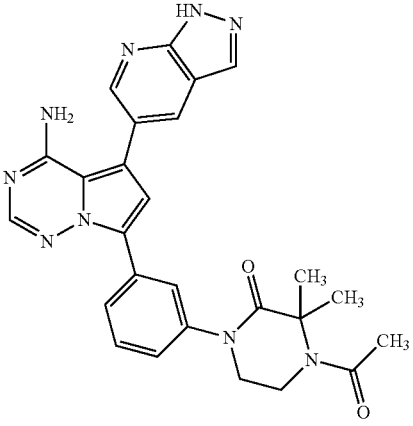 | 4-acetyl-1-[3-(4-amino-5-{1H-pyrazolo[3,4-b]pyridin-5-yl}pyrrolo[2,1-f][1,2,4]triazin-7-yl)phenyl]-3,3-dimethylpiperazin-2-one | 497 |
| 491 | 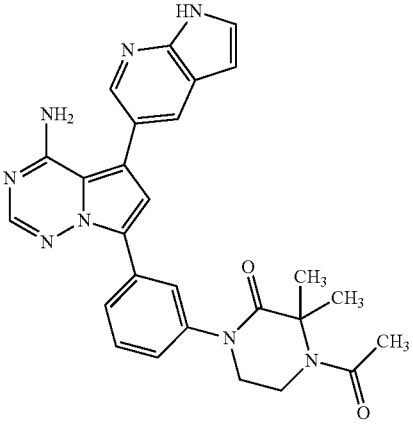 [SMILES: CC(=O)N1CCN(c2cccc(-c3cc(-c4cnc5[nH]ccc5c4)c4c(N)ncnn34)c2)C(=O)C1(C)C] | 4-acetyl-1-[3-(4-amino-5-{1H-pyrrolo[2,3-b]pyridin-5-yl}pyrrolo[2,1-f][1,2,4]triazin-7-yl)phenyl]-3,3-dimethylpiperazin-2-one | 496 |

TABLE 40-continued

| Ex. No. | Structure | Name | [M + 1] |
|---|---|---|---|
| 492 | 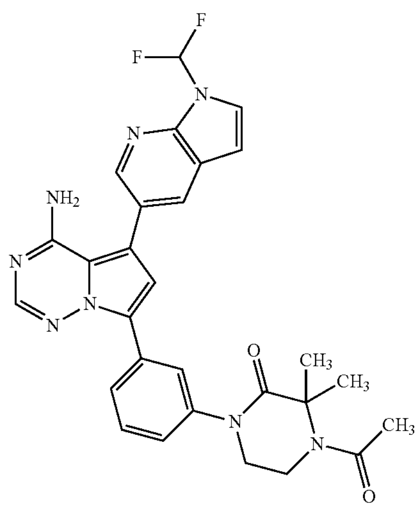 [SMILES: CC(=O)N1CCN(c2cccc(-c3cc(-c4cnc5c(ccn5C(F)F)c4)c4c(N)ncnn34)c2)C(=O)C1(C)C] | 4-acetyl-1-(3-{4-amino-5-[1-(difluoromethyl)-1H-pyrrolo[2,3-b]pyridin-5-yl]pyrrolo[2,1-f][1,2,4]triazin-7-yl}phenyl)-3,3-dimethylpiperazin-2-one | 546 |
| 493 | 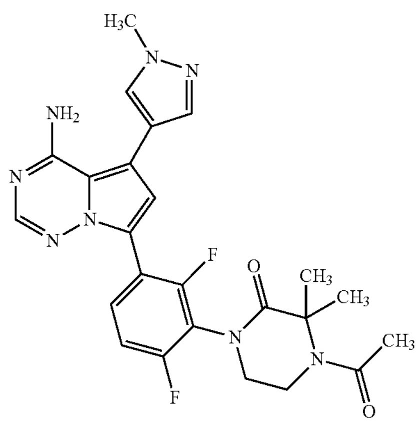 [SMILES: CC(=O)N1CCN(c2c(F)ccc(-c3cc(-c4cnn(C)c4)c4c(N)ncnn34)c2F)C(=O)C1(C)C] | 4-acetyl-1-{3-[4-amino-5-(1-methyl-1H-pyrazol-4-yl)pyrrolo[2,1-f][1,2,4]triazin-7-yl]-2,6-difluorophenyl}-3,3-dimethylpiperazin-2-one | 496 |
| 494 | 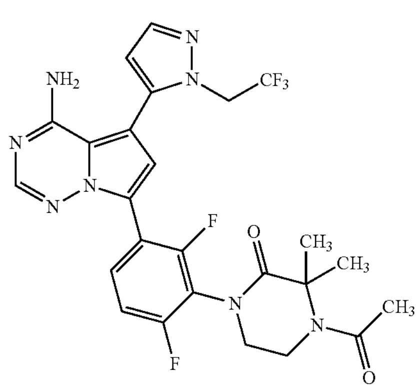 [SMILES: CC(=O)N1CCN(c2c(F)ccc(-c3cc(-c4ccnn4CC(F)(F)F)c4c(N)ncnn34)c2F)C(=O)C1(C)C] | 4-acetyl-1-(3-{4-amino-5-[1-(2,2,2-trifluoroethyl)-1H-pyrazol-5-yl]pyrrolo[2,1-f][1,2,4]triazin-7-yl}-2,6-difluorophenyl)-3,3-dimethylpiperazin-2-one | 564 |

TABLE 40-continued

| Ex. No. | Structure | Name | [M + 1] |
|---|---|---|---|
| 495 | 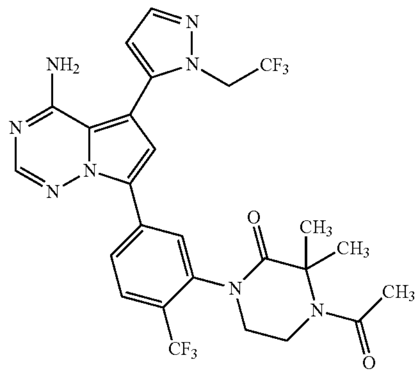 | 4-acetyl-1-(5-{4-amino-5-[1-(2,2,2-trifluoroethyl)-1H-pyrazol-5-yl]pyrrolo[2,1-f][1,2,4]triazin-7-yl}-2-(trifluoromethyl)phenyl)-3,3-dimethylpiperazin-2-one | 596 |
| 496 | 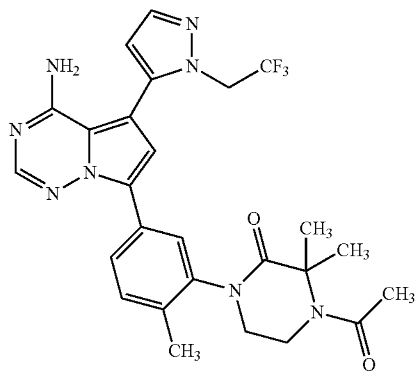 [SMILES: CC(=O)N1CCN(c2cc(-c3cc(-c4ccnn4CC(F)(F)F)c4c(N)ncnn34)ccc2C(F)(F)F)C(=O)C1(C)C] | 4-acetyl-1-(5-{4-amino-5-[1-(2,2,2-trifluoroethyl)-1H-pyrazol-5-yl]pyrrolo[2,1-f][1,2,4]triazin-7-yl}-2-methylphenyl)-3,3-dimethylpiperazin-2-one | 542 |
| 497 | 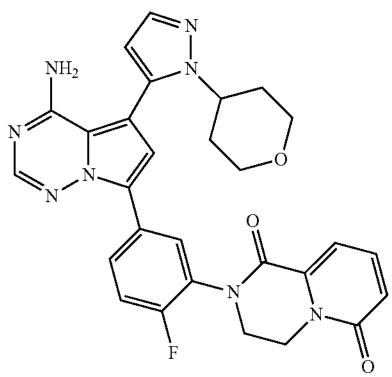 [SMILES: Nc1ncnn2c(-c3ccc(F)c(N4CCn5c(cccc5=O)C4=O)c3)cc(-c3ccnn3C3CCOCC3)c12] | 2-(5-{4-amino-5-[1-(oxan-4-yl)-1H-pyrazol-5-yl]pyrrolo[2,1-f][1,2,4]triazin-7-yl}-2-fluorophenyl)-1H,2H,3H,4H,6H-pyrido[1,2-a]piperazine-1,6-dione | 542 |
| 498 | 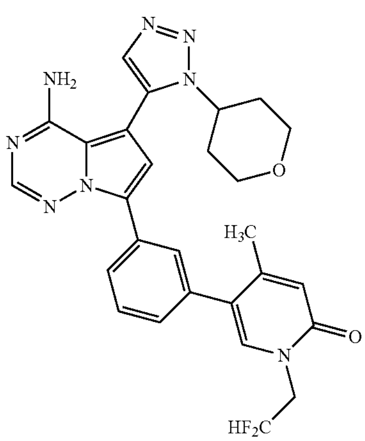 | 5-(3-{4-amino-5-[1-(oxan-4-yl)-1H-1,2,3-triazol-5-yl]pyrrolo[2,1-f][1,2,4]triazin-7-yl}phenyl)-1-(2,2-difluoroethyl)-4-methyl-1,2-dihydropyridin-2-one | 534 |

TABLE 40-continued

| Ex. No. | Structure | Name | [M + 1] |
|---|---|---|---|
| 499 | 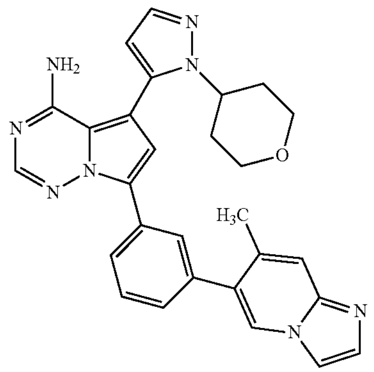 [SMILES: Cc1cc2nccn2cc1-c1cccc(-c2cc(-c3ccnn3C3CCOCC3)c3c(N)ncnn23)c1] | 7-(3-{7-methylimidazo[1,2-a]pyridin-6-yl}phenyl)-5-[1-(oxan-4-yl)-1H-pyrazol-5-yl]pyrrolo[2,1-f][1,2,4]triazin-4-amine | 492 |
| 500 | 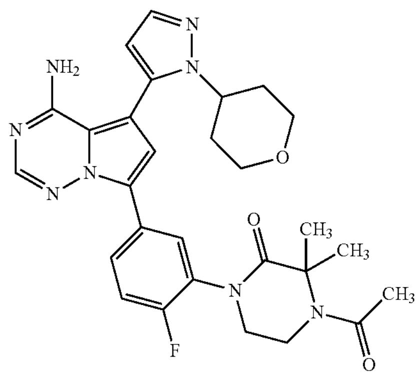 [SMILES: CC(=O)N1CCN(c2cc(-c3cc(-c4ccnn4C4CCOCC4)c4c(N)ncnn34)ccc2F)C(=O)C1(C)C] | 4-acetyl-1-(5-{4-amino-5-[1-(oxan-4-yl)-1H-pyrazol-5-yl]pyrrolo[2,1-f][1,2,4]triazin-7-yl}-2-fluorophenyl)-3,3-dimethylpiperazin-2-one | 548 |
| 501 | 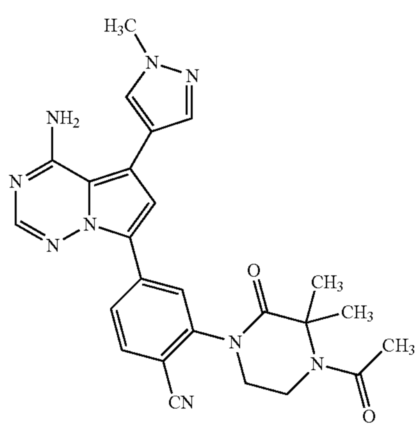 [SMILES: CC(=O)N1CCN(c2cc(-c3cc(-c4cnn(C)c4)c4c(N)ncnn34)ccc2C#N)C(=O)C1(C)C] | 2-(4-acetyl-3,3-dimethyl-2-oxopiperazin-1-yl)-4-[4-amino-5-(1-methyl-1H-pyrazol-4-yl)pyrrolo[2,1-f][1,2,4]triazin-7-yl]benzonitrile | 485 |
| 502 | 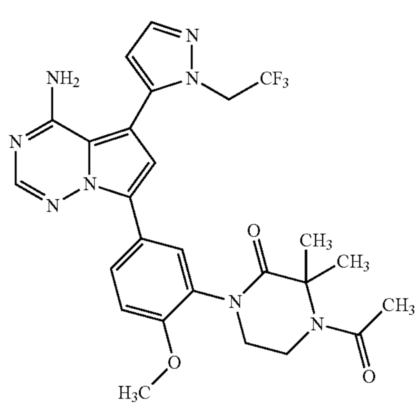 [SMILES: COc1ccc(-c2cc(-c3ccnn3CC(F)(F)F)c3c(N)ncnn23)cc1N1CCN(C(C)=O)C(C)(C)C1=O] | 4-acetyl-1-(5-{4-amino-5-[1-(2,2,2-trifluoroethyl)-1H-pyrazol-5-yl]pyrrolo[2,1-f][1,2,4]triazin-7-yl}-2-methoxyphenyl)-3,3-dimethylpiperazin-2-one | 558 |

TABLE 40-continued

| Ex. No. | Structure | Name | [M + 1] |
|---|---|---|---|
| 503 | 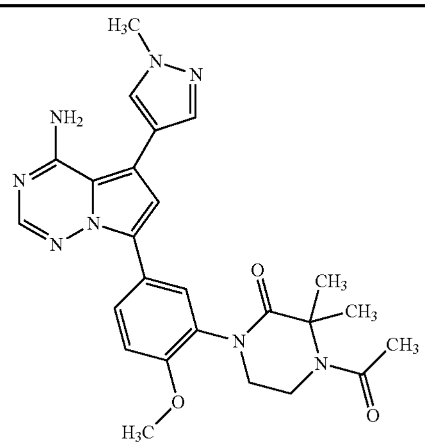 | 4-acetyl-1-{5-[4-amino-5-(1-methyl-1H-pyrazol-4-yl)pyrrolo[2,1-f][1,2,4]triazin-7-yl]-2-methoxyphenyl}-3,3-dimethylpiperazin-2-one | 490 |
| 504 | 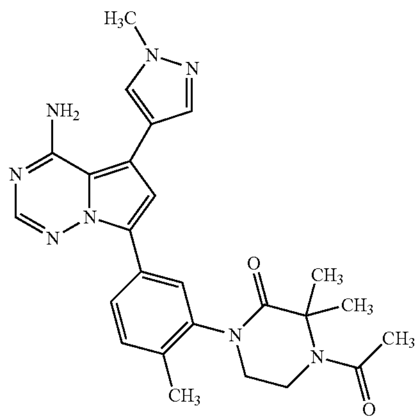 | 4-acetyl-1-{5-[4-amino-5-(1-methyl-1H-pyrazol-4-yl)pyrrolo[2,1-f][1,2,4]triazin-7-yl]-2-methylphenyl}-3,3-dimethylpiperazin-2-one | 474 |
| 505 | 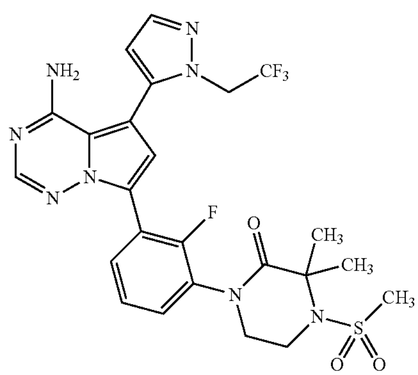 [SMILES: CC1(C)C(=O)N(c2cccc(-c3cc(-c4ccnn4CC(F)(F)F)c4c(N)ncnn34)c2F)CCN1S(C)(=O)=O] | 1-(3-{4-amino-5-[1-(2,2,2-trifluoroethyl)-1H-pyrazol-5-yl]pyrrolo[2,1-f][1,2,4]triazin-7-yl}-2-fluorophenyl)-4-methanesulfonyl-3,3-dimethylpiperazin-2-one | 582 |
| 506 | 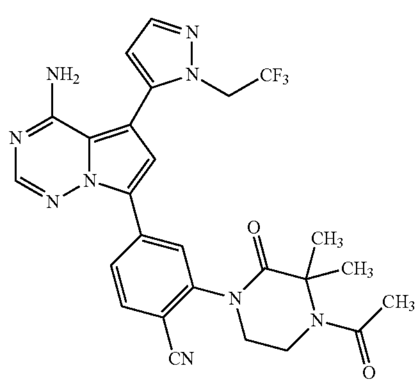 [SMILES: CC(=O)N1CCN(c2cc(-c3cc(-c4ccnn4CC(F)(F)F)c4c(N)ncnn34)ccc2C#N)C(=O)C1(C)C] | 2-(4-acetyl-3,3-dimethyl-2-oxopiperazin-1-yl)-4-{4-amino-5-[1-(2,2,2-trifluoroethyl)-1H-pyrazol-5-yl]pyrrolo[2,1-f][1,2,4]triazin-7-yl}benzonitrile | 553 |

TABLE 40-continued

| Ex. No. | Structure | Name | [M + 1] |
|---|---|---|---|
| 507 | 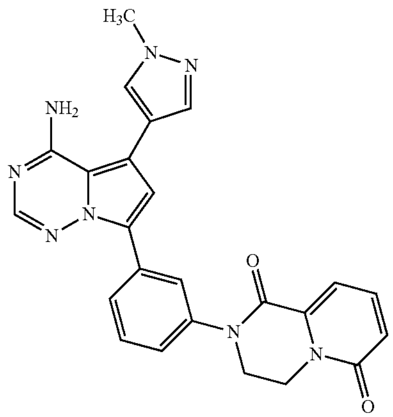 [SMILES: Cn1cc(-c2cc(-c3cccc(N4CCn5c(cccc5=O)C4=O)c3)n3ncnc(N)c23)cn1] | 2-{3-[4-amino-5-(1-methyl-1H-pyrazol-4-yl)pyrrolo[2,1-f][1,2,4]triazin-7-yl]phenyl}-1H,2H,3H,4H,6H-pyrido[1,2-a]piperazine-1,6-dione | 453 |
| 508 | 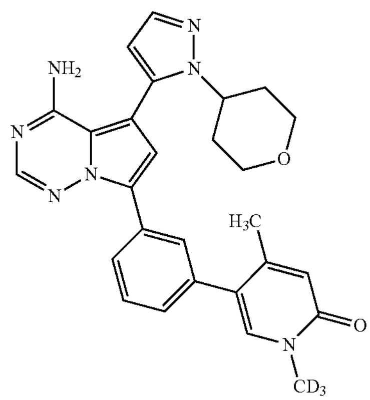 [SMILES: [2H]C([2H])([2H])n1cc(-c2cccc(-c3cc(-c4ccnn4C4CCOCC4)c4c(N)ncnn34)c2)c(C)cc1=O] | 5-(3-{4-amino-5-[1-(oxan-4-yl)-1H-pyrazol-5-yl]pyrrolo[2,1-f][1,2,4]triazin-7-yl}phenyl)-1-($^{2}H_{3}$)methyl-4-methyl-1,2-dihydropyridin-2-one | 486 |
| 509 | 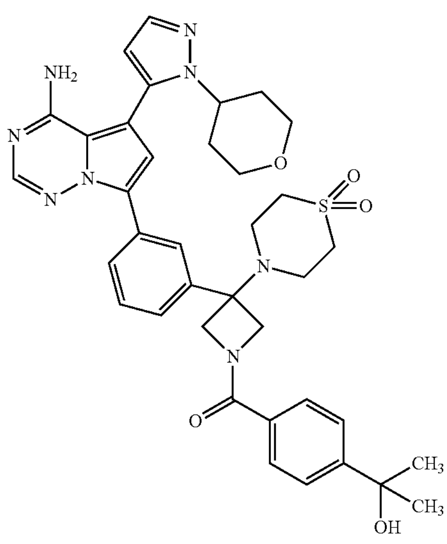 [SMILES: CC(C)(O)c1ccc(C(=O)N2CC(c3cccc(-c4cc(-c5ccnn5C5CCOCC5)c5c(N)ncnn45)c3)(N3CCS(=O)(=O)CC3)C2)cc1] | 4-[3-(3-{4-amino-5-[1-(oxan-4-yl)-1H-pyrazol-5-yl]pyrrolo[2,1-f][1,2,4]triazin-7-yl}phenyl)-1-[4-(2-hydroxypropan-2-yl)benzoyl]azetidin-3-yl]-1$\lambda^{6}$,4-thiomorpholine-1,1-dione | 712 |

TABLE 40-continued

| Ex. No. | Structure | Name | [M + 1] |
|---|---|---|---|
| 510 | 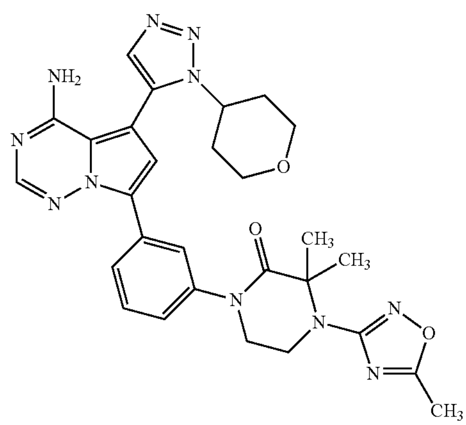 [SMILES: Cc1nc(N2CCN(c3cccc(-c4cc(-c5cnnn5C5CCOCC5)c5c(N)ncnn45)c3)C(=O)C2(C)C)no1] | 1-(3-{4-amino-5-[1-(oxan-4-yl)-1H-1,2,3-triazol-5-yl]pyrrolo[2,1-f][1,2,4]triazin-7-yl}phenyl)-3,3-dimethyl-4-(5-methyl-1,2,4-oxadiazol-3-yl)piperazin-2-one | 571 |
| 511 | 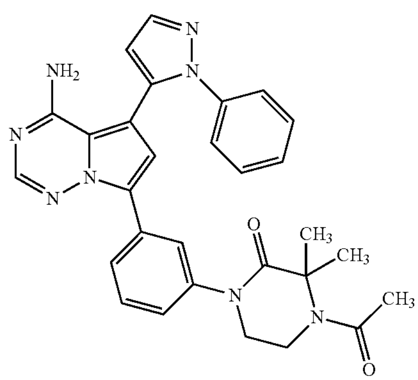 [SMILES: CC(=O)N1CCN(c2cccc(-c3cc(-c4ccnn4-c4ccccc4)c4c(N)ncnn34)c2)C(=O)C1(C)C] | 4-acetyl-1-{3-[4-amino-5-(1-phenyl-1H-pyrazol-5-yl)pyrrolo[2,1-f][1,2,4]triazin-7-yl]phenyl}-3,3-dimethylpiperazin-2-one | 522 |
| 512 | 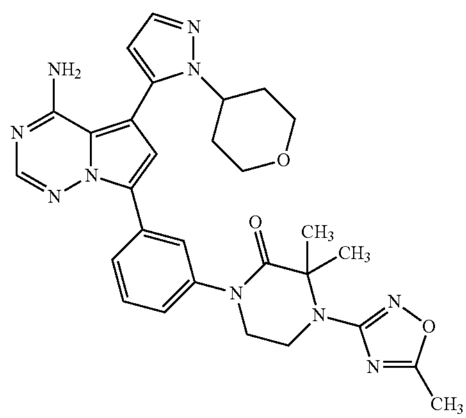 [SMILES: Cc1nc(N2CCN(c3cccc(-c4cc(-c5ccnn5C5CCOCC5)c5c(N)ncnn45)c3)C(=O)C2(C)C)no1] | 1-(3-{4-amino-5-[1-(oxan-4-yl)-1H-pyrazol-5-yl]pyrrolo[2,1-f][1,2,4]triazin-7-yl}phenyl)-3,3-dimethyl-4-(5-methyl-1,2,4-oxadiazol-3-yl)piperazin-2-one | 570 |

TABLE 40-continued
| Ex. No. | Structure | Name | [M + 1] |
|---|---|---|---|
| 513 | 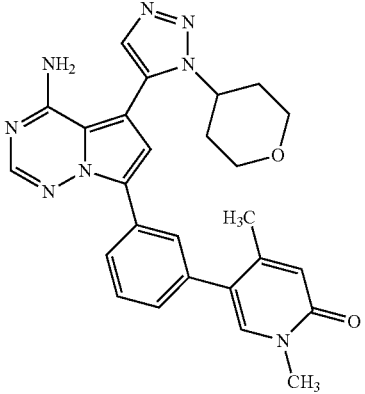 [SMILES: Cc1cc(=O)n(C)cc1-c1cccc(-c2cc(-c3cnnn3C3CCOCC3)c3c(N)ncnn23)c1] | 5-(3-{4-amino-5-[1-(oxan-4-yl)-1H-1,2,3-triazol-5-yl]pyrrolo[2,1-f][1,2,4]triazin-7-yl}phenyl)-1,4-dimethyl-1,2-dihydropyridin-2-one | 484 |
| 514 | 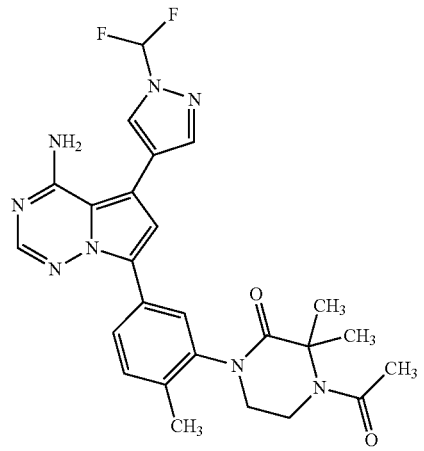 [SMILES: CC(=O)N1CCN(c2cc(-c3cc(-c4cnn(C(F)F)c4)c4c(N)ncnn34)ccc2C)C(=O)C1(C)C] | 4-acetyl-1-(5-{4-amino-5-[1-(difluoromethyl)-1H-pyrazol-4-yl]pyrrolo[2,1-f][1,2,4]triazin-7-yl}-2-methylphenyl)-3,3-dimethylpiperazin-2-one | 509 |
| 515 | 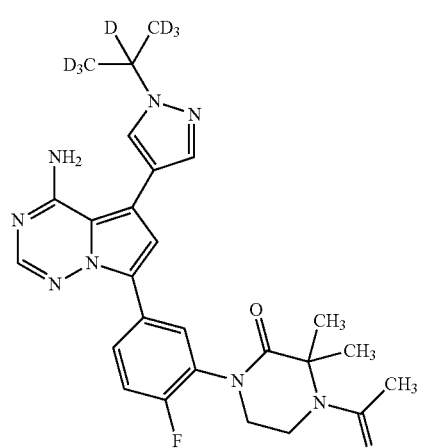 | 4-acetyl-1-[5-(4-amino-5-{1-[($^2$H$_7$)propan-2-yl]-1H-pyrazol-4-yl}pyrrolo[2,1-f][1,2,4]triazin-7-yl)-2-fluorophenyl]-3,3-dimethylpiperazin-2-one | 512 |

TABLE 40-continued

| Ex. No. | Structure | Name | [M + 1] |
|---|---|---|---|
| 516 | 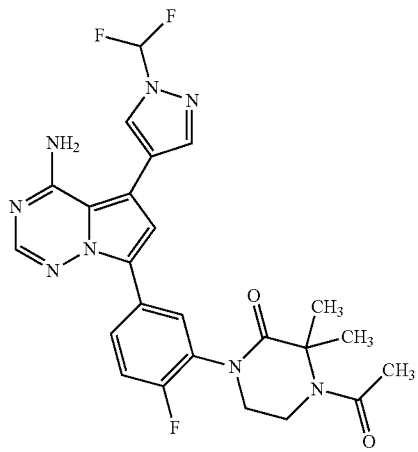 [SMILES: CC(=O)N1CCN(c2cc(-c3cc(-c4cnn(C(F)F)c4)c4c(N)ncnn34)ccc2F)C(=O)C1(C)C] | 4-acetyl-1-(5-{4-amino-5-[1-(difluoromethyl)-1H-pyrazol-4-yl]pyrrolo[2,1-f][1,2,4]triazin-7-yl}-2-fluorophenyl)-3,3-dimethylpiperazin-2-one | 513 |
| 517 | 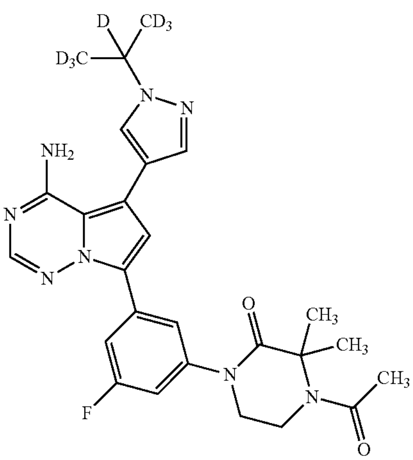 [SMILES: [2H]C([2H])([2H])C([2H])(n1cc(-c2cc(-c3cc(F)cc(N4CCN(C(C)=O)C(C)(C)C4=O)c3)n3ncnc(N)c23)cn1)C([2H])([2H])[2H]] | 4-acetyl-1-[3-(4-amino-5-{1-[($^2$H$_7$)propan-2-yl]-1H-pyrazol-4-yl}pyrrolo[2,1-f][1,2,4]triazin-7-yl)-5-fluorophenyl]-3,3-dimethylpiperazin-2-one | 512 |
| 518 | 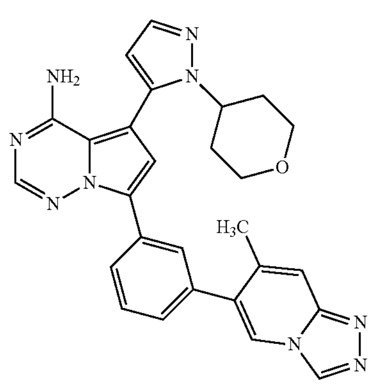 [SMILES: Cc1cc2nncn2cc1-c1cccc(-c2cc(-c3ccnn3C3CCOCC3)c3c(N)ncnn23)c1] | 7-(3-{7-methyl-[1,2,4]triazolo[4,3-a]pyridin-6-yl}phenyl)-5-[1-(oxan-4-yl)-1H-pyrazol-5-yl]pyrrolo[2,1-f][1,2,4]triazin-4-amine | 492 |

TABLE 40-continued

| Ex. No. | Structure | Name | [M + 1] |
|---|---|---|---|
| 519 | 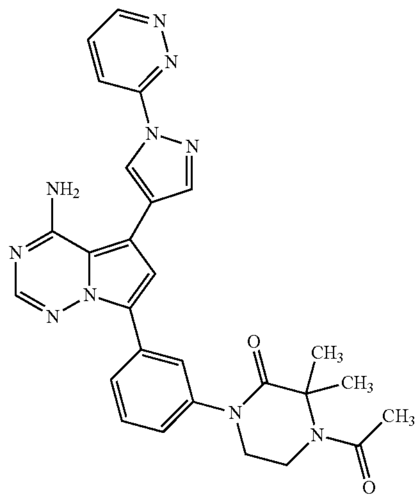 [SMILES: CC(=O)N1CCN(c2cccc(-c3cc(-c4cnn(-c5cccnn5)c4)c4c(N)ncnn34)c2)C(=O)C1(C)C] | 4-acetyl-1-(3-{4-amino-5-[1-(pyridazin-3-yl)-1H-pyrazol-4-yl]pyrrolo[2,1-f][1,2,4]triazin-7-yl}phenyl)-3,3-dimethylpiperazin-2-one | 523 |
| 520 | 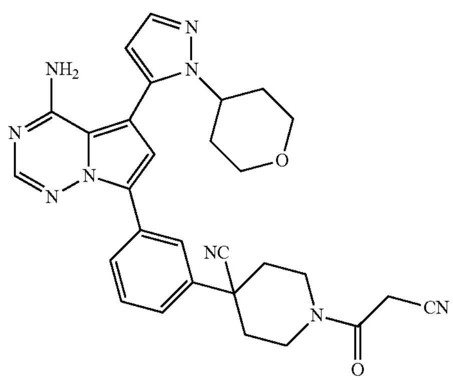 [SMILES: N#CCC(=O)N1CCC(C#N)(c2cccc(-c3cc(-c4ccnn4C4CCOCC4)c4c(N)ncnn34)c2)CC1] | 4-(3-{4-amino-5-[1-(oxan-4-yl)-1H-pyrazol-5-yl]pyrrolo[2,1-f][1,2,4]triazin-7-yl}phenyl)-1-(2-cyanoacetyl)piperidine-4-carbonitrile | 536 |
| 521 | 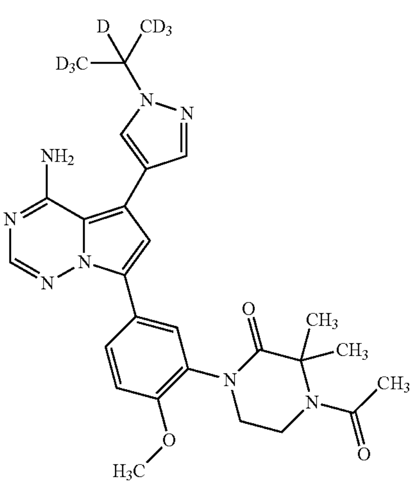 [SMILES: [2H]C([2H])([2H])C([2H])(n1cc(-c2cc(-c3ccc(OC)c(N4CCN(C(C)=O)C(C)(C)C4=O)c3)n3ncnc(N)c23)cn1)C([2H])([2H])[2H]] | 4-acetyl-1-[5-(4-amino-5-{1-[($^2$H$_7$)propan-2-yl]-1H-pyrazol-4-yl}pyrrolo[2,1-f][1,2,4]triazin-7-yl)-2-methoxyphenyl]-3,3-dimethylpiperazin-2-one | 524 |

TABLE 40-continued

| Ex. No. | Structure | Name | [M + 1] |
|---|---|---|---|
| 522 | 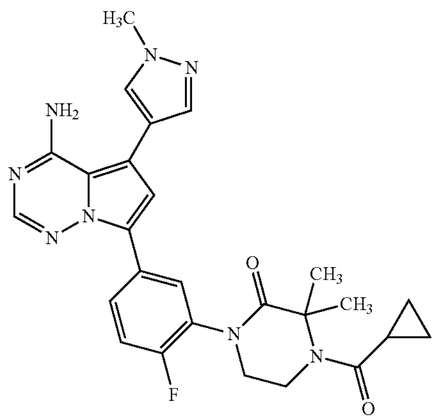 [SMILES: Cn1cc(-c2cc(-c3ccc(F)c(N4CCN(C(=O)C5CC5)C(C)(C)C4=O)c3)n3ncnc(N)c23)cn1] | 1-{5-[4-amino-5-(1-methyl-1H-pyrazol-4-yl)pyrrolo[2,1-f][1,2,4]triazin-7-yl]-2-fluorophenyl}-4-cyclopropanecarbonyl-3,3-dimethylpiperazin-2-one | 503 |
| 523 | 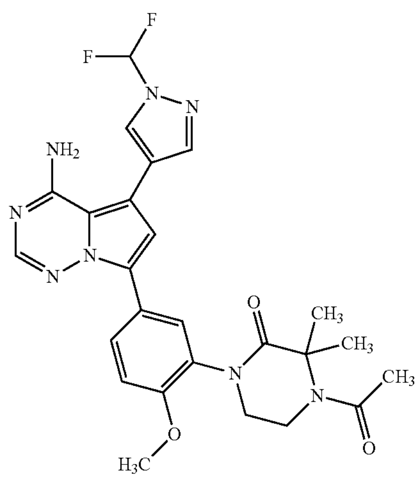 [SMILES: COc1ccc(-c2cc(-c3cnn(C(F)F)c3)c3c(N)ncnn23)cc1N1CCN(C(C)=O)C(C)(C)C1=O] | 4-acetyl-1-(5-{4-amino-5-[1-(difluoromethyl)-1H-pyrazol-4-yl]pyrrolo[2,1-f][1,2,4]triazin-7-yl}-2-methoxyphenyl)-3,3-dimethylpiperazin-2-one | 525 |
| 524 | 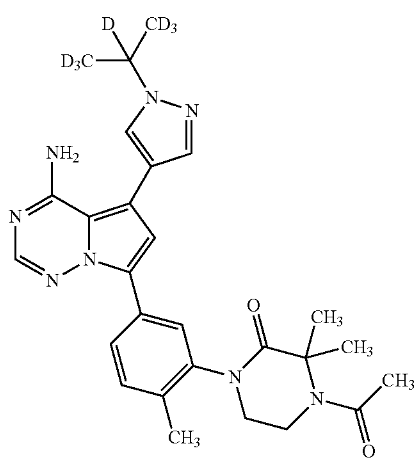 [SMILES: [2H]C([2H])([2H])C([2H])(n1cc(-c2cc(-c3ccc(C)c(N4CCN(C(C)=O)C(C)(C)C4=O)c3)n3ncnc(N)c23)cn1)C([2H])([2H])[2H]] | 4-acetyl-1-[5-(4-amino-5-{1-[($^2$H$_7$)propan-2-yl]-1H-pyrazol-4-yl}pyrrolo[2,1-f][1,2,4]triazin-7-yl)-2-methylphenyl]-3,3-dimethylpiperazin-2-one | 508 |

TABLE 40-continued

| Ex. No. | Structure | Name | [M + 1] |
|---|---|---|---|
| 525 | 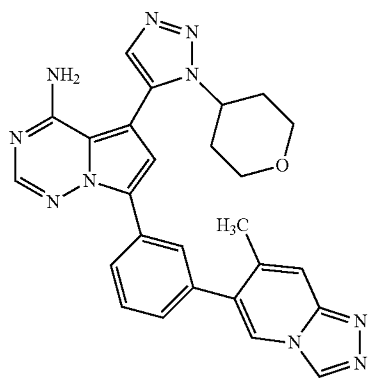 [SMILES: Cc1cc2nncn2cc1-c1cccc(-c2cc(-c3cnnn3C3CCOCC3)c3c(N)ncnn23)c1] | 7-(3-{7-methyl-[1,2,4]triazolo[4,3-a]pyridin-6-yl}phenyl)-5-[1-(oxan-4-yl)-1H-1,2,3-triazol-5-yl]pyrrolo[2,1-f][1,2,4]triazin-4-amine | 493 |
| 526 | 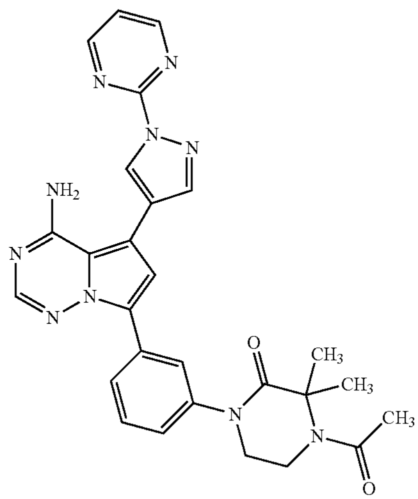 [SMILES: CC(=O)N1CCN(c2cccc(-c3cc(-c4cnn(-c5ncccn5)c4)c4c(N)ncnn34)c2)C(=O)C1(C)C] | 4-acetyl-1-(3-{4-amino-5-[1-(pyrimidin-2-yl)-1H-pyrazol-4-yl]pyrrolo[2,1-f][1,2,4]triazin-7-yl}phenyl)-3,3-dimethylpiperazin-2-one | 523 |
| 527 | 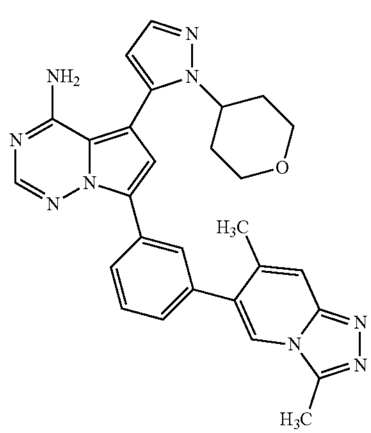 [SMILES: Cc1cc2nnc(C)n2cc1-c1cccc(-c2cc(-c3ccnn3C3CCOCC3)c3c(N)ncnn23)c1] | 7-(3-{3,7-dimethyl-[1,2,4]triazolo[4,3-a]pyridin-6-yl}phenyl)-5-[1-(oxan-4-yl)-1H-pyrazol-5-yl]pyrrolo[2,1-f][1,2,4]triazin-4-amine | 506 |

TABLE 40-continued

| Ex. No. | Structure | Name | [M + 1] |
|---|---|---|---|
| 528 | 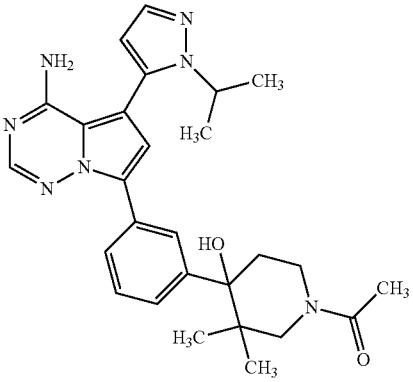 [SMILES: CC(=O)N1CCC(O)(c2cccc(-c3cc(-c4ccnn4C(C)C)c4c(N)ncnn34)c2)C(C)(C)C1] | 1-[4-(3-{4-amino-5-[1-(propan-2-yl)-1H-pyrazol-5-yl]pyrrolo[2,1-f][1,2,4]triazin-7-yl}phenyl)-4-hydroxy-3,3-dimethylpiperidin-1-yl]ethan-1-one | 488 |
| 529 | 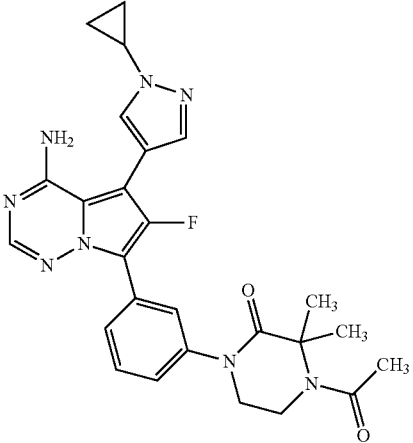 [SMILES: CC(=O)N1CCN(c2cccc(-c3c(F)c(-c4cnn(C5CC5)c4)c4c(N)ncnn34)c2)C(=O)C1(C)C] | 4-acetyl-1-{3-[4-amino-5-(1-cyclopropyl-1H-pyrazol-4-yl)-6-fluoropyrrolo[2,1-f][1,2,4]triazin-7-yl]-phenyl}-3,3-dimethylpiperazin-2-one | 503 |
| 530 | 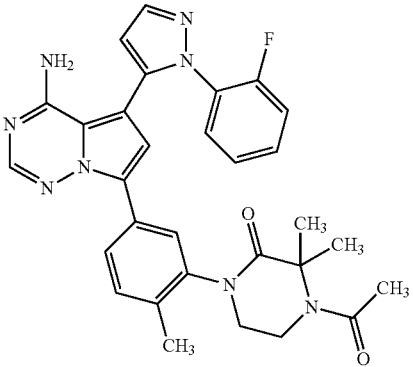 [SMILES: CC(=O)N1CCN(c2cc(-c3cc(-c4ccnn4-c4ccccc4F)c4c(N)ncnn34)ccc2C)C(=O)C1(C)C] | 4-acetyl-1-(5-{4-amino-5-[1-(2-fluorophenyl)-1H-pyrazol-5-yl]pyrrolo[2,1-f][1,2,4]triazin-7-yl}-2-methylphenyl)-3,3-dimethylpiperazin-2-one | 553 |
| 531 | 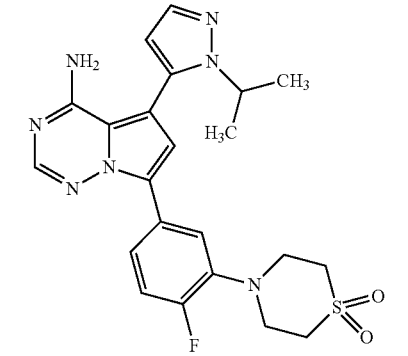 [SMILES: CC(C)n1nccc1-c1cc(-c2ccc(F)c(N3CCS(=O)(=O)CC3)c2)n2ncnc(N)c12] | 4-(5-{4-amino-5-[1-(propan-2-yl)-1H-pyrazol-5-yl]pyrrolo[2,1-f][1,2,4]triazin-7-yl}-2-fluorophenyl)-1$\lambda^6$,4-thiomorpholine-1,1-dione | 470 |

TABLE 40-continued

| Ex. No. | Structure | Name | [M + 1] |
|---|---|---|---|
| 532 | 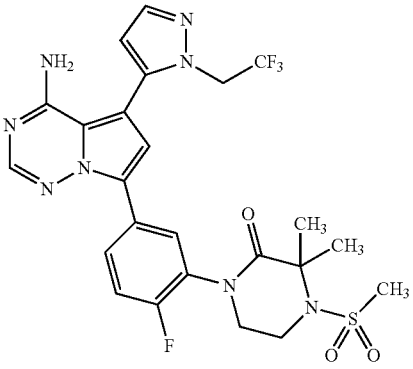 [SMILES: CC1(C)C(=O)N(c2cc(-c3cc(-c4ccnn4CC(F)(F)F)c4c(N)ncnn34)ccc2F)CCN1S(C)(=O)=O] | 1-(5-{4-amino-5-[1-(2,2,2-trifluoroethyl)-1H-pyrazol-5-yl]pyrrolo[2,1-f][1,2,4]triazin-7-yl}-2-fluorophenyl)-4-methanesulfonyl-3,3-dimethylpiperazin-2-one | 581 |
| 533 | 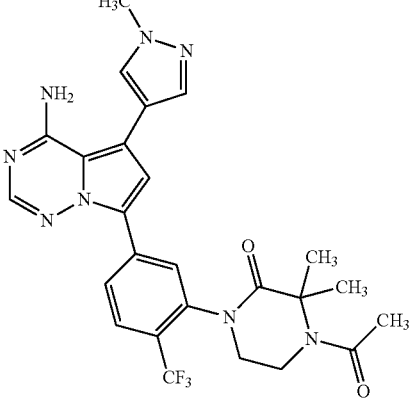 | 4-acetyl-1-{5-[4-amino-5-(1-methyl-1H-pyrazol-4-yl)pyrrolo[2,1-f][1,2,4]triazin-7-yl]-2-(trifluoromethyl)phenyl}-3,3-dimethylpiperazin-2-one | 527 |
| 534 | 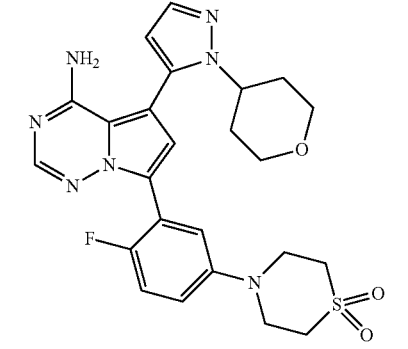 [SMILES: Nc1ncnn2c(-c3cc(N4CCS(=O)(=O)CC4)ccc3F)cc(-c3ccnn3C3CCOCC3)c12] | 4-(3-{4-amino-5-[1-(oxan-4-yl)-1H-pyrazol-5-yl]pyrrolo[2,1-f][1,2,4]triazin-7-yl}-4-fluorophenyl)-1λ$^6$,4-thiomorpholine-1,1-dione | 512 |
| 535 | 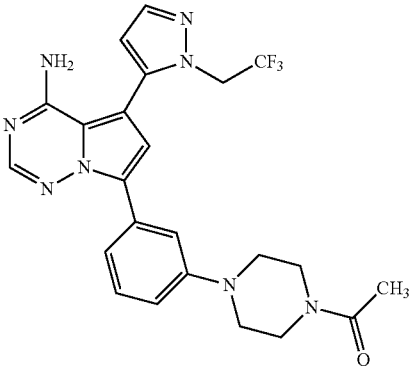 [SMILES: CC(=O)N1CCN(c2cccc(-c3cc(-c4ccnn4CC(F)(F)F)c4c(N)ncnn34)c2)CC1] | 1-[4-(3-{4-amino-5-[1-(2,2,2-trifluoroethyl)-1H-pyrazol-5-yl]pyrrolo[2,1-f][1,2,4]triazin-7-yl}phenyl)piperazin-1-yl]ethan-1-one | 485 |

TABLE 40-continued

| Ex. No. | Structure | Name | [M + 1] |
|---|---|---|---|
| 536 | 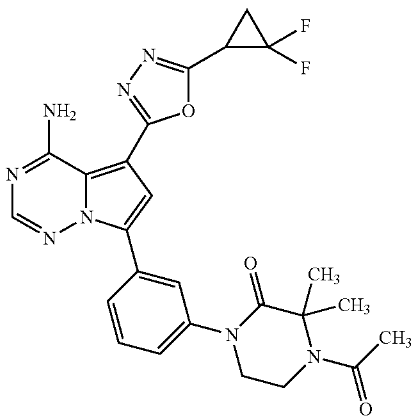 [SMILES: CC(=O)N1CCN(c2cccc(-c3cc(-c4nnc(C5CC5(F)F)o4)c4c(N)ncnn34)c2)C(=O)C1(C)C] | 4-acetyl-1-(3-{4-amino-5-[5-(2,2-difluorocyclopropyl)-1,3,4-oxadiazol-2-yl]pyrrolo[2,1-f][1,2,4]triazin-7-yl}phenyl)-3,3-dimethylpiperazin-2-one | 523 |
| 537 | 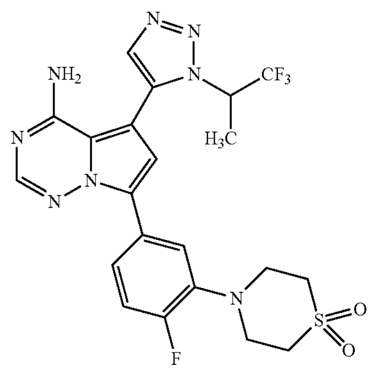 [SMILES: CC(n1nncc1-c1cc(-c2ccc(F)c(N3CCS(=O)(=O)CC3)c2)n2ncnc(N)c12)C(F)(F)F] | 4-(5-{4-amino-5-[1-(propan-2-yl)-1H-1,2,3-triazol-5-yl]pyrrolo[2,1-f][1,2,4]triazin-7-yl}-2-fluorophenyl)-1$\lambda^6$,4-thiomorpholine-1,1-dione | 471 |

Example 538

4-Acetyl-1-(3-(4-amino-5-(1-(1,1,1-trifluoropropan-2-yl)-1H-pyrazol-5-yl)pyrrolo[2,1-f][1,2,4]triazin-7-yl)phenyl)-3,3-dimethylpiperazin-2-one (538)

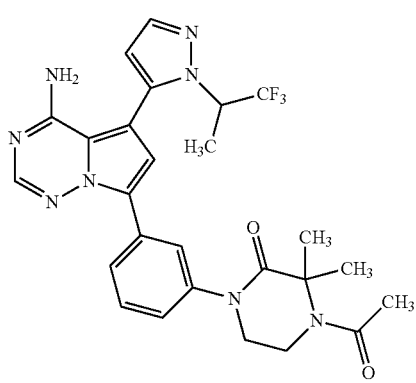

Intermediate 538A: tert-Butyl 2-(1,1,1-trifluoropropan-2-yl)hydrazinecarboxylate

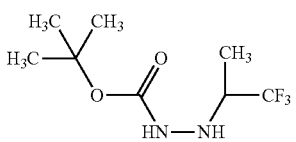

(538A)

A mixture of tert-butyl hydrazinecarboxylate (400 mg, 3.03 mmol), 1,1,1-trifluoropropan-2-one (339 mg, 3.03 mmol) and titanium(IV) isopropoxide (1.774 mL, 6.05 mmol) was stirred at room temperature for 2.5 days. To the yellow cloudy reaction mixture was added dry MeOH (1 mL) followed by NaBH$_4$ (115 mg, 3.03 mmol). After 1 h, the reaction mixture was quenched with 1N NaOH, with a white precipitate forming. The resulting mixture was filtered through CELITE® and the filter cake was washed repeatedly with dichloromethane. The organic phase of the filtrate was separated and concentrated. The residue was chromatographed on an ISCO Companion 40 g silica gel column and eluted with an EtOAc/Hexane gradient (0-100%). The product containing fractions were collected and concentrated to give tert-butyl 2-(1,1,1-trifluoropropan-2-yl) hydrazinecarboxylate (177 mg, 0.78 mmol, 26% yield). Mass spectrum m/z 214 (M-tBu+ACN+H)$^+$. $^1$H NMR (400 MHz, chloroform-d) δ 6.21 (br. s., 1H), 3.95 (br. s., 1H), 3.57-3.41 (m, 1H), 1.49 (s, 9H), 1.30 (d, J=7.0 Hz, 3H).

Intermediate 538B:
(1,1,1-Trifluoropropan-2-yl)hydrazine

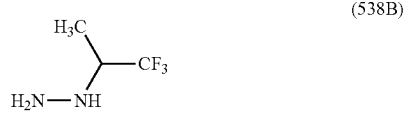

(538B)

A solution of tert-butyl 2-(1,1,1-trifluoropropan-2-yl)hydrazinecarboxylate (177 mg, 0.78 mmol) in TFA (2 mL) was stirred at room temperature for 16 h. The TFA solution was concentrated to give 340 mg yellow oil. Used without further purification.

Intermediate 538C: (E)-4-Acetyl-1-(3-(4-amino-5-(3-(dimethylamino)acryloyl)pyrrolo [2,1-f][1,2,4]triazin-7-yl)phenyl)-3,3-dimethylpiperazin-2-one

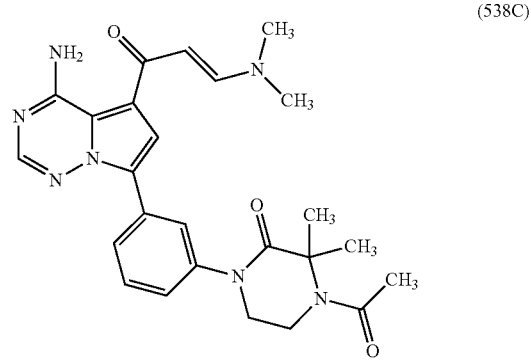 [SMILES: CC(=O)N1CCN(c2cccc(-c3cc(C(=O)/C=C/N(C)C)c4c(N)ncnn34)c2)C(=O)C1(C)C]

(538C)

A mixture of (E)-1-(4-amino-7-bromopyrrolo[2,1-f][1,2,4]triazin-5-yl)-3-(dimethylamino)prop-2-en-1-one (700 mg, 2.257 mmol) (Intermediate N3-A), 4-acetyl-3,3-dimethyl-1-(3-(4,4,5,5-tetramethyl-1,3,2-dioxaborolan-2-yl)phenyl)piperazin-2-one (840 mg, 2.257 mmol) (Intermediate Q53A), PdCl$_2$(dppf)-CH$_2$Cl$_2$ adduct (92 mg, 0.113 mmol) and tripotassium phosphate (2.257 mL, 4.51 mmol) in dioxane (10 mL) in a pressure reaction vial was degassed by vacuum then back filled with nitrogen. The degassing process was repeated twice. The vial was placed in a 90° C. heating block and heated for 3 h. The organic phase of the reaction mixture was separated and concentrated. The residue was triturated with dichloromethane to give a gray solid of (E)-4-acetyl-1-(3-(4-amino-5-(3-(dimethylamino)acryloyl)pyrrolo[2,1-f][1,2,4]triazin-7-yl)phenyl)-3,3-dimethylpiperazin-2-one (940 mg, 1.98 mmol, 88% yield). Mass spectrum m/z 476 (M+H)$^+$. $^1$H NMR (400 MHz, DMSO-d$_6$) δ 10.97 (d, J=4.0 Hz, 1H), 8.07 (d, J=4.2 Hz, 1H), 8.03-7.95 (m, 3H), 7.82 (d, J=12.1 Hz, 1H), 7.76 (s, 1H), 7.52 (t, J=8.0 Hz, 1H), 7.34 (dt, J=7.6, 1.3 Hz, 1H), 6.05 (d, J=12.1 Hz, 1H), 3.87-3.73 (m, 4H), 3.19 (br. s., 3H), 3.00 (br. s., 3H), 2.10 (s, 3H), 1.72 (s, 6H).

Example 538

A suspension of (E)-4-acetyl-1-(3-(4-amino-5-(3-(dimethylamino)acryloyl) pyrrolo[2,1-f][1,2,4]triazin-7-yl)phenyl)-3,3-dimethylpiperazin-2-one (100 mg, 0.210 mmol), (1,1,1-trifluoropropan-2-yl)hydrazine (56.8 mg, 0.252 mmol) and 2 drops of TFA in ethanol (2 mL) was heated at 90° C. for 2 h. The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-85% B over 20 minutes; then a 5-minute hold at 100% B; Flow: 20 mL/min. Fractions containing the desired product were combined and dried via centrifugal evaporation to give 4-acetyl-1-(3-(4-amino-5-(1-(1,1,1-trifluoropropan-2-yl)-1H-pyrazol-5-yl)pyrrolo[2,1-f][1,2,4]triazin-7-yl)phenyl)-3,3-dimethylpiperazin-2-one (83.5 mg, 96% purity, 0.15 mmol, 71% yield). Mass spectrum m/z 541 (M+H)$^+$. $^1$H NMR (500 MHz, DMSO-d$_6$) δ 8.05-7.90 (m, 4H), 7.79 (s, 1H), 7.53 (t, J=7.9 Hz, 1H), 7.32 (d, J=7.7 Hz, 1H), 7.17 (br. s., 1H), 6.59 (s, 1H), 5.10 (br. s., 1H), 3.89-3.72 (m, 5H), 2.51 (br. s., 4H), 2.08 (s, 3H), 1.67 (s, 6H).

Examples 539 and 540

(R)- and (S)-4-Acetyl-1-(3-(4-amino-5-(1-(1,1,1-trifluoropropan-2-yl)-1H-pyrazol-5-yl)pyrrolo[2,1-f][1,2,4]triazin-7-yl)phenyl)-3,3-dimethylpiperazin-2-one

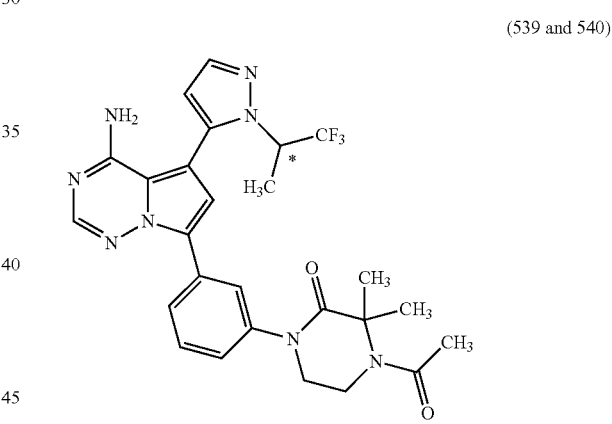

(539 and 540)

Racemic 4-acetyl-1-(3-(4-amino-5-(1-(1,1,1-trifluoropropan-2-yl)-1H-pyrazol-5-yl)pyrrolo[2,1-f][1,2,4]triazin-7-yl)phenyl)-3,3-dimethylpiperazin-2-one (65 mg, 0.12 mmol) (Example 538) was resolved by chiral preparative SFC chromatography to give two peaks. Peak 1 was concentrated to give 15 mg of chiral Example 539. Peak 2 was concentrated to give 16 mg of chiral Example 540. The stereoisomeric purity of each fraction was determined to be greater than 98%. The absolute configuration of the stereocenter was not determined. Examples 539 and 540 had identical mass spectrum and $^1$H NMR with their parent racemic compound Example 538. Preparative Chromatographic Conditions: Instrument: Berger SFC MGII (LVL-L4021 Lab); Column: Chiral OD-H 25×3 cm ID, 5 µm; Flow rate: 85.0 mL/min; Mobile Phase: 80/20 CO$_2$/MeOH; Detector Wavelength: 220 nm; Sample Prep and Injection Volume: 500 µL of 65 mg dissolved in 5 mL MeOH. Analytical Chromatographic Conditions: Instrument: Berger analytical SFC; Column: Chiral OD-H 250×4.6 mm ID, 5 µm; Flow rate: 2.0 mL/min; Mobile Phase: 80/20 CO$_2$/MeOH.

Example 541

3-(4-Amino-5-bromopyrrolo[2,1-f][1,2,4]triazin-7-yl)-N-cyclopropyl-N-(tetrahydro-2H-pyran-4-yl)benzamide

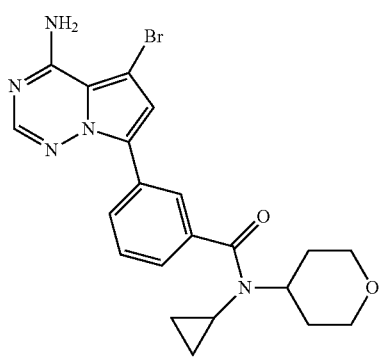
(541)

Intermediate 541A: 3-(4-Aminopyrrolo[2,1-f][1,2,4]triazin-7-yl)benzoic acid

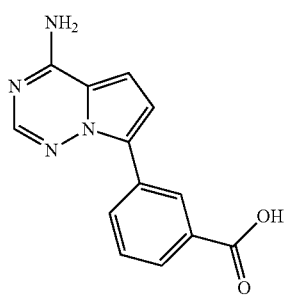
(541A)

To a solution of 7-bromopyrrolo[2,1-f][1,2,4]triazin-4-amine (2.5 g, 11.74 mmol) in dioxane (60 mL) and water (30 mL), were added 3-boronobenzoic acid (2.34 g, 14.08 mmol) and phosphoric acid, potassium salt (8.72 g, 41.1 mmol). The vessel was evacuated, backfilled with $N_2$ and then degassed by bubbling $N_2$ while being sonicated. Tetrakis triphenylphosphine (1.36 g, 1.174 mmol) was added and the degassing process was repeated. The reaction mixture was heated at 90° C. for 10 h, cooled, filtered and concentrated. The pH value of the crude residue was adjusted to 3 with 1N HCl and the precipitate formed was filtered and washed with water and MeOH, then dried under vacuum. The crude product (with small amount of $Ph_3PO$), 3-(4-aminopyrrolo[2,1-f][1,2,4]triazin-7-yl)benzoic acid was used for next step without further purification.

Intermediate 541B: 3-(4-Amino-5-bromopyrrolo[2,1-f][1,2,4]triazin-7-yl)benzoic acid

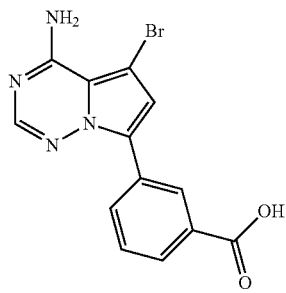
(541B)

To a suspension of 3-(4-aminopyrrolo[2,1-f][1,2,4]triazin-7-yl)benzoic acid (1.43 g, 5.61 mmol) in DMF (5 mL) at 0° C. was added TFA (0.12 mL, 1.573 mmol), followed by NBS (1.0 g, 5.61 mmol) in one portion. After 1 h, the mixture was diluted with water and the precipitate was filtered and the white solid was washed with cold MeOH. The crude product, 3-(4-amino-5-bromopyrrolo[2,1-f][1,2,4]triazin-7-yl)benzoic acid, was dried with air-flow and used as is (1.8 g) in the next step. $M^+=332.97, 334.97$ (1,1 ratio).

Example 541

To a suspension of 3-(4-amino-5-bromopyrrolo[2,1-f][1,2,4]triazin-7-yl)benzoic acid, (1 g, 3.0 mmol) in DMF (50 mL) was added HATU (1.141 g, 3.0 mmol) and DIEA (1.57 mL, 9.01 mmol). After stirring for 5 min, N-cyclopropyltetrahydro-2H-pyran-4-amine (0.424 g, 3.0 mmol) was added and the mixture was heated to 50° C. After 10 min, the mixture became homogenous. After 30 min, the mixture was diluted with water and then extracted with DCM (3×). The combined organic layer was washed with brine (2×), dried over $Na_2SO_4$ and concentrated. The residue was suspended in methanol, and the precipitate was filtered and washed with MeOH. LC/MS showed 3-(4-amino-5-bromopyrrolo[2,1-f][1,2,4] triazin-7-yl)-N-cyclopropyl-N-(tetrahydro-2H-pyran-4-yl)benzamide (1.0 g). LC-MS m/z $(M+H)^+=456.2, 458.2$.

Example 542

1-(4-(3-(4-Amino-5-bromopyrrolo[2,1-f][1,2,4]triazin-7-yl)phenoxy)piperidin-1-yl) ethanone

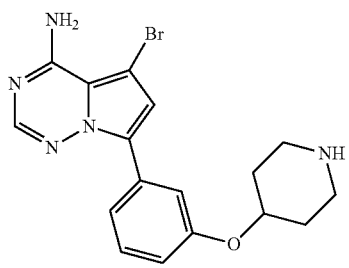
(542)

Intermediate 542A: 7-(3-(Piperidin-4-yloxy)phenyl)pyrrolo[2,1-f][1,2,4]triazin-4-amine

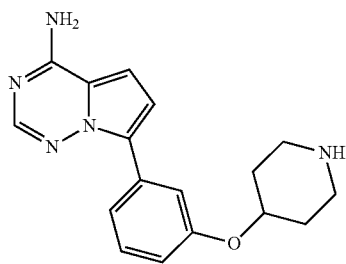

(542A)

To a solution of 4-(3-bromophenoxy)piperidine (361 mg, 1.408 mmol) in dioxane (8 mL) was added 4,4,4',4',5,5,5',5'-octamethyl-2,2'-bi(1,3,2-dioxaborolane) (381 mg, 1.5 mmol), potassium acetate (369 mg, 3.76 mmol), and PdCl$_2$(dppf)-CH$_2$Cl$_2$ adduct (153 mg, 0.188 mmol) under anhydrous conditions in a microwave reaction vessel. The mixture was evacuated, backfilled with N$_2$ and then degassed by bubbling N$_2$ while the flask was immersed in a sonicator and then heated at 120° C. in a microwave instrument for 30 min. The reaction mixture was cooled. Next, water (3 mL), 7-bromopyrrolo[2,1-f][1,2,4]triazin-4-amine (200 mg, 0.939 mmol), Na$_2$CO$_3$ (299 mg, 2.82 mmol) and additional PdCl$_2$(dppf)-CH$_2$Cl$_2$ adduct (153 mg, 0.188 mmol) were added. The degassing procedure was repeated as above by bubbling N$_2$ and the sealed reaction vessel was heated at 120° C. in a microwave for 40 min. The reaction mixture was cooled, filtered, and the solids were washed with water. The filtrate was extracted with ethyl acetate (10 mL×3 times). The organic layers were combined, dried, and concentrated. The crude mixture was dissolved in DMF, and purified by preparative LC method C to obtain 7-(3-(piperidin-4-yloxy)phenyl)pyrrolo[2,1-f][1,2,4]triazin-4-amine (253 mg, 0.818 mmol, 87% yield). LCMS (M+H)$^+$=310.30.

Example 542

To a white suspension of 7-(3-(piperidin-4-yloxy)phenyl)pyrrolo[2,1-f][1,2,4]triazin-4-amine, TFA salt (253 mg, 0.598 mmol) in CH$_2$Cl$_2$ (10 ml) at 0° C. was added TFA (4.60 µl, 0.060 mmol), followed by NBS (117 mg, 0.657 mmol) in one portion. The mixture was worked up as described in the bromination reaction in the synthesis of Example 541 to afford the desired product. The crude mixture could be used without further purification in subsequent functionalizations.

Example 543

1-(4-(3-(4-Amino-5-bromopyrrolo[2,1-f][1,2,4]triazin-7-yl)phenoxy)piperidin-1-yl) ethanone

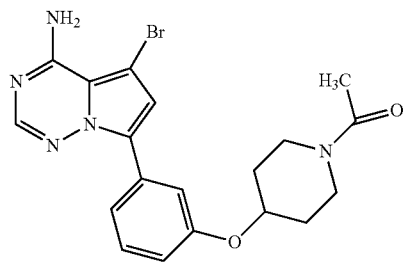

(543)

Intermediate 543A: 7-(3-(Piperidin-4-yloxy)phenyl)pyrrolo[2,1-f][1,2,4]triazin-4-amine

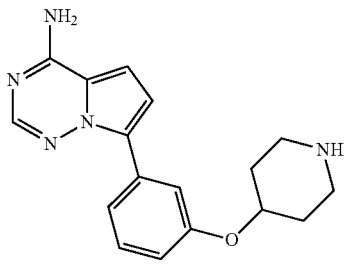

(543A)

To a solution of 4-(3-bromophenoxy)piperidine (361 mg, 1.408 mmol) in dioxane (8 mL) was added 4,4,4',4',5,5,5',5'-octamethyl-2,2'-bi(1,3,2-dioxaborolane) (381 mg, 1.5 mmol), potassium acetate (369 mg, 3.76 mmol), and PdCl$_2$(dppf)-CH$_2$Cl$_2$ adduct (153 mg, 0.188 mmol) under anhydrous conditions in a microwave reaction vessel. The mixture was evacuated, backfilled with N$_2$ and then degassed by bubbling N$_2$ while the flask was immersed in a sonicator and then heated at 120° C. in a microwave instrument for 30 min. The reaction mixture was cooled. Next, water (3 mL), 7-bromopyrrolo[2,1-f][1,2,4]triazin-4-amine (200 mg, 0.939 mmol), Na$_2$CO$_3$ (299 mg, 2.82 mmol) and additional PdCl$_2$(dppf)-CH$_2$Cl$_2$ adduct (153 mg, 0.188 mmol) were added. The degassing procedure was repeated as above by bubbling N$_2$ and the sealed reaction vessel was heated at 120° C. in a microwave for 40 min. The reaction mixture was cooled, filtered, and the solids were washed with water. The filtrate was extracted with ethyl acetate (10 mL×3 times). The organic layers were combined, dried, and concentrated. The crude mixture was dissolved in DMF, and purified by preparative LC method C to obtain 7-(3-(piperidin-4-yloxy)phenyl)pyrrolo[2,1-f][1,2,4]triazin-4-amine (253 mg, 0.818 mmol, 87% yield). LCMS (M+H)$^+$=310.30.

Intermediate 543B: 5-Bromo-7-(3-(piperidin-4-yloxy)phenyl)pyrrolo[2,1-f][1,2,4]triazin-4-amine

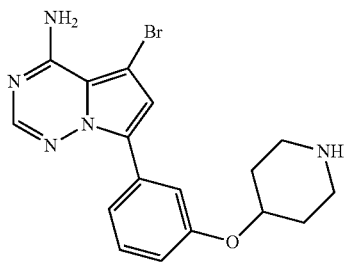

(543B)

To a white suspension of 7-(3-(piperidin-4-yloxy)phenyl) pyrrolo[2,1-f][1,2,4]triazin-4-amine, TFA salt (253 mg, 0.598 mmol) in CH₂Cl₂ (10 ml) at 0° C. was added TFA (4.60 µl, 0.060 mmol), followed by NBS (117 mg, 0.657 mmol) in one portion. The mixture was worked up as described in the bromination reaction in the synthesis of Example 541 to afford the desired product and some bis-brominated impurity. The crude mixture was used without further purification.

Example 543

To a solution of acetic acid (180 mg, 2.99 mmol) in DCM (6 mL) was added HATU (455 mg, 1.196 mmol). After stirring the mixture for 5 min, a solution of crude mixture of Intermediate 543B containing 5-bromo-7-(3-(piperidin-4-yloxy)phenyl) pyrrolo[2,1-f][1,2,4]triazin-4-amine in DMF (2 mL) and DIPEA (104 µl, 0.598 mmol) was added. After stirring for 1 h, the mixture was treated as described in the preparation of Intermediate R3 to obtain 1-(4-(3-(4-amino-5-bromopyrrolo[2,1-f][1,2,4]triazin-7-yl) phenoxy)piperidin-1-yl)ethanone (118 mg, 50% yield in two steps) LCMS (M+H)⁺=430.20, 432.20 (1:1 ratio).

Example 544

5-Bromo-7-(3-((methyl(tetrahydro-2H-pyran-4-yl) amino)methyl)phenyl)pyrrolo[2,1-f][1,2,4]triazin-4-amine

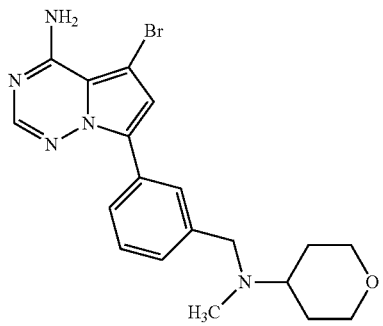

(544)

Intermediate 544A: 7-(3-((Methyl(tetrahydro-2H-pyran-4-yl)amino)methyl)phenyl) pyrrolo[2,1-f][1,2,4]triazin-4-amine

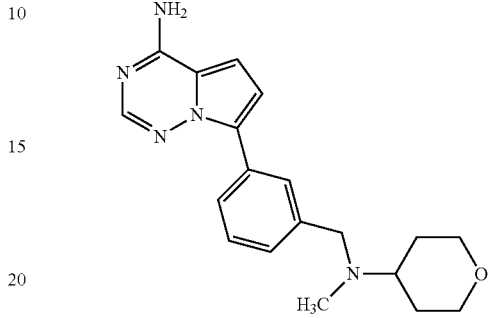

(544A)

To a suspension of N-methyltetrahydro-2H-pyran-4-amine (541 mg, 4.69 mmol) and (3-(bromomethyl)phenyl) boronic acid (756 mg, 3.52 mmol) in acetonitrile (8 mL) was added K₂CO₃ (973 mg, 7.04 mmol) under anhydrous conditions. After stirring at room temperature for 10 h, the reaction mixture was concentrated, phosphoric acid, potassium salt (1.50 g, 2.35 mmol), 7-bromopyrrolo[2,1-f][1,2,4]triazin-4-amine (500 mg, 2.347 mmol), dioxane (8 mL) and water (4 mL) were added. The reaction vessel was evacuated, backfilled with N₂ and then degassed by bubbling N₂ with sonication. Tetrakis triphenylphosphine (271 mg, 0.235 mol) was added and the degassing process was repeated. The resulting reaction mixture was heated at 140° C. in a microwave for 45 min. The reaction complex was cooled, filtered, and washed with water. The filtrate was extracted with ethyl acetate (10 mL×3). The organic layers were combined, dried and concentrated. The crude mixture was dissolved in DMF, and purified by preparative LC Method C to obtain 7-(3-((methyl(tetrahydro-2H-pyran-4-yl)amino)methyl)phenyl) pyrrolo[2,1-f][1,2,4]triazin-4-amine, TFA (636 mg, 60% yield). LC/MS (M+H)=338.30.

Example 544

To a suspension of 7-(3-((methyl(tetrahydro-2H-pyran-4-yl)amino)methyl) phenyl)pyrrolo[2,1-f][1,2,4]triazin-4-amine, TFA (374 mg, 0.828 mmol) in DCM (10 mL) at 0° C. was added TFA (0.1 ml), followed by NBS (147 mg, 0.828 mmol) in one portion. After 20 min, the reaction mixture was concentrated and then purified by ISCO purification (12 g column, 0-5% MeOH/DCM solvent, 20 min gradient) to provide 5-bromo-7-(3-((methyl(tetrahydro-2H-pyran-4-yl)amino)methyl)phenyl)pyrrolo[2,1-f][1,2,4]triazin-4-amine (230 mg, 66.7% yield). (M+H)⁺=416.20, 418.20 (1,1 ratio).

The Examples in Table 41 were prepared according to the general synthesis procedures for Examples 541-543 using NBS or NIS in halogenation step and other appropriate starting materials.

TABLE 41

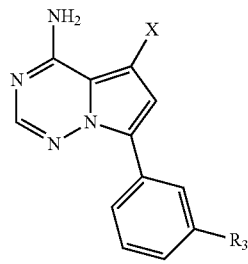

| Ex. No. | X | R₃ | Name |
|---|---|---|---|
| 545 | I | | 3-(4-amino-5-iodopyrrolo[2,1-f][1,2,4]triazin-7-yl)-N-cyclopropyl-N-(tetrahydro-2H-pyran-4-yl)benzamide |
| 546 | Br | | N-(1-acetylpiperidin-4-yl)-3-(4-amino-5-bromopyrrolo[2,1-f][1,2,4]triazin-7-yl)-N-cyclopropylbenzamide |
| 547 | Br | | 3-(4-amino-5-bromopyrrolo[2,1-f][1,2,4]triazin-7-yl)-N-cyclopropyl-N-(1-methylpiperidin-4-yl)benzamide |

Example 548

4-Acetyl-1-(3-(4-amino-5-bromopyrrolo[1,2-f][1,2,4]triazin-7-yl)phenyl)-3,3-dimethylpiperazin-2-one

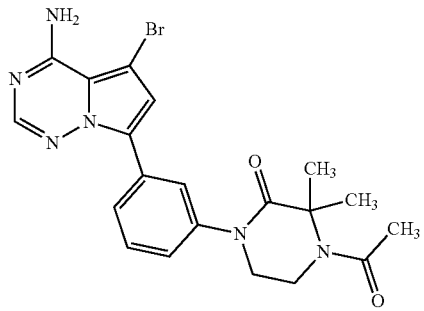

(548)

A solution of 4-acetyl-1-(3-(4-aminopyrrolo[2,1-f][1,2,4]triazin-7-yl)phenyl)-3,3-dimethylpiperazin-2-one (1 g, 2.64 mmol) and NBS (0.400 g, 2.246 mmol) in THF (10 mL) was stirred at room temperature for 2 h. The reaction mixture was diluted with ethyl acetate, washed with 1.5 M K₂HPO₄ aqueous solution, with water, and then concentrated to give 4-acetyl-1-(3-(4-amino-5-bromopyrrolo[2,1-f][1,2,4]triazin-7-yl)phenyl)-3,3-dimethylpiperazin-2-one (1.03 g, 2.25 mmol, 85% yield) as a gray solid. Mass spectrum m/z 457, 459 (M+H)⁺. ¹H NMR (500 MHz, DMSO-d₆) δ 8.03-7.91 (m, 3H), 7.53-7.46 (m, 1H), 7.35-7.29 (m, 1H), 7.29 (s, 1H), 3.85-3.71 (m, 4H), 2.10 (s, 3H), 1.70 (s, 6H).

Example 549

4-Acetyl-1-(3-(4-amino-5-bromopyrrolo[2,1-f][1,2,4]triazin-7-yl)phenyl)-6,6-dimethylpiperazin-2-one (549)

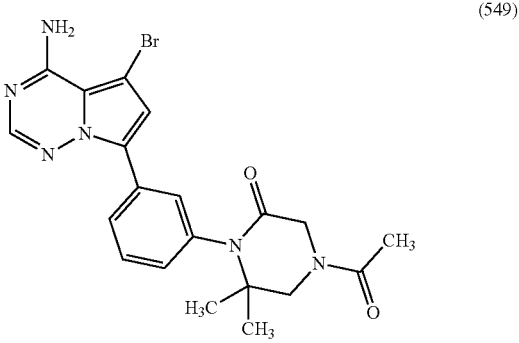 [SMILES: CC(=O)N1CC(=O)N(c2cccc(-c3cc(Br)c4c(N)ncnn34)c2)C(C)(C)C1]

Example 549 was prepared according to the general procedure for the preparation of Example 548. LCMS M+=457.15/459.15. Method G. Retention time 2.48 min.

Example 550

4-Acetyl-1-(3-(4-amino-5-iodopyrrolo[1,2-f][1,2,4]triazin-7-yl)phenyl)-3,3-dimethylpiperazin-2-one

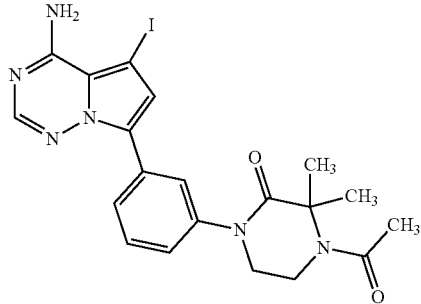

(550)

A solution of 4-acetyl-1-(3-(4-aminopyrrolo[2,1-f][1,2,4]triazin-7-yl)phenyl)-3,3-dimethylpiperazin-2-one (300 mg, 0.793 mmol) and NIS (178 mg, 0.793 mmol) in DMF (10 mL) was stirred under nitrogen at room temperature for 15 h. More NIS (44.6 mg, 0.198 mmol) and TFA (1 drop) were added to the reaction mixture and continued stirring for 2 h to completion. The reaction mixture was diluted with saturated NaHCO₃ (50 mL) and stirred vigorously for 15 min. The precipitated solid was collected by filtration, washed with water, and then ether. The solid was dried in vacuo to give 4-acetyl-1-(3-(4-amino-5-iodopyrrolo[2,1-f][1,2,4]triazin-7-yl)phenyl)-3,3-dimethylpiperazin-2-one (350 mg, 0.694 mmol, 88% yield) as a light brown solid. Mass spectrum m/z 505.0 (M+H)+. ¹H NMR (500 MHz, DMSO-d₆) δ 8.01-7.96 (m, 2H), 7.93 (s, 1H), 7.50 (t, J=7.9 Hz, 1H), 7.37-7.31 (m, 2H), 3.84-3.73 (m, 4H), 2.10 (s, 3H), 1.70 (s, 6H).

Example 551

4-Acetyl-1-(5-(4-amino-5-iodopyrrolo[2,1-f][1,2,4]triazin-7-yl)-2-fluorophenyl)-3,3-dimethylpiperazin-2-one

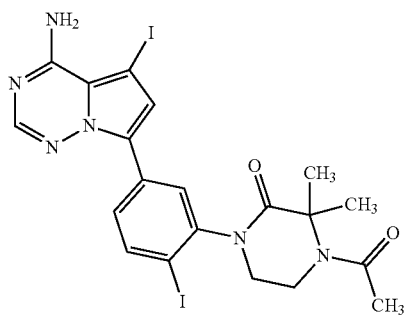

(551)

Intermediate 551A: 4-Acetyl-1-(2-fluoro-5-(4,4,5,5-tetramethyl-1,3,2-dioxaborolan-2-yl)phenyl)-3,3-dimethylpiperazin-2-one

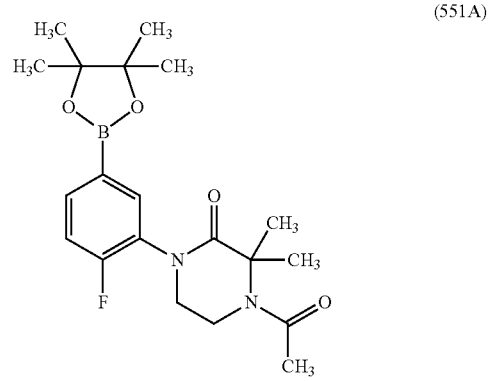 [SMILES: CC(=O)N1CCN(c2cc(B3OC(C)(C)C(C)(C)O3)ccc2F)C(=O)C1(C)C]

(551A)

A mixture of 4-acetyl-1-(5-bromo-2-fluorophenyl)-3,3-dimethylpiperazin-2-one (1.7 g, 3.47 mmol, Intermediate Q53F4), potassium acetate (0.85 g, 8.67 mmol), BISPIN (1.2 g, 4.85 mmol), and 1,1'-bis(diphenylphosphino)ferrocene-palladium(II)dichloride dichloromethane complex (0.28 g, 0.347 mmol) was degassed. Dioxane (29 mL) was added to the mixture and the vessel flushed with nitrogen. The mixture was stirred at 100° C. for 3.5 h and filtered through a bed of CELITE®, washing with EtOAc. The filtrate were adsorbed unto silica gel and purified by flash chromatography using a 40 g ISCO silica gel cartridge eluted with 30-85% Teac/hexane to give 4-acetyl-1-(2-fluoro-5-(4,4,5,5-tetramethyl-1,3,2-dioxaborolan-2-yl)phenyl)-3,3-dimethylpiperazin-2-one as (1.0 g, 75%) as a pale brown solid. LC-MS: m/z=391.1, (M+H)+. ¹H NMR (400 MHz, DMSO-d₆) δ 7.70-7.63 (m, 2H), 7.32 (did, J=10.5, 8.5 Hz, 1H), 3.78-3.65 (m, 4H), 2.08 (s, 3H), 1.68 (s, 6H), 1.30 (s, 12H).

Intermediate 551B: 4-Acetyl-1-(5-(4-aminopyrrolo[2,1-f][1,2,4]triazin-7-yl)-2-fluorophenyl)-3,3-dimethylpiperazin-2-one

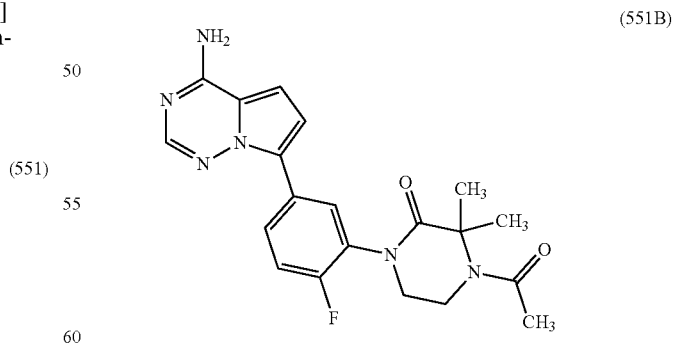

(551B)

A mixture of 7-bromopyrrolo[2,1-f][1,2,4]triazin-4-amine (100 mg, 0.469 mmol), 4-acetyl-1-(2-fluoro-5-(4,4,5,5-tetramethyl-1,3,2-dioxaborolan-2-yl)phenyl)-3,3-dimethylpiperazin-2-one (220 mg, 0.56 mmol), 2 M potassium phosphate tribasic (2.3 mL, 4.69 mmol) and DMF (10 mL) was placed in a 20 mL pressure reaction vial and purged of air by bubbling nitrogen through the mixture for 5 min. 1,1'-bis(diphenylphosphino)ferrocene-palladium(ii)dichloride dichloromethane complex (38 mg, 0.047 mmol) was added to the mixture, the vial flushed with nitrogen and capped and the mixture stirred at 100° C. for 15 min. The mixture was cooled to room temperature, diluted with EtOAc (50 mL) and washed with saturated NaHCO₃ (20 mL), water, (20 mL) and brine (20 mL), dried (Na₂SO₄) and concentrated under reduced pressure to give the crude product. The crude product was absorbed unto silica and purified by flash chromatography using a 24 g ISCO silica gel cartridge by solid loading method and eluted with 0-10% MeOH/DCM to give 4-acetyl-1-(5-(4-aminopyrrolo[2,1-f][1,2,4]triazin-7-yl)-2-fluorophenyl)-3,3-dimethylpiperazin-2-one (110 mg, 59% yield). LC-MS: m/z=397.1, (M+H)⁺. ¹H NMR (400 MHz, DMSO-d₆) δ 8.14 (ddd, J=8.7, 4.8, 2.3 Hz, 1H), 8.06 (dd, J=7.4, 2.3 Hz, 1H), 7.94 (s, 1H), 7.78 (d, J=5.7 Hz, 2H), 7.39 (dd, J=9.9, 8.8 Hz, 1H), 7.07 (d, J=4.6 Hz, 1H), 7.01 (d, J=4.4 Hz, 1H), 3.77 (d, J=2.0 Hz, 4H), 2.10 (s, 3H), 1.70 (s, 6H).

Example 551

A solution of 4-acetyl-1-(5-(4-aminopyrrolo[2,1-f][1,2,4]triazin-7-yl)-2-fluorophenyl)-3,3-dimethylpiperazin-2-one (105 mg, 0.27 mmol) in anhydrous DMF (6 mL) was treated with N-iodosuccinimide (65.6 mg, 0.29 mmol) and the mixture stirred at room temperature in the dark for 15 h. More N-iodosuccinimide (8.94 mg, 0.040 mmol) and TFA (0.020 mL, 0.265 mmol) were added to the mixture and the reaction continued at room temperature for 7 h. The mixture was diluted with water (30 mL), stirred for 5 min and filtered to collect the product which was dried in vacuo to give 4-acetyl-1-(5-(4-amino-5-iodopyrrolo[2,1-f][1,2,4]triazin-7-yl)-2-fluorophenyl)-3,3-dimethylpiperazin-2-one (120 mg, 0.230 mmol, 87% yield). LC-MS: m/z=523.1, (M+H)⁺.

The Examples in Table 42 were prepared according to the general synthesis procedures for Examples 548-551 using NBS or NIS in halogenation step and other appropriate starting materials.

TABLE 42

| Ex. No. | Structure | Name | M + H |
|---|---|---|---|
| 552 | 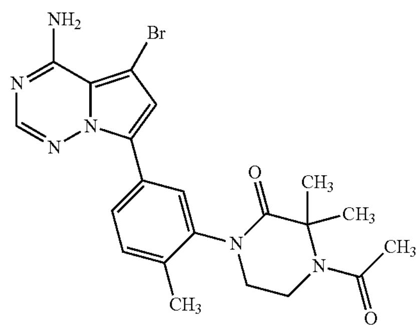 | 4-acetyl-1-(5-{4-amino-5-bromopyrrolo[2,1-f][1,2,4]triazin-7-yl}-2-methylphenyl)-3,3-dimethylpiperazin-2-one | 471 473 |
| 553 | 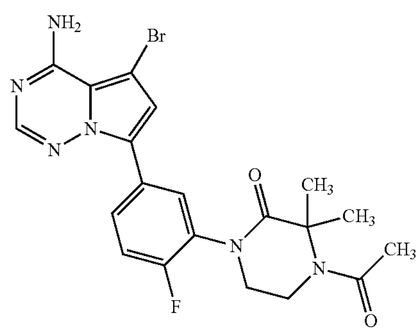 [SMILES: CC(=O)N1CCN(c2cc(-c3cc(Br)c4c(N)ncnn34)ccc2F)C(=O)C1(C)C] | 4-acetyl-1-(5-{4-amino-5-bromopyrrolo[2,1-f][1,2,4]triazin-7-yl}-2-fluorophenyl)-3,3-dimethylpiperazin-2-one | 475 477 |
| 554 | 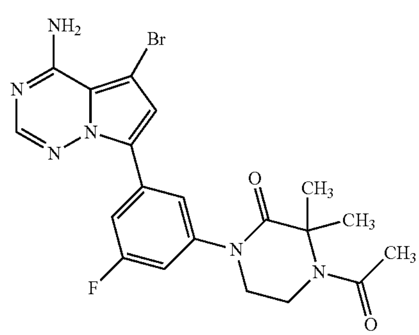 [SMILES: CC(=O)N1CCN(c2cc(F)cc(-c3cc(Br)c4c(N)ncnn34)c2)C(=O)C1(C)C] | 4-acetyl-1-(3-{4-amino-5-bromopyrrolo[2,1-f][1,2,4]triazin-7-yl}-5-fluorophenyl)-3,3-dimethylpiperazin-2-one | 475 477 |

TABLE 42-continued

| Ex. No. | Structure | Name | M + H |
|---|---|---|---|
| 555 | 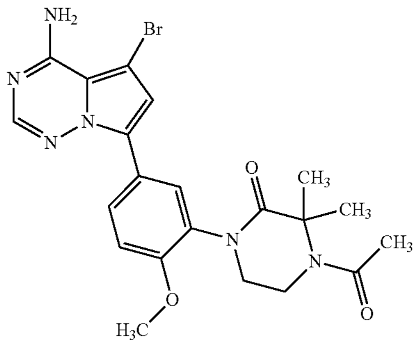 [SMILES: COc1ccc(-c2cc(Br)c3c(N)ncnn23)cc1N1CCN(C(C)=O)C(C)(C)C1=O] | 4-acetyl-1-(5-{4-amino-5-bromopyrrolo[2,1-f][1,2,4]triazin-7-yl}-2-methoxyphenyl)-3,3-dimethylpiperazin-2-one | 487 489 |
| 556 | 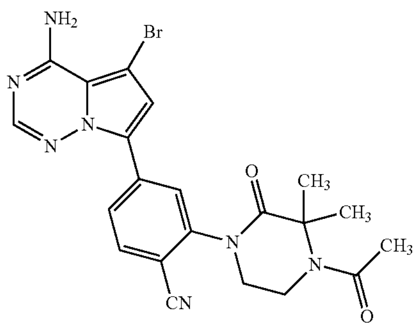 [SMILES: CC(=O)N1CCN(c2cc(-c3cc(Br)c4c(N)ncnn34)ccc2C#N)C(=O)C1(C)C] | 2-(4-acetyl-3,3-dimethyl-2-oxopiperazin-1-yl)-4-{4-amino-5-bromopyrrolo[2,1-f][1,2,4]triazin-7-yl}benzonitrile | 482 484 |

Example 557

7-(3-(4-Acetyl-3,3-dimethyl-2-oxopiperazin-1-yl)-4-fluorophenyl)-4-aminopyrrolo[2,1-f][1,2,4]triazine-5-carbonitrile

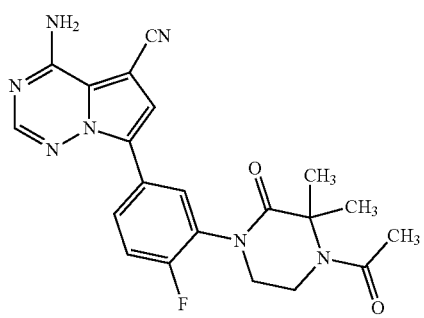

(557)

A mixture of 4-acetyl-1-(5-(4-amino-5-iodopyrrolo[2,1-f][1,2,4]triazin-7-yl)-2-fluorophenyl)-3,3-dimethylpiperazin-2-one (20 mg, 0.038 mmol, Example 551), copper(I) cyanide (34 mg, 0.38 mmol) and pyridine was placed in a 5-mL BIOTAGE® microwave pressure vial, the vial flushed with nitrogen, capped and heated at 150° C. for 30 min. The cooled mixture was partitioned between DCM (25 mL) and water (15 mL). The organic phase was washed with water and concentrated under reduced pressure. The residue was dissolved in DMF (2 mL) and submitted for HPLC purification: The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-70% B over 20 minutes, then a 5-minute hold at 100% B; Flow: 20 mL/min. Fractions containing the desired product were combined and dried via centrifugal evaporation to give 7-(3-(4-acetyl-3,3-dimethyl-2-oxopiperazin-1-yl)-4-fluorophenyl)-4-aminopyrrolo[2,1-f][1,2,4]triazine-5-carbonitrile (7 mg, 43%). LC-MS: m/z=422.2, (M+H)⁺. $^1$H NMR (500 MHz, DMSO-d$_6$) δ 8.18 (s, 1H), 8.12-8.01 (m, 2H), 7.67 (s, 1H), 7.44 (t, J=9.3 Hz, 1H), 3.76 (s, 4H), 2.09 (s, 3H), 1.69 (s, 6H).

Example 558

7-(3-(4-Acetyl-3,3-dimethyl-2-oxopiperazin-1-yl)phenyl)-4-aminopyrrolo[2,1-f][1,2,4]triazine-5-carbonitrile

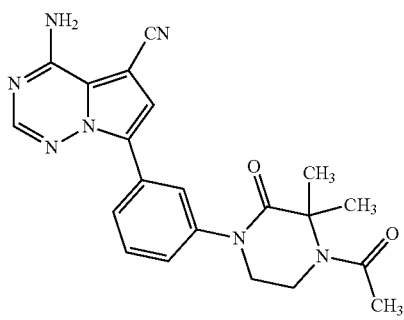

(558)

A mixture of 4-acetyl-1-(3-(4-amino-5-iodopyrrolo[2,1-f] [1,2,4]triazin-7-yl) phenyl)-3,3-dimethylpiperazin-2-one (30 mg, 0.059 mmol, Example 550), copper(I) cyanide (53 mg, 0.60 mmol) and anhydrous pyridine (0.6 mL) was placed in a 5-mL conical microwave vial, the vial flushed with nitrogen, capped and the mixture stirred at 120° C. in an oil bath. After 3 h, the reaction mixture was concentrated under reduced pressure and the residue was partitioned between DCM (10 mL), DMF (3 mL) and 1 M HCl (10 mL). The organic phase was separated and concentrated under reduced pressure and the residue submitted for preparative HPLC separation. The crude material was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 5-100% B over 25 minutes, then a 5-minute hold at 100% B; Flow: 20 mL/min. Fractions containing the desired product were combined and dried via centrifugal evaporation to give 7-(3-(4-acetyl-3,3-dimethyl-2-oxopiperazin-1-yl) phenyl)-4-aminopyrrolo[2,1-f][1,2,4]triazine-5-carbonitrile (8 mg, 33%). LC-MS: m/z=404.3, (M+H)$^+$. $^1$H NMR (500 MHz, DMSO-d$_6$) δ 8.17 (s, 1H), 7.99-7.87 (m, 2H), 7.66 (s, 1H), 7.53 (t, J=7.9 Hz, 1H), 7.37 (d, J=8.1 Hz, 1H), 3.80 (br. s., 2H), 3.74 (br. s., 2H), 3.49 (d, J=5.4 Hz, 2H), 2.08 (s, 3H), 1.69 (s, 6H).

The Examples in Table 43 were prepared according to the general synthesis procedures for Examples 557-558 using other exemplified chemistry with appropriate starting materials.

TABLE 43

| Ex. No. | Structure | Name | M + H |
|---|---|---|---|
| 559 | 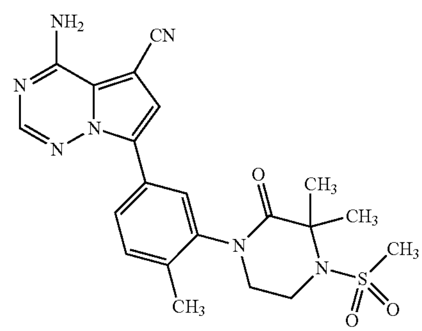 [SMILES: Cc1ccc(-c2cc(C#N)c3c(N)ncnn23)cc1N1CCN(S(C)(=O)=O)C(C)(C)C1=O] | 4-amino-7-[3-(4-methanesulfonyl-3,3-dimethyl-2-oxopiperazin-1-yl)-4-methylphenyl]pyrrolo[2,1-f][1,2,4]triazine-5-carbonitrile | 455 |
| 560 | 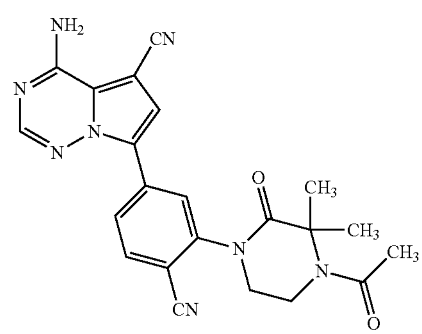 [SMILES: CC(=O)N1CCN(c2cc(-c3cc(C#N)c4c(N)ncnn34)ccc2C#N)C(=O)C1(C)C] | 7-[3-(4-acetyl-3,3-dimethyl-2-oxopiperazin-1-yl)-4-cyanophenyl]-4-aminopyrrolo[2,1-f][1,2,4]triazine-5-carbonitrile | 429 |
| 561 | 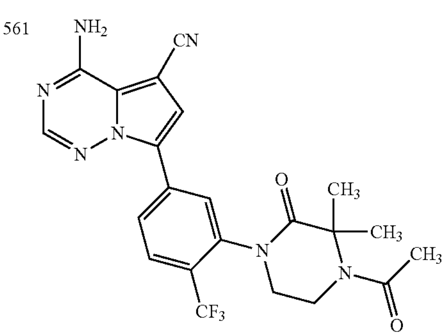 | 7-[3-(4-acetyl-3,3-dimethyl-2-oxopiperazin-1-yl)-4-(trifluoromethyl)phenyl]-4-aminopyrrolo[2,1-f][1,2,4]triazine-5-carbonitrile | 472 |

TABLE 43-continued

| Ex. No. | Structure | Name | M + H |
|---|---|---|---|
| 562 | 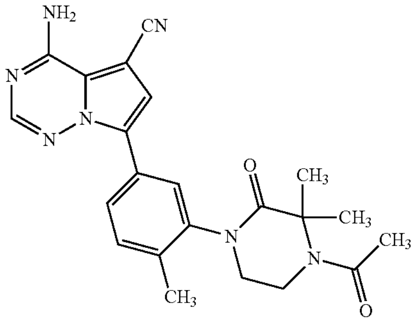 [SMILES: CC(=O)N1CCN(c2cc(-c3cc(C#N)c4c(N)ncnn34)ccc2C)C(=O)C1(C)C] | 7-[3-(4-acetyl-3,3-dimethyl-2-oxopiperazin-1-yl)-4-methylphenyl]-4-aminopyrrolo[2,1-f][1,2,4]triazine-5-carbonitrile | 418 |
| 563 | 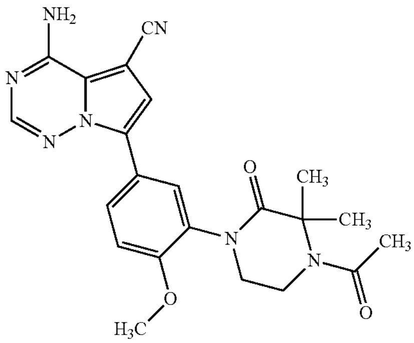 [SMILES: COc1ccc(-c2cc(C#N)c3c(N)ncnn23)cc1N1CCN(C(C)=O)C(C)(C)C1=O] | 7-[3-(4-acetyl-3,3-dimethyl-2-oxopiperazin-1-yl)-4-methoxyphenyl]-4-aminopyrrolo[2,1-f][1,2,4]triazine-5-carbonitrile | 434 |

Example 564

4-Acetyl-1-(3-(4-amino-5-(trifluoromethyl)pyrrolo[2,1-f][1,2,4]triazin-7-yl)phenyl)-3,3-dimethylpiperazin-2-one

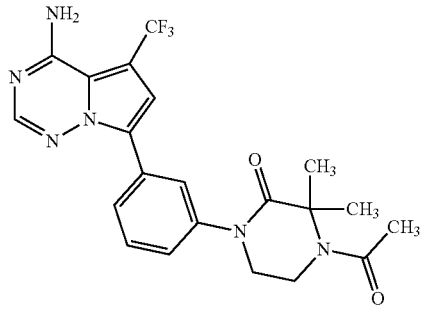

(564)

A mixture of copper(I) iodide (27 mg, 0.142 mmol) and di-tert-butyl (7-(3-(4-acetyl-3,3-dimethyl-2-oxopiperazin-1-yl)phenyl)-5-iodopyrrolo[2,1-f][1,2,4]triazin-4-yl) biscarbamate (100 mg, 0.142 mmol) (Intermediate M33) in a capped pressure reaction vial was degassed by vacuum then filled in with nitrogen, repeating twice more. DMF (1 mL) and HMPA (0.1 mL) were added and the degassing procedure repeated again 3 times. Methyl 2,2-difluoro-2-(fluorosulfonyl)acetate (136 mg, 0.710 mmol) was added and the reaction mixture was heated at 80° C. for 2 days. The reaction mixture was diluted with ethyl acetate, washed with saturated NH$_4$Cl once, 1.5 M NaHPO$_4$ once, water once, then concentrated. The crude material was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 25 minutes, then a 5-minute hold at 100% B; Flow: 20 mL/min. Fractions containing the desired product were combined and dried via centrifugal evaporation to give 4-acetyl-1-(3-(4-amino-5-(trifluoromethyl)pyrrolo[2,1-f][1,2,4]triazin-7-yl)phenyl)-3,3-dimethylpiperazin-2-one (7.7 mg, 95% purity, 0.016 mg, 12% yield). Mass spectrum m/z 447.1 (M+H)$^+$. $^1$H NMR (500 MHz, DMSO-d$_6$) δ 8.16 (s, 1H), 8.02 (d, J=8.1 Hz, 1H), 7.96 (s, 1H), 7.58-7.50 (m, 2H), 7.37 (d, J=7.7 Hz, 1H), 3.85-3.73 (m, 4H), 2.10 (s, 3H), 1.70 (s, 6H).

Example 565

2-(4-Acetyl-3,3-dimethyl-2-oxopiperazin-1-yl)-4-(4-amino-5-(trifluoromethyl)pyrrolo[1,2-f][1,2,4]triazin-7-yl)benzonitrile

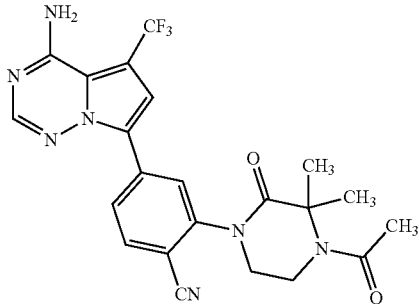

(565)

A mixture of 7-bromo-5-(trifluoromethyl)pyrrolo[2,1-f][1,2,4]triazin-4-amine (20 mg, 0.071 mmol, intermediate M2), 2-(4-acetyl-3,3-dimethyl-2-oxopiperazin-1-yl)-4-(4,4,5,5-tetramethyl-1,3,2-dioxaborolan-2-yl)benzonitrile (synthesized from Intermediate Q53CN4 according to the preparation procedure of Intermediate Q53A), and 1,1'-bis(diphenylphosphino)ferrocene-palladium(II)dichloride dichloromethane complex (8.72 mg, 10.67 µmol) in a 10 mL microwave vial was degassed, then DMF (890 µl) and sodium carbonate, 2M aqueous (89 µl, 0.178 mmol) were added. It was degassed for additional 2 min, flushed with nitrogen, and stirred at 90° C. for 2 hrs, then heating stopped.

It was filtered and purified by prep HPLC. The title compound (18.3 mg) was obtained in 55% yield. LCMS M+H=420.0. $^1$H NMR (500 MHz, DMSO-$d_6$) δ 8.43 (d, J=8.4 Hz, 1H), 8.25 (s, 1H), 8.22 (s, 1H), 8.01 (d, J=8.4 Hz, 1H), 7.79 (s, 1H), 3.82 (d, J=3.0 Hz, 4H), 2.11 (s, 3H), 1.72 (s, 6H).

The Examples in Table 44 were prepared according to the general synthesis procedures for Examples 564-565 using other exemplified chemistry with appropriate starting materials.

TABLE 44

| Ex. No. | Structure | Name | M + H |
|---|---|---|---|
| 566 | 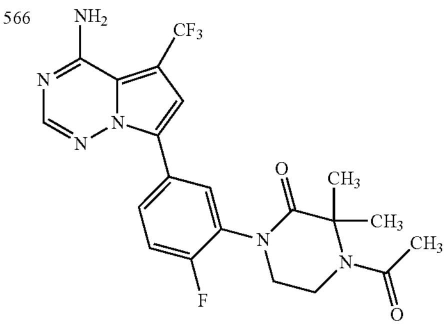 | 4-acetyl-1-{5-[4-amino-5-(trifluoromethyl)pyrrolo[2,1-f][1,2,4]triazin-7-yl]-2-fluorophenyl}-3,3-dimethylpiperazin-2-one | 465 |
| 567 | 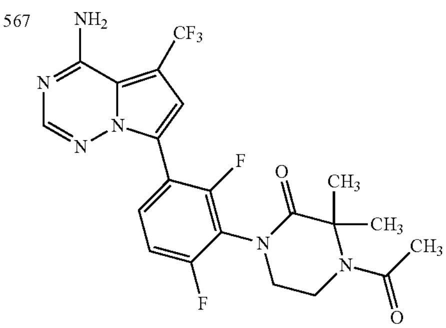 | 4-acetyl-1-{3-[4-amino-5-(trifluoromethyl)pyrrolo[2,1-f][1,2,4]triazin-7-yl]-2,6-difluorophenyl}-3,3-dimethylpiperazin-2-one | 483 |
| 568 | 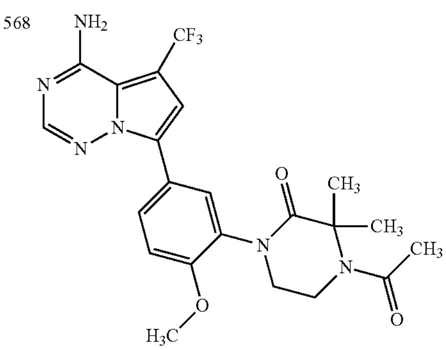 | 4-acetyl-1-{5-[4-amino-5-(trifluoromethyl)pyrrolo[2,1-f][1,2,4]triazin-7-yl]-2-methoxyphenyl}-3,3-dimethylpiperazin-2-one | 477 |
| 569 | 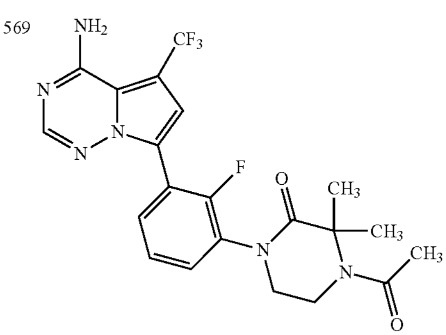 | 4-acetyl-1-{3-[4-amino-5-(trifluoromethyl)pyrrolo[2,1-f][1,2,4]triazin-7-yl]-2-fluorophenyl}-3,3-dimethylpiperazin-2-one | 465 |

TABLE 44-continued

| Ex. No. | Structure | Name | M + H |
|---|---|---|---|
| 570 | 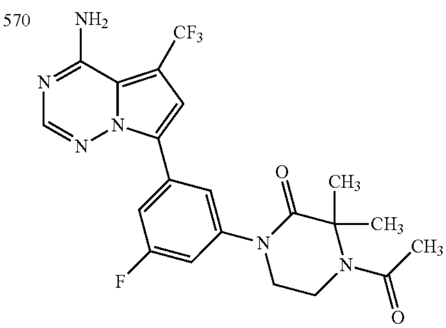 | 4-acetyl-1-{3-[4-amino-5-(trifluoromethyl)pyrrolo[2,1-f][1,2,4]triazin-7-yl]-5-fluorophenyl}-3,3-dimethylpiperazin-2-one | 465 |
| 571 | 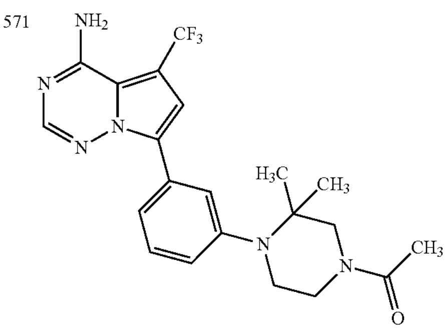 | 1-(4-{3-[4-amino-5-(trifluoromethyl)pyrrolo[2,1-f][1,2,4]triazin-7-yl]phenyl}-3,3-dimethylpiperazin-1-yl)ethan-1-one | 433 |
| 572 | 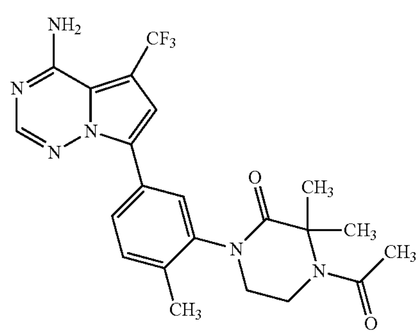 | 4-acetyl-1-{5-[4-amino-5-(trifluoromethyl)pyrrolo[2,1-f][1,2,4]triazin-7-yl]-2-methylphenyl}-3,3-dimethylpiperazin-2-one | 461 |
| 573 | 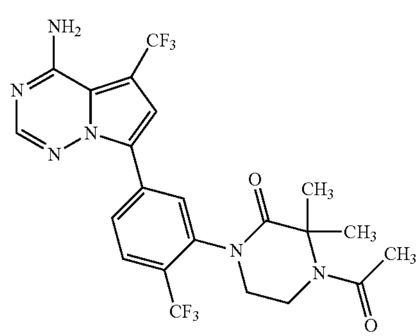 | 4-acetyl-1-{5-[4-amino-5-(trifluoromethyl)pyrrolo[2,1-f][1,2,4]triazin-7-yl]-2-(trifluoromethyl)phenyl}-3,3-dimethylpiperazin-2-one | 515 |

Example 574

4-Acetyl-1-(3-(4-amino-5-methylpyrrolo[2,1-f][1,2,4]triazin-7-yl)phenyl)-3,3-dimethylpiperazin-2-one

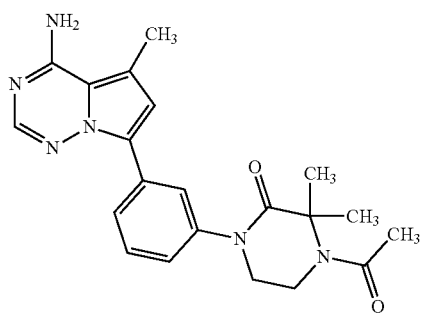

(574)

A mixture of 7-iodo-5-methylpyrrolo[2,1-f][1,2,4]triazin-4-amine (23 mg, 0.084 mmol) (Intermediate M1), 4-acetyl-3,3-dimethyl-1-(3-(4,4,5,5-tetramethyl-1,3,2-dioxaborolan-2-yl)phenyl)piperazin-2-one (37.5 mg, 0.101 mmol) (Intermediate Q53A), $PdCl_2(dppf)$-$CH_2Cl_2$ adduct (3.43 mg, 4.20 μmol) and tripotassium phosphate (0.084 mL, 0.168 mmol) in DMF (1 mL) in a capped pressure reaction vial was degassed by vacuum then filled in with nitrogen. The degassing process was repeated twice. The vial was placed in a 90° C. heating block and heated for 2 h. The reaction mixture was filtered and the crude material was purified via preparative LC/MS with the following conditions: Column: Waters XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-40% B over 25 minutes, then a 5-minute hold at 40% B; Flow: 20 mL/min. Fractions containing the desired product were combined and dried via centrifugal evaporation to give 4-acetyl-1-(3-(4-amino-5-methylpyrrolo[2,1-f][1,2,4]triazin-7-yl)phenyl)-3,3-dimethylpiperazin-2-one (20.5 mg, 98% purity, 0.052 mmol, 62% yield). Mass spectrum m/z 393.4 $(M+H)^+$. $^1H$ NMR (500 MHz, DMSO-$d_6$) δ 8.02 (s, 1H), 7.96-7.89 (m, 2H), 7.55-7.50 (m, 1H), 7.38-7.33 (m, 1H), 7.03 (s, 1H), 3.84-3.74 (m, 4H), 2.56 (s, 3H), 2.10 (s, 3H), 1.70 (s, 6H).

The Examples in Table 45 were prepared according to the general synthesis procedures for Example 574 using other exemplified chemistry with appropriate starting materials.

TABLE 45

| Ex. No. | Structure | Name | M + H |
|---|---|---|---|
| 575 | 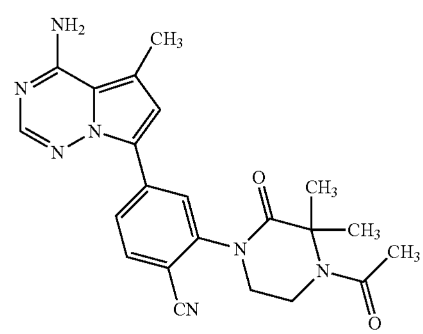 | 2-(4-acetyl-3,3-dimethyl-2-oxopiperazin-1-yl)-4-{4-amino-5-methylpyrrolo[2,1-f][1,2,4]triazin-7-yl}benzonitrile | 418 |
| 576 | 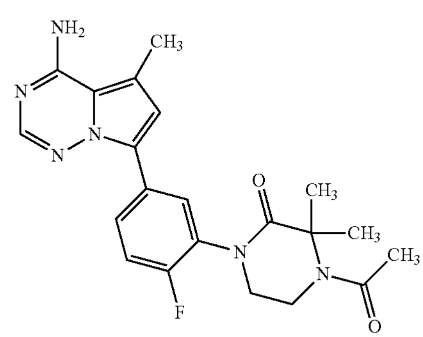 [SMILES: CC(=O)N1CCN(c2cc(-c3cc(C(F)(F)F)c4c(N)ncnn34)ccc2F)C(=O)C1(C)C] | 4-acetyl-1-(5-{4-amino-5-methylpyrrolo[2,1-f][1,2,4]triazin-7-yl}-2-fluorophenyl)-3,3-dimethylpiperazin-2-one | 411 |

TABLE 45-continued

| Ex. No. | Structure | Name | M + H |
|---|---|---|---|
| 577 | 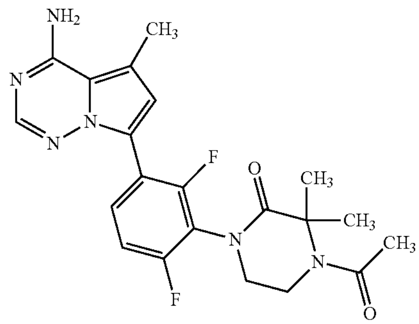 [SMILES: CC(=O)N1CCN(c2c(F)ccc(-c3cc(C(F)(F)F)c4c(N)ncnn34)c2F)C(=O)C1(C)C] | 4-acetyl-1-(3-{4-amino-5-methylpyrrolo[2,1-f][1,2,4]triazin-7-yl}-2,6-difluorophenyl)-3,3-dimethylpiperazin-2-one | 429 |
| 578 | 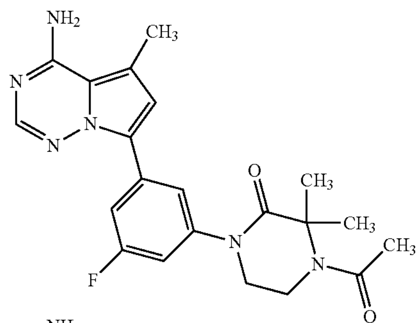 | 4-acetyl-1-(3-{4-amino-5-methylpyrrolo[2,1-f][1,2,4]triazin-7-yl}-5-fluorophenyl)-3,3-dimethylpiperazin-2-one | 411 |
| 579 | 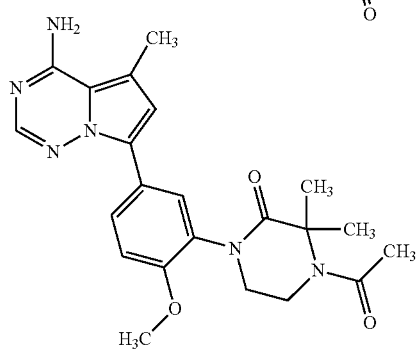 | 4-acetyl-1-(5-{4-amino-5-methylpyrrolo[2,1-f][1,2,4]triazin-7-yl}-2-methoxyphenyl)-3,3-dimethylpiperazin-2-one | 423 |

Example 580

2-(4-Acetyl-3,3-dimethyl-2-oxopiperazin-1-yl)-4-(4-amino-5-chloropyrrolo[1,2-f][1,2,4]triazin-7-yl)benzonitrile (580)

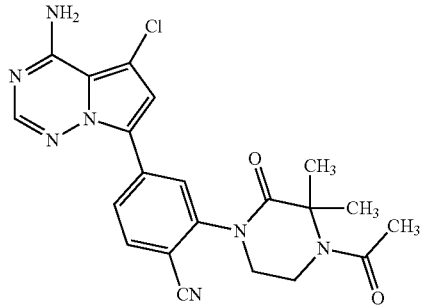

2-(4-Acetyl-3,3-dimethyl-2-oxopiperazin-1-yl)-4-(4-amino-5-chloropyrrolo[1,2-f][1,2,4]triazin-7-yl)benzonitrile was synthesized from 7-bromo-5-chloropyrrolo[2,1-f][1,2,4]triazin-4-amine (Intermediate M4) and 2-(4-acetyl-3,3-dimethyl-2-oxopiperazin-1-yl)-4-(4,4,5,5-tetramethyl-1,3,2-dioxaborolan-2-yl)benzonitrile (Intermediate Q53CN4), according to the procedure of Example 566. LCMS M+H=438.0 and 440.0. $^1$H NMR (500 MHz, DMSO-$d_6$) δ 8.39 (d, J=8.4 Hz, 1H), 8.35-8.11 (m, 2H), 8.03-7.96 (m, 2H), 7.46 (s, 1H), 7.13 (br. s., 1H), 3.81 (br. s., 4H), 2.11 (s, 3H), 1.72 (s, 6H).

Example 581

4-Acetyl-1-(3-(4-amino-5-chloropyrrolo[1,2-f][1,2,4]triazin-7-yl)phenyl)-3,3-dimethylpiperazin-2-one (581)

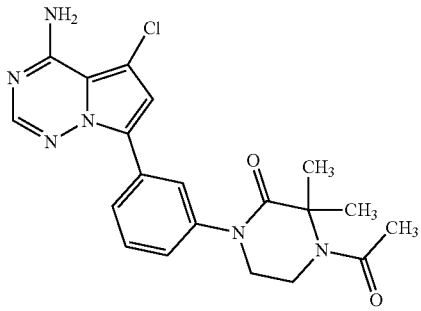

To a solution of 4-acetyl-1-(3-(4-aminopyrrolo[2,1-f][1,2,4]triazin-7-yl)phenyl)-3,3-dimethylpiperazin-2-one (100 mg, 0.264 mmol) in DMF (2643 μl) was added NCS (42.3 mg, 0.317 mmol) and the reaction mixture was stirred overnight at room temperature. The reaction mixture was diluted with DMF and purified on HPLC affording 4-acetyl-1-(3-(4-amino-5-chloropyrrolo[2,1-f][1,2,4]triazin-7-yl)phenyl)-3,3-dimethylpiperazin-2-one (63 mg, 0.148 mmol, 56.0% yield). LCMS M+=302.8. Method G. Retention time 0.66 min. $^1$H NMR (500 MHz, DMSO-$d_6$) δ 7.99 (d, J=7.7 Hz, 1H), 7.94 (s, 2H), 7.51 (t, J=8.1 Hz, 1H), 7.33 (d, J=7.7 Hz, 1H), 7.22 (s, 1H), 3.86-3.71 (m, 4H), 2.10 (s, 3H), 1.70 (s, 6H).

The Examples in Table 46 were prepared according to the general synthesis procedures for Examples 580-581 using other exemplified chemistry with appropriate starting materials.

TABLE 46

| Ex. No. | Structure | Name | M + H |
|---|---|---|---|
| 582 | 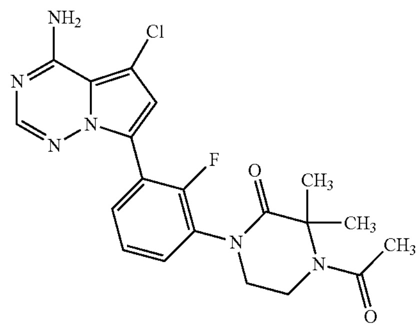 [SMILES: CC(=O)N1CCN(c2cccc(-c3cc(C(F)(F)F)c4c(N)ncnn34)c2F)C(=O)C1(C)C] | 4-acetyl-1-(3-{4-amino-5-chloropyrrolo[2,1-f][1,2,4]triazin-7-yl}-2-fluorophenyl)-3,3-dimethylpiperazin-2-one | 432 |
| 583 | 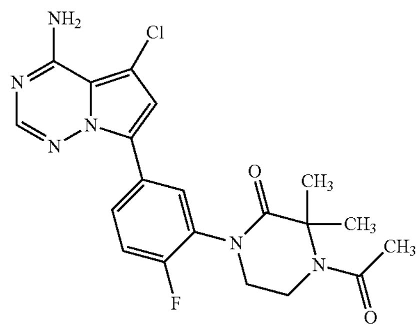 | 4-acetyl-1-(5-{4-amino-5-chloropyrrolo[2,1-f][1,2,4]triazin-7-yl}-2-fluorophenyl)-3,3-dimethylpiperazin-2-one | 432 |
| 584 | 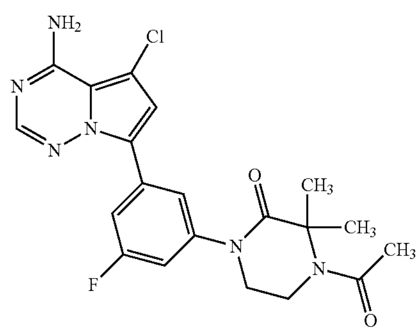 [SMILES: CC(=O)N1CCN(c2cc(F)cc(-c3cc(C(F)(F)F)c4c(N)ncnn34)c2)C(=O)C1(C)C] | 4-acetyl-1-(3-{4-amino-5-chloropyrrolo[2,1-f][1,2,4]triazin-7-yl}-5-fluorophenyl)-3,3-dimethylpiperazin-2-one | 432 |
| 585 | 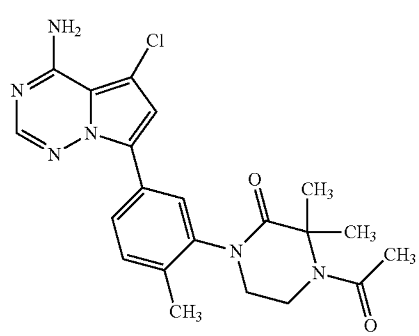 | 4-acetyl-1-(5-{4-amino-5-chloropyrrolo[2,1-f][1,2,4]triazin-7-yl}-2-methylphenyl)-3,3-dimethylpiperazin-2-one | 428 |

TABLE 46-continued

| Ex. No. | Structure | Name | M + H |
|---|---|---|---|
| 586 | 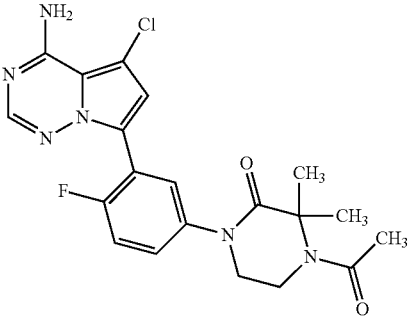 [SMILES: CC(=O)N1CCN(c2ccc(F)c(-c3cc(Cl)c4c(N)ncnn34)c2)C(=O)C1(C)C] | 4-acetyl-1-(3-{4-amino-5-chloropyrrolo[2,1-f][1,2,4]triazin-7-yl}-4-fluorophenyl)-3,3-dimethylpiperazin-2-one | 432 |
| 587 | 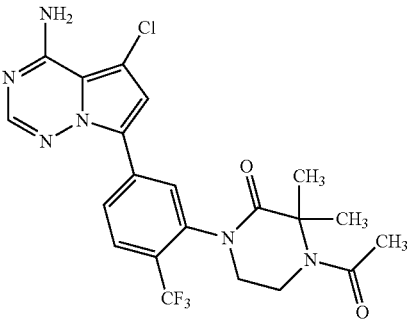 | 4-acetyl-1-(5-{4-amino-5-chloropyrrolo[2,1-f][1,2,4]triazin-7-yl}-2-(trifluoromethyl)phenyl)-3,3-dimethylpiperazin-2-one | 482 |
| 588 | 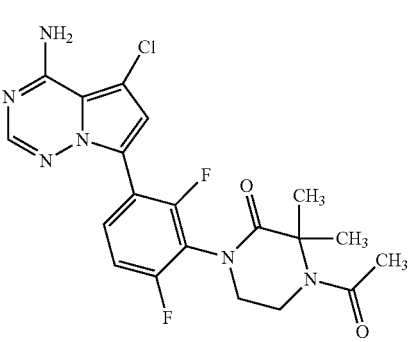 | 4-acetyl-1-(3-{4-amino-5-chloropyrrolo[2,1-f][1,2,4]triazin-7-yl}-2,6-difluorophenyl)-3,3-dimethylpiperazin-2-one | 450 |
| 589 | 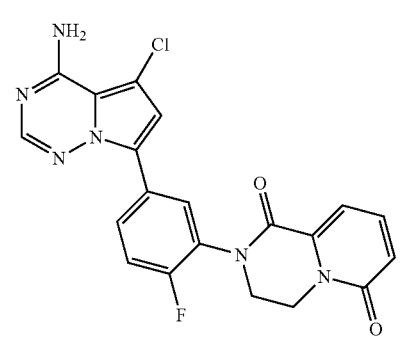 [SMILES: Nc1ncnn2c(-c3ccc(F)c(N4CCn5c(cccc5=O)C4=O)c3)cc(Cl)c12] | 2-(5-{4-amino-5-chloropyrrolo[2,1-f][1,2,4]triazin-7-yl}-2-fluorophenyl)-1H,2H,3H,4H,6H-pyrido[1,2-a]piperazine-1,6-dione | 426 |

TABLE 46-continued

| Ex. No. | Structure | Name | M + H |
|---|---|---|---|
| 590 | 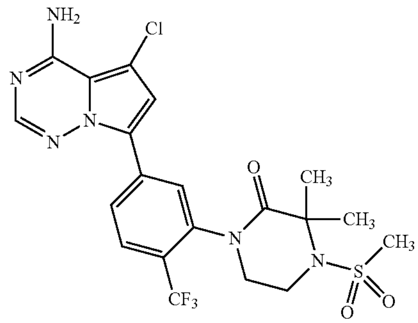 [SMILES: CC1(C)C(=O)N(c2cc(-c3cc(Cl)c4c(N)ncnn34)ccc2C(F)(F)F)CCN1S(C)(=O)=O] | 1-(5-{4-amino-5-chloropyrrolo[2,1-f][1,2,4]triazin-7-yl}-2-(trifluoromethyl)phenyl)-4-methanesulfonyl-3,3-dimethylpiperazin-2-one | 518 |
| 591 | 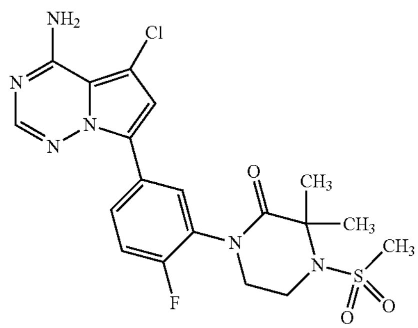 [SMILES: CC1(C)C(=O)N(c2cc(-c3cc(Cl)c4c(N)ncnn34)ccc2F)CCN1S(C)(=O)=O] | 1-(5-{4-amino-5-chloropyrrolo[2,1-f][1,2,4]triazin-7-yl}-2-fluorophenyl)-4-methanesulfonyl-3,3-dimethylpiperazin-2-one | 468 |
| 592 | 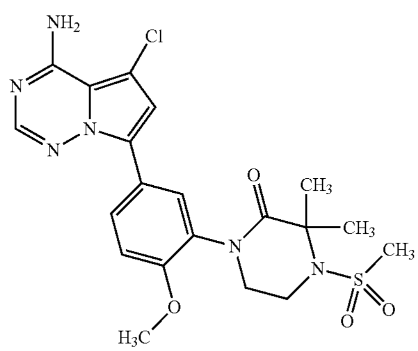 [SMILES: COc1ccc(-c2cc(Cl)c3c(N)ncnn23)cc1N1CCN(S(C)(=O)=O)C(C)(C)C1=O] | 1-(5-{4-amino-5-chloropyrrolo[2,1-f][1,2,4]triazin-7-yl}-2-methoxyphenyl)-4-methanesulfonyl-3,3-dimethylpiperazin-2-one | 480 |
| 593 | 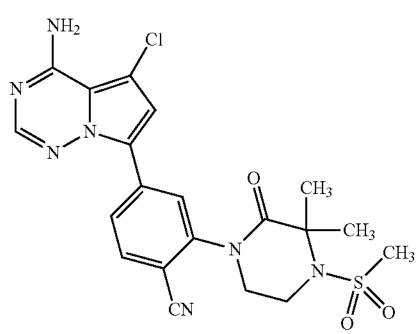 | 4-{4-amino-5-chloropyrrolo[2,1-f][1,2,4]triazin-7-yl}-2-(4-methanesulfonyl-3,3-dimethyl-2-oxopiperazin-1-yl)benzonitrile | 475 |

TABLE 46-continued

| Ex. No. | Structure | Name | M + H |
|---|---|---|---|
| 594 | 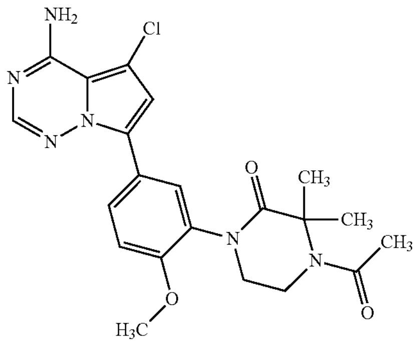 | 4-acetyl-1-(5-(4-amino-5-chloropyrrolo[1,2-f][1,2,4]triazin-7-yl)-2-methoxyphenyl)-3,3-dimethylpiperazin-2-one | 443 |
| 595 | 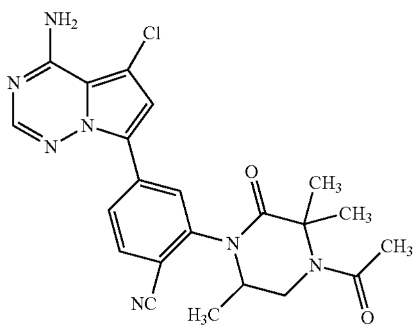 [SMILES: CC(=O)N1CC(C)N(c2cc(-c3cc(Cl)c4c(N)ncnn34)ccc2C#N)C(=O)C1(C)C] | 2-(4-acetyl-3,3,6-trimethyl-2-oxopiperazin-1-yl)-4-{4-amino-5-chloropyrrolo[2,1-f][1,2,4]triazin-7-yl}benzonitrile (racemic) | 452, 454 |
| 596 | 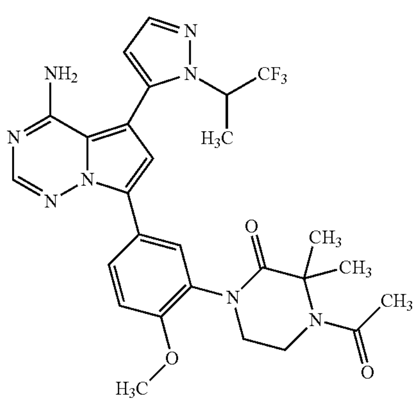 [SMILES: COc1ccc(-c2cc(-c3ccnn3C(C)C(F)(F)F)c3c(N)ncnn23)cc1N1CCN(C(C)=O)C(C)(C)C1=O] | 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-methoxyphenyl)-3,3-dimethylpiperazin-2-one; chiral-Isomer A | 571 |
| 597 | 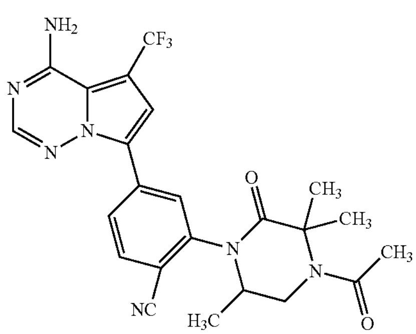 [SMILES: CC(=O)N1CC(C)N(c2cc(-c3cc(C(F)(F)F)c4c(N)ncnn34)ccc2C#N)C(=O)C1(C)C] | 2-(4-acetyl-3,3,6-trimethyl-2-oxopiperazin-1-yl)-4-[4-amino-5-(trifluoromethyl)pyrrolo[2,1-f][1,2,4]triazin-7-yl]benzonitrile; racemic R,S | 486 |

TABLE 46-continued

| Ex. No. | Structure | Name | M + H |
|---|---|---|---|
| 598 | 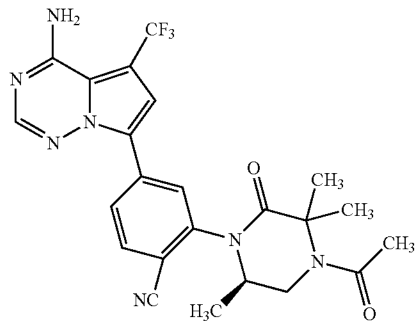 [SMILES: CC(=O)N1C[C@@H](C)N(c2cc(-c3cc(C(F)(F)F)c4c(N)ncnn34)ccc2C#N)C(=O)C1(C)C] | (R)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile | 486 |
| 599 | 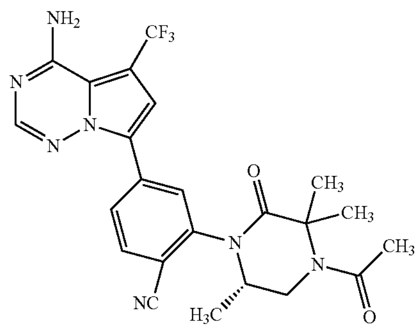 [SMILES: CC(=O)N1C[C@H](C)N(c2cc(-c3cc(C(F)(F)F)c4c(N)ncnn34)ccc2C#N)C(=O)C1(C)C] | (S)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile | 486 |
| 600 | 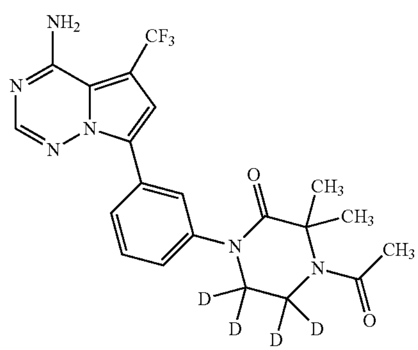 [SMILES: [2H]C1([2H])N(c2cccc(-c3cc(C(F)(F)F)c4c(N)ncnn34)c2)C(=O)C(C)(C)N(C(C)=O)C1([2H])[2H]] | 4-acetyl-1-{3-[4-amino-5-(trifluoromethyl)pyrrolo[2,1-f][1,2,4]triazin-7-yl]phenyl}-3,3-dimethyl-5,5,6,6-tetradeuteropiperazin-2-one | 451 |
| 601 | 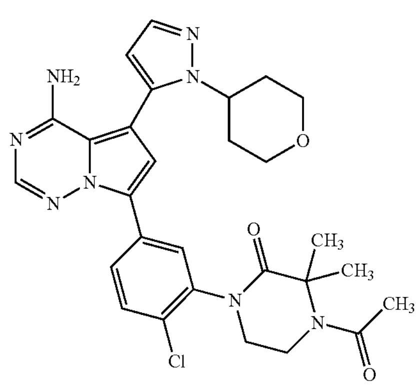 [SMILES: CC(=O)N1CCN(c2cc(-c3cc(-c4ccnn4C4CCOCC4)c4c(N)ncnn34)ccc2Cl)C(=O)C1(C)C] | 4-acetyl-1-(5-(4-amino-5-(1-(tetrahydro-2H-pyran-4-yl)-1H-pyrazol-5-yl)pyrrolo[2,1-f][1,2,4]triazin-7-yl)-2-chlorophenyl)-3,3-dimethylpiperazin-2-one | 563, 564, 565 |

TABLE 46-continued

| Ex. No. | Structure | Name | M + H |
|---|---|---|---|
| 602 | 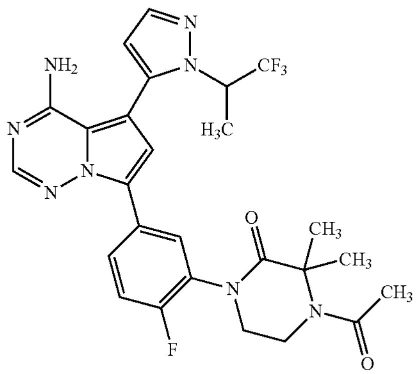 [SMILES: CC(=O)N1CCN(c2cc(-c3cc(-c4ccnn4C(C)C(F)(F)F)c4c(N)ncnn34)ccc2F)C(=O)C1(C)C] | 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one; racemate, R,S | 559 |
| 603 | 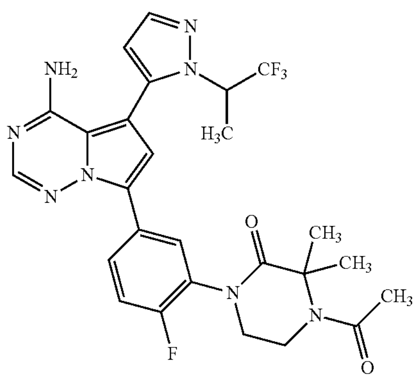 [SMILES: CC(=O)N1CCN(c2cc(-c3cc(-c4ccnn4C(C)C(F)(F)F)c4c(N)ncnn34)ccc2F)C(=O)C1(C)C] | 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one; chiral, Isomer A | 559 |
| 604 | 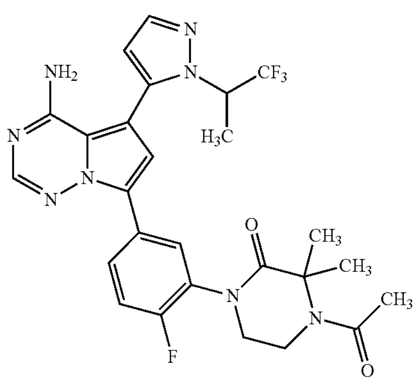 [SMILES: CC(=O)N1CCN(c2cc(-c3cc(-c4ccnn4C(C)C(F)(F)F)c4c(N)ncnn34)ccc2F)C(=O)C1(C)C] | 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one; chiral, Isomer B | 559 |
| 605 | 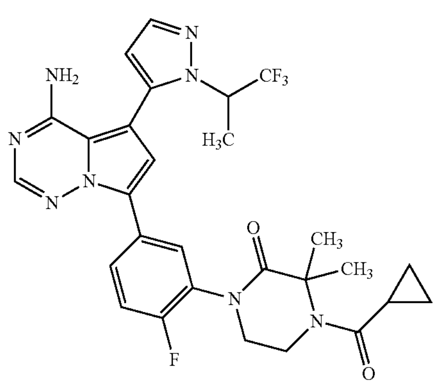 [SMILES: CC(n1nccc1-c1cc(-c2ccc(F)c(N3CCN(C(=O)C4CC4)C(C)(C)C3=O)c2)n2ncnc(N)c12)C(F)(F)F] | 1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-4-cyclopropanecarbonyl-3,3-dimethylpiperazin-2-one; chiral Isomer A | 585 |

TABLE 46-continued

| Ex. No. | Structure | Name | M + H |
|---|---|---|---|
| 606 | 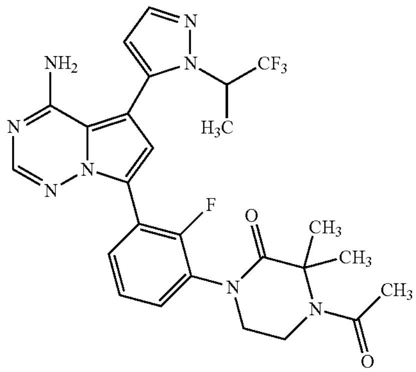 [SMILES: CC(=O)N1CCN(c2cccc(-c3cc(-c4ccnn4C(C)C(F)(F)F)c4c(N)ncnn34)c2F)C(=O)C1(C)C] | 4-acetyl-1-(3-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one; chiral, Isomer A | 559 |
| 607 | 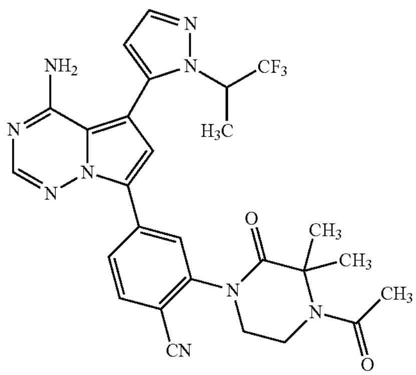 [SMILES: CC(=O)N1CCN(c2cc(-c3cc(-c4ccnn4C(C)C(F)(F)F)c4c(N)ncnn34)ccc2C#N)C(=O)C1(C)C] | 2-(4-acetyl-3,3-dimethyl-2-oxopiperazin-1-yl)-4-{4-amino-5-[1-(1,1,1-trifluoropropan-2-yl)-1H-pyrazol-5-yl]pyrrolo[2,1-f][1,2,4]triazin-7-yl}benzonitrile; chiral, Isomer A | 566 |
| 608 | 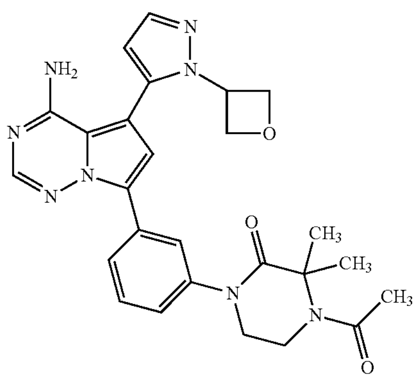 [SMILES: CC(=O)N1CCN(c2cccc(-c3cc(-c4ccnn4C4COC4)c4c(N)ncnn34)c2)C(=O)C1(C)C] | 4-acetyl-1-(3-{4-amino-5-[1-(oxetan-3-yl)-1H-pyrazol-5-yl]pyrrolo[2,1-f][1,2,4]triazin-7-yl}phenyl)-3,3-dimethylpiperazin-2-one | 501 |
| 609 | 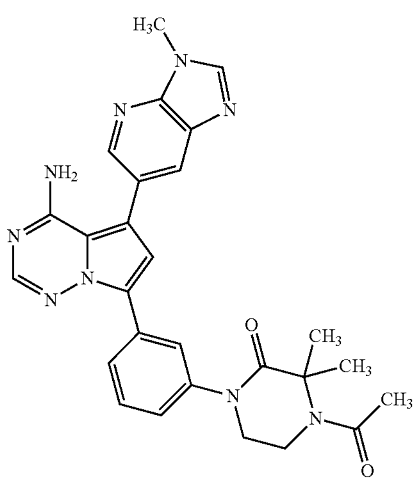 [SMILES: CC(=O)N1CCN(c2cccc(-c3cc(-c4cnc5c(c4)ncn5C)c4c(N)ncnn34)c2)C(=O)C1(C)C] | 4-acetyl-1-[3-(4-amino-5-{3-methyl-3H-imidazo[4,5-b]pyridin-6-yl}pyrrolo[2,1-f][1,2,4]triazin-7-yl)phenyl]-3,3-dimethylpiperazin-2-one | 510 |

TABLE 46-continued

| Ex. No. | Structure | Name | M + H |
|---|---|---|---|
| 610 | 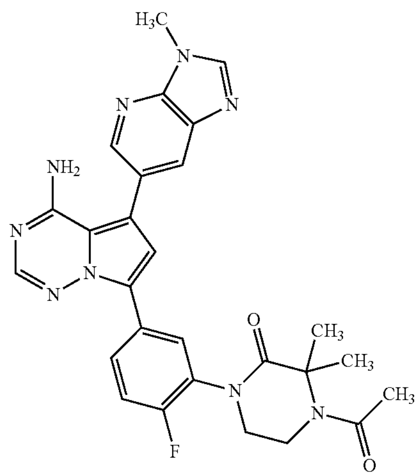 [SMILES: CC(=O)N1CCN(c2cc(-c3cc(-c4cnc5c(c4)ncn5C)c4c(N)ncnn34)ccc2F)C(=O)C1(C)C] | 4-acetyl-1-[5-(4-amino-5-{3-methyl-3H-imidazo[4,5-b]pyridin-6-yl}pyrrolo[2,1-f][1,2,4]triazin-7-yl)-2-fluorophenyl]-3,3-dimethylpiperazin-2-one | 528 |
| 611 | 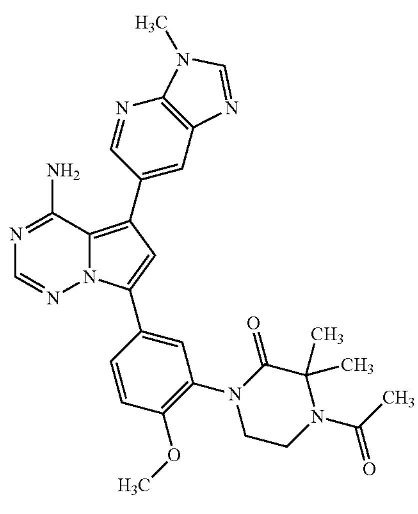 [SMILES: COc1ccc(-c2cc(-c3cnc4c(c3)ncn4C)c3c(N)ncnn23)cc1N1CCN(C(C)=O)C(C)(C)C1=O] | 4-acetyl-1-[5-(4-amino-5-{3-methyl-3H-imidazo[4,5-b]pyridin-6-yl}pyrrolo[2,1-f][1,2,4]triazin-7-yl)-2-methoxyphenyl]-3,3-dimethylpiperazin-2-one | 540 |
| 612 | 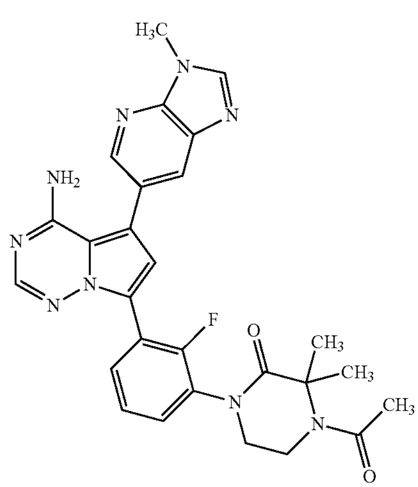 [SMILES: CC(=O)N1CCN(c2cccc(-c3cc(-c4cnc5c(c4)ncn5C)c4c(N)ncnn34)c2F)C(=O)C1(C)C] | 4-acetyl-1-[3-(4-amino-5-{3-methyl-3H-imidazo[4,5-b]pyridin-6-yl}pyrrolo[2,1-f][1,2,4]triazin-7-yl)-2-fluorophenyl]-3,3-dimethylpiperazin-2-one | 528 |

TABLE 46-continued

| Ex. No. | Structure | Name | M + H |
|---|---|---|---|
| 613 | 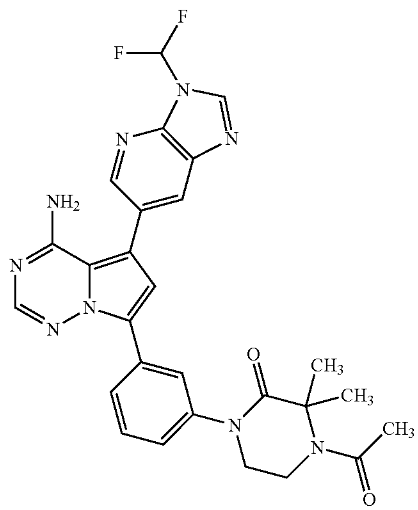 [SMILES: CC(=O)N1CCN(c2cccc(-c3cc(-c4cnc5c(c4)ncn5C(F)F)c4c(N)ncnn34)c2)C(=O)C1(C)C] | 4-acetyl-1-(3-{4-amino-5-[3-(difluoromethyl)-3H-imidazo[4,5-b]pyridin-6-yl]pyrrolo[2,1-f][1,2,4]triazin-7-yl}phenyl)-3,3-dimethylpiperazin-2-one | 546 |
| 614 | 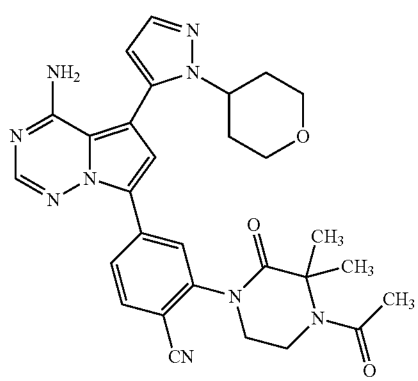 [SMILES: CC(=O)N1CCN(c2cc(-c3cc(-c4ccnn4C4CCOCC4)c4c(N)ncnn34)ccc2C#N)C(=O)C1(C)C] | 2-(4-acetyl-3,3-dimethyl-2-oxopiperazin-1-yl)-4-{4-amion-5-[1-(oxan-4-yl)-1H-pyrazol-5-yl]pyrrolo[2,1-f][1,2,4]triazin-7-yl}benzonitrile | 554 |
| 615 | 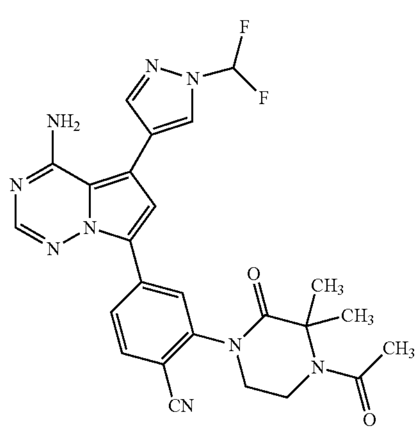 [SMILES: CC(=O)N1CCN(c2cc(-c3cc(-c4cnn(C(F)F)c4)c4c(N)ncnn34)ccc2C#N)C(=O)C1(C)C] | 2-(4-acetyl-3,3-dimethyl-2-oxopiperazin-1-yl)-4-{4-amino-5-[1-(difluoromethyl)-1H-pyrazol-4-yl]pyrrolo[2,1-f][1,2,4]triazin-7-yl}benzonitrile | 520 |

| Ex. No. | Structure | Name | M + H |
|---|---|---|---|
| 616 | 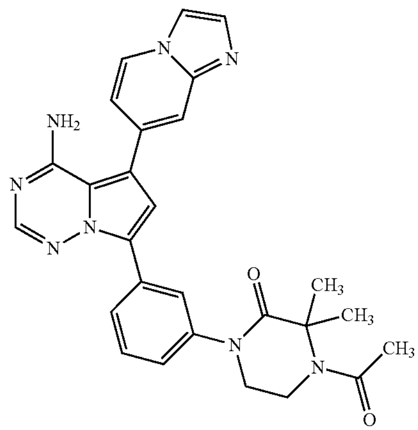 [SMILES: CC(=O)N1CCN(c2cccc(-c3cc(-c4ccn5ccnc5c4)c4c(N)ncnn34)c2)C(=O)C1(C)C] | 4-acetyl-1-[3-(4-amino-5-{imidazo[1,2-a]pyridin-7-yl}pyrrolo[2,1-f][1,2,4]triazin-7-yl)phenyl]-3,3-dimethylpiperazin-2-one | 495 |
| 617 | 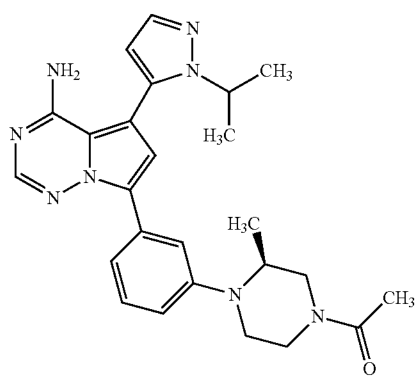 [SMILES: CC(=O)N1CCN(c2cccc(-c3cc(-c4ccnn4C(C)C)c4c(N)ncnn34)c2)[C@@H](C)C1] | 1-[(3S)-4-(3-{4-amino-5-[1-(propan-2-yl)-1H-pyrazol-5-yl]pyrrolo[2,1-f][1,2,4]triazin-7-yl}phenyl)-3-methylpiperazin-1-yl]ethan-1-one | 459 |
| 618 | 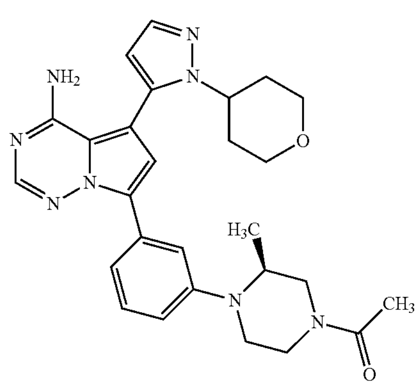 [SMILES: CC(=O)N1CCN(c2cccc(-c3cc(-c4ccnn4C4CCOCC4)c4c(N)ncnn34)c2)[C@@H](C)C1] | 1-[(3S)-4-(3-{4-amino-5-[1-(oxan-4-yl)-1H-pyrazol-5-yl]pyrrolo[2,1-f][1,2,4]triazin-7-yl}phenyl)-3-methylpiperazin-1-yl]ethan-1-one | 501 |

Example 619

4-Acetyl-1-(3-(1-amino-8-(1-(tetrahydro-2H-pyran-4-yl)-1H-pyrazol-5-yl)pyrrolo[1,2-a]pyrazin-6-yl)phenyl)-3,3-dimethylpiperazin-2-one

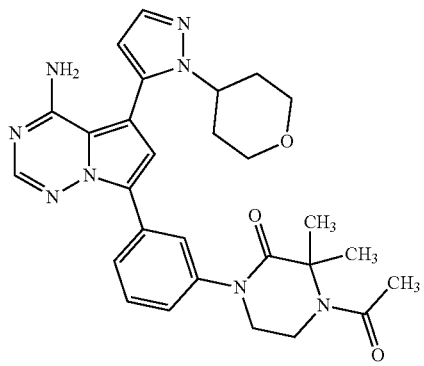

(619)

4-Acetyl-1-(3-bromophenyl)-3,3-dimethylpiperazin-2-one (0.02 g, 0.062 mmol), 4,4,4',4',5,5,5',5'-octamethyl-2,2'-bi(1,3,2-dioxaborolane) (0.017 g, 0.068 mmol) and potassium acetate (0.024 g, 0.246 mmol) were combined in a pressure tube. Dioxane (0.308 ml) was added and the suspension was degassed by bubbling with nitrogen while sonicating. PdCl$_2$(dppf)-CH$_2$Cl$_2$ adduct (5.02 mg, 6.15 µmol) was added and the mixture was sealed and heated at 80° C. overnight and then cooled to room temperature. Water (0.5 mL), sodium carbonate (0.020 g, 0.185 mmol) and 6-bromo-8-(1-(tetrahydro-2H-pyran-4-yl)-1H-pyrazol-5-yl)pyrrolo[1,2-a]pyrazin-1-amine (18 mg, 0.049 mmol, Intermediate C2) were added and the resulting solution was degassed by bubbling with nitrogen while sonicating. PdCl$_2$(dppf)-CH$_2$Cl$_2$ adduct (5.02 mg, 6.15 µmol) was added and the reaction mixture was heated at 80° C. for 1 h. The reaction mixture was filtered and purified by preparative HPLC (Method B) providing 4-acetyl-1-(3-(1-amino-8-(1-(tetrahydro-2H-pyran-4-yl)-1H-pyrazol-5-yl)pyrrolo[1,2-a]pyrazin-6-yl)phenyl)-3,3-dimethylpiperazin-2-one (6.5 mg, 0.012 mmol, 19.83% yield). $^1$H NMR (500 MHz, DMSO-d$_6$) δ 7.74 (d, J=4.3 Hz, 1H), 7.69-7.50 (m, 4H), 7.41 (d, J=7.3 Hz, 1H), 7.12 (br. s., 1H), 6.97 (s, 1H), 6.41 (s, 1H), 5.70 (br. s., 2H), 4.30 (br. s., 1H), 3.92-3.83 (m, 2H), 3.33-3.25 (m, 2H), 2.08 (m, 5H), 1.90 (m, 2H), 1.69 (s, 6H). LC/MS: 1.26 min, [M+1]$^+$=528 Method P.

The Examples in Table 47 were prepared according to the general procedure for the preparation of Example 619, and other Examples exemplified above, using appropriate intermediates.

TABLE 47

| Ex. No. | Structure | Name | M + H |
|---|---|---|---|
| 620 | 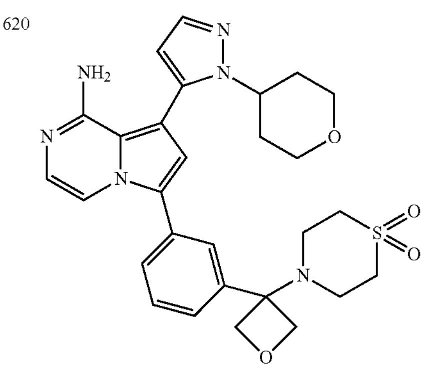 | 4-[3-(3-{1-amino-8-[1-(oxan-4-yl)-1H-pyrazol-5-yl]pyrrolo[1,2-a]pyrazin-6-yl}phenyl)oxetan-3-yl]-1λ$^6$,4-thiomorpholine-1,1-dione | 550 |
| 621 | 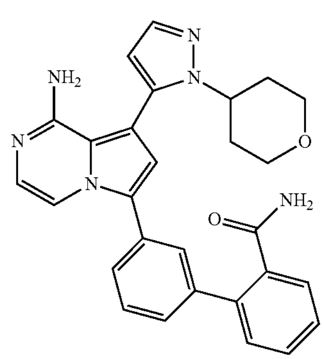 [SMILES: NC(=O)c1ccccc1-c1cccc(-c2cc(-c3ccnn3C3CCOCC3)c3c(N)nccn23)c1] | 2-(3-{1-amino-8-[1-(oxan-4-yl)-1H-pyrazol-5-yl]pyrrolo[1,2-a]pyrazin-6-yl}phenyl)benzamide | 480 |

The Examples in Table 48 were prepared according to the general synthesis procedures for all Examples above using other exemplified chemistry with appropriate starting materials.

TABLE 48

| Ex. No. | Structure | Name | M + H |
|---|---|---|---|
| 622 | 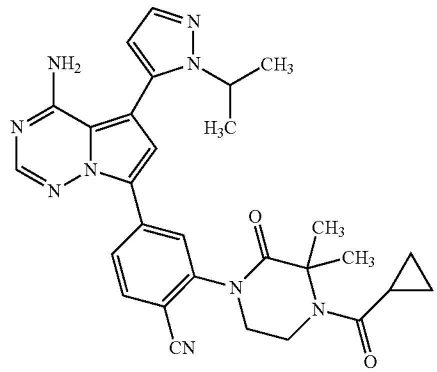 [SMILES: CC(C)n1nccc1-c1cc(-c2ccc(C#N)c(N3CCN(C(=O)C4CC4)C(C)(C)C3=O)c2)n2ncnc(N)c12] | 4-(4-amino-5-(1-(1,1,1-trifluoropropan-2-yl)-1H-pyrazol-5-yl)pyrrolo[2,1-f][1,2,4]triazin-7-yl)-2-(4-(cyclopropanecarbonyl)-3,3-dimethyl-2-oxopiperazin-1-yl)benzonitrile, Isomer A | 592 |
| 623 | 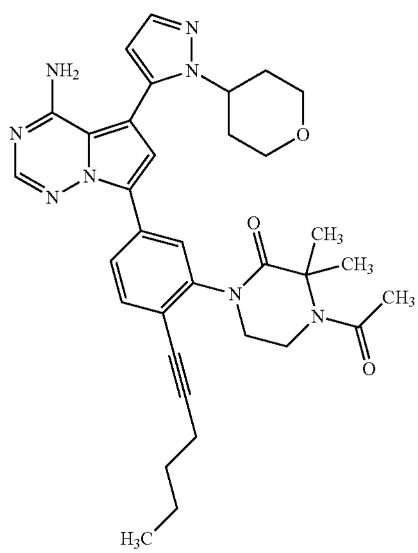 [SMILES: CCCCC#Cc1ccc(-c2cc(-c3ccnn3C3CCOCC3)c3c(N)ncnn23)cc1N1CCN(C(C)=O)C(C)(C)C1=O] | 4-acetyl-1-(5-(4-amino-5-(1-(tetrahydro-2H-pyran-4-yl)-1H-pyrazol-5-yl)pyrrolo[2,1-f][1,2,4]triazin-7-yl)-2-(hex-1-yn-1-yl)phenyl)-3,3-dimethylpiperazin-2-one | 610 |
| 624 | 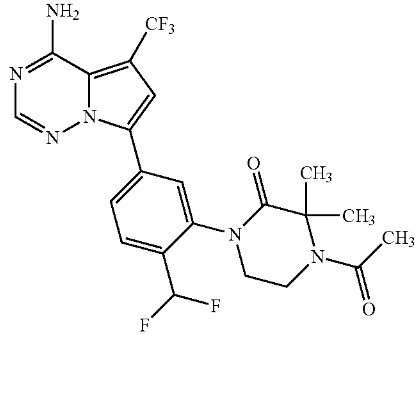 [SMILES: CC(=O)N1CCN(c2cc(-c3cc(C(F)(F)F)c4c(N)ncnn34)ccc2C(F)F)C(=O)C1(C)C] | 4-acetyl-1-(5-(4-amino-5-(trifluoromethyl)pyrrolo[2,1-f][1,2,4]triazin-7-yl)-2-(difluoromethyl)phenyl)-3,3-dimethylpiperazin-2-one | 497 |

TABLE 48-continued

| Ex. No. | Structure | Name | M + H |
|---|---|---|---|
| 625 | 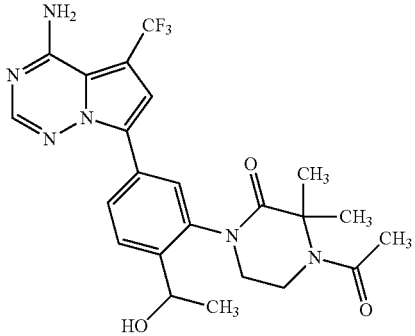 | 4-acetyl-1-(5-(4-amino-5-(trifluoromethyl)pyrrolo[2,1-f][1,2,4]triazin-7-yl)-2-(1-hydroxyethyl)phenyl)-3,3-dimethylpiperazin-2-one | 491 |
| 626 | 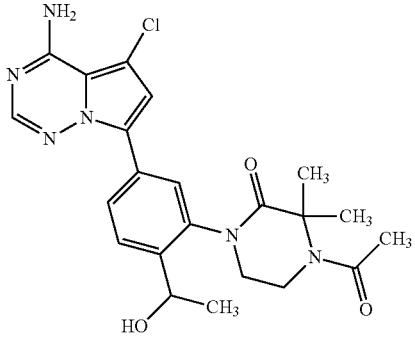 [SMILES: CC(=O)N1CCN(c2cc(-c3cc(C(F)(F)F)c4c(N)ncnn34)ccc2C(C)O)C(=O)C1(C)C] | 4-acetyl-1-(5-(4-amino-5-chloropyrrolo[2,1-f][1,2,4]triazin-7-yl)-2-(1-hydroxyethyl)phenyl)-3,3-dimethylpiperazin-2-one | 458 |
| 627 | 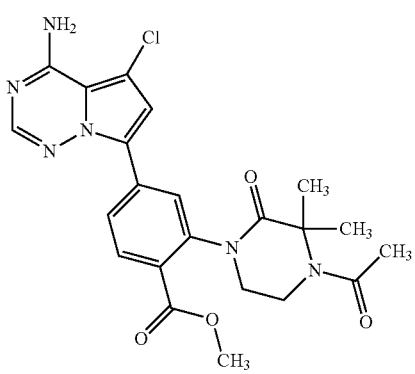 [SMILES: COC(=O)c1ccc(-c2cc(Cl)c3c(N)ncnn23)cc1N1CCN(C(C)=O)C(C)(C)C1=O] | methyl 2-(4-acetyl-3,3-dimethyl-2-oxopiperazin-1-yl)-4-(4-amino-5-chloropyrrolo[2,1-f][1,2,4]triazin-7-yl)benzoate | 472 |
| 628 | 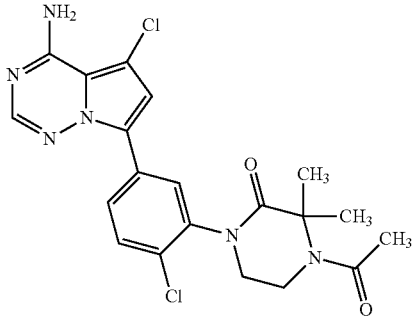 [SMILES: CC(=O)N1CCN(c2cc(-c3cc(Cl)c4c(N)ncnn34)ccc2Cl)C(=O)C1(C)C] | 7-(3-(4-acetyl-3,3-dimethyl-2-oxopiperazin-1-yl)-4-chlorophenyl)-4-aminopyrrolo[2,1-f][1,2,4]triazine-5-carbonitrile | 439 |

TABLE 48-continued

| Ex. No. | Structure | Name | M + H |
|---|---|---|---|
| 629 | 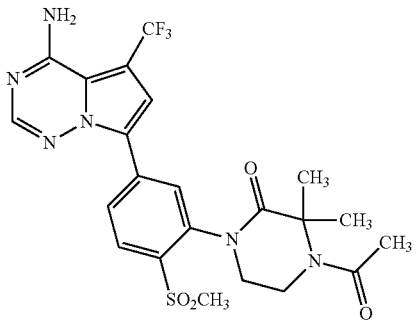 [SMILES: CC(=O)N1CCN(c2cc(-c3cc(C(F)(F)F)c4c(N)ncnn34)ccc2S(C)(=O)=O)C(=O)C1(C)C] | 4-acetyl-1-(5-(4-amino-5-(trifluoromethyl)pyrrolo[2,1-f][1,2,4]triazin-7-yl)-2-(methylsulfonyl)phenyl)-3,3-dimethylpiperazin-2-one | 526 |
| 630 | 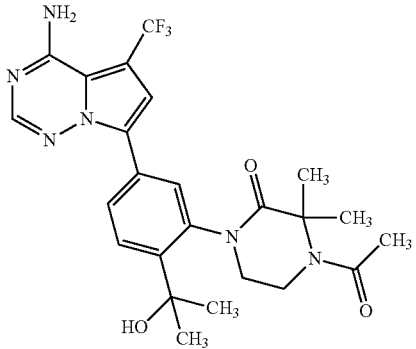 [SMILES: CC(=O)N1CCN(c2cc(-c3cc(C(F)(F)F)c4c(N)ncnn34)ccc2C(C)(C)O)C(=O)C1(C)C] | 4-acetyl-1-(5-(4-amino-5-(trifluoromethyl)pyrrolo[2,1-f][1,2,4]triazin-7-yl)-2-(2-hydroxypropan-2-yl)phenyl)-3,3-dimethylpiperazin-2-one | 506 |
| 631 | 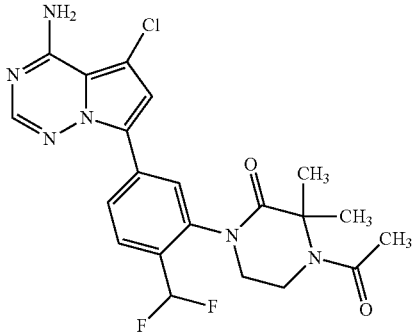 [SMILES: CC(=O)N1CCN(c2cc(-c3cc(Cl)c4c(N)ncnn34)ccc2C(F)F)C(=O)C1(C)C] | 4-acetyl-1-(5-(4-amino-5-chloropyrrolo[2,1-f][1,2,4]triazin-7-yl)-2-(difluoromethyl)phenyl)-3,3-dimethylpiperazin-2-one | 464 |
| 632 | 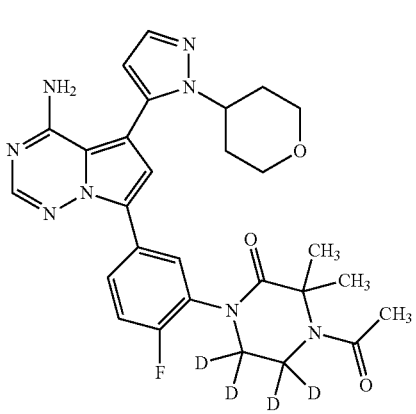 [SMILES: [2H]C1([2H])N(c2cc(-c3cc(-c4ccnn4C4CCOCC4)c4c(N)ncnn34)ccc2F)C(=O)C(C)(C)N(C(C)=O)C1([2H])[2H]] | 4-acetyl-1-(5-(4-amino-5-(1-(tetrahydro-2H-pyran-4-yl)-1H-pyrazol-5-yl)-pyrrolo[2,1-f][1,2,4]triazin-7-yl)-2-fluoro-phenyl)-3,3-dimethyl-5,5,6,6-tetradeuteropiperazin-2-one | 552 |

TABLE 48-continued

| Ex. No. | Structure | Name | M + H |
|---|---|---|---|
| 633 | 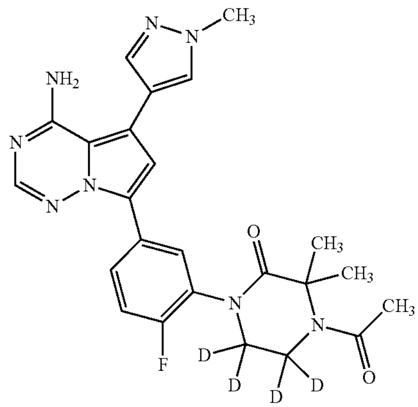 [SMILES: [2H]C1([2H])N(c2cc(-c3cc(-c4cnn(C)c4)c4c(N)ncnn34)ccc2F)C(=O)C(C)(C)N(C(C)=O)C1([2H])[2H]] | 4-acetyl-1-(5-(4-amino-5-(1-methyl-1H-pyrazol-4-yl)pyrrolo[2,1-f][1,2,4]triazin-7-yl)-2-fluorophenyl)-3,3-dimethyl-5,5,6,6-tetradeuteropiperazin-2-one | 482 |
| 634 | 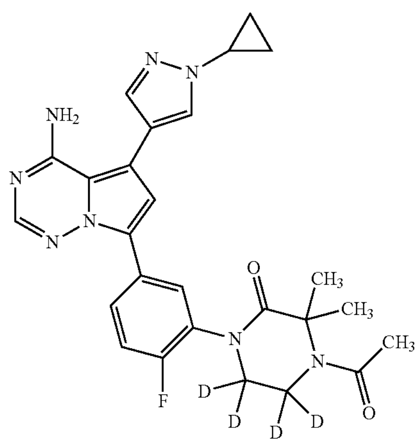 [SMILES: [2H]C1([2H])N(c2cc(-c3cc(-c4cnn(C5CC5)c4)c4c(N)ncnn34)ccc2F)C(=O)C(C)(C)N(C(C)=O)C1([2H])[2H]] | 4-acetyl-1-(5-(4-amino-5-(1-cyclopropyl-1H-pyrazol-4-yl)pyrrolo[2,1-f][1,2,4]triazin-7-yl)-2-fluorophenyl)-3,3-dimethyl-5,5,6,6-tetradeuteropiperazin-2-one | 508 |
| 635 | 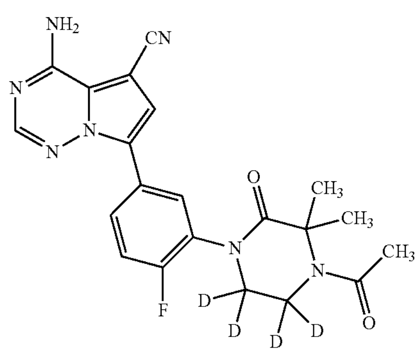 [SMILES: [2H]C1([2H])N(c2cc(-c3cc(C#N)c4c(N)ncnn34)ccc2F)C(=O)C(C)(C)N(C(C)=O)C1([2H])[2H]] | 7-(3-(4-acetyl-3,3-dimethyl-2-oxo-5,5,6,6-tetradeuteropiperazin-1-yl)-4-fluorophenyl)-4-aminopyrrolo[2,1-f][1,2,4]triazine-5-carbonitrile | 426 |
| 636 | 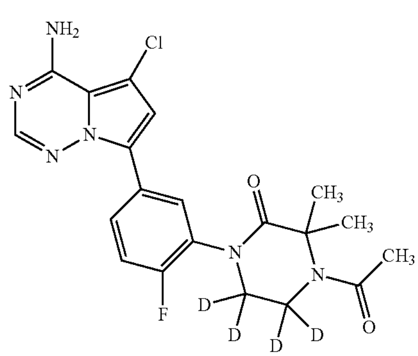 [SMILES: [2H]C1([2H])N(c2cc(-c3cc(Cl)c4c(N)ncnn34)ccc2F)C(=O)C(C)(C)N(C(C)=O)C1([2H])[2H]] | 4-acetyl-1-(5-(4-amino-5-chloropyrrolo[2,1-f][1,2,4]triazin-7-yl)-2-fluorophenyl)-3,3-dimethyl-5,5,6,6-tetradeuteropiperazin-2-one | 436 |

TABLE 48-continued

| Ex. No. | Structure | Name | M + H |
|---|---|---|---|
| 637 | 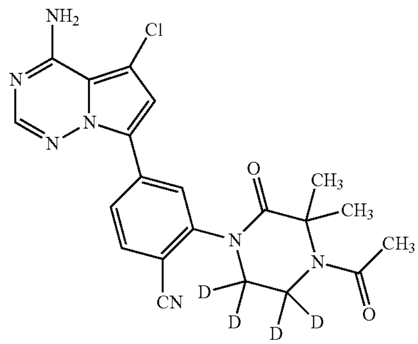 [SMILES: [2H]C1([2H])N(c2cc(-c3cc(Cl)c4c(N)ncnn34)ccc2C#N)C(=O)C(C)(C)N(C(C)=O)C1([2H])[2H]] | 2-(4-acetyl-3,3-dimethyl-2-oxo-5,5,6,6-tetradeuteropiperazin-1-yl)-4-(4-amino-5-chloropyrrolo[2,1-f][1,2,4]triazin-7-yl)benzonitrile | 443 |
| 638 | 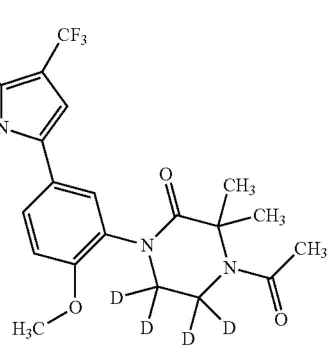 | 4-acetyl-1-(5-(4-amino-5-(trifluoromethyl)pyrrolo[2,1-f][1,2,4]triazin-7-yl)-2-methoxyphenyl)-3,3-dimethyl-5,5,6,6-tetradeuteropiperazin-2-one | 481 |
| 639 | 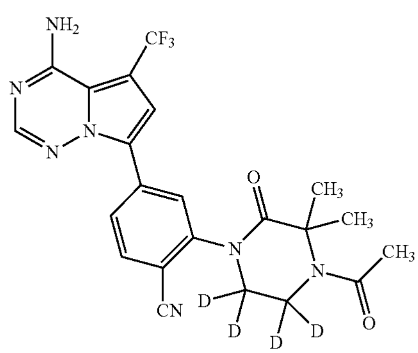 [SMILES: [2H]C1([2H])N(c2cc(-c3cc(C(F)(F)F)c4c(N)ncnn34)ccc2C#N)C(=O)C(C)(C)N(C(C)=O)C1([2H])[2H]] | 2-(4-acetyl-3,3-dimethyl-2-oxo-5,5,6,6-tetradeuteropiperazin-1-yl)-4-(4-amino-5-(trifluoromethyl)pyrrolo[2,1-f][1,2,4]triazin-7-yl)benzonitrile | 476 |
| 640 | 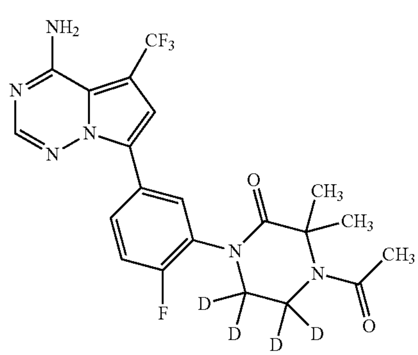 | 4-acetyl-1-(5-(4-amino-5-(trifluoromethyl)pyrrolo[2,1-f][1,2,4]triazin-7-yl)-2-fluorophenyl)-3,3-dimethyl-5,5,6,6-tetradeuteropiperazin-2-one | 469 |

TABLE 48-continued

| Ex. No. | Structure | Name | M + H |
|---|---|---|---|
| 641 | 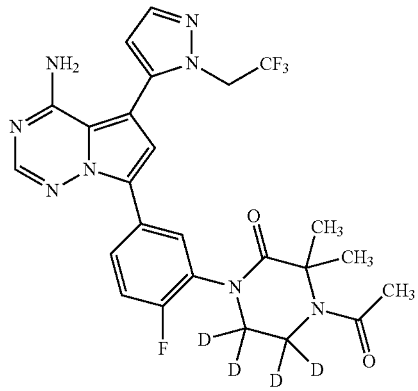 [SMILES: [2H]C1([2H])N(c2cc(-c3cc(-c4ccnn4CC(F)(F)F)c4c(N)ncnn34)ccc2F)C(=O)C(C)(C)N(C(C)=O)C1([2H])[2H]] | 4-acetyl-1-(5-(4-amino-5-(1-(2,2,2-trifluoroethyl)-1H-pyrazol-5-yl)pyrrolo[2,1-f][1,2,4]triazin-7-yl)-2-fluorophenyl)-3,3-dimethyl-5,5,6,6-tetradeuteropiperazin-2-one | 550 |
| 642 | 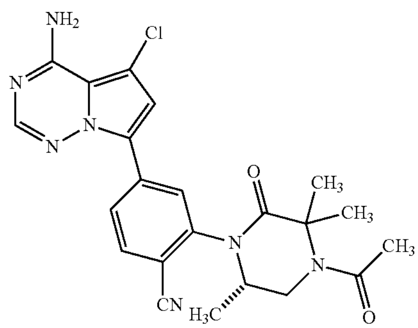 [SMILES: CC(=O)N1C[C@H](C)N(c2cc(-c3cc(Cl)c4c(N)ncnn34)ccc2C#N)C(=O)C1(C)C] | (S)-2-(4-acetyl-3,3,6-trimethyl-2-oxopiperazin-1-yl)-4-(4-amino-5-chloropyrrolo[2,1-f][1,2,4]triazin-7-yl)benzonitrile | 453 |
| 643 | 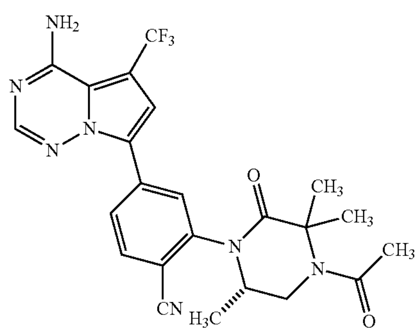 [SMILES: CC(=O)N1C[C@H](C)N(c2cc(-c3cc(C(F)(F)F)c4c(N)ncnn34)ccc2C#N)C(=O)C1(C)C] | (S)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile | 486 |
| 644 | 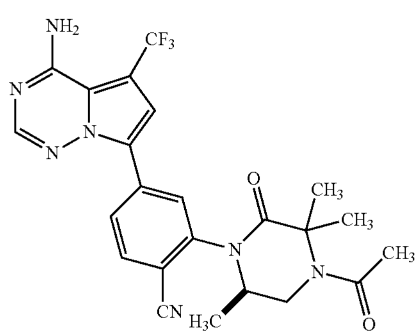 [SMILES: CC(=O)N1C[C@@H](C)N(c2cc(-c3cc(C(F)(F)F)c4c(N)ncnn34)ccc2C#N)C(=O)C1(C)C] | (R)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile | 486 |

TABLE 48-continued

| Ex. No. | Structure | Name | M + H |
|---|---|---|---|
| 645 | 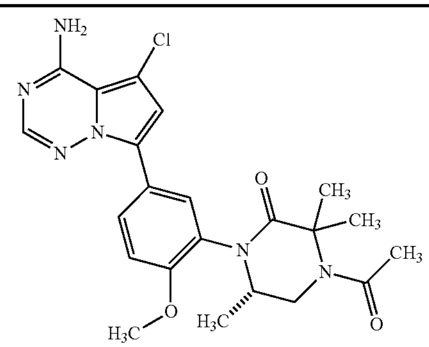 | (S)-4-acetyl-1-(5-(4-amino-5-chloropyrrolo[2,1-f][1,2,4]triazin-7-yl)-2-methoxyphenyl)-3,3,6-trimethylpiperazin-2-one | 458 |
| 646 | 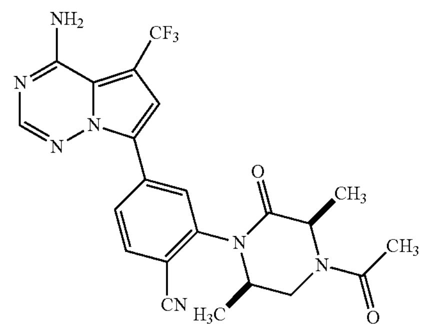 [SMILES: CC(=O)N1C[C@@H](C)N(c2cc(-c3cc(C(F)(F)F)c4c(N)ncnn34)ccc2C#N)C(=O)[C@H]1C] | 2-((3R,6R)-4-acetyl-3,6-dimethyl-2-oxopiperazin-1-yl)-4-(4-amino-5-(trifluoromethyl)pyrrolo[2,1-f][1,2,4]triazin-7-yl)benzonitrile | 472 |
| 647 | 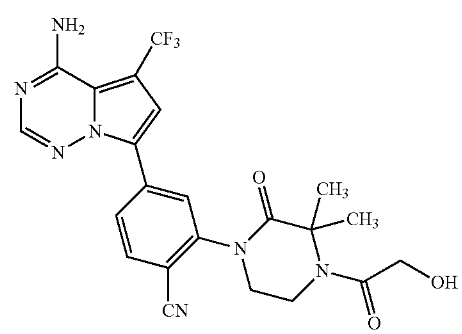 [SMILES: CC1(C)C(=O)N(c2cc(-c3cc(C(F)(F)F)c4c(N)ncnn34)ccc2C#N)CCN1C(=O)CO] | 4-(4-amino-5-(trifluoromethyl)pyrrolo[2,1-f][1,2,4]triazin-7-yl)-2-(4-(2-hydroxyacetyl)-3,3-dimethyl-2-oxopiperazin-1-yl)benzonitrile | 488 |
| 648 | 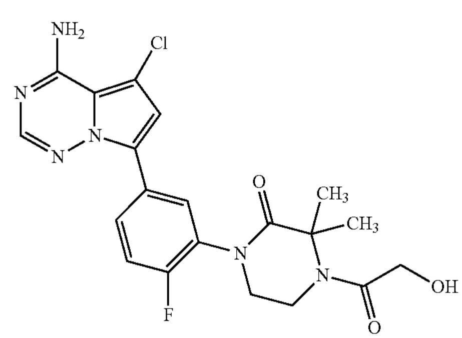 [SMILES: CC1(C)C(=O)N(c2cc(-c3cc(Cl)c4c(N)ncnn34)ccc2F)CCN1C(=O)CO] | 1-(5-(4-amino-5-chloropyrrolo[2,1-f][1,2,4]triazin-7-yl)-2-fluorophenyl)-4-(2-hydroxyacetyl)-3,3-dimethylpiperazin-2-one | 448 |

TABLE 48-continued

| Ex. No. | Structure | Name | M + H |
|---|---|---|---|
| 649 | 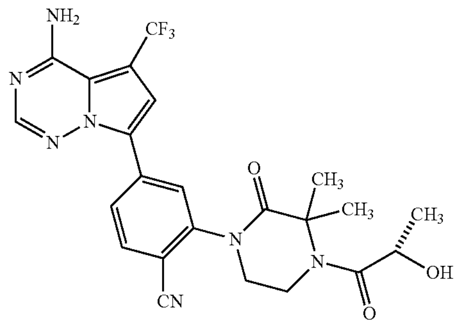 [SMILES: C[C@H](O)C(=O)N1CCN(c2cc(-c3cc(C(F)(F)F)c4c(N)ncnn34)ccc2C#N)C(=O)C1(C)C] | (S)-4-(4-amino-5-(trifluoromethyl)pyrrolo[2,1-f][1,2,4]triazin-7-yl)-2-(4-(2-hydroxypropanoyl)-3,3-dimethyl-2-oxopiperazin-1-yl)benzonitrile | 502 |
| 650 | 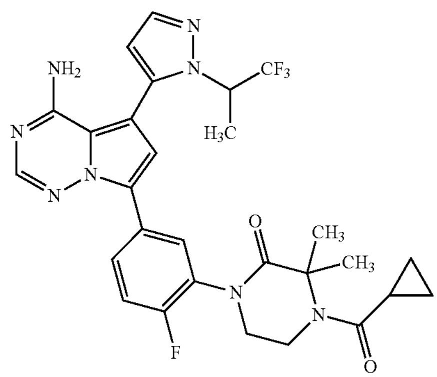 [SMILES: CC(n1nccc1-c1cc(-c2ccc(F)c(N3CCN(C(=O)C4CC4)C(C)(C)C3=O)c2)n2ncnc(N)c12)C(F)(F)F] | 1-(5-(4-amino-5-(1-(1,1,1-trifluoropropan-2-yl)-1H-pyrazol-5-yl)pyrrolo[2,1-f][1,2,4]triazin-7-yl)-2-fluorophenyl)-4-(cyclopropanecarbonyl)-3,3-dimethylpiperazin-2-one (chiral) | 586 |
| 651 | 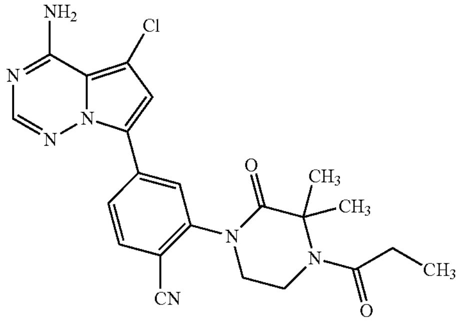 [SMILES: CCC(=O)N1CCN(c2cc(-c3cc(Cl)c4c(N)ncnn34)ccc2C#N)C(=O)C1(C)C] | 4-(4-amino-5-chloropyrrolo[2,1-f][1,2,4]triazin-7-yl)-2-(3,3-dimethyl-2-oxo-4-propionylpiperazin-1-yl)benzonitrile | 453 |
| 652 | 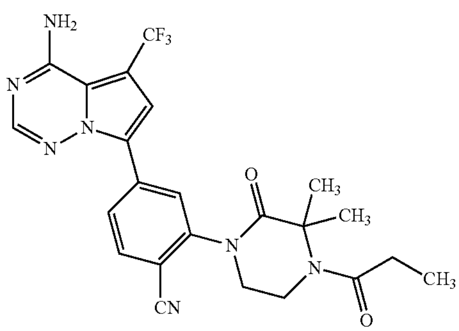 [SMILES: CCC(=O)N1CCN(c2cc(-c3cc(C(F)(F)F)c4c(N)ncnn34)ccc2C#N)C(=O)C1(C)C] | 4-(4-amino-5-(trifluoromethyl)pyrrolo[2,1-f][1,2,4]triazin-7-yl)-2-(3,3-dimethyl-2-oxo-4-propionylpiperazin-1-yl)benzonitrile | 486 |

TABLE 48-continued

| Ex. No. | Structure | Name | M + H |
|---|---|---|---|
| 653 | 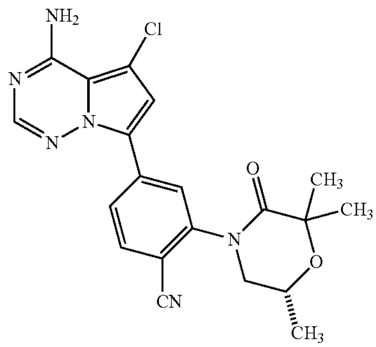 [SMILES: C[C@@H]1CN(c2cc(-c3cc(Cl)c4c(N)ncnn34)ccc2C#N)C(=O)C(C)(C)O1] | (R)-4-(4-amino-5-chloropyrrolo[2,1-f][1,2,4]triazin-7-yl)-2-(2,2,6-trimethyl-3-oxomorpholino)benzonitrile | 412 |
| 654 | 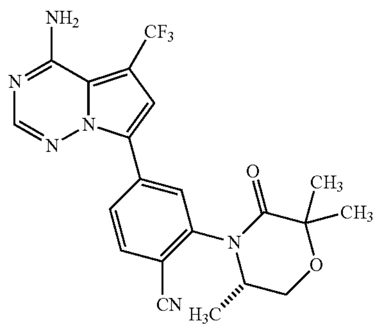 [SMILES: C[C@H]1COC(C)(C)C(=O)N1c1cc(-c2cc(C(F)(F)F)c3c(N)ncnn23)ccc1C#N] | (S)-4-(4-amino-5-(trifluoromethyl)pyrrolo[2,1-f][1,2,4]triazin-7-yl)-2-(2,2,5-trimethyl-3-oxomorpholino)benzonitrile | 445 |
| 655 | 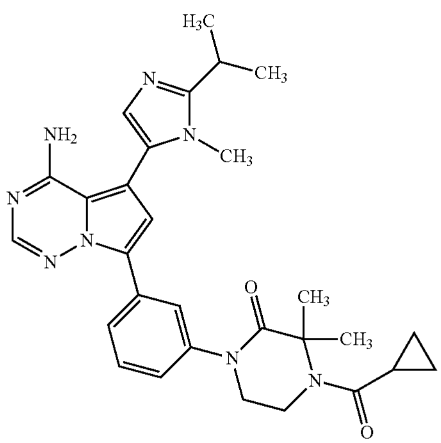 [SMILES: CC(C)c1ncc(-c2cc(-c3cccc(N4CCN(C(=O)C5CC5)C(C)(C)C4=O)c3)n3ncnc(N)c23)n1C] | 1-(3-(4-amino-5-(2-isopropyl-1-methyl-1H-imidazol-5-yl)pyrrolo[2,1-f][1,2,4]triazin-7-yl)phenyl)-4-(cyclopropanecarbonyl)-3,3-dimethylpiperazin-2-one | 527 |
| 656 | 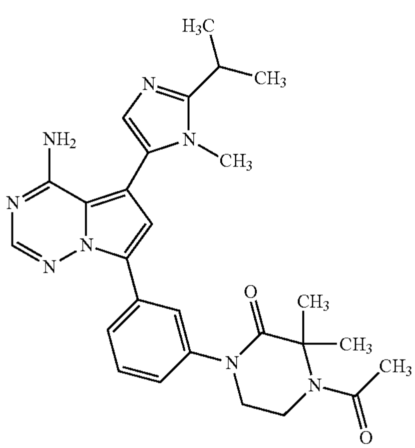 [SMILES: CC(=O)N1CCN(c2cccc(-c3cc(-c4cnc(C(C)C)n4C)c4c(N)ncnn34)c2)C(=O)C1(C)C] | 4-acetyl-1-(3-(4-amino-5-(2-isopropyl-1-methyl-1H-imidazol-5-yl)pyrrolo[2,1-f][1,2,4]triazin-7-yl)phenyl)-3,3-dimethylpiperazin-2-one | 501 |

TABLE 48-continued

| Ex. No. | Structure | Name | M + H |
|---|---|---|---|
| 657 | 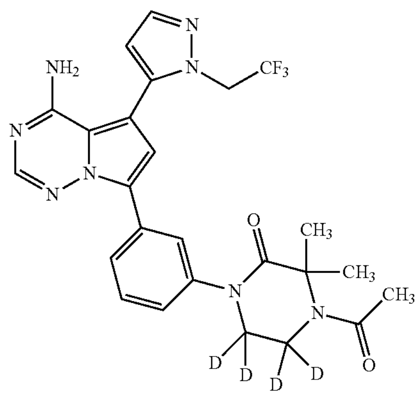 [SMILES: [2H]C1([2H])N(c2cccc(-c3cc(-c4ccnn4CC(F)(F)F)c4c(N)ncnn34)c2)C(=O)C(C)(C)N(C(C)=O)C1([2H])[2H]] | 4-acetyl-1-(3-(4-amino-5-(1-(2,2,2-trifluoroethyl)-1H-pyrazol-5-yl)pyrrolo[2,1-f][1,2,4]triazin-7-yl)phenyl)-3,3-dimethyl-5,5,6,6-tetradeuteropiperazin-2-one | 531 |
| 658 | 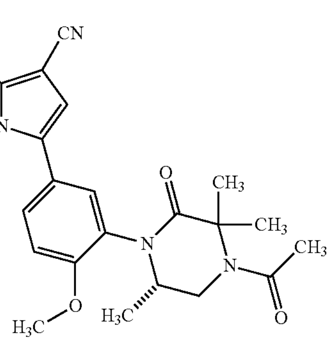 | (S)-7-(3-(4-acetyl-3,3,6-trimethyl-2-oxopiperazin-1-yl)-4-methoxyphenyl)-4-aminopyrrolo[2,1-f][1,2,4]triazine-5-carbonitrile | 448 |
| 659 | 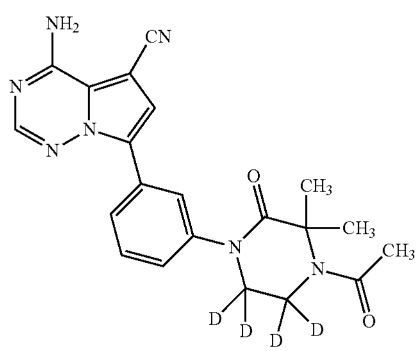 [SMILES: [2H]C1([2H])N(c2cccc(-c3cc(C#N)c4c(N)ncnn34)c2)C(=O)C(C)(C)N(C(C)=O)C1([2H])[2H]] | 7-(3-(4-acetyl-3,3-dimethyl-2-oxo-5,5,6,6-tetradeutero-piperazin-1-yl)phenyl)-4-aminopyrrolo[2,1-f][1,2,4]triazine-5-carbonitrile | 408 |
| 660 | 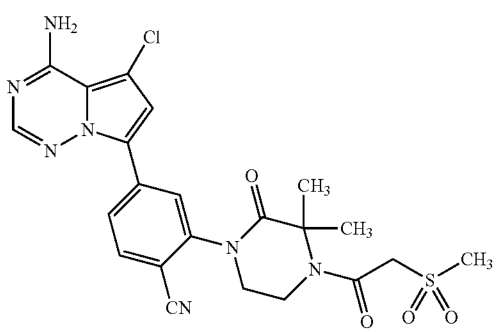 [SMILES: CC1(C)C(=O)N(c2cc(-c3cc(Cl)c4c(N)ncnn34)ccc2C#N)CCN1C(=O)CS(C)(=O)=O] | 4-(4-amino-5-chloropyrrolo[2,1-f][1,2,4]triazin-7-yl)-2-(3,3-dimethyl-4-(2-(methylsulfonyl)acetyl)-2-oxopiperazin-1-yl)benzonitrile | 517 |

TABLE 48-continued

| Ex. No. | Structure | Name | M + H |
|---|---|---|---|
| 661 | 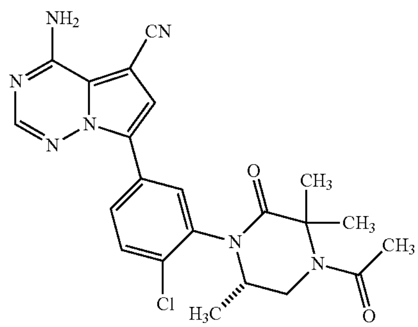 [SMILES: CC(=O)N1C[C@H](C)N(c2cc(-c3cc(C#N)c4c(N)ncnn34)ccc2Cl)C(=O)C1(C)C] | (S)-7-(3-(4-acetyl-3,3,6-trimethyl-2-oxopiperazin-1-yl)-4-chlorophenyl)-4-aminopyrrolo[2,1-f][1,2,4]triazine-5-carbonitrile | 453 |
| 662 | 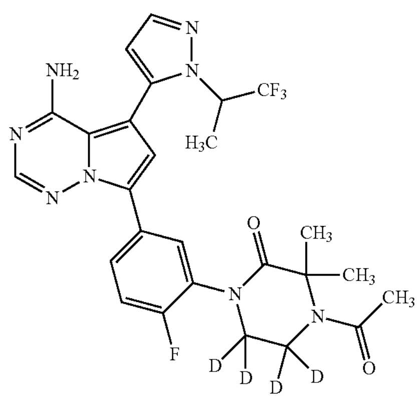 [SMILES: [2H]C1([2H])N(c2cc(-c3cc(-c4ccnn4C(C)C(F)(F)F)c4c(N)ncnn34)ccc2F)C(=O)C(C)(C)N(C(C)=O)C1([2H])[2H]] | 4-acetyl-1-(3-(4-amino-5-(1-(1,1,1-trifluoropropan-2-yl)-1H-pyrazol-5-yl)pyrrolo[2,1-f][1,2,4]triazin-7-yl)-2-fluorophenyl)-3,3-dimethyl-5,5,6,6-tetradeuteropiperazin-2-one (chiral) | 564 |
| 663 | 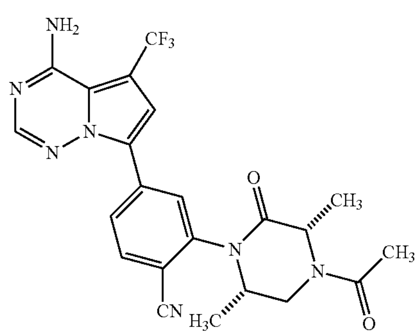 [SMILES: CC(=O)N1C[C@H](C)N(c2cc(-c3cc(C(F)(F)F)c4c(N)ncnn34)ccc2C#N)C(=O)[C@@H]1C] | 2-((3S,6S)-4-acetyl-3,6-dimethyl-2-oxopiperazin-1-yl)-4-(4-amino-5-(trifluoromethyl)pyrrolo[2,1-f][1,2,4]triazin-7-yl)benzonitrile | 472 |

TABLE 49

| Ex. No. | Structure | Name | M + H |
|---|---|---|---|
| 664 | 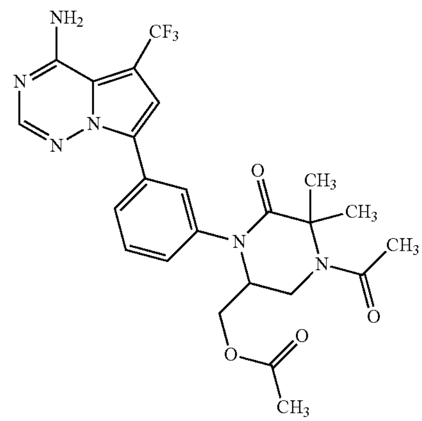 [SMILES: CC(=O)OCC1CN(C(C)=O)C(C)(C)C(=O)N1c1cccc(-c2cc(C(F)(F)F)c3c(N)ncnn23)c1] | (4-acetyl-1-(3-(4-amino-5-(trifluoromethyl)pyrrolo[2,1-f][1,2,4]triazin-7-yl)phenyl)-5,5-dimethyl-6-oxopiperazin-2-yl)methyl acetate | 518 |
| 665 | 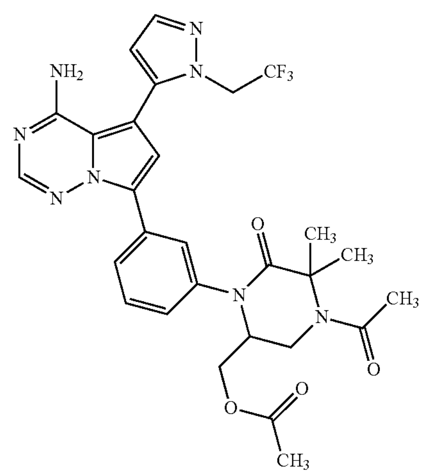 [SMILES: CC(=O)OCC1CN(C(C)=O)C(C)(C)C(=O)N1c1cccc(-c2cc(-c3ccnn3CC(F)(F)F)c3c(N)ncnn23)c1] | (4-acetyl-1-(3-(4-amino-5-(1-(2,2,2-trifluoroethyl)-1H-pyrazol-5-yl)pyrrolo[2,1-f][1,2,4]triazin-7-yl)phenyl)-5,5-dimethyl-6-oxopiperazin-2-yl)methyl acetate | 599 |
| 666 | 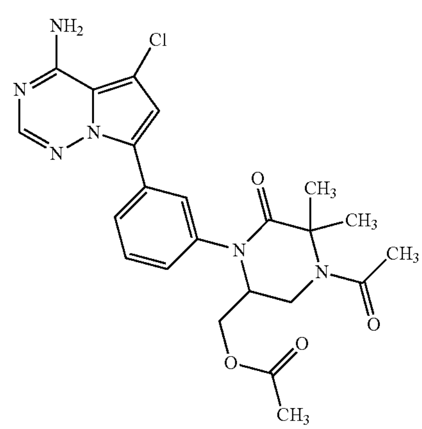 [SMILES: CC(=O)OCC1CN(C(C)=O)C(C)(C)C(=O)N1c1cccc(-c2cc(Cl)c3c(N)ncnn23)c1] | (4-acetyl-1-(3-(4-amino-5-chloropyrrolo[2,1-f][1,2,4]triazin-7-yl)phenyl)-5,5-dimethyl-6-oxopiperazin-2-yl)methyl acetate | 531 |

| Ex. No. | Structure | Name | M + H |
|---|---|---|---|
| 667 | 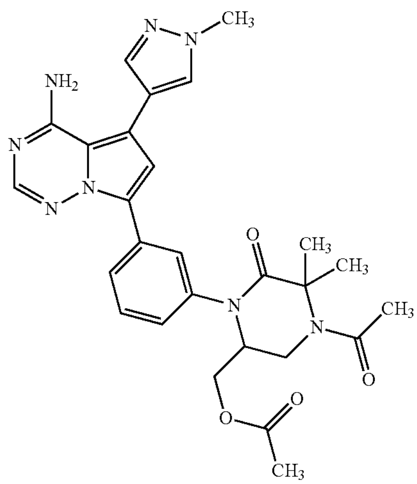 [SMILES: CC(=O)OCC1CN(C(C)=O)C(C)(C)C(=O)N1c1cccc(-c2cc(-c3cnn(C)c3)c3c(N)ncnn23)c1] | (4-acetyl-1-(3-(4-amino-5-(1-methyl-1H-pyrazol-4-yl)pyrrolo[2,1-f][1,2,4]triazin-7-yl)phenyl)-5,5-dimethyl-6-oxopiperazin-2-yl)methyl acetate | 530 |
| 668 | 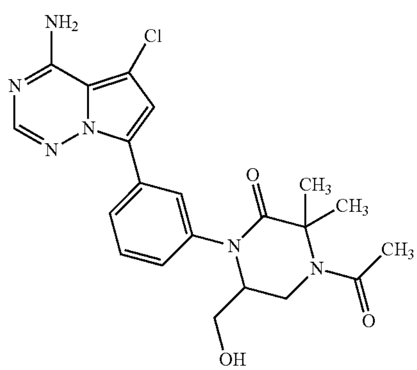 [SMILES: CC(=O)N1CC(CO)N(c2cccc(-c3cc(Cl)c4c(N)ncnn34)c2)C(=O)C1(C)C] | 4-acetyl-1-(3-(4-amino-5-chloropyrrolo[2,1-f][1,2,4]triazin-7-yl)phenyl)-6-(hydroxymethyl)-3,3-dimethylpiperazin-2-one | 443 |
| 669 | 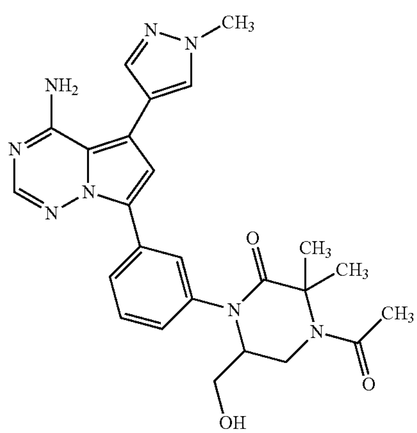 [SMILES: CC(=O)N1CC(CO)N(c2cccc(-c3cc(-c4cnn(C)c4)c4c(N)ncnn34)c2)C(=O)C1(C)C] | 4-acetyl-1-(3-(4-amino-5-(1-methyl-1H-pyrazol-4-yl)pyrrolo[2,1-f][1,2,4]triazin-7-yl)phenyl)-6-(hydroxymethyl)-3,3-dimethylpiperazin-2-one | 489 |

TABLE 49-continued

| Ex. No. | Structure | Name | M + H |
|---|---|---|---|
| 670 | 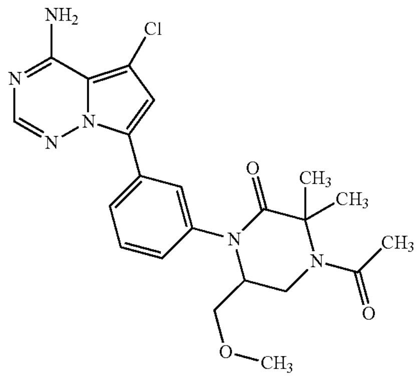 [SMILES: COCC1CN(C(C)=O)C(C)(C)C(=O)N1c1cccc(-c2cc(Cl)c3c(N)ncnn23)c1] | 4-acetyl-1-(3-(4-amino-5-chloropyrrolo[2,1-f][1,2,4]triazin-7-yl)phenyl)-6-(methoxymethyl)-3,3-dimethylpiperazin-2-one | 457 |
| 671 | 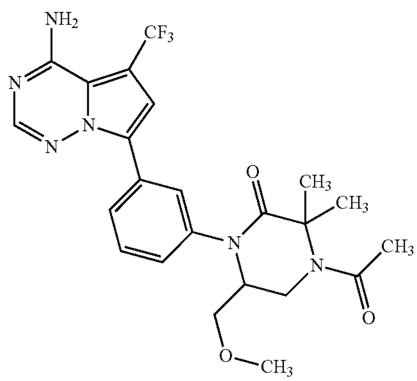 [SMILES: COCC1CN(C(C)=O)C(C)(C)C(=O)N1c1cccc(-c2cc(C(F)(F)F)c3c(N)ncnn23)c1] | 4-acetyl-1-(3-(4-amino-5-(trifluoromethyl)pyrrolo[2,1-f][1,2,4]triazin-7-yl)phenyl)-6-(methoxymethyl)-3,3-dimethylpiperazin-2-one | 490 |
| 672 | 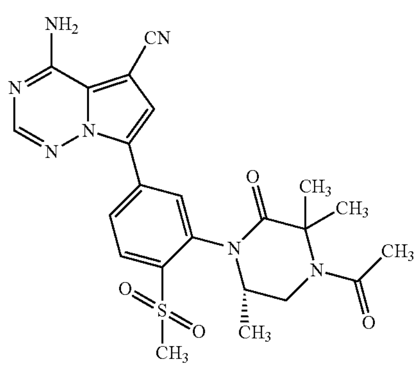 | (S)-7-(3-(4-acetyl-3,3,6-trimethyl-2-oxopiperazin-1-yl)-4-(methylsulfonyl)phenyl)-4-aminopyrrolo[2,1-f][1,2,4]triazine-5-carbonitrile | 496 |
| 673 | 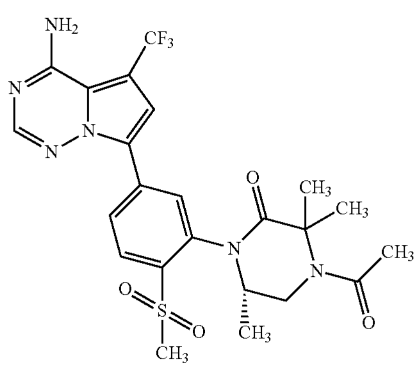 [SMILES: CC(=O)N1C[C@H](C)N(c2cc(-c3cc(C#N)c4c(N)ncnn34)ccc2S(C)(=O)=O)C(=O)C1(C)C] | (S)-4-acetyl-1-(5-(4-amino-5-(trifluoromethyl)pyrrolo[2,1-f][1,2,4]triazin-7-yl)-2-(methylsulfonyl)phenyl)-3,3,6-trimethylpiperazin-2-one | 539 |

TABLE 49-continued

| Ex. No. | Structure | Name | M + H |
|---|---|---|---|
| 674 | 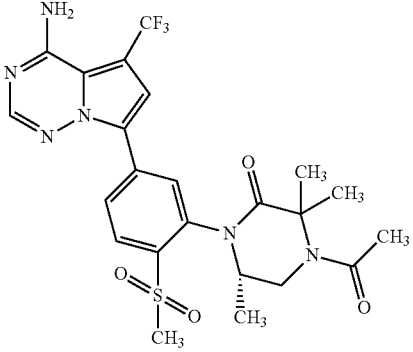 | (S)-4-acetyl-1-(5-(4-amino-5-(trifluoromethyl)pyrrolo[2,1-f][1,2,4]triazin-7-yl)-2-(methylsulfonyl)phenyl)-3,3,6-trimethylpiperazin-2-one | 539 |
| 675 | 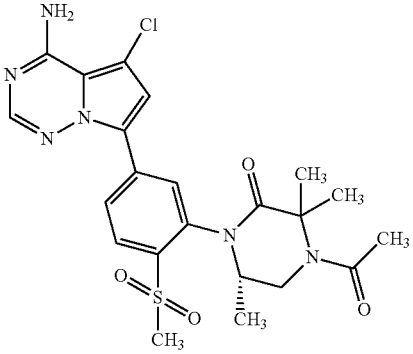 [SMILES: CC(=O)N1C[C@H](C)N(c2cc(-c3cc(Cl)c4c(N)ncnn34)ccc2S(C)(=O)=O)C(=O)C1(C)C] | (S)-4-acetyl-1-(5-(4-amino-5-chloropyrrolo[2,1-f][1,2,4]triazin-7-yl)-2-(methylsulfonyl)phenyl)-3,3,6-trimethylpiperazin-2-one | 505 |
| 676 | 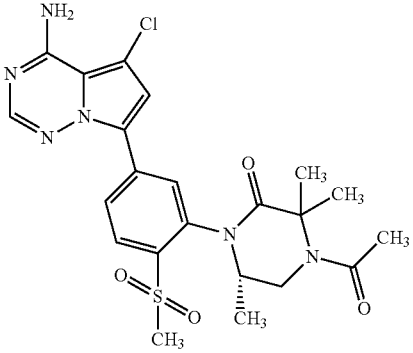 [SMILES: CC(=O)N1C[C@H](C)N(c2cc(-c3cc(Cl)c4c(N)ncnn34)ccc2S(C)(=O)=O)C(=O)C1(C)C] | (S)-4-acetyl-1-(5-(4-amino-5-chloropyrrolo[2,1-f][1,2,4]triazin-7-yl)-2-(methylsulfonyl)phenyl)-3,3,6-trimethylpiperazin-2-one | 505 |
| 677 | 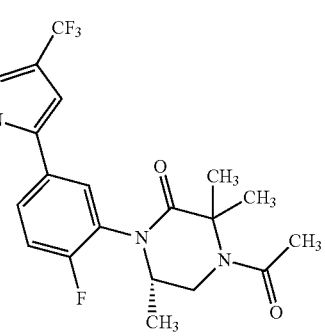 | (S)-4-acetyl-1-(5-(4-amino-5-(trifluoromethyl)pyrrolo[2,1-f][1,2,4]triazin-7-yl)-2-fluorophenyl)-3,3,6-trimethylpiperazin-2-one | 478 |

TABLE 49-continued

| Ex. No. | Structure | Name | M + H |
|---|---|---|---|
| 678 | 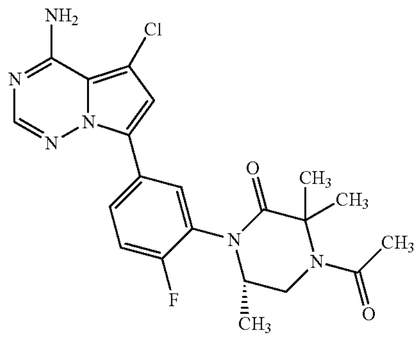 [SMILES: CC(=O)N1C[C@H](C)N(c2cc(-c3cc(Cl)c4c(N)ncnn34)ccc2F)C(=O)C1(C)C] | (S)-4-acetyl-1-(5-(4-amino-5-chloropyrrolo[2,1-f][1,2,4]triazin-7-yl)-2-fluorophenyl)-3,3,6-trimethylpiperazin-2-one | 445 |
| 679 | 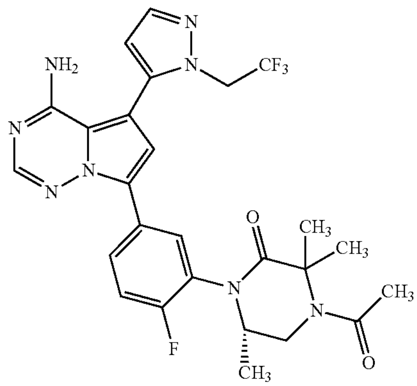 [SMILES: CC(=O)N1C[C@H](C)N(c2cc(-c3cc(-c4ccnn4CC(F)(F)F)c4c(N)ncnn34)ccc2F)C(=O)C1(C)C] | (S)-4-acetyl-1-(5-(4-amino-5-(1-(2,2,2-trifluoroethyl)-1H-pyrazol-5-yl)pyrrolo[2,1-f][1,2,4]triazin-7-yl)-2-fluorophenyl)-3,3,6-trimethylpiperazin-2-one | 559 |
| 680 | 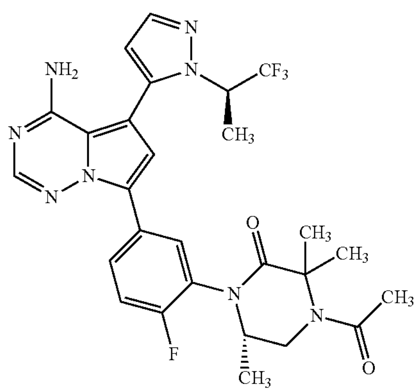 [SMILES: CC(=O)N1C[C@H](C)N(c2cc(-c3cc(-c4ccnn4[C@H](C)C(F)(F)F)c4c(N)ncnn34)ccc2F)C(=O)C1(C)C] | (S)-4-acetyl-1-(5-(4-amino-5-(1-((R)-1,1,1-trifluoropropan-2-yl)-1H-pyrazol-5-yl)pyrrolo[2,1-f][1,2,4]triazin-7-yl)-2-fluoropehnyl)-3,3,6-trimethylpiperazin-2-one | 573 |
| 681 | 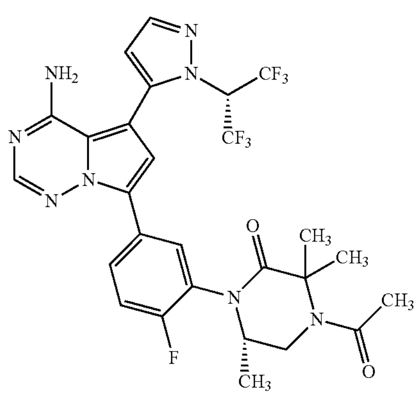 | (S)-4-acetyl-1-(5-(4-amino-5-(1-((S)-1,1,1-trifluoropropan-2-yl)-1H-pyrazol-5-yl)pyrrolo[2,1-f][1,2,4]triazin-7-yl)-2-fluorophenyl)-3,3,6-trimethylpiperazin-2-one | 573 |

TABLE 49-continued

| Ex. No. | Structure | Name | M + H |
|---|---|---|---|
| 682 | 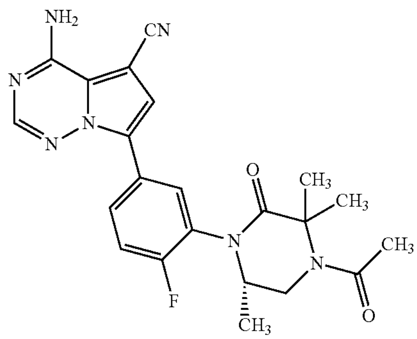 [SMILES: CC(=O)N1C[C@H](C)N(c2cc(-c3cc(C#N)c4c(N)ncnn34)ccc2F)C(=O)C1(C)C] | (S)-7-(3-(4-acetyl-3,3,6-trimethyl-2-oxopiperazin-1-yl)-4-fluorophenyl)-4-aminopyrrolo[2,1-f][1,2,4]triazine-5-carbonitrile | 435 |
| 683 | 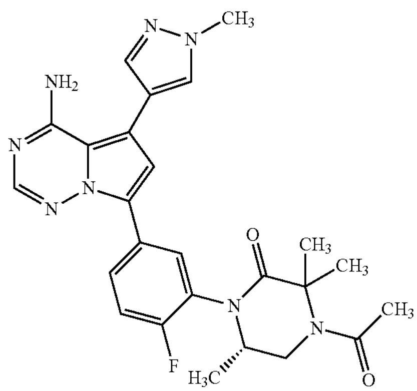 [SMILES: CC(=O)N1C[C@H](C)N(c2cc(-c3cc(-c4cnn(C)c4)c4c(N)ncnn34)ccc2F)C(=O)C1(C)C] | (S)-4-acetyl-1-(5-(4-amino-5-(1-methyl-1H-pyrazol-4-yl)pyrrolo[2,1-f][1,2,4]triazin-7-yl)-2-fluorophenyl)-3,3,6-trimethylpiperazin-2-one | 491 |
| 684 | 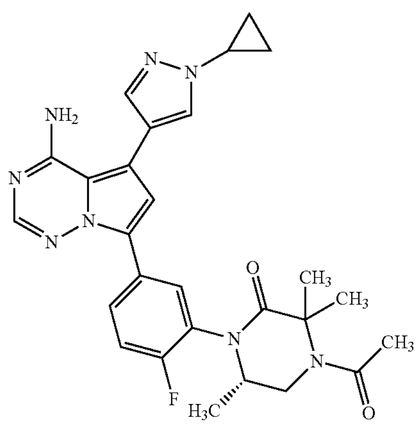 [SMILES: CC(=O)N1C[C@H](C)N(c2cc(-c3cc(-c4cnn(C5CC5)c4)c4c(N)ncnn34)ccc2F)C(=O)C1(C)C] | (S)-4-acetyl-1-(5-(4-amino-5-(1-cyclopropyl-1H-pyrazol-4-yl)pyrrolo[2,1-f][1,2,4]triazin-7-yl)-2-fluorophenyl)-3,3,6-trimethylpiperazin-2-one | 517 |
| 685 | 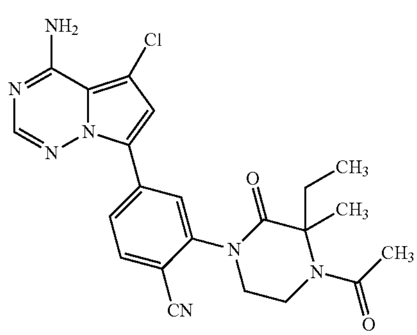 [SMILES: CCC1(C)C(=O)N(c2cc(-c3cc(Cl)c4c(N)ncnn34)ccc2C#N)CCN1C(C)=O] | 2-(4-acetyl-3-ethyl-3-methyl-2-oxopiperazin-1-yl)-4-(4-amino-5-chloropyrrolo[2,1-f][1,2,4]triazin-7-yl)benzonitrile | 452 |

TABLE 49-continued

| Ex. No. | Structure | Name | M + H |
|---|---|---|---|
| 686 | 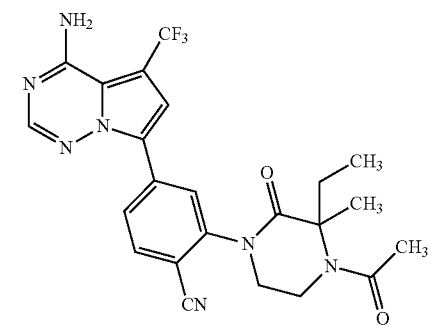 [SMILES: CCC1(C)C(=O)N(c2cc(-c3cc(C(F)(F)F)c4c(N)ncnn34)ccc2C#N)CCN1C(C)=O] | 2-(4-acetyl-3-ethyl-3-methyl-2-oxopiperazin-1-yl)-4-(4-amino-5-(trifluoromethyl)pyrrolo[2,1-f][1,2,4]triazin-7-yl)benzonitrile | 485 |
| 687 | 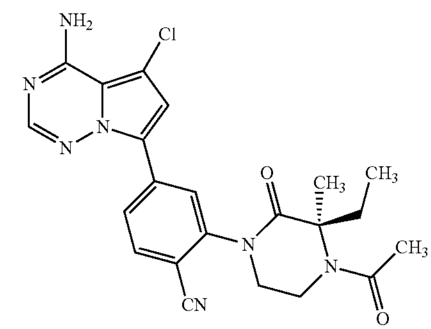 [SMILES: CC[C@]1(C)C(=O)N(c2cc(-c3cc(Cl)c4c(N)ncnn34)ccc2C#N)CCN1C(C)=O] | (R)-2-(4-acetyl-3-ethyl-3-methyl-2-oxopiperazin-1-yl)-4-(4-amino-5-chloropyrrolo[2,1-f][1,2,4]triazin-7-yl)benzonitrile | 452 |
| 689 | 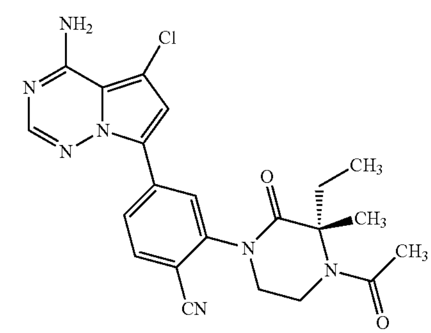 [SMILES: CC[C@@]1(C)C(=O)N(c2cc(-c3cc(Cl)c4c(N)ncnn34)ccc2C#N)CCN1C(C)=O] | (S)-2-(4-acetyl-3-ethyl-3-methyl-2-oxopiperazin-1-yl)-4-(4-amino-5-chloropyrrolo[2,1-f][1,2,4]triazin-7-yl)benzonitrile | 452 |
| 690 | 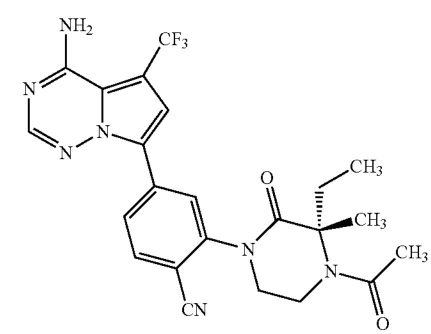 [SMILES: CC[C@@]1(C)C(=O)N(c2cc(-c3cc(C(F)(F)F)c4c(N)ncnn34)ccc2C#N)CCN1C(C)=O] | (S)-2-(4-acetyl-3-ethyl-3-methyl-2-oxopiperazin-1-yl)-4-(4-amino-5-(trifluoromethyl)pyrrolo[2,1-f][1,2,4]triazin-7-yl)benzonitrile | 485 |

TABLE 49-continued

| Ex. No. | Structure | Name | M + H |
|---|---|---|---|
| 691 | 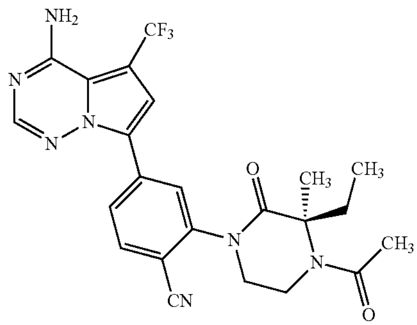 [SMILES: CC[C@]1(C)C(=O)N(c2cc(-c3cc(C(F)(F)F)c4c(N)ncnn34)ccc2C#N)CCN1C(C)=O] | (R)-2-(4-acetyl-3-ethyl-3-methyl-2-oxopiperazin-1-yl)-4-(4-amino-5-(trifluoromethyl)pyrrolo[2,1-f][1,2,4]triazin-7-yl)benzonitrile | 485 |
| 692 | 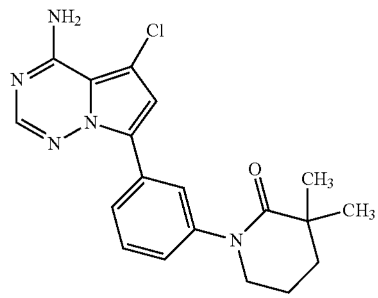 [SMILES: CC1(C)CCCN(c2cccc(-c3cc(Cl)c4c(N)ncnn34)c2)C1=O] | 1-(3-(4-amino-5-chloropyrrolo[2,1-f][1,2,4]triazin-7-yl)phenyl)-3,3-diemthylpiperidin-2-one | 370 |
| 693 | 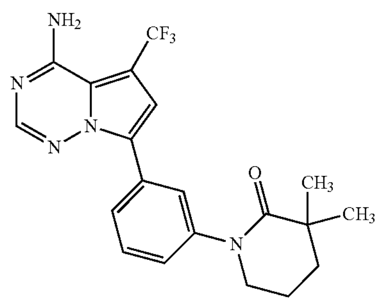 [SMILES: CC1(C)CCCN(c2cccc(-c3cc(C(F)(F)F)c4c(N)ncnn34)c2)C1=O] | 1-(3-(4-amio-5-(trifluoromethyl)pyrrolo[2,1-f][1,2,4]triazin-7-yl)phenyl)-3,3-dimethylpiperidin-2-one | 403 |
| 694 | 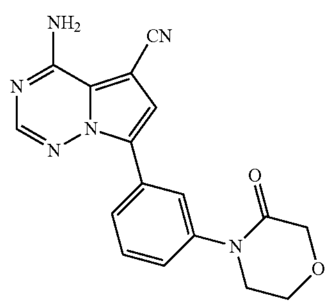 [SMILES: N#Cc1cc(-c2cccc(N3CCOCC3=O)c2)n2ncnc(N)c12] | 4-amino-7-(3-(3-oxomorpholino)phenyl)pyrrolo[2,1-f][1,2,4]triazine-5-carbonitrile | 334 |
| 695 | 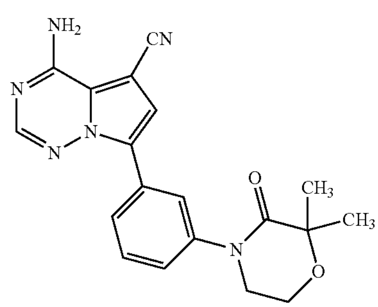 [SMILES: CC1(C)OCCN(c2cccc(-c3cc(C#N)c4c(N)ncnn34)c2)C1=O] | 4-amino-7-(3-(2,2-dimethyl-3-oxomorpholino)phenyl)pyrrolo[2,1-f][1,2,4]triazine-5-carbonitrile | 362 |

TABLE 49-continued

| Ex. No. | Structure | Name | M + H |
|---|---|---|---|
| 696 | 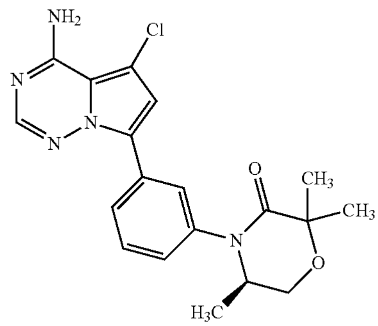 [SMILES: C[C@@H]1COC(C)(C)C(=O)N1c1cccc(-c2cc(Cl)c3c(N)ncnn23)c1] | (R)-4-(3-(4-amino-5-chloropyrrolo[2,1-f][1,2,4]triazin-7-yl)phenyl)-2,2,5-trimethylmorpholin-3-one | 386 |
| 697 | 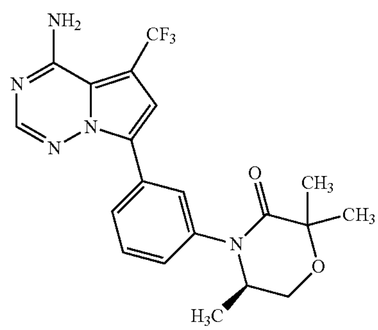 | (R)-4-(3-(4-amino-5-(trifluoromethyl)pyrrolo[2,1-f][1,2,4]triazin-7-yl)phenyl)-2,2,5-trimethylmorpholin-3-one | 419 |
| 698 | 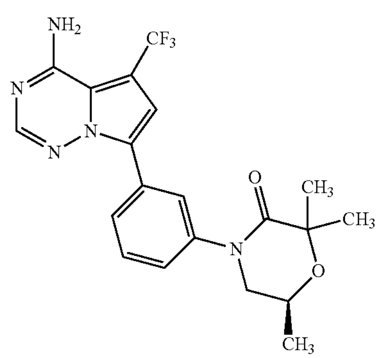 [SMILES: C[C@H]1CN(c2cccc(-c3cc(C(F)(F)F)c4c(N)ncnn34)c2)C(=O)C(C)(C)O1] | (S)-4-(3-(4-amino-5-(trifluoromethyl)pyrrolo[2,1-f][1,2,4]triazin-7-yl)phenyl)-2,2,6-trimethylmorpholin-3-one | 419 |
| 699 | 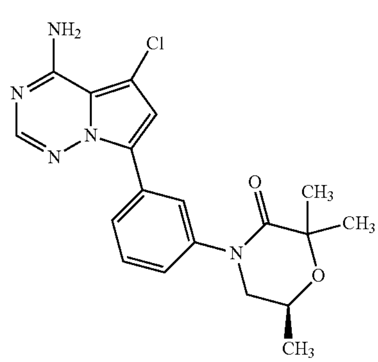 [SMILES: C[C@H]1CN(c2cccc(-c3cc(Cl)c4c(N)ncnn34)c2)C(=O)C(C)(C)O1] | (S)-4-(3-(4-amino-5-chloropyrrolo[2,1-f][1,2,4]triazin-7-yl)phenyl)-2,2,6-trimethylmorpholin-3-one | 386 |

TABLE 49-continued

| Ex. No. | Structure | Name | M + H |
|---|---|---|---|
| 700 | 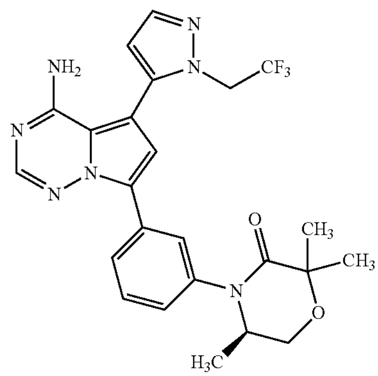 [SMILES: C[C@@H]1COC(C)(C)C(=O)N1c1cccc(-c2cc(-c3ccnn3CC(F)(F)F)c3c(N)ncnn23)c1] | (R)-4-(3-(4-amino-5-(1-(2,2,2-trifluoroethyl)-1H-pyrazol-5-yl)pyrrolo[2,1-f][1,2,4]triazin-7-yl)phenyl)-2,2,5-trimethylmorpholin-3-one | 499 |
| 701 | 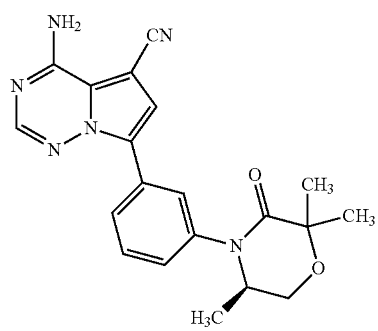 [SMILES: C[C@@H]1COC(C)(C)C(=O)N1c1cccc(-c2cc(C#N)c3c(N)ncnn23)c1] | (R)-4-amino-7-(3-(2,2,5-trimethyl-3-oxomorpholino)phenyl)pyrrolo[2,1-f][1,2,4]triazine-5-carbonitrile | 376 |
| 702 | 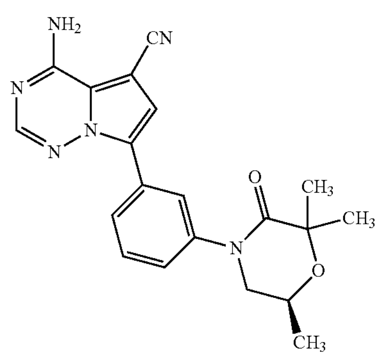 [SMILES: C[C@H]1CN(c2cccc(-c3cc(C#N)c4c(N)ncnn34)c2)C(=O)C(C)(C)O1] | (S)-4-amino-7-(3-(2,2,6-trimethyl-3-oxomorpholino)phenyl)pyrrolo[2,1-f][1,2,4]triazine-5-carbonitrile | 376 |
| 703 | 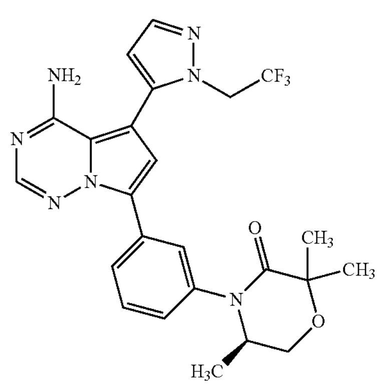 [SMILES: C[C@@H]1COC(C)(C)C(=O)N1c1cccc(-c2cc(-c3ccnn3CC(F)(F)F)c3c(N)ncnn23)c1] | (R)-4-(3-(4-amino-5-(1-(2,2,2-trifluoroethyl)-1H-pyrazol-5-yl)pyrrolo[2,1-f][1,2,4]triazin-7-yl)phenyl)-2,2,5-trimethylmorpholin-3-one | 499 |

TABLE 49-continued

| Ex. No. | Structure | Name | M + H |
|---|---|---|---|
| 704 | 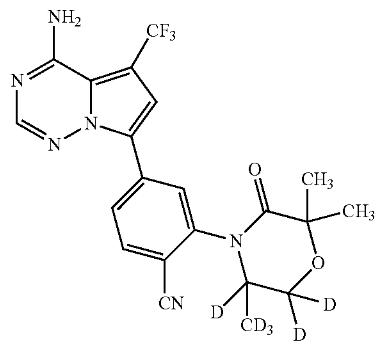 [SMILES: [2H]C([2H])([2H])C1([2H])N(c2cc(-c3cc(C(F)(F)F)c4c(N)ncnn34)ccc2C#N)C(=O)C(C)(C)OC1([2H])[2H]] | 4-(4-amino-5-(trifluoromethyl)pyrrolo[2,1-f][1,2,4]triazin-7-yl)-2-(2,2-dimethyl-5-(methyl-d₃)-3-oxomorpholino-5,6,6-d₃)benzonitrile | 450 |
| 705 | 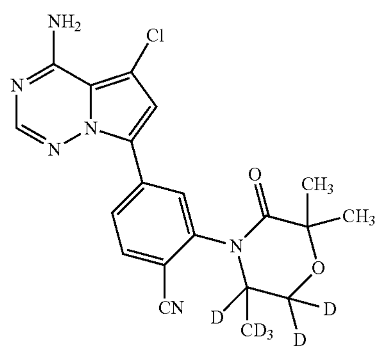 [SMILES: [2H]C([2H])([2H])C1([2H])N(c2cc(-c3cc(Cl)c4c(N)ncnn34)ccc2C#N)C(=O)C(C)(C)OC1([2H])[2H]] | 4-(4-amino-5-chloropyrrolo[2,1-f][1,2,4]triazin-7-yl)-2-(2,2-dimethyl-5-(methyl-d₃)-3-oxomorpholino-5,6,6-d₃)benzonitrile | 417 |
| 706 | 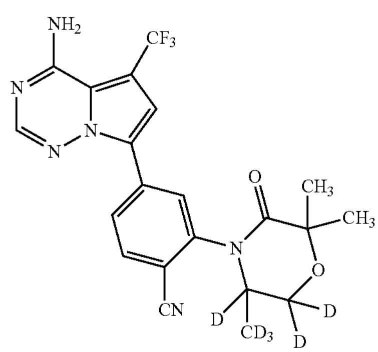 [SMILES: [2H]C([2H])([2H])C1([2H])N(c2cc(-c3cc(C(F)(F)F)c4c(N)ncnn34)ccc2C#N)C(=O)C(C)(C)OC1([2H])[2H]] | 4-(4-amino-5-(trifluoromethyl)pyrrolo[2,1-f][1,2,4]triazin-7-yl)-2-(2,2-dimethyl-5-(methyl-d₃)-3-oxomorpholino-5,6,6-d₃)benzonitrile | 450 |
| 707 | 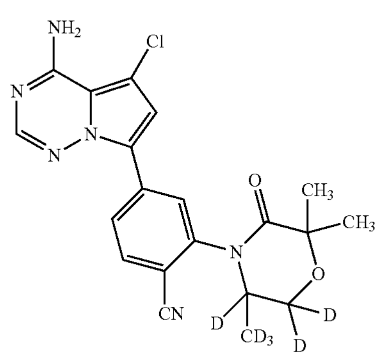 [SMILES: [2H]C([2H])([2H])C1([2H])N(c2cc(-c3cc(Cl)c4c(N)ncnn34)ccc2C#N)C(=O)C(C)(C)OC1([2H])[2H]] | 4-(4-amino-5-chloropyrrolo[2,1-f][1,2,4]triazin-7-yl)-2-(2,2-dimethyl-5-(methyl-d₃)-3-oxomorpholino-5,6,6-d₃)benzonitrile | 417 |

TABLE 49-continued

| Ex. No. | Structure | Name | M + H |
|---|---|---|---|
| 708 | 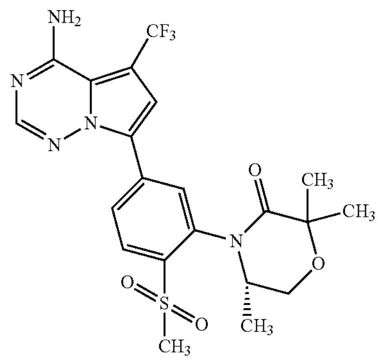 [SMILES: C[C@H]1COC(C)(C)C(=O)N1c1cc(-c2cc(C(F)(F)F)c3c(N)ncnn23)ccc1S(C)(=O)=O] | (S)-4-(5-(4-amino-5-(trifluoromethyl) pyrrolo[2,1-f][1,2,4]triazin-7-yl)-2-(methylsulfonyl)phenyl)-2,2,5-trimethylmorpholin-3-one | 497 |
| 709 | 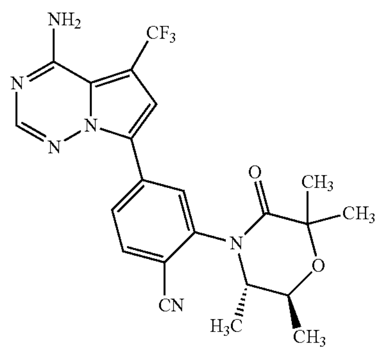 [SMILES: C[C@@H]1OC(C)(C)C(=O)N(c2cc(-c3cc(C(F)(F)F)c4c(N)ncnn34)ccc2C#N)[C@H]1C] | 4-(4-amino-5-(trifluoromethyl)pyrrolo [2,1-f][1,2,4]triazin-7-yl)-2-((5S,6S)-2,2,5,6-tetramethyl-3-oxomorpholino) benzonitrile | 458 |
| 710 | 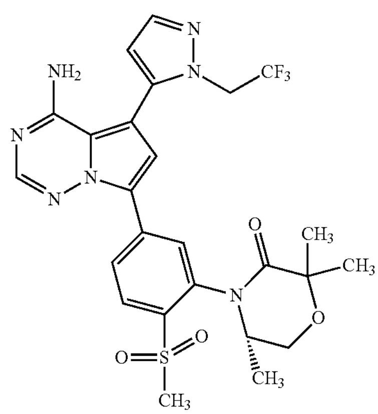 [SMILES: C[C@H]1COC(C)(C)C(=O)N1c1cc(-c2cc(-c3ccnn3CC(F)(F)F)c3c(N)ncnn23)ccc1S(C)(=O)=O] | (S)-4-(5-(4-amino-5-(1-(2,2,2-trifluoroethyl)-1H-pyrazol-5-yl)pyrrolo [2,1-f][1,2,4]triazin-7-yl)-2-(methylsulfonyl)phenyl)-2,2,5-trimethylmorpholin-3-one | 578 |
| 711 | 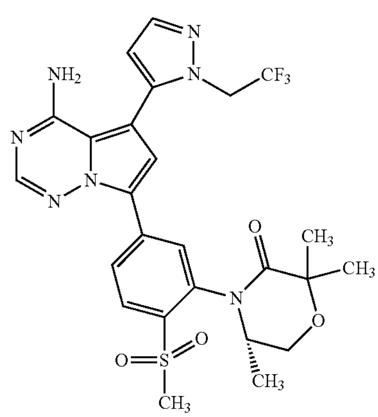 [SMILES: C[C@H]1COC(C)(C)C(=O)N1c1cc(-c2cc(-c3ccnn3CC(F)(F)F)c3c(N)ncnn23)ccc1S(C)(=O)=O] | (S)-4-(5-(4-amino-5-(1-(2,2,2-trifluoroethyl)-1H-pyrazol-5-yl)pyrrolo[2,1-f][1,2,4]triazin-7-yl)-2-(methylsulfonyl)phenyl)-2,2,5-trimethylmorpholin-3-one | 578 |

TABLE 49-continued

| Ex. No. | Structure | Name | M + H |
|---|---|---|---|
| 712 | 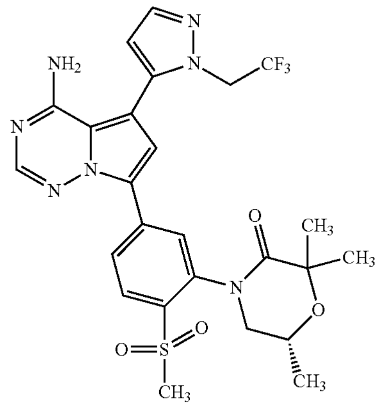 [SMILES: C[C@@H]1CN(c2cc(-c3cc(-c4ccnn4CC(F)(F)F)c4c(N)ncnn34)ccc2S(C)(=O)=O)C(=O)C(C)(C)O1] | (R)-4-(5-(4-amino-5-(1-(2,2,2-trifluoroethyl)-1H-pyrazol-5-yl)pyrrolo[2,1-f][1,2,4]triazin-7-yl)-2-(methylsulfonyl)phenyl)-2,2,6-trimethylmorpholin-3-one | 578 |
| 713 | 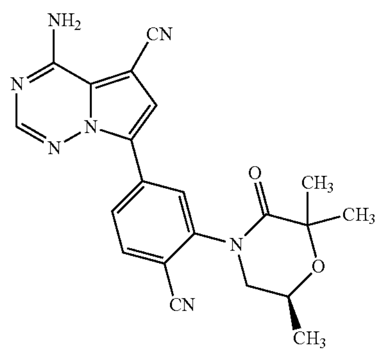 [SMILES: C[C@H]1CN(c2cc(-c3cc(C#N)c4c(N)ncnn34)ccc2C#N)C(=O)C(C)(C)O1] | (S)-4-amino-7-(4-cyano-3-(2,2,6-trimethyl-3-oxomorpholino)phenyl)pyrrolo[2,1-f][1,2,4]triazine-5-carbonitrile | 401 |
| 714 | 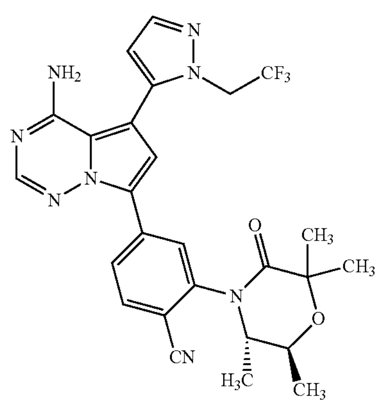 [SMILES: C[C@@H]1OC(C)(C)C(=O)N(c2cc(-c3cc(-c4ccnn4CC(F)(F)F)c4c(N)ncnn34)ccc2C#N)[C@H]1C] | 4-(4-amino-5-(1-(2,2,2-trifluoroethyl)-1H-pyrazol-5-yl)pyrrolo[2,1-f][1,2,4]triazin-7-yl)-2-((5S,6S)-2,2,5,6-tetramethyl-3-oxomorpholino)benzonitrile | 539 |
| 715 | 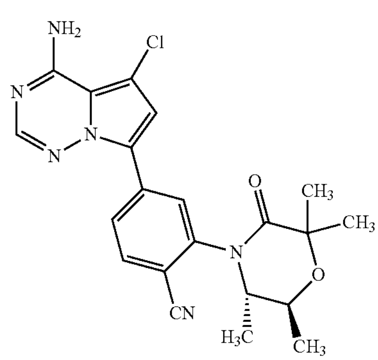 [SMILES: C[C@@H]1OC(C)(C)C(=O)N(c2cc(-c3cc(Cl)c4c(N)ncnn34)ccc2C#N)[C@H]1C] | 4-(4-amino-5-chloropyrrolo[2,1-f][1,2,4]triazin-7-yl)-2-((5S,6S)-2,2,5,6-tetramethyl-3-oxomorpholino)benzonitrile | 425 |

TABLE 49-continued

| Ex. No. | Structure | Name | M + H |
|---|---|---|---|
| 716 | 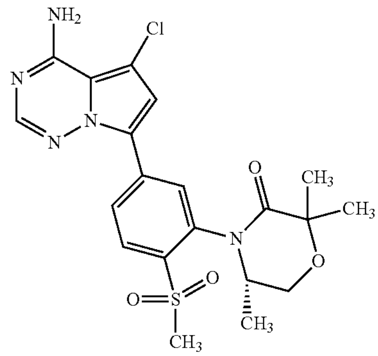 [SMILES: C[C@H]1COC(C)(C)C(=O)N1c1cc(-c2cc(Cl)c3c(N)ncnn23)ccc1S(C)(=O)=O] | (S)-4-(5-(4-amino-5-chloropyrrolo[2,1-f][1,2,4]triazin-7-yl)-2-(methylsulfonyl)phenyl)-2,2,5-trimethylmorpholin-3-one | 464 |
| 717 | 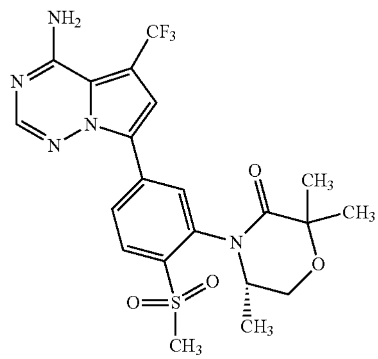 [SMILES: C[C@H]1COC(C)(C)C(=O)N1c1cc(-c2cc(C(F)(F)F)c3c(N)ncnn23)ccc1S(C)(=O)=O] | (S)-4-(5-(4-amino-5-(trifluoromethyl)pyrrolo[2,1-f][1,2,4]triazin-7-yl)-2-(methylsulfonyl)phenyl)-2,2,5-trimethylmorpholin-3-one | 498 |
| 718 | 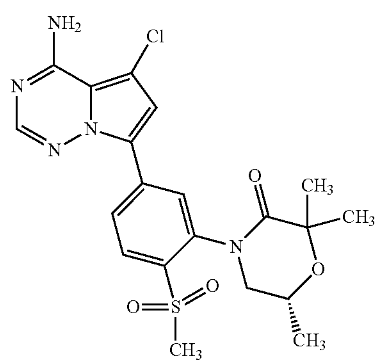 [SMILES: C[C@@H]1CN(c2cc(-c3cc(Cl)c4c(N)ncnn34)ccc2S(C)(=O)=O)C(=O)C(C)(C)O1] | (R)-4-(5-(4-amino-5-chloropyrrolo[2,1-f][1,2,4]triazin-7-yl)-2-(methylsulfonyl)phenyl)-2,2,6-trimethylmorpholin-3-one | 464 |
| 719 | 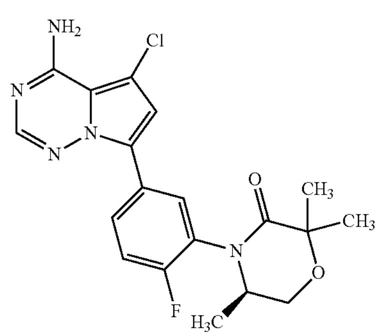 [SMILES: C[C@@H]1COC(C)(C)C(=O)N1c1cc(-c2cc(Cl)c3c(N)ncnn23)ccc1F] | (R)-4-(5-(4-amino-5-chloropyrrolo[2,1-f][1,2,4]triazin-7-yl)-2-fluorophenyl)-2,2,5-trimethylmorpholin-3-one | 404 |

TABLE 49-continued

| Ex. No. | Structure | Name | M + H |
|---|---|---|---|
| 720 | 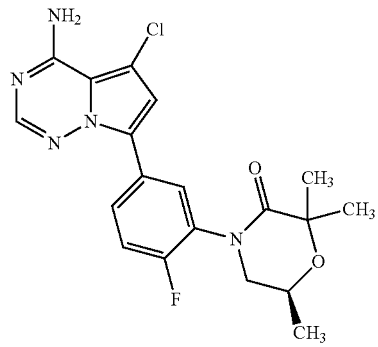 [SMILES: C[C@H]1CN(c2cc(-c3cc(Cl)c4c(N)ncnn34)ccc2F)C(=O)C(C)(C)O1] | (S)-4-(5-(4-amino-5-chloropyrrolo[2,1-f][1,2,4]triazin-7-yl)-2-fluorophenyl)-2,2,6-trimethylmorpholin-3-one | 404 |
| 721 | 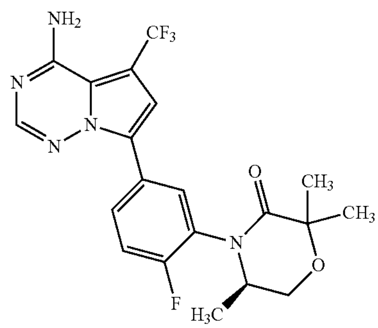 [SMILES: C[C@@H]1COC(C)(C)C(=O)N1c1cc(-c2cc(C(F)(F)F)c3c(N)ncnn23)ccc1F] | (R)-4-(5-(4-amino-5-(trifluoromethyl)pyrrolo[2,1-f][1,2,4]triazin-7-yl)-2-fluorophenyl)-2,2,5-trimethylmorpholin-3-one | 437 |
| 722 | 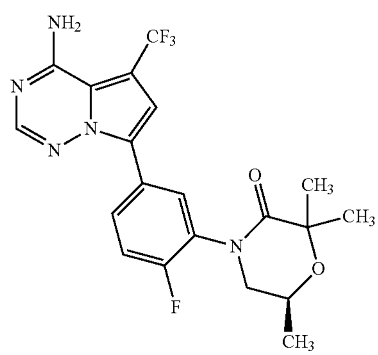 [SMILES: C[C@H]1CN(c2cc(-c3cc(C(F)(F)F)c4c(N)ncnn34)ccc2F)C(=O)C(C)(C)O1] | (S)-4-(5-(4-amino-5-(trifluoromethyl)pyrrolo[2,1-f][1,2,4]triazin-7-yl)-2-fluorophenyl)-2,2,6-trimethylmorpholin-3-one | 437 |
| 723 | 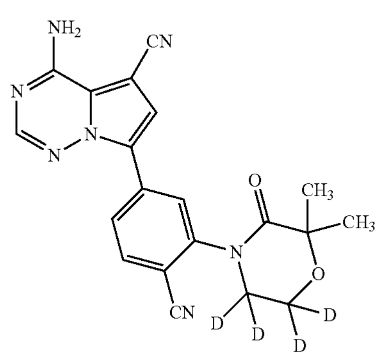 [SMILES: [2H]C1([2H])OC(C)(C)C(=O)N(c2cc(-c3cc(C#N)c4c(N)ncnn34)ccc2C#N)C1([2H])[2H]] | 4-amino-7-(4-cyano-3-(2,2-dimethyl-3-oxomorpholino-5,5,6,6-$d_4$)phenyl)pyrrolo[2,1-f][1,2,4]triazine-5-carbonitrile | 391 |

TABLE 49-continued

| Ex. No. | Structure | Name | M + H |
|---|---|---|---|
| 724 | 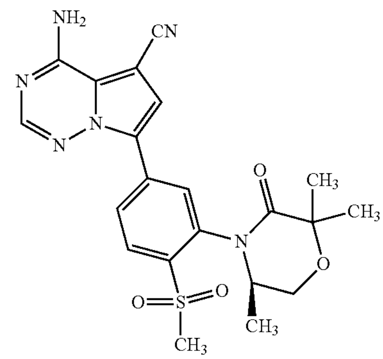 [SMILES: C[C@@H]1COC(C)(C)C(=O)N1c1cc(-c2cc(C#N)c3c(N)ncnn23)ccc1S(C)(=O)=O] | (R)-4-amino-7-(4-(methylsulfonyl)-3-(2,2,5-trimethyl-3-oxomorpholino)phenyl)pyrrolo[2,1-f][1,2,4]triazine-5-carbonitrile | 455 |
| 725 | 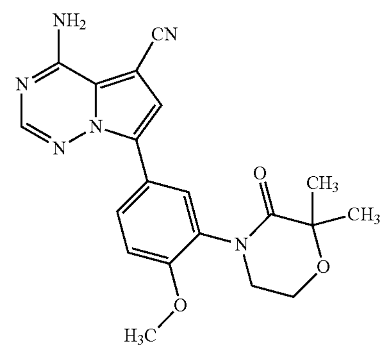 [SMILES: COc1ccc(-c2cc(C#N)c3c(N)ncnn23)cc1N1CCOC(C)(C)C1=O] | 4-amino-7-(3-(2,2-dimethyl-3-oxomorpholino)-4-methoxyphenyl)pyrrolo[2,1-f][1,2,4]triazine-5-carbonitrile | 392 |
| 726 | 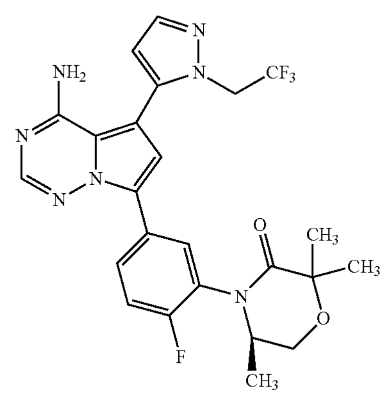 [SMILES: C[C@@H]1COC(C)(C)C(=O)N1c1cc(-c2cc(-c3ccnn3CC(F)(F)F)c3c(N)ncnn23)ccc1F] | (R)-4-(5-(4-amino-5-(1-(2,2,2-trifluoroethyl)-1H-pyrazol-5-yl)pyrrolo[2,1-f][1,2,4]triazin-7-yl)-2-fluorophenyl)-2,2,5-trimethylmorpholin-3-one | 517 |
| 727 | 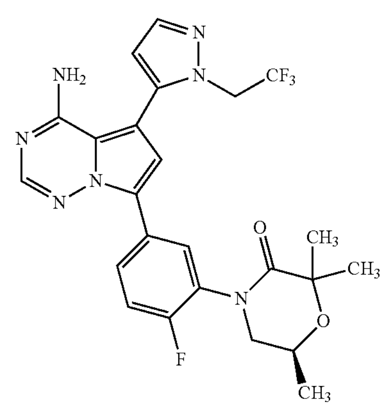 [SMILES: C[C@H]1CN(c2cc(-c3cc(-c4ccnn4CC(F)(F)F)c4c(N)ncnn34)ccc2F)C(=O)C(C)(C)O1] | (S)-4-(5-(4-amino-5-(1-(2,2,2-trifluoroethyl)-1H-pyrazol-5-yl)pyrrolo[2,1-f][1,2,4]triazin-7-yl)-2-fluorophenyl)-2,2,6-trimethylmorpholin-3-one | 517 |

TABLE 49-continued

| Ex. No. | Structure | Name | M + H |
|---|---|---|---|
| 728 | 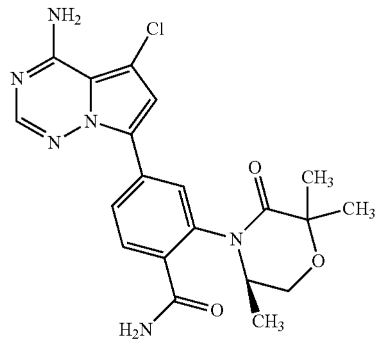 [SMILES: C[C@@H]1COC(C)(C)C(=O)N1c1cc(-c2cc(Cl)c3c(N)ncnn23)ccc1C(N)=O] | (R)-4-(4-amino-5-chloropyrrolo[2,1-f][1,2,4]triazin-7-yl)-2-(2,2,5-trimethyl-3-oxomorpholino)benzamide | 429 |
| 729 | 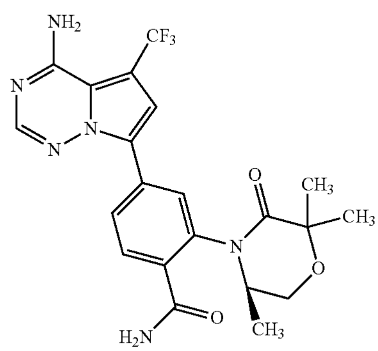 [SMILES: C[C@@H]1COC(C)(C)C(=O)N1c1cc(-c2cc(C(F)(F)F)c3c(N)ncnn23)ccc1C(N)=O] | (R)-4-(4-amino-5-(trifluoromethyl)pyrrolo[2,1-f][1,2,4]triazin-7-yl)-2-(2,2,5-trimethyl-3-oxomorpholino)benzamide | 462 |
| 730 | 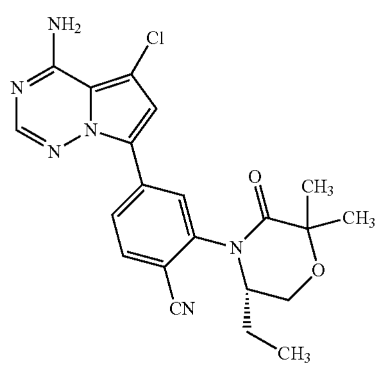 [SMILES: CC[C@H]1COC(C)(C)C(=O)N1c1cc(-c2cc(Cl)c3c(N)ncnn23)ccc1C#N] | (S)-4-(4-amino-5-chloropyrrolo[2,1-f][1,2,4]triazin-7-yl)-2-(5-ethyl-2,2-dimethyl-3-oxomorpholino)benzonitrile | 425 |
| 731 | 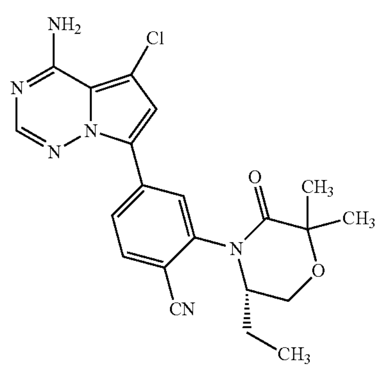 [SMILES: CC[C@H]1COC(C)(C)C(=O)N1c1cc(-c2cc(Cl)c3c(N)ncnn23)ccc1C#N] | (S)-4-(4-amino-5-chloropyrrolo[2,1-f][1,2,4]triazin-7-yl)-2-(5-ethyl-2,2-dimethyl-3-oxomorpholino)benzonitrile | 425 |

TABLE 49-continued

| Ex. No. | Structure | Name | M + H |
|---|---|---|---|
| 732 | 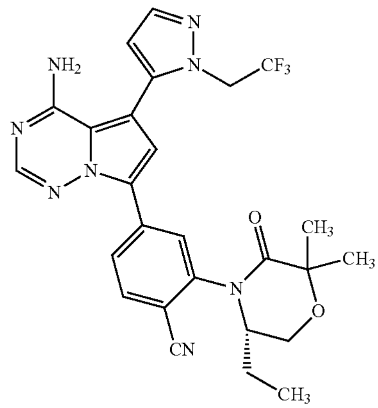 [SMILES: CC[C@H]1COC(C)(C)C(=O)N1c1cc(-c2cc(-c3ccnn3CC(F)(F)F)c3c(N)ncnn23)ccc1C#N] | (S)-4-(4-amino-5-(1-(2,2,2-trifluoroethyl)-1H-pyrazol-5-yl)pyrrolo[2,1-f][1,2,4]triazin-7-yl)-2-(5-ethyl-2,2-dimethyl-3-oxomorpholino)benzonitrile | 539 |
| 733 | 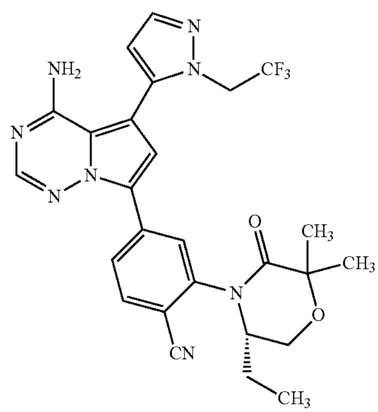 [SMILES: CC[C@H]1COC(C)(C)C(=O)N1c1cc(-c2cc(-c3ccnn3CC(F)(F)F)c3c(N)ncnn23)ccc1C#N] | (S)-4-(4-amino-5-(1-(2,2,2-trifluoroethyl)-1H-pyrazol-5-yl)pyrrolo[2,1-f][1,2,4]triazin-7-yl)-2-(5-ethyl-2,2-dimethyl-3-oxomorpholino)benzonitrile | 539 |
| 734 | 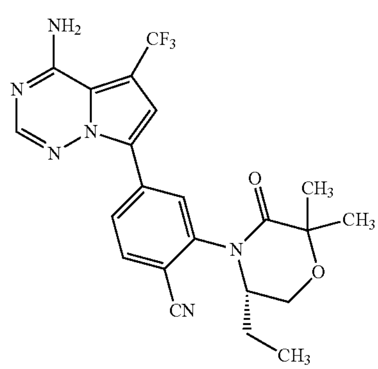 [SMILES: CC[C@H]1COC(C)(C)C(=O)N1c1cc(-c2cc(C(F)(F)F)c3c(N)ncnn23)ccc1C#N] | (S)-4-(4-amino-5-(trifluoromethyl)pyrrolo[2,1-f][1,2,4]triazin-7-yl)-2-(5-ethyl-2,2-dimethyl-3-oxomorpholino)benzonitrile | 458 |
| 735 | 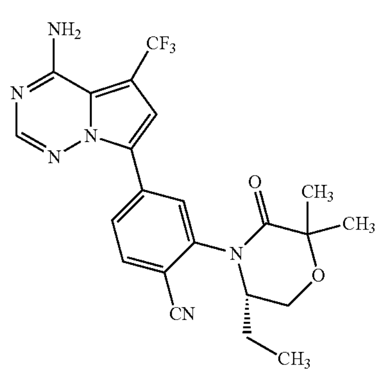 [SMILES: CC[C@H]1COC(C)(C)C(=O)N1c1cc(-c2cc(C(F)(F)F)c3c(N)ncnn23)ccc1C#N] | (S)-4-(4-amino-5-(trifluoromethyl)pyrrolo[2,1-f][1,2,4]triazin-7-yl)-2-(5-ethyl-2,2-dimethyl-3-oxomorpholino)benzonitrile | 458 |

TABLE 49-continued

| Ex. No. | Structure | Name | M + H |
|---|---|---|---|
| 736 | 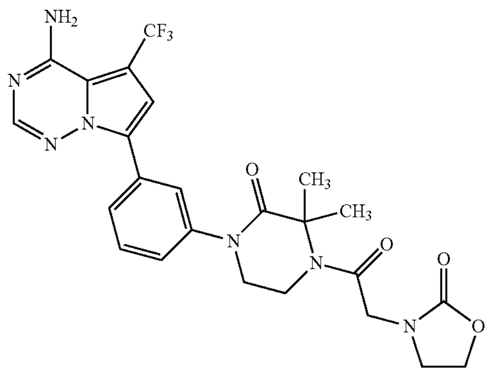 | 3-(2-(4-(3-(4-amino-5-(trifluoromethyl)pyrrolo[2,1-f][1,2,4]triazin-7-yl)phenyl)-2,2-dimethyl-3-oxopiperazin-1-yl)-2-oxoethyl)oxazolidin-2-one | 531 |
| 737 | 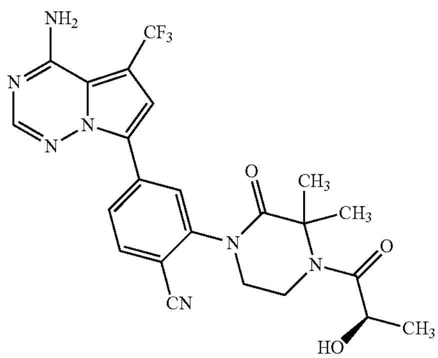 [SMILES: C[C@@H](O)C(=O)N1CCN(c2cc(-c3cc(C(F)(F)F)c4c(N)ncnn34)ccc2C#N)C(=O)C1(C)C] | (R)-4-(4-amino-5-(trifluoromethyl)pyrrolo[2,1-f][1,2,4]triazin-7-yl)-2-(4-(2-hydroxypropanoyl)-3,3-dimethyl-2-oxopiperazin-1-yl)benzonitrile | 501 |
| 738 | 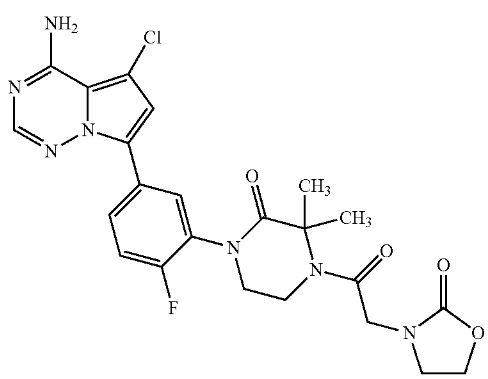 | 3-(2-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl)oxazolidin-2-one | 516 |
| 739 | 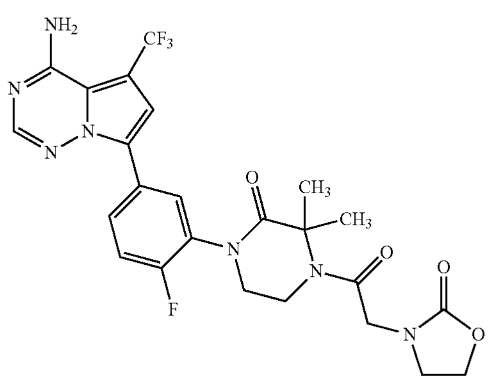 [SMILES: CC1(C)C(=O)N(c2cc(-c3cc(Cl)c4c(N)ncnn34)ccc2F)CCN1C(=O)CN1CCOC1=O] | 3-(2-(4-(5-(4-amino-5-(trifluoromethyl)pyrrolo[2,1-f][1,2,4]triazin-7-yl)-2-fluorophenyl)-2,2-dimethyl-3-oxopiperazin-1-yl)-2-oxoethyl)oxazolidin-2-one | 549 |

TABLE 49-continued

| Ex. No. | Structure | Name | M + H |
|---|---|---|---|
| 740 | 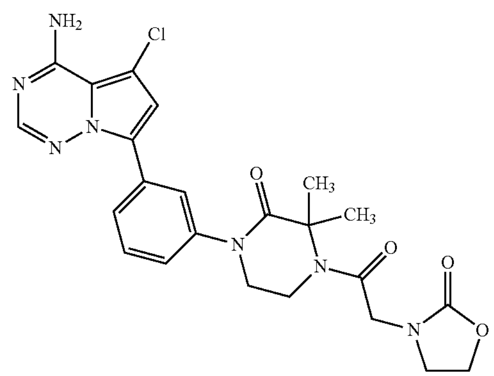 [SMILES: CC1(C)C(=O)N(c2cccc(-c3cc(Cl)c4c(N)ncnn34)c2)CCN1C(=O)CN1CCOC1=O] | 3-(2-(4-(3-(4-amino-5-chloropyrrolo[2,1-f][1,2,4]triazin-7-yl)phenyl)-2,2-dimethyl-3-oxopiperazin-1-yl)-2-oxoethyl)oxazolidin-2-one | 498 |
| 741 | 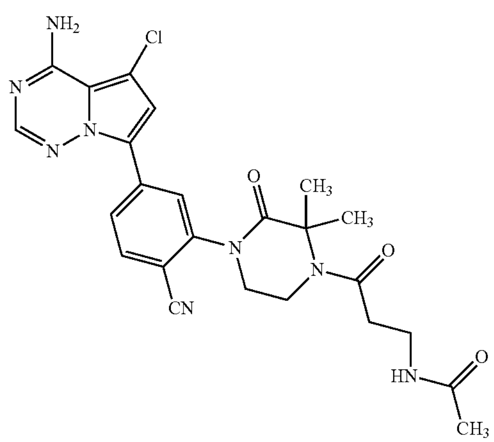 [SMILES: CC(=O)NCCC(=O)N1CCN(c2cc(-c3cc(Cl)c4c(N)ncnn34)ccc2C#N)C(=O)C1(C)C] | N-(3-(4-(5-(4-amino-5-chloropyrrolo[2,1-f][1,2,4]triazin-7-yl)-2-cyanophenyl)-2,2-dimethyl-3-oxopiperazin-1-yl)-3-oxopropyl)acetamide | 509 |
| 742 | 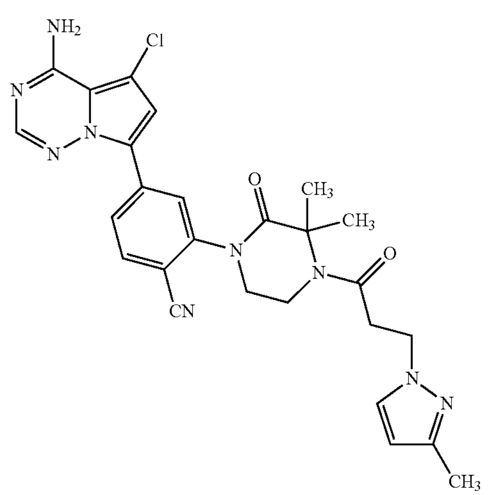 [SMILES: Cc1ccn(CCC(=O)N2CCN(c3cc(-c4cc(Cl)c5c(N)ncnn45)ccc3C#N)C(=O)C2(C)C)n1] | 4-(4-amino-5-chloropyrrolo[2,1-f][1,2,4]triazin-7-yl)-2-(3,3-dimethyl-4-(3-(3-methyl-1H-pyrazol-1-yl)propanoyl)-2-oxopiperazin-1-yl)benzonitrile | 532 |

TABLE 49-continued

| Ex. No. | Structure | Name | M + H |
|---|---|---|---|
| 743 | 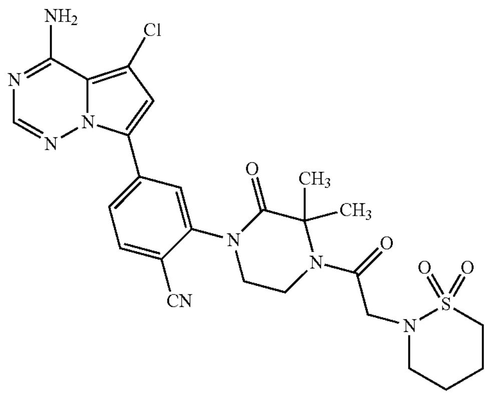 [SMILES: CC1(C)C(=O)N(c2cc(-c3cc(Cl)c4c(N)ncnn34)ccc2C#N)CCN1C(=O)CN1CCCCS1(=O)=O] | 4-(4-amino-5-chloropyrrolo[2,1-f][1,2,4]triazin-7-yl)-2-(4-(2-(1,1-dioxido-1,2-thiazinan-2-yl)acetyl)-3,3-dimethyl-2-oxopiperazin-1-yl)benzonitrile | 571 |
| 744 | 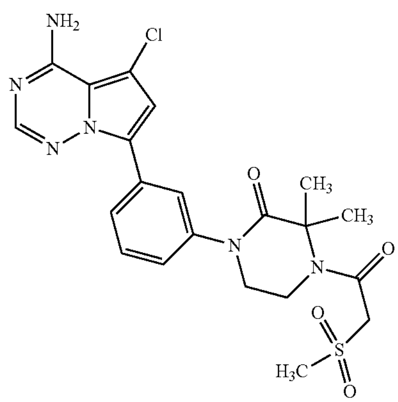 [SMILES: CC1(C)C(=O)N(c2cccc(-c3cc(Cl)c4c(N)ncnn34)c2)CCN1C(=O)CS(C)(=O)=O] | 1-(3-(4-amino-5-chloropyrrolo[2,1-f][1,2,4]triazin-7-yl)phenyl)-3,3-dimethyl-4-(2-(methylsulfonyl)acetyl)piperazin-2-one | 491 |
| 745 | 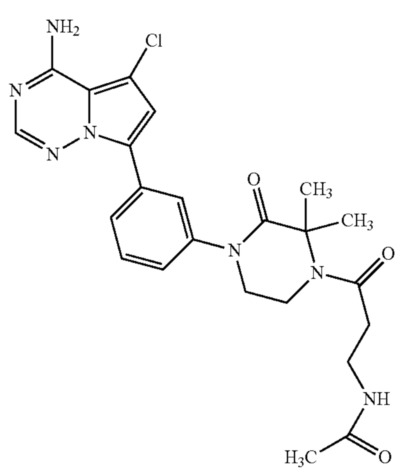 [SMILES: CC(=O)NCCC(=O)N1CCN(c2cccc(-c3cc(Cl)c4c(N)ncnn34)c2)C(=O)C1(C)C] | N-(3-(4-(3-(4-amino-5-chloropyrrolo[2,1-f][1,2,4]triazin-7-yl)phenyl)-2,2-dimethyl-3-oxopiperazin-1-yl)-3-oxopropyl)acetamide | 484 |

TABLE 49-continued

| Ex. No. | Structure | Name | M + H |
|---|---|---|---|
| 746 | 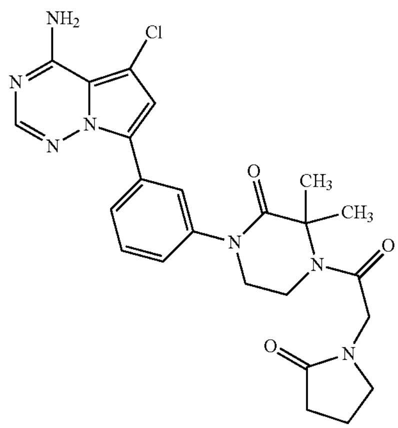 [SMILES: CC1(C)C(=O)N(c2cccc(-c3cc(Cl)c4c(N)ncnn34)c2)CCN1C(=O)CN1CCCC1=O] | 1-(3-(4-amino-5-chloropyrrolo[2,1-f][1,2,4]triazin-7-yl)phenyl)-3,3-dimethyl-4-(2-(2-oxopyrrolidin-1-yl)acetyl)piperazin-2-one | 496 |
| 747 | 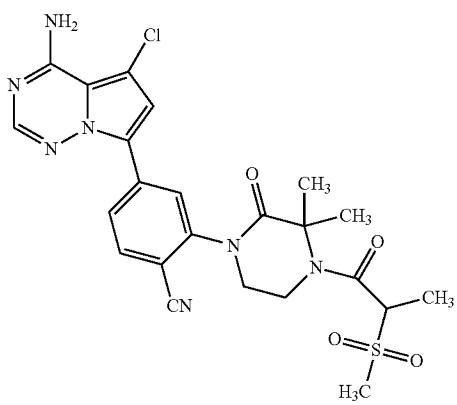 [SMILES: CC(C(=O)N1CCN(c2cc(-c3cc(Cl)c4c(N)ncnn34)ccc2C#N)C(=O)C1(C)C)S(C)(=O)=O] | 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile | 530 |
| 748 | 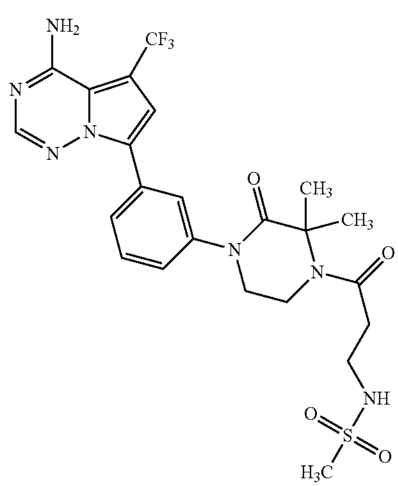 [SMILES: CC1(C)C(=O)N(c2cccc(-c3cc(Cl)c4c(N)ncnn34)c2)CCN1C(=O)CCNS(C)(=O)=O] | N-(3-(4-(3-(4-amino-5-(trifluoromethyl)pyrrolo[2,1-f][1,2,4]triazin-7-yl)phenyl)-2,2-dimethyl-3-oxopiperazin-1-yl)-3-oxopropyl)methanesulfonamide | 554 |

TABLE 49-continued

| Ex. No. | Structure | Name | M + H |
|---|---|---|---|
| 749 | 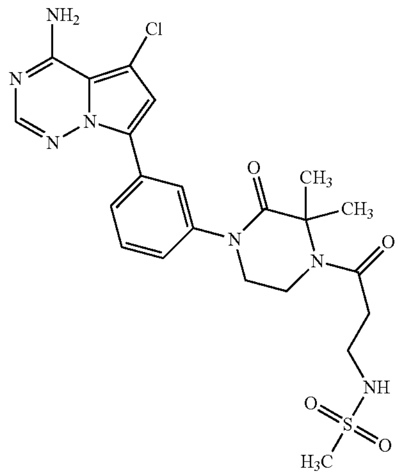 | N-(3-(4-(3-(4-amino-5-chloropyrrolo[2,1-f][1,2,4]triazin-7-yl)phenyl)-2,2-dimethyl-3-oxopiperazin-1-yl)-3-oxopropyl)methanesulfonamide | 520 |
| 750 | 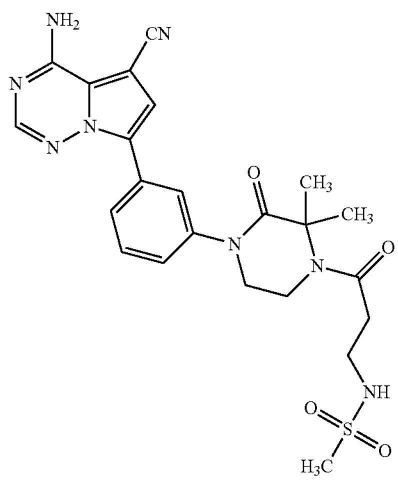 | N-(3-(4-(3-(4-amino-5-cyanopyrrolo[2,1-f][1,2,4]triazin-7-yl)phenyl)-2,2-dimethyl-3-oxopiperazin-1-yl)-3-oxopropyl)methanesulfonamide | 511 |
| 751 | 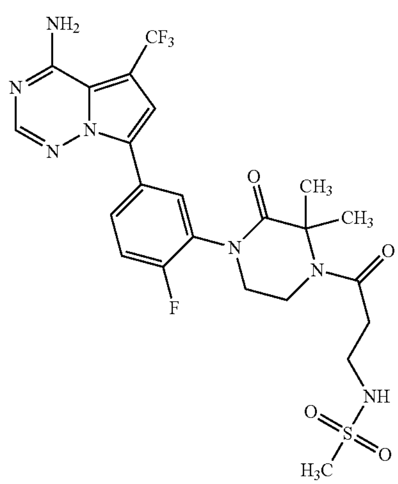 | N-(3-(4-(5-(4-amino-5-(trifluoromethyl)pyrrolo[2,1-f][1,2,4]triazin-7-yl)-2-fluorophenyl)-2,2-dimethyl-3-oxopiperazin-1-yl)-3-oxopropyl)methanesulfonamide | 572 |

TABLE 49-continued

| Ex. No. | Structure | Name | M + H |
|---|---|---|---|
| 752 | 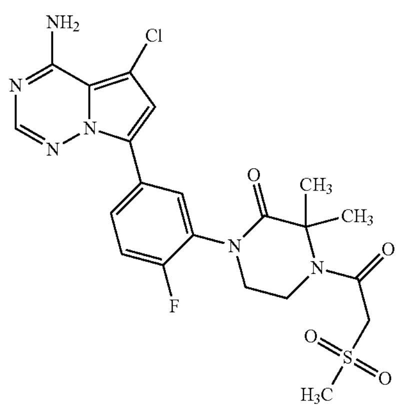 [SMILES: CC1(C)C(=O)N(c2cc(-c3cc(Cl)c4c(N)ncnn34)ccc2F)CCN1C(=O)CS(C)(=O)=O] | 1-(5-(4-amino-5-chloropyrrolo[2,1-f][1,2,4]triazin-7-yl)-2-fluorophenyl)-3,3-dimethyl-4-(2-(methylsulfonyl)acetyl)piperazin-2-one | 509 |
| 753 | 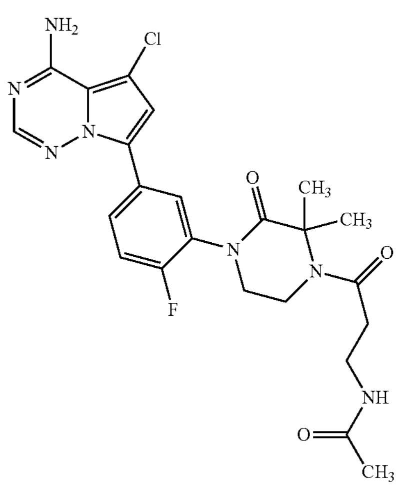 [SMILES: CC(=O)NCCC(=O)N1CCN(c2cc(-c3cc(Cl)c4c(N)ncnn34)ccc2F)C(=O)C1(C)C] | N-(3-(4-(5-(4-amino-5-chloropyrrolo[2,1-f][1,2,4]triazin-7-yl)-2-fluorophenyl)-2,2-dimethyl-3-oxopiperazin-1-yl)-3-oxopropyl)acetamide | 502 |
| 754 | 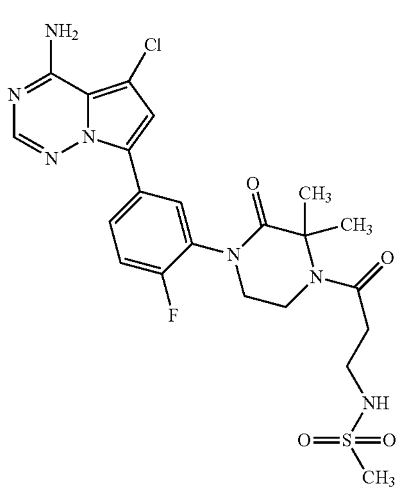 [SMILES: CC1(C)C(=O)N(c2cc(-c3cc(Cl)c4c(N)ncnn34)ccc2F)CCN1C(=O)CCNS(C)(=O)=O] | N-(3-(4-(5-(4-amino-5-chloropyrrolo[2,1-f][1,2,4]triazin-7-yl)-2-fluorophenyl)-2,2-dimethyl-3-oxopiperazin-1-yl)-3-oxopropyl)methanesulfonamide | 538 |

TABLE 49-continued

| Ex. No. | Structure | Name | M + H |
|---|---|---|---|
| 755 | 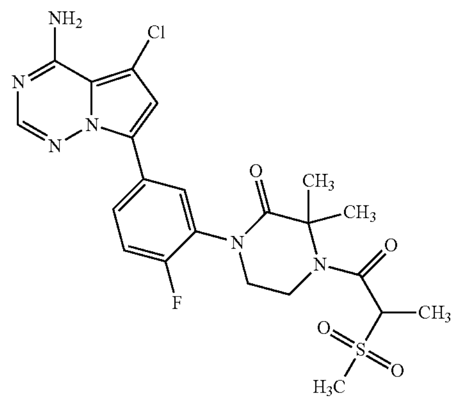 [SMILES: CC(C(=O)N1CCN(c2cc(-c3cc(Cl)c4c(N)ncnn34)ccc2F)C(=O)C1(C)C)S(C)(=O)=O] | 1-(5-(4-amino-5-chloropyrrolo[2,1-f][1,2,4]triazin-7-yl)-2-fluorophenyl)-3,3-dimethyl-4-(2-(methylsulfonyl)propanoyl)piperazin-2-one | 523 |
| 756 | 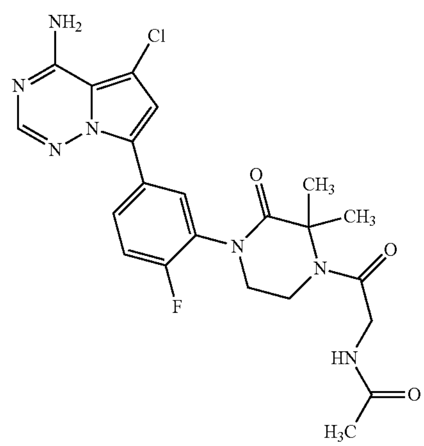 [SMILES: CC(=O)NCC(=O)N1CCN(c2cc(-c3cc(Cl)c4c(N)ncnn34)ccc2F)C(=O)C1(C)C] | N-(2-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl)acetamide | 488 |
| 757 | 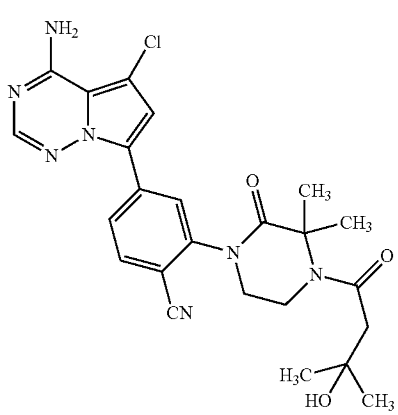 [SMILES: CC(C)(O)CC(=O)N1CCN(c2cc(-c3cc(Cl)c4c(N)ncnn34)ccc2C#N)C(=O)C1(C)C] | 4-(4-amino-5-chloropyrrolo[2,1-f][1,2,4]triazin-7-yl)-2-(4-(3-hydroxy-3-methylbutanoyl)-3,3-dimethyl-2-oxopiperazin-1-yl)benzonitrile | 496 |

TABLE 49-continued

| Ex. No. | Structure | Name | M + H |
|---|---|---|---|
| 758 | 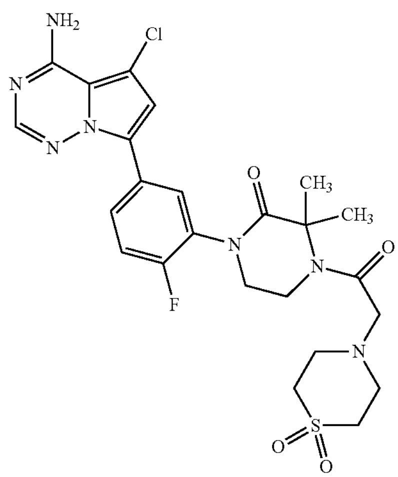 [SMILES: CC1(C)C(=O)N(c2cc(-c3cc(Cl)c4c(N)ncnn34)ccc2F)CCN1C(=O)CN1CCS(=O)(=O)CC1] | 1-(5-(4-amino-5-chloropyrrolo[2,1-f][1,2,4]triazin-7-yl)-2-fluorophenyl)-4-(2-(1,1-dioxidothiomorpholino)acetyl)-3,3-dimethylpiperazin-2-one | 564 |
| 759 | 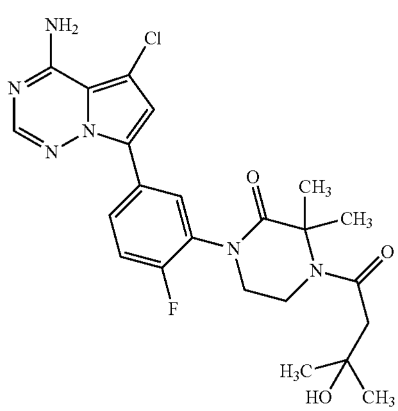 [SMILES: CC(C)(O)CC(=O)N1CCN(c2cc(-c3cc(Cl)c4c(N)ncnn34)ccc2F)C(=O)C1(C)C] | 1-(5-(4-amino-5-chloropyrrolo[2,1-f][1,2,4]triazin-7-yl)-2-fluorophenyl)-4-(3-hydroxy-3-methylbutanoyl)-3,3-dimethylpiperazin-2-one | 489 |
| 760 | 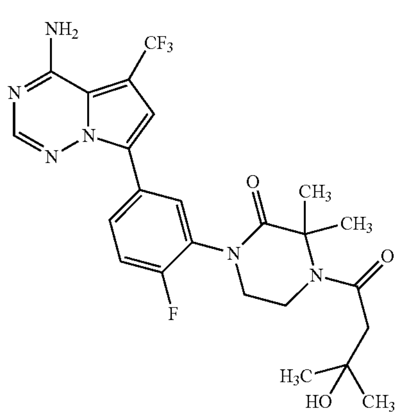 [SMILES: CC(C)(O)CC(=O)N1CCN(c2cc(-c3cc(C(F)(F)F)c4c(N)ncnn34)ccc2F)C(=O)C1(C)C] | 1-(5-(4-amino-5-(trifluoromethyl)pyrrolo[2,1-f][1,2,4]triazin-7-yl)-2-fluorophenyl)-4-(3-hydroxy-3-methylbutanoyl)-3,3-dimethylpiperazin-2-one | 523 |

TABLE 49-continued

| Ex. No. | Structure | Name | M + H |
|---|---|---|---|
| 761 | 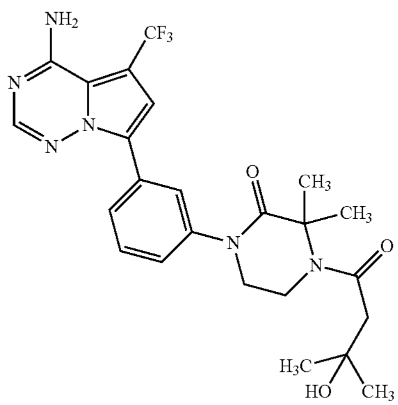 [SMILES: CC(C)(O)CC(=O)N1CCN(c2cccc(-c3cc(C(F)(F)F)c4c(N)ncnn34)c2)C(=O)C1(C)C] | 1-(3-(4-amino-5-(trifluoromethyl) pyrrolo[2,1-f][1,2,4]triazin-7-yl)phenyl)-4-(3-hydroxy-3-methylbutanoyl)-3,3-dimethylpiperazin-2-one | 505 |
| 762 | 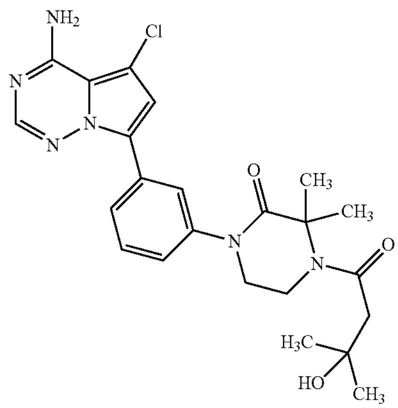 [SMILES: CC(C)(O)CC(=O)N1CCN(c2cccc(-c3cc(Cl)c4c(N)ncnn34)c2)C(=O)C1(C)C] | 1-(3-(4-amino-5-chloropyrrolo[2,1-f][1,2,4]triazin-7-yl)phenyl)-4-(3-hydroxy-3-methylbutanoyl)-3,3-dimethylpiperazin-2-one | 471 |
| 763 | 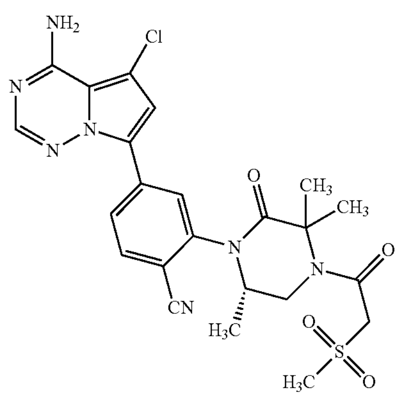 [SMILES: C[C@H]1CN(C(=O)CS(C)(=O)=O)C(C)(C)C(=O)N1c1cc(-c2cc(Cl)c3c(N)ncnn23)ccc1C#N] | (S)-4-(4-amino-5-chloropyrrolo[2,1-f][1,2,4]triazin-7-yl)-2-(3,3,6-trimethyl-4-(2-(methylsulfonyl)acetyl)-2-oxopiperazin-1-yl)benzonitrile | 530 |
| 764 | 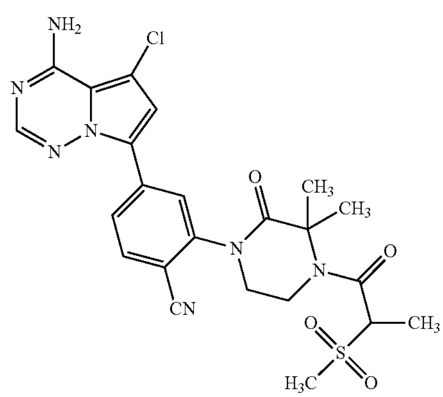 [SMILES: CC(C(=O)N1CCN(c2cc(-c3cc(Cl)c4c(N)ncnn34)ccc2C#N)C(=O)C1(C)C)S(C)(=O)=O] | 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile | 530 |

TABLE 49-continued

| Ex. No. | Structure | Name | M + H |
|---|---|---|---|
| 765 | 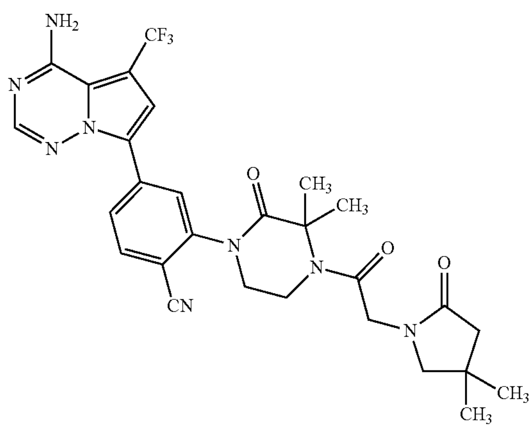 [SMILES: CC1(C)CC(=O)N(CC(=O)N2CCN(c3cc(-c4cc(C(F)(F)F)c5c(N)ncnn45)ccc3C#N)C(=O)C2(C)C)C1] | 4-(4-amino-5-(trifluoromethyl)pyrrolo[2,1-f][1,2,4]triazin-7-yl)-2-(4-(2-(4,4-dimethyl-2-oxopyrrolidin-1-yl)acetyl)-3,3-dimethyl-2-oxopiperaizn-1-yl)benzonitrile | 583 |
| 766 | 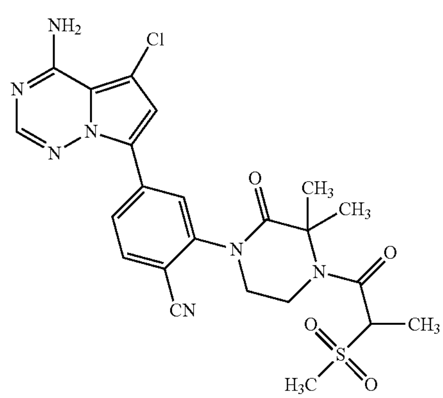 [SMILES: CC(C(=O)N1CCN(c2cc(-c3cc(Cl)c4c(N)ncnn34)ccc2C#N)C(=O)C1(C)C)S(C)(=O)=O] | 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile | 530 |
| 767 | 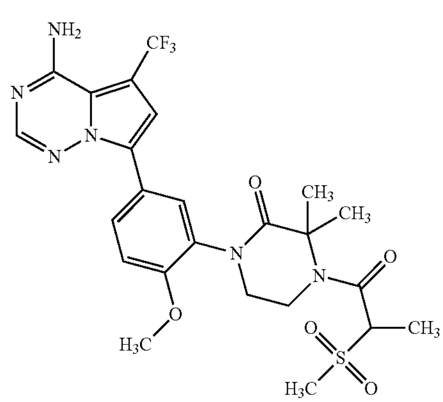 [SMILES: COc1ccc(-c2cc(C(F)(F)F)c3c(N)ncnn23)cc1N1CCN(C(=O)C(C)S(C)(=O)=O)C(C)(C)C1=O] | 1-(5-(4-amino-5-(trifluoromethyl)pyrrolo[2,1-f][1,2,4]triazin-7-yl)-2-methoxyphenyl)-3,3-dimethyl-4-(2-(methylsulfonyl)propanoyl)piperazin-2-one | 569 |

TABLE 49-continued

| Ex. No. | Structure | Name | M + H |
|---|---|---|---|
| 768 | 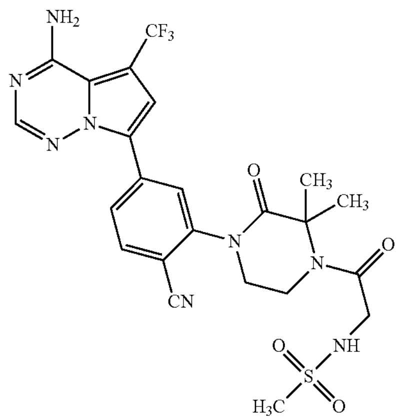 [SMILES: CC1(C)C(=O)N(c2cc(-c3cc(C(F)(F)F)c4c(N)ncnn34)ccc2C#N)CCN1C(=O)CNS(C)(=O)=O] | N-(2-(4-(5-(4-amino-5-(trifluoromethyl)pyrrolo[2,1-f][1,2,4]triazin-7-yl)-2-cyanophenyl)-2,2-dimethyl-3-oxopiperazin-1-yl)-2-oxoethyl)methanesulfonamide | 565 |
| 769 | 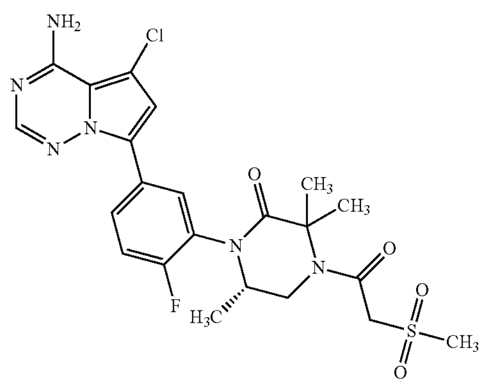 [SMILES: C[C@H]1CN(C(=O)CS(C)(=O)=O)C(C)(C)C(=O)N1c1cc(-c2cc(Cl)c3c(N)ncnn23)ccc1F] | (S)-1-(5-(4-amino-5-chloropyrrolo[2,1-f][1,2,4]triazin-7-yl)-2-fluorophenyl)-3,3,6-trimethyl-4-(2-(methylsulfonyl)acetyl)piperazin-2-one | 523 |
| 770 | 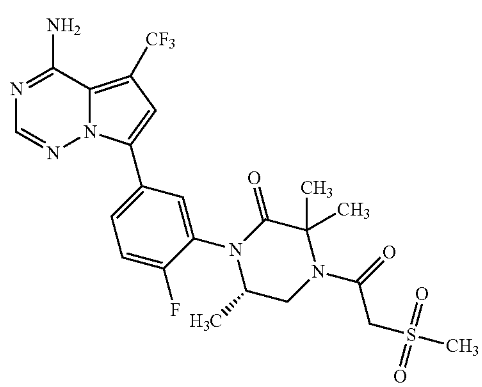 | (S)-1-(5-(4-amino-5-(trifluoromethyl)pyrrolo[2,1-f][1,2,4]triazin-7-yl)-2-fluorophenyl)-3,3,6-trimethyl-4-(2-(methylsulfonyl)acetyl)piperazin-2-one | 557 |

TABLE 49-continued

| Ex. No. | Structure | Name | M + H |
|---|---|---|---|
| 771 | 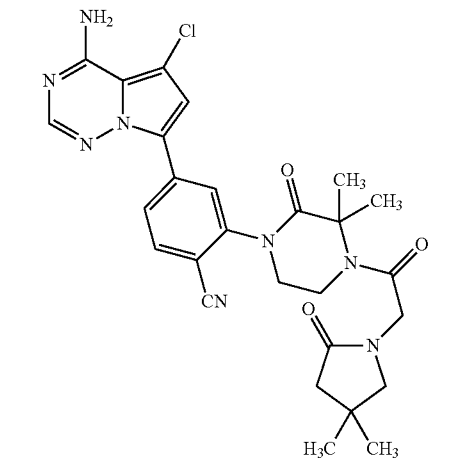 [SMILES: CC1(C)CC(=O)N(CC(=O)N2CCN(c3cc(-c4cc(Cl)c5c(N)ncnn45)ccc3C#N)C(=O)C2(C)C)C1] | 4-(4-amino-5-chloropyrrolo[2,1-f][1,2,4]triazin-7-yl)-2-(4-(2-(4,4-dimethyl-2-oxopyrrolidin-1-yl)acetyl)-3,3-dimethyl-2-oxopiperazin-1-yl)benzonitrile | 549 |
| 772 | 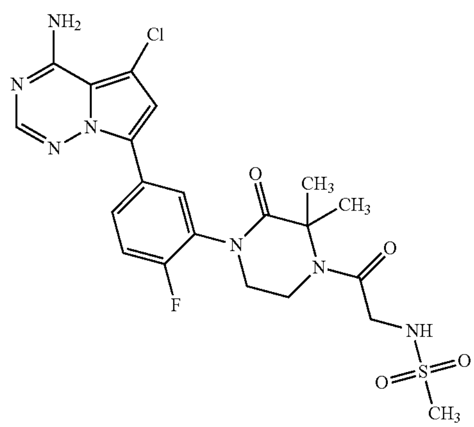 [SMILES: CC1(C)C(=O)N(c2cc(-c3cc(Cl)c4c(N)ncnn34)ccc2F)CCN1C(=O)CNS(C)(=O)=O] | N-(4-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl)methanesulfonamide | 524 |
| 773 | 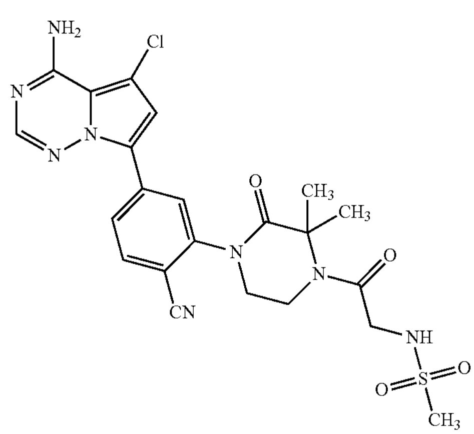 [SMILES: CC1(C)C(=O)N(c2cc(-c3cc(Cl)c4c(N)ncnn34)ccc2C#N)CCN1C(=O)CNS(C)(=O)=O] | N-(2-(4-(5-(4-amino-5-chloropyrrolo[2,1-f][1,2,4]triazin-7-yl)-2-cyanophenyl)-2,2-dimethyl-3-oxopiperazin-1-yl)-2-oxoethyl)methanesulfonamide | 531 |

TABLE 49-continued

| Ex. No. | Structure | Name | M + H |
|---|---|---|---|
| 774 | 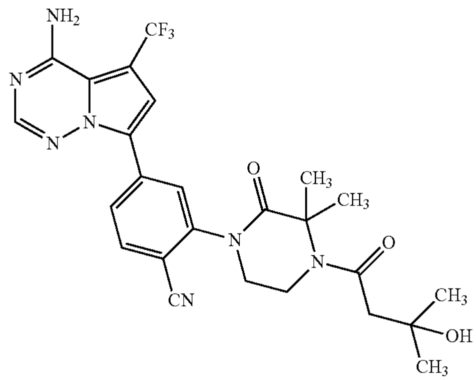 [SMILES: CC(C)(O)CC(=O)N1CCN(c2cc(-c3cc(C(F)(F)F)c4c(N)ncnn34)ccc2C#N)C(=O)C1(C)C] | 4-(4-amino-5-(trifluoromethyl)pyrrolo[2,1-f][1,2,4]triazin-7-yl)-2-(4-(3-hydroxy-3-methylbutanoyl)-3,3-dimethyl-2-oxopiperazin-1-yl)benzonitrile | 530 |
| 775 | 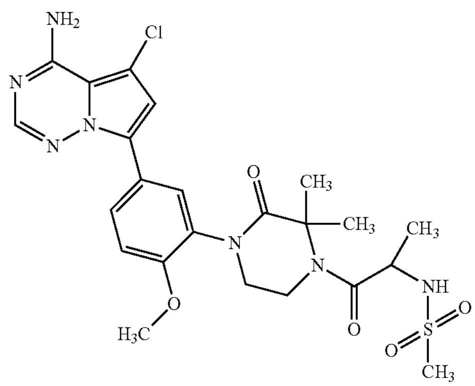 [SMILES: COc1ccc(-c2cc(Cl)c3c(N)ncnn23)cc1N1CCN(C(=O)C(C)NS(C)(=O)=O)C(C)(C)C1=O] | N-(1-(4-(5-(4-amino-5-chloropyrrolo[2,1-f][1,2,4]triazin-7-yl)-2-methoxyphenyl)-2,2-dimethyl-3-oxopiperazin-1-yl)-1-oxopropan-2-yl)methanesulfonamide | 535 |
| 776 | 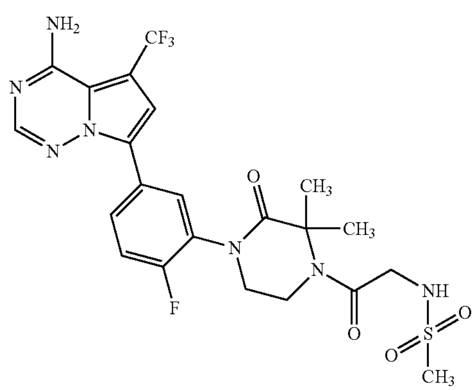 [SMILES: CC1(C)C(=O)N(c2cc(-c3cc(C(F)(F)F)c4c(N)ncnn34)ccc2F)CCN1C(=O)CNS(C)(=O)=O] | N-(2-(4-(5-(4-amino-5-(trifluoromethyl)pyrrolo[2,1-f][1,2,4]triazin-7-yl)-2-fluorophenyl)-2,2-dimethyl-3-oxopiperazin-1-yl)-2-oxoethyl)methanesulfonamide | 558 |
| 777 | 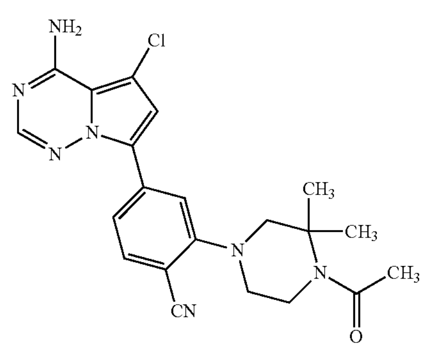 [SMILES: CC(=O)N1CCN(c2cc(-c3cc(Cl)c4c(N)ncnn34)ccc2C#N)CC1(C)C] | 2-(4-acetyl-3,3-dimethylpiperazin-1-yl)-4-(4-amino-5-chloropyrrolo[2,1-f][1,2,4]triazin-7-yl)benzonitrile | 424 |

TABLE 49-continued

| Ex. No. | Structure | Name | M + H |
|---|---|---|---|
| 778 | 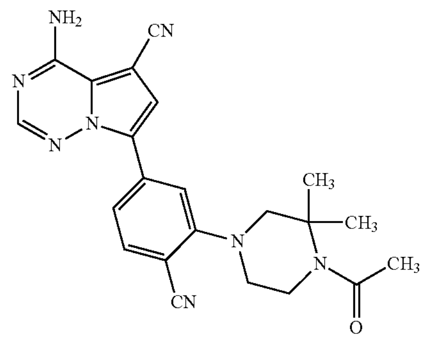 [SMILES: CC(=O)N1CCN(c2cc(-c3cc(C#N)c4c(N)ncnn34)ccc2C#N)CC1(C)C] | 7-(3-(4-acetyl-3,3-dimethylpiperazin-1-yl)-4-cyanophenyl)-4-aminopyrrolo[2,1-f][1,2,4]triazine-5-carbonitrile | 414 |
| 779 | 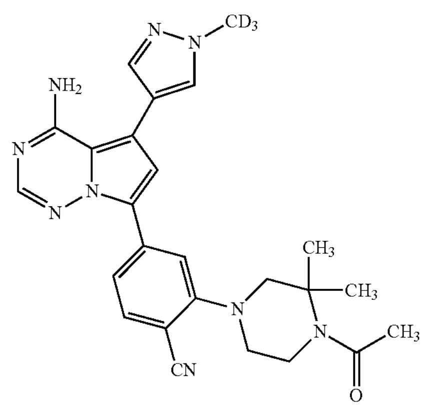 [SMILES: [2H]C([2H])([2H])n1cc(-c2cc(-c3ccc(C#N)c(N4CCN(C(C)=O)C(C)(C)C4)c3)n3ncnc(N)c23)cn1] | 2-(4-acetyl-3,3-dimethylpiperazin-1-yl)-4-(4-amino-5-(1-(methyl-d$_3$)-1H-pyrazol-4-yl)pyrrolo[2,1-f][1,2,4]triazin-7-yl)benzonitrile | 473 |
| 780 | 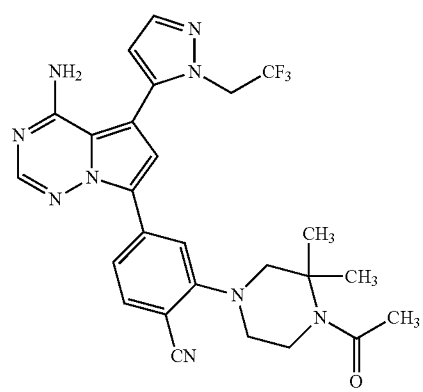 [SMILES: CC(=O)N1CCN(c2cc(-c3cc(-c4ccnn4CC(F)(F)F)c4c(N)ncnn34)ccc2C#N)CC1(C)C] | 2-(4-acetyl-3,3-dimethylpiperazin-1-yl)-4-(4-amino-5-(1-(2,2,2-trifluoroethyl)-1H-pyrazol-5-yl)pyrrolo[2,1-f][1,2,4]triazin-7-yl)benzonitrile | 538 |
| 781 | 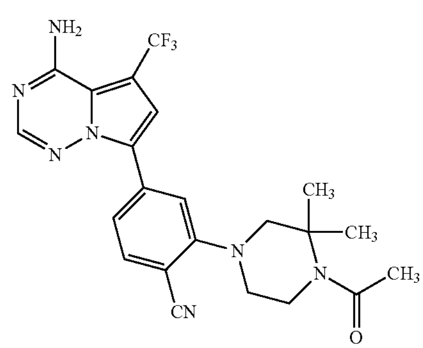 [SMILES: CC(=O)N1CCN(c2cc(-c3cc(C(F)(F)F)c4c(N)ncnn34)ccc2C#N)CC1(C)C] | 2-(4-acetyl-3,3-dimethylpiperazin-1-yl)-4-(4-amino-5-(trifluoromethyl)pyrrolo[2,1-f][1,2,4]triazin-7-yl)benzonitrile | 457 |

TABLE 49-continued

| Ex. No. | Structure | Name | M + H |
|---|---|---|---|
| 782 | 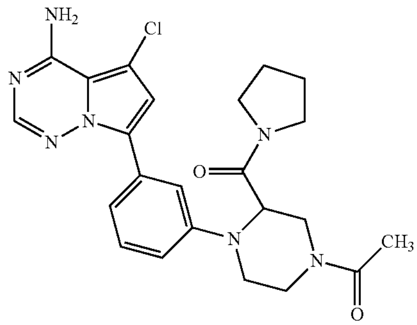 [SMILES: CC(=O)N1CCN(c2cccc(-c3cc(Cl)c4c(N)ncnn34)c2)C(C(=O)N2CCCC2)C1] | 1-(4-(3-(4-amino-5-chloropyrrolo[2,1-f][1,2,4]triazin-7-yl)phenyl)-3-(pyrrolidine-1-carbonyl)piperazin-1-yl)ethan-1-one | 468 |
| 783 | 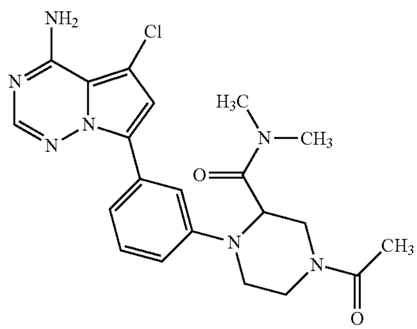 [SMILES: CC(=O)N1CCN(c2cccc(-c3cc(Cl)c4c(N)ncnn34)c2)C(C(=O)N(C)C)C1] | 4-acetyl-1-(3-(4-amino-5-chloropyrrolo[2,1-f][1,2,4]triazin-7-yl)phenyl)-N,N-dimethylpiperazine-2-carboxamide | 442 |
| 784 | 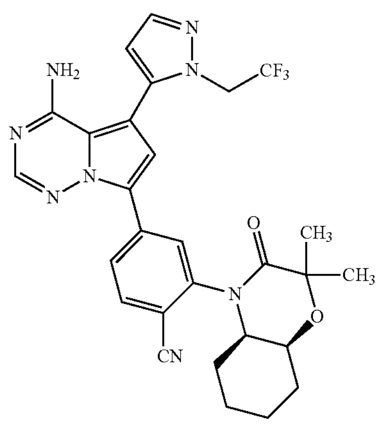 [SMILES: CC1(C)O[C@H]2CCCC[C@H]2N(c2cc(-c3cc(-c4ccnn4CC(F)(F)F)c4c(N)ncnn34)ccc2C#N)C1=O] | 4-(4-amino-5-(1-(2,2,2-trifluoroethyl)-1H-pyrazol-5-yl)pyrrolo[2,1-f][1,2,4]triazin-7-yl)-2-((4aR,8aS)-2,2-dimethyl-3-oxooctahydro-4H-benzo[b][1,4]oxazin-4-yl)benzonitrile | 565 |
| 785 | 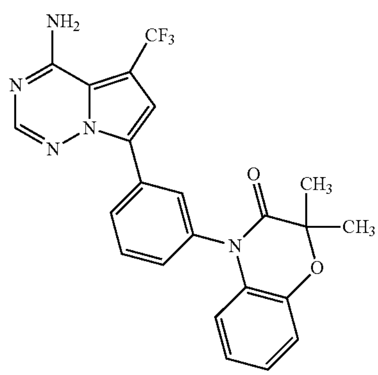 [SMILES: CC1(C)Oc2ccccc2N(c2cccc(-c3cc(C(F)(F)F)c4c(N)ncnn34)c2)C1=O] | 4-(3-(4-amino-5-(trifluoromethyl)pyrrolo[2,1-f][1,2,4]triazin-7-yl)phenyl)-2,2-dimethyl-2H-benzo[b][1,4]oxazin-3(4H)-one | 453 |

TABLE 49-continued

| Ex. No. | Structure | Name | M + H |
|---|---|---|---|
| 786 | 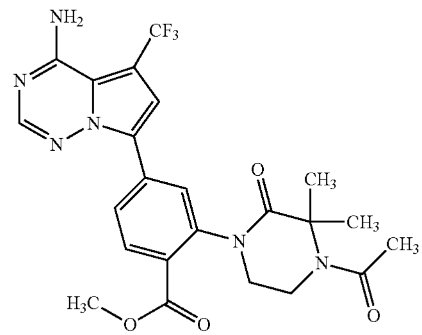 [SMILES: COC(=O)c1ccc(-c2cc(C(F)(F)F)c3c(N)ncnn23)cc1N1CCN(C(C)=O)C(C)(C)C1=O] | methyl 2-(4-acetyl-3,3-dimethyl-2-oxopiperazin-1-yl)-4-(4-amino-5-(trifluoromethyl)pyrrolo[2,1-f][1,2,4]triazin-7-yl)benzoate | 504 |
| 787 | 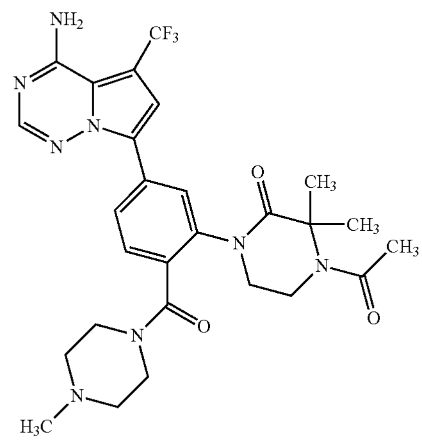 [SMILES: CC(=O)N1CCN(c2cc(-c3cc(C(F)(F)F)c4c(N)ncnn34)ccc2C(=O)N2CCN(C)CC2)C(=O)C1(C)C] | 4-acetyl-1-(5-(4-amino-5-(trifluoromethyl)pyrrolo[2,1-f][1,2,4]triazin-7-yl)-2-(4-methylpiperazine-1-carbonyl)phenyl)-3,3-dimethylpiperazin-2-one | 573 |
| 788 | 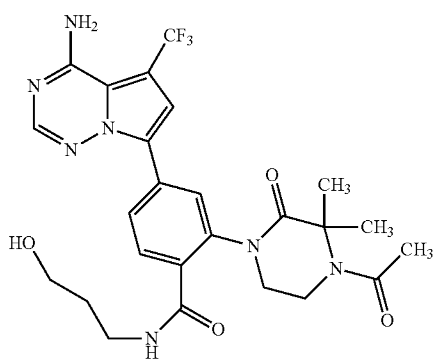 [SMILES: CC(=O)N1CCN(c2cc(-c3cc(C(F)(F)F)c4c(N)ncnn34)ccc2C(=O)NCCCO)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(3-hydroxypropyl)benzamide | 548 |
| 789 | 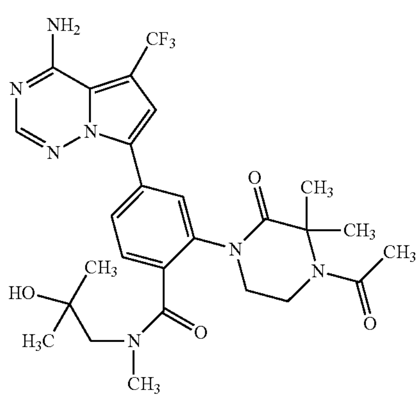 [SMILES: CC(=O)N1CCN(c2cc(-c3cc(C(F)(F)F)c4c(N)ncnn34)ccc2C(=O)N(C)CC(C)(C)O)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-hydroxy-2-methylpropyl)-N-methylbenzamide | 562 |

TABLE 49-continued

| Ex. No. | Structure | Name | M + H |
|---|---|---|---|
| 790 | 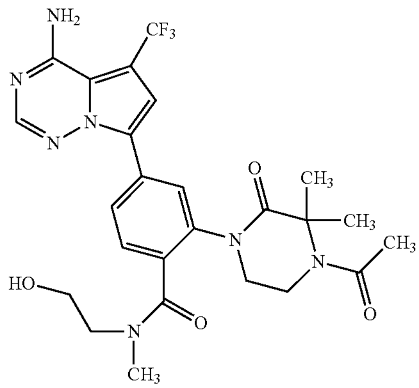 [SMILES: CC(=O)N1CCN(c2cc(-c3cc(C(F)(F)F)c4c(N)ncnn34)ccc2C(=O)N(C)CCO)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-hydroxyethyl)-N-methylbenzamide | 548 |
| 791 | 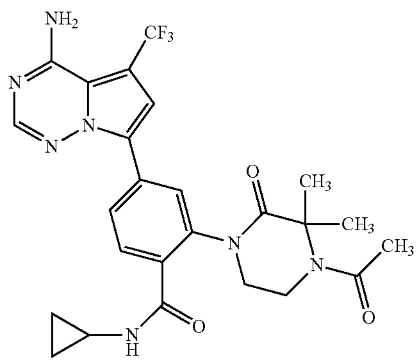 [SMILES: CC(=O)N1CCN(c2cc(-c3cc(C(F)(F)F)c4c(N)ncnn34)ccc2C(=O)NC2CC2)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-cyclopropylbenzamide | 530 |
| 792 | 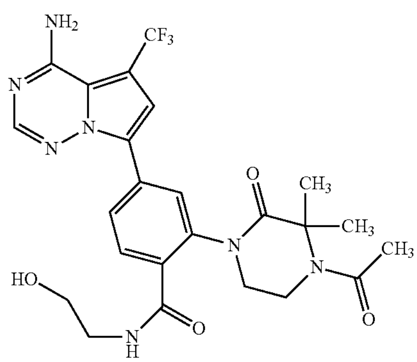 [SMILES: CC(=O)N1CCN(c2cc(-c3cc(C(F)(F)F)c4c(N)ncnn34)ccc2C(=O)NCCO)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-hydroxyethyl)benzamide | 534 |
| 793 | 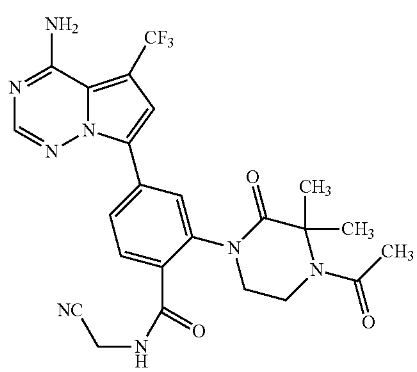 [SMILES: CC(=O)N1CCN(c2cc(-c3cc(C(F)(F)F)c4c(N)ncnn34)ccc2C(=O)NCC#N)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(cyanomethyl)benzamide | 528 |

TABLE 49-continued

| Ex. No. | Structure | Name | M + H |
|---|---|---|---|
| 794 | 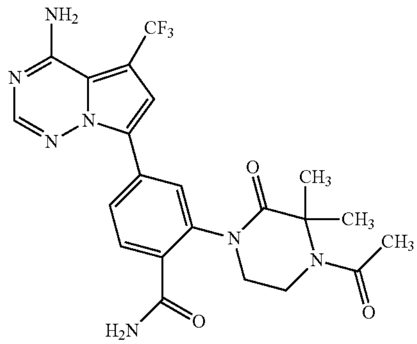 [SMILES: CC(=O)N1CCN(c2cc(-c3cc(C(F)(F)F)c4c(N)ncnn34)ccc2C(N)=O)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)benzamide | 489 |
| 795 | 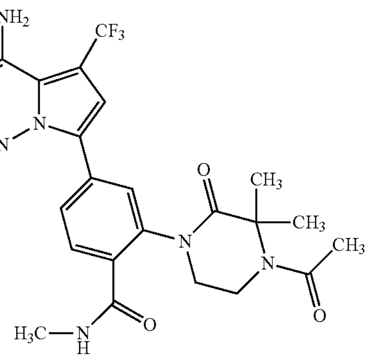 | 2-(4-acetyl-3,3-dimethyl-2-oxopiperazin-1-yl)-4-(4-amino-5-(trifluoromethyl)pyrrolo[2,1-f][1,2,4]triazin-7-yl)-N-methylbenzamide | 503 |
| 796 | 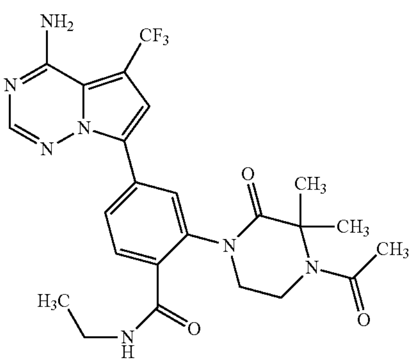 [SMILES: CCNC(=O)c1ccc(-c2cc(C(F)(F)F)c3c(N)ncnn23)cc1N1CCN(C(C)=O)C(C)(C)C1=O] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-ethylbenzamide | 518 |
| 797 | 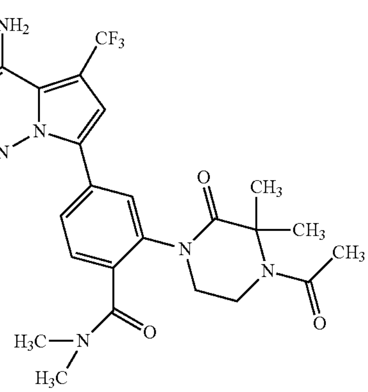 | 2-(4-acetyl-3,3-dimethyl-2-oxopiperazin-1-yl)-4-(4-amino-5-(tirfluoromethyl)pyrrolo[2,1-f][1,2,4]triazin-7-yl)-N,N-dimethylbenzamide | 376 |

TABLE 49-continued

| Ex. No. | Structure | Name | M + H |
|---|---|---|---|
| 798 | 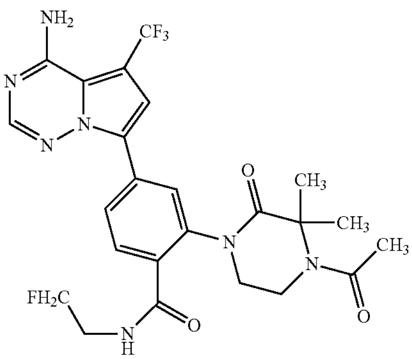 | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-fluoroethyl)benzamide | 535 |
| 799 | 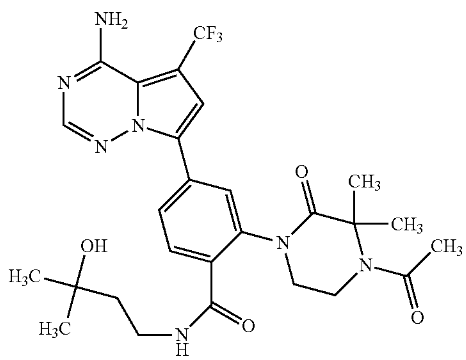 [SMILES: CC(=O)N1CCN(c2cc(-c3cc(C(F)(F)F)c4c(N)ncnn34)ccc2C(=O)NCCC(C)(C)O)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(3-hydroxy-3-methylbutyl))benzamide | 576 |
| 800 | 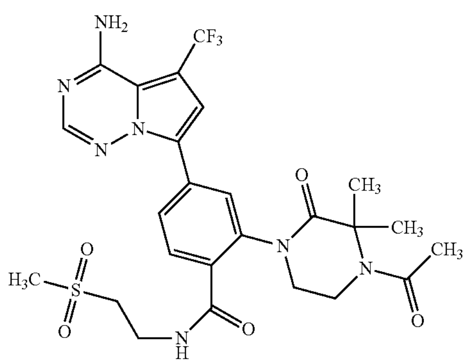 [SMILES: CC(=O)N1CCN(c2cc(-c3cc(C(F)(F)F)c4c(N)ncnn34)ccc2C(=O)NCCS(C)(=O)=O)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-(methylsulfonyl)ethyl)benzamide | 596 |
| 801 | 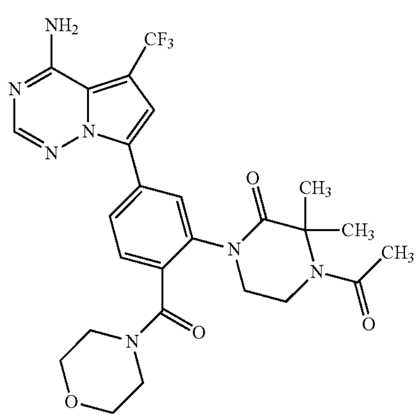 [SMILES: CC(=O)N1CCN(c2cc(-c3cc(C(F)(F)F)c4c(N)ncnn34)ccc2C(=O)N2CCOCC2)C(=O)C1(C)C] | 4-acetyl-1-(5-(4-amino-5-(trifluoromethyl)pyrrolo[2,1-f][1,2,4]triazin-7-yl)-2-(morpholine-4-carbonyl)phenyl)-3,3-dimethylpiperazin-2-one | 560 |

TABLE 49-continued

| Ex. No. | Structure | Name | M + H |
|---|---|---|---|
| 802 | 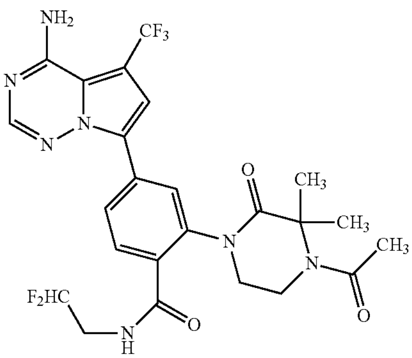 [SMILES: CC(=O)N1CCN(c2cc(-c3cc(C(F)(F)F)c4c(N)ncnn34)ccc2C(=O)NCC(F)F)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2,2-difluoroethyl)benzamide | 533 |
| 803 | 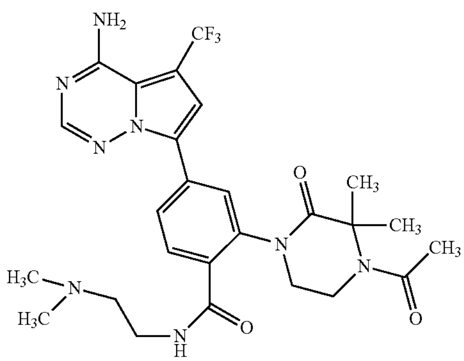 [SMILES: CC(=O)N1CCN(c2cc(-c3cc(C(F)(F)F)c4c(N)ncnn34)ccc2C(=O)NCCN(C)C)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-(dimethylamino)ethyl)-N-methylbenzamide | 575 |
| 804 | 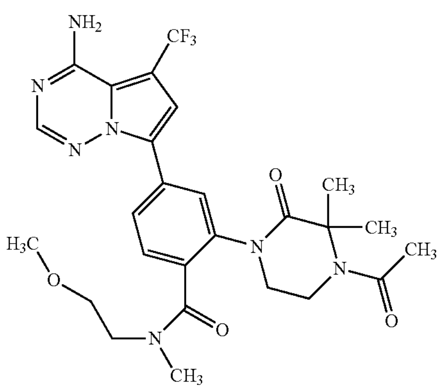 [SMILES: COCCN(C)C(=O)c1ccc(-c2cc(C(F)(F)F)c3c(N)ncnn23)cc1N1CCN(C(C)=O)C(C)(C)C1=O] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-methoxyethyl)-N-methylbenzamide | 562 |
| 805 | 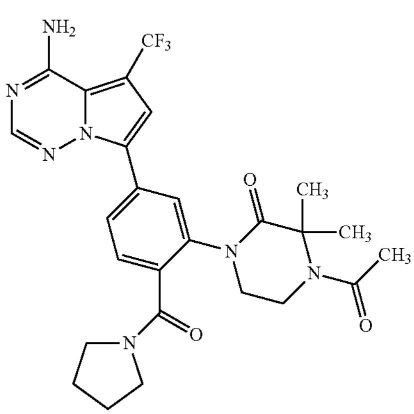 [SMILES: CC(=O)N1CCN(c2cc(-c3cc(C(F)(F)F)c4c(N)ncnn34)ccc2C(=O)N2CCCC2)C(=O)C1(C)C] | 4-acetyl-1-(5-(4-amino-5-(trifluoromethyl)pyrrolo[2,1-f][1,2,4]triazin-7-yl)-2-(pyrrolidine-1-carbonyl)phenyl)-3,3-dimethylpiperazin-2-one | 544 |

TABLE 49-continued

| Ex. No. | Structure | Name | M + H |
|---|---|---|---|
| 806 | 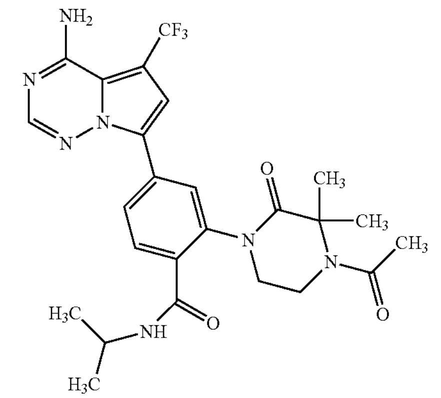 [SMILES: CC(=O)N1CCN(c2cc(-c3cc(C(F)(F)F)c4c(N)ncnn34)ccc2C(=O)NC(C)C)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-isopropylbenzamide | 532 |
| 807 | 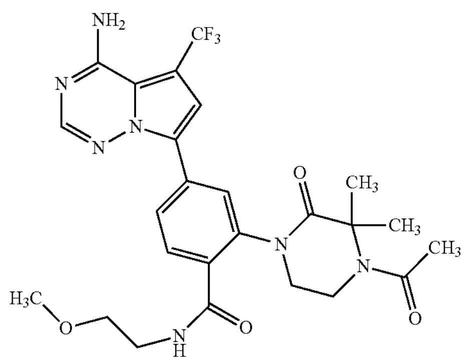 [SMILES: COCCNC(=O)c1ccc(-c2cc(C(F)(F)F)c3c(N)ncnn23)cc1N1CCN(C(C)=O)C(C)(C)C1=O] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-methoxyethyl)benzamide | 548 |
| 808 | 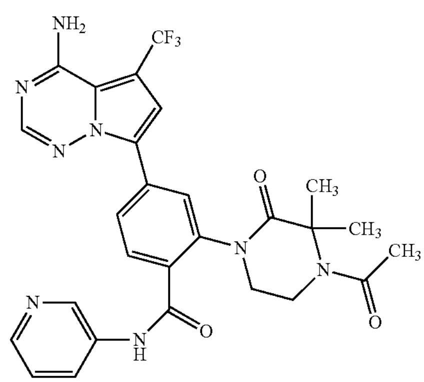 [SMILES: CC(=O)N1CCN(c2cc(-c3cc(C(F)(F)F)c4c(N)ncnn34)ccc2C(=O)Nc2cccnc2)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(pyridin-3-yl)benzamide | 567 |
| 809 | 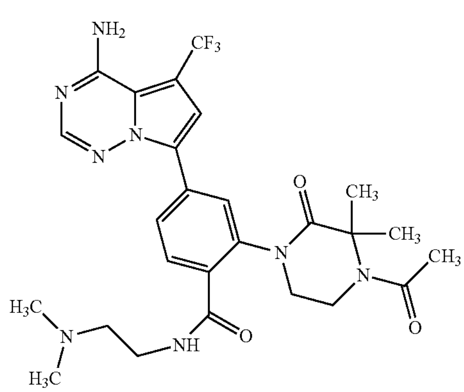 [SMILES: CC(=O)N1CCN(c2cc(-c3cc(C(F)(F)F)c4c(N)ncnn34)ccc2C(=O)NCCN(C)C)C(=O)C1(C)C] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-(dimethylamino)ethyl)benzamide | 561 |

| Ex. No. | Structure | Name | M + H |
|---|---|---|---|
| 810 | 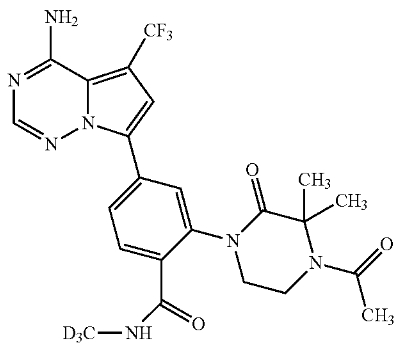 [SMILES: [2H]C([2H])([2H])NC(=O)c1ccc(-c2cc(C(F)(F)F)c3c(N)ncnn23)cc1N1CCN(C(C)=O)C(C)(C)C1=O] | 2-(4-acetyl-3,3-dimethyl-2-oxopiperazin-1-yl)-4-(4-amino-5-(trifluoromethyl)pyrrolo[2,1-f][1,2,4]triazin-7-yl)-N-(methyl-d₃)benzamide | 507 |
| 811 | 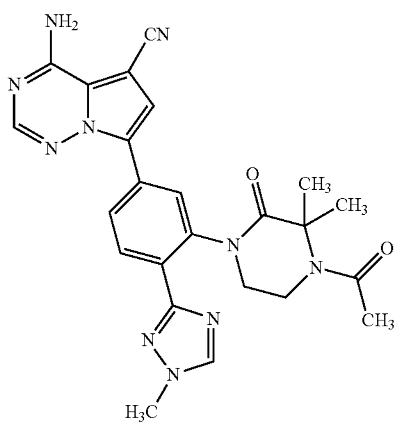 [SMILES: CC(=O)N1CCN(c2cc(-c3cc(C#N)c4c(N)ncnn34)ccc2-c2ncn(C)n2)C(=O)C1(C)C] | 7-(3-(4-acetyl-3,3-dimethyl-2-oxopiperazin-1-yl)-4-(1-methyl-1H-1,2,4-triazol-3-yl)phenyl)-4-aminopyrrolo[2,1-f][1,2,4]triazine-5-carbonitrile | 485 |
| 812 | 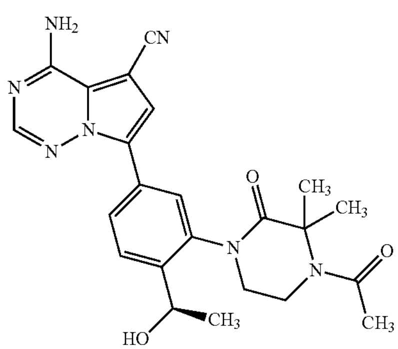 [SMILES: CC(=O)N1CCN(c2cc(-c3cc(C#N)c4c(N)ncnn34)ccc2[C@@H](C)O)C(=O)C1(C)C] | (R)-4-acetyl-1-(5-(4-amino-5-(trifluoromethyl)pyrrolo[2,1-f][1,2,4]triazin-7-yl)-2-(1-hydroxyethyl)phenyl)-3,3-dimethylpiperazin-2-one | 490 |
| 813 | 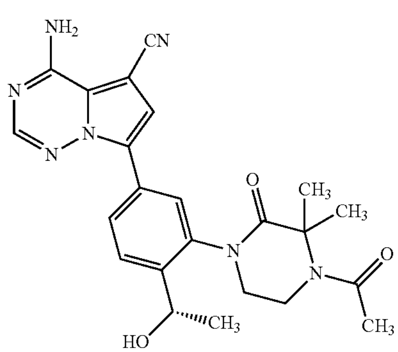 [SMILES: CC(=O)N1CCN(c2cc(-c3cc(C#N)c4c(N)ncnn34)ccc2[C@H](C)O)C(=O)C1(C)C] | (S)-4-acetyl-1-(5-(4-amino-5-(trifluoromethyl)pyrrolo[2,1-f][1,2,4]triazin-7-yl)-2-(1-hydroxyethyl)phenyl)-3,3-dimethylpiperazin-2-one | 490 |

TABLE 49-continued

| Ex. No. | Structure | Name | M + H |
|---|---|---|---|
| 814 | 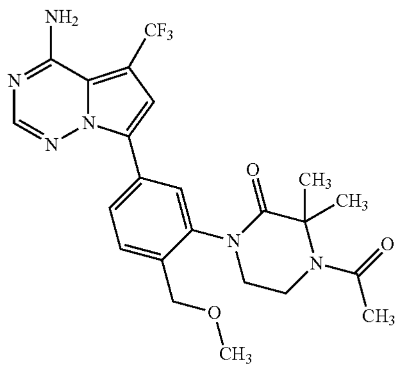 [SMILES: COCc1ccc(-c2cc(C(F)(F)F)c3c(N)ncnn23)cc1N1CCN(C(C)=O)C(C)(C)C1=O] | 4-acetyl-1-(5-(4-amino-5-(trifluoromethyl)pyrrolo[2,1-f][1,2,4]triazin-7-yl)-2-(methoxymethyl)phenyl)-3,3-dimethylpiperazin-2-one | 490 |
| 815 | 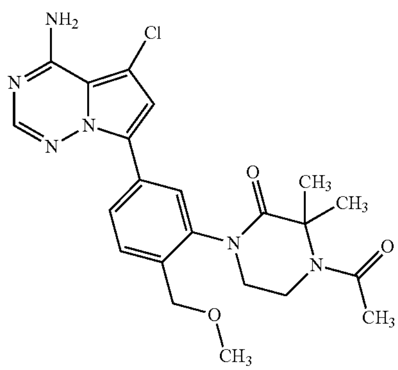 | 4-acetyl-1-(5-(4-amino-5-chloropyrrolo[2,1-f][1,2,4]triazin-7-yl)-2-(methoxymethyl)phenyl)-3,3-dimethylpiperazin-2-one | 457 |
| 816 | 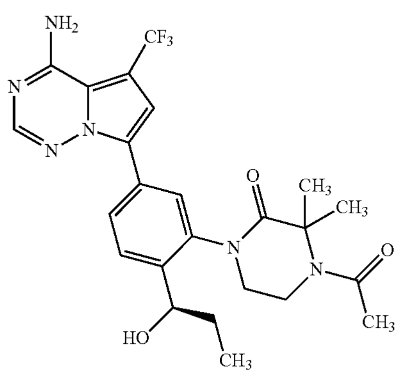 [SMILES: CC[C@@H](O)c1ccc(-c2cc(C(F)(F)F)c3c(N)ncnn23)cc1N1CCN(C(C)=O)C(C)(C)C1=O] | (R)-4-acetyl-1-(5-(4-amino-5-(trifluoromethyl)pyrrolo[2,1-f][1,2,4]triazin-7-yl)-2-(1-hydroxypropyl)phenyl)-3,3-dimethylpiperazin-2-one | 505 |
| 817 | 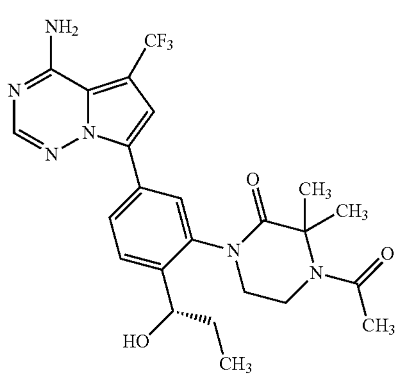 [SMILES: CC[C@H](O)c1ccc(-c2cc(C(F)(F)F)c3c(N)ncnn23)cc1N1CCN(C(C)=O)C(C)(C)C1=O] | (S)-4-acetyl-1-(5-(4-amino-5-(trifluoromethyl)pyrrolo[2,1-f][1,2,4]triazin-7-yl)-2-(1-hydroxypropyl)phenyl)-3,3-dimethylpiperazin-2-one | 505 |

TABLE 49-continued

| Ex. No. | Structure | Name | M + H |
|---|---|---|---|
| 818 | 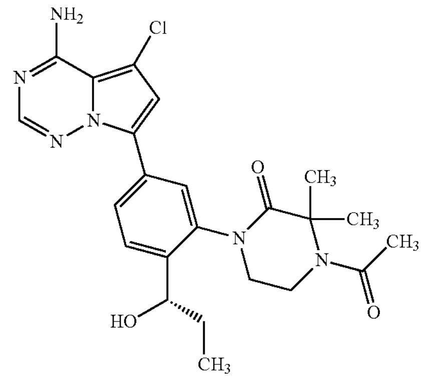 [SMILES: CC[C@H](O)c1ccc(-c2cc(Cl)c3c(N)ncnn23)cc1N1CCN(C(C)=O)C(C)(C)C1=O] | (S)-4-acetyl-1-(5-(4-amino-5-chloropyrrolo[2,1-f][1,2,4]triazin-7-yl)-2-(1-hydroxypropyl)phenyl)-3,3-dimethylpiperazin-2-one | 471 |
| 819 | 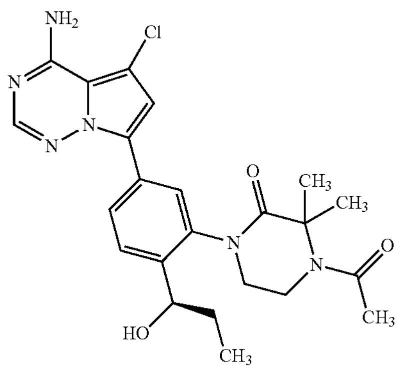 [SMILES: CC[C@@H](O)c1ccc(-c2cc(Cl)c3c(N)ncnn23)cc1N1CCN(C(C)=O)C(C)(C)C1=O] | (R)-4-acetyl-1-(5-(4-amino-5-chloropyrrolo[2,1-f][1,2,4]triazin-7-yl)-2-(1-hydroxypropyl)phenyl)-3,3-dimethylpiperazin-2-one | 471 |
| 820 | 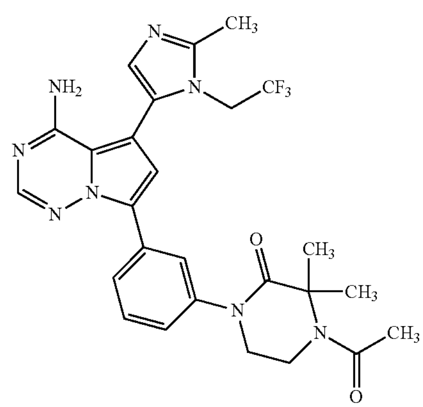 [SMILES: CC(=O)N1CCN(c2cccc(-c3cc(-c4cnc(C)n4CC(F)(F)F)c4c(N)ncnn34)c2)C(=O)C1(C)C] | 4-acetyl-1-(3-(4-amino-5-(2-methyl-1-(2,2,2-trifluoroethyl)-1H-imidazol-5-yl)pyrrolo[2,1-f][1,2,4]triazin-7-yl)phenyl)-3,3-dimethylpiperazin-2-one | 541 |
| 821 | 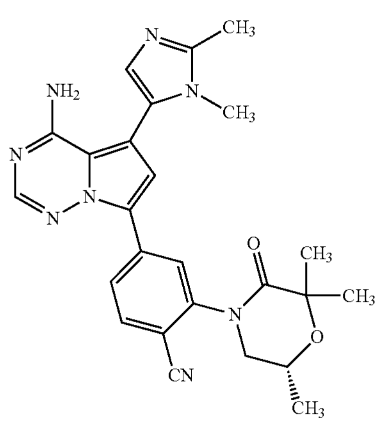 [SMILES: Cc1ncc(-c2cc(-c3ccc(C#N)c(N4C[C@@H](C)OC(C)(C)C4=O)c3)n3ncnc(N)c23)n1C] | (R)-4-(4-amino-5-(1,2-dimethyl-1H-imidazol-5-yl)pyrrolo[2,1-f][1,2,4]triazin-7-yl)-2-(2,2,6-trimethyl-3-oxomorpholino)benzonitrile | 471 |

TABLE 49-continued

| Ex. No. | Structure | Name | M + H |
|---|---|---|---|
| 822 | 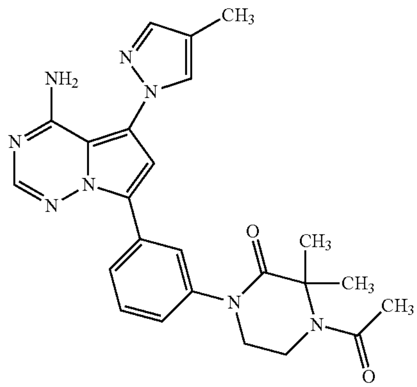 [SMILES: CC(=O)N1CCN(c2cccc(-c3cc(-n4cc(C)cn4)c4c(N)ncnn34)c2)C(=O)C1(C)C] | 4-acetyl-1-(3-(4-amino-5-(4-methyl-1H-pyrazol-1-yl)pyrrolo[2,1-f][1,2,4]triazin-7-yl)phenyl)-3,3-dimethylpiperazin-2-one | 459 |
| 823 | 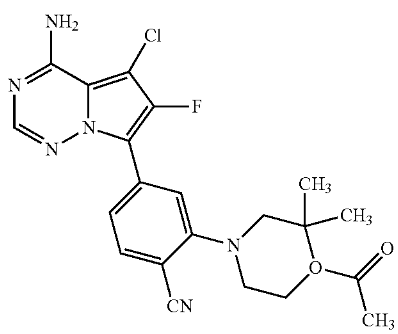 | 2-(4-acetyl-3,3-dimethylpiperazin-1-yl)-4-(4-amino-5-chloro-6-fluoropyrrolo[2,1-f][1,2,4]triazin-7-yl)benzonitrile | 442 |
| 824 | 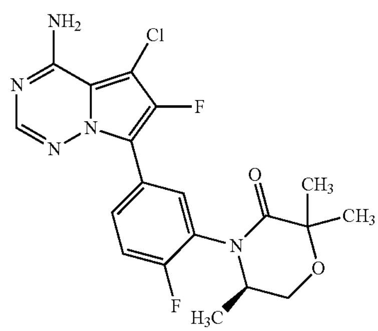 [SMILES: C[C@@H]1COC(C)(C)C(=O)N1c1cc(-c2c(F)c(Cl)c3c(N)ncnn23)ccc1F] | (R)-4-(5-(4-amino-5-chloro-6-fluoropyrrolo[2,1-f][1,2,4]triazin-7-yl)-2-fluorophenyl)-2,2,5-trimethylmorpholin-3-one | 422 |
| 825 | 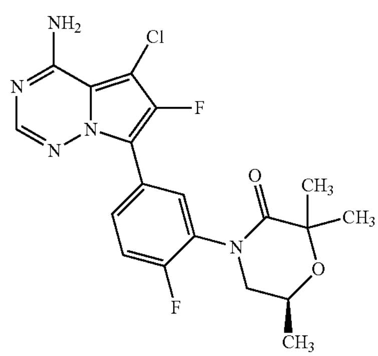 [SMILES: C[C@H]1CN(c2cc(-c3c(F)c(Cl)c4c(N)ncnn34)ccc2F)C(=O)C(C)(C)O1] | (S)-4-(5-(4-amino-5-chloro-6-fluoropyrrolo[2,1-f][1,2,4]triazin-7-yl)-2-fluorophenyl)-2,2,6-trimethylmorpholin-3-one | 422 |

TABLE 49-continued

| Ex. No. | Structure | Name | M + H |
|---|---|---|---|
| 826 | 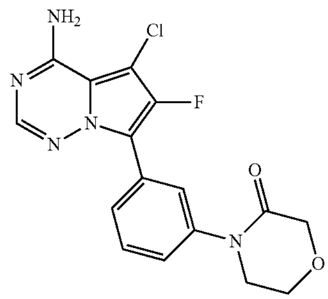 [SMILES: Nc1ncnn2c(-c3cccc(N4CCOCC4=O)c3)c(F)c(Cl)c12] | 4-(3-(4-amino-5-chloro-6-fluoropyrrolo[2,1-f][1,2,4]triazin-7-yl)phenyl)morpholin-3-one | 362 |
| 827 | 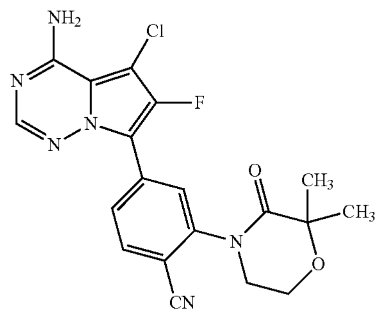 [SMILES: CC1(C)OCCN(c2cc(-c3c(F)c(Cl)c4c(N)ncnn34)ccc2C#N)C1=O] | 4-(4-amino-5-chloro-6-fluoropyrrolo[2,1-f][1,2,4]triazin-7-yl)-2-(2,2-dimethyl-3-oxomorpholino)benzonitrile | 415 |
| 828 | 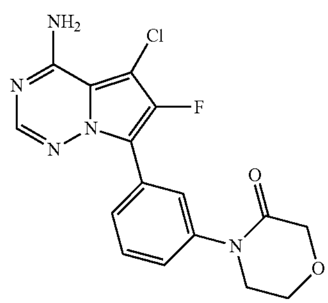 [SMILES: Nc1ncnn2c(-c3cccc(N4CCOCC4=O)c3)c(F)c(Cl)c12] | 4-(3-(4-amino-5-chloro-6-fluoropyrrolo[2,1-f][1,2,4]triazin-7-yl)phenyl)morpholin-3-one | 362 |
| 829 | 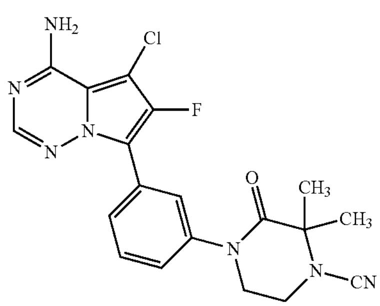 [SMILES: CC1(C)C(=O)N(c2cccc(-c3c(F)c(Cl)c4c(N)ncnn34)c2)CCN1C#N] | 4-(3-(4-amino-5-chloro-6-fluoropyrrolo[2,1-f][1,2,4]triazin-7-yl)phenyl)-2,2-dimethyl-3-oxopiperazine-1-carbonitrile | 414 |
| 830 | 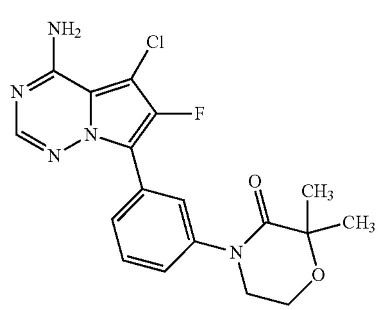 [SMILES: CC1(C)OCCN(c2cccc(-c3c(F)c(Cl)c4c(N)ncnn34)c2)C1=O] | 4-(3-(4-amino-5-chloro-6-fluoropyrrolo[2,1-f][1,2,4]triazin-7-yl)phenyl)-2,2-dimethylmorpholin-3-one | 390 |

TABLE 49-continued

| Ex. No. | Structure | Name | M + H |
|---|---|---|---|
| 831 | 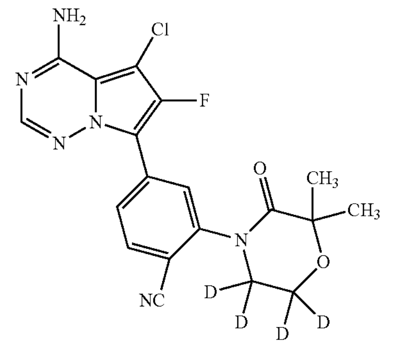 [SMILES: [2H]C1([2H])OC(C)(C)C(=O)N(c2cc(-c3c(F)c(Cl)c4c(N)ncnn34)ccc2C#N)C1([2H])[2H]] | 4-(4-amino-5-chloro-6-fluoropyrrolo[2,1-f][1,2,4]triazin-7-yl)-2-(2,2-dimethyl-3-oxomorpholino-5,5,6,6-d₄)benzonitrile | 419 |
| 832 | 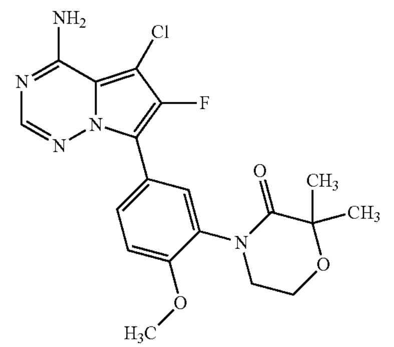 [SMILES: COc1ccc(-c2c(F)c(Cl)c3c(N)ncnn23)cc1N1CCOC(C)(C)C1=O] | 4-(5-(4-amino-5-chloro-6-fluoropyrrolo[2,1-f][1,2,4]triazin-7-yl)-2-methoxyphenyl)-2,2-dimethylmorpholin-3-one | 420 |
| 833 | 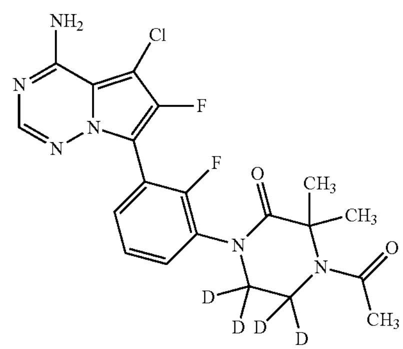 [SMILES: [2H]C1([2H])N(c2cccc(-c3c(F)c(Cl)c4c(N)ncnn34)c2F)C(=O)C(C)(C)N(C(C)=O)C1([2H])[2H]] | 4-acetyl-1-(3-(4-amino-5-chloro-6-fluoropyrrolo[2,1-f][1,2,4]triazin-7-yl)-2-fluorophenyl)-3,3-dimethylpiperazin-2-one-5,5,6,6-d₄ | 453 |
| 834 | 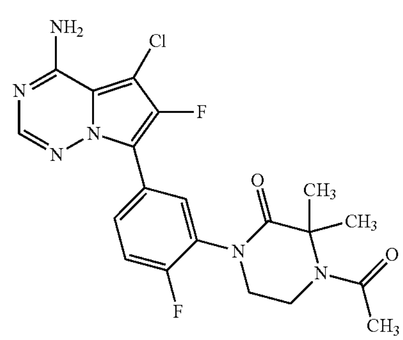 [SMILES: CC(=O)N1CCN(c2cc(-c3c(F)c(Cl)c4c(N)ncnn34)ccc2F)C(=O)C1(C)C] | 4-acetyl-1-(5-(4-amino-5-chloro-6-fluoropyrrolo[2,1-f][1,2,4]triazin-7-yl)-2-fluorophenyl)-3,3-dimethylpiperazin-1-one | 457 |

TABLE 49-continued

| Ex. No. | Structure | Name | M + H |
|---|---|---|---|
| 835 | 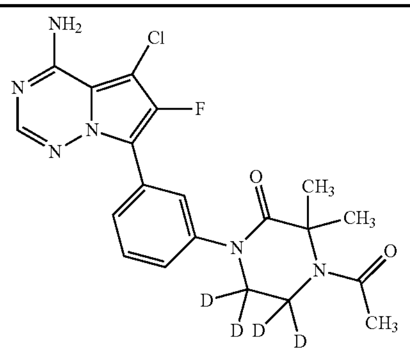 | 4-acetyl-1-(3-(4-amino-5-chloro-6-fluoropyrrolo[2,1-f][1,2,4]triazin-7-yl)phenyl)-3,3-dimethylpiperazin-2-one-5,5,6,6-$d_4$ | 435 |
| 836 | 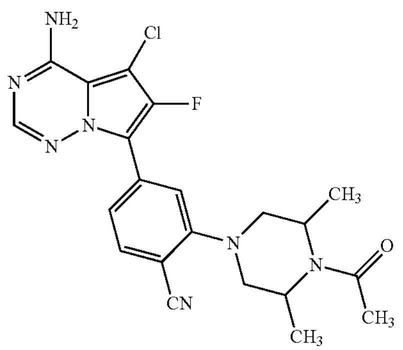 [SMILES: CC(=O)N1C(C)CN(c2cc(-c3c(F)c(Cl)c4c(N)ncnn34)ccc2C#N)CC1C] | 2-(4-acetyl-3,5-dimethylpiperazin-1-yl)-4-(4-amino-5-chloro-6-fluoropyrrolo[2,1-f][1,2,4]triazin-7-yl)benzonitrile | 442 |
| 837 | 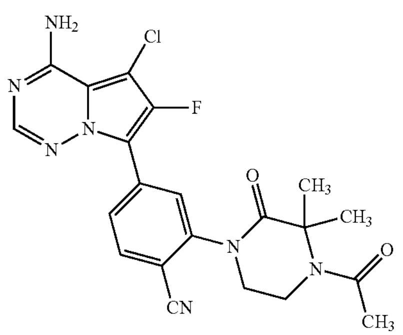 [SMILES: CC(=O)N1CCN(c2cc(-c3c(F)c(Cl)c4c(N)ncnn34)ccc2C#N)C(=O)C1(C)C] | 2-(4-acetyl-3,3-dimethyl-2-oxopiperazin-1-yl)-4-(4-amino-5-chloro-6-fluoropyrrolo[2,1-f][1,2,4]triazin-7-yl)benzonitrile | 456 |

Biological Assays

The pharmacological properties of the compounds of this invention may be confirmed by a number of biological assays. The exemplified biological assays, which follow, have been carried out with compounds of the invention.

ADP-Glo Format PI3K Assays

The ADP-Glo format PI3K assays were performed in Proxiplate 384-well plates (Perkin Elmer #6008280). The final assay volume was 2 µl prepared from 1 µl additions of enzyme/PIP2:PS lipid (Invitrogen #PV5100) mixture and 1 µl ATP (provided in kit, Promega #V9101) and test compounds in assay buffer (50 mM HEPES pH 7.5, 3 mM MgCl$_2$, 100 mM NaCl, 0.5 mM EGTA, 2 mM DTT, 0.03% CHAPS). The reaction was initiated by the combination of enzyme/lipid, ATP, and test compounds. The reaction mixture was incubated at room temperature for 30 minutes (PI3K Alpha, Beta, Gamma) or 3 hours for PI3K Delta. ADP-Glo (2 µl), followed by Kinase Detection reagent (4 µl), were added to reactions following the initial incubation and allowed to incubate 40 minutes at room temperature. The reaction mixture was analyzed on the TOPCOUNT® (Perkin Elmer). Inhibition data were calculated by comparison to no enzyme control reactions for 100% inhibition and vehicle-only reactions for 0% inhibition. The final concentration of enzyme in the assays are PI3K Alpha [0.5 nM], PI3K Beta [2 nM], PI3K Gamma [20 nM], PI3K Delta [0.5 nM]. ATP final concentrations are as follows: for Alpha [10 µM], for Beta [12.5 µM], for Gamma [6.5 µM], for Delta [100 µM]. Lipid final concentration was the same for all enzymes, [25 µM]. Dose response curves were generated to determine the concentration required to inhibit 50% of activity. Compounds were dissolved at 0.12 mM in dimethylsulfoxide (DMSO) and evaluated at eleven concentrations. The IC$_{50}$ values were derived by non-linear regression analysis.

Whole Blood Assay of BCR-Stimulated CD69 Expression on B Cells

The efficacy of PI3K inhibitor compounds in suppressing CD69 expression on B cells human in whole blood assays is useful for predicting efficacious doses in the clinic and minimizing potential side-effects. PI3K inhibitor compounds having higher activity in the whole blood CD69 expression assay are expected to require lower doses than compounds having lower activity, and are expected to cause fewer unwanted side-effects. (Uetrecht, *Chem. Res. Toxicol.*, 12:387-395 (1999); Nakayama, *Drug Metabolism and Disposition*, 37(9):1970-1977 (2009); Sakatis, *Chemical Research in Toxicology* (2012)).

To measure BCR-stimulated B cells, ACD-A human whole blood was treated with various concentrations of test compound and stimulated with 30 μg/mL AffiniPure F(ab')2 fragment goat anti human IgM (Jackson 109-006-1299—endotoxin cleared) and 10 ng/mL human IL-4 (PeproTech 200-04) for 18 h at 37° C. with agitation. The cells were blocked with human gamma globulin (Jackson 009-000-002) and stained with FITC-conjugated mouse anti-human CD20 (BD Pharmingen 555622) and PE-conjugated mouse anti-human CD69 monoclonal antibody (BD Pharmingen 555531), lysed and fixed, then washed. The amount of CD69 expression was quantitated by the median fluorescence intensity (MFI) after gating on the CD20-positive B cell population as measured by FACS analysis.

In the whole blood assay of BCR-Stimulated CD69 expression on B cells, increased efficacy of a PI3K inhibitor compound is indicated by a lower CD69 $IC_{50}$ value.

The exemplified Examples disclosed below were tested in one or both of the ADP-Glo format PI3K assays and the Whole Blood Assay of BCR-Stimulated CD69 Expression on B Cells, each described above. The exemplified Examples disclosed below were found to have PI3K delta inhibitory activity. Table 11 lists the $IC_{50}$ values measured in the ADP-Glo format PI3K delta assay and CD69 $IC_{50}$ values measured the Whole Blood Assay of BCR-Stimulated CD69 Expression on B Cells for the following examples.

TABLE 11

| Ex. No. | PI3K delta $IC_{50}$ value (nM) | CD69 $IC_{50}$ value (nM) |
| --- | --- | --- |
| 1 | 13 | — |
| 2 | 16 | — |
| 3 | 3 | — |
| 4 | 2 | — |
| 5 | 5 | — |
| 6 | 3 | — |
| 7 | 12 | — |
| 8 | 11 | — |
| 9 | 18 | — |
| 10 | 4 | — |
| 11 | 7 | — |
| 12 | 19 | — |
| 13 | 16 | — |
| 14 | 2 | — |
| 15 | 6 | — |
| 16 | 25 | — |
| 17 | 2 | — |
| 18 | 10 | — |
| 19 | 1 | — |
| 20 | 16 | — |
| 21 | 10 | — |
| 22 | 2 | — |
| 23 | 1 | — |
| 24 | 8 | — |
| 25 | 8 | — |
| 26 | 5 | — |
| 27 | 1 | — |
| 28 | 1 | — |
| 29 | 6 | — |
| 30 | 6 | — |
| 31 | 1 | — |
| 32 | 3 | — |
| 33 | 7 | — |
| 34 | 6 | — |
| 35 | 2 | — |
| 36 | 6 | — |
| 37 | 3 | — |
| 38 | 5 | — |
| 39 | 2 | — |
| 40 | 3 | — |
| 41 | 4 | — |
| 42 | 3 | — |
| 43 | 4 | — |
| 44 | 4 | — |
| 45 | 1 | — |
| 46 | 4 | — |
| 47 | 4 | — |
| 48 | 6 | — |
| 49 | 3 | — |
| 50 | 2 | — |
| 51 | 1 | — |
| 52 | 2 | — |
| 53 | 4 | — |
| 54 | 2 | — |
| 55 | 2 | — |
| 56 | 4 | — |
| 57 | 4 | — |
| 59 | 2 | — |
| 60 | 2 | — |
| 61 | 2 | — |
| 62 | 2 | — |
| 63 | 2 | — |
| 64 | 1 | — |
| 65 | 7 | — |
| 66 | 2 | — |
| 67 | 22 | — |
| 68 | 8 | — |
| 69 | 2 | — |
| 70 | 4 | — |
| 71 | 3 | — |
| 72 | 2 | — |
| 73 | 3 | — |
| 74 | 7 | — |
| 75 | 2 | — |
| 76 | 3 | — |
| 77 | 4 | — |
| 78 | 4 | — |
| 79 | 3 | — |
| 80 | 2 | — |
| 81 | 6 | — |
| 82 | 3 | — |
| 83 | 6 | — |
| 84 | 2 | — |
| 85 | 2 | — |
| 86 | 2 | — |
| 87 | 7 | — |
| 88 | 5 | — |
| 89 | 6 | — |
| 90 | 1 | — |
| 91 | 2 | — |
| 92 | 1 | — |
| 93 | 1 | — |
| 94 | 2 | 23 |
| 95 | 2 | — |
| 96 | 0.4 | — |
| 97 | 2 | — |
| 98 | 3 | 30 |
| 99 | 1 | — |
| 100 | 4 | — |
| 101 | 4 | — |
| 102 | 4 | — |
| 103 | 7 | — |
| 104 | 3 | — |
| 105 | 3 | — |
| 106 | 6 | — |
| 107 | 3 | — |
| 108 | 4 | |
| 109 | 58 | — |
| 110 | 1 | — |

TABLE 11-continued

| Ex. No. | PI3K delta IC$_{50}$ value (nM) | CD69 IC$_{50}$ value (nM) |
|---|---|---|
| 111 | 1 | — |
| 112 | 3 | — |
| 113 | 3 | — |
| 114 | 5 | — |
| 115 | 3 | — |
| 116 | 2 | — |
| 117 | 2 | — |
| 118 | 1 | 26 |
| 119 | 4 | — |
| 120 | 2 | — |
| 121 | 1 | — |
| 122 | 4 | — |
| 123 | 2 | — |
| 124 | 2 | — |
| 125 | 2 | — |
| 126 | 4 | — |
| 127 | 8 | — |
| 128 | 1 | — |
| 129 | 4 | — |
| 130 | 4 | — |
| 131 | 5 | — |
| 132 | 3 | 1335 |
| 132 Enant. 1 | 2 | 284 |
| 132 Enant. 2 | 5 | — |
| 133 | 6 | — |
| 134 | 1 | — |
| 135 | 5 | — |
| 136 | 1 | — |
| 137 | 5 | — |
| 138 | 1 | — |
| 139 | 2 | — |
| 140 | 4 | — |
| 141 | 0.5 | 6 |
| 142 | 1 | — |
| 143 | 1 | — |
| 144 | 2 | — |
| 145 | 2 | — |
| 146 | 3 | — |
| 147 | 1 | — |
| 148 | 2 | — |
| 149 | 4 | — |
| 150 | 3 | — |
| 151 | 4 | — |
| 152 | 2 | — |
| 153 | 3 | — |
| 154 | 3 | — |
| 155 | 4 | — |
| 156 | 9 | — |
| 157 | 4 | — |
| 158 | 2 | — |
| 159 | 5 | — |
| 160 | 2 | — |
| 161 | 3 | — |
| 162 | 2 | — |
| 163 | 2 | — |
| 164 | 4 | — |
| 165 | 3 | — |
| 166 | 4 | — |
| 167 | 4 | — |
| 168 | 4 | — |
| 169 | 2 | — |
| 170 | 2 | — |
| 171 | 2 | — |
| 172 | 5 | — |
| 173 | 2 | — |
| 174 | 3 | — |
| 175 | 2 | — |
| 176 | 3 | — |
| 177 | 3 | — |
| 178 | 2 | — |
| 179 | 3 | — |
| 180 | 2 | — |
| 181 | 14 | — |
| 182 | 8 | — |
| 183 | 4 | — |
| 184 | 2 | — |
| 185 | 5 | — |
| 186 | 2 | — |
| 187 | 7 | — |
| 188 | 7 | — |
| 189 | 8 | — |
| 190 | 3 | — |
| 191 | 4 | — |
| 192 | 4 | — |
| 193 | 4 | — |
| 194 | 4 | — |
| 195 | 4 | — |
| 196 | 4 | — |
| 197 | 4 | — |
| 198 | 2 | — |
| 199 | 12 | — |
| 200 | 9 | — |
| 201 | 4 | — |
| 202 | 4 | — |
| 203 | 4 | — |
| 204 | 4 | — |
| 205 | 2 | — |
| 206 | 3 | — |
| 207 | 5 | — |
| 208 | 6 | 1185 |
| 209 | 9 | 1677 |
| 210 | 2 | 88 |
| 211 | 4 | — |
| 212 | 2 | — |
| 213 | 2 | — |
| 214 | 3 | — |
| 215 | 3 | — |
| 216 | 2 | — |
| 217 | 3 | — |
| 218 | 2 | — |
| 219 | 6 | — |
| 220 | 3 | — |
| 221 | 2 | — |
| 222 | 3 | — |
| 223 | 1 | — |
| 224 | 2 | — |
| 225 | 1 | — |
| 226 | 1 | — |
| 227 | 2 | — |
| 228 | 0.4 | — |
| 229 | 1 | — |
| 230 | 1 | — |
| 231 | 8 | — |
| 232 | 8 | — |
| 233 | 2 | — |
| 234 | 8 | — |
| 235 | 3 | — |
| 236 | 3 | — |
| 237 | 5 | — |
| 238 | 2 | — |
| 239 | 6 | — |
| 240 | 3 | — |
| 241 | 7 | — |
| 242 | 4 | — |
| 243 | 4 | — |
| 244 | 1 | — |
| 245 | 1 | — |
| 246 | 1 | 61 |
| 247 | 2 | — |
| 248 | 2 | — |
| 249 | 2 | — |
| 250 | 4 | — |
| 251 | 2 | — |
| 252 | 1 | — |
| 253 | 1 | — |
| 254 | 3 | — |
| 255 | 1 | — |
| 256 | 0.5 | — |
| 257 | 0.4 | — |
| 258 | 1 | — |

TABLE 11-continued

| Ex. No. | PI3K delta IC$_{50}$ value (nM) | CD69 IC$_{50}$ value (nM) |
|---|---|---|
| 259 | 1 | — |
| 260 | 1 | — |
| 261 | 4 | — |
| 262 | 3 | 35 |
| 263 | 6 | — |
| 264 | 1 | — |
| 265 | 1 | — |
| 266 | 4 | 81 |
| 267 | 2 | — |
| 268 | 1 | — |
| 269 | 2 | — |
| 270 | 1 | — |
| 271 | 4 | — |
| 272 | 4 | — |
| 273 | 5 | — |
| 274 | 1 | — |
| 275 | 1 | — |
| 276 | 3 | — |
| 277 | 2 | — |
| 278 | 3 | — |
| 279 | 5 | — |
| 280 | 4 | — |
| 281 | 4 | — |
| 282 | 1 | — |
| 283 | 2 | — |
| 284 | 6 | — |
| 285 | 6 | — |
| 286 | 5 | — |
| 287 | 5 | — |
| 288 | 2 | 4 |
| 289 | 1 | — |
| 290 | 1 | — |
| 291 | 1 | — |
| 292 | 3 | — |
| 293 | 1 | — |
| 294 | 2 | — |
| 295 | 2 | — |
| 296 | 2 | — |
| 297 | 2 | — |
| 298 | 2 | — |
| 299 | 3 | — |
| 300 | 1 | — |
| 301 | 4 | — |
| 302 | 5 | — |
| 303 | 2 | — |
| 304 | 7 | — |
| 305 | 5 | — |
| 306 | 3 | 208 |
| 307 | 3 | — |
| 308 | 3 | — |
| 309 | 2 | — |
| 310 | 3 | — |
| 311 | 2 | — |
| 312 | 1 | — |
| 313 | 2 | — |
| 314 | 1 | — |
| 315 | 6 | — |
| 316 | 4 | — |
| 317 | 8 | — |
| 318 | 5 | — |
| 319 | 2 | — |
| 320 | 5 | — |
| 321 | 3 | — |
| 322 | 5 | — |
| 323 | 2 | — |
| 324 | 0.5 | 7 |
| 325 | 2 | — |
| 326 | 2 | — |
| 327 | 2 | — |
| 328 | 2 | 38 |
| 329 | 3 | 48 |
| 330 | 3 | 87 |
| 331 | 4 | — |
| 332 | 4 | 52 |
| 333 | 4 | 22 |
| 334 | 6 | 44 |
| 335 | 4 | 24 |
| 336 | 5 | — |
| 337 | 3 | — |
| 338 | 2 | — |
| 339 | 1 | — |
| 340 | 1 | — |
| 341 | 1 | — |
| 342 | 2 | — |
| 343 | 2 | 237 |
| 344 | 3 | — |
| 345 | 7 | — |
| 346 | 3 | — |
| 347 | 3 | 94 |
| 348 | 2 | — |
| 349 | 2 | 31 |
| 350 | 3 | — |
| 351 | 2 | — |
| 352 | 2 | — |
| 353 | 4 | — |
| 354 | 2 | 180 |
| 355 | 2 | 208 |
| 356 | 7 | — |
| 357 | 7 | 121 |
| 358 | 5 | — |
| 359 | 2 | — |
| 360 | 8 | — |
| 361 | 3 | — |
| 362 | 3 | — |
| 363 | 2 | — |
| 364 | 1 | — |
| 365 | 2 | — |
| 366 | 4 | 229 |
| 367 | 3 | — |
| 368 | 4 | — |
| 369 | 3 | — |
| 370 | 5 | — |
| 371 | 4 | — |
| 372 | 4 | — |
| 373 | 3 | — |
| 374 | 3 | — |
| 375 | 5 | — |
| 376 | 4 | — |
| 377 | 4 | 182 |
| 378 | 6 | — |
| 379 | 3 | — |
| 380 | 3 | — |
| 381 | 4 | — |
| 382 | 7 | — |
| 383 | 3 | — |
| 384 | 6 | — |
| 385 | 2 | — |
| 386 | 2 | — |
| 387 | 3 | — |
| 388 | 5 | — |
| 389 | 4 | 424 |
| 390 | 4 | 201 |
| 391 | 3 | — |
| 392 | 2 | — |
| 393 | 4 | — |
| 394 | 4 | — |
| 395 | 2 | — |
| 396 | 3 | — |
| 397 | 1 | — |
| 398 | 5 | — |
| 399 | 4 | — |
| 400 | 7 | — |
| 401 | 12 | — |
| 402 | 4 | — |
| 403 | 2 | — |
| 404 | 1 | 160 |
| 405 | 1 | — |
| 406 | 1 | — |
| 407 | 2 | 17 |
| 408 | 2 | 11 |
| 409 | 2 | 52 |
| 410 | 2 | 36 |

TABLE 11-continued

| Ex. No. | PI3K delta IC$_{50}$ value (nM) | CD69 IC$_{50}$ value (nM) |
|---|---|---|
| 411 | 2 | — |
| 412 | 2 | 41 |
| 413 | 2 | — |
| 414 | 3 | — |
| 415 | 3 | 112 |
| 416 | 4 | — |
| 417 | 4 | — |
| 418 | 4 | — |
| 419 | 4 | — |
| 420 | 5 | 149 |
| 421 | 5 | 191 |
| 422 | 8 | 11 |
| 423 | 8 | — |
| 425 | 9 | — |
| 426 | 5 | 77 |
| 427 | 3 | 129 |
| 428 | 0.5 | 15 |
| 429 | 1 | 32 |
| 430 | 1 | — |
| 431 | 1 | — |
| 432 | 2 | 83 |
| 433 | 0.4 | 96 |
| 434 | 2 | 323 |
| 435 | 1 | 113 |
| 436 | 2 | 28 |
| 437 | 3 | 44 |
| 438 | 2 | 66 |
| 439 | 1 | 33 |
| 440 | 2 | 141 |
| 441 | 4 | 127 |
| 442 | 4 | 62 |
| 443 | 4 | 168 |
| 444 | 5 | 80 |
| 445 | 2 | 64 |
| 446 | 3 | 98 |
| 447 | 2 | 102 |
| 448 | 2 | 111 |
| 449 | 2 | 129 |
| 450 | 2 | 337 |
| 451 | 1 | 13 |
| 452 | 2 | 66 |
| 453 | 1 | 16 |
| 454 | 2 | 54 |
| 455 | 1 | 16 |
| 456 | 4 | 31 |
| 457 | 2 | 24 |
| 458 | 2 | 50 |
| 459 | 1 | 21 |
| 460 | 3 | 84 |
| 461 | 2 | 28 |
| 462 | 3 | 30 |
| 463 | 21 | 34 |
| 464 | 2 | 49 |
| 465 | 3 | 113 |
| 466 | 2 | 115 |
| 467 | 2 | 121 |
| 468 | 1 | 17 |
| 469 | 3 | 211 |
| 470 | 3 | 69 |
| 471 | 3 | 91 |
| 472 | 2 | — |
| 473 | 1 | 123 |
| 474 | 4 | 459 |
| 475 | 1 | 59 |
| 476 | 1 | 16 |
| 477 | 1 | 29 |
| 478 | 1 | 139 |
| 479 | 3 | 105 |
| 480 | 3 | 161 |
| 481 | 6 | 499 |
| 482 | 3 | 237 |
| 483 | 10 | 372 |
| 484 | 6 | 568 |
| 485 | 6 | 400 |
| 486 | 15 | 415 |
| 487 | 2 | 6 |
| 488 | 2 | 32 |
| 489 | 2 | 15 |
| 490 | 3 | 35 |
| 491 | 1 | — |
| 492 | 1 | 35 |
| 493 | 2 | 151 |
| 494 | 1 | 158 |
| 495 | 3 | 238 |
| 496 | 2 | 148 |
| 497 | 4 | 239 |
| 498 | 1 | 254 |
| 499 | 2 | 237 |
| 500 | 1 | 22 |
| 501 | 1 | 35 |
| 502 | 2 | 217 |
| 503 | 2 | 220 |
| 504 | 2 | 268 |
| 505 | 2 | 271 |
| 506 | 1 | 39 |
| 507 | 4 | 249 |
| 508 | 2 | 257 |
| 509 | 1 | 270 |
| 510 | 1 | 176 |
| 511 | 2 | 109 |
| 512 | 1 | 112 |
| 513 | 2 | 146 |
| 514 | 1 | 72 |
| 515 | 1 | 87 |
| 516 | 1 | 77 |
| 517 | 3 | 217 |
| 518 | 1 | 51 |
| 519 | 1 | 205 |
| 520 | 4 | 223 |
| 521 | 2 | 59 |
| 522 | 2 | 172 |
| 523 | 2 | 66 |
| 524 | 1 | 68 |
| 525 | 1 | 90 |
| 526 | 1 | 98 |
| 527 | 1 | 100 |
| 528 | 4 | 100 |
| 529 | 1 | 129 |
| 530 | 1 | 118 |
| 531 | 2 | 155 |
| 532 | 2 | 128 |
| 533 | 1 | 129 |
| 534 | 3 | 285 |
| 535 | 6 | 143 |
| 536 | 1 | 172 |
| 537 | 2 | 88 |
| 538 | 2 | 42 |
| 539 | 1 | 25 |
| 540 | 3 | 293 |
| 545 | 4 | — |
| 546 | 4 | — |
| 548 | 2 | 39 |
| 550 | 2 | 35 |
| 552 | 1 | 46 |
| 553 | 2 | 62 |
| 554 | 2 | 250 |
| 555 | 3 | 123 |
| 556 | 1 | 73 |
| 557 | 3 | 59 |
| 558 | 5 | 36 |
| 559 | 2 | 254 |
| 560 | 2 | 135 |
| 561 | 2 | 208 |
| 562 | 3 | 337 |
| 563 | 3 | 283 |
| 564 | 2 | 72 |
| 565 | 2 | 35 |
| 566 | 2 | 29 |
| 567 | 2 | 316 |
| 568 | 3 | 92 |
| 569 | 3 | 865 |
| 570 | 5 | 394 |

TABLE 11-continued

| Ex. No. | PI3K delta IC$_{50}$ value (nM) | CD69 IC$_{50}$ value (nM) |
|---|---|---|
| 571 | 6 | 1137 |
| 572 | 2 | 179 |
| 573 | 2 | 225 |
| 574 | 9 | 74 |
| 575 | 2 | 428 |
| 576 | 3 | 141 |
| 577 | 8 | 773 |
| 578 | 8 | 756 |
| 579 | 9 | 297 |
| 580 | 1 | 108 |
| 581 | 3 | 95 |
| 582 | 5 | 761 |
| 583 | 2 | 41 |
| 584 | 1 | 884 |
| 585 | 1 | 38 |
| 586 | 5 | 222 |
| 587 | 2 | 222 |
| 588 | 2 | — |
| 589 | 7 | 382 |
| 590 | 6 | 547 |
| 591 | 1 | 113 |
| 592 | 3 | 513 |
| 593 | 2 | 53 |
| 594 | 2 | 226 |
| 595 | 1 | 46 |
| 596 | 1 | 51 |
| 597 | 1 | 50 |
| 598 | 2 | 1189 |
| 599 | 1 | 18 |
| 600 | 4 | 37 |
| 601 | 2 | 11 |
| 602 | 3 | 82 |
| 603 | 2 | 14 |
| 604 | 2 | 38 |
| 605 | 1 | 47 |
| 606 | 2 | 46 |
| 607 | 2 | 33 |
| 608 | 2 | 18 |
| 609 | 1 | 21 |
| 610 | 1 | 24 |
| 611 | 1 | 35 |
| 612 | 1 | 35 |
| 613 | 2 | 38 |
| 614 | 2 | 9 |
| 615 | 1 | 70 |
| 616 | 1 | 30 |
| 617 | 2 | 54 |
| 618 | 1 | 38 |
| 619 | 3 | 199 |
| 620 | 4 | 299 |
| 621 | 6 | 3949 |
| 622 | 1 | 27 |
| 623 | 2 | 45 |
| 624 | 2 | 153 |
| 625 | 4 | 16 |
| 626 | 5 | 27 |
| 627 | 2 | 24 |
| 628 | 3 | 72 |
| 629 | 2 | 74 |
| 630 | 2 | 72 |
| 631 | 2 | 71 |
| 632 | 1 | 4 |
| 633 | 2 | 15 |
| 634 | 2 | 20 |
| 635 | 4 | 73 |
| 636 | 3 | 28 |
| 637 | 2 | 37 |
| 638 | 2 | 68 |
| 639 | 2 | 50 |
| 640 | 3 | 39 |
| 641 | 1 | 8 |
| 642 | 2 | 6 |
| 643 | 1 | 18 |
| 644 | 2 | 1189 |
| 645 | 3 | 53 |
| 646 | 3 | 91 |
| 647 | 3 | 21 |
| 648 | 3 | 61 |
| 649 | 3 | 88 |
| 650 | 1 | 47 |
| 651 | 1 | 127 |
| 652 | 2 | 69 |
| 653 | 2 | 14 |
| 654 | 2 | 32 |
| 655 | 2 | 16 |
| 656 | 3 | 67 |
| 657 | 3 | 66 |
| 658 | 4 | 52 |
| 659 | 5 | 48 |
| 660 | 2 | 9 |
| 661 | 2 | 10 |
| 662 | 1.5 | 5 |
| 663 | 3 | 11 |

TABLE 12

| Ex. No. | PI3K delta IC$_{50}$ value (nM) | CD69 IC$_{50}$ values (nM) |
|---|---|---|
| 664 | 4 | 210 |
| 665 | 4 | 1800 |
| 666 | 2 | 70 |
| 667 | 5 | 230 |
| 668 | 0.6 | 20 |
| 669 | 1 | 30 |
| 670 | 0.8 | 360 |
| 671 | 2 | 410 |
| 672 | 1 | 90 |
| 673 | 0.6 | 60 |
| 674 | 0.9 | 40 |
| 675 | 0.8 | 140 |
| 676 | 2 | 150 |
| 677 | 0.2 | 10 |
| 678 | 0.2 | 13 |
| 679 | 0.6 | 80 |
| 680 | 1 | 250 |
| 681 | 0.2 | 20 |
| 682 | 0.4 | 14 |
| 683 | 0.2 | 12 |
| 684 | 0.3 | 12 |
| 685 | 0.2 | 80 |
| 686 | 0.3 | 50 |
| 687 | 0.2 | 30 |
| 688 | 0.5 | 40 |
| 689 | 0.9 | 100 |
| 690 | 0.2 | 40 |
| 691 | 8 | 2780 |
| 692 | 7 | 1210 |
| 693 | 36 | 2620 |
| 694 | 16 | 1610 |
| 695 | 5 | 2110 |
| 696 | 4 | 890 |
| 697 | 11 | 2830 |
| 698 | 4 | 2150 |
| 699 | 11 | 1340 |
| 700 | 6 | 160 |
| 701 | 10 | 630 |
| 702 | 16 | 220 |
| 703 | 0.5 | 30 |
| 704 | 0.7 | 160 |
| 705 | 1 | 160 |
| 706 | 0.2 | 20 |
| 707 | 3 | 110 |
| 708 | 0.7 | 30 |
| 709 | 5 | 270 |
| 710 | 7 | 140 |
| 711 | 10 | 330 |
| 712 | 4 | 230 |

TABLE 12-continued

| Ex. No. | PI3K delta IC$_{50}$ value (nM) | CD69 IC$_{50}$ values (nM) |
|---|---|---|
| 713 | 0.8 | 40 |
| 714 | 0.2 | 30 |
| 715 | 2 | 190 |
| 716 | 2 | 420 |
| 717 | 1 | 230 |
| 718 | 2 | 1200 |
| 719 | 2 | 320 |
| 720 | 2 | 630 |
| 721 | 3 | 750 |
| 722 | 7 | 550 |
| 723 | 1 | 530 |
| 724 | 25 | 2540 |
| 725 | 5 | 870 |
| 726 | 4 | 40 |
| 727 | 1 | 30 |
| 728 | 2 | 60 |
| 729 | 0.2 | 40 |
| 730 | 0.4 | 50 |
| 731 | 0.6 | 100 |
| 732 | 2 | 80 |
| 733 | 1 | 120 |
| 734 | 0.4 | 40 |
| 735 | 2 | 40 |
| 736 | 1 | 90 |
| 737 | 1 | 80 |
| 738 | 2 | 70 |
| 739 | 1 | 20 |
| 740 | 0.5 | 110 |
| 741 | 0.3 | 160 |
| 742 | 0.7 | 60 |
| 743 | 0.4 | 120 |
| 744 | 1 | 210 |
| 745 | 2 | 80 |
| 746 | 0.4 | 40 |
| 747 | 1 | 170 |
| 748 | 0.7 | 140 |
| 749 | 2 | 80 |
| 750 | 0.6 | 90 |
| 751 | 0.5 | 130 |
| 752 | 0.6 | 210 |
| 753 | 0.5 | 120 |
| 754 | 1 | 170 |
| 755 | 2 | 80 |
| 756 | 0.2 | 60 |
| 757 | — | 260 |
| 758 | 1 | 250 |
| 759 | 0.8 | 260 |
| 760 | 2 | 40 |
| 761 | 1 | 90 |
| 762 | 0.2 | 14 |
| 763 | 0.5 | 170 |
| 764 | 0.8 | 530 |
| 765 | 0.4 | 150 |
| 766 | 3 | 120 |
| 767 | 0.7 | 120 |
| 768 | 0.2 | 130 |
| 769 | 0.2 | 340 |
| 770 | 1 | 90 |
| 771 | 1 | 550 |
| 772 | 0.4 | 110 |
| 773 | 1 | 370 |
| 774 | 1 | 360 |
| 775 | 1 | 220 |
| 776 | 1 | 590 |
| 777 | 5 | 420 |
| 778 | 2 | 270 |
| 779 | 6 | 500 |
| 780 | 4 | 1110 |
| 781 | 18 | 2710 |
| 782 | 20 | 2100 |
| 783 | — | 2730 |
| 784 | 59 | 2110 |
| 785 | 1 | 90 |
| 786 | 3 | 60 |
| 787 | 2 | 360 |
| 788 | 6 | 90 |
| 789 | 2 | 30 |
| 790 | 2 | 30 |
| 791 | 1 | 40 |
| 792 | 3 | 20 |
| 793 | 0.5 | 20 |
| 794 | 1 | 90 |
| 795 | 3 | 13 |
| 796 | 6 | — |
| 797 | 4 | 20 |
| 798 | 3 | 190 |
| 799 | 4 | 890 |
| 800 | 8 | 260 |
| 801 | 3 | 80 |
| 802 | 4 | 150 |
| 803 | 7 | 60 |
| 804 | 4 | 330 |
| 805 | 5 | 120 |
| 806 | 4 | 6 |
| 807 | 1 | 380 |
| 808 | 3 | 70 |
| 809 | 2 | 150 |
| 810 | 1 | 90 |
| 811 | 2 | 120 |
| 812 | 2 | 300 |
| 813 | 0.9 | 80 |
| 814 | 0.2 | 290 |
| 815 | 1 | 130 |
| 816 | 2 | 100 |
| 817 | 1 | 950 |
| 818 | 0.5 | 50 |
| 819 | 4 | 330 |
| 820 | 8 | 1450 |
| 821 | 5 | 1230 |
| 822 | 29 | 630 |
| 823 | 2 | 770 |
| 824 | 3 | 1340 |
| 825 | 31 | 1940 |
| 826 | 4 | 530 |
| 827 | 1514 | 10000 |
| 828 | 4 | 1710 |
| 829 | 14 | 1290 |
| 830 | 3 | 390 |
| 831 | 8 | 1340 |
| 832 | 14 | 1070 |
| 833 | 0.7 | — |
| 834 | 2 | 420 |
| 835 | — | 2070 |
| 836 | 2 | 190 |

The compounds of the present invention possess activity as inhibitors of PI3K delta, and therefore, may be used in the treatment of diseases associated with PI3K activity.

The invention claimed is:

1. A compound of Formula (I):

(I)

or a salt thereof; wherein:

X is N or CH;

$Q_1$ is:
(i) Cl, I, —CN, —CH$_3$, —CD$_3$, or —CF$_3$;
(ii) a 5-membered heteroaryl selected from pyrrolyl, pyrazolyl, imidazolyl, isoxazolyl, thiazolyl, triazolyl, oxadiazolyl, and thiadiazolyl;
(iii) a 6-membered heteroaryl selected from pyridinyl, pyridazinyl, and pyrimidinyl; or
(iv) a bicyclic heteroaryl selected from indolyl, imidazopyridinyl, pyrrolopyridinyl, pyrazolopyridinyl and benzo[d]oxazolyl;
wherein each of said 5-membered, 6-membered, and bicyclic heteroaryls is substituted with zero to 1 $R_a$ and zero to 1 $R_b$;

$R_a$ is $C_{1-6}$ alkyl, $C_{1-6}$ deuteroalkyl, $C_{1-4}$ fluoroalkyl, $C_{1-4}$ hydroxyalkyl, $C_{1-4}$ alkoxyalkyl, $C_{1-4}$ hydroxyfluoroalkyl, —CH$_2$(C$_{3-6}$ cycloalkyl), —CH$_2$(oxetanyl), —CH$_2$(methyloxetanyl), —NH$_2$, —S(O)$_2$(C$_{1-4}$ alkyl), —S(O)$_2$(C$_{3-6}$ cycloalkyl), C$_{3-6}$ cycloalkyl, C$_{3-6}$ fluorocycloalkyl, oxetanyl, tetrahydropyranyl, pyridinyl, pyrimidinyl, pyridazinyl, phenyl, or fluorophenyl substituted with zero to 1 substituent selected from F, —CF$_3$, and —OCF$_3$;

$R_b$ is Cl, $C_{1-4}$ alkyl, $C_{1-3}$ haloalkyl, or $C_{3-5}$ cycloalkyl;

$R_1$ is H or F;

$R_2$ is H or F;

$R_3$ is H or $R_x$;

$R_4$ is H, F, Cl, —CN, —CH$_3$, —CHF$_2$, —CF$_3$, —OCH$_3$, —OCD$_3$, —(CH$_2$)$_{1-3}$OR$_c$, —CHR$_c$OH, —C(CH$_3$)$_2$OH, —C(O)OCH$_3$, —C(O)N(R$_w$)$_2$, —C(O)—NR$_w$R$_7$, —C(O)R$_8$, —C≡C—(C$_{1-4}$ alkyl), —S(O)$_{0-2}$(C$_{1-4}$ alkyl), or —S(O)$_{0-2}$(C$_{3-6}$ cycloalkyl), or triazolyl, wherein the triazolyl is substituted with 0 to 1-CH$_3$;

$R_c$ is H, —CH$_3$, —CD$_3$, —CH$_2$CH$_3$, —CH(CH$_3$)$_2$, or cyclopropyl;

$R_5$ is H, F, Cl, —CH$_3$, or —OCH$_3$;

$R_6$ is H or F;

$R_7$ is CD$_3$, $C_{1-6}$alkyl, $C_{1-4}$haloalkyl, $C_{1-6}$alkyl substituted with 0-1 $R_{7a}$, cyclopropyl, cyano$C_{1-6}$alkyl, or pyridinyl;

$R_{7a}$ is —CN, —N(R$_w$)$_2$, —OCH$_3$, or —S(O)$_2$CH$_3$;

$R_8$ is $C_{1-6}$alkyl, hydroxy$C_{1-6}$alkyl, morpholinyl, or piperazinyl, wherein the piperazinyl is substituted with 0 to 1-CH$_3$;

$R_w$ is H or —CH$_3$;

$R_x$ is:
(i) $C_{1-4}$ hydroxyalkyl, $C_{1-4}$ alkoxyalkyl, $C_{1-4}$ aminoalkyl, —CR$_w$R$_w$NH(C$_{1-4}$ alkyl), —CR$_w$R$_w$N(C$_{1-4}$ alkyl)$_2$, —CR$_w$R$_w$NR$_w$(CH$_2$)$_{1-3}$O(C$_{1-3}$ alkyl), —CR$_w$R$_w$CR$_w$R$_w$N(C$_{1-3}$ alkyl)$_2$, —CR$_w$R$_w$CR$_w$R$_w$NR$_w$C(O)(C$_{1-3}$ alkyl), —CR$_w$R$_w$C(O)(C$_{1-3}$ alkyl), —CR$_w$R$_w$NR$_w$C(O)(C$_{1-4}$ hydroxyalkyl), —(CR$_w$R$_w$)$_2$R$_{3a}$, —CR$_w$(CF$_3$)R$_{3a}$, —CR$_w$R$_w$NR$_w$R$_{3a}$, —CH$_2$NHS(O)$_2$CH$_3$ —CH$_2$OR$_{3a}$, —CH$_2$(8-oxa-3-azabicyclo[3.2.1]octanyl), —CH(CH$_3$)(dimethylazetidinyl), —CH(CH$_3$)(methyl hydroxyazetidinyl), or —CR$_w$R$_w$NR$_w$C(O)R$_{3a}$, wherein $R_{3a}$ is tetrahydropyran, morpholinyl, morpholinonyl, oxazinanonyl, oxazolidinonyl, pyrrolidinyl, pyrrolidinonyl, piperazinyl, pyridinyl, pyrrolidinium, or phenyl, each substituted with zero to 1 substituent selected from F, Cl, $C_{1-4}$ alkyl, and —C(O)CH$_3$;
(ii) —C(O)OH or —C(O)R$_{3b}$, wherein $R_{3b}$ is pyrrolidinyl, pyrrolidinonyl, azetidinyl, morpholinyl, dioxidothiomorpholinyl, thiadiazolyl, piperazinyl, piperazinonyl, 8-oxa-3-azabicyclo[3.2.1]octanyl, or piperidinyl, each substituted with zero to 2 substituents independently selected from F, —OH, —CN, $C_{1-2}$ alkyl, $C_{1-3}$ hydroxyalkyl, —C(O)(C$_{1-3}$ alkyl), —C(O)NR$_w$R$_w$, —C(O)O(C$_{1-3}$ alkyl), —NR$_w$C(O)(C$_{1-3}$ alkyl), —C(O)NH(C$_{1-3}$ hydroxyalkyl), and —C(O)tetrahydrofuranyl; —C(O)NR$_w$R$_w$, —C(O)NH(C$_{1-4}$ alkyl), —C(O)N(C$_{1-4}$ alkyl)$_2$, —C(O)NR$_w$(C$_{1-3}$ fluoroalkyl), —C(O)NR$_w$(C$_{1-3}$ hydroxyalkyl), —C(O)NR$_w$(C$_{1-4}$ alkoxyalkyl), —C(O)NR$_w$(CR$_w$R$_w$C(O)NR$_w$R$_w$), —C(O)NR$_w$CR$_w$(C$_{1-4}$ alkyl)C(O)NR$_w$R$_w$, —C(O)NR$_w$(C$_{1-6}$ hydroxyalkyl), —C(O)NR$_w$R$_{3c}$, —C(O)NR$_w$(CR$_w$R$_w$)$_{1-2}$R$_{3c}$, —C(O)NR$_w$CR$_w$R$_w$C(O)R$_{3c}$, —C(O)N(C$_{1-4}$ alkyl)(C$_{3-6}$ cycloalkyl), —C(O)N(C$_{3-6}$ cycloalkyl)$_2$, —C(O)N(C$_{3-6}$ cycloalkyl)R$_{3c}$, —C(O)N(C$_{3-6}$ cycloalkyl)(CH$_2$R$_{3c}$), or —C(O)CR$_w$R$_w$S(O)$_2$(C$_{1-4}$ alkyl), wherein $R_{3c}$ is phenyl, oxazolyl, oxopiperidinyl, oxopyrrolidinyl, tetrahydropyranyl, tetrazolyl, thiazolyl, piperidinyl, pyrazolyl, oxetanyl, morpholinyl, pyrrolidinyl, or isoxazolyl, each substituted with zero to 2 substituents independently selected from —CH$_3$, —C(O)CH$_3$, —C(O)NH$_2$, cyclopropyl, and —CH$_2$OH;
(iii) —OR$_{3d}$ wherein $R_{3d}$ is tetrahydropyranyl, tetrahydrothiopyranyl, piperidinyl, or pyridinyl, each substituted with zero to 3 substituents independently selected from —CH$_3$, =O, —C(O)CH$_3$, and —C(O)CH(CH$_3$)$_2$;
(iv) —NR$_w$C(O)(C$_{1-3}$ alkyl), —NR$_w$S(O)$_2$(C$_{1-3}$ alkyl), or —S(O)$_2$NR$_w$R$_w$;
(v) $C_{3-6}$ cycloalkyl substituted with zero to 3 substituents independently selected from F, —OH, $C_{1-3}$ alkyl, $C_{1-3}$ fluoroalkyl, $C_{1-3}$ alkoxy, $C_{1-3}$ fluoroalkoxy, —C(O)NR$_w$(C$_{1-4}$ alkyl), —C(O)NR$_w$(C$_{1-4}$ fluoroalkyl), —C(O)NR$_w$(C$_{3-6}$ cycloalkyl), and —C(O)NR$_w$R$_{3d}$, wherein $R_{3d}$ is oxetanyl, azetidinyl, morpholinyl, piperidinyl, pyrrolidinyl, cyclobutyl, or tetrahydropyranyl, each substituted with zero to 2 substituents independently selected from F, —CH$_3$, and —OCH$_3$; or
(vi) azetidinyl, oxetanyl, tetrahydropyranyl, piperazinyl, pyrrolidinyl, piperidinyl, 1,2-dihydropyridinonyl, morpholinyl, 4,7-diazaspiro[2.5]octanyl, octahydrobenzo[b][1,4]oxazinyl, or benzo[b][1,4]oxazinyl, each substituted with zero to 8 substituents independently selected from D, —OH, —CN, $C_{1-4}$ alkyl, $C_{1-3}$ deuteroalkyl, $C_{1-3}$ fluoroalkyl, $C_{1-4}$ cyanoalkyl, $C_{1-4}$ hydroxyalkyl, $C_{1-3}$ alkoxy, =O, —(CH$_2$)O(O)CH$_3$, —C(O)(C$_{1-4}$ alkyl), —C(O)(C$_{1-4}$ hydroxyalkyl), —C(O)NR$_w$R$_w$, —C(O)CH$_2$CN, —C(O)CH$_2$OH, —C(O)(C$_{3-4}$ cycloalkyl), —C(O)NH$_2$, —S(O)$_2$CH$_3$, —C(O)OCH$_3$, —NHC(O)(C$_{1-4}$ alkyl), —NR$_w$S(O)(C$_{1-3}$ alkyl), —NR$_w$S(O)$_2$(C$_{1-3}$ alkyl), —C(O)CR$_w$R$_w$S(O)$_2$(C$_{1-4}$ alkyl), —C(O)(phenyl), —C(O)(fluorophenyl), —C(O)(chlorophenyl), —C(O)(hydroxypropyl phenyl), —C(O)(difluorocyclopropyl), —C(O)(oxazolyl), —C(O)(pyrazinyl), —C(O)(pyrazolyl), —C(O)(pyridazinyl), —C(O)(pyridinyl), —C(O)(pyrimidinyl), —C(O)(pyrrolidinyl), —C(O)(tetrahydropyranyl), —C(O)(thiazolyl), —C(O)(methyl thiazolyl), —C(O)(imidazolyl), —C(O)(methyl imidazolyl), —C(O)(methyl oxazolyl), —C(O)(methyl phenyl), —C(O)(methyl pyrazolyl), —C(O)(morpholinyl), —C(O)(acetophenonyl), —C(O)CH$_2$(oxazolidinonyl), —C(O)CH$_2$(pyrrolidinyl), —C(O)CH$_2$(dioxidothiazinanyl), —C(O)CH$_2$(dioxidothiomorpholinyl), —C(O)

CH₂ (dimethyl-oxopyrrolidinyl), —C(O)CH₂ (trimethyl-oxopyrrolidinyl), —C(O)CH₂NHC(O)CH₃, —C(O)CH₂CH₂NHC(O)CH₃, —C(O)CH₂CH₂S(O)₂CH₃, —C(O)CH₂S(O)₂CH₃, —C(O)CH(CH₃)S(O)₂CH₃, —C(O)CH₂CH₂NHS(O)₂CH₃, —C(O)CH₂NHS(O)₂CH₃, —C(O)CH₂CH₂NHS(O)₂CH₃, —C(O)CH(CH₃)NHS(O)₂CH₃, —C(O)CH₂CH₂(methyl-pyrazolyl), —N(CH₃)₂, —N(CH₃)(acetyl piperidinyl), —CH₂C(O)NHCH₂C(CH₃)₂OH, —N(CH₃)C(O)CH₃, —N(CH₃)C(O)C(CH₃)₂OH, —N(CH₃)C(O)NH(CH(CH₃)₂), —N(CH₃)C(O)(furanyl), —N(CH₃)C(O)CH₂(pyrazinyl), —N(CH₃)C(O)(cyanocyclopropyl), —N(CH₃)C(O)CH(CH₃)OH, benzyl, carbamoyl azepanyl, carbamoyl-morpholinyl, chlorophenyl, cyclopropyl, cyclobutyl, dioxothiomorpholinyl, fluorobenzoyl, fluorophenyl, hydroxypiperidinyl, hydroxypyrrolidinyl, hydroxytetrahydropyranyl, methoxytetrahydropyranyl, methyl imidazol[1,2a]pyridinyl, methyloxadiazolyl, methylpiperazinyl, methylpiperazinonyl, methyl pyridinonyl, morpholinyl, oxetanyl, phenyl, piperidinonyl, pyridinyl, and pyrimidinyl;
(vii) phenyl, pyrazolyl, dioxothiazinanyl, pyrrolidinonyl, dimethyloxazolindinonyl, oxazolyl, tetrazolyl, pyridinyl, dioxothiomorpholinyl, quinazolinyl, thiazolyl, octahydropyrrolo[3,4-c]pyrrole, 1H-pyrido[1,2-c]pyrimidine-1,3(2H)-dione, 1,3-oxazinan-2-onyl, 1H,2H,3H,4H,6H-pyrido[1,2-a]piperazinone-1,6-dionyl, 2,3-dihydroquinazolin-4(1H)-onyl, methoxy 2,3-dihydroquinazolin-4(1H)-onyl, 2-azaspiro[4.5]decan-3-onyl, 2-oxa-6-azaspiro[3.3]heptanyl, acetyl 3,8-diazabicyclo[3.2.1]octanyl, acetyl-3,4-dihydroquinoxalin-1(2H)-yl, methyl [1,2,4]triazolo[4,3-a]pyridinyl), or dimethyl[1,2,4]triazolo[4,3-a]pyridinyl, each substituted with zero to 4 substituents independently selected from D, F, Cl, —OH, —CN, —NH₂, C₁₋₃ alkyl, C₁₋₅ hydroxyalkyl, C₁₋₅ alkoxyalkyl, —C(O)CH₃, —C(O)C(CH₃)₂OH, —C(O)NH₂, —C(O)NH(C₁₋₄ alkyl), —CH(R_w)CH₂NR_wR_w, —C(O)NR_wR_w, —S(O)₂NH₂, —S(O)₂(C₁₋₄ alkyl), —NR_wC(O)(C₁₋₄ alkyl), —NR_wS(O)₀₋₂(C₁₋₄ alkyl), =O, C₃₋₆ cycloalkyl, —O(piperidinyl-S(O)₂CH₃), —O(piperidinyl-C(O)NR_w(C₁₋₄ alkyl), and —O(piperidinyl-C(O)(C₁₋₄ hydroxyalkyl);
provided that if R₃ is H, then R₄ is —C(O)N(CH₃)₂; and if Q₁ is Br, then R₃ is not —CH₂OH.

2. The compound according to claim 1 or a salt thereof; wherein:
R_a is —CH₃, —CH₂CH₂CH₃, —CH(CH₃)₂, —C(CH₃)₃, —CH₂CH(CH₃)₂, —CH(CH₃)CH₂CH₃, —CH₂C(CH₃)₃, —CD₃, —CD₂CD₃, —CH(CD₃)₂, —CD(CD₃)₂, —CF₂H, —CF₃, —CH₂CHF₂, —CH₂CF₃, —CH(CH₂F)₂, —CH(CH₃)(CF₃), —CH(CF₃)₂, —CH₂CH₂OCH₃, —CH₂C(CH₃)₂OH, —CH₂CH(OH)CF₃, —CH₂(cyclopropyl), —CH₂(cyclobutyl), —CH₂(oxetanyl), —CH₂(methyloxetanyl), —NH₂, —S(O)₂CH₃, —S(O)₂CH(CH₃)₂, —S(O)₂(cyclopropyl), cyclopropyl, cyclobutyl, cyclohexyl, difluorocyclopropyl, difluorocyclohexyl, oxetanyl, tetrahydropyranyl, pyridinyl, pyrimidinyl, pyridazinyl, phenyl, or fluorophenyl;
R_x is:
(i) —CH₂OH, —CH₂NH₂, —CH₂N(CH₃)₂, —CH₂NHS(O)₂CH₃, —CH₂N(CH₃)CH₂CH₂OCH₃, —CH₂CH(CH₃)NHCH₂CH₂OCH₃, —C(CH₃)₂N(CH₃)₂, —C(CH₃)₂N(CH₂CH₃)₂, —CH₂CH(CH₃)NH(tetrahydropyranyl), —C(CH₃)₂N(CH₃)(tetrahydropyran), —CH₂CH(CH₃)N(CH₃)₂, —C(CH₃)₂CH₂N(CH₃)₂, —CH₂ (morpholinyl), —CH₂(morpholinonyl), —CH₂(oxazinanonyl), —CH₂(pyrrolidinonyl), —CH₂(hydroxypyrrolidinyl), —CH₂(t-butyl oxazolidinonyl), —CH₂(dimethyl oxazolidinonyl), —CH₂(i-propyl oxazolidinonyl), —CH₂(acetyl piperazinyl), —CH₂(methyl piperazinonyl), —CH₂(methyl pyrrolidinonyl), —CH₂ (8-oxa-3-azabicyclo[3.2.1]octanyl), —CH₂N(tetrahydropyranyl)₂, —CH₂NHC(O)(methoxyphenyl), —CH₂N(cyclopropyl)(methylsulfonyl azetidinyl), —CH₂N(CH₃)(tetrahydropyranyl), —CH₂N(CH₃)(oxetanyl), —CH₂N(C(O)CH₃)(morpholinyl), —CH₂CH(CH₃)(morpholinyl), —CH₂CH(CH₃)(pyrrolidinyl), —CH(CH₃)(morpholinyl), —CH(CH₃)(dimethylazetidinyl), —CH(CH₃)(dimethylmorpholinyl), —CH(CH₃)(hydroxypyrrolidinyl), —CH(CH₃)(methoxypyrrolidinyl), —CH(CH₃)(methyl hydroxyazetidinyl), —CH(CH₃)(acetopiperazinyl), —CH(CH₃)NH(tetrahydropyranyl), —CH(CF₃)(morpholinyl), —CH₂C(O)(dioxoidothiomorpholinyl), —CH₂CH(CH₃)N(CH₃)(tetrahydropyranyl), —C(CH₃)₂(pyrrolidinyl), —C(CH₃)₂(morpholinyl), —C(CH₃)₂(oxazolidinonyl), —C(CH₃)₂(methyl pyrrolidinium), —C(CH₃)₂NHC(O)CH₂C(CH₃)₂OH, or —CH₂O(pyridinyl);
(ii) —C(O)OH, —C(O)NH₂, —C(O)NHCH₃, —C(O)NHC(CH₃)₂C(O)NHCH₃, —C(O)(cyanoazetidinyl), —C(O)(methyl, hydroxyazetidinyl), —C(O)(morpholinyl), —C(O)(dioxidothiomorpholinyl), —C(O)(piperazinyl) wherein said piperazinyl is substituted with —C(O)CH₃, —C(O)CH₂CH₃, —C(O)C(CH₃)₂H, —C(O)OCH₃, or —C(O)tetrahydrofuranyl; —C(O)(methyl piperazinonyl), —C(O)(piperidinyl) wherein said piperidinyl is substituted with 1 to 2 substituents independently selected from —OH, —CH₂OH, —C(CH₃)₂OH, —C(O)NH₂—C(O)NHCH₃, —N(CH₃)₂, and —NHC(O)CH₃; —C(O)(pyrrolidinyl), —C(O)(8-oxa-3-azabicyclo[3.2.1]octanyl), —C(O)NHCH₃, —C(O)NH(oxopiperidinyl), —C(O)NH(oxopyrrolidinyl), —C(O)NH(benzamide), —C(O)NH(carbamoyl thiazolyl), —C(O)NH(acetyl piperidinyl), —C(O)NH(methyl piperidinyl), —C(O)NH(methyl, cyclopropyl-pyrazolyl), —C(O)NH(tetrahydropyranyl), —C(O)NH(hydroxymethyl tetrahydropyranyl), —C(O)N(CH₃)(methyl pyrrolidinyl), —C(O)N(CH₃)(oxetanyl), —C(O)N(CH₃)(tetrahydropyran), —C(O)N(CH₃)₂, —C(O)N(CH₃)C(O)CH₂NH₂, —C(O)N(CH₃)CH₂(dimethylisoxazolyl), —C(O)N(CH₃)CH₂(methyl pyrrolidinyl), —C(O)N(CH₃)CH₂C(CH₃)₂CH₂OH, —C(O)N(CH₃)CH₂CF₂H, —C(O)N(CH₂CH₃)₂, —C(O)N(cyclopropyl)(methyl piperidinyl), —C(O)N(cyclopropyl)(methyl pyrazolyl), —C(O)N(cyclopropyl)(acetyl piperidinyl), —C(O)N(cyclopropyl)(methyl piperidinyl), —C(O)N(cyclopropyl)(tetrahydropyranyl), —C(O)N(cyclopropyl)(thiazolyl), —C(O)N(cyclopropyl)₂, —C(O)N(cyclopropyl)(CH₂(methyl pyrazolyl)), or —C(O)N(cyclopropyl)(CH₂-thiazolyl);
(iii) —O(tetrahydropyranyl), —O(dimethyltetrahydropyranyl), —O(dioxotetrahydrothiopyranyl), —O(piperidinyl) wherein said piperidinyl is substituted with zero to 1 substituent selected from —CH₃, —C(O)CH₃, and —C(O)CH(CH₃)₂; —O(dimethylpyridinonyl), or —O(methyl pyridinonyl);
(iv) —NHC(O)CH₃ or —NHS(O)₂CH₃;
(v) cyclopropyl substituted with —C(O)NH(CH₂CH₃), —C(O)NH(CH(CH₃)₂), —C(O)NH(cyclopropyl), —C(O)NH(oxetanyl), —C(O)NH(difluorocyclobutyl), or —CH₂NH(tetrahydropyranyl); or cyclobutyl substituted with 1 to 3 substituents independently selected from F, —OH, —CH₃, —CF₃, —OCH₃, —OCHF₂, —C(O)NH(CH₃), —C(O)NH(CH₂CH₃), —C(O)NH(CH(CH₃)₂), —C(O)NH(CH₂CF₃), —C(O)NH(cyclopropyl), —C(O)NH(difluorocyclobutyl), —C(O)N(CH₃)(oxetanyl), —C(O)(morpholinyl), —C(O)(methoxypyrrolidinyl), and —C(O)(difluoroazetidinyl); or (vi) azetidinyl substituted with 1 to 2 substituents independently selected from fluorobenzoyl, dioxothiomorpholinyl, and —C(O)(hydroxypropyl phenyl); octahydropyrrolo[3,4-c]pyrrole substituted with zero to 1 substituent selected from —CH₃, —C(O)CH₃, —CH(CH₃)₂), —CH(CH₃)C(CH₃)₂OH, —CH(CH₃)CH₂OCH₃, —S(O)₂CH₃, and cyclobutyl; 1,2-dihydropyridinonyl substituted with 1 to 3 substituents independently selected from —CH₃, —CD₃, —CH₂CH₃, =O, and —CH₂CHF₂; 4,7-diazaspiro[2.5]octanyl substituted with zero to 1 substituent selected from —C(O)CH₃, —C(O)OCH₃, cyclobutyl, and oxetanyl; tetrahydropyranyl substituted with —OH, —CN, —OCH₃, —C(O)NH₂, or —NHC(O)CH₃; oxetanyl substituted with —N(CH₃)₂, —NHC(O)C(CH₃)₃, —NHS(O)C(CH₃)₃, —N(CH₃)S(O)C(CH₃)₃, —N(CH₃)(acetyl piperidinyl), piperidinonyl, hydroxypiperidinyl, hydroxypyrrolidinyl, morpholinyl, or dioxothiomorpholinyl; piperazinyl substituted with zero to 8 substituents independently selected from D, —OH, —CH₃, —CH(CH₃)₂, —CF₃, =O, —C(O)(cyclopropyl), —C(O)(cyclobutyl), —S(O)₂CH₃, —C(O)CH₂S(O)₂CH₃, —C(O)CH₃, —C(O)CH(CH₃)₂, —C(O)OCH₃, —C(O)CH₂CN, —C(O)CH₂OH, —C(O)CH₂CH₃, —C(O)CH(CH₃)OH, —C(O)C(CH₃)₂OH, —C(O)(phenyl), —N(CH₃)C(O)CH₃, cyclopropyl, cyclobutyl, oxetanyl, phenyl, fluorophenyl, chlorophenyl, pyridinyl, pyrimidinyl, and methyloxadiazolyl; pyrrolidinyl substituted with zero to 2 substituents independently selected from —OH, —CH₃, —C(CH₃)₂OH, —C(O)CH₃, —C(O)CH(CH₃)₂, —C(O)C(CH₃)₃, —NHC(O)CH₃, —N(CH₃)C(O)CH₃, —N(CH₃)C(O)C(CH₃)₂OH, —N(CH₃)C(O)CH₂(pyrazinyl), —C(O)(phenyl), —C(O)(fluorophenyl), —C(O)(methyl phenyl), —C(O)(cyclopropyl), —C(O)(difluorocyclopropyl), —C(O)(oxazolyl), —C(O)(pyrazolyl), —C(O)(pyridazinyl), —C(O)(pyridinyl), —C(O)(tetrahydropyranyl), —C(O)(thiazolyl), —C(O)(methyl thiazolyl), —C(O)(methyl pyrazolyl), and morpholinyl; piperidinyl substituted with zero to 4 substituents independently selected from —OH, —CH₃, —CN, —OCH₃, =O, —C(O)CH₃, —C(O)CH₂CN, —C(O)(morpholinyl), —C(O)NH₂, —NHC(O)CH₃, —N(CH₃)S(O)₂CH₃, —N(CH₃)C(O)NH(CH(CH₃)₂), —N(CH₃)C(O)CH₂(pyrazinyl), —N(CH₃)C(O)(furanyl), —N(CH₃)C(O)(cyanocyclopropyl), oxetanyl, morpholinyl, and piperidinonyl; phenyl substituted with 1 to 2 substituents independently selected from F and —C(O)NH₂; quinazolinyl substituted with zero to 4 substituents independently selected from F, —CH₃, and =O; carbamoyl azepanyl, imidazolyl, dimethyloxazolindinonyl, methyl imidazol[1,2a]pyridinyl, morpholinyl, carbamoyl-morpholinyl, morpholinonyl, methyl pyridinonyl, dimethyl morpholinonyl, trimethyl morpholinonyl, dioxothiomorpholinyl, methyl [1,2,4]triazolo[4,3-a]pyridinyl], dimethyl [1,2,4]triazolo[4,3-a]pyridinyl], 1-(3,4-dihydroquinoxalin-1(2H)-yl)ethanone, 2,3-dihydroquinazolin-4(1H)-one, oxetan-3-yl-1λ6,4-thiomorpholine-1,1-dione, 1,3-oxazinan-2-one, 1H,2H,3H,4H,6H-pyrido[1,2-a]piperazinone-1,6-dionyl, 1H-pyrido[1,2-c]pyrimidine-1,3(2H)-dione, or 3,8-diazabicyclo[3.2.1]octanyl ethanone;

provided that if R₃ is H, then R₄ is —CH₂OH, —CH₂CH₂OH, —CH₂NH₂, —C(O)N(CH₃)₂, —C(O)NHCH₂CH₂OH, —C(O)(morpholinyl), or —C(O)NH(cyclopropyl); and provided that if R₃ is R_x, then R₄ is H, F, Cl, —CN, —CH₃, —CHF₂, —CF₃, —OCH₃, —CH(CH₃)OH, —C(CH₃)₂OH, —C(O)OCH₃, —C(O)N(CH₃)₂, —C≡C(CH₂)₃CH₃, or —S(O)₂CH₃.

3. The compound according to claim 1 or a salt thereof, wherein X is N.

4. The compound according to claim 1 or a salt thereof, wherein Q₁ is Cl, I, —CN, —CH₃, or —CF₃.

5. The compound according to claim 1 or a salt thereof, wherein Q₁ is:
   (i) a 5-membered heteroaryl selected from pyrrolyl, pyrazolyl, imidazolyl, isoxazolyl, thiazolyl, triazolyl, oxadiazolyl, and thiadiazolyl;
   (ii) a 6-membered heteroaryl selected from pyridinyl, pyridazinyl, and pyrimidinyl; or
   (iii) a bicyclic heteroaryl selected from indolyl, imidazopyridinyl, pyrrolopyridinyl, pyrazolopyridinyl and benzo[d]oxazolyl;
   wherein each of said 5-membered, 6-membered, and bicyclic heteroaryls is substituted with zero to 1 R_a and zero to 1 R_b.

6. The compound according to claim 1 or a salt thereof, wherein X is CH.

7. A compound, or a salt thereof, wherein said compound is selected from 5-(4-amino-5-(1-cyclohexyl-1H-pyrazol-5-yl)pyrrolo[2,1-f][1,2,4]triazin-7-yl)-2-fluorobenzamide (1); 7-(3-(aminomethyl)phenyl)-5-(1-cyclohexyl-1H-pyrazol-5-yl)pyrrolo[2,1-f][1,2,4]triazin-4-amine (2); 5-(1-cyclohexyl-1H-pyrazol-5-yl)-7-(3-((dimethylamino)methyl)phenyl)pyrrolo[2,1-f][1,2,4]triazin-4-amine (3); (3-(4-amino-5-(1-(tetrahydro-2H-pyran-4-yl)-1H-pyrazol-5-yl)pyrrolo[2,1-f][1,2,4]triazin-7-yl)phenyl) (pyrrolidin-1-yl)methanone (4); N-(3-(4-amino-5-(1-cyclohexyl-1H-pyrazol-5-yl)pyrrolo[2,1-f][1,2,4]triazin-7-yl)benzyl)methanesulfonamide (5); 5-(1-cyclohexyl-1H-pyrazol-5-yl)-7-(3-(morpholinomethyl)phenyl)pyrrolo[2,1-f][1,2,4]triazin-4-amine (6); (5-(4-amino-5-(1-cyclohexyl-1H-pyrazol-5-yl)pyrrolo[2,1-f][1,2,4]triazin-7-yl)-2-fluorophenyl) methanol (7); N-(3-(4-amino-5-(1-cyclohexyl-1H-pyrazol-5-yl)pyrrolo[2,1-f][1,2,4] triazin-7-yl)phenyl)acetamide (8); N-(3-(4-amino-5-(1-cyclohexyl-1H-pyrazol-5-yl)pyrrolo[2,1-f][1,2,4]triazin-7-yl)phenyl)methanesulfonamide (9); 3-(4-amino-5-(1-cyclohexyl-1H-pyrazol-5-yl)pyrrolo[2,1-f][1,2,4]triazin-7-yl)-N-methylbenzamide (10); 3-(4-amino-5-(1-cyclohexyl-1H-pyrazol-5-yl)pyrrolo[2,1-f][1,2,4]triazin-7-yl)-N,N-dimethylbenzamide (11); 4-(4-amino-5-(1-cyclohexyl-1H-pyrazol-5-yl)pyrrolo[2,1-f][1,2,4]triazin-7-yl)-N,N-dimethylbenzamide (12); 3-(4-amino-5-(1-cyclohexyl-1H-pyrazol-5-yl)pyrrolo[2,1-f][1,2,4]triazin-7-yl)benzoic acid (13); 7-(3-(morpholinomethyl) phenyl)-5-(1-(tetrahydro-2H-pyran-4-yl)-1H-pyrazol-5-yl)pyrrolo[2,1-f][1,2,4]triazin-4-amine (14); (3-(4-amino-5-(1-(tetrahydro-2H-pyran-4-yl)-1H-pyrazol-5-yl)pyrrolo[2,1-f][1,2,4]triazin-7-yl)phenyl)(pyrrolidin-1-yl)methanone (15); 7-(3-((dimethyl amino) methyl)phenyl)-5-(1-(tetrahydro-2H-pyran-4-yl)-1H-pyrazol-5-yl)pyrrolo[2,1-f][1,2,4] triazin-4-amine (16); 7-(3-(2-(dimethylamino)propan-2-yl)phenyl)-5-(1-(tetrahydro-2H-pyran-4-yl)-1H-pyrazol-5-yl)pyrrolo[2,1-f][1,2,4]triazin-4-amine (17); N-(3-(4-amino-5-(1-(tetrahydro-2H-pyran-4-yl)-1H-pyrazol-5-yl)pyrrolo[2,1-f][1,2,4]triazin-7-yl)benzyl) methanesulfonamide (18); (3-(4-amino-5-(1-cyclohexyl-1H-pyrazol-5-yl)pyrrolo[2,1-f][1,2,4]triazin-7-yl)phenyl)(morpholino)methanone (19); (3-(4-amino-5-(1-cyclohexyl-1H-pyrazol-5-yl)pyrrolo[2,1-f][1,2,4]triazin-7-yl)phenyl)(4-(2-hydroxypropan-2-yl)piperidin-1-yl)methanone 20); 2-(3-(4-amino-5-(1-cyclohexyl-1H-pyrazol-5-yl)pyrrolo[2,1-f][1,2,4]triazin-7-yl)benzamido)thiazole-5-carboxamide (21); N-(1-acetylpiperidin-4-yl)-3-(4-amino-5-(1-cyclohexyl-1H-pyrazol-5-yl)pyrrolo[2,1-f][1,2,4]triazin-7-yl)benzamide (22); 3-(4-amino-5-(1-cyclohexyl-1H-pyrazol-5-yl)pyrrolo[2,1-f][1,2,4] triazin-7-yl)-N-(1-methylpiperidin-3-yl)benzamide (23); 1-(4-(3-(4-amino-5-(1-cyclohexyl-1H-pyrazol-5-yl)pyrrolo[2,1-f][1,2,4]triazin-7-yl)benzoyl)piperazin-1-yl)-2-methylpropan-1-one (24); (S)-1-(3-(4-amino-5-(1-cyclohexyl-1H-pyrazol-5-yl)pyrrolo[2,1-f][1,2,4]triazin-7-yl)benzoyl)piperidine-2-carboxamide (25); 1-(3-(4-amino-5-(1-cyclohexyl-1H-pyrazol-5-yl)pyrrolo[2,1-f][1,2,4]triazin-7-yl)benzoyl)azetidine-3-carbonitrile (26); 4-(3-(4-amino-5-(1-cyclohexyl-1H-pyrazol-5-yl)pyrrolo[2,1-f][1,2,4] triazin-7-yl)benzoyl)-1-methylpiperazin-2-one (27); 3-(4-amino-5-(1-cyclohexyl-1H-pyrazol-5-yl)pyrrolo[2,1-f][1,2,4]triazin-7-yl)-N-(2-oxopiperidin-4-yl)benzamide (28); 1-(4-(3-(4-amino-5-(1-cyclohexyl-1H-pyrazol-5-yl)pyrrolo[2,1-f][1,2,4]triazin-7-yl)benzoyl)piperazin-1-yl)propan-1-one (29); N-(1-(3-(4-amino-5-(1-cyclohexyl-1H-pyrazol-5-yl)pyrrolo[2,1-f][1,2,4]triazin-7-yl)benzoyl)piperidin-4-yl)acetamide (30); (4-(3-(4-amino-5-(1-cyclohexyl-1H-pyrazol-5-yl)pyrrolo[2,1-f][1,2,4]triazin-7-yl)benzoyl) piperazin-1-yl)(tetrahydrofuran-2-yl)methanone (31); (3-(4-amino-5-(1-cyclohexyl-1H-pyrazol-5-yl)pyrrolo[2,1-f][1,2,4]triazin-7-yl)phenyl)(3-(dimethylamino)piperidin-1-yl)methanone (32); 1-(3-(4-amino-5-(1-cyclohexyl-1H-pyrazol-5-yl)pyrrolo[2,1-f][1,2,4] triazin-7-yl)benzoyl)piperidine-4-carboxamide (33); (3-(4-amino-5-(1-cyclohexyl-1H-pyrazol-5-yl)pyrrolo[2,1-f][1,2,4]triazin-7-yl)phenyl)(3-hydroxy-3-methylazetidin-1-yl)methanone (34); 1-(4-(3-(4-amino-5-(1-cyclohexyl-1H-pyrazol-5-yl)pyrrolo[2,1-f][1,2,4]triazin-7-yl)benzoyl)piperazin-1-yl)ethanone (35); 3-(4-amino-5-(1-cyclohexyl-1H-pyrazol-5-yl)pyrrolo[2,1-f][1,2,4]triazin-7-yl)-N-(3-carbamoylphenyl)benzamide (36); 3-(4-amino-5-(1-cyclohexyl-1H-pyrazol-5-yl)pyrrolo[2,1-f][1,2,4]triazin-7-yl)-N-(tetrahydro-2H-pyran-4-yl)benzamide (37); 1-(3-(4-amino-5-(1-cyclohexyl-1H-pyrazol-5-yl)pyrrolo[2,1-f][1,2,4]triazin-7-yl)benzoyl)-N-methylpiperidine-4-carboxamide (38); (3-(4-amino-5-(1-cyclohexyl-1H-pyrazol-5-yl)pyrrolo[2,1-f][1,2,4]triazin-7-yl)phenyl)(4-hydroxy-4-(hydroxymethyl)piperidin-1-yl)methanone (39); 3-(4-amino-5-(1-cyclohexyl-1H-pyrazol-5-yl)pyrrolo[2,1-f][1,2,4]triazin-7-yl)-N-(3-cyclopropyl-1-methyl-1H-pyrazol-5-yl)benzamide (40); methyl 4-(3-(4-amino-5-(1-cyclohexyl-1H-pyrazol-5-yl)pyrrolo[2,1-f][1,2,4]triazin-7-yl)benzoyl) piperazine-1-carboxylate (41); 3-(4-amino-5-(1-cyclohexyl-1H-pyrazol-5-yl)pyrrolo[2,1-f][1,2,4]triazin-7-yl)-N-(2-oxopyrrolidin-3-yl)benzamide (42); 3-(4-amino-5-(1-cyclohexyl-1H-pyrazol-5-yl)pyrrolo[2,1-f][1,2,4] triazin-7-yl)-N-(2-methyl-1-(methylamino)-1-oxopropan-2-yl)benzamide (43); 3-(4-amino-5-(1-cyclohexyl-1H-pyrazol-5-yl)pyrrolo[2,1-f][1,2,4]triazin-7-yl)-N-(4-(hydroxymethyl)tetrahydro-2H-pyran-4-yl)benzamide (44); 3-(4-amino-5-(1-cyclohexyl-1H-pyrazol-5-yl)pyrrolo[2,1-f][1,2,4]triazin-7-yl)-N-cyclopropyl-N-(tetrahydro-2H-pyran-4-yl)benzamide (45); (3-(4-amino-5-(1-cyclohexyl-1H-pyrazol-5-yl)pyrrolo[2,1-f][1,2,4]triazin-7-yl)phenyl)(1,1-dioxidothiomorpholino)methanone (46); 3-(4-amino-5-(1-cyclohexyl-1H-pyrazol-5-yl)pyrrolo[2,1-f][1,2,4]triazin-7-yl)-N-(2H-tetrazol-5-yl)benzamide (47); 5-(1-(4,4-difluorocyclohexyl)-1H-pyrazol-5-yl)-7-(3-((dimethylamino)methyl)phenyl)pyrrolo[2,1-f][1,2,4]triazin-4-amine (48); 5-(1-(4,4-difluorocyclohexyl)-1H-pyrazol-5-yl)-'7-(3-(2-(dimethylamino)propan-2-yl)phenyl)pyrrolo[2,1-f][1,2,4]triazin-4-amine (49); 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-fluoro-N-(tetrahydro-2H-pyran-4-yl)benzamide (50); 5-(4-amino-5-(1-(tetrahydro-2H-pyran-4-yl)-1H-pyrazol-5-yl)pyrrolo[2,1-f][1,2,4]triazin-7-yl)-N-((3,5-dimethylisoxazol-4-yl)methyl)-2-fluoro-N-methylbenzamide (51); 5-(4-amino-5-(1-(tetrahydro-2H-pyran-4-yl)-1H-pyrazol-5-yl)pyrrolo[2,1-f][1,2,4]triazin-7-yl)-N,N-dicyclopropyl-2-fluorobenzamide (52); (5-(4-amino-5-(1-(tetrahydro-2H-pyran-4-yl)-1H-pyrazol-5-yl)pyrrolo[2,1-f][1,2,4] triazin-7-yl)-2-fluorophenyl)((1R,5R)-8-oxa-3-azabicyclo[3.2.1]octan-3-yl)methanone (53); 5-(4-amino-5-(1-(tetrahydro-2H-pyran-4-yl)-1H-pyrazol-5-yl)pyrrolo[2,1-f][1,2,4] triazin-7-yl)-2-fluoro-N-methyl-N-((1-methylpyrrolidin-2-yl)methyl)benzamide (54); N-(1-acetylpiperidin-4-yl)-5-(4-amino-5-(1-(tetrahydro-2H-pyran-4-yl)-1H-pyrazol-5-yl)pyrrolo[2,1-f][1,2,4]triazin-7-yl)-N-cyclopropyl-2-fluorobenzamide (55); 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-methoxy-N-(tetrahydro-2H-pyran-4-yl)benzamide (56); 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-methyl-N-(tetrahydro-2H-pyran-4-yl)benzamide (57); 5-(4-amino-5-(1-(tetrahydro-2H-pyran-4-yl)-1H-pyrazol-5-yl)pyrrolo[2,1-f][1,2,4]triazin-7-yl)-2-chlorobenzoic acid (58); 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-(tetrahydro-2H-pyran-4-yl)benzamide (59); 5-(4-amino-5-(1-(tetrahydro-2H-pyran-4-yl)-1H-pyrazol-5-yl)pyrrolo [2,1-f][1,2,4]triazin-7-yl)-2-chloro-N-(2,2-difluoroethyl)-N-methylbenzamide (60); 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-((1-methyl-1H-pyrazol-4-yl)methyl)benzamide (61); 5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropyl-N-(thiazol-2-ylmethyl)benzamide (62); 5-(4-amino-5-(1-(tetrahydro-2H-pyran-4-yl)-1H-pyrazol-5-yl)pyrrolo[2,1-f][1,2,4]triazin-7-yl)-2-chloro-N-methyl-N-(tetrahydro-2H-pyran-4-yl)benzamide (63); N-(1-acetylpiperidin-4-yl)-5-(4-amino-5-(1-(tetrahydro-2H-pyran-4-yl)-1H-pyrazol-5-yl)pyrrolo[2,1-f][1,2,4]triazin-7-yl)-2-chloro-N-cyclopropylbenzamide (64); 5-(4-amino-5-(1-(tetrahydro-2H-pyran-4-yl)-1H-pyrazol-5-yl)pyrrolo[2,1-f][1,2,4]triazin-7-yl)-2-chloro-N-(3-hydroxy-2,2-dimethylpropyl)-N-methylbenzamide (65); 5-(4-amino-5-(1-(tetrahydro-2H-pyran-4-yl)-1H-pyrazol-5-yl)pyrrolo[2,1-f][1,2,4]triazin-7-yl)-2-chloro-N,N-diethylbenzamide (66); 3-(4-amino-5-(1-methyl-1H-pyrrol-2-yl)pyrrolo[2,1-f][1,2,4]triazin-7-yl)-N-cyclopropyl-N-(tetrahydro-2H-pyran-4-yl)benzamide (67); 3-(4-amino-5-(1-phenyl-1H-pyrrol-2-yl)pyrrolo[2,1-f][1,2,4]triazin-7-yl)-N-cyclopropyl-N-(tetrahydro-2H-pyran-4-yl)benzamide (68); 3-(4-amino-5-(1-(tetrahydro-2H-pyran-4-yl)-1H-pyrazol-5-yl)pyrrolo [2,1-f][1,2,4]triazin-7-yl)-N,N-dicyclopropylbenzamide (69); 3-(4-amino-5-(1-(tetrahydro-2H-pyran-4-yl)-1H-pyrazol-5-yl)pyrrolo[2,1-f][1,2,4]triazin-7-yl)-N-cyclopropyl-N-((1-methyl-1H-pyrazol-5-yl)methyl)benzamide (70); 3-(4-amino-5-(1-(tetrahydro-2H-pyran-4-yl)-1H-pyrazol-5-yl)pyrrolo[2,1-f][1,2,4]triazin-7-yl)-N-(3- hydroxy-2,2-dimethylpropyl)-N-methylbenzamide (71); 3-(4-amino-5-(1-(tetrahydro-2H-pyran-4-yl)-1H-pyrazol-5-yl)pyrrolo[2,1-f][1,2,4]triazin-7-yl)-N-cyclopropyl-N-(thiazol-2-ylmethyl)benzamide (72); 3-(4-amino-5-(1-(tetrahydro-2H-pyran-4-yl)-1H-pyrazol-5-yl)pyrrolo[2,1-f][1,2,4]triazin-7-yl)-N-methyl-N-((1-methylpyrrolidin-2-yl)methyl) benzamide (73); 3-(4-amino-5-(1-(tetrahydro-2H-pyran-4-yl)-1H-pyrazol-5-yl)pyrrolo [2,1-f][1,2,4]triazin-7-yl)-N,N-diethylbenzamide (74); N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-N-cyclopropylbenzamide (75); 3-(4-amino-5-(1-(tetrahydro-2H-pyran-4-yl)-1H-pyrazol-5-yl)pyrrolo[2,1-f][1,2,4]triazin-7-yl)-N-((3,5-dimethylisoxazol-4-yl)methyl)-N-methylbenzamide (76); 3-(4-amino-5-(1-(tetrahydro-2H-pyran-4-yl)-1H-pyrazol-5-yl)pyrrolo[2,1-f][1,2,4]triazin-7-yl)-5-chloro-N-(3-hydroxy-2,2-dimethylpropyl)-N-methylbenzamide (77); 3-(4-amino-5-(1-(tetrahydro-2H-pyran-4-yl)-1H-pyrazol-5-yl)pyrrolo[2,1-f][1,2,4]triazin-7-yl)-5-chloro-N-cyclopropyl-N-(1-methylpiperidin-4-yl)benzamide (78); 3-(4-amino-5-(1-(tetrahydro-2H-pyran-4-yl)-1H-pyrazol-5-yl)pyrrolo [2,1-f][1,2,4]triazin-7-yl)-5-chloro-N-(tetrahydro-2H-pyran-4-yl)benzamide (79); N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-5-chloro-N-cyclopropylbenzamide (80); 3-(4-amino-5-(1-(tetrahydro-2H-pyran-4-yl)-1H-pyrazol-5-yl)pyrrolo[2,1-f][1,2,4]triazin-7-yl)-5-chloro-N-methyl-N-(oxetan-3-yl)benzamide (81); 3-(4-amino-5-(1-(tetrahydro-2H-pyran-4-yl)-1H-pyrazol-5-yl)pyrrolo[2,1-f][1,2,4]triazin-7-yl)-5-chloro-N-methyl-N-((1-methylpyrrolidin-2-yl)methyl) benzamide (82); 3-(4-amino-5-(1-(tetrahydro-2H-pyran-4-yl)-1H-pyrazol-5-yl)pyrrolo[2,1-f][1,2,4]triazin-7-yl)-5-fluoro-N-(3-hydroxy-2,2-dimethylpropyl)-N-methylbenzamide (83); 3-(4-amino-5-(1-(tetrahydro-2H-pyran-4-yl)-1H-pyrazol-5-yl)pyrrolo[2,1-f][1,2,4]triazin-7-yl)-N-cyclopropyl-5-fluoro-N-(thiazol-2-ylmethyl)benzamide (84); N-(1-acetylpiperidin-4-yl)-3-(4-amino-5-(1-(tetrahydro-2H-pyran-4-yl)-1H-pyrazol-5-yl)pyrrolo[2,1-f][1,2,4]triazin-7-yl)-N-cyclopropyl-5-fluorobenzamide (85); 3-(4-amino-5-(1-(tetrahydro-2H-pyran-4-yl)-1H-pyrazol-5-yl)pyrrolo[2,1-f][1,2,4]triazin-7-yl)-5-fluoro-N-methyl-N-((1-methylpyrrolidin-2-yl)methyl)benzamide (86); 5-(4-amino-5-(1-(tetrahydro-2H-pyran-4-yl)-1H-pyrazol-5-yl)pyrrolo[2,1-f][1,2,4]triazin-7-yl)-N-(2,2-difluoroethyl)-2-fluoro-N-methylbenzamide (87); 5-(4-amino-5-(1-(tetrahydro-2H-pyran-4-yl)-1H-pyrazol-5-yl)pyrrolo[2,1-f][1,2,4] triazin-7-yl)-2-fluoro-N-methyl-N-(tetrahydro-2H-pyran-4-yl)benzamide (88); 5-(4-amino-5-(1-(tetrahydro-2H-pyran-4-yl)-1H-pyrazol-5-yl)pyrrolo[2,1-f][1,2,4]triazin-7-yl)-N-cyclopropyl-2-fluoro-N-(thiazol-2-ylmethyl)benzamide (89); 7-(3-(3-(dimethylamino)oxetan-3-yl)phenyl)-5-(1-(tetrahydro-2H-pyran-4-yl)-1H-pyrazol-5-yl)pyrrolo[2,1-f][1,2,4]triazin-4-amine (90); N-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)-2-methylpropane-2-sulfinamide (91); 1-[3-(3-{4-amino-5-[1-(oxan-4-yl)-1H-pyrazol-5-yl]pyrrolo[2,1-f][1,2,4]triazin-7-yl}phenyl)oxetan-3-yl]piperidin-4-one (92); 1-(3-(3-(4-amino-5-(1-(tetrahydro-2H-pyran-4-yl)-1H-1,2,3-triazol-5-yl)pyrrolo[2,1-f][1,2,4]triazin-7-yl)phenyl)oxetan-3-yl) piperidin-4-one (93); 1-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)pyrrolidin-3-ol (94); 1-[3-(3-{4-amino-5-[1-(oxan-4-yl)-1H-1,2,3-triazol-5-yl]pyrrolo[2,1-f][1,2,4]triazin-7-yl}phenyl)oxetan-3-yl]piperidin-4-ol (95); 4-(3-(3-(4-amino-5-(1-(tetrahydro-2H-pyran-4-yl)-1H-pyrazol-5-yl)pyrrolo[2,1-f][1,2,4]triazin-7-yl)phenyl) oxetan-3-yl)thiomorpholine 1,1-dioxide (96); 4-(3-(3-(4-amino-5-(1-(2,2,2-trifluoroethyl)-1H-pyrazol-5-yl)pyrrolo [2,1-f][1,2,4]triazin-7-yl)phenyl)oxetan-3-yl)thiomorpholine 1,1-dioxide (97); 7-(3-(3-morpholinooxetan-3-yl) phenyl)-5-(1-(tetrahydro-2H-pyran-4-yl)-1H-pyrazol-5-yl)pyrrolo[2,1-f][1,2,4]triazin-4-amine (98); 1-(3-(3-(4-amino-5-(1-(tetrahydro-2H-pyran-4-yl)-1H-pyrazol-5-yl)pyrrolo[2,1-f][1,2,4] triazin-7-yl)phenyl)oxetan-3-yl)pyrrolidin-3-ol (99); 1-(3-(3-(4-amino-5-(1-isopropyl-1H-1,2,3-triazol-5-yl)pyrrolo[2,1-f][1,2,4]triazin-7-yl)phenyl)oxetan-3-yl) pyrrolidin-3-ol (100); 1-(4-((3-(3-(4-amino-5-(1-(tetrahydro-2H-pyran-4-yl)-1H-pyrazol-5-yl)pyrrolo [2,1-f][1,2,4]triazin-7-yl)phenyl)oxetan-3-yl)(methyl)amino) piperidin-1-yl)ethanone (101); N-(3-(3-(4-amino-5-(1-(tetrahydro-2H-pyran-4-yl)-1H-pyrazol-5-yl)pyrrolo[2,1-f][1,2,4]triazin-7-yl)phenyl)oxetan-3-yl)-N,2-dimethylpropane-2-sulfinamide (102); N-(3-(3-(4-amino-5-(1-(tetrahydro-2H-pyran-4-yl)-1H-pyrazol-5-yl)pyrrolo[2,1-f][1,2,4] triazin-7-yl)phenyl)oxetan-3-yl)pivalamide (103); (cis)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-methylcyclobutanecarboxamide (104); (trans)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-methylcyclobutanecarboxamide (105); (trans)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxy-3-(trifluoromethyl)cyclobutanecarboxamide (106); (cis)-1-(3-(4-amino-5-(1-cyclobutyl-1H-pyrazol-5-yl)pyrrolo[2,1-f][1,2,4]triazin-7-yl)phenyl)-3-hydroxy-N,3-dimethylcyclobutanecarboxamide (107); (cis)-1-(3-(4-amino-5-(1-isopropyl-1H-pyrazol-5-yl)pyrrolo[2,1-f][1,2,4]triazin-7-yl)phenyl)-3-hydroxy-N,3-dimethylcyclobutanecarboxamide (108); 1-(3-(4-amino-5-(1-cyclopropyl-1H-pyrazol-5-yl)pyrrolo[2,1-f][1,2,4]triazin-7-yl)phenyl)-N-(3,3-difluorocyclobutyl)-3,3-difluorocyclobutanecarboxamide (109); (cis)-1-(3-(4-amino-5-(1-(tetrahydro-2H-pyran-4-yl)-1H-pyrazol-5-yl) pyrrolo[2,1-f][1,2,4]triazin-7-yl)phenyl)-N-cyclopropyl-3-methoxycyclobutanecarboxamide (110); (cis)-1-(3-(4-amino-5-(1-cyclopropyl-1H-pyrazol-5-yl)pyrrolo[2,1-f][1,2,4]triazin-7-yl)phenyl)-N-cyclopropyl-3-methoxycyclobutanecarboxamide (111); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-(difluoromethoxy)-N-methylcyclobutanecarboxamide (112); ((cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutyl) (morpholino)methanone (113); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-methyl-N-(oxetan-3-yl)cyclobutanecarboxamide (114); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-methylcyclobutanecarboxamide (115); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropyl-3-hydroxycyclobutanecarboxamide (116); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxy-N-isopropylcyclobutanecarboxamide (117); (cis)-1-(3-(4-amino-5-(1-(tetrahydro-2H-pyran-4-yl)-1H-pyrazol-5-yl)pyrrolo[2,1-f][1,2,4]triazin-7-yl)phenyl)-N-ethyl-3-hydroxycyclobutanecarboxamide (118); ((1s,3 s)-1-(3-(4-amino-5-(1-(tetrahydro-2H-pyran-4-yl)-1H-pyrazol-5-yl) pyrrolo[2,1-f][1,2,4]triazin-7-yl)phenyl)-3- hydroxycyclobutyl)(3-methoxypyrrolidin-1-yl)methanone (119); ((cis)-1-(3-(4-amino-5-(1-(tetrahydro-2H-pyran-4-yl)-1H-pyrazol-5-yl)pyrrolo[2,1-f][1,2,4]triazin-7-yl)phenyl)-3-hydroxycyclobutyl)(3,3-difluoroazetidin-1-yl) methanone (120); (cis)-1-(3-(4-amino-5-(1-cyclopropyl-1H-pyrazol-5-yl)pyrrolo[2,1-f][1,2,4]triazin-7-yl)phenyl)-N-ethyl-3-hydroxycyclobutanecarboxamide (121); (cis)-1-(3-(4-amino-5-(1-cyclopropyl-1H-pyrazol-5-yl)pyrrolo[2,1-f][1,2,4] triazin-7-yl)phenyl)-3-hydroxy-N-isopropylcyclobutanecarboxamide (122); (cis)-1-(3-(4-amino-5-(1-cyclopropyl-1H-pyrazol-5-yl)pyrrolo[2,1-f][1,2,4]triazin-7-yl)phenyl)-3-hydroxy-N-(2,2,2-trifluoroethyl) cyclobutanecarboxamide (123); (cis)-1-(3-(4-amino-5-(1-cyclopropyl-1H-pyrazol-5-yl)pyrrolo[2,1-f][1,2,4]triazin-7-yl)phenyl)-N-cyclopropyl-3-hydroxycyclobutanecarboxamide (124); 1-(3-(4-amino-5-(1-(tetrahydro-2H-pyran-4-yl)-1H-pyrazol-5-yl)pyrrolo[2,1-f][1,2,4]triazin-7-yl)phenyl)-N-(3,3-difluorocyclobutyl) cyclopropanecarboxamide (125); 1-(3-(4-amino-5-(1-(tetrahydro-2H-pyran-4-yl)-1H-pyrazol-5-yl)pyrrolo[2,1-f][1,2,4]triazin-7-yl)phenyl)-N-ethylcyclopropanecarboxamide (126); 1-(3-(4-amino-5-(1-(tetrahydro-2H-pyran-4-yl)-1H-pyrazol-5-yl)pyrrolo[2,1-f][1,2,4]triazin-7-yl)phenyl)-N-isopropylcyclopropanecarboxamide (127); 1-(3-(4-amino-5-(1-(tetrahydro-2H-pyran-4-yl)-1H-pyrazol-5-yl)pyrrolo[2,1-f][1,2,4]triazin-7-yl)phenyl)-N-cyclopropylcyclopropanecarboxamide (128); 1-(3-(4-amino-5-(1-cyclopropyl-1H-pyrazol-5-yl)pyrrolo[2,1-f][1,2,4]triazin-7-yl)phenyl)-N-(oxetan-3-yl) cyclopropanecarboxamide (129); 1-(3-(4-amino-5-(1-cyclopropyl-1H-pyrazol-5-yl)pyrrolo[2,1-f][1,2,4]triazin-7-yl)phenyl)-N-ethylcyclopropanecarboxamide (130); 1-(3-(4-amino-5-(1-cyclopropyl-1H-pyrazol-5-yl)pyrrolo[2,1-f][1,2,4]triazin-7-yl)phenyl)-N-isopropylcyclopropanecarboxamide (131); 4-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethyloxazolidin-2-one (132); (3R,5S)-5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyrrolidin-3-ol (133); (3S,5R)-5-(3-(4-amino-5-(1-(tetrahydro-2H-pyran-4-yl)-1H-pyrazol-5-yl) pyrrolo[2,1-f][1,2,4]triazin-7-yl)phenyl)-1-methylpyrrolidin-3-ol (134); (3R,5R)-5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyrrolidin-3-ol (135); 1-((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)ethanone (136); 1-((2S,4S)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)ethanone (137); 1-((2S,4R)-2-(3-(4-amino-5-(1-(tetrahydro-2H-pyran-4-yl)-1H-pyrazol-5-yl) pyrrolo[2,1-f][1,2,4]triazin-7-yl)phenyl)-4-hydroxypyrrolidin-1-yl)-2,2-dimethylpropan-1-one (138); 1-((2S,4R)-2-(3-(4-amino-5-(1-cyclopropyl-1H-pyrazol-5-yl)pyrrolo[2,1-f][1,2,4]triazin-7-yl)phenyl)-4-hydroxypyrrolidin-1-yl)ethanone (139); (2S,4R)-tert-butyl 2-(3-(4-amino-5-(1-(tetrahydro-2H-pyran-4-yl)-1H-pyrazol-5-yl) pyrrolo[2,1-f][1,2,4]triazin-7-yl)phenyl)-4-hydroxypyrrolidine-1-carboxylate (140); ((2S,4R)-2-(3-(4-amino-5-(1-(tetrahydro-2H-pyran-4-yl)-1H-pyrazol-5-yl) pyrrolo[2,1-f][1,2,4]triazin-7-yl)phenyl)-4-hydroxypyrrolidin-1-yl)(cyclopropyl)methanone (141); 1-((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)-2-methylpropan-1-one (142); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(2,2-difluorocyclopropyl) methanone (143); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(tetrahydro-2H-pyran-4-yl)methanone (144); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(phenyl)methanone (145); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(4-methylthiazol-5-yl)methanone (146); ((2S,4R)-2-(3-(4-amino-5-(1-(tetrahydro-2H-pyran-4-yl)-1H-pyrazol-5-yl) pyrrolo[2,1-f][1,2,4]triazin-7-yl)phenyl)-4-hydroxypyrrolidin-1-yl)(oxazol-4-yl)methanone (147); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(thiazol-5-yl)methanone (148); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridin-4-yl)methanone (149); ((2 S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridin-3-yl)methanone (150); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(o-tolyl)methanone (151); ((2S, 4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(1H-pyrazol-3-yl)methanone (152); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(3-fluorophenyl)methanone (153); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(1-methyl-1H-pyrazol-5-yl)methanone (154); ((2S,4R)-2-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypyrrolidin-1-yl)(pyridazin-4-yl)methanone (155); (S)-3-(3-(4-amino-5-(1-(tetrahydro-2H-pyran-4-yl)-1H-pyrazol-5-yl)pyrrolo[2,1-f][1,2,4]triazin-7-yl)benzyl)-4-(tert-butyl)oxazolidin-2-one (156); 3-(3-(4-amino-5-(1-(tetrahydro-2H-pyran-4-yl)-1H-pyrazol-5-yl)pyrrolo[2,1-f][1,2,4]triazin-7-yl)benzyl)-1,3-oxazinan-2-one (157); (S)-3-(3-(4-amino-5-(1-(tetrahydro-2H-pyran-4-yl)-1H-pyrazol-5-yl)pyrrolo[2,1-f][1,2,4]triazin-7-yl)benzyl)-4-isopropyloxazolidin-2-one (158); 1-(3-(4-amino-5-(1-(tetrahydro-2H-pyran-4-yl)-1H-pyrazol-5-yl) pyrrolo[2,1-f][1,2,4]triazin-7-yl)benzyl)pyrrolidin-2-one (159); N-(3-(4-amino-5-(1-(tetrahydro-2H-pyran-4-yl)-1H-pyrazol-5-yl)pyrrolo[2,1-f][1,2,4] triazin-7-yl)benzyl)-N-(tetrahydro-2H-pyran-4-yl)acetamide (160); 1-(3-(4-amino-5-(1-(tetrahydro-2H-pyran-4-yl)-1H-pyrazol-5-yl)pyrrolo[2,1-f][1,2,4]triazin-7-yl)benzyl)-3-methylpyrrolidin-2-one (161); 3-(3-(4-amino-5-(1-(tetrahydro-2H-pyran-4-yl)-1H-pyrazol-5-yl)pyrrolo[2,1-f][1,2,4]triazin-7-yl)benzyl)-5,5-dimethyloxazolidin-2-one (162); 3-(2-(3-(4-amino-5-(1-(tetrahydro-2H-pyran-4-yl)-1H-pyrazol-5-yl)pyrrolo[2,1-f][1,2,4]triazin-7-yl)phenyl)propan-2-yl)oxazolidin-2-one (163); 7-(34(1S,5S)-8-oxa-3-azabicyclo[3.2.1]octan-3-ylmethyl)phenyl)-5-(1-(tetrahydro-2H-pyran-4-yl)-1H-pyrazol-5-yl)pyrrolo[2,1-f][1,2,4]triazin-4-amine (164); N-(3-(4-amino-5-(1-(tetrahydro-2H-pyran-4-yl)-1H-pyrazol-5-yl) pyrrolo[2,1-f][1,2,4]triazin-7-yl)benzyl)-4-methoxybenzamide (165); N-(2-(3-(4-amino-5-(1-(tetrahydro-2H-pyran-4-yl)-1H-pyrazol-5-yl) pyrrolo[2,1-f][1,2,4]triazin-7-yl)phenyl)propan-2-yl)-3-hydroxy-3- methylbutanamide (166); 1-(4-(3-(4-amino-5-(1-(tetrahydro-2H-pyran-4-yl)-1H-pyrazol-5-yl)pyrrolo[2,1-f][1,2,4]triazin-7-yl)benzyl)piperazin-1-yl)ethanone (167); 4-(3-(4-amino-5-(1-(tetrahydro-2H-pyran-4-yl)-1H-pyrazol-5-yl)pyrrolo[2,1-f][1,2,4]triazin-7-yl)benzyl)-1-methylpiperazin-2-one (168); 7-(3-((methyl(tetrahydro-2H-pyran-4-yl)amino)methyl)phenyl)-5-(1-(tetrahydro-2H-pyran-4-yl)-1H-pyrazol-5-yl)pyrrolo[2,1-f][1,2,4]triazin-4-amine (169); 7-(3-(((2-methoxyethyl)(methyl)amino)methyl)phenyl)-5-(1-(tetrahydro-2H-pyran-4-yl)-1H-pyrazol-5-yl)pyrrolo[2,1-f][1,2,4]triazin-4-amine (170); (3R)-1-(1-(3-(4-amino-5-(1-(tetrahydro-2H-pyran-4-yl)-1H-pyrazol-5-yl)pyrrolo [2,1-f][1,2,4]triazin-7-yl)phenyl)ethyl)pyrrolidin-3-ol (171); 7-(3-(1-(3,3-dimethylmorpholino)ethyl)phenyl)-5-(1-(tetrahydro-2H-pyran-4-yl)-1H-pyrazol-5-yl)pyrrolo[2,1-f][1,2,4]triazin-4-amine (172); 1-(4-(1-(3-(4-amino-5-(1-(tetrahydro-2H-pyran-4-yl)-1H-pyrazol-5-yl)pyrrolo[2,1-f][1,2,4]triazin-7-yl)phenyl)ethyl)piperazin-1-yl)ethanone (173); 7-(3-(1-(3-methoxypyrrolidin-1-yl)ethyl)phenyl)-5-(1-(tetrahydro-2H-pyran-4-yl)-1H-pyrazol-5-yl)pyrrolo[2,1-f][1,2,4]triazin-4-amine (174); 7-(3-(1-morpholinoethyl)phenyl)-5-(1-(tetrahydro-2H-pyran-4-yl)-1H-pyrazol-5-yl)pyrrolo[2,1-f][1,2,4]triazin-4-amine (175); 7-(3-(1-((cis)-2,6-dimethylmorpholino)ethyl)phenyl)-5-(1-(tetrahydro-2H-pyran-4-yl)-1H-pyrazol-5-yl)pyrrolo[2,1-f][1,2,4]triazin-4-amine (176); 7-(3-(1-(methyl(tetrahydro-2H-pyran-4-yl)amino)ethyl)phenyl)-5-(1-(tetrahydro-2H-pyran-4-yl)-1H-pyrazol-5-yl)pyrrolo[2,1-f][1,2,4]triazin-4-amine (177); 7-(3-(1-(3,3-dimethylazetidin-1-yl)ethyl)phenyl)-5-(1-(tetrahydro-2H-pyran-4-yl)-1H-pyrazol-5-yl)pyrrolo[2,1-f][1,2,4]triazin-4-amine (178); 1-(1-(3-(4-amino-5-(1-(tetrahydro-2H-pyran-4-yl)-1H-pyrazol-5-yl)pyrrolo[2,1-f][1,2,4]triazin-7-yl)phenyl)ethyl)-3-methylazetidin-3-ol (179); 7-(3-(2-morpholinopropan-2-yl)phenyl)-5-(1-(tetrahydro-2H-pyran-4-yl)-1H-pyrazol-5-yl)pyrrolo[2,1-f][1,2,4]triazin-4-amine (180); 5-(1-(tetrahydro-2H-pyran-4-yl)-1H-pyrazol-5-yl)-'7-(3-(2,2,2-trifluoro-1-morpholinoethyl)phenyl)pyrrolo [2,1-f][1,2,4]triazin-4-amine (181); 7-(3-(2-(dimethylamino)propan-2-yl)phenyl)-5-(1-(tetrahydro-2H-pyran-4-yl)-1H-1,2,3-triazol-5-yl)pyrrolo[2,1-f][1,2,4]triazin-4-amine (182); 7-(3-(2-(diethylamino)propan-2-yl)phenyl)-5-(1-(tetrahydro-2H-pyran-4-yl)-1H-1,2,3-triazol-5-yl)pyrrolo[2,1-f][1,2,4]triazin-4-amine (183); 1-((2S,4R)-2-(3-(4-amino-5-(1-isopropyl-1H-1,2,3-triazol-5-yl)pyrrolo[2,1-f][1,2,4]triazin-7-yl)phenyl)-4-hydroxypyrrolidin-1-yl)ethanone (184); 7-(3-(piperidin-4-yl)phenyl)-5-(1-(tetrahydro-2H-pyran-4-yl)-1H-1,2,3-triazol-5-yl)pyrrolo[2,1-f][1,2,4]triazin-4-amine (185); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-1-yl)ethanone (186); 7-(3-(1-methylpiperidin-4-yl)phenyl)-5-(1-(tetrahydro-2H-pyran-4-yl)-1H-1,2,3-triazol-5-yl)pyrrolo[2,1-f][1,2,4]triazin-4-amine (187); 5-(1-isopropyl-1H-1,2,3-triazol-5-yl)-7-(3-(1-methylpiperidin-4-yl)phenyl) pyrrolo[2,1-f][1,2,4]triazin-4-amine (188); 4-(3-(4-amino-5-(1-(tetrahydro-2H-pyran-4-yl)-1H-1,2,3-triazol-5-yl)pyrrolo[2,1-f][1,2,4]triazin-7-yl)benzyl)morpholin-3-one (189); 7-(3-((methyl(tetrahydro-2H-pyran-4-yl)amino)methyl)phenyl)-5-(1-(tetrahydro-2H-pyran-4-yl)-1H-1,2,3-triazol-5-yl)pyrrolo[2,1-f][1,2,4]triazin-4-amine (190); 7-(3-((methyl(oxetan-3-yl)amino)methyl)phenyl)-5-(1-(tetrahydro-2H-pyran-4-yl)-1H-pyrazol-5-yl)pyrrolo[2,1-f][1,2,4]triazin-4-amine (191); 7-(3-((cyclopropyl(1-(methylsulfonyl)azetidin-3-yl)amino)methyl)phenyl)-5-(1-(tetrahydro-2H-pyran-4-yl)-1H-1,2,3-triazol-5-yl)pyrrolo[2,1-f][1,2,4]triazin-4-amine (192); 7-(3-((bis(tetrahydro-2H-pyran-4-yl)amino)methyl)phenyl)-5-(1-(tetrahydro-2H-pyran-4-yl)-1H-pyrazol-5-yl)pyrrolo[2,1-f][1,2,4]triazin-4-amine (193); 7-(3-(morpholinomethyl)phenyl)-5-(1-(tetrahydro-2H-pyran-4-yl)-1H-1,2,3-triazol-5-yl)pyrrolo[2,1-f][1,2,4]triazin-4-amine (194); (R)-1-(3-(4-amino-5-(1-isopropyl-1H-1,2,3-triazol-5-yl)pyrrolo[2,1-f][1,2,4] triazin-7-yl)benzyl)pyrrolidin-3-ol (195); 4-(3-(4-amino-5-(1-(tetrahydro-2H-pyran-4-yl)-1H-pyrazol-5-yl)pyrrolo[2,1-f][1,2,4]triazin-7-yl)phenoxy)tetrahydro-2H-thiopyran 1,1-dioxide (196); 5-(1-(tetrahydro-2H-pyran-4-yl)-1H-pyrazol-5-yl)-'7-(3-((tetrahydro-2H-pyran-4-yl)oxy)phenyl)pyrrolo[2,1-f][1,2,4]triazin-4-amine (197); 7-(1-(2,6-dimethyltetrahydro-2H-pyran-4-yl)-1H-indazol-6-yl)-5-(1-(tetrahydro-2H-pyran-4-yl)-1H-pyrazol-5-yl)pyrrolo[2,1-f][1,2,4]triazin-4-amine (198); 7-(3-(piperidin-4-yloxy) phenyl)-5-(1-(tetrahydro-2H-pyran-4-yl)-1H-1,2,3-triazol-5-yl)pyrrolo[2,1-f][1,2,4] triazin-4-amine (199); 7-(3-(piperidin-4-yloxy)phenyl)-5-(1-(tetrahydro-2H-pyran-4-yl)-1H-pyrazol-5-yl)pyrrolo[2,1-f][1,2,4]triazin-4-amine (200); 7-(3-((1-methylpiperidin-4-yl)oxy)phenyl)-5-(1-(tetrahydro-2H-pyran-4-yl)-1H-1,2,3-triazol-5-yl) pyrrolo[2,1-f][1,2,4]triazin-4-amine (201); 7-(3-((1-methylpiperidin-4-yl)oxy)phenyl)-5-(1-(tetrahydro-2H-pyran-4-yl)-1H-pyrazol-5-yl)pyrrolo[2,1-f][1,2,4]triazin-4-amine (202); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenoxy)piperidin-1-yl)-2-methylpropan-1-one (203); 1-(4-(3-(4-amino-5-(1-isopropyl-1H-1,2,3-triazol-5-yl)pyrrolo[2,1-f][1,2,4]triazin-7-yl)phenoxy) piperidin-1-yl)-2-methylpropan-1-one (204); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenoxy)piperidin-1-yl)ethanone (205); 1-(4-(3-(4-amino-5-(1-isopropyl-1H-1,2,3-triazol-5-yl)pyrrolo[2,1-f][1,2,4]triazin-7-yl)phenoxy)piperidin-1-yl)ethanone (206); 5-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyridin-2(1H)-one (207); 5-(3-(4-amino-5-(1-isopropyl-1H-1,2,3-triazol-5-yl)pyrrolo[2,1-f][1,2,4]triazin-7-yl)phenyl)-1-methylpyridin-2(1H)-one (208); 5-(3-(4-amino-5-(1-cyclopropyl-1H-pyrazol-5-yl)pyrrolo[2,1-f][1,2,4]triazin-7-yl)phenyl)-1-methylpyridin-2(1H)-one (209); 5-(3-(4-amino-5-(1-(tetrahydro-2H-pyran-4-yl)-1H-pyrazol-5-yl)pyrrolo[2,1-f][1,2,4]triazin-7-yl)phenyl)-1,4-dimethylpyridin-2(1H)-one (210); 4-(3-(4-amino-5-(1-(tetrahydro-2H-pyran-4-yl)-1H-pyrazol-5-yl)pyrrolo[2,1-f][1,2,4]triazin-7-yl)phenyl)-1-methylpyridin-2(1H)-one (211); 4-(3-(4-amino-5-(1-isopropyl-1H-1,2,3-triazol-5-yl)pyrrolo[2,1-f][1,2,4]triazin-7-yl)phenyl)-1-methylpyridin-2(1H)-one (212); 4-(3-(4-amino-5-(1-(tetrahydro-2H-pyran-4-yl)-1H-1,2,3-triazol-5-yl)pyrrolo[2,1-f][1,2,4]triazin-7-yl) phenyl)-1-methylpyridin-2(1H)-one (213); 4-(3-(4-amino-5-(1-isopropyl-1H-1,2,3-triazol-5-yl)pyrrolo[2,1-f][1,2,4] triazin-7-yl)phenyl)thiomorpholine 1,1-dioxide (214); 7-(3-morpholinophenyl)-5-(1-(tetrahydro-2H-pyran-4-yl)-1H-1,2,3-triazol-5-yl)pyrrolo[2,1-f][1,2,4]triazin-4-amine, TFA (215); 4-(3-(4-amino-5-(1-cyclohexyl-1H-1,2,3-triazol-5-yl)pyrrolo[2,1-f][1,2,4]triazin-7-yl)phenyl)thiomorpholine 1,1-dioxide (216); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-fluorophenyl)-2,6-dimethylpiperazin-1-yl) ethanone (217); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-fluorophenyl)-2,6-dimethylpiperazin-1-yl) ethanone (218); 1-((cis)-4-(3-(4-amino-5-(1-(tetrahydro-2H-pyran-4-yl)-1H-1,2,3-triazol-5-yl)pyrrolo[2,1-f][1,2,4] triazin-7-yl)-5-chlorophenyl)-2,6-dimethylpiperazin-1-yl) ethanone (219); 1-((cis)-4-(3-(4-amino-5-(1-(tetrahydro-2H-pyran-4-yl)-1H-pyrazol-5-yl)pyrrolo[2,1-f][1,2,4]

triazin-7-yl)-5-methylphenyl)-2,6-dimethylpiperazin-1-yl)ethanone (220); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-methylphenyl)-2,6-dimethylpiperazin-1-yl)ethanone (221); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methoxyphenyl)-2,6-dimethylpiperazin-1-yl)ethanone (222); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-methoxyphenyl)-2,6-dimethylpiperazin-1-yl)ethanone (223); 1-(4-(3-(4-amino-5-(1-isopropyl-1H-1,2,3-triazol-5-yl)pyrrolo[2,1-f][1,2,4]triazin-7-yl)phenyl)-3,5-dimethylpiperazin-1-yl)ethanone (224); 1-((cis)-4-(3-(4-amino-5-(1-(tetrahydro-2H-pyran-4-yl)-1H-pyrazol-5-yl)pyrrolo [2,1-f][1,2,4]triazin-7-yl)-5-fluorophenyl)-3,5-dimethylpiperazin-1-yl)ethanone (225); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-fluorophenyl)-3,5-dimethylpiperazin-1-yl)ethanone (226); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methylphenyl)-3,5-dimethylpiperazin-1-yl)ethanone (227); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)-5-methylphenyl)-3,5-dimethylpiperazin-1-yl)ethanone (228); 1-((cis)-4-(3-(4-amino-5-(1-(tetrahydro-2H-pyran-4-yl)-1H-pyrazol-5-yl)pyrrolo[2,1-f][1,2,4]triazin-7-yl)-5-methoxyphenyl)-3,5-dimethylpiperazin-1-yl)ethanone (229); 1-(4-(3-(4-amino-5-(1-isopropyl-1H-1,2,3-triazol-5-yl)pyrrolo[2,1-f][1,2,4]triazin-7-yl)phenyl)-3,3-dimethylpiperazin-1-yl)ethanone (230); 1-(4-(3-(4-amino-5-(thiazol-5-yl)pyrrolo[2,1-f][1,2,4]triazin-7-yl)phenoxy)piperidin-1-yl)ethanone (231); 3-(4-amino-5-(1-phenyl-1H-pyrrol-2-yl)pyrrolo[2,1-f][1,2,4]triazin-7-yl)-N-cyclopropyl-N-(tetrahydro-2H-pyran-4-yl)benzamide (232); N-(1-acetylpiperidin-4-yl)-3-(4-amino-5-(thiazol-5-yl)pyrrolo[2,1-f][1,2,4]triazin-7-yl)-N-cyclopropylbenzamide (233); 3-(4-amino-5-(1-(tetrahydro-2H-pyran-4-yl)-1H-1,2,3-triazol-5-yl)pyrrolo[2,1-f][1,2,4]triazin-7-yl)-N-cyclopropyl-N-(tetrahydro-2H-pyran-4-yl)benzamide (234); (3-(4-amino-5-(1-isopropyl-1H-1,2,3-triazol-5-yl)pyrrolo[2,1-f][1,2,4]triazin-7-yl)phenyl)(pyrrolidin-1-yl)methanone (235); (3-(4-amino-5-(1-(tetrahydro-2H-pyran-4-yl)-1H-1,2,3-triazol-5-yl)pyrrolo[2,1-f][1,2,4]triazin-7-yl)phenyl)(pyrrolidin-1-yl)methanone (236); 3-(4-amino-5-(1-(tetrahydro-2H-pyran-4-yl)-1H-1,2,3-triazol-5-yl)pyrrolo[2,1-f][1,2,4]triazin-7-yl)-N,N-dicyclopropylbenzamide (237); 2-(3-(4-amino-5-(1-(tetrahydro-2H-pyran-4-yl)-1H-1,2,3-triazol-5-yl)pyrrolo[2,1-f][1,2,4]triazin-7-yl)phenyl)-1-(1,1-dioxidothiomorpholino)ethanone (238); 2-(3-(4-amino-5-(1-(tetrahydro-2H-pyran-4-yl)-1H-pyrazol-5-yl)pyrrolo [2,1-f][1,2,4]triazin-7-yl)phenyl)-N-cyclopropylcyclopropane carboxamide (239); 1-(3-(4-amino-5-(1-(tetrahydro-2H-pyran-4-yl)-1H-pyrazol-5-yl)pyrrolo[2,1-f][1,2,4]triazin-7-yl)phenyl)-4-methylpiperidin-4-ol (240); 7-(3-morpholinophenyl)-5-(1-(tetrahydro-2H-pyran-4-yl)-1H-pyrazol-5-yl)pyrrolo[2,1-f][1,2,4]triazin-4-amine (241); 7-(3-(4-methoxypiperidin-1-yl)phenyl)-5-(1-(tetrahydro-2H-pyran-4-yl)-1H-pyrazol-5-yl)pyrrolo [2,1-f][1,2,4]triazin-4-amine (242); 4-(3-(4-amino-5-(1-(tetrahydro-2H-pyran-4-yl)-1H-pyrazol-5-yl)pyrrolo[2,1-f][1,2,4]triazin-7-yl)phenyl)thiomorpholine 1,1-dioxide (243); 1-(4-(3-(4-amino-5-(1-(tetrahydro-2H-pyran-4-yl)-1H-pyrazol-5-yl)pyrrolo[2,1-f][1,2,4] triazin-7-yl)phenyl)-3-(trifluoromethyl)piperazin-1-yl)ethanone (244); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(trifluoromethyl)piperazin-1-yl)ethanone (245); 1-((2S,6R)-4-(3-(4-amino-5-(1-(tetrahydro-2H-pyran-4-yl)-1H-pyrazol-5-yl)pyrrolo[2,1-f][1,2,4]triazin-7-yl)phenyl)-2,6-dimethylpiperazin-1-yl)ethanone (246); 1-((2S,6R)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,6-dimethylpiperazin-1-yl)ethanone (247); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2-cyclopropyl-6-isopropylpiperazin-1-yl)ethanone (248); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2,6-dicyclopropylpiperazin-1-yl)ethanone (249); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2-cyclopropyl-6-isopropylpiperazin-1-yl)ethanone (250); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2-phenylpiperazin-1-yl)ethanone (251); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2-(pyridin-3-yl)piperazin-1-yl)ethanone (252); 1-(4-(3-(4-amino-5-(1-(tetrahydro-2H-pyran-4-yl)-1H-1,2,3-triazol-5-yl)pyrrolo [2,1-f][1,2,4]triazin-7-yl)phenyl)-2-(pyridin-3-yl)piperazin-1-yl)ethanone (253); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(2-fluorophenyl)piperazin-1-yl)ethanone (254); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(2-fluorophenyl)piperazin-1-yl)ethanone (255); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-(pyridin-3-yl)piperazin-1-yl)ethanone (256); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-(pyridin-3-yl)piperazin-1-yl)ethanone (257); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-2,3-dimethylpiperazin-1-yl)ethanone (258); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,3-dimethylpiperazin-1-yl)ethanone (259); 1-(4-(3-(4-amino-5-(1-(tetrahydro-2H-pyran-4-yl)-1H-pyrazol-5-yl)pyrrolo[2,1-f][1,2,4] triazin-7-yl)phenyl)-3-(4-chlorophenyl)piperazin-1-yl)ethanone (260); N-(1-(3-(4-amino-5-(1-(tetrahydro-2H-pyran-4-yl)-1H-pyrazol-5-yl)pyrrolo[2,1-f][1,2,4]triazin-7-yl)phenyl)-4-methylpiperidin-4-yl)acetamide (261); 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)ethanone (262); 5-(1-(tetrahydro-2H-pyran-4-yl)-1H-pyrazol-5-yl)-7-(3-((cis)-2,4,6-trimethylpiperazin-1-yl)phenyl)pyrrolo[2,1-f][1,2,4]triazin-4-amine (263); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)ethanone (264); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)-2-hydroxyethanone (265); (cis)-methyl 4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazine-1-carboxylate (266); 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)-2-hydroxyethanone (267); 1-((cis)-4-(3-(4-amino-5-(1-isopropyl-1H-pyrazol-5-yl)pyrrolo[2,1-f][1,2,4]triazin-7-yl)phenyl)-3,5-dimethylpiperazin-1-yl)ethanone (268); 7-(3-((cis)-2,6-dimethyl-4-(methylsulfonyl)piperazin-1-yl)phenyl)-5-(1-(tetrahydro-2H-pyran-4-yl)-1H-pyrazol-5-yl)

pyrrolo[2,1-f][1,2,4]triazin-4-amine (269); (cis)-methyl 4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazine-1-carboxylate (270); 1-((cis)-4-(3-(4-amino-5-(1-(tetrahydro-2H-pyran-4-yl)-1H-pyrazol-5-yl)pyrrolo[2,1-f][1,2,4]triazin-7-yl)phenyl)-3,5-dimethylpiperazin-1-yl)-2-hydroxy-2-methylpropan-1-one (271); 1-((cis)-4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,5-dimethylpiperazin-1-yl)-2-hydroxy-2-methyl-propan-1-one (272); 1-((cis)-4-(3-(4-amino-5-(1-(2,2,2-trifluoroethyl)-1H-pyrazol-5-yl)pyrrolo[2,1-f][1,2,4]triazin-7-yl)phenyl)-3,5-dimethylpiperazin-1-yl)ethanone (273); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)ethanone (274); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3,3-dimethylpiperazin-1-yl)ethanone (275); methyl 4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazine-1-carboxylate (276); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)-2-hydroxyethanone (277); 7-(3-(2,2-dimethyl-4-(methylsulfonyl)piperazin-1-yl)phenyl)-5-(1-(tetrahydro-2H-pyran-4-yl)-1H-pyrazol-5-yl)pyrrolo[2,1-f][1,2,4]triazin-4-amine (278); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-4,7-diazaspiro[2.5]octan-7-yl)ethanone (279); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-4,7-diazaspiro[2.5]octan-7-yl)ethanone (280); 1-(4-(3-(4-amino-5-(1-isopropyl-1H-1,2,3-triazol-5-yl)pyrrolo[2,1-f][1,2,4]triazin-7-yl)phenyl)-4,7-diazaspiro[2.5]octan-7-yl)ethanone (281); (S)-1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-1-yl)-2-hydroxypropan-1-one (282); 1-(4-(3-(4-amino-5-(1-cyclohexyl-1H-1,2,3-triazol-5-yl)pyrrolo[2,1-f][1,2,4]triazin-7-yl)phenyl)-3,3-dimethylpiperazin-1-yl)-2-hydroxyethanone (283); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3,4-dihydroquinoxalin-1(2H)-yl)ethanone (284); 7-(3-(piperidin-4-yl)phenyl)-5-(1-(tetrahydro-2H-pyran-4-yl)-1H-pyrazol-5-yl)pyrrolo[2,1-f][1,2,4]triazin-4-amine (285); 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperidin-1-yl)ethanone (286); 7-(3-(1-(oxetan-3-yl)piperidin-4-yl)phenyl)-5-(1-(tetrahydro-2H-pyran-4-yl)-1H-pyrazol-5-yl)pyrrolo[2,1-f][1,2,4]triazin-4-amine (287); 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)ethanone (288); 7-(3-(4-(oxetan-3-yl)piperazin-1-yl)phenyl)-5-(1-(tetrahydro-2H-pyran-4-yl)-1H-pyrazol-5-yl)pyrrolo[2,1-f][1,2,4]triazin-4-amine (289); 7-(3-(4-methylpiperazin-1-yl)phenyl)-5-(1-(tetrahydro-2H-pyran-4-yl)-1H-pyrazol-5-yl)pyrrolo[2,1-f][1,2,4]triazin-4-amine (290); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-3-phenylpiperazin-1-yl)ethanone (291); methyl 4-(3-(4-amino-5-(1-(tetrahydro-2H-pyran-4-yl)-1H-pyrazol-5-yl)pyrrolo[2,1-f][1,2,4]triazin-7-yl)phenyl)piperazine-1-carboxylate (292); methyl 4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperazine-1-carboxylate (293); 7-(3-(4-(methylsulfonyl)piperazin-1-yl)phenyl)-5-(1-(tetrahydro-2H-pyran-4-yl)-1H-pyrazol-5-yl)pyrrolo[2,1-f][1,2,4]triazin-4-amine (294); 7-(3-(4-(methylsulfonyl)piperazin-1-yl)phenyl)-5-(1-(tetrahydro-2H-pyran-4-yl)-1H-1,2,3-triazol-5-yl)pyrrolo[2,1-f][1,2,4] triazin-4-amine (295); 1-(4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)-2-methylpropan-1-one (296); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperazin-1-yl)-2-methylpropan-1-one (297); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)piperazin-1-yl)ethanone (298); (4-(3-(4-amino-5-(1-(tetrahydro-2H-pyran-4-yl)-1H-pyrazol-5-yl)pyrrolo[2,1-f][1,2,4]triazin-7-yl)phenyl)piperazin-1-yl)(phenyl) methanone (299); 1-(4-(3-(4-amino-5-(1-(tetrahydro-2H-pyran-4-yl)-1H-1,2,3-triazol-5-yl)pyrrolo[2,1-f][1,2,4]triazin-7-yl)phenyl)-3-phenylpiperazin-1-yl) ethanone (300); N-(1-(3-(4-amino-5-(1-(tetrahydro-2H-pyran-4-yl)-1H-pyrazol-5-yl)pyrrolo[2,1-f][1,2,4] triazin-7-yl)phenyl)piperidin-4-yl)-N-methylacetamide (301); 1-(4-(3-(4-amino-5-(1-isopropyl-1H-pyrazol-5-yl)pyrrolo[2,1-f][1,2,4]triazin-7-yl)phenyl)piperazin-1-yl)ethanone (302); 1-(4-(3-(4-amino-5-(1-cyclopropyl-1H-pyrazol-5-yl)pyrrolo[2,1-f][1,2,4]triazin-7-yl)phenyl)piperazin-1-yl)ethanone (303); 3-(3-(4-amino-5-(1-(tetrahydro-2H-pyran-4-yl)-1H-pyrazol-5-yl)pyrrolo[2,1-f][1,2,4]triazin-7-yl)phenyl)-1,3-oxazinan-2-one (304); 3-(3-(4-amino-5-(1-(tetrahydro-2H-pyran-4-yl)-1H-1,2,3-triazol-5-yl)pyrrolo[2,1-f][1,2,4] triazin-7-yl)phenyl)-1,3-oxazinan-2-one (305); 4-(3-(4-amino-5-(1H-indol-2-yl)pyrrolo[2,1-f][1,2,4]triazin-7-yl)phenyl)-2,2-dimethylmorpholin-3-one (306); 4-(3-(4-amino-5-(1-(tetrahydro-2H-pyran-4-yl)-1H-pyrazol-5-yl)pyrrolo[2,1-f][1,2,4]triazin-7-yl)phenyl)-2,2-dimethylmorpholin-3-one (307); 4-(3-(4-amino-5-(1-(4,4-difluorocyclohexyl)-1H-pyrazol-5-yl)pyrrolo[2,1-f][1,2,4] triazin-7-yl)phenyl)-2,2-dimethylmorpholin-3-one (308); 4-(3-(4-amino-5-(1-(tetrahydro-2H-pyran-4-yl)-1H-1,2,3-triazol-5-yl)pyrrolo[2,1-f][1,2,4]triazin-7-yl)phenyl)-2,2-dimethylmorpholin-3-one (309); 7-(3-(2-(methyl (tetrahydro-2H-pyran-4-yl)amino)propan-2-yl)phenyl)-5-(1-(tetrahydro-2H-pyran-4-yl)-1H-pyrazol-5-yl)pyrrolo[2,1-f][1,2,4]triazin-4-amine (310); 7-(3-(2-(methyl(tetrahydro-2H-pyran-4-yl)amino)propan-2-yl)phenyl)-5-(1-(tetrahydro-2H-pyran-4-yl)-1H-1,2,3-triazol-5-yl)pyrrolo[2,1-f][1,2,4]triazin-4-amine (311); 7-(3-(2-(pyrrolidin-1-yl)propan-2-yl)phenyl)-5-(1-(tetrahydro-2H-pyran-4-yl)-1H-pyrazol-5-yl)pyrrolo[2,1-f][1,2,4]triazin-4-amine (312); 7-(3-(2-(pyrrolidin-1-yl)propan-2-yl)phenyl)-5-(1-(tetrahydro-2H-pyran-4-yl)-1H-1,2,3-triazol-5-yl)pyrrolo[2,1-f][1,2,4] triazin-4-amine (313); 1-(2-(3-(4-amino-5-(1-(tetrahydro-2H-pyran-4-yl)-1H-pyrazol-5-yl)pyrrolo[2,1-f][1,2,4]triazin-7-yl)phenyl)propan-2-yl)-1-methylpyrrolidin-1-ium (314); 4-(3-(4-amino-5-(1-(tetrahydro-2H-pyran-4-yl)-1H-pyrazol-5-yl)pyrrolo[2,1-f][1,2,4] triazin-7-yl)phenyl)-1-methylpiperidin-4-ol (315); 1-(4-(3-(4-amino-5-(1-(tetrahydro-2H-pyran-4-yl)-1H-pyrazol-5-yl)pyrrolo[2,1-f][1,2,4]triazin-7-yl)phenyl)-4-hydroxypiperidin-1-yl) ethanone (316); 4-(3-(4-amino-5-(1-(tetrahydro-2H-pyran-4-yl)-1H-1,2,3-triazol-5-yl)pyrrolo[2,1-f][1,2,4]triazin-7-yl)phenyl)tetrahydro-2H-pyran-4-ol (317); 7-(3-(4-methoxytetrahydro-2H-pyran-4-yl)phenyl)-5-(1-(tetrahydro-2H-pyran-4-yl)-1H-pyrazol-5-yl)pyrrolo[2,1-f][1,2,4]triazin-4-amine (318); 7-(3-(4-methoxytetrahydro-2H-pyran-4-yl)phenyl)-5-(1-(tetrahydro-2H-pyran-4-yl)-1H-1,2,3-triazol-5-yl)pyrrolo[2,1-f][1,2,4]triazin-4-amine (319); N-(4-(3-(4-amino-5-(1-(tetrahydro-2H-pyran-4-yl)-1H-pyrazol-5-yl)pyrrolo[2,1-f][1,2,4]triazin-7-yl)phenyl)

tetrahydro-2H-pyran-4-yl)acetamide (320); N-(1-acetyl-4-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)acetamide (321); 4-(3-(4-amino-5-(1-(tetrahydro-2H-pyran-4-yl)-1H-pyrazol-5-yl)pyrrolo[2,1-f][1,2,4]triazin-7-yl)phenyl)tetrahydro-2H-pyran-4-carbonitrile (322); 4-(3-(4-amino-5-(1-(tetrahydro-2H-pyran-4-yl)-1H-pyrazol-5-yl)pyrrolo[2,1-f][1,2,4] triazin-7-yl)phenyl)tetrahydro-2H-pyran-4-carboxamide (323); 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-2-one (324); 4-acetyl-1-(3-(4-amino-5-(1-(4,4-difluorocyclohexyl)-1H-pyrazol-5-yl)pyrrolo[2,1-f][1,2,4]triazin-7-yl)phenyl)-3,3-dimethylpiperazin-2-one (325); 1-(3-(4-amino-5-(1-(tetrahydro-2H-pyran-4-yl)-1H-pyrazol-5-yl)pyrrolo[2,1-f][1,2,4]triazin-7-yl)phenyl)-3,3-dimethylpiperazin-2-one (326); 4-acetyl-1-(3-(4-amino-5-(1H-indol-2-yl)pyrrolo[2,1-f][1,2,4]triazin-7-yl)phenyl)-3,3-dimethylpiperazin-2-one (327); 4-acetyl-1-(3-(4-amino-5-(1-cyclopropyl-1H-pyrazol-5-yl)pyrrolo[2,1-f][1,2,4]triazin-7-yl)phenyl)-3,3-dimethylpiperazin-2-one (328); 4-acetyl-1-(3-(4-amino-5-(1-(2,2,2-trifluoroethyl)-1H-pyrazol-5-yl)pyrrolo[2,1-f][1,2,4]triazin-7-yl)phenyl)-3,3-dimethylpiperazin-2-one (329); 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-5,5-dimethylpiperazin-2-one (330); 4-acetyl-1-(3-(4-amino-5-(1-(4,4-difluorocyclohexyl)-1H-pyrazol-5-yl)pyrrolo[2,1-f][1,2,4]triazin-7-yl)phenyl)-6,6-dimethylpiperazin-2-one (331); 4-acetyl-1-(3-(4-amino-5-(1-isopropyl-1H-pyrazol-5-yl)pyrrolo[2,1-f][1,2,4] triazin-7-yl)phenyl)-6,6-dimethylpiperazin-2-one (332); 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)-6,6-dimethylpiperazin-2-one (333); 4-acetyl-1-(3-(4-amino-5-(1-(tetrahydro-2H-pyran-4-yl)-1H-pyrazol-5-yl)pyrrolo[2,1-f][1,2,4]triazin-7-yl)phenyl)piperazin-2-one (334); 4-acetyl-1-(3-(4-amino-5-(1-methyl-1H-pyrazol-4-yl)pyrrolo[2,1-f][1,2,4]triazin-7-yl)phenyl)-3,3-dimethylpiperazin-2-one (335); 4-acetyl-1-(3-(4-amino-5-(1-cyclopropyl-1H-pyrazol-5-yl)pyrrolo[2,1-f][1,2,4] triazin-7-yl)phenyl)-6,6-dimethylpiperazin-2-one (336); 1-(3-(4-amino-5-(1-(tetrahydro-2H-pyran-4-yl)-1H-pyrazol-5-yl)pyrrolo[2,1-f][1,2,4]triazin-7-yl)phenyl)-3,3,4-trimethylpiperazin-2-one (337); 4-acetyl-1-(3-(4-amino-5-(1-isopropyl-1H-pyrazol-4-yl)pyrrolo[2,1-f][1,2,4]triazin-7-yl)phenyl)-3,3-dimethylpiperazin-2-one (338); 4-acetyl-1-(3-(4-amino-5-(5-methyl-1-phenyl-1H-pyrazol-4-yl)pyrrolo[2,1-f][1,2,4]triazin-7-yl)phenyl)-3,3-dimethylpiperazin-2-one (339); 4-acetyl-1-(3-(4-amino-5-(1-phenyl-1H-pyrazol-4-yl)pyrrolo[2,1-f][1,2,4]triazin-7-yl)phenyl)-3,3-dimethylpiperazin-2-one (340); 4-acetyl-1-(3-(4-amino-5-(3-(trifluoromethyl)-1H-pyrazol-4-yl)pyrrolo[2,1-f][1,2,4]triazin-7-yl)phenyl)-3,3-dimethylpiperazin-2-one (341); 4-acetyl-1-(3-(4-amino-5-(1-methyl-1H-indol-2-yl)pyrrolo[2,1-f][1,2,4]triazin-7-yl)phenyl)-3,3-dimethylpiperazin-2-one (342); 4-acetyl-1-(3-(4-amino-5-(1-isobutyl-1H-pyrazol-4-yl)pyrrolo[2,1-f][1,2,4]triazin-7-yl)phenyl)-3,3-dimethylpiperazin-2-one (343); 4-acetyl-1-(3-(4-amino-5-(3-(trifluoromethyl)-1H-pyrazol-4-yl)pyrrolo[2,1-f][1,2,4] triazin-7-yl)phenyl)-6,6-dimethylpiperazin-2-one (344); 4-acetyl-1-(3-(4-amino-5-(1-methyl-3-(trifluoromethyl)-1H-pyrazol-4-yl)pyrrolo[2,1-f][1,2,4]triazin-7-yl)phenyl)-3,3-dimethylpiperazin-2-one (345); 4-acetyl-1-(3-(4-amino-5-(1H-indol-2-yl)pyrrolo[2,1-f][1,2,4]triazin-7-yl)phenyl)-6,6-dimethylpiperazin-2-one (346); 4-acetyl-1-(3-(4-amino-5-(1-(cyclopropylmethyl)-1H-pyrazol-4-yl)pyrrolo[2,1-f][1,2,4]triazin-7-yl)phenyl)-3,3-dimethylpiperazin-2-one (347); 4-acetyl-1-(3-(4-amino-5-(1-methyl-5-phenyl-1H-pyrazol-4-yl)pyrrolo[2,1-f][1,2,4]triazin-7-yl)phenyl)-3,3-dimethylpiperazin-2-one (348); 4-acetyl-1-(3-(4-amino-5-(1-cyclopropyl-1H-pyrazol-4-yl)pyrrolo[2,1-f][1,2,4]triazin-7-yl)phenyl)-3,3-dimethylpiperazin-2-one (349); 4-acetyl-1-(3-(4-amino-5-(1-(2-hydroxy-2-methylpropyl)-1H-pyrazol-4-yl)pyrrolo[2,1-f][1,2,4]triazin-7-yl)phenyl)-3,3-dimethylpiperazin-2-one (350); 1-(3-(4-amino-5-(1-(tetrahydro-2H-pyran-4-yl)-1H-pyrazol-5-yl)pyrrolo[2,1-f][1,2,4]triazin-7-yl)phenyl)-4-(4-fluorophenyl)-3,3-dimethylpiperazine-2,5-dione (351); 1-(3-(4-amino-5-(1-(tetrahydro-2H-pyran-4-yl)-1H-1,2,3-triazol-5-yl)pyrrolo[2,1-f][1,2,4]triazin-7-yl)phenyl)-4-(4-fluorophenyl)-3,3-dimethylpiperazine-2,5-dione (352); 4-acetyl-1-(3-(4-amino-5-(1-(tetrahydrofuran-3-yl)-1H-pyrazol-4-yl)pyrrolo[2,1-f][1,2,4]triazin-7-yl)phenyl)-3,3-dimethylpiperazin-2-one (353); 4-acetyl-1-(3-(4-amino-5-(1-(pyridin-3-yl)-1H-pyrazol-4-yl)pyrrolo[2,1-f][1,2,4]triazin-7-yl)phenyl)-3,3-dimethylpiperazin-2-one (354); 4-acetyl-1-(3-(4-amino-5-(1-(pyridin-2-yl)-1H-pyrazol-4-yl)pyrrolo[2,1-f][1,2,4]triazin-7-yl)phenyl)-3,3-dimethylpiperazin-2-one (355); 4-acetyl-1-(3-(4-amino-5-(1-(sec-butyl)-1H-pyrazol-4-yl)pyrrolo[2,1-f][1,2,4]triazin-7-yl)phenyl)-3,3-dimethylpiperazin-2-one (356); 1-(3-(4-amino-5-(1-(tetrahydro-2H-pyran-4-yl)-1H-pyrazol-5-yl)pyrrolo[2,1-f][1,2,4]triazin-7-yl)phenyl)-4-isopropyl-3,6-dimethylpiperazine-2,5-dione (357); 3-(3-(4-amino-5-(1-(tetrahydro-2H-pyran-4-yl)-1H-pyrazol-5-yl)pyrrolo[2,1-f][1,2,4]triazin-7-yl)phenyl)-8-fluoro-1-methylquinazoline-2,4(1H,3H)-dione (358); 3-(3-(4-amino-5-(1-(tetrahydro-2H-pyran-4-yl)-1H-pyrazol-5-yl)pyrrolo[2,1-f][1,2,4]triazin-7-yl)phenyl)-1-methylquinazoline-2,4(1H,3H)-dione (359); 3-(3-(4-amino-5-(1-(tetrahydro-2H-pyran-4-yl)-1H-pyrazol-5-yl)pyrrolo[2,1-f][1,2,4]triazin-7-yl)phenyl)quinazolin-4(3H)-one (360); 2-(3-(4-amino-5-(1-(tetrahydro-2H-pyran-4-yl)-1H-pyrazol-5-yl)pyrrolo[2,1-f][1,2,4] triazin-7-yl)phenyl)-1H-pyrido[1,2-c]pyrimidine-1,3(2H)-dione (361); 3-(3-(4-amino-5-(1-(tetrahydro-2H-pyran-4-yl)-1H-1,2,3-triazol-5-yl)pyrrolo[2,1-f][1,2,4]triazin-7-yl)phenyl)-1-methylquinazoline-2,4(1H,3H)-dione (362); 3-(3-(4-amino-5-(1-(tetrahydro-2H-pyran-4-yl)-1H-1,2,3-triazol-5-yl)pyrrolo[2,1-f][1,2,4]triazin-7-yl)phenyl)quinazolin-4(3H)-one (363); 3-(3-(4-amino-5-(1-(tetrahydro-2H-pyran-4-yl)-1H-1,2,3-triazol-5-yl)pyrrolo[2,1-f][1,2,4]triazin-7-yl)phenyl)-8-fluoro-1-methylquinazoline-2,4(1H,3H)-dione (364); 5-(1-isopropyl-1H-1,2,3-triazol-5-yl)-7-(3-(5-(methylsulfonyl) hexahydropyrrolo[3,4-c]pyrrol-2(1H)-yl)phenyl)pyrrolo[2,1-f][1,2,4]triazin-4-amine (365); 7-(3-(5-(methylsulfonyl)hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (366); 7-(3-(5-methylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (367); 1-(5-(3-(4-amino-5-(1-(tetrahydro-2H-pyran-4-yl)-1H-1,2,3-triazol-5-yl)pyrrolo[2,1-f][1,2,4]triazin-7-yl)phenyl)hexahydropyrrolo[3,4-c]pyrrol-2(1H)-yl)ethanone (368); 1-(5-(3-(4-amino-5-(1-(tetrahydro-2H-pyran-4-yl)-1H-pyrazol-5-yl)pyrrolo[2,1-f][1,2,4]triazin-7-yl)phenyl) hexahydropyrrolo[3,4-c]pyrrol-2(1H)-yl)ethanone (369); 7-(3-(hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (370); 7-(3-(5-isopropylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (371); 7-(3-(5-cyclobutylhexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (372); 3-(5-(3-(4-amino-5-(1-

(tetrahydro-2H-pyran-4-yl)-1H-pyrazol-5-yl)pyrrolo[2,1-f][1,2,4] triazin-7-yl)phenyl)hexahydropyrrolo[3,4-c]pyrrol-2 (1H)-yl)-2-methylbutan-2-ol (373); 7-(3-(5-(1-methoxypropan-2-yl)hexahydropyrrolo[3,4-c]pyrrol-2(1H)-yl)phenyl)-5-(1-(tetrahydro-2H-pyran-4-yl)-1H-pyrazol-5-yl)pyrrolo[2,1-f][1,2,4]triazin-4-amine (374); N-(1-(3-(4-amino-5-(1-(tetrahydro-2H-pyran-4-yl)-1H-pyrazol-5-yl)pyrrolo[2,1-f][1,2,4] triazin-7-yl)phenyl)piperidin-4-yl)-N-methylmethanesulfonamide (375); N-(1-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-4-yl)-N-methylmethanesulfonamide (376); N-(1-(3-(4-amino-5-(1-isopropyl-1H-1,2,3-triazol-5-yl)pyrrolo[2,1-f][1,2,4]triazin-7-yl)phenyl)piperidin-4-yl)-N-methylmethanesulfonamide (377); 1'-(3-(4-amino-5-(1-(tetrahydro-2H-pyran-4-yl)-1H-1,2,3-triazol-5-yl)pyrrolo[2,1-f][1,2,4]triazin-7-yl)phenyl)-[1,4'-bipiperidin]-2-one (378); N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methylfuran-2-carboxamide (379); N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-N-methyl-2-(pyrazin-2-yl)acetamide (380); 1-(1-(3-(4-amino-5-(1-(tetrahydro-2H-pyran-4-yl)-1H-pyrazol-5-yl)pyrrolo[2,1-f][1,2,4]triazin-7-yl)phenyl) piperidin-4-yl)-3-isopropyl-1-methylurea (381); N-(1-(3-(4-amino-5-(1-(tetrahydro-2H-pyran-4-yl)-1H-pyrazol-5-yl)pyrrolo[2,1-f][1,2,4]triazin-7-yl)phenyl)piperidin-4-yl)-1-cyano-N-methylcyclopropanecarboxamide (382); 7-(3-(4-morpholinopiperidin-1-yl)phenyl)-5-(1-(tetrahydro-2H-pyran-4-yl)-1H-pyrazol-5-yl)pyrrolo[2,1-f][1,2,4]triazin-4-amine (383); 1-(3-(4-amino-5-(1-(tetrahydro-2H-pyran-4-yl)-1H-pyrazol-5-yl)pyrrolo[2,1-f][1,2,4]triazin-7-yl)phenyl)-3-(morpholine-4-carbonyl)piperidin-2-one (384); N-(1-(3-(4-amino-5-(1-(tetrahydro-2H-pyran-4-yl)-1H-pyrazol-5-yl)pyrrolo[2,1-f][1,2,4] triazin-7-yl)phenyl)pyrrolidin-3-yl)-2-hydroxy-N,2-dimethylpropanamide (385); N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)-N-methyl-2-(pyrazin-2-yl)acetamide (386); N-(1-(3-(4-amino-5-(1-(tetrahydro-2H-pyran-4-yl)-1H-pyrazol-5-yl)pyrrolo[2,1-f][1,2,4]triazin-7-yl)phenyl)pyrrolidin-3-yl)-N-methylacetamide (387); S)—N-(1-(3-(4-amino-5-(1-(tetrahydro-2H-pyran-4-yl)-1H-pyrazol-5-yl)pyrrolo[2,1-f][1,2,4]triazin-7-yl)phenyl) pyrrolidin-3-yl)acetamide (388); 7-(3-((pyridin-3-yloxy)methyl)phenyl)-5-(1-(tetrahydro-2H-pyran-4-yl)-1H-pyrazol-5-yl)pyrrolo[2,1-f][1,2,4]triazin-4-amine (389); 7-(3-((pyridin-2-yloxy)methyl)phenyl)-5-(1-(tetrahydro-2H-pyran-4-yl)-1H-pyrazol-5-yl)pyrrolo[2,1-f][1,2,4]triazin-4-amine (390); 7-(3-(2-morpholinopropyl)phenyl)-5-(1-(tetrahydro-2H-pyran-4-yl)-1H-pyrazol-5-yl)pyrrolo[2,1-f][1,2,4]triazin-4-amine (391); 7-(3-(2-(pyrrolidin-1-yl)propyl)phenyl)-5-(1-(tetrahydro-2H-pyran-4-yl)-1H-pyrazol-5-yl)pyrrolo[2,1-f][1,2,4]triazin-4-amine (392); 7-(3-(2-((2-methoxyethyl)amino) propyl) phenyl)-5-(1-(tetrahydro-2H-pyran-4-yl)-1H-pyrazol-5-yl)pyrrolo[2,1-f][1,2,4]triazin-4-amine (393); 5-(1-(tetrahydro-2H-pyran-4-yl)-1H-pyrazol-5-yl)-7-(3-(2-((tetrahydro-2H-pyran-4-yl)amino)propyl)phenyl)pyrrolo[2,1-f][1,2,4]triazin-4-amine (394); 7-(3-(2-(methyl(tetrahydro-2H-pyran-4-yl)amino)propyl)phenyl)-5-(1-(tetrahydro-2H-pyran-4-yl)-1H-pyrazol-5-yl)pyrrolo[2,1-f][1,2,4]triazin-4-amine (395); 7-(3-(2-(dimethylamino)propyl)phenyl)-5-(1-(tetrahydro-2H-pyran-4-yl)-1H-pyrazol-5-yl)pyrrolo[2,1-f][1,2,4] triazin-4-amine (396); 7-(3-(1-(dimethylamino)-2-methylpropan-2-yl)phenyl)-5-(1-(tetrahydro-2H-pyran-4-yl)-1H-pyrazol-5-yl)pyrrolo[2,1-f][1, 2,4]triazin-4-amine (397); 5-(1-(tetrahydro-2H-pyran-4-yl)-1H-pyrazol-5-yl)-7-(3-(1-(((tetrahydro-2H-pyran-4-yl)amino)methyl)cyclopropyl)phenyl)pyrrolo[2,1-f][1,2,4] triazin-4-amine (398); 7-(3-(3-morpholinopyrrolidin-1-yl) phenyl)-5-(1-(tetrahydro-2H-pyran-4-yl)-1H-pyrazol-5-yl) pyrrolo[2,1-f][1,2,4]triazin-4-amine (399); 2-(1-(3-(4-amino-5-(1-(tetrahydro-2H-pyran-4-yl)-1H-1,2,3-triazol-5-yl)pyrrolo[2,1-f][1,2,4]triazin-7-yl)phenyl)piperidin-4-yl) propan-2-ol (400); 7-(3-(1H-imidazol-2-yl)phenyl)-5-(1-(tetrahydro-2H-pyran-4-yl)-1H-pyrazol-5-yl)pyrrolo[2,1-f][1,2,4]triazin-4-amine (401); 4-(3-(4-amino-5-(1-(tetrahydro-2H-pyran-4-yl)-1H-pyrazol-5-yl)pyrrolo[2,1-f][1,2,4]triazin-7-yl)phenyl) morpholine-3-carboxamide (402); 3'-(4-amino-5-(2-methylthiazol-5-yl)pyrrolo[2,1-f][1,2,4]triazin-7-yl)-[1,1'-biphenyl]-2-carboxamide (403); 3'-(4-amino-5-(thiazol-5-yl)pyrrolo[2,1-f][1,2,4]triazin-7-yl)-[1,1'-biphenyl]-2-carboxamide (404); 3'-(4-amino-5-(1-(tetrahydro-2H-pyran-4-yl)-1H-pyrazol-5-yl)pyrrolo[2,1-f][1,2,4]triazin-7-yl)-3-fluoro-[1,1'-biphenyl]-2-carboxamide (405); 4-acetyl-1-(3-(4-amino-5-(2-propylthiazol-5-yl)pyrrolo[2,1-f][1,2,4]triazin-7-yl)phenyl)-3,3-dimethylpiperazin-2-one (406); 4-acetyl-1-(3-(4-amino-5-(1H-pyrazol-4-yl)pyrrolo[2,1-f][1,2,4]triazin-7-yl)phenyl)-3,3-dimethylpiperazin-2-one (407); 4-acetyl-1-(3-(4-amino-5-(1-(difluoromethyl)-1H-pyrazol-4-yl)pyrrolo[2,1-f][1,2,4] triazin-7-yl)phenyl)-3,3-dimethylpiperazin-2-one (408); 4-acetyl-1-(3-(4-amino-5-(thiazol-5-yl)pyrrolo[2,1-f][1,2,4] triazin-7-yl)phenyl)-3,3-dimethylpiperazin-2-one (409); 4-acetyl-1-(3-(4-amino-5-(2-methylthiazol-5-yl)pyrrolo [2,1-f][1,2,4]triazin-7-yl)phenyl)-3,3-dimethylpiperazin-2-one (410); 3'-(4-amino-5-(1-methyl-1H-pyrazol-4-yl)pyrrolo[2,1-f][1,2,4]triazin-7-yl)-[1,1'-biphenyl]-2-carboxamide (411); 4-acetyl-1-(3-(4-amino-5-(1-trideuteromethyl-1H-pyrazol-4-yl)pyrrolo[2,1-f][1,2,4]triazin-7-yl)phenyl)-3,3-dimethylpiperazin-2-one (412); 3'-(4-amino-5-(1-(tetrahydro-2H-pyran-4-yl)-1H-pyrazol-5-yl)pyrrolo[2,1-f][1,2,4]triazin-7-yl)-6-fluoro-[1,1'-biphenyl]-2-carboxamide (413); 1-(3-(4-amino-5-(1-(tetrahydro-2H-pyran-4-yl)-1H-pyrazol-5-yl)pyrrolo[2,1-f][1,2,4]triazin-7-yl)phenyl)piperidine-2-carboxamide (414); 4-acetyl-1-(3-(4-amino-5-(1-(2,2-difluoroethyl)-1H-pyrazol-4-yl)pyrrolo[2,1-f][1,2,4] triazin-7-yl)phenyl)-3,3-dimethylpiperazin-2-one (415); 4-acetyl-1-(3-(4-amino-5-(2-phenylthiazol-5-yl)pyrrolo[2,1-f][1,2,4]triazin-7-yl)phenyl)-3,3-dimethylpiperazin-2-one (416); 4-acetyl-1-(3-(4-amino-5-(2-isobutylthiazol-5-yl) pyrrolo[2,1-f][1,2,4]triazin-7-yl)phenyl)-3,3-dimethylpiperazin-2-one (417); 4-acetyl-1-(3-(4-amino-5-(benzo[d] oxazol-2-yl)pyrrolo[2,1-f][1,2,4]triazin-7-yl)phenyl)-3,3-dimethylpiperazin-2-one (418); 4-acetyl-1-(3-(4-amino-5-(1-(cyclobutylmethyl)-1H-pyrazol-4-yl)pyrrolo[2,1-f][1,2,4] triazin-7-yl)phenyl)-3,3-dimethylpiperazin-2-one (419); 4-acetyl-1-(3-(4-amino-5-(thiazol-2-yl)pyrrolo[2,1-f][1,2,4] triazin-7-yl)phenyl)-3,3-dimethylpiperazin-2-one (420); 4-acetyl-1-(3-(4-amino-5-(1-neopentyl-1H-pyrazol-4-yl) pyrrolo[2,1-f][1,2,4]triazin-7-yl)phenyl)-3,3-dimethylpiperazin-2-one (421); 4-acetyl-1-(3-(4-amino-5-(1-(2-methoxyethyl)-1H-pyrazol-4-yl)pyrrolo[2,1-f][1,2,4]triazin-7-yl) phenyl)-3,3-dimethylpiperazin-2-one (422); 4-acetyl-1-(3-(4-amino-5-(1-(oxetan-3-ylmethyl)-1H-pyrazol-4-yl) pyrrolo[2,1-f][1,2,4]triazin-7-yl)phenyl)-3,3-dimethylpiperazin-2-one (423); 4-acetyl-1-(3-(4-amino-5-(1-((3-methyloxetan-3-yl)methyl)-1H-pyrazol-4-yl)pyrrolo[2,1-f][1,2,4]triazin-7-yl)phenyl)-3,3-dimethylpiperazin-2-one (424); 1-(3-(4-amino-5-(1-(tetrahydro-2H-pyran-4-yl)-1H-pyrazol-5-yl)pyrrolo[2,1-f][1,2,4]triazin-7-yl)phenyl) azepane-2-carboxamide (425); 4-acetyl-1-{3-[4-amino-6-fluoro-5-(1-methyl-1H-pyrazol-4-yl)pyrrolo[2,1-f][1,2,4]

triazin-7-yl]phenyl}-3,3-dimethylpiperazin-2-one (426); 4-acetyl-1-(3-{4-amino-5-[1-(2,2-difluoroethyl)-1H-pyrazol-4-yl]-6-fluoropyrrolo[2,1-f][1,2,4]triazin-7-yl}phenyl)-3,3-dimethylpiperazin-2-one (427); 4-acetyl-1-{3-[4-amino-5-(1-methanesulfonyl-1H-pyrazol-4-yl)pyrrolo[2,1-f][1,2,4]triazin-7-yl]phenyl}-3,3-dimethylpiperazin-2-one (428); 4-acetyl-1-{5-[4-amino-5-(1-methanesulfonyl-1H-pyrazol-4-yl)pyrrolo[2,1-f][1,2,4]triazin-7-yl]-2-fluorophenyl}-3,3-dimethylpiperazin-2-one (429); 4-acetyl-1-(3-{4-amino-5-[1-(cyclopropanesulfonyl)-1H-pyrazol-4-yl]pyrrolo [2,1-f][1,2,4]triazin-7-yl} phenyl)-3,3-dimethylpiperazin-2-one (430); 4-acetyl-1-(5-{4-amino-5-[1-(cyclopropanesulfonyl)-1H-pyrazol-4-yl]pyrrolo[2,1-f][1,2,4]triazin-7-yl}-2-fluorophenyl)-3,3-dimethylpiperazin-2-one (431); 4-acetyl-1-(3-{4-amino-5-[1-(propane-2-sulfonyl)-1H-pyrazol-4-yl]pyrrolo[2,1-f][1,2,4]triazin-7-yl}phenyl)-3,3-dimethylpiperazin-2-one (432); 4-acetyl-1-(5-{4-amino-5-[1-(propane-2-sulfonyl)-1H-pyrazol-4-yl]pyrrolo[2,1-f][1,2,4]triazin-7-yl}-2-fluorophenyl)-3,3-dimethylpiperazin-2-one (433); 4-acetyl-1-(3-{4-amino-5-[1-(1,3-difluoropropan-2-yl)-1H-pyrazol-4-yl]pyrrolo[2,1-f][1,2,4]triazin-7-yl}phenyl)-3,3-dimethylpiperazin-2-one (434); 4-acetyl-1-[3-(4-amino-5-{1-[($^2$H$_7$)propan-2-yl]-1H-pyrazol-4-yl}pyrrolo[2,1-f][1,2,4]triazin-7-yl)phenyl]-3,3-dimethylpiperazin-2-one (435); 4-acetyl-1-{3-[4-amino-5-(1-cyclobutyl-1H-pyrazol-4-yl)pyrrolo[2,1-f][1,2,4]triazin-7-yl]phenyl}-3,3-dimethylpiperazin-2-one (436); 4-acetyl-1-(3-{4-amino-5-[1-($^2$H$_5$)ethyl-1H-pyrazol-4-yl]pyrrolo[2,1-f][1,2,4] triazin-7-yl}phenyl)-3,3-dimethylpiperazin-2-one (437); 4-acetyl-1-{3-[4-amino-5-(1-methyl-1H-pyrazol-4-yl)pyrrolo[2,1-f][1,2,4]triazin-7-yl]-5-fluorophenyl}-3,3-dimethylpiperazin-2-one (438); 4-acetyl-1-{5-[4-amino-5-(1-methyl-1H-pyrazol-4-yl)pyrrolo[2,1-f][1,2,4]triazin-7-yl]-2-fluorophenyl}-3,3-dimethylpiperazin-2-one (439); 4-acetyl-1-{3-[4-amino-5-(1-methyl-1H-pyrazol-4-yl)pyrrolo[2,1-f][1,2,4]triazin-7-yl]-4-fluorophenyl}-3,3-dimethylpiperazin-2-one (440); 4-acetyl-1-{3-[4-amino-5-(1-methyl-1H-pyrazol-4-yl)pyrrolo[2,1-f][1,2,4]triazin-7-yl]-2-fluorophenyl}-3,3-dimethylpiperazin-2-one (441); 1-{3-[4-amino-5-(1-methyl-1H-pyrazol-4-yl)pyrrolo[2,1-f][1,2,4]triazin-7-yl]phenyl}-4-cyclobutanecarbonyl-3,3-dimethylpiperazin-2-one (442); 1-{3-[4-amino-5-(1-methyl-1H-pyrazol-4-yl)pyrrolo[2,1-f][1,2,4]triazin-7-yl]phenyl}-4-cyclopropanecarbonyl-3,3-dimethylpiperazin-2-one (443); 3-(4-{3-[4-amino-5-(1-methyl-1H-pyrazol-4-yl)pyrrolo[2,1-f][1,2,4]triazin-7-yl]phenyl}-2,2-dimethyl-3-oxopiperazin-1-yl)-3-oxopropanenitrile (444); 4-acetyl-1-[3-(4-amino-5-{1-[(2S)-3,3,3-trifluoro-2-hydroxypropyl]-1H-pyrazol-4-yl}pyrrolo[2,1-f][1,2,4]triazin-7-yl)phenyl]-3,3-dimethylpiperazin-2-one (445); 4-acetyl-1-[3-(4-amino-5-{1-[(2R)-3,3,3-trifluoro-2-hydroxypropyl]-1H-pyrazol-4-yl}pyrrolo[2,1-f][1,2,4]triazin-7-yl)phenyl]-3,3-dimethylpiperazin-2-one (446); 4-acetyl-1-[3-(4-amino-5-{1-[(2S)-2-hydroxypropyl]-1H-pyrazol-4-yl}pyrrolo[2,1-f][1,2,4]triazin-7-yl)phenyl]-3,3-dimethylpiperazin-2-one (447); 4-acetyl-1-(3-{4-amino-5-[1-(2,2,2-trifluoroethyl)-1H-pyrazol-5-yl]pyrrolo[2,1-f][1,2,4] triazin-7-yl}-2-fluorophenyl)-3,3-dimethylpiperazin-2-one (448); 4-acetyl-1-(3-{4-amino-5-[1-(2,2,2-trifluoroethyl)-1H-pyrazol-5-yl]pyrrolo[2,1-f][1,2,4]triazin-7-yl}-4-fluorophenyl)-3,3-dimethylpiperazin-2-one (449); 4-acetyl-1-(3-{4-amino-5-[1-(2,2,2-trifluoroethyl)-1H-pyrazol-5-yl]pyrrolo[2,1-f][1,2,4]triazin-7-yl}-5-fluorophenyl)-3,3-dimethylpiperazin-2-one (450); 4-acetyl-1-(5-{4-amino-5-[1-(2,2,2-trifluoroethyl)-1H-pyrazol-5-yl]pyrrolo[2,1-f][1,2,4]triazin-7-yl}-2-fluorophenyl)-3,3-dimethylpiperazin-2-one (451); 4-acetyl-1-(3-{4-amino-5-[1-(1,3-difluoropropan-2-yl)-1H-pyrazol-5-yl]pyrrolo[2,1-f][1,2,4]triazin-7-yl}phenyl)-3,3-dimethylpiperazin-2-one (452); 4-acetyl-1-[3-(4-amino-5-{1-[(1,1,1,3,3,3-$^2$H$_6$)propan-2-yl]-1H-pyrazol-5-yl}pyrrolo[2,1-f][1,2,4] triazin-7-yl)phenyl]-3,3-dimethylpiperazin-2-one (453); 4-acetyl-1-[3-(4-amino-5-{1-[($^2$H$_7$)propan-2-yl]-1H-pyrazol-5-yl}pyrrolo[2,1-f][1,2,4]triazin-7-yl)phenyl]-3,3-dimethylpiperazin-2-one (454); 4-acetyl-1-(3-{4-amino-5-[1-(propan-2-yl)-1H-pyrazol-5-yl]pyrrolo[2,1-f][1,2,4]triazin-7-yl}phenyl)-3,3-dimethylpiperazin-2-one (455); 4-acetyl-1-(3-{4-amino-5-[1-(2,2-difluoroethyl)-1H-pyrazol-5-yl]pyrrolo[2,1-f][1,2,4]triazin-7-yl}phenyl)-3,3-dimethylpiperazin-2-one (456); 4-acetyl-1-(3-{4-amino-5-[1-(oxan-4-yl)-1H-pyrazol-5-yl]pyrrolo[2,1-f][1,2,4]triazin-7-yl}phenyl)-3-(propan-2-yl)piperazin-2-one (457); 4-acetyl-1-(3-{4-amino-5-[1-(oxan-4-yl)-1H-pyrazol-5-yl]pyrrolo[2,1-f][1,2,4] triazin-7-yl}phenyl)-3-(propan-2-yl)piperazin-2-one, chiral (458); 4-acetyl-1-(3-{4-amino-5-[1-(oxan-4-yl)-1H-pyrazol-5-yl]pyrrolo[2,1-f][1,2,4]triazin-7-yl}phenyl)-3-(propan-2-yl)piperazin-2-one, chiral (459); 4-acetyl-1-(3-{4-amino-5-[1-(2,2,2-trifluoroethyl)-1H-pyrazol-5-yl]pyrrolo[2,1-f][1,2,4]triazin-7-yl} phenyl)-3-(propan-2-yl)piperazin-2-one (460); 4-acetyl-1-(3-{4-amino-5-[1-(oxan-4-yl)-1H-pyrazol-5-yl]pyrrolo[2,1-f][1,2,4]triazin-7-yl}phenyl)-3-methylpiperazin-2-one (461); 4-acetyl-1-(3-{4-amino-5-[1-(propan-2-yl)-1H-pyrazol-5-yl]pyrrolo[2,1-f][1,2,4]triazin-7-yl}phenyl)-3-methylpiperazin-2-one (462); 1-(3-{4-amino-5-[1-(oxan-4-yl)-1H-pyrazol-5-yl]pyrrolo[2,1-f][1,2,4]triazin-7-yl} phenyl)-4-methanesulfonyl-3-methylpiperazin-2-one (463); 7-(3-{4-amino-5-[1-(oxan-4-yl)-1H-pyrazol-5-yl]pyrrolo[2,1-f][1,2,4]triazin-7-yl}phenyl)-4,7-diazaspiro[2.5]octan-8-one (464); 4-acetyl-7-(3-{4-amino-5-[1-(oxan-4-yl)-1H-pyrazol-5-yl]pyrrolo[2,1-f][1,2,4]triazin-7-yl}phenyl)-4,7-diazaspiro[2.5]octan-8-one (465); 7-(3-{4-amino-5-[1-(oxan-4-yl)-1H-pyrazol-5-yl]pyrrolo[2,1-f][1,2,4]triazin-7-yl}phenyl)-4-cyclobutyl-4,7-diazaspiro[2.5]octan-8-one (466); 4-acetyl-7-(3-{4-amino-5-[1-(propan-2-yl)-1H-pyrazol-5-yl]pyrrolo[2,1-f][1,2,4]triazin-7-yl}phenyl)-4,7-diazaspiro[2.5]octan-8-one (467); 7-(3-{4-amino-5-[1-(oxan-4-yl)-1H-pyrazol-5-yl]pyrrolo[2,1-f][1,2,4]triazin-7-yl}phenyl)-4-(oxetan-3-yl)-4,7-diazaspiro[2.5]octan-8-one (468); methyl 4-(3-{4-amino-5-[1-(2,2,2-trifluoroethyl)-1H-pyrazol-5-yl]pyrrolo[2,1-f][1,2,4]triazin-7-yl}phenyl)-2,2-dimethyl-3-oxopiperazine-1-carboxylate (469); 2-(3-{4-amino-5-[1-(oxan-4-yl)-1H-pyrazol-5-yl]pyrrolo[2,1-f][1,2,4]triazin-7-yl}phenyl)-1H,2H,3H,4H,6H-pyrido[1,2-a]piperazine-1,6-dione (470); 1-[8-(3-{4-amino-5-[1-(oxan-4-yl)-1H-pyrazol-5-yl]pyrrolo[2,1-f][1,2,4]triazin-7-yl}phenyl)-3,8-diazabicyclo[3.2.1] octan-3-yl]ethan-1-one (471); 1-[3-(3-{4-amino-5-[1-(oxan-4-yl)-1H-pyrazol-5-yl]pyrrolo[2,1-f][1,2,4]triazin-7-yl}phenyl)-3,8-diazabicyclo [3.2.1]octan-8-yl]ethan-1-one (472); 4-[3-(3-{4-amino-5-[1-(oxan-4-yl)-1H-pyrazol-5-yl]pyrrolo[2,1-f][1,2,4] triazin-7-yl}phenyl)-1-(4-fluorobenzoyl)azetidin-3-yl]-1$\lambda^6$, 4-thiomorpholine-1,1-dione (473); 1-(3-{4-amino-5-[1-(oxan-4-yl)-1H-pyrazol-5-yl]pyrrolo[2,1-f][1,2,4]triazin-7-yl}phenyl)-4-(pyrimidin-2-yl)piperazin-2-one (474); 5-(3-{4-amino-5-[1-(oxan-4-yl)-1H-pyrazol-5-yl]pyrrolo[2,1-f][1,2,4]triazin-7-yl}phenyl)-1-ethyl-4-methyl-1,2-dihydropyridin-2-one (475); 5-(3-{4-amino-5-[1-(oxan-4-yl)-1H-1,2,3-triazol-5-yl]pyrrolo[2,1-f][1,2,4]triazin-7-yl}phenyl)-1-ethyl-4-methyl-1,2-dihydropyridin-2-one (476); 4-acetyl-1-(3-{4-amino-5-[1-(propan-2-yl)-1H-1,2,3-triazol-5-yl]pyrrolo[2,1-f][1,2,4]triazin-7-yl}phenyl)-3,3-dimethylpiperazin-2-one (477); 4-acetyl-1-(3-{4-amino-5-[5-(propan-2-yl)-1,3,4-oxadiazol-2-yl]pyrrolo[2,1-f][1,2,4]triazin-7-yl}phenyl)-3,3-dimethylpiperazin-2-one (478);

4-acetyl-1-{3-[4-amino-5-(2-chloro-1-methyl-1H-imidazol-5-yl)pyrrolo[2,1-f][1,2,4]triazin-7-yl]phenyl}-3,3-dimethylpiperazin-2-one (479); 4-acetyl-1-{3-[4-amino-5-(1,3-thiazol-4-yl)pyrrolo[2,1-f][1,2,4]triazin-7-yl]phenyl}-3,3-dimethylpiperazin-2-one (480); 4-acetyl-1-{3-[4-amino-5-(5-methyl-1,3,4-thiadiazol-2-yl)pyrrolo[2,1-f][1,2,4]triazin-7-yl]phenyl}-3,3-dimethylpiperazin-2-one (481); 4-acetyl-1-{3-[4-amino-5-(3-methyl-1,2-oxazol-5-yl)pyrrolo[2,1-f][1,2,4]triazin-7-yl]phenyl}-3,3-dimethylpiperazin-2-one (482); 4-acetyl-1-(3-{4-amino-5-[1-(cyclopropylmethyl)-1H-1,2,3-triazol-4-yl]pyrrolo[2,1-f][1,2,4]triazin-7-yl}phenyl)-3,3-dimethylpiperazin-2-one (483); 4-acetyl-1-(3-{4-amino-5-[1-(propan-2-yl)-1H-1,2,3-triazol-4-yl]pyrrolo[2,1-f][1,2,4]triazin-7-yl}phenyl)-3,3-dimethylpiperazin-2-one (484); 4-acetyl-1-{3-[4-amino-5-(1-methyl-1H-1,2,3-triazol-4-yl)pyrrolo[2,1-f][1,2,4]triazin-7-yl]phenyl}-3,3-dimethylpiperazin-2-one (485); 4-acetyl-1-{3-[4-amino-5-(6-methylpyridazin-4-yl)pyrrolo[2,1-f][1,2,4]triazin-7-yl]phenyl}-3,3-dimethylpiperazin-2-one (486); 4-acetyl-1-{3-[4-amino-5-(6-aminopyridin-3-yl)pyrrolo[2,1-f][1,2,4]triazin-7-yl]phenyl}-3,3-dimethylpiperazin-2-one (487); 4-acetyl-1-{3-[4-amino-5-(2-amino-1,3-thiazol-5-yl)pyrrolo[2,1-f][1,2,4]triazin-7-yl]phenyl}-3,3-dimethylpiperazin-2-one (488); 4-acetyl-1-[3-(4-amino-5-{1-methyl-1H-pyrrolo[2,3-b]pyridin-5-yl}pyrrolo[2,1-f][1,2,4]triazin-7-yl)phenyl]-3,3-dimethylpiperazin-2-one (489); 4-acetyl-1-[3-(4-amino-5-{1H-pyrazolo[3,4-b]pyridin-5-yl}pyrrolo[2,1-f][1,2,4]triazin-7-yl)phenyl]-3,3-dimethylpiperazin-2-one (490); 4-acetyl-1-[3-(4-amino-5-{1H-pyrrolo[2,3-b]pyridin-5-yl}pyrrolo[2,1-f][1,2,4]triazin-7-yl)phenyl]-3,3-dimethylpiperazin-2-one (491); 4-acetyl-1-(3-{4-amino-5-[1-(difluoromethyl)-1H-pyrrolo[2,3-b]pyridin-5-yl]pyrrolo[2,1-f][1,2,4]triazin-7-yl}phenyl)-3,3-dimethylpiperazin-2-one (492); 4-acetyl-1-{3-[4-amino-5-(1-methyl-1H-pyrazol-4-yl)pyrrolo[2,1-f][1,2,4]triazin-7-yl]-2,6-difluorophenyl}-3,3-dimethylpiperazin-2-one (493); 4-acetyl-1-(3-{4-amino-5-[1-(2,2,2-trifluoroethyl)-1H-pyrazol-5-yl]pyrrolo[2,1-f][1,2,4]triazin-7-yl}-2,6-difluorophenyl)-3,3-dimethylpiperazin-2-one (494); 4-acetyl-1-(5-{4-amino-5-[1-(2,2,2-trifluoroethyl)-1H-pyrazol-5-yl]pyrrolo[2,1-f][1,2,4]triazin-7-yl}-2-(trifluoromethyl)phenyl)-3,3-dimethylpiperazin-2-one (495); 4-acetyl-1-(5-{4-amino-5-[1-(2,2,2-trifluoroethyl)-1H-pyrazol-5-yl]pyrrolo[2,1-f][1,2,4]triazin-7-yl}-2-methylphenyl)-3,3-dimethylpiperazin-2-one (496); 2-(5-{4-amino-5-[1-(oxan-4-yl)-1H-pyrazol-5-yl]pyrrolo[2,1-f][1,2,4]triazin-7-yl}-2-fluorophenyl)-1H,2H,3H,4H,6H-pyrido[1,2-a]piperazine-1,6-dione (497); 5-(3-{4-amino-5-[1-(oxan-4-yl)-1H-1,2,3-triazol-5-yl]pyrrolo[2,1-f][1,2,4]triazin-7-yl}phenyl)-1-(2,2-difluoroethyl)-4-methyl-1,2-dihydropyridin-2-one (498); 7-(3-{7-methylimidazo[1,2-a]pyridin-6-yl}phenyl)-5-[1-(oxan-4-yl)-1H-pyrazol-5-yl]pyrrolo[2,1-f][1,2,4]triazin-4-amine (499); 4-acetyl-1-(5-{4-amino-5-[1-(oxan-4-yl)-1H-pyrazol-5-yl]pyrrolo[2,1-f][1,2,4]triazin-7-yl}-2-fluorophenyl)-3,3-dimethylpiperazin-2-one (500); 2-(4-acetyl-3,3-dimethyl-2-oxopiperazin-1-yl)-4-[4-amino-5-(1-methyl-1H-pyrazol-4-yl)pyrrolo[2,1-f][1,2,4]triazin-7-yl]benzonitrile (501); 4-acetyl-1-(5-{4-amino-5-[1-(2,2,2-trifluoroethyl)-1H-pyrazol-5-yl]pyrrolo[2,1-f][1,2,4]triazin-7-yl}-2-methoxyphenyl)-3,3-dimethylpiperazin-2-one (502); 4-acetyl-1-{5-[4-amino-5-(1-methyl-1H-pyrazol-4-yl)pyrrolo[2,1-f][1,2,4]triazin-7-yl]-2-methoxyphenyl}-3,3-dimethylpiperazin-2-one (503); 4-acetyl-1-{5-[4-amino-5-(1-methyl-1H-pyrazol-4-yl)pyrrolo[2,1-f][1,2,4]triazin-7-yl]-2-methylphenyl}-3,3-dimethylpiperazin-2-one (504); 1-(3-{4-amino-5-[1-(2,2,2-trifluoroethyl)-1H-pyrazol-5-yl]pyrrolo[2,1-f][1,2,4]triazin-7-yl}-2-fluorophenyl)-4-methanesulfonyl-3,3-dimethylpiperazin-2-one (505); 2-(4-acetyl-3,3-dimethyl-2-oxopiperazin-1-yl)-4-{4-amino-5-[1-(2,2,2-trifluoroethyl)-1H-pyrazol-5-yl]pyrrolo[2,1-f][1,2,4]triazin-7-yl}benzonitrile (506); 2-{3-[4-amino-5-(1-methyl-1H-pyrazol-4-yl)pyrrolo[2,1-f][1,2,4]triazin-7-yl]phenyl}-1H,2H,3H,4H,6H-pyrido[1,2-a]piperazine-1,6-dione (507); 5-(3-{4-amino-5-[1-(oxan-4-yl)-1H-pyrazol-5-yl]pyrrolo[2,1-f][1,2,4]triazin-7-yl}phenyl)-1-($^2$H$_3$)methyl-4-methyl-1,2-dihydropyridin-2-one (508); 4-[3-(3-{4-amino-5-[1-(oxan-4-yl)-1H-pyrazol-5-yl]pyrrolo[2,1-f][1,2,4]triazin-7-yl}phenyl)-1-[4-(2-hydroxypropan-2-yl)benzoyl]azetidin-3-yl]-1$\lambda^6$,4-thiomorpholine-1,1-dione (509); 1-(3-{4-amino-5-[1-(oxan-4-yl)-1H-1,2,3-triazol-5-yl]pyrrolo[2,1-f][1,2,4]triazin-7-yl}phenyl)-3,3-dimethyl-4-(5-methyl-1,2,4-oxadiazol-3-yl)piperazin-2-one (510); 4-acetyl-1-{3-[4-amino-5-(1-phenyl-1H-pyrazol-5-yl)pyrrolo[2,1-f][1,2,4]triazin-7-yl]phenyl}-3,3-dimethylpiperazin-2-one (511); 1-(3-{4-amino-5-[1-(oxan-4-yl)-1H-pyrazol-5-yl]pyrrolo[2,1-f][1,2,4]triazin-7-yl}phenyl)-3,3-dimethyl-4-(5-methyl-1,2,4-oxadiazol-3-yl)piperazin-2-one (512); 5-(3-{4-amino-5-[1-(oxan-4-yl)-1H-1,2,3-triazol-5-yl]pyrrolo[2,1-f][1,2,4]triazin-7-yl}phenyl)-1,4-dimethyl-1,2-dihydropyridin-2-one (513); 4-acetyl-1-(5-{4-amino-5-[1-(difluoromethyl)-1H-pyrazol-4-yl]pyrrolo[2,1-f][1,2,4]triazin-7-yl}-2-methylphenyl)-3,3-dimethylpiperazin-2-one (514); 4-acetyl-1-[5-(4-amino-5-{1-[($^2$H$_7$)propan-2-yl]-1H-pyrazol-4-yl}pyrrolo[2,1-f][1,2,4]triazin-7-yl)-2-fluorophenyl]-3,3-dimethylpiperazin-2-one (515); 4-acetyl-1-(5-{4-amino-5-[1-(difluoromethyl)-1H-pyrazol-4-yl]pyrrolo[2,1-f][1,2,4]triazin-7-yl}-2-fluorophenyl)-3,3-dimethylpiperazin-2-one (516); 4-acetyl-1-[3-(4-amino-5-{1-[($^2$H$_7$)propan-2-yl]-1H-pyrazol-4-yl}pyrrolo[2,1-f][1,2,4]triazin-7-yl)-5-fluorophenyl]-3,3-dimethylpiperazin-2-one (517); 7-(3-{7-methyl-[1,2,4]triazolo[4,3-a]pyridin-6-yl}phenyl)-5-[1-(oxan-4-yl)-1H-pyrazol-5-yl]pyrrolo[2,1-f][1,2,4]triazin-4-amine (518); 4-acetyl-1-(3-{4-amino-5-[1-(pyridazin-3-yl)-1H-pyrazol-4-yl]pyrrolo[2,1-f][1,2,4]triazin-7-yl}phenyl)-3,3-dimethylpiperazin-2-one (519); 4-(3-{4-amino-5-[1-(oxan-4-yl)-1H-pyrazol-5-yl]pyrrolo[2,1-f][1,2,4]triazin-7-yl}phenyl)-1-(2-cyanoacetyl)piperidine-4-carbonitrile (520); 4-acetyl-1-[5-(4-amino-5-{1-[($^2$H$_7$)propan-2-yl]-1H-pyrazol-4-yl}pyrrolo[2,1-f][1,2,4]triazin-7-yl)-2-methoxyphenyl]-3,3-dimethylpiperazin-2-one (521); 1-{5-[4-amino-5-(1-methyl-1H-pyrazol-4-yl)pyrrolo[2,1-f][1,2,4]triazin-7-yl]-2-fluorophenyl}-4-cyclopropanecarbonyl-3,3-dimethylpiperazin-2-one (522); 4-acetyl-1-(5-{4-amino-5-[1-(difluoromethyl)-1H-pyrazol-4-yl]pyrrolo[2,1-f][1,2,4]triazin-7-yl}-2-methoxyphenyl)-3,3-dimethylpiperazin-2-one (523); 4-acetyl-1-[5-(4-amino-5-{1-[($^2$H$_7$)propan-2-yl]-1H-pyrazol-4-yl}pyrrolo[2,1-f][1,2,4]triazin-7-yl)-2-methylphenyl]-3,3-dimethylpiperazin-2-one (524); 7-(3-{7-methyl-[4,2,4]triazolo[4,3-a]pyridin-6-yl}phenyl)-5-[1-(oxan-4-yl)-1H-1,2,3-triazol-5-yl]pyrrolo[2,1-f][1,2,4]triazin-4-amine (525); 4-acetyl-1-(3-{4-amino-5-[1-(pyrimidin-2-yl)-1H-pyrazol-4-yl]pyrrolo[2,1-f][1,2,4]triazin-7-yl}phenyl)-3,3-dimethylpiperazin-2-one (526); 7-(3-{3,7-dimethyl-[1,2,4]triazolo[4,3-a]pyridin-6-yl}phenyl)-5-[1-(oxan-4-yl)-1H-pyrazol-5-yl]pyrrolo[2,1-f][1,2,4]triazin-4-amine (527); 1-[4-(3-{4-amino-5-[1-(propan-2-yl)-1H-pyrazol-5-yl]pyrrolo[2,1-f][1,2,4]triazin-7-yl}phenyl)-4-hydroxy-3,3-dimethylpiperidin-1-yl]ethan-1-one (528); 4-acetyl-1-{3-[4-amino-5-(1-cyclopropyl-1H-pyrazol-4-yl)-6-fluoropyrrolo[2,1-f][1,2,4]triazin-7-yl]phenyl}-3,3-dimethylpiperazin-2-one (529); 4-acetyl-1-(5-{4-amino-5-[1-(2-fluorophenyl)-1H-pyrazol-5-yl]pyrrolo[2,1-f][1,2,4]triazin-7-yl}-2-methylphenyl)-3,3- dimethylpiperazin-2-one (530); 4-(5-{4-amino-5-[1-(propan-2-yl)-1H-pyrazol-5-yl]pyrrolo[2,1-f][1,2,4]triazin-7-yl}-2-fluorophenyl)-1λ⁶,4-thiomorpholine-1,1-dione (531); 1-(5-{4-amino-5-[1-(2,2,2-trifluoroethyl)-1H-pyrazol-5-yl]pyrrolo[2,1-f][1,2,4] triazin-7-yl}-2-fluorophenyl)-4-methanesulfonyl-3,3-dimethylpiperazin-2-one (532); 4-acetyl-1-{5-[4-amino-5-(1-methyl-1H-pyrazol-4-yl)pyrrolo[2,1-f][1,2,4]triazin-7-yl]-2-(trifluoromethyl)phenyl}-3,3-dimethylpiperazin-2-one (533); 4-(3-{4-amino-5-[1-(oxan-4-yl)-1H-pyrazol-5-yl]pyrrolo[2,1-f][1,2,4]triazin-7-yl}-4-fluorophenyl)-1λ⁶,4-thiomorpholine-1,1-dione (534); 1-[4-(3-{4-amino-5-[1-(2,2,2-trifluoroethyl)-1H-pyrazol-5-yl]pyrrolo[2,1-f][1,2,4]triazin-7-yl}phenyl)piperazin-1-yl]ethan-1-one (535); 4-acetyl-1-(3-{4-amino-5-[5-(2,2-difluorocyclopropyl)-1,3,4-oxadiazol-2-yl]pyrrolo[2,1-f][1,2,4]triazin-7-yl}phenyl)-3,3-dimethylpiperazin-2-one (536); 4-(5-{4-amino-5-[1-(propan-2-yl)-1H-1,2,3-triazol-5-yl]pyrrolo[2,1-f][1,2,4]triazin-7-yl}-2-fluorophenyl)-1λ⁶,4-thiomorpholine-1,1-dione (537); 4-acetyl-1-(3-(4-amino-5-(1-(1,1,1-trifluoropropan-2-yl)-1H-pyrazol-5-yl)pyrrolo[2,1-f][1,2,4]triazin-7-yl)phenyl)-3,3-dimethylpiperazin-2-one (538); (R)- and (S)-4-acetyl-1-(3-(4-amino-5-(1-(1,1,1-trifluoropropan-2-yl)-1H-pyrazol-5-yl)pyrrolo[2,1-f][1,2,4]triazin-7-yl)phenyl)-3,3-dimethylpiperazin-2-one (539 and 540); 3-(4-amino-5-bromopyrrolo[2,1-f][1,2,4]triazin-7-yl)-N-cyclopropyl-N-(tetrahydro-2H-pyran-4-yl)benzamide (541); 1-(4-(3-(4-amino-5-bromopyrrolo[2,1-f][1,2,4]triazin-7-yl)phenoxy)piperidin-1-yl)ethanone (542); 1-(4-(3-(4-amino-5-bromopyrrolo[2,1-f][1,2,4]triazin-7-yl)phenoxy)piperidin-1-yl)ethanone (543); 5-bromo-7-(3-((methyl(tetrahydro-2H-pyran-4-yl)amino)methyl)phenyl)pyrrolo[2,1-f][1,2,4]triazin-4-amine (544); 3-(4-amino-5-iodopyrrolo[2,1-f][1,2,4]triazin-7-yl)-N-cyclopropyl-N-(tetrahydro-2H-pyran-4-yl)benzamide (545); N-(1-acetylpiperidin-4-yl)-3-(4-amino-5-bromopyrrolo[2,1-f][1,2,4]triazin-7-yl)-N-cyclopropylbenzamide (546); 3-(4-amino-5-bromopyrrolo[2,1-f][1,2,4]triazin-7-yl)-N-cyclopropyl-N-(1-methylpiperidin-4-yl)benzamide (547); 4-acetyl-1-(3-(4-amino-5-bromopyrrolo[1,2-f][1,2,4]triazin-7-yl)phenyl)-3,3-dimethylpiperazin-2-one (548); 4-acetyl-1-(3-(4-amino-5-bromopyrrolo[2,1-f][1,2,4]triazin-7-yl)phenyl)-6,6-dimethylpiperazin-2-one (549); 4-acetyl-1-(3-(4-amino-5-iodopyrrolo[1,2-f][1,2,4]triazin-7-yl)phenyl)-3,3-dimethylpiperazin-2-one (550); 4-acetyl-1-(5-(4-amino-5-iodopyrrolo[2,1-f][1,2,4] triazin-7-yl)-2-fluorophenyl)-3,3-dimethylpiperazin-2-one (551); 4-acetyl-1-(5-{4-amino-5-bromopyrrolo[2,1-f][1,2,4]triazin-7-yl}-2-methylphenyl)-3,3-dimethylpiperazin-2-one (552); 4-acetyl-1-(5-{4-amino-5-bromopyrrolo[2,1-f][1,2,4]triazin-7-yl}-2-fluorophenyl)-3,3-dimethylpiperazin-2-one (553); 4-acetyl-1-(3-{4-amino-5-bromopyrrolo[2,1-f][1,2,4] triazin-7-yl}-5-fluorophenyl)-3,3-dimethylpiperazin-2-one (554); 4-acetyl-1-(5-{4-amino-5-bromopyrrolo[2,1-f][1,2,4]triazin-7-yl}-2-methoxyphenyl)-3,3-dimethylpiperazin-2-one (555); 2-(4-acetyl-3,3-dimethyl-2-oxopiperazin-1-yl)-4-{4-amino-5-bromopyrrolo[2,1-f][1,2,4]triazin-7-yl}benzonitrile (556); 7-(3-(4-acetyl-3,3-dimethyl-2-oxopiperazin-1-yl)-4-fluorophenyl)-4-aminopyrrolo[2,1-f][1,2,4]triazine-5-carbonitrile (557); 7-(3-(4-acetyl-3,3-dimethyl-2-oxopiperazin-1-yl)phenyl)-4-aminopyrrolo[2,1-f][1,2,4]triazine-5-carbonitrile (558); 4-amino-7-[3-(4-methanesulfonyl-3,3-dimethyl-2-oxopiperazin-1-yl)-4-methylphenyl]pyrrolo[2,1-f][1,2,4]triazine-5-carbonitrile (559); 7-[3-(4-acetyl-3,3-dimethyl-2-oxopiperazin-1-yl)-4-cyanophenyl]-4-aminopyrrolo[2,1-f][1,2,4]triazine-5-carbonitrile (560); 7-[3-(4-acetyl-3,3-dimethyl-2-oxopiperazin-1-yl)-4-(trifluoromethyl)phenyl]-4-aminopyrrolo[2,1-f][1,2,4]triazine-5-carbonitrile (561); 7-[3-(4-acetyl-3,3-dimethyl-2-oxopiperazin-1-yl)-4-methylphenyl]-4-aminopyrrolo[2,1-f][1,2,4]triazine-5-carbonitrile (562); 7-[3-(4-acetyl-3,3-dimethyl-2-oxopiperazin-1-yl)-4-methoxyphenyl]-4-aminopyrrolo[2,1-f][1,2,4] triazine-5-carbonitrile (563); 4-acetyl-1-(3-(4-amino-5-(trifluoromethyl)pyrrolo[2,1-f][1,2,4]triazin-7-yl)phenyl)-3,3-dimethylpiperazin-2-one (564); 2-(4-acetyl-3,3-dimethyl-2-oxopiperazin-1-yl)-4-(4-amino-5-(trifluoromethyl)pyrrolo[1,2-f][1,2,4] triazin-7-yl)benzonitrile (565); 4-acetyl-1-{5-[4-amino-5-(trifluoromethyl)pyrrolo[2,1-f][1,2,4]triazin-7-yl]-2-fluorophenyl}-3,3-dimethylpiperazin-2-one (566); 4-acetyl-1-{3-[4-amino-5-(trifluoromethyl)pyrrolo[2,1-f][1,2,4]triazin-7-yl]-2,6-difluorophenyl}-3,3-dimethylpiperazin-2-one (567); 4-acetyl-1-{5-[4-amino-5-(trifluoromethyl)pyrrolo[2,1-f][1,2,4]triazin-7-yl]-2-methoxyphenyl}-3,3-dimethylpiperazin-2-one (568); 4-acetyl-1-{3-[4-amino-5-(trifluoromethyl)pyrrolo[2,1-f][1,2,4]triazin-7-yl]-2-fluorophenyl}-3,3-dimethylpiperazin-2-one (569); 4-acetyl-1-{3-[4-amino-5-(trifluoromethyl)pyrrolo[2,1-f][1,2,4]triazin-7-yl]-5-fluorophenyl}-3,3-dimethylpiperazin-2-one (570); 1-(4-{3-[4-amino-5-(trifluoromethyl)pyrrolo[2,1-f][1,2,4]triazin-7-yl]phenyl}-3,3-dimethylpiperazin-1-yl)ethan-1-one (571); 4-acetyl-1-{5-[4-amino-5-(trifluoromethyl) pyrrolo[2,1-f][1,2,4]triazin-7-yl]-2-methylphenyl}-3,3-dimethylpiperazin-2-one (572); 4-acetyl-1-{5-[4-amino-5-(trifluoromethyl)pyrrolo[2,1-f][1,2,4]triazin-7-yl]-2-(trifluoromethyl)phenyl}-3,3-dimethylpiperazin-2-one (573); 4-acetyl-1-(3-(4-amino-5-methylpyrrolo[2,1-f][1,2,4]triazin-7-yl)phenyl)-3,3-dimethylpiperazin-2-one (574); 2-(4-acetyl-3,3-dimethyl-2-oxopiperazin-1-yl)-4-{4-amino-5-methylpyrrolo[2,1-f][1,2,4] triazin-7-yl}benzonitrile (575); 4-acetyl-1-(5-{4-amino-5-methylpyrrolo[2,1-f][1,2,4] triazin-7-yl}-2-fluorophenyl)-3,3-dimethylpiperazin-2-one (576); 4-acetyl-1-(3-{4-amino-5-methylpyrrolo[2,1-f][1,2,4]triazin-7-yl}-2,6-difluorophenyl)-3,3-dimethylpiperazin-2-one (577); 4-acetyl-1-(3-{4-amino-5-methylpyrrolo[2,1-f][1,2,4] triazin-7-yl}-5-fluorophenyl)-3,3-dimethylpiperazin-2-one (578); 4-acetyl-1-(5-{4-amino-5-methylpyrrolo[2,1-f][1,2,4]triazin-7-yl}-2-methoxyphenyl)-3,3-dimethylpiperazin-2-one (579); 2-(4-acetyl-3,3-dimethyl-2-oxopiperazin-1-yl)-4-(4-amino-5-chloropyrrolo[1,2-f][1,2,4]triazin-7-yl)benzonitrile (580); 4-acetyl-1-(3-(4-amino-5-chloropyrrolo[1,2-f][1,2,4]triazin-7-yl)phenyl)-3,3-dimethylpiperazin-2-one (581); 4-acetyl-1-(3-{4-amino-5-chloropyrrolo[2,1-f][1,2,4]triazin-7-yl}-2-fluorophenyl)-3,3-dimethylpiperazin-2-one (582); 4-acetyl-1-(5-{4-amino-5-chloropyrrolo[2,1-f][1,2,4] triazin-7-yl}-2-fluorophenyl)-3,3-dimethylpiperazin-2-one (583); 4-acetyl-1-(3-{4-amino-5-chloropyrrolo[2,1-f][1,2,4]triazin-7-yl}-5-fluorophenyl)-3,3-dimethylpiperazin-2-one (584); 4-acetyl-1-(5-{4-amino-5-chloropyrrolo[2,1-f][1,2,4]triazin-7-yl}-2-methylphenyl)-3,3-dimethylpiperazin-2-one (585); 4-acetyl-1-(3-{4-amino-5-chloropyrrolo[2,1-f][1,2,4]triazin-7-yl}-4-fluorophenyl)-3,3-dimethylpiperazin-2-one (586); 4-acetyl-1-(5-{4-amino-5-chloropyrrolo[2,1-f][1,2,4]triazin-7-yl}-2-(trifluoromethyl)phenyl)-3,3-dimethylpiperazin-2-one (587); 4-acetyl-1-(3-{4-amino-5-chloropyrrolo[2,1-f][1,2,4]triazin-7-yl}-2,6-difluorophenyl)-3,3-dimethylpiperazin-2-one (588); 2-(5-{4-amino-5-chloropyrrolo[2,1-f][1,2,4]triazin-7-yl}-2-fluorophenyl)-1H,2H,3H,4H,6H-pyrido[1,2-a]piperazine-1,6-dione (589); 1-(5-{4-amino-5-chloropyrrolo[2,1-f][1,2,4]triazin-7-yl}-2-(trifluoromethyl)phenyl)-4-methanesulfonyl-3,3-dimethylpiperazin-2-one (590); 1-(5-{4-amino-5-chloropyrrolo[2,1-f][1,2,4]triazin-7-yl}-2-fluorophenyl)-4-methanesulfonyl-3,3-dimethylpiperazin-2-one (591); 1-(5-{4-amino-5-chloropyrrolo[2,1-f][1,2,4]

triazin-7-yl}-2-methoxyphenyl)-4-methanesulfonyl-3,3-dimethylpiperazin-2-one (592); 4-{4-amino-5-chloropyrrolo[2,1-f][1,2,4]triazin-7-yl}-2-(4-methanesulfonyl-3,3-dimethyl-2-oxopiperazin-1-yl)benzonitrile (593); 4-acetyl-1-(5-(4-amino-5-chloropyrrolo[1,2-f][1,2,4]triazin-7-yl)-2-methoxyphenyl)-3,3-dimethylpiperazin-2-one (594); 2-(4-acetyl-3,3,6-trimethyl-2-oxopiperazin-1-yl)-4-{4-amino-5-chloropyrrolo[2,1-f][1,2,4]triazin-7-yl}benzonitrile (595); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-methoxyphenyl)-3,3-dimethylpiperazin-2-one (596); 2-(4-acetyl-3,3,6-trimethyl-2-oxopiperazin-1-yl)-4-[4-amino-5-(trifluoromethyl)pyrrolo[2,1-f][1,2,4]triazin-7-yl]benzonitrile, racemic R,S (597); (R)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile (598); (S)-2-(4-acetyl-3,3,6-trimethyl-2-oxopiperazin-1-yl)-4-(4-amino-5-(trifluoromethyl)pyrrolo[2,1-f][1,2,4]triazin-7-yl)benzonitrile (599); 4-acetyl-1-{3-[4-amino-5-(trifluoromethyl)pyrrolo[2,1-f][1,2,4]triazin-7-yl]phenyl}-3,3-dimethyl-5,5,6,6-tetradeuteropiperazin-2-one (600); 4-acetyl-1-(5-(4-amino-5-(1-(tetrahydro-2H-pyran-4-yl)-1H-pyrazol-5-yl)pyrrolo[2,1-f][1,2,4]triazin-7-yl)-2-chlorophenyl)-3,3-dimethylpiperazin-2-one (601); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one, racemate, R,S (602); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one (603); 4-acetyl-1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one (604); 1-(5-{4-amino-5-[1-(1,1,1-trifluoropropan-2-yl)-1H-pyrazol-5-yl]pyrrolo[2,1-f][1,2,4]triazin-7-yl}-2-fluorophenyl)-4-cyclopropanecarbonyl-3,3-dimethylpiperazin-2-one (605); 4-acetyl-1-(3-{4-amino-5-[1-(1,1,1-trifluoropropan-2-yl)-1H-pyrazol-5-yl]pyrrolo[2,1-f][1,2,4]triazin-7-yl}-2-fluorophenyl)-3,3-dimethylpiperazin-2-one (606); 2-(4-acetyl-3,3-dimethyl-2-oxopiperazin-1-yl)-4-{4-amino-5-[1-(1,1,1-trifluoropropan-2-yl)-1H-pyrazol-5-yl]pyrrolo [2,1-f][1,2,4]triazin-7-yl}benzonitrile (607); 4-acetyl-1-(3-{4-amino-5-[1-(oxetan-3-yl)-1H-pyrazol-5-yl]pyrrolo[2,1-f][1,2,4]triazin-7-yl}phenyl)-3,3-dimethylpiperazin-2-one (608); 4-acetyl-1-[3-(4-amino-5-{3-methyl-3H-imidazo[4,5-b]pyridin-6-yl}pyrrolo[2,1-f][1,2,4]triazin-7-yl)phenyl]-3,3-dimethylpiperazin-2-one (609); 4-acetyl-1-[5-(4-amino-5-{3-methyl-3H-imidazo[4,5-b]pyridin-6-yl}pyrrolo[2,1-f][1,2,4]triazin-7-yl)-2-fluorophenyl]-3,3-dimethylpiperazin-2-one (610); 4-acetyl-1-[5-(4-amino-5-{3-methyl-3H-imidazo[4,5-b]pyridin-6-yl}pyrrolo[2,1-f][1,2,4]triazin-7-yl)-2-methoxyphenyl]-3,3-dimethylpiperazin-2-one (611); 4-acetyl-1-[3-(4-amino-5-{3-methyl-3H-imidazo[4,5-b]pyridin-6-yl}pyrrolo[2,1-f][1,2,4]triazin-7-yl)-2-fluorophenyl]-3,3-dimethylpiperazin-2-one (612); 4-acetyl-1-(3-{4-amino-5-[3-(difluoromethyl)-3H-imidazo[4,5-b]pyridin-6-yl]pyrrolo[2,1-f][1,2,4]triazin-7-yl}phenyl)-3,3-dimethylpiperazin-2-one (613); 2-(4-acetyl-3,3-dimethyl-2-oxopiperazin-1-yl)-4-{4-amino-5-[1-(oxan-4-yl)-1H-pyrazol-5-yl]pyrrolo[2,1-f][1,2,4]triazin-7-yl}benzonitrile (614); 2-(4-acetyl-3,3-dimethyl-2-oxopiperazin-1-yl)-4-{4-amino-5-[1-(difluoromethyl)-1H-pyrazol-4-yl]pyrrolo[2,1-f][1,2,4]triazin-7-yl}benzonitrile (615); 4-acetyl-1-[3-(4-amino-5-{imidazo[1,2-a]pyridin-7-yl}pyrrolo[2,1-f][1,2,4]triazin-7-yl)phenyl]-3,3-dimethylpiperazin-2-one (616); 1-[(3S)-4-(3-{4-amino-5-[1-(propan-2-yl)-1H-pyrazol-5-yl]pyrrolo[2,1-f][1,2,4]triazin-7-yl}phenyl)-3-methylpiperazin-1-yl]ethan-1-one (617); 1-[(3S)-4-(3-{4-amino-5-[1-(oxan-4-yl)-1H-pyrazol-5-yl]pyrrolo[2,1-f][1,2,4]triazin-7-yl}phenyl)-3-methylpiperazin-1-yl]ethan-1-one (618); 4-acetyl-1-(3-(1-amino-8-(1-(tetrahydro-2H-pyran-4-yl)-1H-pyrazol-5-yl)pyrrolo[1,2-a]pyrazin-6-yl)phenyl)-3,3-dimethylpiperazin-2-one (619); 4-[3-(3-{1-amino-8-[1-(oxan-4-yl)-1H-pyrazol-5-yl]pyrrolo[1,2-a]pyrazin-6-yl}phenyl)oxetan-3-yl]-1$\lambda^6$,4-thiomorpholine-1,1-dione (620); 2-(3-{1-amino-8-[1-(oxan-4-yl)-1H-pyrazol-5-yl]pyrrolo[1,2-a]pyrazin-6-yl}phenyl)benzamide (621); 4-(4-amino-5-(1-(1,1,1-trifluoropropan-2-yl)-1H-pyrazol-5-yl)pyrrolo[2,1-f][1,2,4]triazin-7-yl)-2-(4-(cyclopropanecarbonyl)-3,3-dimethyl-2-oxopiperazin-1-yl)benzonitrile, (622); 4-acetyl-1-(5-(4-amino-5-(1-(tetrahydro-2H-pyran-4-yl)-1H-pyrazol-5-yl)pyrrolo[2,1-f][1,2,4] triazin-7-yl)-2-(hex-1-yn-1-yl)phenyl)-3,3-dimethylpiperazin-2-one (623); 4-acetyl-1-(5-(4-amino-5-(trifluoromethyl)pyrrolo[2,1-f][1,2,4]triazin-7-yl)-2-(difluoromethyl)phenyl)-3,3-dimethylpiperazin-2-one (624); 4-acetyl-1-(5-(4-amino-5-(trifluoromethyl)pyrrolo[2,1-f][1,2,4]triazin-7-yl)-2-(1-hydroxyethyl)phenyl)-3,3-dimethylpiperazin-2-one (625); 4-acetyl-1-(5-(4-amino-5-chloropyrrolo[2,1-f][1,2,4]triazin-7-yl)-2-(1-hydroxyethyl) phenyl)-3,3-dimethylpiperazin-2-one (626); methyl 2-(4-acetyl-3,3-dimethyl-2-oxopiperazin-1-yl)-4-(4-amino-5-chloropyrrolo[2,1-f][1,2,4]triazin-7-yl)benzoate (627); 7-(3-(4-acetyl-3,3-dimethyl-2-oxopiperazin-1-yl)-4-chlorophenyl)-4-aminopyrrolo[2,1-f][1,2,4]triazine-5-carbonitrile (628); 4-acetyl-1-(5-(4-amino-5-(trifluoromethyl)pyrrolo[2,1-f][1,2,4]triazin-7-yl)-2-(methylsulfonyl)phenyl)-3,3-dimethylpiperazin-2-one (629); 4-acetyl-1-(5-(4-amino-5-(trifluoromethyl)pyrrolo[2,1-f][1,2,4]triazin-7-yl)-2-(2-hydroxypropan-2-yl)phenyl)-3,3-dimethylpiperazin-2-one (630); 4-acetyl-1-(5-(4-amino-5-chloropyrrolo[2,1-f][1,2,4]triazin-7-yl)-2-(difluoromethyl)phenyl)-3,3-dimethylpiperazin-2-one (631); 4-acetyl-1-(5-(4-amino-5-(1-(tetrahydro-2H-pyran-4-yl)-1H-pyrazol-5-yl)-pyrrolo[2,1-f][1,2,4]triazin-7-yl)-2-fluorophenyl)-3,3-dimethyl-5,5,6,6-tetradeuteropiperazin-2-one (632); 4-acetyl-1-(5-(4-amino-5-(1-methyl-1H-pyrazol-4-yl)pyrrolo[2,1-f][1,2,4]triazin-7-yl)-2-fluorophenyl)-3,3-dimethyl-5,5,6,6-tetradeuteropiperazin-2-one (633); 4-acetyl-1-(5-(4-amino-5-(1-cyclopropyl-1H-pyrazol-4-yl)pyrrolo[2,1-f][1,2,4]triazin-7-yl)-2-fluorophenyl)-3,3-dimethyl-5,5,6,6-tetradeuteropiperazin-2-one (634); 7-(3-(4-acetyl-3,3-dimethyl-2-oxo-5,5,6,6-tetradeuteropiperazin-1-yl)-4-fluorophenyl)-4-aminopyrrolo[2,1-f][1,2,4]triazine-5-carbonitrile (635); 4-acetyl-1-(5-(4-amino-5-chloropyrrolo[2,1-f][1,2,4]triazin-7-yl)-2-fluorophenyl)-3,3-dimethyl-5,5,6,6-tetradeuteropiperazin-2-one (636); 2-(4-acetyl-3,3-dimethyl-2-oxo-5,5,6,6-tetradeuteropiperazin-1-yl)-4-(4-amino-5-chloropyrrolo[2,1-f][1,2,4]triazin-7-yl)benzonitrile (637); 4-acetyl-1-(5-(4-amino-5-(trifluoromethyl)pyrrolo[2,1-f][1,2,4]triazin-7-yl)-2-methoxyphenyl)-3,3-dimethyl-5,5,6,6-tetradeuteropiperazin-2-one (638); 2-(4-acetyl-3,3-dimethyl-2-oxo-5,5,6,6-tetradeuteropiperazin-1-yl)-4-(4-amino-5-(trifluoromethyl)pyrrolo[2,1-f][1,2,4]triazin-7-yl)benzonitrile (639); 4-acetyl-1-(5-(4-amino-5-(trifluoromethyl)pyrrolo[2,1-f][1,2,4]triazin-7-yl)-2-fluorophenyl)-3,3-dimethyl-5,5,6,6-tetradeuteropiperazin-2-one (640); 4-acetyl-1-(5-(4-amino-5-(1-(2,2,2-trifluoroethyl)-1H-pyrazol-5-yl)pyrrolo[2,1-f][1,2,4]triazin-7-yl)-2-fluorophenyl)-3,3-dimethyl-5,5,6,6-tetradeuteropiperazin-2-one (641); (S)-2-(4-acetyl-3,3,6-trimethyl-2-oxopiperazin-1-yl)-4-(4-amino-5-chloropyrrolo[2,1-f][1,2,4]triazin-7-yl)benzonitrile (642); (S)-2-(4-acetyl-3,3,6-trimethyl-2-oxopiperazin-1-yl)-4-(4-amino-5-

(trifluoromethyl)pyrrolo[2,1-f][1,2,4]triazin-7-yl) benzonitrile (643); (R)-2-(4-acetyl-3,3,6-trimethyl-2-oxopiperazin-1-yl)-4-(4-amino-5-(trifluoromethyl)pyrrolo [2,1-f][1,2,4]triazin-7-yl)benzonitrile (644); (S)-4-acetyl-1-(5-(4-amino-5-chloropyrrolo[2,1-f][1,2,4]triazin-7-yl)-2-methoxyphenyl)-3,3,6-trimethylpiperazin-2-one (645); 2-((3R,6R)-4-acetyl-3,6-dimethyl-2-oxopiperazin-1-yl)-4-(4-amino-5-(trifluoromethyl) pyrrolo[2,1-f][1,2,4]triazin-7-yl)benzonitrile (646); 4-(4-amino-5-(trifluoromethyl) pyrrolo[2,1-f][1,2,4]triazin-7-yl)-2-(4-(2-hydroxyacetyl)-3,3-dimethyl-2-oxopiperazin-1-yl)benzonitrile (647); 1-(5-(4-amino-5-chloropyrrolo[2,1-f][1,2,4]triazin-7-yl)-2-fluorophenyl)-4-(2-hydroxyacetyl)-3,3-dimethylpiperazin-2-one (648); (S)-4-(4-amino-5-(trifluoromethyl)pyrrolo[2,1-f][1,2,4]triazin-7-yl)-2-(4-(2-hydroxypropanoyl)-3,3-dimethyl-2-oxopiperazin-1-yl)benzonitrile (649); 1-(5-(4-amino-5-(1-(1,1,1-trifluoropropan-2-yl)-1H-pyrazol-5-yl)pyrrolo[2,1-f][1,2,4]triazin-7-yl)-2-fluorophenyl)-4-(cyclopropanecarbonyl)-3,3-dimethylpiperazin-2-one (650); 4-(4-amino-5-chloropyrrolo[2,1-f][1,2,4]triazin-7-yl)-2-(3,3-dimethyl-2-oxo-4-propionylpiperazin-1-yl)benzonitrile (651); 4-(4-amino-5-(trifluoromethyl)pyrrolo[2,1-f][1,2,4]triazin-7-yl)-2-(3,3-dimethyl-2-oxo-4-propionylpiperazin-1-yl)benzonitrile (652); (R)-4-(4-amino-5-chloropyrrolo[2,1-f][1,2,4]triazin-7-yl)-2-(2,2,6-trimethyl-3-oxomorpholino)benzonitrile (653); (S)-4-(4-amino-5-(trifluoromethyl)pyrrolo[2,1-f][1,2,4]triazin-7-yl)-2-(2,2,5-trimethyl-3-oxomorpholino)benzonitrile (654); 1-(3-(4-amino-5-(2-isopropyl-1-methyl-1H-imidazol-5-yl)pyrrolo [2,1-f][1,2,4]triazin-7-yl)phenyl)-4-(cyclopropanecarbonyl)-3,3-dimethylpiperazin-2-one (655); 4-acetyl-1-(3-(4-amino-5-(2-isopropyl-1-methyl-1H-imidazol-5-yl)pyrrolo[2,1-f][1,2,4]triazin-7-yl)phenyl)-3,3-dimethylpiperazin-2-one (656); 4-acetyl-1-(3-(4-amino-5-(1-(2,2,2-trifluoroethyl)-1H-pyrazol-5-yl)pyrrolo[2,1-f][1,2,4]triazin-7-yl)phenyl)-3,3-dimethyl-5,5,6,6-tetradeuteropiperazin-2-one (657); (S)-7-(3-(4-acetyl-3,3,6-trimethyl-2-oxopiperazin-1-yl)-4-methoxyphenyl)-4-aminopyrrolo [2,1-f][1,2,4]triazine-5-carbonitrile (658); 7-(3-(4-acetyl-3,3-dimethyl-2-oxo-5,5,6,6-tetradeutero-piperazin-1-yl)phenyl)-4-aminopyrrolo[2,1-f][1,2,4]triazine-5-carbonitrile (659); 4-(4-amino-5-chloropyrrolo[2,1-f][1,2,4]triazin-7-yl)-2-(3,3-dimethyl-4-(2-(methylsulfonyl)acetyl)-2-oxopiperazin-1-yl)benzonitrile (660); (S)-7-(3-(4-acetyl-3,3,6-trimethyl-2-oxopiperazin-1-yl)-4-chlorophenyl)-4-aminopyrrolo[2,1-f][1,2,4]triazine-5-carbonitrile (661); 4-acetyl-1-(3-(4-amino-5-(1-(1,1,1-trifluoropropan-2-yl)-1H-pyrazol-5-yl)pyrrolo[2,1-f][1,2,4]triazin-7-yl)-2-fluorophenyl)-3,3-dimethyl-5,5,6,6-tetradeuteropiperazin-2-one (chiral)(662); 2-((3S,6S)-4-acetyl-3,6-dimethyl-2-oxopiperazin-1-yl)-4-(4-amino-5-(trifluoromethyl)pyrrolo[2,1-f][1,2,4]triazin-7-yl)benzonitrile (663); (4-acetyl-1-(3-(4-amino-5-(trifluoromethyl)pyrrolo[2,1-f][1,2,4] triazin-7-yl)phenyl)-5,5-dimethyl-6-oxopiperazin-2-yl)methyl acetate (664); (4-acetyl-1-(3-(4-amino-5-(1-(2,2,2-trifluoroethyl)-1H-pyrazol-5-yl)pyrrolo[2,1-f][1,2,4]triazin-7-yl)phenyl)-5,5-dimethyl-6-oxopiperazin-2-yl)methyl acetate (665); (4-acetyl-1-(3-(4-amino-5-chloropyrrolo[2,1-f][1,2,4]triazin-7-yl)phenyl)-5,5-dimethyl-6-oxopiperazin-2-yl)methyl acetate (666); (4-acetyl-1-(3-(4-amino-5-(1-methyl-1H-pyrazol-4-yl)pyrrolo [2,1-f][1,2,4]triazin-7-yl)phenyl)-5,5-dimethyl-6-oxopiperazin-2-yl)methyl acetate (667); 4-acetyl-1-(3-(4-amino-5-chloropyrrolo[2,1-f][1,2,4]triazin-7-yl)phenyl)-6-(hydroxymethyl)-3,3-dimethylpiperazin-2-one (668); 4-acetyl-1-(3-(4-amino-5-(1-methyl-1H-pyrazol-4-yl)pyrrolo[2,1-f][1,2,4]triazin-7-yl)phenyl)-6-(hydroxymethyl)-3,3-dimethylpiperazin-2-one (669); 4-acetyl-1-(3-(4-amino-5-chloropyrrolo[2,1-f][1,2,4] triazin-7-yl)phenyl)-6-(methoxymethyl)-3,3-dimethylpiperazin-2-one (670); 4-acetyl-1-(3-(4-amino-5-(trifluoromethyl)pyrrolo[2,1-f][1,2,4]triazin-7-yl)phenyl)-6-(methoxymethyl)-3,3-dimethylpiperazin-2-one (671); (S)-7-(3-(4-acetyl-3,3,6-trimethyl-2-oxopiperazin-1-yl)-4-(methylsulfonyl)phenyl)-4-aminopyrrolo[2,1-f][1,2,4] triazine-5-carbonitrile (672); (S)-4-acetyl-1-(5-(4-amino-5-(trifluoromethyl)pyrrolo[2,1-f][1,2,4] triazin-7-yl)-2-(methylsulfonyl)phenyl)-3,3,6-trimethylpiperazin-2-one (673); (S)-4-acetyl-1-(5-(4-amino-5-(trifluoromethyl)pyrrolo[2,1-f][1,2,4]triazin-7-yl)-2-(methylsulfonyl)phenyl)-3,3,6-trimethylpiperazin-2-one (674); (S)-4-acetyl-1-(5-(4-amino-5-chloropyrrolo[2,1-f][1,2,4]triazin-7-yl)-2-(methylsulfonyl)phenyl)-3,3,6-trimethylpiperazin-2-one (675); (S)-4-acetyl-1-(5-(4-amino-5-chloropyrrolo[2,1-f][1,2,4] triazin-7-yl)-2-(methylsulfonyl)phenyl)-3,3,6-trimethylpiperazin-2-one (676); (S)-4-acetyl-1-(5-(4-amino-5-(trifluoromethyl)pyrrolo[2,1-f][1,2,4]triazin-7-yl)-2-fluorophenyl)-3,3,6-trimethylpiperazin-2-one (677); (S)-4-acetyl-1-(5-(4-amino-5-chloropyrrolo[2,1-f][1,2,4]triazin-7-yl)-2-fluorophenyl)-3,3,6-trimethylpiperazin-2-one (678); (S)-4-acetyl-1-(5-(4-amino-5-(1-(2,2,2-trifluoroethyl)-1H-pyrazol-5-yl)pyrrolo [2,1-f][1,2,4]triazin-7-yl)-2-fluorophenyl)-3,3,6-trimethylpiperazin-2-one (679); (S)-4-acetyl-1-(5-(4-amino-5-(1-((R)-1,1,1-trifluoropropan-2-yl)-1H-pyrazol-5-yl)pyrrolo[2,1-f][1,2,4]triazin-7-yl)-2-fluorophenyl)-3,3,6-trimethylpiperazin-2-one (680); (S)-4-acetyl-1-(5-(4-amino-5-(1-((S)-1,1,1-trifluoropropan-2-yl)-1H-pyrazol-5-yl)pyrrolo[2,1-f][1,2,4] triazin-7-yl)-2-fluorophenyl)-3,3,6-trimethylpiperazin-2-one (681); (S)-7-(3-(4-acetyl-3,3,6-trimethyl-2-oxopiperazin-1-yl)-4-fluorophenyl)-4-aminopyrrolo[2,1-f][1,2,4] triazine-5-carbonitrile (682); (S)-4-acetyl-1-(5-(4-amino-5-(1-methyl-1H-pyrazol-4-yl)pyrrolo[2,1-f][1,2,4]triazin-7-yl)-2-fluorophenyl)-3,3,6-trimethylpiperazin-2-one (683); (S)-4-acetyl-1-(5-(4-amino-5-(1-cyclopropyl-1H-pyrazol-4-yl) pyrrolo[2,1-f][1,2,4] triazin-7-yl)-2-fluorophenyl)-3,3,6-trimethylpiperazin-2-one (684); 2-(4-acetyl-3-ethyl-3-methyl-2-oxopiperazin-1-yl)-4-(4-amino-5-chloropyrrolo [2,1-f][1,2,4]triazin-7-yl)benzonitrile (685); 2-(4-acetyl-3-ethyl-3-methyl-2-oxopiperazin-1-yl)-4-(4-amino-5-(trifluoromethyl)pyrrolo[2,1-f][1,2,4]triazin-7-yl) benzonitrile (686); (R)-2-(4-acetyl-3-ethyl-3-methyl-2-oxopiperazin-1-yl)-4-(4-amino-5-chloropyrrolo[2,1-f][1,2,4]triazin-7-yl)benzonitrile (687); (S)-2-(4-acetyl-3-ethyl-3-methyl-2-oxopiperazin-1-yl)-4-(4-amino-5-chloropyrrolo [2,1-f][1,2,4]triazin-7-yl)benzonitrile (689); (S)-2-(4-acetyl-3-ethyl-3-methyl-2-oxopiperazin-1-yl)-4-(4-amino-5-(trifluoromethyl)pyrrolo[2,1-f][1,2,4]triazin-7-yl) benzonitrile (690); (R)-2-(4-acetyl-3-ethyl-3-methyl-2-oxopiperazin-1-yl)-4-(4-amino-5-(trifluoromethyl)pyrrolo [2,1-f][1,2,4]triazin-7-yl)benzonitrile (691); 1-(3-(4-amino-5-chloropyrrolo[2,1-f][1,2,4]triazin-7-yl)phenyl)-3,3-dimethylpiperidin-2-one (692); 1-(3-(4-amino-5-(trifluoromethyl)pyrrolo[2,1-f][1,2,4]triazin-7-yl)phenyl)-3,3-dimethylpiperidin-2-one (693); 4-amino-7-(3-(3-oxomorpholino)phenyl)pyrrolo[2,1-f][1,2,4]triazine-5-carbonitrile (694); 4-amino-7-(3-(2,2-dimethyl-3-oxomorpholino) phenyl)pyrrolo[2,1-f][1,2,4]triazine-5-carbonitrile (695); (R)-4-(3-(4-amino-5-chloropyrrolo[2,1-f][1,2,4]triazin-7-yl)phenyl)-2,2,5-trimethylmorpholin-3-one (696); (R)-4-(3-(4-amino-5-(trifluoromethyl)pyrrolo[2,1-f][1,2,4]triazin-7-yl)phenyl)-2,2,5-trimethylmorpholin-3-one (697); (S)-4-(3-(4-amino-5-(trifluoromethyl)pyrrolo[2,1-f][1,2,4]triazin-7-yl)phenyl)-2,2,6-trimethylmorpholin-3-one (698); (S)-4-(3-(4-amino-5-chloropyrrolo[2,1-f][1,2,4]

triazin-7-yl)phenyl)-2,2,6-trimethylmorpholin-3-one (699); (R)-4-(3-(4-amino-5-(1-(2,2,2-trifluoroethyl)-1H-pyrazol-5-yl)pyrrolo[2,1-f][1,2,4] triazin-7-yl)phenyl)-2,2,5-trimethylmorpholin-3-one (700); (R)-4-amino-7-(3-(2,2,5-trimethyl-3-oxomorpholino)phenyl)pyrrolo[2,1-f][1,2,4] triazine-5-carbonitrile (701); (S)-4-amino-7-(3-(2,2,6-trimethyl-3-oxomorpholino)phenyl)pyrrolo[2,1-f][1,2,4] triazine-5-carbonitrile (702); (R)-4-(3-(4-amino-5-(1-(2,2,2-trifluoroethyl)-1H-pyrazol-5-yl)pyrrolo [2,1-f][1,2,4] triazin-7-yl)phenyl)-2,2,5-trimethylmorpholin-3-one (703); 4-(4-amino-5-(trifluoromethyl)pyrrolo[2,1-f][1,2,4]triazin-7-yl)-2-(2,2-dimethyl-5-(methyl-$d_3$)-3-oxomorpholino-5,6,6-$d_3$)benzonitrile (704); 4-(4-amino-5-chloropyrrolo[2,1-f][1,2,4] triazin-7-yl)-2-(2,2-dimethyl-5-(methyl-$d_3$)-3-oxomorpholino-5,6,6-$d_3$)benzonitrile (705); 4-(4-amino-5-(trifluoromethyl)pyrrolo[2,1-f][1,2,4]triazin-7-yl)-2-(2,2-dimethyl-5-(methyl-$d_3$)-3-oxomorpholino-5,6,6-$d_3$) benzonitrile (706); 4-(4-amino-5-chloropyrrolo [2,1-f][1,2,4]triazin-7-yl)-2-(2,2-dimethyl-5-(methyl-$d_3$)-3-oxomorpholino-5,6,6-$d_3$)benzonitrile (707); (S)-4-(5-(4-amino-5-(trifluoromethyl)pyrrolo[2,1-f][1,2,4]triazin-7-yl)-2-(methylsulfonyl)phenyl)-2,2,5-trimethylmorpholin-3-one (708); 4-(4-amino-5-(trifluoromethyl)pyrrolo[2,1-f][1,2,4]triazin-7-yl)-2-((5S,6S)-2,2,5,6-tetramethyl-3-oxomorpholino)benzonitrile (709); (S)-4-(5-(4-amino-5-(1-(2,2,2-trifluoroethyl)-1H-pyrazol-5-yl)pyrrolo[2,1-f][1,2,4]triazin-7-yl)-2-(methylsulfonyl)phenyl)-2,2,5-trimethylmorpholin-3-one (710); (S)-4-(5-(4-amino-5-(1-(2,2,2-trifluoroethyl)-1H-pyrazol-5-yl)pyrrolo[2,1-f][1,2,4]triazin-7-yl)-2-(methylsulfonyl)phenyl)-2,2,5-trimethylmorpholin-3-one (711); (R)-4-(5-(4-amino-5-(1-(2,2,2-trifluoroethyl)-1H-pyrazol-5-yl)pyrrolo[2,1-f][1,2,4]triazin-7-yl)-2-(methylsulfonyl)phenyl)-2,2,6-trimethylmorpholin-3-one (712); (S)-4-amino-7-(4-cyano-3-(2,2,6-trimethyl-3-oxomorpholino)phenyl)pyrrolo[2,1-f][1,2,4]triazine-5-carbonitrile (713); 4-(4-amino-5-(1-(2,2,2-trifluoroethyl)-1H-pyrazol-5-yl)pyrrolo[2,1-f][1,2,4]triazin-7-yl)-2-((5S,6S)-2,2,5,6-tetramethyl-3-oxomorpholino)benzonitrile (714); 4-(4-amino-5-chloropyrrolo [2,1-f][1,2,4]triazin-7-yl)-2-((5S,6S)-2,2,5,6-tetramethyl-3-oxomorpholino)benzonitrile (715); (S)-4-(5-(4-amino-5-chloropyrrolo[2,1-f][1,2,4]triazin-7-yl)-2-(methylsulfonyl) phenyl)-2,2,5-trimethylmorpholin-3-one (716); (S)-4-(5-(4-amino-5-(trifluoromethyl) pyrrolo[2,1-f][1,2,4]triazin-7-yl)-2-(methylsulfonyl)phenyl)-2,2,5-trimethylmorpholin-3-one (717); (R)-4-(5-(4-amino-5-chloropyrrolo[2,1-f][1,2,4]triazin-7-yl)-2-(methylsulfonyl)phenyl)-2,2,6-trimethylmorpholin-3-one (718); (R)-4-(5-(4-amino-5-chloropyrrolo[2,1-f][1,2,4]triazin-7-yl)-2-fluorophenyl)-2,2,5-trimethylmorpholin-3-one (719); (S)-4-(5-(4-amino-5-chloropyrrolo[2,1-f][1,2,4]triazin-7-yl)-2-fluorophenyl)-2,2,6-trimethylmorpholin-3-one (720); (R)-4-(5-(4-amino-5-(trifluoromethyl)pyrrolo[2,1-f][1,2,4]triazin-7-yl)-2-fluorophenyl)-2,2,5-trimethylmorpholin-3-one (721); (S)-4-(5-(4-amino-5-(trifluoromethyl)pyrrolo[2,1-f][1,2,4]triazin-7-yl)-2-fluorophenyl)-2,2,6-trimethylmorpholin-3-one (722); 4-amino-7-(4-cyano-3-(2,2-dimethyl-3-oxomorpholino-5,5,6,6-$d_4$)phenyl)pyrrolo[2,1-f][1,2,4]triazine-5-carbonitrile (723); (R)-4-amino-7-(4-(methylsulfonyl)-3-(2,2,5-trimethyl-3-oxomorpholino)phenyl)pyrrolo[2,1-f][1,2,4] triazine-5-carbonitrile (724); 4-amino-7-(3-(2,2-dimethyl-3-oxomorpholino)-4-methoxyphenyl)pyrrolo[2,1-f][1,2,4]triazine-5-carbonitrile (725); (R)-4-(5-(4-amino-5-(1-(2,2,2-trifluoroethyl)-1H-pyrazol-5-yl)pyrrolo[2,1-f][1,2,4]triazin-7-yl)-2-fluorophenyl)-2,2,5-trimethylmorpholin-3-one (726); (S)-4-(5-(4-amino-5-(1-(2,2,2-trifluoroethyl)-1H-pyrazol-5-yl)pyrrolo[2,1-f][1,2,4]triazin-7-yl)-2-fluorophenyl)-2,2,6-trimethylmorpholin-3-one (727); (R)-4-(4-amino-5-chloropyrrolo[2,1-f][1,2,4]triazin-7-yl)-2-(2,2,5-trimethyl-3-oxomorpholino)benzamide (728); (R)-4-(4-amino-5-(trifluoromethyl)pyrrolo[2,1-f][1,2,4]triazin-7-yl)-2-(2,2,5-trimethyl-3-oxomorpholino) benzamide (729); (S)-4-(4-amino-5-chloropyrrolo[2,1-f][1,2,4]triazin-7-yl)-2-(5-ethyl-2,2-dimethyl-3-oxomorpholino)benzonitrile (730); (S)-4-(4-amino-5-chloropyrrolo[2,1-f][1,2,4]triazin-7-yl)-2-(5-ethyl-2,2-dimethyl-3-oxomorpholino)benzonitrile (731); (S)-4-(4-amino-5-(1-(2,2,2-trifluoroethyl)-1H-pyrazol-5-yl) pyrrolo[2,1-f][1,2,4]triazin-7-yl)-2-(5-ethyl-2,2-dimethyl-3-oxomorpholino)benzonitrile (732); (S)-4-(4-amino-5-(1-(2,2,2-trifluoroethyl)-1H-pyrazol-5-yl)pyrrolo[2,1-f][1,2,4] triazin-7-yl)-2-(5-ethyl-2,2-dimethyl-3-oxomorpholino) benzonitrile (733); (S)-4-(4-amino-5-(trifluoromethyl) pyrrolo[2,1-f][1,2,4]triazin-7-yl)-2-(5-ethyl-2,2-dimethyl-3-oxomorpholino)benzonitrile (734); (S)-4-(4-amino-5-(trifluoromethyl)pyrrolo[2,1-f][1,2,4]triazin-7-yl)-2-(5-ethyl-2,2-dimethyl-3-oxomorpholino)benzonitrile (735); 3-(2-(4-(3-(4-amino-5-(trifluoromethyl)pyrrolo[2,1-f][1,2,4]triazin-7-yl)phenyl)-2,2-dimethyl-3-oxopiperazin-1-yl)-2-oxoethyl)oxazolidin-2-one (736); (R)-4-(4-amino-5-(trifluoromethyl)pyrrolo[2,1-f][1,2,4]triazin-7-yl)-2-(4-(2-hydroxypropanoyl)-3,3-dimethyl-2-oxopiperazin-1-yl) benzonitrile (737); 3-(2-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl)oxazolidin-2-one (738); 3-(2-(4-(5-(4-amino-5-(trifluoromethyl)pyrrolo[2,1-f][1,2,4]triazin-7-yl)-2-fluorophenyl)-2,2-dimethyl-3-oxopiperazin-1-yl)-2-oxoethyl)oxazolidin-2-one (739); 3-(2-(4-(3-(4-amino-5-chloropyrrolo[2,1-f][1,2,4]triazin-7-yl)phenyl)-2,2-dimethyl-3-oxopiperazin-1-yl)-2-oxoethyl)oxazolidin-2-one (740); N-(3-(4-(5-(4-amino-5-chloropyrrolo[2,1-f][1,2,4] triazin-7-yl)-2-cyanophenyl)-2,2-dimethyl-3-oxopiperazin-1-yl)-3-oxopropyl)acetamide (741); 4-(4-amino-5-chloropyrrolo[2,1-f][1,2,4]triazin-7-yl)-2-(3,3-dimethyl-4-(3-(3-methyl-1H-pyrazol-1-yl)propanoyl)-2-oxopiperazin-1-yl)benzonitrile (742); 4-(4-amino-5-chloropyrrolo[2,1-f][1,2,4]triazin-7-yl)-2-(4-(2-(1,1-dioxido-1,2-thiazinan-2-yl)acetyl)-3,3-dimethyl-2-oxopiperazin-1-yl)benzonitrile (743); 1-(3-(4-amino-5-chloropyrrolo[2,1-f][1,2,4]triazin-7-yl)phenyl)-3,3-dimethyl-4-(2-(methylsulfonyl)acetyl)piperazin-2-one (744); N-(3-(4-(3-(4-amino-5-chloropyrrolo[2,1-f][1,2,4]triazin-7-yl)phenyl)-2,2-dimethyl-3-oxopiperazin-1-yl)-3-oxopropyl)acetamide (745); 1-(3-(4-amino-5-chloropyrrolo[2,1-f][1,2,4]triazin-7-yl)phenyl)-3,3-dimethyl-4-(2-(2-oxopyrrolidin-1-yl)acetyl)piperazin-2-one (746); 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile (747); N-(3-(4-(3-(4-amino-5-(trifluoromethyl)pyrrolo[2,1-f][1,2,4]triazin-7-yl)phenyl)-2,2-dimethyl-3-oxopiperazin-1-yl)-3-oxopropyl) methanesulfonamide (748); N-(3-(4-(3-(4-amino-5-chloropyrrolo[2,1-f][1,2,4]triazin-7-yl)phenyl)-2,2-dimethyl-3-oxopiperazin-1-yl)-3-oxopropyl) methanesulfonamide (749); N-(3-(4-(3-(4-amino-5-cyanopyrrolo[2,1-f][1,2,4]triazin-7-yl)phenyl)-2,2-dimethyl-3-oxopiperazin-1-yl)-3-oxopropyl) methanesulfonamide (750); N-(3-(4-(5-(4-amino-5-(trifluoromethyl)pyrrolo[2,1-f][1,2,4] triazin-7-yl)-2-fluorophenyl)-2,2-dimethyl-3-oxopiperazin-1-yl)-3-oxopropyl) methanesulfonamide (751); 1-(5-(4-amino-5-chloropyrrolo[2,1-f][1,2,4]triazin-7-yl)-2-fluorophenyl)-3,3-dimethyl-4-(2-(methylsulfonyl)acetyl)piperazin-2-one (752); N-(3-(4-(5-(4-amino-5-chloropyrrolo[2,1-f][1,2,4]triazin-7-yl)-2-fluorophenyl)-2,2-dimethyl-3-oxopiperazin-1-yl)-3-oxopropyl)acetamide (753); N-(3-(4-(5-(4-amino-5- chloropyrrolo [2,1-f][1,2,4]triazin-7-yl)-2-fluorophenyl)-2,2-dimethyl-3-oxopiperazin-1-yl)-3-oxopropyl)methanesulfonamide (754); 1-(5-(4-amino-5-chloropyrrolo[2,1-f][1,2,4] triazin-7-yl)-2-fluorophenyl)-3,3-dimethyl-4-(2-(methylsulfonyl)propanoyl)piperazin-2-one (755); N-(2-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl)acetamide (756); 4-(4-amino-5-chloropyrrolo[2,1-f][1,2,4]triazin-7-yl)-2-(4-(3-hydroxy-3-methylbutanoyl)-3,3-dimethyl-2-oxopiperazin-1-yl)benzonitrile (757); 1-(5-(4-amino-5-chloropyrrolo[2,1-f][1,2,4]triazin-7-yl)-2-fluorophenyl)-4-(2-(1,1-dioxidothiomorpholino)acetyl)-3,3-dimethylpiperazin-2-one (758); 1-(5-(4-amino-5-chloropyrrolo[2,1-f][1,2,4]triazin-7-yl)-2-fluorophenyl)-4-(3-hydroxy-3-methylbutanoyl)-3,3-dimethylpiperazin-2-one (759); 1-(5-(4-amino-5-(trifluoromethyl)pyrrolo[2,1-f][1,2,4]triazin-7-yl)-2-fluorophenyl)-4-(3-hydroxy-3-methylbutanoyl)-3,3-dimethylpiperazin-2-one (760); 1-(3-(4-amino-5-(trifluoromethyl)pyrrolo[2,1-f][1,2,4]triazin-7-yl)phenyl)-4-(3-hydroxy-3-methylbutanoyl)-3,3-dimethylpiperazin-2-one (761); 1-(3-(4-amino-5-chloropyrrolo[2,1-f][1,2,4]triazin-7-yl)phenyl)-4-(3-hydroxy-3-methylbutanoyl)-3,3-dimethylpiperazin-2-one (762); (S)-4-(4-amino-5-chloropyrrolo[2,1-f][1,2,4]triazin-7-yl)-2-(3,3,6-trimethyl-4-(2-(methylsulfonyl)acetyl)-2-oxopiperazin-1-yl)benzonitrile (763); 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile (764); 4-(4-amino-5-(trifluoromethyl)pyrrolo[2,1-f][1,2,4]triazin-7-yl)-2-(4-(2-(4,4-dimethyl-2-oxopyrrolidin-1-yl)acetyl)-3,3-dimethyl-2-oxopiperazin-1-yl)benzonitrile (765); 4-(4-amino-5-chloropyrrolo[2,1-f][1,2,4]triazin-7-yl)-2-(3,3-dimethyl-4-(2-(methylsulfonyl)propanoyl)-2-oxopiperazin-1-yl)benzonitrile (766); 1-(5-(4-amino-5-(trifluoromethyl)pyrrolo[2,1-f][1,2,4]triazin-7-yl)-2-methoxyphenyl)-3,3-dimethyl-4-(2-(methylsulfonyl)propanoyl)piperazin-2-one (767); N-(2-(4-(5-(4-amino-5-(trifluoromethyl)pyrrolo[2,1-f][1,2,4]triazin-7-yl)-2-cyanophenyl)-2,2-dimethyl-3-oxopiperazin-1-yl)-2-oxoethyl)methanesulfonamide (768); (S)-1-(5-(4-amino-5-chloropyrrolo[2,1-f][1,2,4]triazin-7-yl)-2-fluorophenyl)-3,3,6-trimethyl-4-(2-(methylsulfonyl)acetyl)piperazin-2-one (769); (S)-1-(5-(4-amino-5-(trifluoromethyl) pyrrolo[2,1-f][1,2,4]triazin-7-yl)-2-fluorophenyl)-3,3,6-trimethyl-4-(2-(methylsulfonyl) acetyl)piperazin-2-one (770); 4-(4-amino-5-chloropyrrolo[2,1-f][1,2,4]triazin-7-yl)-2-(4-(2-(4,4-dimethyl-2-oxopyrrolidin-1-yl)acetyl)-3,3-dimethyl-2-oxopiperazin-1-yl)benzonitrile (771); N-(2-(4-(5-(4-amino-5-chloropyrrolo[2,1-f][1,2,4]triazin-7-yl)-2-fluorophenyl)-2,2-dimethyl-3-oxopiperazin-1-yl)-2-oxoethyl)methanesulfonamide (772); N-(2-(4-(5-(4-amino-5-chloropyrrolo[2,1-f][1,2,4]triazin-7-yl)-2-cyanophenyl)-2,2-dimethyl-3-oxopiperazin-1-yl)-2-oxoethyl)methanesulfonamide (773); 4-(4-amino-5-(trifluoromethyl)pyrrolo[2,1-f][1,2,4]triazin-7-yl)-2-(4-(3-hydroxy-3-methylbutanoyl)-3,3-dimethyl-2-oxopiperazin-1-yl)benzonitrile (774); N-(1-(4-(5-(4-amino-5-chloropyrrolo[2,1-f][1,2,4]triazin-7-yl)-2-methoxyphenyl)-2,2-dimethyl-3-oxopiperazin-1-yl)-1-oxopropan-2-yl)methanesulfonamide (775); N-(2-(4-(5-(4-amino-5-(trifluoromethyl)pyrrolo[2,1-f][1,2,4]triazin-7-yl)-2-fluorophenyl)-2,2-dimethyl-3-oxopiperazin-1-yl)-2-oxoethyl)methanesulfonamide (776); 2-(4-acetyl-3,3-dimethylpiperazin-1-yl)-4-(4-amino-5-chloropyrrolo[2,1-f][1,2,4]triazin-7-yl)benzonitrile (777); 7-(3-(4-acetyl-3,3-dimethylpiperazin-1-yl)-4-cyanophenyl)-4-aminopyrrolo[2,1-f][1,2,4]triazine-5-carbonitrile (778); 2-(4-acetyl-3,3-dimethylpiperazin-1-yl)-4-(4-amino-5-(1-(methyl-d$_3$)-1H-pyrazol-4-yl)pyrrolo[2,1-f][1,2,4]triazin-7-yl)benzonitrile (779); 2-(4-acetyl-3,3-dimethylpiperazin-1-yl)-4-(4-amino-5-(1-(2,2,2-trifluoroethyl)-1H-pyrazol-5-yl)pyrrolo[2,1-f][1,2,4]triazin-7-yl)benzonitrile (780); 2-(4-acetyl-3,3-dimethylpiperazin-1-yl)-4-(4-amino-5-(trifluoromethyl)pyrrolo[2,1-f][1,2,4]triazin-7-yl) benzonitrile (781); 1-(4-(3-(4-amino-5-chloropyrrolo[2,1-f][1,2,4]triazin-7-yl)phenyl)-3-(pyrrolidine-1-carbonyl)piperazin-1-yl)ethan-1-one (782); 4-acetyl-1-(3-(4-amino-5-chloropyrrolo[2,1-f][1,2,4]triazin-7-yl)phenyl)-N,N-dimethylpiperazine-2-carboxamide (783); 4-(4-amino-5-(1-(2,2,2-trifluoroethyl)-1H-pyrazol-5-yl)pyrrolo[2,1-f][1,2,4]triazin-7-yl)-2-((4aR,8aS)-2,2-dimethyl-3-oxooctahydro-4H-benzo[b][1,4]oxazin-4-yl)benzonitrile (784); 4-(3-(4-amino-5-(trifluoromethyl)pyrrolo[2,1-f][1,2,4]triazin-7-yl)phenyl)-2,2-dimethyl-2H-benzo[b][1,4]oxazin-3(4H)-one (785); methyl 2-(4-acetyl-3,3-dimethyl-2-oxopiperazin-1-yl)-4-(4-amino-5-(trifluoromethyl)pyrrolo[2,1-f][1,2,4] triazin-7-yl)benzoate (786); 4-acetyl-1-(5-(4-amino-5-(trifluoromethyl)pyrrolo[2,1-f][1,2,4]triazin-7-yl)-2-(4-methylpiperazine-1-carbonyl)phenyl)-3,3-dimethylpiperazin-2-one (787); 2-(4-acetyl-3,3-dimethyl-2-oxopiperazin-1-yl)-4-(4-amino-5-(trifluoromethyl) pyrrolo[2,1-f][1,2,4]triazin-7-yl)-N-(3-hydroxypropyl)benzamide (788); 2-(4-acetyl-3,3-dimethyl-2-oxopiperazin-1-yl)-4-(4-amino-5-(trifluoromethyl)pyrrolo[2,1-f][1,2,4] triazin-7-yl)-N-(2-hydroxy-2-methylpropyl)-N-methylbenzamide (789); 2-(4-acetyl-3,3-dimethyl-2-oxopiperazin-1-yl)-4-(4-amino-5-(trifluoromethyl)pyrrolo[2,1-f][1,2,4] triazin-7-yl)-N-(2-hydroxyethyl)-N-methylbenzamide (790); 2-(4-acetyl-3,3-dimethyl-2-oxopiperazin-1-yl)-4-(4-amino-5-(trifluoromethyl)pyrrolo[2,1-f][1,2,4]triazin-7-yl)-N-cyclopropylbenzamide (791); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-hydroxyethyl)benzamide (792); 2-(4-acetyl-3,3-dimethyl-2-oxopiperazin-1-yl)-4-(4-amino-5-(trifluoromethyl)pyrrolo [2,1-f][1,2,4]triazin-7-yl)-N-(cyanomethyl)benzamide (793); 2-(4-acetyl-3,3-dimethyl-2-oxopiperazin-1-yl)-4-(4-amino-5-(trifluoromethyl) pyrrolo[2,1-f][1,2,4]triazin-7-yl)benzamide (794); 2-(4-acetyl-3,3-dimethyl-2-oxopiperazin-1-yl)-4-(4-amino-5-(trifluoromethyl)pyrrolo[2,1-f][1,2,4]triazin-7-yl)-N-methylbenzamide (795); 2-(4-acetyl-3,3-dimethyl-2-oxopiperazin-1-yl)-4-(4-amino-5-(trifluoromethyl)pyrrolo [2,1-f][1,2,4] triazin-7-yl)-N-ethylbenzamide (796); 2-(4-acetyl-3,3-dimethyl-2-oxopiperazin-1-yl)-4-(4-amino-5-(trifluoromethyl)pyrrolo[2,1-f][1,2,4]triazin-7-yl)-N,N-dimethylbenzamide (797); 2-(4-acetyl-3,3-dimethyl-2-oxopiperazin-1-yl)-4-(4-amino-5-(trifluoromethyl) pyrrolo [2,1-f][1,2,4]triazin-7-yl)-N-(2-fluoroethyl)benzamide (798); 2-(4-acetyl-3,3-dimethyl-2-oxopiperazin-1-yl)-4-(4-amino-5-(trifluoromethyl)pyrrolo[2,1-f][1,2,4] triazin-7-yl)-N-(3-hydroxy-3-methylbutyl)benzamide (799); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-(methylsulfonyl)ethyl)benzamide (800); 4-acetyl-1-(5-(4-amino-5-(trifluoromethyl) pyrrolo[2,1-f][1,2,4]triazin-7-yl)-2-(morpholine-4-carbonyl)phenyl)-3,3-dimethylpiperazin-2-one (801); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2,2-difluoroethyl) benzamide (802); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-(dimethylamino)ethyl)-N-methylbenzamide (803); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-methoxyethyl)-N-methylbenzamide (804); 4-acetyl-1-(5-(4- amino-5-(trifluoromethyl)pyrrolo[2,1-f][1,2,4] triazin-7-yl)-2-(pyrrolidine-1-carbonyl)phenyl)-3,3-dimethylpiperazin-2-one (805); 2-(4-acetyl-3,3-dimethyl-2-oxopiperazin-1-yl)-4-(4-amino-5-(trifluoromethyl)pyrrolo[2,1-f][1,2,4]triazin-7-yl)-N-isopropylbenzamide (806); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(2-methoxyethyl)benzamide (807); 2-(4-acetyl-3,3-dimethyl-2-oxopiperazin-1-yl)-4-(4-amino-5-(trifluoromethyl) pyrrolo[2,1-f][1,2,4]triazin-7-yl)-N-(pyridin-3-yl) benzamide (808); 2-(4-acetyl-3,3-dimethyl-2-oxopiperazin-1-yl)-4-(4-amino-5-(trifluoromethyl) pyrrolo[2,1-f][1,2,4]triazin-7-yl)-N-(2-(dimethylamino)ethyl)benzamide (809); 2-(4-acetyl-3,3-dimethyl-2-oxopiperazin-1-yl)-4-(4-amino-5-(trifluoromethyl)pyrrolo[2,1-f][1,2,4]triazin-7-yl)-N-(methyl-d$_3$)benzamide (810); 7-(3-(4-acetyl-3,3-dimethyl-2-oxopiperazin-1-yl)-4-(1-methyl-1H-1,2,4-triazol-3-yl)phenyl)-4-aminopyrrolo[2,1-f][1,2,4]triazine-5-carbonitrile (811); (R)-4-acetyl-1-(5-(4-amino-5-(trifluoromethyl) pyrrolo[2,1-f][1,2,4]triazin-7-yl)-2-(1-hydroxyethyl)phenyl)-3,3-dimethylpiperazin-2-one (812); (S)-4-acetyl-1-(5-(4-amino-5-(trifluoromethyl)pyrrolo[2,1-f][1,2,4]triazin-7-yl)-2-(1-hydroxyethyl)phenyl)-3,3-dimethylpiperazin-2-one (813); 4-acetyl-1-(5-(4-amino-5-(trifluoromethyl)pyrrolo[2,1-f][1,2,4]triazin-7-yl)-2-(methoxymethyl)phenyl)-3,3-dimethylpiperazin-2-one (814); 4-acetyl-1-(5-(4-amino-5-chloropyrrolo[2,1-f][1,2,4] triazin-7-yl)-2-(methoxymethyl)phenyl)-3,3-dimethylpiperazin-2-one (815); (R)-4-acetyl-1-(5-(4-amino-5-(trifluoromethyl)pyrrolo[2,1-f][1,2,4]triazin-7-yl)-2-(1-hydroxypropyl) phenyl)-3,3-dimethylpiperazin-2-one (816); (S)-4-acetyl-1-(5-(4-amino-5-(trifluoromethyl)pyrrolo[2,1-f][1,2,4]triazin-7-yl)-2-(1-hydroxypropyl) phenyl)-3,3-dimethylpiperazin-2-one (817); (S)-4-acetyl-1-(5-(4-amino-5-chloropyrrolo[2,1-f][1,2,4] triazin-7-yl)-2-(1-hydroxypropyl)phenyl)-3,3-dimethylpiperazin-2-one (818); (R)-4-acetyl-1-(5-(4-amino-5-chloropyrrolo[2,1-f][1,2,4]triazin-7-yl)-2-(1-hydroxypropyl) phenyl)-3,3-dimethylpiperazin-2-one (819); 4-acetyl-1-(3-(4-amino-5-(2-methyl-1-(2,2,2-trifluoroethyl)-1H-imidazol-5-yl)pyrrolo[2,1-f][1,2,4]triazin-7-yl)phenyl)-3,3-dimethylpiperazin-2-one (820); (R)-4-(4-amino-5-(1,2-dimethyl-1H-imidazol-5-yl)pyrrolo[2,1-f][1,2,4]triazin-7-yl)-2-(2,2,6-trimethyl-3-oxomorpholino)benzonitrile (821); 4-acetyl-1-(3-(4-amino-5-(4-methyl-1H-pyrazol-1-yl)pyrrolo[2,1-f][1,2,4]triazin-7-yl)phenyl)-3,3-dimethylpiperazin-2-one (822); 2-(4-acetyl-3,3-dimethylpiperazin-1-yl)-4-(4-amino-5-chloro-6-fluoropyrrolo[2,1-f][1,2,4]triazin-7-yl)benzonitrile (823); (R)-4-(5-(4-amino-5-chloro-6-fluoropyrrolo[2,1-f][1,2,4]triazin-7-yl)-2-fluorophenyl)-2,2,5-trimethylmorpholin-3-one (824); (S)-4-(5-(4-amino-5-chloro-6-fluoropyrrolo[2,1-f][1,2,4]triazin-7-yl)-2-fluorophenyl)-2,2,6-trimethylmorpholin-3-one (825); 4-(3-(4-amino-5-chloro-6-fluoropyrrolo[2,1-f][1,2,4]triazin-7-yl)phenyl)morpholin-3-one (826); 4-(4-amino-5-chloro-6-fluoropyrrolo[2,1-f][1,2,4]triazin-7-yl)-2-(2,2-dimethyl-3-oxomorpholino) benzonitrile (827); 4-(3-(4-amino-5-chloro-6-fluoropyrrolo [2,1-f][1,2,4] triazin-7-yl)phenyl)morpholin-3-one (828); 4-(3-(4-amino-5-chloro-6-fluoropyrrolo[2,1-f][1,2,4]triazin-7-yl)phenyl)-2,2-dimethyl-3-oxopiperazine-1-carbonitrile (829); 4-(3-(4-amino-5-chloro-6-fluoropyrrolo[2,1-f][1,2,4]triazin-7-yl)phenyl)-2,2-dimethylmorpholin-3-one (830); 4-(4-amino-5-chloro-6-fluoropyrrolo[2,1-f][1,2,4]triazin-7-yl)-2-(2,2-dimethyl-3-oxomorpholino-5,5,6,6-d$_4$) benzonitrile (831); 4-(5-(4-amino-5-chloro-6-fluoropyrrolo [2,1-f][1,2,4]triazin-7-yl)-2-methoxyphenyl)-2,2-dimethylmorpholin-3-one (832); 4-acetyl-1-(3-(4-amino-5-chloro-6-fluoropyrrolo[2,1-f][1,2,4]triazin-7-yl)-2-fluorophenyl)-3,3-dimethylpiperazin-2-one-5,5,6,6-d$_4$ (833); 4-acetyl-1-(5-(4-amino-5-chloro-6-fluoropyrrolo[2,1-f][1,2,4]triazin-7-yl)-2-fluorophenyl)-3,3-dimethylpiperazin-2-one (834); 4-acetyl-1-(3-(4-amino-5-chloro-6-fluoropyrrolo[2,1-f][1,2,4]triazin-7-yl)phenyl)-3,3-dimethylpiperazin-2-one-5,5,6,6-d$_4$ (835); 2-(4-acetyl-3,5-dimethylpiperazin-1-yl)-4-(4-amino-5-chloro-6-fluoropyrrolo[2,1-f][1,2,4]triazin-7-yl)benzonitrile (836); 2-(4-acetyl-3,3-dimethyl-2-oxopiperazin-1-yl)-4-(4-amino-5-chloro-6-fluoropyrrolo[2,1-f][1,2,4]triazin-7-yl)benzonitrile (837); and a salt thereof.

8. A pharmaceutical composition comprising a compound according to claim 1 and a pharmaceutically acceptable carrier.

9. A method of treating a disease, comprising administering to a patient a therapeutically-effective amount of a compound according to claim 1, wherein the disease is autoimmune disease or chronic inflammatory disease wherein said autoimmune disease or chronic inflammatory disease is systemic lupus erythematosus, lupus nephritis, rheumatoid arthritis, multiple vasculitides, idiopathic thrombocytopenic purpura, myasthenia gravis, allergic rhinitis, or multiple sclerosis.

* * * * *

UNITED STATES PATENT AND TRADEMARK OFFICE
CERTIFICATE OF CORRECTION

PATENT NO. : 10,214,537 B2  
APPLICATION NO. : 15/521202  
DATED : February 26, 2019  
INVENTOR(S) : Rajeev S. Bhide et al.

Page 1 of 2

It is certified that error appears in the above-identified patent and that said Letters Patent is hereby corrected as shown below:

On the Title Page

<u>In the Abstract:</u>
Column 2 (Abstract), Line 5, delete "6?membered" and insert -- 6-membered --, therefor.

In the Claims

Claim 1, Column 667, Line 25, delete "$C_{1-3}$ haloalkyl," and insert -- $C_{1-3}$haloalkyl, --, therefor.

Claim 1, Column 667, Line 56, "—$CH_2NHS(O)_2CH_3$—$CH_2OR_{3a}$,", should read "—$CH_2NHS(O)_2CH_3$, —$CH_2OR_{3a}$,".

Claim 1, Column 669, Line 1, delete "$CH_2$ (dimethyl-," and insert -- $CH_2$(dimethyl-, --, therefor.

Claim 1, Column 669, Lines 1-2, delete "$CH_2$ (trimethyl-" and insert -- $CH_2$(trimethyl- --, therefor.

Claim 1, Column 669, Lines 43-44, should read "—$O(piperidinyl-C(O)NR_w(C_{1-4}$ alkyl)), and —$O(piperidinyl-C(O)(C_{1-4}$ hydroxyalkyl))".

Claim 2, Column 670, Line 2, delete "—$CH_2$ (morpholinyl)," and insert -- —$CH_2$(morpholinyl), --, therefor.

Claim 2, Column 670, Line 8, delete "—$CH_2$ (" and insert -- —$CH_2$( --, therefor.

Claim 2, Column 671, Lines 15-16, delete "—$CH(CH_3)_2$)," and insert -- —$CH(CH_3)_2$, --, therefor.

Claim 2, Column 671, Lines 66-67, should read "methyl [1,2,4]triazolo[4,3-a]pyridinyl, dimethyl [1,2,4]triazolo[4,3-a]pyridinyl".

Signed and Sealed this  
Fifth Day of November, 2019

Andrei Iancu  
*Director of the United States Patent and Trademark Office*

CERTIFICATE OF CORRECTION (continued)
U.S. Pat. No. 10,214,537 B2

Claim 7, Column 672, Lines 64-65, delete "-((dimethyl amino)" and insert -- -((dimethylamino) --, therefor.

Claim 7, Column 673, Line 9, delete "20);" and insert -- (20); --, therefor.

Claim 7, Column 674, Line 7, delete "-′7-" and insert -- -7- --, therefor.

Claim 7, Column 676, Line 65, delete "((1s,3 s)-" and insert -- ((1s,3s)- --, therefor.

Claim 7, Column 677, Line 9, delete "] triazin-" and insert -- ]triazin- --, therefor.

Claim 7, Column 679, Line 37, delete "-′7-" and insert -- -7- --, therefor.

Claim 7, Column 680, Line 10, delete "-′7-" and insert -- -7- --, therefor.

Claim 7, Column 687, Line 43, delete "S)—" and insert -- (S)— --, therefor.

Claim 7, Column 692, Line 53, delete "-[4,2,4]" and insert -- -[1,2,4] --, therefor.

Claim 7, Column 696, Line 13, delete ")benzonitrile," and insert -- )benzonitrile --, therefor.

Claim 9, Column 704, Line 43, delete "vasculitides," and insert -- vasculitis, --, therefor.